(12) United States Patent
Binder et al.

(10) Patent No.: US 9,468,672 B2
(45) Date of Patent: *Oct. 18, 2016

(54) PROSTATE-ASSOCIATED ANTIGENS AND VACCINE-BASED IMMUNOTHERAPY REGIMENS

(71) Applicant: Pfizer Inc, New York, NY (US)

(72) Inventors: Joseph John Binder, San Diego, CA (US); Helen Kim Cho, San Diego, CA (US); Michael Robert Dermyer, Carlsbad, CA (US); Karin Ute Jooss, San Diego, CA (US); Brian Gregory Pierce, Wayland, MA (US); Joyce Tsi Tan, Chapel Hill, NC (US); Van To Tsai, San Diego, CA (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/657,302

(22) Filed: Mar. 13, 2015

(65) Prior Publication Data

US 2015/0246106 A1 Sep. 3, 2015

Related U.S. Application Data

(62) Division of application No. 13/875,162, filed on May 1, 2013, now Pat. No. 9,066,898.

(60) Provisional application No. 61/642,844, filed on May 4, 2012.

(51) Int. Cl.

| A61K 39/00 | (2006.01) |
|---|---|
| C07H 21/04 | (2006.01) |
| A61K 39/39 | (2006.01) |
| A61K 39/395 | (2006.01) |
| C12N 9/48 | (2006.01) |
| A61K 31/404 | (2006.01) |
| C07K 14/47 | (2006.01) |
| C12N 9/64 | (2006.01) |

(52) U.S. Cl.
CPC ......... *A61K 39/0011* (2013.01); *A61K 31/404* (2013.01); *A61K 39/39* (2013.01); *A61K 39/3955* (2013.01); *C07K 14/4748* (2013.01); *C12N 9/485* (2013.01); *C12N 9/6445* (2013.01); *C12Y 304/17021* (2013.01); *A61K 2039/53* (2013.01); *A61K 2039/55561* (2013.01)

(58) Field of Classification Search
None
See application file for complete search history.

(56) References Cited

U.S. PATENT DOCUMENTS

| 5,538,866 | A | 7/1996 | Israeli et al. |
|---|---|---|---|
| 6,541,212 | B2 | 4/2003 | Reiter et al. |
| 6,825,326 | B2 | 11/2004 | Reiter et al. |
| 7,005,498 | B1 | 2/2006 | Steinaa |
| 7,109,003 | B2 | 9/2006 | Hanson et al. |
| 7,288,251 | B2 | 10/2007 | Bedian et al. |
| 7,288,636 | B2 | 10/2007 | Mikolajczyk |
| 8,435,516 | B2 | 5/2013 | Huang et al. |
| 9,066,898 | B2 | 6/2015 | Binder et al. |
| 2003/0086930 | A1 | 5/2003 | Mueller et al. |
| 2005/0136055 | A1 | 6/2005 | Gladue et al. |
| 2005/0226875 | A1 | 10/2005 | Gomez-Navaro et al. |
| 2005/0272755 | A1 | 12/2005 | Denis et al. |
| 2007/0059315 | A1 | 3/2007 | Jaffee et al. |
| 2008/0193448 | A1 | 8/2008 | Baum et al. |
| 2008/0279865 | A1 | 11/2008 | Gomez et al. |
| 2009/0004213 | A1 | 1/2009 | Singh et al. |
| 2009/0074787 | A1 | 3/2009 | Gomez et al. |
| 2009/0117132 | A1 | 5/2009 | Readett et al. |
| 2010/0305196 | A1* | 12/2010 | Probst ............... A61K 39/0011 514/44 R |
| 2010/3005196 | | 12/2010 | Probst et al. |
| 2012/0263677 | A1 | 10/2012 | Eagle et al. |

FOREIGN PATENT DOCUMENTS

| WO | WO2006048749 | 5/2006 |
|---|---|---|
| WO | WO2007113648 | 10/2007 |
| WO | WO20120042421 | 4/2012 |
| WO | WO2012065164 | 5/2012 |
| WO | WO2013006050 | 1/2013 |

OTHER PUBLICATIONS

Qin et al (Immunology Letter, 2005, 99:85-93, IDS).*
Waeckerle-Men et al (Cancer Immunol Immunother, 2006, 55:1524-1533).*
Schmittgen, T., et al., "Expression of Prostate Specific Membrane Antigen and Three Alternatively Spliced Variants of PSMA in Prostate Cancer Patients," Int. J. Cancer, 2003, vol. 107(2):323-9.
Schoenfeld, J. et al., "Active immunotherapy induces antibody responses that target tumor angiogenesis," Cancer Research, 2010, vol. 70:10150-10160.
Schroers, R., et al., "Identification of MHC class II-restricted T-cell epitopes in prostate-specific membrane antigen," Clinical Cancer Research, 2003, vol. 9(9):3260-71.
Sharma, R. et al., "4-1BB Ligand As an Effective Multifunctional Immunomodulator and Antigen Delivery Vehicle for the Development of Therapeutic Cancer Vaccines," Cancer Research, 2010, vol. 70(10):3945-3954.
Shen, L., et al., "Cellular Protein Is the Source of Cross-Priming Antigen in Vivo," Proc Natl Acad Sci U S A 2004, vol. 101(9):3035-3040.

(Continued)

Primary Examiner — Laura B Goddard
(74) Attorney, Agent, or Firm — Austin W. Zhang

(57) ABSTRACT

The present disclosure provides (a) isolated immunogenic PAA polypeptides; (b) isolated nucleic acid molecules encoding immunogenic PAA polypeptides; (c) vaccine compositions comprising an immunogenic PAA polypeptide or an isolated nucleic acid molecule encoding an immunogenic PAA polypeptide; (d) methods relating to uses of the polypeptides, nucleic acid molecules, and compositions; and (e) vaccine-based immunotherapy regimens which involve co-administration of a vaccine in combination with an immune-suppressive-cell inhibitor and an immune-effector-cell enhancer.

20 Claims, 55 Drawing Sheets

(56) References Cited

OTHER PUBLICATIONS

Sonpavde, G., et al., "Recent Advances in Immunotherapy for the Treatment of Prostate Cancer." Expert Opinion on Biol. Ther., 2011, vol. 11(8):997-1009.

Stura E., et al., "Crystal Structure of Human Prostate-Specific Antigen in a Sandwich Antibody Complex.," Journal of Molecular Biology, 2011, vol. 414:530-544.

Terasawa, H. et al., "Identification and Characterization of a Human Agonist Cytotoxic T-Lymphocyte Epitope of Human Prostate-specific Antigen," Clinical Cancer Research, 2002, vol. 8:41-53.

Thomas-Kaskel, A., et al., "Vaccination of Advanced Prostate Cancer Patients With PSCA and PSA Peptide-Loaded Dendritic Cells Induces DTH Responses That Correlate With Superior Overall Survival," International Journal against Cancer, 2006, vol. 119, 2428-2434.

van den Eertwegh, A., et al., "Combined Immunotherapy With Granulocyte-Macrophage Colony-Stimulating Factor-Transduced Allogeneic Prostate Cancer Cells and Ipilimumab in Patients With Metastatic Castration-Resistant Prostate Cancer: A Phase 1 Dose-Escalation Trial," Lancet Oncology, 2012, vol. 13:509-17.

Villoutreix, B., et al., "A Structural Model for the Prostate Disease Marker, Human Prostate-Specific Antigen," Protein Science, 1994, vol. 3(11):2033-2044.

Zhang, J., et al., "A Small Composite Probasin Promoter Confers High Levels of Prostate-Specific Gene Expression Through Regulation by Androgens and Glucocorticoids In Vitro and In Vivo" Endocrinology, 2000, vol. 141 (12):4698-4710.

Houot, R., et al., "T-cell modulation combined with intratumoral CpG cures lymphoma in a mouse model without the need for chemotherapy," Blood, 2009, 3546-3552, vol. 113.

Olson, W., et al., "Clinical Trials of Cancer Therapies Targeting Prostate-Specific Membrane Antigen," Reviews on Recent Clinical Trials, 2007, 182-190, vol. 2.

Ying, W., et al., "Dendritic cell-based multi-epitope immunotherapy of hormone-refractory prostate carcinoma", Cancer Immunology Immunotherapy, 2006, 1524-1533, vol. 55.

Sutmuller, R., et al., "Synergism of Cytotoxic T Lymphocyte—associated Antigen 4 Blockade and Depletion of CD25 Regulatory T Cells in Antitumor Therapy Reveals Alternative Pathways for Suppression of Autoreactive Cytotoxic T Lymphocyte Responses", J. Exp. Med., 2001, 823-832, vol. 194, No. 6.

Ahlers, J., et al., "A push—pull approach to maximize vaccine efficacy: Abrogating suppression with an IL-13 inhibitor while augmenting help with granulocyte/macrophage colony-stimulating factor and CD40L", PNAS, 2002, 13020-13025, vol. 99, No. 20.

Berzofsky, J., et al., "Progress on new vaccine strategies for the immunotherapy and prevention of cancer", The Journal of Clinical Investigation, 2004, 1515-1525, vol. 113, No. 11.

Mangsbo, S., et al., "Enhanced Tumor Eradication by Combining CTLA-4 or PD-1 Blockade with CpG Therapy," Journal of Immunotherapy, 2010, 225-235, vol. 33.

Database UniProt [Online], "Glutamate carboxypeptidase 2; EC=3. 4.17.21; Cell growth-inhibiting gene 27 protein; Folate hydrolase 1; Folylpoly-gama-glutamate carboxypeptidase", retrieved from EBI accession No. UNIPROT:Q04609 Database accession No. Q04609 sequence, Jun. 1, 1994.

Ahmad, S. et al., "Prostate Stem Cell Antigen DNA Vaccination Breaks Tolerance to Self-Antigen and Inhibits Prostate Cancer Growth," American Society of Gene Therapy, 2009; vol. 17(6):1101-8.

Arlen, P. et al., "Clinical Safety of a Viral Vector Based Prostate Cancer Vaccine Strategy." The Journal of Urology, 2007, vol. 178:1515-1520.

Balk, S. et al., "Biology of Prostate-Specific Antigen," Journal of Clinical Onoclogy, 2003, vol. 21(2):383-391.

Bar$^V$inka, C.et al., "Amino Acids At the N- and C-Termini of Human Glutamate Carboxypeptidase II Are Required for Enzymatic Activity and Proper Folding," Eur. J. Biochem, 2004, vol. 271:2782-2790.

Barinka, C. et al. "Identification of the N-glycosylation sites on glutamate carboxypeptidase II necessary for proteolytic activity." Protein Science, 2004, vol. 13(6): 1627-1635.

Bose, A. et al., "Combined Vaccine + Axitinib Therapy Yields Superior Antitumor Efficacy in a Murine Melanoma Model," Melanoma Research, 2012, vol. 22:236-243.

Cha, E., et al., "Therapeutic Vaccines for Prostate Cancer." Current Opinion in Molecular Therapeutics, 2010, vol. 12 (1): 77-85.

Chakraborty, M. et al., "The Combined Activation of Positive Costimulatory Signals With Modulation of a Negative Costimulatory Signal for the Enhancement of Vaccine-Mediated T-Cell Responses," Cancer Immunol Immunother, 2007, vol. 56:1471-1484.

Collins, D., et al., "Trastuzumab Induces Antibody-Dependent Cell-Mediated Cytotoxicity (ADCC) in HER-2-Non-Amplified Breast Cancer Cell Lines" Annals of Oncology, 2011, vol. 23:1788-1795.

Dall'Ozzo, S., et al.,"Rituximab-Dependent Cytotoxicity by Natural Killer Cells: Influence of FCGR3A Polymorphism on the Concentration-Effect Relationship." Cancer Research, 2004, vol. 64(13): 4664-4669.

Dannull J. et al., "Prostate Stem Cell Antigen is a Promising Candidate for Immunotherapy of Advanced Prostate Cancer.," Cancer Research, 2000, vol. 60:5522-28.

Davis, M., et al., "Crystal Structure of Prostate-Specific Membrane Antigen, a Tumor Marker and Peptidase," Proc Natl Acad Science, 2005, vol. 102(17):5981-6.

Drake, C. et al., "Update: immunological strategies for prostate cancer," Curr Urol Rep, 2010, vol. 11(3):202-7.

Durso, R., et al., "A Novel Alphavirus Vaccine Encoding Prostate-Specific Membrane Antigen Elicits Potent Cellular and Humoral Immune Responses." Clinical Cancer Research, 2007, vol. 13(13):3999-4008.

Elsasser-Beile, U., et al., "Targeted Therapies for Prostate Cancer Against the Prostate Specific Membrane Antigen," Current Drug Targets, 2009, vol. 10(2):118-25.

Farsaci, B. et al., "Consequence of Dose Scheduling of Sunitinib on Host Immune Response Elements and Vaccine Combination Therapy," International Journal of Cancer, 2011, vol. 0:1-12.

Ferraro, B., et al., "Co-delivery of PSA and PSMA DNA Vaccines With Electroporation Induces Potent Immune Responses," Human Vaccines, 2011, vol. 7:120-127.

Garcia-Hernandez , M.,, et al., "Prostate Stem Cell Antigen Vaccination Induces a Long-Term Protective Immune Response Against Prostate Cancer in the Absence of Autoimmunity." Cancer Research, 2008, vol. 68(3): 861-869.

Goodman, O., et al. "Interaction of prostate specific membrane antigen with clathrin and the adaptor protein complex-2," International Journal of Oncology , 2007, vol. 31(5): 1199-1203.

Gregor, P., et al., "Induction of autoantibodies to syngeneic prostate-specific membrane antigen by xenogeneic vaccination.," International Journal of Cancer, 2005, vol. 116(3): 415-21.

Gu, Z., et al., "Prostate Stem Cell Antigen (PSCA) Expression Increases With High Gleason Score, Advanced Stage and Bone Metastasis in Prostate Cancer." Oncogene, 2000, vol. 19(10): 1288-1296.

Harada, M., et al., "Prostate-Specific Antigen-Derived Epitopes Capable of Inducing Cellular and Humoral Responses in HLA-A24+ Prostate Cancer Patients," The Prostate, 2003, vol. 57:152-159.

Hirao, L. et al., "Immune Modulation through 4-1BB Enhances SIV Vaccine Protection in Non-Human Primates against SIVmac251 Challenge," PLoS One, 2011, vol. 6(9): 1-11.

Hodge, J.. et al., "Multiple Costimulatory Modalities Enhance CTL Activity," The Journal of Immunology, 2005, vol. 174;5994-6004.

Horig , H. et al., "Prostate-Specific Antigen Vaccines for Prostate Cancer," Expert Opininion, 2002, vol. 2(4):395-408.

Houghton, C., et al., "Immunological validation of the EpitOptimizer program for streamlined design of heteroclitic epitopes." Vaccine, 2007, vol. 25(29): 5330-5342.

Karan, D., et al., "Dual Antigen Target-Based Immunotherapy for Prostate Cancer Eliminates the Growth of Established Tumors in Mice." Immunotherapy, 2011, vol. 3(6): 735-746.

(56) References Cited

OTHER PUBLICATIONS

Keler, T. et al., "Activity and Safety of CTLA-4 Blockade Combined with Vaccines in Cynomolgus Macaques.," The Journal of Immunology, 2003, vol. 171:6251-6259.
Kiessling, A., et al., "Advances in specific immunotherapy for prostate cancer.," European Urology, 2008. vol. 53 (4):694-708.
Kim, S., et al., "Vaccination With Recombinant Adenoviruses and Dendritic Cells Expressing Prostate-Specific Antigens Is Effective in Eliciting CTL and Suppresses Tumor Growth in the Experimental Prostate Cancer." The Prostate, 2009, vol. 69(9): 938-948.
Kobayashi, K., et al., "Identification of a Prostate-Specific Membrane Antigen-Derived Peptide Capable of Eliciting Both Cellular and Humoral Immune Responses in HLA-A24+ Prostate Cancer Patients," Cancer Sci, 2003, vol. 94(7): 622-7.
Kumar, A., et al. "Expression of Pro Form of Prostate-Specific Antigen by Mammalian Cells and Its Conversion to Mature, Active Form by Human Kallikrein 2," Cancer Research, 1997, vol. 57(15): 3111-3114.
Li, Betty et al., "Established B16 Tumors Are Rejected Following Treatment With GM-CSF-Secreting Tumor Cell Immunotherapy in Combination With Anti-4-1BB Mab," Clinical Immunology, 2007, vol. 125:76-87.
Li, Y. et al "Cytotoxicity of Human Prostate Cancer Cell Lines In Vitro and Induction of Apoptosis Using 213Bi-Herceptin Alpha-Conjugate." Cancer Letters, 2004, vol. 205(2): 161-171.
Li, Y., et al "Promising Tumor-Associated Antigens for Future Prostate Cancer Therapy." Medicinal Research Reviews, 2010, vol. 30(1):67-101.
Lu, J., et al. "Recognition of Prostate Tumor Cells by Cytotoxic T Lymphocytes Specific for Prostate-Specific Membrane Antigen," Cancer Research, 2002, vol. 62(20):5807-12.
Lubaroff, D., et al., "Phase I Clinical Trial of an Adenovirus/Prostate-Specific Antigen Vaccine for Prostate Cancer: Safety and Immunologic Results." Clinical Cancer Research, 2009, vol. 15(23): 7375-7380.
Lundwall, A., et al., "Molecular Cloning of Human Prostate Specific Antigen cDNA," FEBS Letters, 1987, vol. 214(2): 317-322.
Madan, R.. et al., "Ipilimumab and a Poxviral Vaccine Targeting Prostate-Specific Antigen in Metastatic Castration-Resistant Prostate Cancer: A Phase 1 Dose-Escalation Trial," Lancet Oncol, 2012; 13: 501-08.
Matsueda, S., et al., "Identification of peptide vaccine candidates for prostate cancer patients with HLA-A3 supertype alleles.," Clinical Cancer Research, 2005, vol. 11:6933-43.
McCormack, R., et al., "Molecular Forms of Prostate-Specific Antigen and the Human Kallikrein Gene Family: A New Era." Urology, 1995, vol. 45(5):729-744.
Mincheff, M., et al., "Immune Responses Against PSMA After Gene-Based Vaccination for Immunotherapy-A: Results From Immunizations in Animals," Cancer Gene Therapy, 2006, 13(4):436-44.
Qin, H., et al., "Specific Antitumor Immune Response Induced by a Novel DNA Vaccine Composed of Multiple CTL and T Helper Cell Epitopes of Prostate Cancer Associated Antigens," Immunology Letters, 2005, vol. 99(1):85-93.
Raff A., et al., "Prostate Stem Cell Antigen: A Prospective Therapeutic and Diagnostic Target," Cancer Letters, 2009, vol. 277:126-132.
Rajasekaran, S., et al., "A novel cytoplasmic tail MXXXL motif mediates the internalization of prostate-specific membrane antigen," Molecular Biology of the Cell, 2003, vol. 14(12):4835-4845.
Reiter, R., et al., "Prostate Stem Cell Antigen: A Cell Surface Marker Overexpressed in Prostate Cancer." Proc Natl Acad Sci U S A , 1994, vol. 95(4):1735-1740.
Rock, K., et al., "Cross-Presentation: Underlying Mechanisms and Role in Immune Surveillance." Immunology Reviews, 2005, vol. 207: 166-183.
Rountree, R., et al.,"Exosome targeting of tumor antigens expressed by cancer vaccines can improve antigen immunogenicity and therapeutic efficacy." Cancer Research, 2011, vol. 71:5235-5244.
Sacha, P., et al., "Expression of glutamate carboxypeptidase II in human brain," Neuroscience, 2007. vol. 144 (4):1361-72.
Sakamoto, H. et al., "Genetic variation in PSCA is associated with susceptibility to diffuse-type gastric cancer," Nature Genetics, 2008, vol.;40(6):730-40.
U.S. Appl. No. 14/527,226, filed Oct. 29, 2014.

* cited by examiner

FIG. 2

```
                    10                  20
----------------------+-------------------+-
Q T L N F D L L K L A G D V E S N P G * P   FMDV 2A
- - E G R G S L L T C G D V E E N P G * P   TAV 2A
H Y A G Y F A D L L I H D I E T N P G * P   EMCV 2A
Q C T N Y A L L K L A G D V E S N P G * P   ERAV 2A
- A T N F S L L K Q A G D V E E N P G * P   PTV 2A
```

FIG. 3

5'UAACGUUACUGGCCGAAGCCGCUUGGAAUAAGGCCGGUGUGCGUUUGUCUAU
AUGUUAUUUUCCACCAUAUUGCCGUCUUUUGGCAAUGUGAGGGCCCGGAAACCU
GGCCCUGUCUUCUUGACGAGCAUUCCAGGGGUCUUUCCCCUCUCGCCAAAGG
AAUGCAAGGUCUGUUGAAUGUCGUGAAGGAAGCAGUUCCUCUGGAAGCUUCUU
GAAGACAAACAACGUCUGUAGCGACCCUUUGCAGGCAGCGGAACCCCCCACCUG
GCGACAGGUGCCUCUGCGGCCAAAAGCCACGUAUAAGAUACACCUGCAAAGG
CGGCACAACCCCAGUGCCACGUUGUGAGUUGGAUAGUUGUGGAAAGAGUCAAAU
GGCUCUCCUCAAGCGUAUUCAACAAGGGCUGAAGGAUGCCCAGAAGGUACCCC
AUUGUAUGGGAUCUGAUCUGGGGCCUCGGUGCACAUGCUUUACAUGUGUUUAG
UCGAGGUUAAAAAACGUCUAGGCCCCCCGAACCACGGGGACGUGGUUUUCCUUU
GAAAAACACGAUGAUAAU*<u>AUGGCCACAACCAUG</u>3'

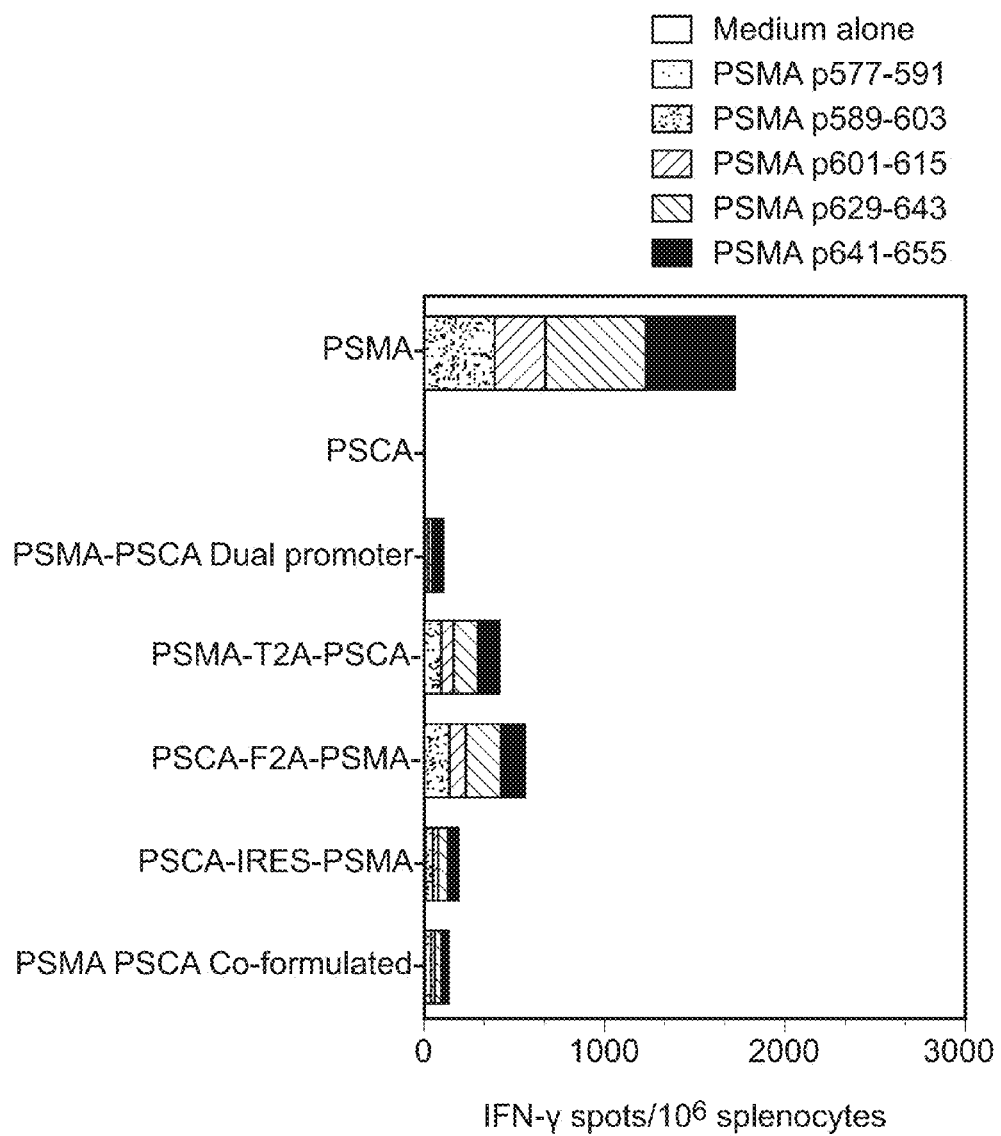

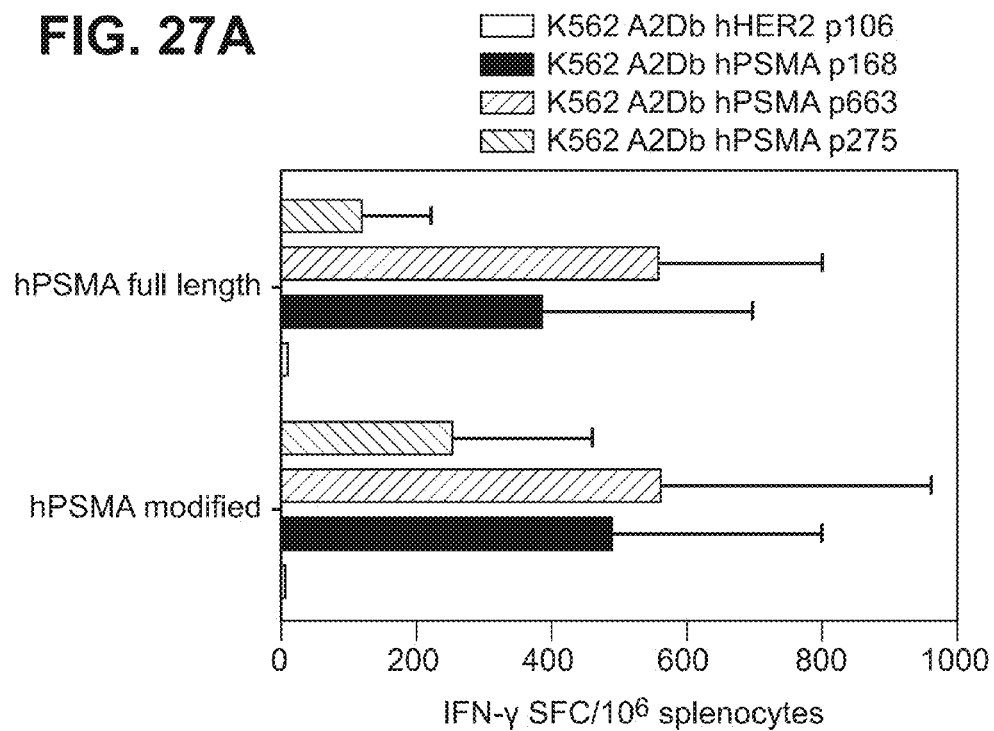
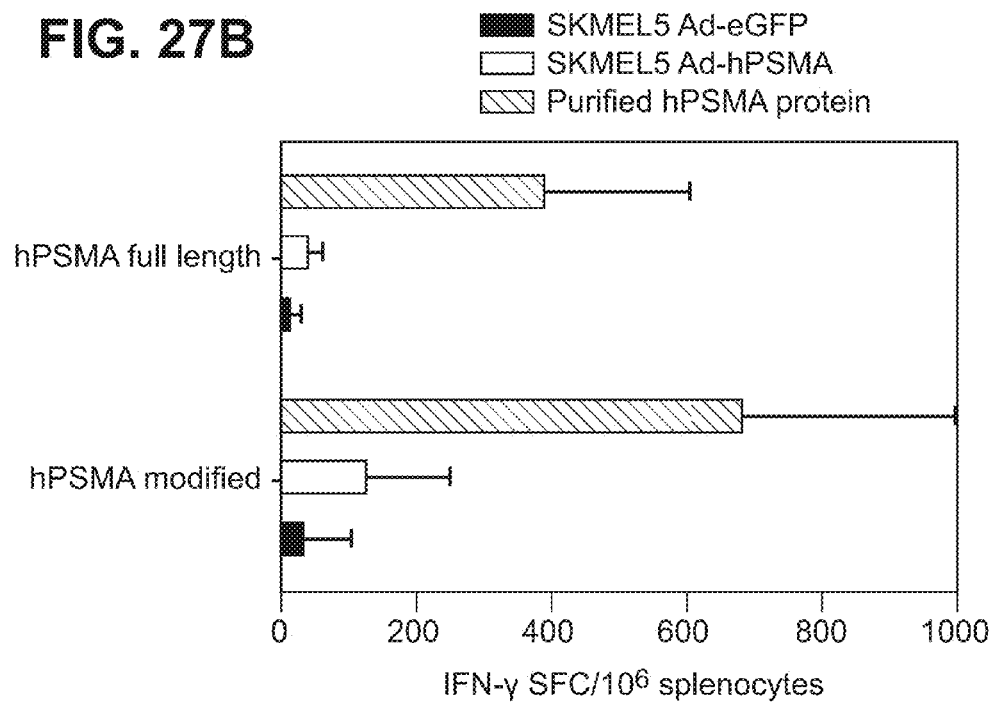

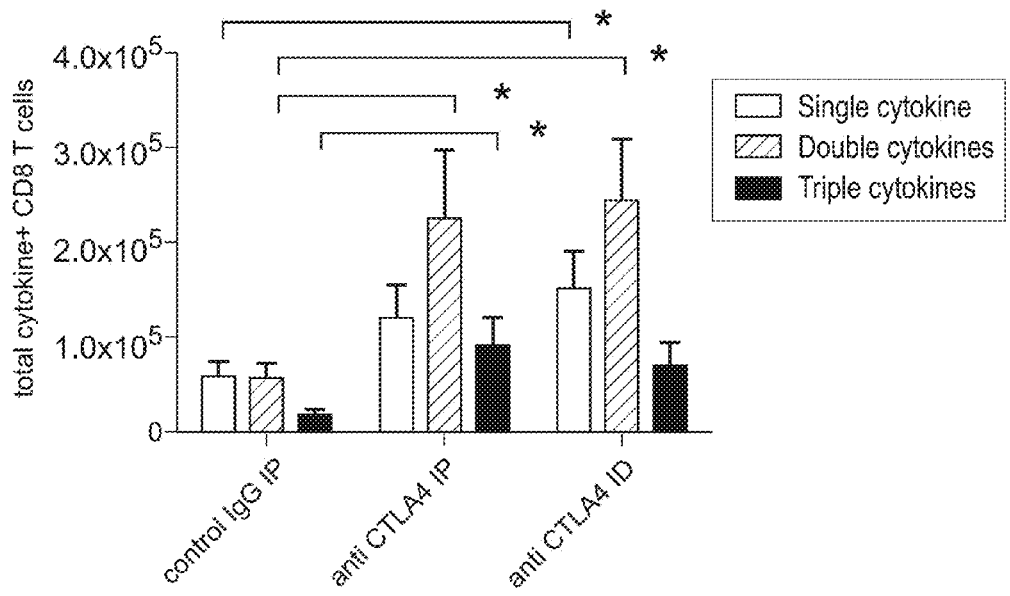
FIG. 31A rHer-2 specific polyfunctional CD8 T cells
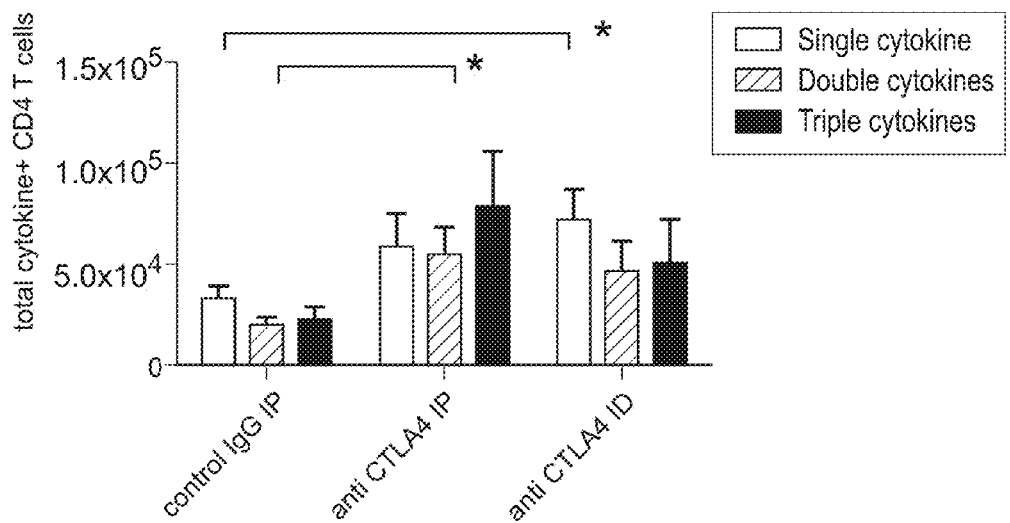
FIG. 31B rHer-2 specific polyfunctional CD4 T cells FIG. 33A — vehicle + control
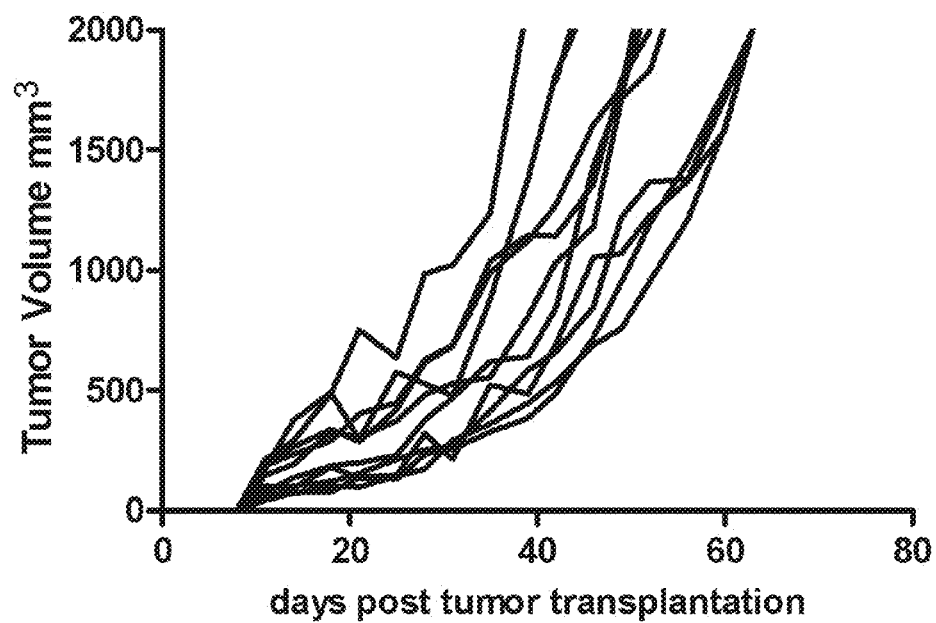
FIG. 33B — Sutent + Control
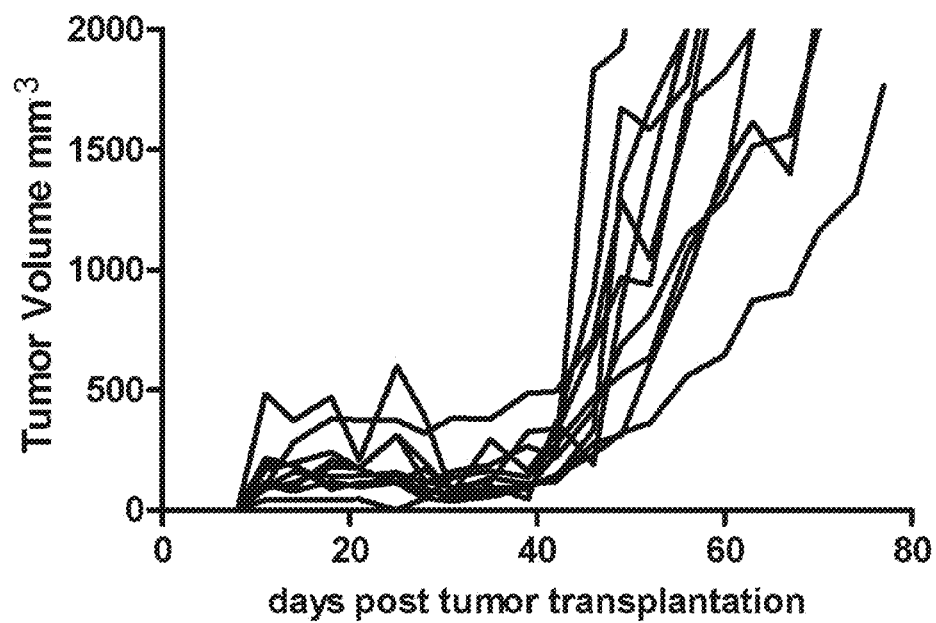

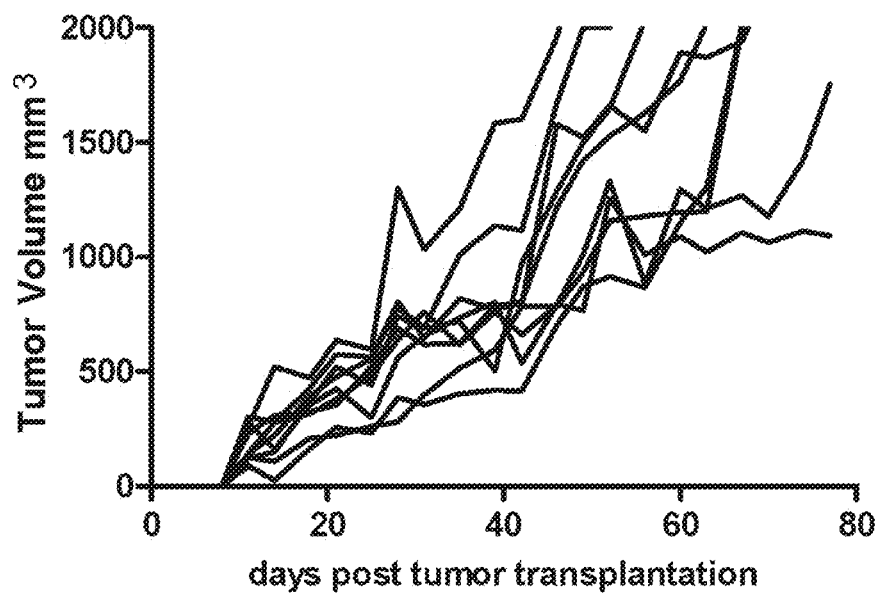
FIG. 33C — vehicle + rHER2
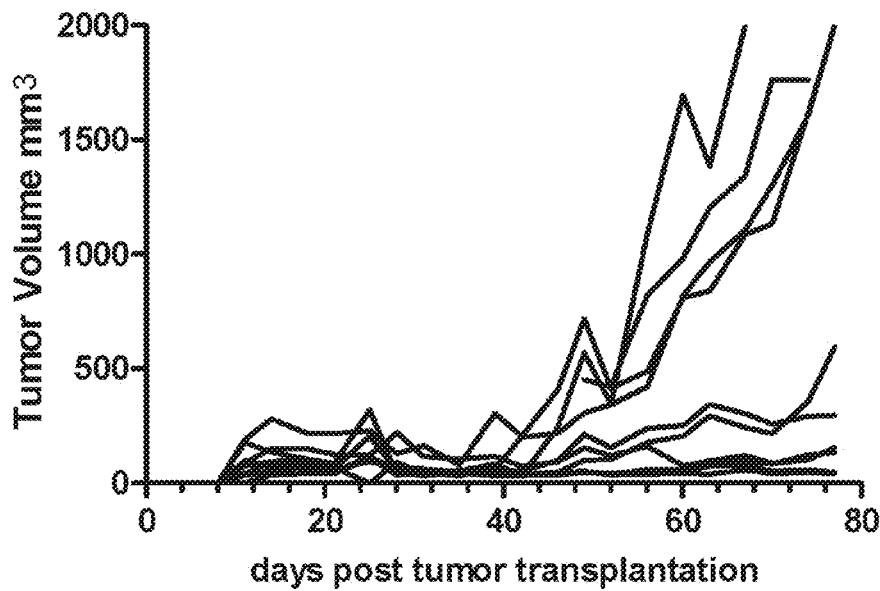
FIG. 33D — Sutent + rHER2

SEQUENCE LISTING

<160> NUMBER OF SEQ ID NOS: 62

<210> SEQ ID NO 1
<211> LENGTH: 750
<212> TYPE: PRT
<213> ORGANISM: Homo sapiens

<400> SEQUENCE: 1

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

-continued

```
Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
    370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
    450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
```

```
              515                 520                 525
Gly Ile Ala Ser Gly Arg Ala Arg Tyr Thr Lys Asn Trp Glu Thr Asn
    530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
    610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
        675                 680                 685

His Val Ile Tyr Ala Pro Ser Ser His Asn Lys Tyr Ala Gly Glu Ser
    690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Glu Thr Leu Ser Glu Val Ala
            740                 745                 750

<210> SEQ ID NO 2
<211> LENGTH: 2250
<212> TYPE: DNA
<213> ORGANISM: Homo sapiens

<400> SEQUENCE: 2
atgtggaatc tccttcacga aaccgactcg gctgtggcca ccgcgcgccg cccgcgctgg     60
ctgtgcgctg gggcgctggt gctggcgggt ggcttctttc cctcggctt cctcttcggg    120 tggtttataa atcctccaa tgaagctact aacattactc caaagcataa atgaaagca    180 tttttggatg aattgaaagc tgagaacatc aagaagttct tatataattt tacacagata    240
ccacatttag caggaacaga acaaaacttt cagcttgcaa agcaaattca atcccagtgg    300
aaagaatttg gcctggattc tgttgagcta gcacattatg atgtcctgtt gtcctaccca    360
aataagactc atcccaacta catctcaata attaatgaag atggaaatga gattttcaac    420
acatcattat ttgaaccacc tcctccagga tatgaaaatg tttcggatat tgtaccacct    480
ttcagtgctt tctctcctca aggaatgcca gagggcgatc tagtgtatgt taactatgca    540
cgaactgaag acttctttaa attggaacgg gacatgaaaa tcaattgctc tgggaaaatt    600
gtaattgcca gatatgggaa agttttcaga ggaaataagg ttaaaaatgc ccagctggca    660
ggggccaaag gagtcattct ctactccgac cctgctgact actttgctcc tggggtgaag    720
tcctatccag atggttggaa tcttcctgga ggtggtgtcc agcgtggaaa tatcctaaat    780
ctgaatggtg caggagaccc tctcacacca ggttacccag caaatgaata tgcttatagg    840
```

```
cgtggaattg cagaggctgt tggtcttcca agtattcctg ttcatccaat tggatactat    900
gatgcacaga agctcctaga aaaaatgggt ggctcagcac caccagatag cagctggaga    960
ggaagtctca aagtgcccta caatgttgga cctggcttta ctggaaactt ttctacacaa   1020
aaagtcaaga tgcacatcca ctctaccaat gaagtgacaa gaatttacaa tgtgataggt   1080
actctcagag gagcagtgga accagacaga tatgtcattc tgggaggtca ccgggactca   1140
tgggtgtttg gtggtattga ccctcagagt ggagcagctg ttgttcatga aattgtgagg   1200
agctttggaa cactgaaaaa ggaagggtgg agacctagaa gaacaatttt gtttgcaagc   1260
tgggatgcag aagaatttgg tcttcttggt tctactgagt gggcagagga gaattcaaga   1320
ctccttcaag agcgtggcgt ggcttatatt aatgctgact catctataga aggaaactac   1380
actctgagag ttgattgtac accgctgatg tacagcttgg tacacaacct aacaaaagag   1440
ctgaaaagcc ctgatgaagg ctttgaaggc aaatctcttt atgaaagttg gactaaaaaa   1500
agtccttccc cagagttcag tggcatgccc aggataagca aattgggatc tggaaatgat   1560
tttgaggtgt tcttccaacg acttggaatt gcttcaggca gagcacggta tactaaaaat   1620
tgggaaacaa acaaattcag cggctatcca ctgtatcaca gtgtctatga acatatgagc   1680
ttggtggaaa agttttatga tccaatgttt aaatatcacc tcactgtggc ccaggttcga   1740
ggagggatgg tgtttgagct agccaattcc atagtgctcc cttttgattg tcgagattat   1800
gctgtagttt aagaaagta tgctgacaaa atctacagta tttctatgaa acatccacag   1860
gaaatgaaga catacagtgt atcatttgat tcactttttt ctgcagtaaa gaattttaca   1920
gaaattgctt ccaagttcag tgagagactc caggactttg acaaaagcaa cccaatagta   1980
ttaagaatga tgaatgatca actcatgttt ctggaaagag catttattga tccattaggg   2040
ttaccagaca ggccttttta taggcatgtc atctatgctc caagcagcca caacaagtat   2100
gcaggggagt cattcccagg aatttatgat gctctgtttg atattgaaag caaagtggac   2160
ccttccaagg cctggggaga agtgaagaga cagatttatg ttgcagcctt cacagtgcag   2220
gcagctgcag agactttgag tgaagtagcc                                    2250
```

<210> SEQ ID NO 3
<211> LENGTH: 739
<212> TYPE: PRT
<213> ORGANISM: Artificial
<220> FEATURE:
<223> OTHER INFORMATION: synthetic construct

<400> SEQUENCE: 3

```
Met Ala Ser Ala Arg Arg Pro Arg Trp Leu Cys Ala Gly Ala Leu Val
1               5                   10                  15

Leu Ala Gly Gly Phe Phe Leu Leu Gly Phe Leu Phe Gly Trp Phe Ile
                20                  25                  30

Lys Ser Ser Ser Glu Ala Thr Asn Ile Ser Pro Gln His Asn Val Lys
            35                  40                  45

Ala Phe Leu Asp Glu Met Lys Ala Glu Asn Ile Lys Lys Phe Leu Tyr
        50                  55                  60

Leu Phe Thr Gln Ile Pro His Leu Ala Gly Thr Glu Gln Asn Phe Gln
65                  70                  75                  80

Leu Ala Lys Gln Ile Gln Ala Glu Trp Lys Glu Phe Gly Leu Asp Ser
                85                  90                  95

Val Glu Leu Ala His Tyr Asp Val Leu Leu Ser Tyr Pro Asn Glu Thr
                100                 105                 110
```

```
His Pro Asn Tyr Ile Ser Ile Ile Asp Glu Asp Gly Asn Glu Ile Phe
            115                 120                 125

Asn Thr Ser Leu Phe Glu Pro Pro Pro Gly Tyr Glu Asn Ile Ser
        130                 135                 140

Asp Val Val Pro Pro Tyr Ser Ala Phe Ser Pro Gln Gly Met Pro Glu
145                 150                 155                 160

Gly Asp Leu Val Tyr Val Asn Tyr Ala Arg Thr Glu Asp Phe Phe Lys
                165                 170                 175

Leu Glu Arg Glu Leu Lys Ile Asn Cys Ser Gly Lys Ile Leu Ile Ala
            180                 185                 190

Arg Tyr Gly Lys Val Phe Arg Gly Asn Lys Val Lys Asn Ala Gln Leu
        195                 200                 205

Ala Gly Ala Lys Gly Ile Ile Leu Tyr Ser Asp Pro Ala Asp Tyr Phe
        210                 215                 220

Ala Pro Gly Val Lys Ser Tyr Pro Asp Gly Trp Asn Leu Pro Gly Gly
225                 230                 235                 240

Gly Val Gln Arg Gly Asn Val Leu Asn Leu Asn Gly Ala Gly Asp Pro
                245                 250                 255

Leu Thr Pro Gly Tyr Pro Ala Asn Glu Tyr Ala Tyr Arg Glu Leu
            260                 265                 270

Ala Glu Ala Val Gly Leu Pro Ser Ile Pro Val His Pro Ile Gly Tyr
        275                 280                 285

Tyr Asp Ala Gln Lys Leu Leu Glu Lys Met Gly Gly Ser Ala Pro Pro
        290                 295                 300

Asp Ser Ser Trp Lys Gly Ser Leu Lys Val Pro Tyr Asn Val Gly Pro
305                 310                 315                 320

Gly Phe Thr Gly Asn Phe Ser Thr Gln Lys Val Lys Met His Ile His
                325                 330                 335

Ser Thr Asn Glu Val Thr Arg Ile Tyr Asn Val Ile Gly Thr Ile Arg
            340                 345                 350

Gly Ala Val Glu Pro Asp Arg Tyr Val Ile Leu Gly Gly His Arg Asp
        355                 360                 365

Ala Trp Val Phe Gly Gly Ile Asp Pro Gln Ser Gly Ala Ala Val Val
        370                 375                 380

His Glu Ile Val Arg Ser Phe Gly Thr Leu Lys Lys Lys Gly Trp Arg
385                 390                 395                 400

Pro Arg Arg Thr Ile Ile Phe Ala Ser Trp Asp Ala Glu Glu Phe Gly
                405                 410                 415

Leu Leu Gly Ser Thr Glu Trp Ala Glu Glu Asn Ser Arg Leu Leu Gln
            420                 425                 430

Glu Arg Gly Val Ala Tyr Ile Asn Ala Asp Ser Ser Ile Glu Gly Asn
        435                 440                 445

Tyr Thr Leu Arg Val Asp Cys Thr Pro Leu Met Tyr Ser Leu Val Tyr
        450                 455                 460

Asn Leu Thr Lys Glu Leu Gln Ser Pro Asp Glu Gly Phe Glu Gly Lys
465                 470                 475                 480

Ser Leu Tyr Glu Ser Trp Thr Lys Lys Ser Pro Ser Pro Glu Phe Ser
                485                 490                 495

Gly Val Pro Arg Ile Asn Lys Leu Gly Ser Gly Asn Asp Phe Glu Val
            500                 505                 510

Phe Phe Gln Arg Leu Gly Ile Ala Ser Gly Arg Ala Arg Tyr Thr Lys
        515                 520                 525
```

```
Asn Trp Lys Thr Asn Lys Phe Ser Gly Tyr Pro Leu Tyr His Ser Val
    530                 535                 540
Tyr Glu Thr Tyr Glu Leu Val Glu Lys Phe Tyr Asp Pro Met Phe Lys
545                 550                 555                 560
Tyr His Leu Thr Val Ala Gln Val Arg Gly Gly Leu Val Phe Glu Leu
                565                 570                 575
Ala Asp Ser Ile Val Leu Pro Phe Asp Cys Gln Asp Tyr Ala Val Val
            580                 585                 590
Leu Arg Lys Tyr Ala Asp Lys Ile Tyr Asn Leu Ala Met Lys His Pro
        595                 600                 605
Glu Glu Leu Lys Thr Tyr Ser Val Ser Phe Asp Ser Leu Phe Ser Ala
    610                 615                 620
Val Lys Asn Phe Thr Glu Ile Ala Ser Lys Phe Asn Gln Arg Leu Gln
625                 630                 635                 640
Asp Phe Asp Lys Asn Asn Pro Leu Leu Val Arg Met Leu Asn Asp Gln
                645                 650                 655
Leu Met Phe Leu Glu Arg Ala Phe Val Asp Pro Leu Gly Leu Pro Asp
            660                 665                 670
Arg Pro Phe Tyr Arg His Val Ile Tyr Ala Pro Ser Ser His Asn Lys
        675                 680                 685
Tyr Ala Gly Glu Ser Phe Pro Gly Ile Tyr Asp Ala Leu Phe Asp Ile
    690                 695                 700
Glu Ser Lys Val Asp Pro Ser Lys Ala Trp Gly Glu Val Lys Arg Gln
705                 710                 715                 720
Ile Tyr Val Ala Ala Phe Thr Val Gln Ala Ala Glu Thr Leu Ser
                725                 730                 735
Glu Val Ala

<210> SEQ ID NO 4
<211> LENGTH: 2217
<212> TYPE: DNA
<213> ORGANISM: Artificial
<220> FEATURE:
<223> OTHER INFORMATION: Synthetic Construct

<400> SEQUENCE: 4
atggctagcg ccagacggcc cagatggctg tgcgccggag ccctggtgct ggccggagga     60
ttcttcctgc tgggcttcct gttcggctgg ttcatcaaga gcagcagcga ggccaccaac    120
atcagccccc agcacaacgt gaaggccttt ctggacgaga tgaaggccga aacatcaag    180
aagtttctgt acctgttcac ccagatcccc cacctggccg gcaccgagca gaacttccag    240
ctggccaagc agattcaggc tgagtggaaa gagttcggcc tggacagcgt ggagctggcc    300
cactacgacg tgctgctgtc ctaccccaac gagacacacc ccaactacat cagcatcatc    360
gacgaggacg gcaacgagat tttcaacacc agcctgttcg agcccctcc cctggctac     420
gagaacatct ccgacgtggt gcccccctac agcgccttca gccctcaggg aatgcctgaa    480
ggcgacctgg tgtacgtgaa ctacgcccgg accgaggact tcttcaagct ggaacgggag    540
ctgaagatca actgcagcgg caagatcctg atcgccagat acggcaaggt gttccgggc     600
aacaaagtga agaacgcaca gctggctgga ccaagggca tcatcctgta cagcgacccc    660
gccgactact tcgcccctgg cgtgaagtcc taccctgacg ctggaacct gcctggcggc    720
ggagtgcagc ggggcaacgt gctgaacctg aacggagccg cgaccctct gaccccaggc    780
taccccgcca acgagtacgc ctaccggcgg gagctggccg aagccgtggg cctgcccagc    840
```

```
atccccgtgc acccccatcgg ctactacgac gcccagaaac tgctggaaaa gatgggcggc    900
agcgcccctc ccgacagcag ctggaagggc agcctgaagg tgccctacaa cgtgggccct    960
ggcttcaccg gcaacttcag cacccagaaa gtgaagatgc acatccacag caccaacgaa   1020
gtgacccgga tctacaacgt gatcggcacc atcagaggcg ccgtggagcc cgacagatac   1080
gtgatcctgg gcggccaccg ggacgcctgg gtgttcggcg catcgaccc ccagagcgga   1140 gccgccgtgg tgcacgagat cgtgcggagc ttcggcaccc tgaagaagaa gggctggcgg   1200
cccagacgga ccatcatctt cgccagctgg gacgccgagg aattcggact gctgggctct   1260
accgagtggg ccgaggaaaa cagcagactg ctgcaggaac ggggcgtcgc ctacatcaac   1320
gccgacagct ccatcgaggg caactacacc ctgcgggtgg actgcacccc cctgatgtac   1380
agcctggtgt acaacctgac caaagagctg cagagcccg acgagggctt cgagggcaag   1440
agcctgtacg agagctggac caagaagtcc cccagccccg agttcagcgg cgtgccccgg   1500
atcaacaagc tgggcagcgg caacgacttc gaggtgttct ccagaggct gggcattgcc   1560 agcggcagag cccggtacac caagaactgg aaaaccaaca agttctccgg ctaccccctg   1620
taccacagcg tgtacgagac atacgaactg gtggagaagt tctacgaccc catgttcaag   1680
taccacctga ccgtggccca ggtccgggga gggctggtgt cgaactggc cgacagcatc   1740 gtgctgccct tcgactgcca ggactatgct gtggtgctgc ggaagtacgc cgacaaaatc   1800
tacaacctgg ccatgaagca ccccgaggaa ctgaaaacct acagcgtgtc cttcgacagc   1860
ctgttcagcg ccgtgaagaa cttcaccgag atcgccagca agttcaacca gcggctgcag   1920
gacttcgaca agaacaaccc cctgctggtc cggatgctga cgaccagct gatgttcctg   1980 gaacgggcct tcgtggaccc cctgggcctg cctgaccggc ccttctaccg gcacgtgatc   2040 tatgcccccca gcagccacaa caagtacgct ggcgagagct ccccggcat ctacgatgcc   2100 ctgttcgaca tcgagagcaa ggtggacccc agcaaggcct ggggcgaagt gaagcggcag   2160
atatacgtgg ccgccttcac agtgcaggcc gctgccgaga cactgagcga ggtggcc      2217
```

<210> SEQ ID NO 5
<211> LENGTH: 739
<212> TYPE: PRT
<213> ORGANISM: Artificial
<220> FEATURE:
<223> OTHER INFORMATION: Synthetic Construct

<400> SEQUENCE: 5

```
Met Ala Ser Ala Arg Arg Pro Arg Trp Leu Cys Ala Gly Ala Leu Val
1               5                   10                  15

Leu Ala Gly Gly Phe Phe Leu Leu Gly Phe Leu Phe Gly Trp Phe Ile
                20                  25                  30

Lys Ser Ser Glu Ala Thr Asn Ile Thr Pro Gln His Asn Val Lys
            35                  40                  45

Ala Phe Leu Asp Glu Leu Lys Ala Glu Asn Ile Lys Lys Phe Leu Tyr
        50                  55                  60

Asn Phe Thr Gln Ile Pro His Leu Ala Gly Thr Glu Gln Asn Phe Glu
65                  70                  75                  80

Leu Ala Lys Gln Ile Gln Ala Gln Trp Lys Glu Phe Gly Leu Asp Ser
                85                  90                  95

Val Glu Leu Ser His Tyr Asp Val Leu Leu Ser Tyr Pro Asn Glu Thr
            100                 105                 110

His Pro Asn Tyr Ile Ser Ile Ile Asp Glu Asp Gly Asn Glu Ile Phe
        115                 120                 125
```

```
Asn Thr Ser Leu Phe Glu Pro Pro Pro Gly Tyr Glu Asn Ile Ser
    130                 135                 140

Asp Val Val Pro Pro Tyr Ser Ala Phe Ser Pro Gln Gly Met Pro Glu
145                 150                 155                 160

Gly Asp Leu Val Tyr Val Asn Tyr Ala Arg Thr Glu Asp Phe Phe Lys
                    165                 170                 175

Leu Glu Arg Asp Met Lys Ile Asn Cys Ser Gly Lys Ile Leu Ile Ala
                180                 185                 190

Arg Tyr Gly Lys Val Phe Arg Gly Asn Lys Val Lys Asn Ala Gln Leu
            195                 200                 205

Ala Gly Ala Lys Gly Ile Ile Leu Tyr Ser Asp Pro Ala Asp Tyr Phe
        210                 215                 220

Ala Pro Gly Val Lys Ser Tyr Pro Asp Gly Trp Asn Leu Pro Gly Gly
225                 230                 235                 240

Gly Val Gln Arg Gly Asn Val Leu Asn Leu Asn Gly Ala Gly Asp Pro
                245                 250                 255

Leu Thr Pro Gly Tyr Pro Ala Asn Glu Tyr Ala Tyr Arg Arg Gly Ile
                260                 265                 270

Ala Glu Ala Val Gly Leu Pro Ser Ile Pro Val His Pro Ile Gly Tyr
            275                 280                 285

Tyr Asp Ala Gln Lys Leu Leu Glu Lys Met Gly Gly Ala Ala Pro Pro
        290                 295                 300

Asp Ser Ser Trp Lys Gly Ser Leu Gln Val Pro Tyr Asn Val Gly Pro
305                 310                 315                 320

Gly Phe Thr Gly Asn Phe Ser Thr Gln Lys Val Lys Met His Ile His
                325                 330                 335

Ser Thr Asn Glu Val Thr Arg Ile Tyr Asn Val Ile Gly Thr Leu Lys
                340                 345                 350

Gly Ala Val Glu Pro Asp Arg Tyr Val Ile Leu Gly Gly His Arg Asp
            355                 360                 365

Ala Trp Val Phe Gly Gly Ile Asp Pro Gln Ser Gly Ala Ala Val Val
        370                 375                 380

His Glu Ile Val Arg Ser Phe Gly Thr Leu Lys Lys Lys Gly Trp Arg
385                 390                 395                 400

Pro Arg Arg Thr Ile Leu Phe Ala Ser Trp Asp Ala Glu Glu Phe Gly
                405                 410                 415

Leu Leu Gly Ser Thr Glu Trp Ala Glu Glu Asn Ser Arg Leu Leu Gln
                420                 425                 430

Glu Arg Gly Val Ala Tyr Ile Asn Ala Asp Ser Ser Ile Glu Gly Asn
            435                 440                 445

Tyr Thr Leu Arg Val Asp Cys Thr Pro Leu Met Tyr Ser Leu Val Tyr
450                 455                 460

Asn Leu Thr Lys Glu Leu Gln Ser Pro Asp Glu Gly Phe Glu Gly Lys
465                 470                 475                 480

Ser Leu Phe Asp Ser Trp Thr Glu Lys Ser Pro Ser Pro Glu Phe Ser
                485                 490                 495

Gly Leu Pro Arg Ile Ser Lys Leu Gly Ser Gly Asn Asp Phe Glu Val
                500                 505                 510

Phe Phe Gln Arg Leu Gly Ile Ala Ser Gly Arg Ala Arg Tyr Thr Lys
            515                 520                 525

Asp Trp Lys Thr Ser Lys Phe Ser Gly Tyr Pro Leu Tyr His Ser Val
530                 535                 540
```

```
Tyr Glu Thr Tyr Glu Leu Val Glu Lys Phe Tyr Asp Pro Met Phe Lys
545                 550                 555                 560

Tyr His Leu Thr Val Ala Gln Val Arg Gly Gly Ile Val Phe Glu Leu
                565                 570                 575

Ala Asn Ser Val Val Leu Pro Phe Asp Cys Gln Asp Tyr Ala Val Val
            580                 585                 590

Leu Lys Lys Tyr Ala Asp Lys Ile Tyr Asn Ile Ser Met Lys His Pro
        595                 600                 605

Gln Glu Met Lys Thr Tyr Ser Val Ser Phe Asp Ser Leu Phe Ser Ala
    610                 615                 620

Val Lys Asn Phe Thr Glu Ile Ala Ser Lys Phe Asn Gln Arg Leu Gln
625                 630                 635                 640

Asp Phe Asp Lys Asn Asn Pro Ile Leu Leu Arg Met Met Asn Asp Gln
                645                 650                 655

Leu Met Phe Leu Glu Arg Ala Phe Ile Asp Pro Leu Gly Leu Pro Asp
            660                 665                 670

Arg Pro Phe Tyr Arg His Val Ile Tyr Ala Pro Ser Ser His Asn Lys
        675                 680                 685

Tyr Ala Gly Glu Ser Phe Pro Gly Ile Tyr Asp Ala Leu Phe Asp Ile
    690                 695                 700

Glu Ser Lys Val Asp Pro Ser Lys Ala Trp Gly Glu Val Lys Arg Gln
705                 710                 715                 720

Ile Tyr Val Ala Ala Phe Thr Val Gln Ala Ala Glu Thr Leu Ser
                725                 730                 735

Glu Val Ala

<210> SEQ ID NO 6
<211> LENGTH: 2217
<212> TYPE: DNA
<213> ORGANISM: Artificial
<220> FEATURE:
<223> OTHER INFORMATION: Synthetic Construct

<400> SEQUENCE: 6
atggctagcg ccagacggcc cagatggctg tgtgctggcg ccctggtgct ggctggcggc    60
ttttcctgc tgggcttcct gttcggctgg ttcatcaaga gcagcagcga ggccaccaac   120
atcacccccc agcacaacgt gaaggccttt ctggacgagc tgaaggccga gaatatcaag   180
aagttcctgt acaacttcac ccagatcccc cacctggccg caccgagca gaacttcgag   240
ctggccaagc agatccaggc ccagtggaaa gagttcggcc tggacagcgt ggaactgagc   300
cactacgacg tgctgctgag ctaccccaac gagacacacc ccaactacat cagcatcatc   360
gacgaggacg gcaacgagat tttcaacacc agcctgttcg agcccctcc acccggctac   420
gagaacatca gcgacgtggt gccccctac agcgcattca gtccacaggg aatgcccgag   480
ggcgacctgg tgtacgtgaa ctacgcccgg accgaggact tcttcaagct ggaacgggac   540
atgaagatca actgcagcgg caagatcctg atcgccagat acggcaaggt gttccggggc   600
aacaaagtga agaacgccca gctggcaggc gccaagggca tcatcctgta cagcgacccc   660
gccgactact cgcccctgg cgtgaagtcc taccccgacg ctggaacct gcctggcggc   720
ggagtgcaga ggggcaacgt gctgaacctg aacggcgctg gcgaccctct gacccctggc   780
taccccgcca acgagtacgc ctacagacgg ggaatcgccg aggccgtggg cctgcctagc   840
atccctgtgc accccatcgg ctactacgac gcccagaaac tgctggaaaa gatgggcgga   900
gccgcccctc ccgacagctc ttggaagggc agcctgcagg tccctacaa cgtgggccct   960
```

```
ggcttcaccg gcaacttcag cacccagaaa gtgaagatgc acatccacag caccaacgaa    1020
gtgacccgga tctacaacgt gatcggcacc ctgaagggcg ccgtggaacc cgacagatac    1080
gtgatcctgg cggccaccg ggacgcctgg gtgttcggag gcatcgaccc tcagagcggc     1140
gctgccgtgt gcacgagat cgtgcggagc ttcggcacac tgaagaagaa gggctggcgg     1200
cccagacgga ccatcctgtt cgccagctgg gacgccgagg aattcggcct gctgggcagc    1260
accgagtggg ccgaggaaaa cagtcggctg ctgcaggaac ggggcgtcgc ctacatcaac    1320
gccgacagca gcatcgaggg caactacacc ctgcgggtgg actgcacccc cctgatgtac    1380
agcctggtgt acaacctgac caaagagctg cagagccccg acgagggctt cgagggcaag    1440
tccctgttcg actcctggac cgagaagtcc cccagccccg agttcagcgg cctgcccaga    1500
atcagcaagc tgggcagcgg caacgacttc gaggtgttct ccagcggct gggaatcgcc     1560 agcggcagag cccggtacac caaggactgg aaaaccagca agttctccgg ctaccccctg    1620
taccacagcg tgtacgagac atacgagctg gtggaaaagt tctacgaccc catgttcaag    1680
taccacctga ccgtggccca ggtccgaggc ggcatcgtgt cgaactggc caacagcgtg     1740 gtgctgccat tcgattgtca ggactacgcc gtggtgctga agaagtacgc cgacaaaatc    1800
tacaacatca gcatgaagca ccccaggaa atgaaaacct acagcgtgtc cttcgacagc     1860
ctgttcagcg ccgtgaagaa tttcaccgag atcgcctcca gttcaacca gagactgcag     1920 gacttcgaca gaacaacccc catcctgctg cggatgatga cgaccagct gatgttcctg     1980 gaacgggcct tcatcgaccc cctgggcctg cccgaccggc cctttaccg gcacgtgatc    2040 tatgccccca gcagccacaa caaatacgcc ggcgagagtt tccccggcat ctacgatgcc    2100
ctgttcgata tcgagagcaa ggtggacccc agcaaggcct ggggcgaagt gaagcggcag    2160
atttacgtgg ccgcattcac agtgcaggct gctgccgaga cactgagcga ggtggcc      2217

<210> SEQ ID NO 7
<211> LENGTH: 739
<212> TYPE: PRT
<213> ORGANISM: Artificial
<220> FEATURE:
<223> OTHER INFORMATION: Synthetic Construct

<400> SEQUENCE: 7

Met Ala Ser Ala Arg Arg Pro Arg Trp Leu Cys Ala Gly Ala Leu Val
1               5                   10                  15

Leu Ala Gly Gly Phe Phe Leu Leu Gly Phe Leu Phe Gly Trp Phe Ile
                20                  25                  30

Lys Ser Ser Asn Glu Ala Thr Asn Ile Thr Pro Lys His Asn Met Lys
            35                  40                  45

Ala Phe Leu Asp Glu Leu Lys Ala Glu Asn Ile Lys Lys Phe Leu Tyr
        50                  55                  60

Asn Phe Thr Gln Ile Pro His Leu Ala Gly Thr Glu Gln Asn Phe Gln
65                  70                  75                  80

Leu Ala Lys Gln Ile Gln Ser Gln Trp Lys Glu Phe Gly Leu Asp Ser
                85                  90                  95

Val Glu Leu Ala His Tyr Asp Val Leu Leu Ser Tyr Pro Asn Lys Thr
            100                 105                 110

His Pro Asn Tyr Ile Ser Ile Ile Asn Glu Asp Gly Asn Glu Ile Phe
        115                 120                 125

Asn Thr Ser Leu Phe Glu Pro Pro Pro Gly Tyr Glu Asn Val Ser
        130                 135                 140
```

```
Asp Ile Val Pro Pro Phe Ser Ala Phe Ser Pro Gln Gly Met Pro Glu
145                 150                 155                 160

Gly Asp Leu Val Tyr Val Asn Tyr Ala Arg Thr Glu Asp Phe Phe Lys
            165                 170                 175

Leu Glu Arg Asp Met Lys Ile Asn Cys Ser Gly Lys Ile Val Ile Ala
        180                 185                 190

Arg Tyr Gly Lys Val Phe Arg Gly Asn Lys Val Lys Asn Ala Gln Leu
    195                 200                 205

Ala Gly Ala Lys Gly Val Ile Leu Tyr Ser Asp Pro Ala Asp Tyr Phe
210                 215                 220

Ala Pro Gly Val Lys Ser Tyr Pro Asp Gly Trp Asn Leu Pro Gly Gly
225                 230                 235                 240

Gly Val Gln Arg Gly Asn Ile Leu Asn Leu Asn Gly Ala Gly Asp Pro
            245                 250                 255

Leu Thr Pro Gly Tyr Pro Ala Asn Glu Tyr Ala Tyr Arg Arg Gly Ile
        260                 265                 270

Ala Glu Ala Val Gly Leu Pro Ser Ile Pro Val His Pro Ile Gly Tyr
    275                 280                 285

Tyr Asp Ala Gln Lys Leu Leu Glu Lys Met Gly Gly Ser Ala Pro Pro
290                 295                 300

Asp Ser Ser Trp Arg Gly Ser Leu Lys Val Pro Tyr Asn Val Gly Pro
305                 310                 315                 320

Gly Phe Thr Gly Asn Phe Ser Ala Gln Lys Leu Lys Leu His Ile His
            325                 330                 335

Ser Asn Thr Lys Val Thr Arg Ile Tyr Asn Val Ile Gly Thr Leu Arg
        340                 345                 350

Gly Ala Val Glu Pro Asp Arg Tyr Val Ile Leu Gly Gly His Arg Asp
    355                 360                 365

Ser Trp Val Phe Gly Gly Ile Asp Pro Gln Ser Gly Ala Ala Val Val
370                 375                 380

His Glu Ile Val Arg Thr Phe Gly Thr Leu Lys Lys Lys Gly Trp Arg
385                 390                 395                 400

Pro Arg Arg Thr Ile Leu Phe Ala Ser Trp Asp Ala Glu Glu Phe Gly
            405                 410                 415

Leu Leu Gly Ser Thr Glu Trp Ala Glu Glu Asn Ser Arg Leu Leu Gln
        420                 425                 430

Glu Arg Gly Val Ala Tyr Ile Asn Ala Asp Ser Ser Ile Glu Gly Asn
    435                 440                 445

Tyr Thr Leu Arg Val Asp Cys Thr Pro Leu Leu His Ser Leu Val Tyr
450                 455                 460

Asn Leu Thr Lys Glu Leu Lys Ser Pro Asp Glu Gly Phe Glu Gly Lys
465                 470                 475                 480

Ser Leu Tyr Glu Ser Trp Thr Lys Lys Ser Pro Ser Pro Glu Leu Ser
            485                 490                 495

Gly Leu Pro Arg Ile Ser Lys Leu Gly Ser Gly Asn Asp Phe Glu Val
        500                 505                 510

Phe Phe Gln Arg Leu Gly Ile Ser Ser Gly Arg Ala Arg Tyr Thr Lys
    515                 520                 525

Asp Trp Lys Thr Ser Lys Phe Ser Ser Tyr Pro Leu Tyr His Ser Ile
530                 535                 540

Tyr Glu Thr Tyr Glu Leu Val Val Lys Phe Tyr Asp Pro Met Phe Lys
545                 550                 555                 560
```

```
Tyr His Leu Thr Val Ala Gln Val Arg Gly Gly Met Val Phe Glu Leu
            565                 570                 575
Ala Asn Ser Ile Val Leu Pro Phe Asp Cys Arg Asp Tyr Ala Val Ala
        580                 585                 590
Leu Lys Asn His Ala Glu Asn Leu Tyr Ser Ile Ser Met Lys His Pro
    595                 600                 605
Gln Glu Met Lys Thr Tyr Ser Val Ser Phe Asp Ser Leu Phe Ser Ala
610                 615                 620
Val Lys Asn Phe Thr Glu Ile Ala Ser Lys Phe Ser Glu Arg Leu Gln
625                 630                 635                 640
Asp Phe Asp Lys Ser Asn Pro Ile Val Leu Arg Met Met Asn Asp Gln
                645                 650                 655
Leu Met Phe Leu Glu Arg Ala Phe Ile Asp Pro Leu Gly Leu Pro Asp
            660                 665                 670
Arg Pro Phe Tyr Arg His Val Ile Tyr Ala Pro Ser Ser His Asn Lys
        675                 680                 685
Tyr Ala Gly Glu Ser Phe Pro Gly Ile Tyr Asp Ala Leu Phe Asp Ile
    690                 695                 700
Glu Ser Lys Val Asp Pro Ser Lys Ala Trp Gly Glu Val Lys Arg Gln
705                 710                 715                 720
Ile Tyr Val Ala Ala Phe Thr Val Gln Ala Ala Ala Glu Thr Leu Ser
                725                 730                 735
Glu Val Ala
```

<210> SEQ ID NO 8
<211> LENGTH: 2217
<212> TYPE: DNA
<213> ORGANISM: Artificial
<220> FEATURE:
<223> OTHER INFORMATION: Synthetic Construct

<400> SEQUENCE: 8

```
atggctagcg ccagacggcc cagatggctg tgtgctggcg ccctggtgct ggctggcggc      60
ttttcctgc  tgggcttcct gttcggctgg ttcatcaaga gcagcaacga ggccaccaac     120
atcacccca  agcacaacat gaaggccttt ctggacgagc tgaaggccga gaatatcaag     180
aagttcctgt acaacttcac ccagatcccc acctggccg  caccgagca gaacttccag     240
ctggccaagc agatccagag ccagtggaaa gagttcggcc tggacagcgt ggaactggcc     300
cactacgacg tgctgctgag ctaccccaac aagacccacc ccaactacat cagcatcatc     360
aacgaggacg caacgagat  tttcaacacc agcctgttcg agccccctcc acccggctac     420
gagaacgtgt ccgacatcgt gcccccattc agcgcattca gtccacaggg aatgcccgag     480
ggcgacctgt gtacgtgaa  ctacgcccgg accgaggact tcttcaagct ggaacgggac     540
atgaagatca actgcagcgg caagatcgtg atcgccagat acggcaaggt gttccggggc     600
aacaaagtga agaacgccca gctggcaggc gccaagggcg tgatcctgta tagcgacccc     660
gccgactact cgcccctgg  cgtgaagtcc taccccgacg gctggaacct gcctggcggc     720
ggagtgcagc ggggcaacat cctgaacctg aacggcgctg cgaccccct  gacccctggc     780
tatcccgcca acgagtacgc ctacagacg  ggaatcgccg aggccgtggg cctgcctagc     840
atccctgtgc accccatcgg ctactacgac gcccagaaac tgctggaaaa gatgggcggc     900
agcgcccctc ccgatagctc ttggagaggc agcctgaagg tgccctacaa cgtgggccct     960
ggcttcaccg gcaacttcag cgcccagaag ctgaagctgc acatccacag caacaccaaa    1020
```

```
gtgacccgga tctacaacgt gatcggcacc ctgagaggcg ccgtggaacc cgacagatac    1080
gtgatcctgg gcggccaccg ggacagctgg gtgttcggcg catcgaccc tcagtctggc    1140 gccgctgtgg tgcacgagat cgtgcggacc tttggcaccc tgaagaagaa gggctggcgg    1200
cccagacgga ccatcctgtt cgccagctgg gacgccgagg aattcggcct gctgggcagc    1260
accgagtggg ccgaggaaaa cagtcggctg ctgcaggaac ggggcgtcgc ctacatcaac    1320
gccgacagca gcatcgaggg caactacacc ctgcgggtgg actgcacccc cctgctgcac    1380
agcctggtgt acaacctgac caaagagctg aagtcccccg acgagggctt cgagggcaag    1440
agcctgtacg agagctggac caagaagtcc cccagccccg agctgagcgg cctgcccaga    1500
atcagcaagc tgggcagcgg caacgacttc gaggtgttct ccagcggct gggcatcagc    1560 agcggcagag cccggtacac caaggactgg aaaaccagca agttcagcag ctaccccctg    1620
taccacagca tctacgagac atacgagctg gtggtcaagt tctacgaccc catgttcaag    1680
taccacctga ccgtggccca ggtccgaggc ggcatggtgt tcgagctggc caacagcatc    1740
gtgctgccct tcgactgccg ggactacgcc gtggccctga gaaccacgc cgagaacctg    1800 tacagcatca gcatgaagca cccccaggaa atgaaaacct acagcgtgtc cttcgacagc    1860
ctgttcagcg ccgtgaagaa tttcaccgag atcgcctcca agttcagcga gcggctgcag    1920
gacttcgaca gagcaaccc catcgtgctg agaatgatga cgaccagct gatgttcctg    1980 gaacgggcct tcatcgaccc cctgggcctg cccgaccggc ccttttaccg gcacgtgatc    2040 tatgcccca gcagccacaa caaatacgcc ggcgagagtt tccccggcat ctacgatgcc    2100
ctgttcgaca tcgagagcaa ggtggacccc agcaaggcct ggggcgaagt gaagcggcag    2160
atttacgtgg ccgcattcac agtgcaggcc gctgccgaga cactgagcga ggtggcc      2217
```

<210> SEQ ID NO 9
<211> LENGTH: 739
<212> TYPE: PRT
<213> ORGANISM: Artificial
<220> FEATURE:
<223> OTHER INFORMATION: Synthetic Construct

<400> SEQUENCE: 9

```
Met Ala Ser Ala Arg Arg Pro Arg Trp Leu Cys Ala Gly Ala Leu Val
1               5                   10                  15

Leu Ala Gly Gly Phe Phe Leu Leu Gly Phe Leu Phe Gly Trp Phe Ile
                20                  25                  30

Lys Ser Ser Asn Glu Ala Thr Asn Ile Thr Pro Lys His Asn Met Lys
            35                  40                  45

Ala Phe Leu Asp Glu Leu Lys Ala Glu Asn Ile Lys Lys Phe Leu Tyr
        50                  55                  60

Asn Phe Thr Gln Ile Pro His Leu Ala Gly Thr Glu Gln Asn Phe Gln
65                  70                  75                  80

Leu Ala Lys Gln Ile Gln Ser Gln Trp Lys Glu Phe Gly Leu Asp Ser
                85                  90                  95

Val Glu Leu Ala His Tyr Asp Val Leu Leu Ser Tyr Pro Asn Lys Thr
            100                 105                 110

His Pro Asn Tyr Ile Ser Ile Ile Asn Glu Asp Gly Asn Glu Ile Phe
        115                 120                 125

Asn Thr Ser Leu Phe Glu Pro Pro Pro Gly Tyr Glu Asn Val Ser
    130                 135                 140

Asp Ile Val Pro Pro Phe Ser Ala Phe Ser Pro Gln Gly Met Pro Glu
145                 150                 155                 160
```

-continued

Gly Asp Leu Val Tyr Val Asn Tyr Ala Arg Thr Glu Asp Phe Phe Lys
            165                 170                 175

Leu Glu Arg Asp Met Lys Ile Asn Cys Ser Gly Lys Ile Val Ile Ala
            180                 185                 190

Arg Tyr Gly Lys Val Phe Arg Gly Asn Lys Val Lys Asn Ala Gln Leu
            195                 200                 205

Ala Gly Ala Lys Gly Val Ile Leu Tyr Ser Asp Pro Ala Asp Tyr Phe
210                 215                 220

Ala Pro Gly Val Lys Ser Tyr Pro Asp Gly Trp Asn Leu Pro Gly Gly
225                 230                 235                 240

Gly Val Gln Arg Gly Asn Ile Leu Asn Leu Asn Gly Ala Gly Asp Pro
            245                 250                 255

Leu Thr Pro Gly Tyr Pro Ala Asn Glu Tyr Ala Tyr Arg Arg Gly Ile
            260                 265                 270

Ala Glu Ala Val Gly Leu Pro Ser Ile Pro Val His Pro Ile Gly Tyr
            275                 280                 285

Tyr Asp Ala Gln Lys Leu Leu Glu Lys Met Gly Gly Ser Ala Pro Pro
290                 295                 300

Asp Ser Ser Trp Arg Gly Ser Leu Lys Val Pro Tyr Asn Val Gly Pro
305                 310                 315                 320

Gly Phe Thr Gly Asn Phe Ser Thr Gln Lys Val Lys Met His Ile His
            325                 330                 335

Ser Thr Asn Glu Val Thr Arg Ile Tyr Asn Val Ile Gly Thr Leu Arg
            340                 345                 350

Gly Ala Val Glu Pro Asp Arg Tyr Val Ile Leu Gly His Arg Asp
            355                 360                 365

Ser Trp Val Phe Gly Gly Ile Asp Pro Gln Ser Gly Ala Ala Val Val
            370                 375                 380

His Glu Ile Val Arg Ser Phe Gly Thr Leu Lys Lys Glu Gly Trp Arg
385                 390                 395                 400

Pro Arg Arg Thr Ile Leu Phe Ala Ser Trp Asp Ala Glu Glu Phe Gly
            405                 410                 415

Leu Leu Gly Ser Thr Glu Trp Ala Glu Glu Asn Ser Arg Leu Leu Gln
            420                 425                 430

Glu Arg Gly Val Ala Tyr Ile Asn Ala Asp Ser Ser Ile Glu Gly Asn
            435                 440                 445

Tyr Thr Leu Arg Val Asp Cys Thr Pro Leu Met Tyr Ser Leu Val His
450                 455                 460

Asn Leu Thr Lys Glu Leu Lys Ser Pro Asp Glu Gly Phe Glu Gly Lys
465                 470                 475                 480

Ser Leu Tyr Glu Ser Trp Thr Lys Lys Ser Pro Ser Pro Glu Phe Ser
            485                 490                 495

Gly Met Pro Arg Ile Ser Lys Leu Gly Ser Gly Asn Asp Phe Glu Val
            500                 505                 510

Phe Phe Gln Arg Leu Gly Ile Ala Ser Gly Arg Ala Arg Tyr Thr Lys
            515                 520                 525

Asn Trp Glu Thr Asn Lys Phe Ser Gly Tyr Pro Leu Tyr His Ser Val
530                 535                 540

Tyr Glu Thr Tyr Glu Leu Val Glu Lys Phe Tyr Asp Pro Met Phe Lys
545                 550                 555                 560

Tyr His Leu Thr Val Ala Gln Val Arg Gly Gly Met Val Phe Glu Leu
            565                 570                 575

```
Ala Asn Ser Ile Val Leu Pro Phe Asp Cys Arg Asp Tyr Ala Val Val
            580                 585                 590

Leu Arg Lys Tyr Ala Asp Lys Ile Tyr Ser Ile Ser Met Lys His Pro
        595                 600                 605

Gln Glu Met Lys Thr Tyr Ser Val Ser Phe Asp Ser Leu Phe Ser Ala
        610                 615                 620

Val Lys Asn Phe Thr Glu Ile Ala Ser Lys Phe Ser Glu Arg Leu Gln
625                 630                 635                 640

Asp Phe Asp Lys Ser Asn Pro Ile Val Leu Arg Met Met Asn Asp Gln
                645                 650                 655

Leu Met Phe Leu Glu Arg Ala Phe Ile Asp Pro Leu Gly Leu Pro Asp
                660                 665                 670

Arg Pro Phe Tyr Arg His Val Ile Tyr Ala Pro Ser Ser His Asn Lys
                675                 680                 685

Tyr Ala Gly Glu Ser Phe Pro Gly Ile Tyr Asp Ala Leu Phe Asp Ile
            690                 695                 700

Glu Ser Lys Val Asp Pro Ser Lys Ala Trp Gly Glu Val Lys Arg Gln
705                 710                 715                 720

Ile Tyr Val Ala Ala Phe Thr Val Gln Ala Ala Glu Thr Leu Ser
                725                 730                 735

Glu Val Ala

<210> SEQ ID NO 10
<211> LENGTH: 2217
<212> TYPE: DNA
<213> ORGANISM: Artificial
<220> FEATURE:
<223> OTHER INFORMATION: Synthetic Construct

<400> SEQUENCE: 10
atggctagcg cgcgccgccc gcgctggctg tgcgctgggg cgctggtgct ggcgggtggc    60
ttctttctcc tcggcttcct cttcgggtgg tttataaaat cctccaatga agctactaac   120
attactccaa agcataatat gaaagcattt ttggatgaat tgaaagctga acatcaag     180 aagttcttat ataattttac acagatacca catttagcag gaacagaaca aaactttcag   240
cttgcaaagc aaattcaatc ccagtggaaa gaatttggcc tggattctgt tgagctggca   300
cattatgatg tcctgttgtc ctacccaaat aagactcatc ccaactacat ctcaataatt   360
aatgaagatg gaaatgagat ttcaacacac tcattatttg aaccacctcc tccaggatat   420
gaaaatgttt cggatattgt accacctttc agtgctttct ctcctcaagg aatgccagag   480
ggcgatctag tgtatgttaa ctatgcacga actgaagact tctttaaatt ggaacgggac   540
atgaaaatca attgctctgg gaaaattgta attgccagat atgggaaagt tttcagagga   600
aataaggtta aaaatgccca gctggcaggg gccaaaggag tcattctcta ctccgaccct   660
gctgactact tgctcctgg ggtgaagtcc tatccagatg ttggaatct tcctggaggt    720 ggtgtccagc gtggaaatat cctaaatctg aatggtgcag gagaccctct cacaccaggt   780
tacccagcaa atgaatatgc ttataggcgt ggaattgcag aggctgttgg tcttccaagt   840
attcctgttc atccaattgg atactatgat gcacagaagc tcctagaaaa atgggtggc    900 tcagcaccac cagatagcag ctggagagga agtctcaaag tgccctacaa tgttggacct   960
ggctttactg gaaacttttc tacacaaaaa gtcaagatgc acatccactc taccaatgaa  1020
gtgacaagaa tttacaatgt gataggtact ctcagaggag cagtggaacc agacagatat  1080
gtcattctgg gaggtcaccg ggactcatgg gtgtttggtg gtattgaccc tcagagtgga  1140
```

-continued

```
gcagctgttg ttcatgaaat tgtgaggagc tttggaacac tgaaaaagga agggtggaga    1200
cctagaagaa caattttgtt tgcaagctgg gatgcagaag aatttggtct tcttggttct    1260
actgagtggg cagaggagaa ttcaagactc cttcaagagc gtggcgtggc ttatattaat    1320
gctgactcat ctatagaagg aaactacact ctgagagttg attgtacacc gctgatgtac    1380
agcttggtac acaacctaac aaaagagctg aaaagccctg atgaaggctt gaaggcaaa     1440 tctctttatg aaagttggac taaaaaaagt ccttccccag agttcagtgg catgcccagg    1500
ataagcaaat tgggatctgg aaatgatttt gaggtgttct tccaacgact tggaattgct    1560
tcaggcagag cacggtatac taaaaattgg gaaacaaaca aattcagcgg ctatccactg    1620
tatcacagtg tctatgaaac atatgagttg gtggaaaagt tttatgatcc aatgtttaaa    1680
tatcacctca ctgtggccca ggttcgagga gggatggtgt tgagctggc caattccata    1740 gtgctccctt tgattgtcg agattatgct gtagttttaa gaaagtatgc tgacaaaatc    1800
tacagtattt ctatgaaaca tccacaggaa atgaagacat acagtgtatc atttgattca    1860
cttttttctg cagtaaagaa ttttacagaa attgcttcca agttcagtga gagactccag    1920
gactttgaca aaagcaaccc aatagtatta agaatgatga atgatcaact catgtttctg    1980
gaaagagcat ttattgatcc attagggtta ccagacaggc cttttatag gcatgtcatc    2040 tatgctccaa gcagccacaa caagtatgca ggggagtcat tcccaggaat ttatgatgct    2100
ctgtttgata ttgaaagcaa agtggaccct tccaaggcct ggggagaagt gaagagacag    2160
atttatgttg cagccttcac agtgcaggca gctgcagaga ctttgagtga agtagcc       2217
```

<210> SEQ ID NO 11
<211> LENGTH: 710
<212> TYPE: PRT
<213> ORGANISM: Artificial
<220> FEATURE:
<223> OTHER INFORMATION: Synthetic Construct

<400> SEQUENCE: 11

```
Met Ala Ser Lys Ser Ser Asn Glu Ala Thr Asn Ile Thr Pro Lys His
1               5                   10                  15

Asn Met Lys Ala Phe Leu Asp Glu Leu Lys Ala Glu Asn Ile Lys Lys
            20                  25                  30

Phe Leu Tyr Asn Phe Thr Gln Ile Pro His Leu Ala Gly Thr Glu Gln
        35                  40                  45

Asn Phe Gln Leu Ala Lys Gln Ile Gln Ser Gln Trp Lys Glu Phe Gly
    50                  55                  60

Leu Asp Ser Val Glu Leu Ala His Tyr Asp Val Leu Leu Ser Tyr Pro
65                  70                  75                  80

Asn Lys Thr His Pro Asn Tyr Ile Ser Ile Ile Asn Glu Asp Gly Asn
                85                  90                  95

Glu Ile Phe Asn Thr Ser Leu Phe Glu Pro Pro Pro Gly Tyr Glu
            100                 105                 110

Asn Val Ser Asp Ile Val Pro Pro Phe Ser Ala Phe Ser Pro Gln Gly
        115                 120                 125

Met Pro Glu Gly Asp Leu Val Tyr Val Asn Tyr Ala Arg Thr Glu Asp
    130                 135                 140

Phe Phe Lys Leu Glu Arg Asp Met Lys Ile Asn Cys Ser Gly Lys Ile
145                 150                 155                 160

Val Ile Ala Arg Tyr Gly Lys Val Phe Arg Gly Asn Lys Val Lys Asn
                165                 170                 175
```

```
Ala Gln Leu Ala Gly Ala Lys Gly Val Ile Leu Tyr Ser Asp Pro Ala
            180                 185                 190

Asp Tyr Phe Ala Pro Gly Val Lys Ser Tyr Pro Asp Gly Trp Asn Leu
        195                 200                 205

Pro Gly Gly Gly Val Gln Arg Gly Asn Ile Leu Asn Leu Asn Gly Ala
    210                 215                 220

Gly Asp Pro Leu Thr Pro Gly Tyr Pro Ala Asn Glu Tyr Ala Tyr Arg
225                 230                 235                 240

Arg Gly Ile Ala Glu Ala Val Gly Leu Pro Ser Ile Pro Val His Pro
                245                 250                 255

Ile Gly Tyr Tyr Asp Ala Gln Lys Leu Leu Glu Lys Met Gly Gly Ser
            260                 265                 270

Ala Pro Pro Asp Ser Ser Trp Arg Gly Ser Leu Lys Val Pro Tyr Asn
        275                 280                 285

Val Gly Pro Gly Phe Thr Gly Asn Phe Ser Thr Gln Lys Val Lys Met
    290                 295                 300

His Ile His Ser Thr Asn Glu Val Thr Arg Ile Tyr Asn Val Ile Gly
305                 310                 315                 320

Thr Leu Arg Gly Ala Val Glu Pro Asp Arg Tyr Val Ile Leu Gly Gly
                325                 330                 335

His Arg Asp Ser Trp Val Phe Gly Gly Ile Asp Pro Gln Ser Gly Ala
            340                 345                 350

Ala Val Val His Glu Ile Val Arg Ser Phe Gly Thr Leu Lys Lys Glu
        355                 360                 365

Gly Trp Arg Pro Arg Arg Thr Ile Leu Phe Ala Ser Trp Asp Ala Glu
    370                 375                 380

Glu Phe Gly Leu Leu Gly Ser Thr Glu Trp Ala Glu Glu Asn Ser Arg
385                 390                 395                 400

Leu Leu Gln Glu Arg Gly Val Ala Tyr Ile Asn Ala Asp Ser Ser Ile
                405                 410                 415

Glu Gly Asn Tyr Thr Leu Arg Val Asp Cys Thr Pro Leu Met Tyr Ser
            420                 425                 430

Leu Val His Asn Leu Thr Lys Glu Leu Lys Ser Pro Asp Glu Gly Phe
        435                 440                 445

Glu Gly Lys Ser Leu Tyr Glu Ser Trp Thr Lys Lys Ser Pro Ser Pro
    450                 455                 460

Glu Phe Ser Gly Met Pro Arg Ile Ser Lys Leu Gly Ser Gly Asn Asp
465                 470                 475                 480

Phe Glu Val Phe Phe Gln Arg Leu Gly Ile Ala Ser Gly Arg Ala Arg
                485                 490                 495

Tyr Thr Lys Asn Trp Glu Thr Asn Lys Phe Ser Gly Tyr Pro Leu Tyr
            500                 505                 510

His Ser Val Tyr Glu Thr Tyr Glu Leu Val Glu Lys Phe Tyr Asp Pro
        515                 520                 525

Met Phe Lys Tyr His Leu Thr Val Ala Gln Val Arg Gly Gly Met Val
    530                 535                 540

Phe Glu Leu Ala Asn Ser Ile Val Leu Pro Phe Asp Cys Arg Asp Tyr
545                 550                 555                 560

Ala Val Val Leu Arg Lys Tyr Ala Asp Lys Ile Tyr Ser Ile Ser Met
                565                 570                 575

Lys His Pro Gln Glu Met Lys Thr Tyr Ser Val Ser Phe Asp Ser Leu
            580                 585                 590
```

```
Phe Ser Ala Val Lys Asn Phe Thr Glu Ile Ala Ser Lys Phe Ser Glu
            595                 600                 605

Arg Leu Gln Asp Phe Asp Lys Ser Asn Pro Ile Val Leu Arg Met Met
    610                 615                 620

Asn Asp Gln Leu Met Phe Leu Glu Arg Ala Phe Ile Asp Pro Leu Gly
625                 630                 635                 640

Leu Pro Asp Arg Pro Phe Tyr Arg His Val Ile Tyr Ala Pro Ser Ser
                645                 650                 655

His Asn Lys Tyr Ala Gly Glu Ser Phe Pro Gly Ile Tyr Asp Ala Leu
            660                 665                 670

Phe Asp Ile Glu Ser Lys Val Asp Pro Ser Lys Ala Trp Gly Glu Val
        675                 680                 685

Lys Arg Gln Ile Tyr Val Ala Ala Phe Thr Val Gln Ala Ala Ala Glu
    690                 695                 700

Thr Leu Ser Glu Val Ala
705                 710

<210> SEQ ID NO 12
<211> LENGTH: 2130
<212> TYPE: DNA
<213> ORGANISM: Artificial
<220> FEATURE:
<223> OTHER INFORMATION: Synthetic Construct

<400> SEQUENCE: 12
atggctagca aatcctccaa tgaagctact aacattactc caaagcataa tatgaaagca      60
tttttggatg aattgaaagc tgagaacatc aagaagttct tatataattt tacacagata     120
ccacatttag caggaacaga acaaaacttt cagcttgcaa agcaaattca atcccagtgg     180
aaagaatttg gcctggattc tgttgagctg gcacattatg atgtcctgtt gtcctaccca     240
aataagactc atcccaacta catctcaata attaatgaag atggaaatga gattttcaac     300
acatcattat ttgaaccacc tcctccagga tatgaaaatg tttcggatat tgtaccacct     360
ttcagtgctt tctctcctca aggaatgcca gagggcgatc tagtgtatgt taactatgca     420
cgaactgaag acttctttaa attggaacgg gacatgaaaa tcaattgctc tgggaaaatt     480
gtaattgcca gatatgggaa agtttttcaga ggaaataagg ttaaaaatgc cagctggca     540
ggggccaaag gagtcattct ctactccgac cctgctgact actttgctcc tggggtgaag     600
tcctatccag atggttggaa tcttcctgga ggtggtgtcc agcgtggaaa tatcctaaat     660
ctgaatggtg caggagaccc tctcacacca ggttacccag caaatgaata tgcttatagg     720
cgtggaattg cagaggctgt tggtcttcca agtattcctg ttcatccaat tggatactat     780
gatgcacaga gctcctaga aaaaatgggt ggctcagcac caccagatag cagctggaga     840
ggaagtctca aagtgcccta caatgttgga cctggcttta ctggaaactt ttctacacaa     900
aaagtcaaga tgcacatcca ctctaccaat gaagtgacaa gaatttacaa tgtgataggt     960
actctcagag gagcagtgga accagacaga tatgtcattc tgggaggtca ccggactca    1020
tgggtgtttg gtggtattga ccctcagagt ggagcagctg ttgttcatga aattgtgagg    1080
agctttggaa cactgaaaaa ggaagggtgg agacctagaa gaacaatttt gtttgcaagc    1140
tgggatgcag aagaatttgg tcttcttggt tctactgagt gggcagagga gaattcaaga    1200
ctccttcaag agcgtggcgt ggcttatatt aatgctgact catctataga aggaaactac    1260
actctgagag ttgattgtac accgctgatg tacagcttgg tacacaacct aacaaaagag    1320
ctgaaaagcc ctgatgaagg ctttgaaggc aaatctcttt atgaaagttg gactaaaaaa    1380
```

```
agtccttccc cagagttcag tggcatgccc aggataagca aattgggatc tggaaatgat    1440
tttgaggtgt tcttccaacg acttggaatt gcttcaggca gagcacggta tactaaaaat    1500
tgggaaacaa acaaattcag cggctatcca ctgtatcaca gtgtctatga aacatatgag    1560
ttggtggaaa agttttatga tccaatgttt aaatatcacc tcactgtggc ccaggttcga    1620
ggagggatgg tgtttgagct ggccaattcc atagtgctcc cttttgattg tcgagattat    1680
gctgtagttt aagaaagta tgctgacaaa atctacagta tttctatgaa acatccacag    1740
gaaatgaaga catacagtgt atcatttgat tcactttttt ctgcagtaaa gaattttaca    1800
gaaattgctt ccaagttcag tgagagactc caggactttg acaaaagcaa cccaatagta    1860
ttaagaatga tgaatgatca actcatgttt ctggaaagag catttattga tccattaggg    1920
ttaccagaca ggccttttta taggcatgtc atctatgctc caagcagcca acaagtat      1980
gcagggagt cattcccagg aatttatgat gctctgtttg atattgaaag caaagtggac    2040
ccttccaagg cctggggaga agtgaagaga cagatttatg ttgcagcctt cacagtgcag    2100
gcagctgcag agactttgag tgaagtagcc                                      2130
```

<210> SEQ ID NO 13
<211> LENGTH: 732
<212> TYPE: PRT
<213> ORGANISM: Artificial
<220> FEATURE:
<223> OTHER INFORMATION: Synthetic Construct

<400> SEQUENCE: 13

```
Met Ala Ser Glu Thr Asp Thr Leu Leu Leu Trp Val Leu Leu Leu Trp
1               5                   10                  15

Val Pro Gly Ser Thr Gly Asp Ala Ala Lys Ser Ser Asn Glu Ala Thr
            20                  25                  30

Asn Ile Thr Pro Lys His Asn Met Lys Ala Phe Leu Asp Glu Leu Lys
        35                  40                  45

Ala Glu Asn Ile Lys Lys Phe Leu Tyr Asn Phe Thr Gln Ile Pro His
    50                  55                  60

Leu Ala Gly Thr Glu Gln Asn Phe Gln Leu Ala Lys Gln Ile Gln Ser
65                  70                  75                  80

Gln Trp Lys Glu Phe Gly Leu Asp Ser Val Glu Leu Ala His Tyr Asp
                85                  90                  95

Val Leu Leu Ser Tyr Pro Asn Lys Thr His Pro Asn Tyr Ile Ser Ile
            100                 105                 110

Ile Asn Glu Asp Gly Asn Glu Ile Phe Asn Thr Ser Leu Phe Glu Pro
        115                 120                 125

Pro Pro Pro Gly Tyr Glu Asn Val Ser Asp Ile Val Pro Pro Phe Ser
    130                 135                 140

Ala Phe Ser Pro Gln Gly Met Pro Glu Gly Asp Leu Val Tyr Val Asn
145                 150                 155                 160

Tyr Ala Arg Thr Glu Asp Phe Phe Lys Leu Glu Arg Asp Met Lys Ile
                165                 170                 175

Asn Cys Ser Gly Lys Ile Val Ile Ala Arg Tyr Gly Lys Val Phe Arg
            180                 185                 190

Gly Asn Lys Val Lys Asn Ala Gln Leu Ala Gly Ala Lys Gly Val Ile
        195                 200                 205

Leu Tyr Ser Asp Pro Ala Asp Tyr Phe Ala Pro Gly Val Lys Ser Tyr
    210                 215                 220
```

-continued

```
Pro Asp Gly Trp Asn Leu Pro Gly Gly Gly Val Gln Arg Gly Asn Ile
225                 230                 235                 240

Leu Asn Leu Asn Gly Ala Gly Asp Pro Leu Thr Pro Gly Tyr Pro Ala
            245                 250                 255

Asn Glu Tyr Ala Tyr Arg Arg Gly Ile Ala Glu Ala Val Gly Leu Pro
        260                 265                 270

Ser Ile Pro Val His Pro Ile Gly Tyr Tyr Asp Ala Gln Lys Leu Leu
    275                 280                 285

Glu Lys Met Gly Gly Ser Ala Pro Pro Asp Ser Ser Trp Arg Gly Ser
290                 295                 300

Leu Lys Val Pro Tyr Asn Val Gly Pro Gly Phe Thr Gly Asn Phe Ser
305                 310                 315                 320

Thr Gln Lys Val Lys Met His Ile His Ser Thr Asn Glu Val Thr Arg
                325                 330                 335

Ile Tyr Asn Val Ile Gly Thr Leu Arg Gly Ala Val Glu Pro Asp Arg
            340                 345                 350

Tyr Val Ile Leu Gly Gly His Arg Asp Ser Trp Val Phe Gly Gly Ile
        355                 360                 365

Asp Pro Gln Ser Gly Ala Ala Val Val His Glu Ile Val Arg Ser Phe
370                 375                 380

Gly Thr Leu Lys Lys Glu Gly Trp Arg Pro Arg Arg Thr Ile Leu Phe
385                 390                 395                 400

Ala Ser Trp Asp Ala Glu Glu Phe Gly Leu Leu Gly Ser Thr Glu Trp
                405                 410                 415

Ala Glu Glu Asn Ser Arg Leu Leu Gln Glu Arg Gly Val Ala Tyr Ile
            420                 425                 430

Asn Ala Asp Ser Ser Ile Glu Gly Asn Tyr Thr Leu Arg Val Asp Cys
        435                 440                 445

Thr Pro Leu Met Tyr Ser Leu Val His Asn Leu Thr Lys Glu Leu Lys
    450                 455                 460

Ser Pro Asp Glu Gly Phe Glu Gly Lys Ser Leu Tyr Glu Ser Trp Thr
465                 470                 475                 480

Lys Lys Ser Pro Ser Pro Glu Phe Ser Gly Met Pro Arg Ile Ser Lys
                485                 490                 495

Leu Gly Ser Gly Asn Asp Phe Glu Val Phe Phe Gln Arg Leu Gly Ile
            500                 505                 510

Ala Ser Gly Arg Ala Arg Tyr Thr Lys Asn Trp Glu Thr Asn Lys Phe
        515                 520                 525

Ser Gly Tyr Pro Leu Tyr His Ser Val Tyr Glu Thr Tyr Glu Leu Val
    530                 535                 540

Glu Lys Phe Tyr Asp Pro Met Phe Lys Tyr His Leu Thr Val Ala Gln
545                 550                 555                 560

Val Arg Gly Gly Met Val Phe Glu Leu Ala Asn Ser Ile Val Leu Pro
                565                 570                 575

Phe Asp Cys Arg Asp Tyr Ala Val Val Leu Arg Lys Tyr Ala Asp Lys
            580                 585                 590

Ile Tyr Ser Ile Ser Met Lys His Pro Gln Glu Met Lys Thr Tyr Ser
        595                 600                 605

Val Ser Phe Asp Ser Leu Phe Ser Ala Val Lys Asn Phe Thr Glu Ile
    610                 615                 620

Ala Ser Lys Phe Ser Glu Arg Leu Gln Asp Phe Asp Lys Ser Asn Pro
625                 630                 635                 640

Ile Val Leu Arg Met Met Asn Asp Gln Leu Met Phe Leu Glu Arg Ala
```

```
              645                 650                 655
Phe Ile Asp Pro Leu Gly Leu Pro Asp Arg Pro Phe Tyr Arg His Val
            660                 665                 670
Ile Tyr Ala Pro Ser Ser His Asn Lys Tyr Ala Gly Glu Ser Phe Pro
            675                 680                 685
Gly Ile Tyr Asp Ala Leu Phe Asp Ile Glu Ser Lys Val Asp Pro Ser
            690                 695                 700
Lys Ala Trp Gly Glu Val Lys Arg Gln Ile Tyr Val Ala Ala Phe Thr
705                 710                 715                 720
Val Gln Ala Ala Ala Glu Thr Leu Ser Glu Val Ala
                725                 730

<210> SEQ ID NO 14
<211> LENGTH: 2196
<212> TYPE: DNA
<213> ORGANISM: Artificial
<220> FEATURE:
<223> OTHER INFORMATION: Synthetic Construct

<400> SEQUENCE: 14
```

| | | | | | |
|---|---|---|---|---|---|
| atggctagcg | aaaccgacac | tttgttgttg | tgggtgcttt | tgctttgggt | acccggatct | 60 |
| actggtgatg | ctgctaaatc | tccaatgaa | gctactaaca | ttactccaaa | gcataatatg | 120 |
| aaagcatttt | tggatgaatt | gaaagctgag | aacatcaaga | agttcttata | taattttaca | 180 |
| cagataccac | atttagcagg | aacagaacaa | aactttcagc | ttgcaaagca | aattcaatcc | 240 |
| cagtggaaag | aatttggcct | ggattctgtt | gagctagcac | attatgatgt | cctgttgtcc | 300 |
| tacccaaata | agactcatcc | caactacatc | tcaataatta | atgaagatgg | aaatgagatt | 360 |
| ttcaacacat | cattatttga | ccacctcct | ccaggatatg | aaaatgtttc | ggatattgta | 420 |
| ccacctttca | gtgctttctc | tcctcaagga | atgccagagg | gcgatctagt | gtatgttaac | 480 |
| tatgcacgaa | ctgaagactt | ctttaaattg | gaacgggaca | tgaaaatcaa | ttgctctggg | 540 |
| aaaattgtaa | ttgccagata | tgggaaagtt | ttcagaggaa | ataaggttaa | aaatgcccag | 600 |
| ctggcagggg | ccaaaggagt | cattctctac | tccgaccctg | ctgactactt | tgctcctggg | 660 |
| gtgaagtcct | atccagatgg | ttggaatctt | cctggaggtg | gtgtccagcg | tggaaatatc | 720 |
| ctaaatctga | atggtgcagg | agaccctctc | acaccaggtt | acccagcaaa | tgaatatgct | 780 |
| tataggcgtg | gaattgcaga | ggctgttggt | cttccaagta | ttcctgttca | tccaattgga | 840 |
| tactatgatg | cacagaagct | cctagaaaaa | atgggtggct | cagcaccacc | agatagcagc | 900 |
| tggagaggaa | gtctcaaagt | gcccctacaat | gttggacctg | gctttactgg | aaacttttct | 960 |
| acacaaaaag | tcaagatgca | catccactct | accaatgaag | tgacaagaat | ttacaatgtg | 1020 |
| ataggtactc | tcagaggagc | agtggaacca | gacagatatg | tcattctggg | aggtcaccgg | 1080 |
| gactcatggg | tgtttggtgg | tattgaccct | cagagtggag | cagctgttgt | tcatgaaatt | 1140 |
| gtgaggagct | ttggaacact | gaaaaaggaa | gggtggagac | ctagaagaac | aattttgttt | 1200 |
| gcaagctggg | atgcagaaga | atttggtctt | cttggttcta | ctgagtgggc | agaggagaat | 1260 |
| tcaagactcc | ttcaagagcg | tggcgtggct | tatattaatg | ctgactcatc | tatagaagga | 1320 |
| aactacactc | tgagagttga | ttgtacaccg | ctgatgtaca | gcttggtaca | caacctaaca | 1380 |
| aaagagctga | aaagccctga | tgaaggcttt | gaaggcaaat | ctctttatga | agttggact | 1440 |
| aaaaaagtc | cttccccaga | gttcagtggc | atgcccagga | taagcaaatt | gggatctgga | 1500 |
| aatgattttg | aggtgttctt | ccaacgactt | ggaattgctt | caggcagagc | acggtatact | 1560 |

```
aaaaattggg aaacaaacaa attcagcggc tatccactgt atcacagtgt ctatgaaaca   1620
tatgagttgg tggaaaagtt ttatgatcca atgtttaaat atcacctcac tgtgggcccag  1680 gttcgaggag ggatggtgtt tgagctagcc aattccatag tgctccctt tgattgtcga    1740 gattatgctg tagttttaag aaagtatgct gacaaaatct acagtatttc tatgaaacat   1800
ccacaggaaa tgaagacata cagtgtatca tttgattcac ttttttctgc agtaaagaat   1860
tttacagaaa ttgcttccaa gttcagtgag agactccagg actttgacaa agcaaccca   1920 atagtattaa gaatgatgaa tgatcaactc atgtttctgg aaagagcatt tattgatcca   1980
ttagggttac cagacaggcc ttttataag catgtcatct atgctccaag cagccacaac    2040
aagtatgcag gggagtcatt cccaggaatt tatgatgctc tgtttgatat tgaaagcaaa   2100 gtggacccctt ccaaggcctg gggagaagtg aagagacaga tttatgttgc agccttcaca 2160
gtgcaggcag ctgcagagac tttgagtgaa gtagcc                           2196
```

<210> SEQ ID NO 15
<211> LENGTH: 263
<212> TYPE: PRT
<213> ORGANISM: Homo sapiens

<400> SEQUENCE: 15

```
Met Ala Ser Trp Val Pro Val Phe Leu Thr Leu Ser Val Thr Trp
1               5                   10                  15

Ile Gly Ala Ala Pro Leu Ile Leu Ser Arg Ile Val Gly Gly Trp Glu
            20                  25                  30

Cys Glu Lys His Ser Gln Pro Trp Gln Val Leu Val Ala Ser Arg Gly
        35                  40                  45

Arg Ala Val Cys Gly Gly Val Leu Val His Pro Gln Trp Val Leu Thr
    50                  55                  60

Ala Ala His Cys Ile Arg Asn Lys Ser Val Ile Leu Leu Gly Arg His
65                  70                  75                  80

Ser Leu Phe His Pro Glu Asp Thr Gly Gln Val Phe Gln Val Ser His
                85                  90                  95

Ser Phe Pro His Pro Leu Tyr Asp Met Ser Leu Leu Lys Asn Arg Phe
            100                 105                 110

Leu Arg Pro Gly Asp Asp Ser Ser His Asp Leu Met Leu Leu Arg Leu
        115                 120                 125

Ser Glu Pro Ala Glu Leu Thr Asp Ala Val Lys Val Met Asp Leu Pro
    130                 135                 140

Thr Gln Glu Pro Ala Leu Gly Thr Thr Cys Tyr Ala Ser Gly Trp Gly
145                 150                 155                 160

Ser Ile Glu Pro Glu Glu Phe Leu Thr Pro Lys Lys Leu Gln Cys Val
                165                 170                 175

Asp Leu His Val Ile Ser Asn Asp Val Cys Ala Gln Val His Pro Gln
            180                 185                 190

Lys Val Thr Lys Phe Met Leu Cys Ala Gly Arg Trp Thr Gly Gly Lys
        195                 200                 205

Ser Thr Cys Ser Gly Asp Ser Gly Gly Pro Leu Val Cys Asn Gly Val
    210                 215                 220

Leu Gln Gly Ile Thr Ser Trp Gly Ser Glu Pro Cys Ala Leu Pro Glu
225                 230                 235                 240

Arg Pro Ser Leu Tyr Thr Lys Val Val His Tyr Arg Lys Trp Ile Lys
                245                 250                 255

Asp Thr Ile Val Ala Asn Pro
```

<210> SEQ ID NO 16
<211> LENGTH: 789
<212> TYPE: DNA
<213> ORGANISM: Homo sapiens

<400> SEQUENCE: 16

```
atggctagct gggtcccggt tgtcttcctc accctgtccg tgacgtggat tggcgctgcg      60
cccctcatcc tgtctcggat tgtgggaggc tgggagtgcg agaagcattc ccaaccctgg     120
caggtgcttg tggcctctcg tggcagggca gtctgcggcg gtgttctggt cacccccag     180
tgggtcctca cagctgccca ctgcatcagg aacaaaagcg tgatcttgct gggtcggcac     240
agcttgtttc atcctgaaga cacaggccag gtatttcagg tcagccacag cttcccacac     300
ccgctctacg atatgagcct cctgaagaat cgattcctca ggccaggtga tgactccagc     360
cacgacctca tgctgctccg cctgtcagag cctgccgagc tcacggatgc tgtgaaggtc     420
atggacctgc ccacccagga gccagcactg ggaccacct gctacgcctc aggctggggc     480
agcattgaac agaggagtt cttgacccca agaaacttc agtgtgtgga cctccatgtt     540
atttccaatg acgtgtgtgc gcaagttcac cctcagaagg tgaccaagtt catgctgtgt     600
gctggacgct ggacaggggg caaaagcacc tgctcgggtg attctggggg cccacttgtc     660
tgtaatggtg tgcttcaagg tatcacgtca tgggcagtga accatgtgc cctgcccgaa     720
aggccttccc tgtacaccaa ggtggtgcat taccggaagt ggatcaagga caccatcgtg     780
gccaacccc                                                             789
```

<210> SEQ ID NO 17
<211> LENGTH: 240
<212> TYPE: PRT
<213> ORGANISM: Artificial
<220> FEATURE:
<223> OTHER INFORMATION: Synthetic Construct

<400> SEQUENCE: 17

```
Met Ala Ser Ile Val Gly Gly Trp Glu Cys Glu Lys His Ser Gln Pro
1               5                  10                  15

Trp Gln Val Leu Val Ala Ser Arg Gly Arg Ala Val Cys Gly Gly Val
            20                  25                  30

Leu Val His Pro Gln Trp Val Leu Thr Ala Ala His Cys Ile Arg Asn
        35                  40                  45

Lys Ser Val Ile Leu Leu Gly Arg His Ser Leu Phe His Pro Glu Asp
    50                  55                  60

Thr Gly Gln Val Phe Gln Val Ser His Ser Phe Pro His Pro Leu Tyr
65                  70                  75                  80

Asp Met Ser Leu Leu Lys Asn Arg Phe Leu Arg Pro Gly Asp Asp Ser
                85                  90                  95

Ser His Asp Leu Met Leu Leu Arg Leu Ser Glu Pro Ala Glu Leu Thr
            100                 105                 110

Asp Ala Val Lys Val Met Asp Leu Pro Thr Gln Glu Pro Ala Leu Gly
        115                 120                 125

Thr Thr Cys Tyr Ala Ser Gly Trp Gly Ser Ile Glu Pro Glu Glu Phe
    130                 135                 140

Leu Thr Pro Lys Lys Leu Gln Cys Val Asp Leu His Val Ile Ser Asn
145                 150                 155                 160

Asp Val Cys Ala Gln Val His Pro Gln Lys Val Thr Lys Phe Met Leu
```

165                 170                 175
Cys Ala Gly Arg Trp Thr Gly Gly Lys Ser Thr Cys Ser Gly Asp Ser
            180                 185                 190

Gly Gly Pro Leu Val Cys Asn Gly Val Leu Gln Gly Ile Thr Ser Trp
        195                 200                 205

Gly Ser Glu Pro Cys Ala Leu Pro Glu Arg Pro Ser Leu Tyr Thr Lys
    210                 215                 220

Val Val His Tyr Arg Lys Trp Ile Lys Asp Thr Ile Val Ala Asn Pro
225                 230                 235                 240

<210> SEQ ID NO 18
<211> LENGTH: 720
<212> TYPE: DNA
<213> ORGANISM: Artificial
<220> FEATURE:
<223> OTHER INFORMATION: Synthetic Construct

<400> SEQUENCE: 18
atggctagca ttgtgggagg ctgggagtgc gagaagcatt cccaaccctg gcaggtgctt    60
gtggcctctc gtggcagggc agtctgcggc ggtgttctgg tgcaccccca gtgggtcctc   120
acagctgccc actgcatcag gaacaaaagc gtgatcttgc tgggtcggca cagcttgttt   180
catcctgaag acacaggcca ggtatttcag gtcagccaca gcttcccaca cccgctctac   240
gatatgagcc tcctgaagaa tcgattcctc aggccaggtg atgactccag ccacgacctc   300
atgctgctcc gcctgtcaga gcctgccgag ctcacggatg ctgtgaaggt catggaccTG   360
cccacccagg agccagcact ggggaccacc tgctacgcct caggctgggg cagcattgaa   420
ccagaggagt tcttgacccc aaagaaactt cagtgtgtgg acctccatgt tatttccaat   480
gacgtgtgtg cgcaagttca ccctcagaag gtgaccaagt tcatgctgtg tgctggacgc   540
tggacagggg gcaaaagcac ctgctcgggt gattctgggg gcccacttgt ctgtaatggt   600
gtgcttcaag gtatcacgtc atggggcagt gaaccatgtg ccctgcccga aaggccttcc   660
ctgtacacca aggtggtgca ttaccggaag tggatcaagg acaccatcgt ggccaacccc   720

<210> SEQ ID NO 19
<211> LENGTH: 281
<212> TYPE: PRT
<213> ORGANISM: Artificial
<220> FEATURE:
<223> OTHER INFORMATION: Synthetic Construct

<400> SEQUENCE: 19

Met Ala Ser Ala Arg Arg Pro Arg Trp Leu Cys Ala Gly Ala Leu Val
1               5                   10                  15

Leu Ala Gly Gly Phe Phe Leu Leu Gly Phe Leu Phe Gly Trp Phe Ile
            20                  25                  30

Lys Ser Ser Asn Glu Ala Thr Asn Ile Thr Pro Gly Ile Val Gly Gly
        35                  40                  45

Trp Glu Cys Glu Lys His Ser Gln Pro Trp Gln Val Leu Val Ala Ser
    50                  55                  60

Arg Gly Arg Ala Val Cys Gly Gly Val Leu Val His Pro Gln Trp Val
65                  70                  75                  80

Leu Thr Ala Ala His Cys Ile Arg Asn Lys Ser Val Ile Leu Leu Gly
                85                  90                  95

Arg His Ser Leu Phe His Pro Glu Asp Thr Gly Gln Val Phe Gln Val
            100                 105                 110

Ser His Ser Phe Pro His Pro Leu Tyr Asp Met Ser Leu Leu Lys Asn
            115                 120                 125

Arg Phe Leu Arg Pro Gly Asp Asp Ser Ser His Asp Leu Met Leu Leu
130                 135                 140

Arg Leu Ser Glu Pro Ala Glu Leu Thr Asp Ala Val Lys Val Met Asp
145                 150                 155                 160

Leu Pro Thr Gln Glu Pro Ala Leu Gly Thr Thr Cys Tyr Ala Ser Gly
                165                 170                 175

Trp Gly Ser Ile Glu Pro Glu Glu Phe Leu Thr Pro Lys Lys Leu Gln
            180                 185                 190

Cys Val Asp Leu His Val Ile Ser Asn Asp Val Cys Ala Gln Val His
            195                 200                 205

Pro Gln Lys Val Thr Lys Phe Met Leu Cys Ala Gly Arg Trp Thr Gly
        210                 215                 220

Gly Lys Ser Thr Cys Ser Gly Asp Ser Gly Gly Pro Leu Val Cys Asn
225                 230                 235                 240

Gly Val Leu Gln Gly Ile Thr Ser Trp Gly Ser Glu Pro Cys Ala Leu
                245                 250                 255

Pro Glu Arg Pro Ser Leu Tyr Thr Lys Val Val His Tyr Arg Lys Trp
            260                 265                 270

Ile Lys Asp Thr Ile Val Ala Asn Pro
            275                 280

<210> SEQ ID NO 20
<211> LENGTH: 846
<212> TYPE: DNA
<213> ORGANISM: Artificial
<220> FEATURE:
<223> OTHER INFORMATION: Synthetic Construct

<400> SEQUENCE: 20
atggctagcg cgcgccgccc gcgctggctg tgcgctgggg cgctggtgct ggcgggtggc      60
ttctttctcc tcggcttcct cttcgggtgg tttataaaat cctccaatga agctactaac     120
attactccag gaattgtggg aggctgggag tgcgagaagc attcccaacc ctggcaggtg     180
cttgtggcct ctcgtggcag ggcagtctgc ggcggtgttc tggtgcaccc ccagtgggtc     240
ctcacagctg cccactgcat caggaacaaa agcgtgatct tgctgggtcg gcacagcttg     300
tttcatcctg aagacacagg ccaggtattt caggtcagcc acagcttccc acaccccgctc    360 tacgatatga gcctcctgaa gaatcgattc ctcaggccag gtgatgactc cagccacgac     420
ctcatgctgc tccgcctgtc agagcctgcc gagctcacgg atgctgtgaa ggtcatggac     480
ctgcccaccc aggagccagc actggggacc acctgctacg cctcaggctg gggcagcatt     540
gaaccagagg agttcttgac cccaaagaaa cttcagtgtg tggacctcca tgttatttcc     600
aatgacgtgt gtgcgcaagt tcaccctcag aaggtgacca gttcatgct gtgtgctgga     660 cgctggacag ggggcaaaag cacctgctcg ggtgattctg ggggcccact tgtctgtaat     720
ggtgtgcttc aaggtatcac gtcatggggc agtgaaccat gtgccctgcc cgaaaggcct     780
tccctgtaca ccaaggtggt gcattaccgg aagtggatca aggacaccat cgtggccaac     840
ccctga                                                                 846

<210> SEQ ID NO 21
<211> LENGTH: 125
<212> TYPE: PRT
<213> ORGANISM: Homo sapiens

<400> SEQUENCE: 21

Met Ala Ser Lys Ala Val Leu Leu Ala Leu Leu Met Ala Gly Leu Ala
1               5                   10                  15

Leu Gln Pro Gly Thr Ala Leu Leu Cys Tyr Ser Cys Lys Ala Gln Val
            20                  25                  30

Ser Asn Glu Asp Cys Leu Gln Val Glu Asn Cys Thr Gln Leu Gly Glu
        35                  40                  45

Gln Cys Trp Thr Ala Arg Ile Arg Ala Val Gly Leu Leu Thr Val Ile
    50                  55                  60

Ser Lys Gly Cys Ser Leu Asn Cys Val Asp Asp Ser Gln Asp Tyr Tyr
65                  70                  75                  80

Val Gly Lys Lys Asn Ile Thr Cys Cys Asp Thr Asp Leu Cys Asn Ala
                85                  90                  95

Ser Gly Ala His Ala Leu Gln Pro Ala Ala Ile Leu Ala Leu Leu
            100                 105                 110

Pro Ala Leu Gly Leu Leu Leu Trp Gly Pro Gly Gln Leu
        115                 120                 125

<210> SEQ ID NO 22
<211> LENGTH: 375
<212> TYPE: DNA
<213> ORGANISM: Homo sapiens

<400> SEQUENCE: 22

```
atggctagca aggctgtgct gcttgccctg ttgatggcag gcttggccct gcagccaggc    60
actgccctgc tgtgctactc ctgcaaagcc caggtgagca acgaggactg cctgcaggtg   120
gagaactgca cccagctggg ggagcagtgc tggaccgcgc gcatccgcgc agttggcctc   180
ctgaccgtca tcagcaaagg ctgcagcttg aactgcgtgg atgactcaca ggactactac   240
gtgggcaaga gaacatcac gtgctgtgac accgacttgt gcaacgccag cggggcccat   300
gccctgcagc cggctgccgc catccttgcg ctgctccctg cactcggcct gctgctctgg   360
ggacccggcc agcta                                                    375
```

<210> SEQ ID NO 23
<211> LENGTH: 5964
<212> TYPE: DNA
<213> ORGANISM: Artificial
<220> FEATURE:
<223> OTHER INFORMATION: Synthetic Construct

<400> SEQUENCE: 23

```
ggcgtaatgc tctgccagtg ttacaaccaa ttaaccaatt ctgattagaa aaactcatcg    60
agcatcaaat gaaactgcaa tttattcata tcaggattat caataccata tttttgaaaa   120
agccgtttct gtaatgaagg agaaaactca ccgaggcagt tccataggat ggcaagatcc   180
tggtatcggt ctgcgattcc gactcgtcca acatcaatac aacctattaa tttcccctcg   240
tcaaaaataa ggttatcaag tgagaaatca ccatgagtga cgactgaatc cggtgagaat   300
ggcaaaagct tatgcatttc tttccagact tgttcaacag gccagccatt acgctcgtca   360
tcaaaatcac tcgcatcaac caaaccgtta ttcattcgtg attgcgcctg agcgagacga   420
aatacgcgat cgctgttaaa aggacaatta caaacaggaa tcaaatgcaa ccggcgcagg   480
aacactgcca gcgcatcaac aatattttca cctgaatcag gatattcttc taatacctgg   540
aatgctgttt tccgggggat cgcagtggtg agtaaccatg catcatcagg agtacggata   600
aaatgcttga tggtcggaag aggcataaat tccgtcagcc agtttagtct gaccatctca   660
```

```
tctgtaacat cattggcaac gctacctttg ccatgtttca gaaacaactc tggcgcatcg      720
ggcttcccat acaatcgata gattgtcgca cctgattgcc cgacattatc gcgagcccat      780
ttatacccat ataaatcagc atccatgttg gaatttaatc gcggcctcga gcaagacgtt      840
tcccgttgaa tatggctcat aacacccctt gtattactgt ttatgtaagc agacaggtcg      900
acaatattgg ctattggcca ttgcatacgt tgtatctata tcataatatg tacatttata      960
ttggctcatg tccaatatga ccgccatgtt gacattgatt attgactagt tattaatagt     1020
aatcaattac ggggtcatta gttcatagcc catatatgga gttccgcgtt acataactta     1080
cggtaaatgg cccgcctggc tgaccgccca acgacccccg cccattgacg tcaataatga     1140
cgtatgttcc catagtaacg ccaataggga ctttccattg acgtcaatgg gtggagtatt     1200
tacggtaaac tgcccacttg gcagtacatc aagtgtatca tatgccaagt ccgcccccta     1260
ttgacgtcaa tgacggtaaa tggcccgcct ggcattatgc ccagtacatg accttacggg     1320
actttcctac ttggcagtac atctacgtat tagtcatcgc tattaccatg gtgatgcggt     1380
tttggcagta caccaatggg cgtggatagc ggtttgactc acggggattt ccaagtctcc     1440
accccattga cgtcaatggg agtttgtttt ggcaccaaaa tcaacgggac tttccaaaat     1500
gtcgtaataa ccccgccccg ttgacgcaaa tgggcggtag cgtgtacgg tgggaggtct     1560 atataagcag agctcgttta gtgaaccgtc agatcgcctg gagacgccat ccacgctgtt     1620
ttgacctcca tagaagacac cgggaccgat ccagcctccg cggccgggaa cggtgcattg     1680
gaacgcggat tccccgtgcc aagagtgact caccgtccgg atctcagcaa gcaggtatgt     1740
actctccagg gtgggcctgg cttccccagt caagactcca gggatttgag gacgctgtg      1800 ggctcttctc ttacatgtac cttttgcttg cctcaaccct gactatcttc caggtcagga     1860
tcccagagtc aggggtctgt attttcctgc tggtggctcc agttcaggaa cagtaaaccc     1920
tgctccgaat attgcctctc acatctcgtc aatctccgcg aggactgggg accctgtgac     1980
gaacatggct agcgcgcgcc gcccgcgctg gctgtgcgct ggggcgctgg tgctggcggg     2040
tggcttcttt ctcctcggct tcctcttcgg gtggtttata aaatcctcca atgaagctac     2100
taacattact ccaaagcata atatgaaagc atttttggat gaattgaaag ctgagaacat     2160
caagaagttc ttatataatt ttacacagat accacattta gcaggaacag aacaaaactt     2220
tcagcttgca aagcaaattc aatcccagtg gaaagaattt ggcctggatt ctgttgagct     2280
ggcacattat gatgtcctgt tgtcctaccc aaataagact catcccaact acatctcaat     2340
aattaatgaa gatggaaatg agattttcaa cacatcatta tttgaaccac ctcctccagg     2400
atatgaaaat gtttcggata ttgtaccacc tttcagtgct ttctctcctc aaggaatgcc     2460
agagggcgat ctagtgtatg ttaactatgc acgaactgaa gacttcttta aattggaacg     2520
ggacatgaaa atcaattgct ctgggaaaat tgtaattgcc agatatggga agttttcag      2580 aggaaataag gttaaaaatg cccagctggc aggggccaaa ggagtcattc tctactccga     2640
ccctgctgac tactttgctc ctgggggtgaa gtcctatcca gatggttgga atcttcctgg     2700
aggtggtgtc cagcgtggaa atatcctaaa tctgaatggt gcaggagacc ctctcacacc     2760
aggttaccca gcaaatgaat atgcttatag gcgtggaatt gcagaggctg ttggtcttcc     2820
aagtattcct gttcatccaa ttggatacta tgatgcacag aagctcctag aaaaaatggg     2880
tggctcagca ccaccagata gcagctggag aggaagtctc aaagtgccct acaatgttgg     2940
acctggcttt actggaaact tttctacaca aaaagtcaag atgcacatcc actctaccaa     3000
```

```
tgaagtgaca agaatttaca atgtgatagg tactctcaga ggagcagtgg aaccagacag     3060
atatgtcatt ctggagggtc accgggactc atgggtgttt ggtggtattg accctcagag     3120
tggagcagct gttgttcatg aaattgtgag gagctttgga acactgaaaa aggaagggtg     3180
gagacctaga agaacaattt tgtttgcaag ctgggatgca gaagaatttg gtcttcttgg     3240
ttctactgag tgggcagagg agaattcaag actccttcaa gagcgtggcg tggcttatat     3300
taatgctgac tcatctatag aaggaaacta cactctgaga gttgattgta caccgctgat     3360
gtacagcttg gtacacaacc taacaaaaga gctgaaaagc cctgatgaag gctttgaagg     3420
caaatctctt tatgaaagtt ggactaaaaa aagtccttcc ccagagttca gtggcatgcc     3480
caggataagc aaattgggat ctggaaatga ttttgaggtg ttcttccaac gacttggaat     3540
tgcttcaggc agagcacggt atactaaaaa ttgggaaaca aacaaattca gcggctatcc     3600
actgtatcac agtgtctatg aaacatatga gttggtggaa aagttttatg atccaatgtt     3660
taaatatcac ctcactgtgg cccaggttcg aggagggatg gtgtttgagc tggccaattc     3720
catagtgctc ccttttgatt gtcgagatta tgctgtagtt ttaagaaagt atgctgacaa     3780
aatctacagt atttctatga aacatccaca ggaaatgaag acatacagtg tatcatttga     3840 ttcactttttt tctgcagtaa agaattttac agaaattgct tccaagttca gtgagagact     3900
ccaggacttt gacaaaagca acccaatagt attaagaatg atgaatgatc aactcatgtt     3960
tctggaaaga gcatttattg atccattagg gttaccagac aggcctttttt ataggcatgt     4020 catctatgct ccaagcagcc acaacaagta tgcaggggag tcattcccag gaatttatga     4080
tgctctgttt gatattgaaa gcaaagtgga cccttccaag gctgggggag aagtgaagag     4140
acagatttat gttgcagcct tcacagtgca ggcagctgca gagactttga gtgaagtagc     4200
ctaaagatct gggccctaac aaaacaaaaa gatggggtta ttccctaaac ttcatgggtt     4260
acgtaattgg aagttggggg acattgccac aagatcatat tgtacaaaag atcaaacact     4320
gttttagaaa acttcctgta aacaggccta ttgattggaa agtatgtcaa aggattgtgg     4380
gtcttttggg ctttgctgct ccatttacac aatgtggata tcctgcctta atgcctttgt     4440
atgcatgtat acaagctaaa caggcttttca cttttctcgcc aacttacaag gccttttctaa     4500 gtaaacagta catgaacctt taccccgttg ctcggcaacg gcctggtctg tgccaagtgt     4560
ttgctgacgc aaccccccact ggctggggct tggccatagg ccatcagcgc atgcgtggaa     4620
cctttgtggc tcctctgccg atccatactg cggaactcct agccgcttgt tttgctcgca     4680
gccggtctgg agcaaagctc ataggaactg acaattctgt cgtcctctcg cggaaatata     4740
catcgtttcg atctacgtat gatcttttttc cctctgccaa aaattatggg gacatcatga     4800
agccccttga gcatctgact tctggctaat aaaggaaatt tatttttcatt gcaatagtgt     4860 gttggaattt tttgtgtctc tcactcggaa ggaattctgc attaatgaat cggccaacgc     4920
gcggggagag gcggtttgcg tattgggcgc tcttccgctt cctcgctcac tgactcgctg     4980
cgctcggtcg ttcggctgcg gcgagcggta tcagctcact caaaggcggt aatacggtta     5040
tccacagaat caggggataa cgcaggaaag aacatgtgag caaaaggcca gcaaaaggcc     5100
aggaaccgta aaaaggccgc gttgctggcg tttttccata ggctccgccc cctgacgag     5160 catcacaaaa atcgacgctc aagtcagagg tggcgaaacc cgacaggact ataaagatac     5220
caggcgtttc ccctggaag ctccctcgtg cgctctcctg ttccgaccct gccgcttacc     5280
ggatacctgt ccgcctttct cccttcggga agcgtggcgc tttctcatag ctcacgctgt     5340
aggtatctca gttcggtgta ggtcgttcgc tccaagctgg gctgtgtgca cgaaccccccc     5400
```

```
gttcagcccg accgctgcgc cttatccggt aactatcgtc ttgagtccaa cccggtaaga      5460
cacgacttat cgccactggc agcagccact ggtaacagga ttagcagagc gaggtatgta      5520
ggcggtgcta cagagttctt gaagtggtgg cctaactacg gctacactag aagaacagta      5580
tttggtatct gcgctctgct gaagccagtt accttcggaa aaagagttgg tagctcttga      5640
tccggcaaac aaaccaccgc tggtagcggt ggttttttg tttgcaagca gcagattacg       5700
cgcagaaaaa aaggatctca agaagatcct ttgatctttt ctacgggtc tgacgctcag       5760 tggaacgaaa actcacgtta agggattttg gtcatgagat tatcaaaaag gatcttcacc      5820
tagatccttt taaattaaaa atgaagtttt aaatcaatct aaagtatata tgagtaaact      5880
tggtctgaca gttaccaatg cttaatcagt gaggcaccta tctcagcgat ctgtctattt      5940
cgttcatcca tagttgcctg actc                                             5964
```

<210> SEQ ID NO 24
<211> LENGTH: 4122
<212> TYPE: DNA
<213> ORGANISM: Artificial
<220> FEATURE:
<223> OTHER INFORMATION: Synthetic Construct

<400> SEQUENCE: 24

```
ggcgtaatgc tctgccagtg ttacaaccaa ttaaccaatt ctgattagaa aaactcatcg        60
agcatcaaat gaaactgcaa tttattcata tcaggattat caataccata ttttttgaaaa     120 agccgtttct gtaatgaagg agaaaactca ccgaggcagt tccataggat ggcaagatcc      180
tggtatcggt ctgcgattcc gactcgtcca acatcaatac aacctattaa tttcccctcg      240
tcaaaaataa ggttatcaag tgagaaatca ccatgagtga cgactgaatc cggtgagaat     300
ggcaaaagct tatgcatttc tttccagact tgttcaacag gccagccatt acgctcgtca      360
tcaaaatcac tcgcatcaac caaaccgtta ttcattcgtg attgcgcctg agcgagacga      420
aatacgcgat cgctgttaaa aggacaatta caaacaggaa tcaaatgcaa ccggcgcagg      480
aacactgcca gcgcatcaac aatattttca cctgaatcag gatattcttc taatacctgg      540
aatgctgttt tcccggggat cgcagtggtg agtaaccatg catcatcagg agtacggata      600
aaatgcttga tggtcggaag aggcataaat tccgtcagcc agtttagtct gaccatctca      660
tctgtaacat cattggcaac gctacctttg ccatgtttca gaaacaactc tggcgcatcg      720
ggcttcccat acaatcgata gattgtcgca cctgattgcc cgacattatc gcgagcccat      780
ttatacccat ataaatcagc atccatgttg gaatttaatc gcggcctcga gcaagacgtt      840
tcccgttgaa tatggctcat aacaccccct tgtattactgt ttatgtaagc agacaggtcg      900
acaatattgg ctattggcca ttgcatacgt tgtatctata tcataatatg tacatttata      960
ttggctcatg tccaatatga ccgccatgtt gacattgatt attgactagt tattaatagt     1020
aatcaattac gggtcatta gttcatagcc catatatgga gttccgcgtt acataactta     1080
cggtaaatgg cccgcctggc tgaccgccca acgacccccg cccattgacg tcaataatga    1140
cgtatgttcc catagtaacg ccaatagga cttttccattg acgtcaatgg gtggagtatt    1200
tacggtaaac tgcccacttg gcagtacatc aagtgtatca tatgccaagt ccgccccta     1260 ttgacgtcaa tgacggtaaa tggcccgcct ggcattatgc ccagtacatg accttacggg    1320
actttcctac ttggcagtac atctacgtat tagtcatcgc tattaccatg gtgatgcggt    1380
tttggcagta caccaatggg cgtggatagc ggtttgactc acgggattt ccaagtctcc    1440
```

-continued

```
accccattga cgtcaatggg agtttgtttt ggcaccaaaa tcaacgggac tttccaaaat    1500
gtcgtaataa ccccgccccg ttgacgcaaa tgggcggtag gcgtgtacgg tgggaggtct    1560
atataagcag agctcgttta gtgaaccgtc agatcgcctg gagacgccat ccacgctgtt    1620
ttgacctcca tagaagacac cgggaccgat ccagcctccg cggccgggaa cggtgcattg    1680
gaacgcggat tccccgtgcc aagagtgact caccgtccgg atctcagcaa gcaggtatgt    1740
actctccagg gtgggcctgg cttcccagt caagactcca gggatttgag ggacgctgtg     1800
ggctcttctc ttacatgtac cttttgcttg cctcaaccct gactatcttc caggtcagga    1860
tcccagagtc aggggtctgt attttcctgc tggtggctcc agttcaggaa cagtaaaccc    1920
tgctccgaat attgcctctc acatctcgtc aatctccgcg aggactgggg accctgtgac    1980
gaacatggct agcaaggctg tgctgcttgc cctgttgatg gcaggcttgg ccctgcagcc    2040
aggcactgcc ctgctgtgct actcctgcaa agcccaggtg agcaacgagg actgcctgca    2100
ggtggagaac tgcacccagc tgggggagca gtgctggacc gcgcgcatcc gcgcagttgg    2160
cctcctgacc gtcatcagca aaggctgcag cttgaactgc gtggatgact cacaggacta    2220
ctacgtgggc aagaagaaca tcacgtgctg tgacaccgac ttgtgcaacg ccagcgggc     2280
ccatgccctg cagccggctg ccgccatcct tgcgctgctc cctgcactcg gctgctgct    2340
ctggggaccc ggccagctat agagatctgg gccctaacaa acaaaaaga tggggttatt    2400
ccctaaactt catgggttac gtaattggaa gttggggaca attgccacaa gatcatattg    2460
tacaaaagat caaacactgt tttagaaaac ttcctgtaaa caggcctatt gattggaaag    2520
tatgtcaaag gattgtgggt cttttgggct ttgctgctcc atttacacaa tgtggatatc    2580
ctgccttaat gcctttgtat gcatgtatac aagctaaaca ggctttcact ttctcgccaa    2640
cttacaaggc ctttctaagt aaacagtaca tgaacccttta ccccgttgct cggcaacggc    2700
ctggtctgtg ccaagtgttt gctgacgcaa ccccccactgg ctggggcttg gccataggcc    2760
atcagcgcat gcgtggaacc tttgtggctc ctctgccgat ccatactgcg gaactcctag    2820
ccgcttgttt tgctcgcagc cggtctggag caaagctcat aggaactgac aattctgtcg    2880
tcctctcgcg gaaatataca tcgtttcgat ctacgtatga tcttttccc tctgccaaaa     2940
attatgggga catcatgaag cccccttgagc atctgacttc tggctaataa aggaaattta    3000
ttttcattgc aatagtgtgt tggaattttt tgtgtctctc actcggaagg aattctgcat    3060
taatgaatcg gccaacgcgc ggggagaggc ggtttgcgta ttgggcgctc ttccgcttcc    3120
tcgctcactg actcgctgcg ctcggtcgtt cggctgcggc gagcggtatc agctcactca    3180
aaggcggtaa tacggttatc cacagaatca ggggataacg caggaaagaa catgtgagca    3240
aaaggccagc aaaaggccag gaaccgtaaa aaggccgcgt tgctggcgtt tttccatagg    3300
ctccgccccc ctgacgagca tcacaaaaat cgacgctcaa gtcagaggtg gcgaaacccg    3360
acaggactat aaagatacca ggcgtttccc cctggaagct ccctcgtgcg ctctcctgtt    3420
ccgaccctgc cgcttaccgg atacctgtcc gcctttctcc cttcgggaag cgtggcgctt    3480
tctcatagct cacgctgtag gtatctcagt tcggtgtagg tcgttcgctc caagctgggc    3540
tgtgtgcacg aaccccccgt tcagcccgac cgctgcgcct tatccggtaa ctatcgtctt    3600
gagtccaacc cggtaagaca cgacttatcg ccactggcag cagccactgg taacaggatt    3660
agcagagcga ggtatgtagg cggtgctaca gagttcttga agtggtggcc taactacggc    3720
tacactagaa gaacagtatt tggtatctgc gctctgctga agccagttac cttcggaaaa    3780
agagttggta gctcttgatc cggcaaacaa accaccgctg gtagcggtgg tttttttgtt    3840
```

-continued

| | |
|---|---|
| tgcaagcagc agattacgcg cagaaaaaaa ggatctcaag aagatccttt gatcttttct | 3900 |
| acggggtctg acgctcagtg gaacgaaaac tcacgttaag ggattttggt catgagatta | 3960 |
| tcaaaaagga tcttcaccta gatccttta aattaaaaat gaagttttaa atcaatctaa | 4020 |
| agtatatatg agtaaacttg gtctgacagt taccaatgct taatcagtga ggcacctatc | 4080 |
| tcagcgatct gtctatttcg ttcatccata gttgcctgac tc | 4122 |

<210> SEQ ID NO 25
<211> LENGTH: 4467
<212> TYPE: DNA
<213> ORGANISM: Artificial
<220> FEATURE:
<223> OTHER INFORMATION: Synthetic Construct

<400> SEQUENCE: 25

| | |
|---|---|
| ggcgtaatgc tctgccagtg ttacaaccaa ttaaccaatt ctgattagaa aaactcatcg | 60 |
| agcatcaaat gaaactgcaa tttattcata tcaggattat caataccata tttttgaaaa | 120 |
| agccgtttct gtaatgaagg agaaaactca ccgaggcagt tccataggat ggcaagatcc | 180 |
| tggtatcggt ctgcgattcc gactcgtcca acatcaatac aacctattaa tttcccctcg | 240 |
| tcaaaaataa ggttatcaag tgagaaatca ccatgagtga cgactgaatc cggtgagaat | 300 |
| ggcaaaagct tatgcatttc tttccagact tgttcaacag gccagccatt acgctcgtca | 360 |
| tcaaaatcac tcgcatcaac caaaccgtta ttcattcgtg attgcgcctg agcgagacga | 420 |
| aatacgcgat cgctgttaaa aggacaatta caaacaggaa tcgaatgcaa ccggcgcagg | 480 |
| aacactgcca gcgcatcaac aatattttca cctgaatcag gatattcttc taatacctgg | 540 |
| aatgctgttt tcccggggat cgcagtggtg agtaaccatg catcatcagg agtacggata | 600 |
| aaatgcttga tggtcggaag aggcataaat tccgtcagcc agtttagtct gaccatctca | 660 |
| tctgtaacat cattggcaac gctacctttg ccatgtttca gaaacaactc tggcgcatcg | 720 |
| ggcttcccat acaatcgata gattgtcgca cctgattgcc cgacattatc gcgagcccat | 780 |
| ttatacccat ataaatcagc atccatgttg gaatttaatc gcggcctcga gcaagacgtt | 840 |
| tcccgttgaa tatggctcat aacacccctt gtattactgt ttatgtaagc agacaggtcg | 900 |
| acaatattgg ctattggcca ttgcatacgt tgtatctata tcataatatg tacatttata | 960 |
| ttggctcatg tccaatatga ccgccatgtt gacattgatt attgactagt tattaatagt | 1020 |
| aatcaattac gggtcatta gttcatagcc catatatgga gttccgcgtt acataactta | 1080 |
| cggtaaatgg cccgcctggc tgaccgccca acgacccccg cccattgacg tcaataatga | 1140 |
| cgtatgttcc catagtaacg ccaataggga ctttccattg acgtcaatgg gtggagtatt | 1200 |
| tacggtaaac tgcccacttg gcagtacatc aagtgtatca tatgccaagt ccgcccccta | 1260 |
| ttgacgtcaa tgacggtaaa tggcccgcct ggcattatgc ccagtacatg accttacggg | 1320 |
| actttcctac ttggcagtac atctacgtat tagtcatcgc tattaccatg gtgatgcggt | 1380 |
| tttggcagta caccaatggg cgtggatagc ggtttgactc acggggattt ccaagtctcc | 1440 |
| accccattga cgtcaatggg agtttgtttt ggcaccaaaa tcaacgggac tttccaaaat | 1500 |
| gtcgtaataa ccccgccccg ttgacgcaaa tgggcggtag cgtgtacgg tgggaggtct | 1560 |
| atataagcag agctcgttta gtgaaccgtc agatcgcctg gagacgccat ccacgctgtt | 1620 |
| ttgacctcca tagaagacac cgggaccgat ccagcctccg cggccgggaa cggtgcattg | 1680 |
| gaacgcggat tccccgtgcc aagagtgact caccgtccgg atctcagcaa gcaggtatgt | 1740 |

```
actctccagg gtgggcctgg cttccccagt caagactcca gggatttgag ggacgctgtg   1800
ggctcttctc ttacatgtac cttttgcttg cctcaaccct gactatcttc caggtcagga   1860
tcccagagtc aggggtctgt attttcctgc tggtggctcc agttcaggaa cagtaaaccc   1920
tgctccgaat attgcctctc acatctcgtc aatctccgcg aggactgggg accctgtgac   1980
gaacatggct agcattgtgg gaggctggga gtgcgagaag cattcccaac cctggcaggt   2040
gcttgtggcc tctcgtggca gggcagtctg cggcggtgtt ctggtgcacc ccagtgggt    2100 cctcacagct gcccactgca tcaggaacaa aagcgtgatc ttgctgggtc ggcacagctt   2160
gtttcatcct gaagacacag gccaggtatt tcaggtcagc cacagcttcc cacacccgct   2220
ctacgatatg agcctcctga agaatcgatt cctcaggcca ggtgatgact ccagccacga   2280
cctcatgctg ctccgcctgt cagagcctgc cgagctcacg gatgctgtga aggtcatgga   2340
cctgcccacc caggagccag cactggggac cacctgctac gcctcaggct ggggcagcat   2400
tgaaccagag gagttcttga ccccaaagaa acttcagtgt gtggacctcc atgttatttc   2460
caatgacgtg tgtgcgcaag ttcaccctca gaaggtgacc aagttcatgc tgtgtgctgg   2520
acgctggaca gggggcaaaa gcacctgctc gggtgattct gggggcccac ttgtctgtaa   2580
tggtgtgctt caaggtatca cgtcatgggg cagtgaacca tgtgccctgc ccgaaaggcc   2640
ttccctgtac accaaggtgg tgcattaccg gaagtggatc aaggacacca tcgtggccaa   2700
cccctgaaga tctgggccct aacaaaacaa aaagatgggg ttattcccta aacttcatgg   2760
gttacgtaat tggaagttgg gggacattgc cacaagatca tattgtacaa aagatcaaac   2820
actgttttag aaaacttcct gtaaacaggc ctattgattg gaaagtatgt caaaggattg   2880
tgggtctttt gggctttgct gctccattta cacaatgtgg atatcctgcc ttaatgcctt   2940
tgtatgcatg tatacaagct aaacaggctt tcactttctc gccaacttac aaggcctttc   3000
taagtaaaca gtacatgaac ctttaccccg ttgctcggca acggcctggt ctgtgccaag   3060
tgtttgctga cgcaaccccc actggctggg gcttggccat aggccatcag cgcatgcgtg   3120
gaacctttgt ggctcctctg ccgatccata ctgcggaact cctagccgct tgttttgctc   3180
gcagccggtc tggagcaaag ctcataggaa ctgacaattc tgtcgtcctc tcgcggaaat   3240
atacatcgtt tcgatctacg tatgatcttt ttccctctgc caaaaattat ggggacatca   3300
tgaagcccct tgagcatctg acttctggct aataaaggaa attttatttc attgcaatag   3360
tgtgttggaa ttttttgtgt ctctcactcg gaaggaattc tgcattaatg aatcggccaa   3420
cgcgcgggga gaggcggttt gcgtattggg cgctcttccg cttcctcgct cactgactcg   3480
ctgcgctcgg tcgttcggct gcggcgagcg gtatcagctc actcaaaggc ggtaatacgg   3540
ttatccacag aatcagggga taacgcagga agaacatgt gagcaaaagg ccagcaaaag    3600
gccaggaacc gtaaaaaggc cgcgttgctg gcgttttcc ataggctccg ccccctgac     3660 gagcatcaca aaaatcgacg ctcaagtcag aggtggcgaa acccgacagg actataaaga   3720
taccaggcgt ttccccctgg aagctccctc gtgcgctctc ctgttccgac cctgccgctt   3780
accggatacc tgtccgcctt tctcccttcg ggaagcgtgg cgctttctca tagctcacgc   3840
tgtaggtatc tcagttcggt gtaggtcgtt cgctccaagc tgggctgtgt gcacgaaccc   3900
cccgttcagc ccgaccgctg cgccttatcc ggtaactatc gtcttgagtc aacccggta    3960 agacacgact tatcgccact ggcagcagcc actggtaaca ggattagcag agcgaggtat   4020
gtaggcggtg ctacagagtt cttgaagtgg tggcctaact acggctacac tagaagaaca   4080
gtatttggta tctgcgctct gctgaagcca gttaccttcg gaaaaagagt tggtagctct   4140
```

| | | |
|---|---|---|
| tgatccggca aacaaaccac cgctggtagc ggtggttttt ttgtttgcaa gcagcagatt | 4200 |
| acgcgcagaa aaaaggatc tcaagaagat cctttgatct tttctacggg gtctgacgct | 4260 |
| cagtggaacg aaaactcacg ttaagggatt ttggtcatga gattatcaaa aaggatcttc | 4320 |
| acctagatcc ttttaaatta aaaatgaagt tttaaatcaa tctaaagtat atatgagtaa | 4380 |
| acttggtctg acagttacca atgcttaatc agtgaggcac ctatctcagc gatctgtcta | 4440 |
| tttcgttcat ccatagttgc ctgactc | 4467 |

<210> SEQ ID NO 26
<211> LENGTH: 7563
<212> TYPE: DNA
<213> ORGANISM: Artificial
<220> FEATURE:
<223> OTHER INFORMATION: Synthetic Construct

<400> SEQUENCE: 26

| | | |
|---|---|---|
| gaattctgca ttaatgaatc ggccaacgcg cggggagagg cggtttgcgt attgggcgct | 60 |
| cttccgcttc ctcgctcact gactcgctgc gctcggtcgt tcggctgcgg cgagcggtat | 120 |
| cagctcactc aaaggcggta atacggttat ccacagaatc aggggataac gcaggaaaga | 180 |
| acatgtgagc aaaaggccag caaaaggcca ggaaccgtaa aaaggccgcg ttgctggcgt | 240 |
| ttttccatag gctccgcccc cctgacgagc atcacaaaaa tcgacgctca agtcagaggt | 300 |
| ggcgaaaccc gacaggacta taaagatacc aggcgtttcc ccctggaagc tccctcgtgc | 360 |
| gctctcctgt tccgaccctg ccgcttaccg gatacctgtc cgcctttctc ccttcgggaa | 420 |
| gcgtggcgct ttctcatagc tcacgctgta ggtatctcag ttcggtgtag gtcgttcgct | 480 |
| ccaagctggg ctgtgtgcac gaaccccccg ttcagcccga ccgctgcgcc ttatccggta | 540 |
| actatcgtct gagtccaacc cggtaagac acgacttatc gccactggca gcagccactg | 600 |
| gtaacaggat tagcagagcg aggtatgtag gcggtgctac agagttcttg aagtggtggc | 660 |
| ctaactacgg ctacactaga agaacagtat ttggtatctg cgctctgctg aagccagtta | 720 |
| ccttcggaaa aagagttggt agctcttgat ccggcaaaca aaccaccgct ggtagcggtg | 780 |
| gtttttttgt ttgcaagcag cagattacgc gcagaaaaaa aggatctcaa gaagatcctt | 840 |
| tgatcttttc tacggggtct gacgctcagt ggaacgaaaa ctcacgttaa gggattttgg | 900 |
| tcatgagatt atcaaaaagg atcttcacct agatcctttt aaattaaaaa tgaagtttta | 960 |
| aatcaatcta agtatatat gagtaaactt ggtctgacag ttaccaatgc ttaatcagtg | 1020 |
| aggcacctat ctcagcgatc tgtctatttc gttcatccat agttgcctga ctcggcgtaa | 1080 |
| tgctctgcca gtgttacaac caattaacca attctgatta gaaaaactca tcgagcatca | 1140 |
| aatgaaactg caatttattc atatcaggat tatcaatacc atattttga aaaagccgtt | 1200 |
| tctgtaatga aggagaaaac tcaccgaggc agttccatag gatggcaaga tcctggtatc | 1260 |
| ggtctgcgat tccgactcgt ccaacatcaa taacctat taattttcccc tcgtcaaaaa | 1320 |
| taaggttatc aagtgagaaa tcaccatgag tgacgactga atccggtgag aatggcaaaa | 1380 |
| gcttatgcat ttctttccag acttgttcaa caggccagcc attacgctcg tcatcaaaat | 1440 |
| cactcgcatc aaccaaaccg ttattcattc gtgattgcgc ctgagcgaga cgaaatacgc | 1500 |
| gatcgctgtt aaaaggacaa ttacaaacag gaatcaaatg caaccggcgc aggaacactg | 1560 |
| ccagcgcatc aacaatatt tcacctgaat caggatattc ttctaatacc tggaatgctg | 1620 |
| ttttcccggg gatcgcagtg gtgagtaacc atgcatcatc aggagtacgg ataaaatgct | 1680 |

| | |
|---|---|
| tgatggtcgg aagaggcata aattccgtca gccagtttag tctgaccatc tcatctgtaa | 1740 |
| catcattggc aacgctacct ttgccatgtt tcagaaacaa ctctggcgca tcgggcttcc | 1800 |
| catacaatcg atagattgtc gcacctgatt gcccgacatt atcgcgagcc catttatacc | 1860 |
| catataaatc agcatccatg ttggaattta atcgcggcct cgagcaagac gtttcccgtt | 1920 |
| gaatatggct cataacaccc cttgtattac tgtttatgta agcagacagg gtaccaatct | 1980 |
| tccgagtgag agacacaaaa aattccaaca cactattgca atgaaaataa atttccttta | 2040 |
| ttagccagaa gtcagatgct caaggggctt catgatgtcc ccataatttt tggcagaggg | 2100 |
| aaaaagatca tacgtagatc gaaacgatgt atatttccgc gagaggacga cagaattgtc | 2160 |
| agttcctatg agctttgctc cagaccggct gcgagcaaaa caagcggcta ggagttccgc | 2220 |
| agtatggatc ggcagaggag ccacaaaggt tccacgcatg cgctgatggc ctatggccaa | 2280 |
| gccccagcca gtgggggttg cgtcagcaaa cacttggcac agaccaggcc gttgccgagc | 2340 |
| aacggggtaa aggttcatgt actgtttact tagaaaggcc ttgtaagttg gcgagaaagt | 2400 |
| gaaagcctgt ttagcttgta tacatgcata caaaggcatt aaggcaggat atccacattg | 2460 |
| tgtaaatgga gcagcaaagc ccaaaagacc cacaatcctt tgacatactt tccaatcaat | 2520 |
| aggcctgttt acaggaagtt ttctaaaaca gtgtttgatc ttttgtacaa tatgatcttg | 2580 |
| tggcaatgtc ccccaacttc caattacgta acccatgaag tttagggaat aaccccatct | 2640 |
| ttttgttttg ttagggccca gatctttagg ctacttcact caaagtctct gcagctgcct | 2700 |
| gcactgtgaa ggctgcaaca taaatctgtc tcttcacttc tccccaggcc ttggaagggt | 2760 |
| ccactttgct ttcaatatca aacagagcat cataaattcc tgggaatgac tcccctgcat | 2820 |
| acttgttgtg gctgcttgga gcatagatga catgcctata aaaaggcctg tctggtaacc | 2880 |
| ctaatggatc aataaatgct cttccagaaa acatgagttg atcattcatc attcttaata | 2940 |
| ctattgggtt gcttttgtca aagtcctgga gtctctcact gaacttggaa gcaatttctg | 3000 |
| taaaattctt tactgcagaa aaaagtgaat caaatgatac actgtatgtc ttcatttcct | 3060 |
| gtggatgttt catagaaata ctgtagattt tgtcagcata cttttcttaaa actacagcat | 3120 |
| aatctcgaca atcaaagggg agcactatgg aattggccag ctcaaacacc atccctcctc | 3180 |
| gaacctgggc cacagtgagg tgatatttaa acattggatc ataaaacttt tccaccaact | 3240 |
| catatgtttc atagacactg tgatacagtg gatagccgct gaatttgttt gtttcccaat | 3300 |
| ttttagtata ccgtgctctg cctgaagcaa ttccaagtcg ttggaagaac acctcaaaat | 3360 |
| catttccaga tcccaatttg cttatcctgg gcatgccact gaactctggg gaaggacttt | 3420 |
| ttttagtcca actttcataa agagatttgc cttcaaagcc ttcatcaggg cttttcagct | 3480 |
| cttttgttag gttgtgtacc aagctgtaca tcagcggtgt acaatcaact ctcagagtgt | 3540 |
| agtttccttc tatagatgag tcagcattaa tataagccac gccacgctct tgaaggagtc | 3600 |
| ttgaattctc ctctgcccac tcagtagaac caagaagacc aaattcttct gcatcccagc | 3660 |
| ttgcaaacaa aattgttctt ctaggtctcc acccttcctt tttcagtgtt ccaaagctcc | 3720 |
| tcacaatttc atgaacaaca gctgctccac tctgagggtc aataccacca acacccatg | 3780 |
| agtcccggtg acctcccaga atgacatatc tgtctggttc cactgctcct ctgagagtac | 3840 |
| ctatcacatt gtaaattctt gtcacttcat ggtagagtg gatgtgcatc ttgacttttt | 3900 |
| gtgtagaaaa gtttccagta aagccaggtc caacattgta gggcactttg agacttcctc | 3960 |
| tccagctgct atctggtggt gctgagccac ccatttttc taggagcttc tgtgcatcat | 4020 |
| agtatccaat tggatgaaca ggaatacttg gaagaccaac agcctctgca attccacgcc | 4080 |

| | | | | | |
|---|---|---|---|---|---|
| tataagcata | ttcatttgct | gggtaacctg | gtgtgagagg | gtctcctgca | ccattcagat | 4140 |
| ttaggatatt | tccacgctgg | acaccacctc | caggaagatt | ccaaccatct | ggataggact | 4200 |
| tcaccccagg | agcaaagtag | tcagcagggt | cggagtagag | aatgactcct | ttggcccctg | 4260 |
| ccagctgggc | atttttaacc | ttatttcctc | tgaaaacttt | cccatatctg | gcaattacaa | 4320 |
| ttttcccaga | gcaattgatt | ttcatgtccc | gttccaattt | aaagaagtct | tcagttcgtg | 4380 |
| catagttaac | atacactaga | tcgccctctg | gcattccttg | aggagagaaa | gcactgaaag | 4440 |
| gtggtacaat | atccgaaaca | ttttcatatc | ctggaggagg | tggttcaaat | aatgatgtgt | 4500 |
| tgaaaatctc | atttccatct | tcattaatta | ttgagatgta | gttgggatga | gtcttatttg | 4560 |
| ggtaggacaa | caggacatca | taatgtgcca | gctcaacaga | atccaggcca | aattctttcc | 4620 |
| actgggattg | aatttgcttt | gcaagctgaa | agttttgttc | tgttcctgct | aaatgtggta | 4680 |
| tctgtgtaaa | attatataag | aacttcttga | tgttctcagc | tttcaattca | tccaaaaatg | 4740 |
| ctttcatatt | atgctttgga | gtaatgttag | tagcttcatt | ggaggatttt | ataaaccacc | 4800 |
| cgaagaggaa | gccgaggaga | aagaagccac | ccgccagcac | cagcgcccca | gcgcacagcc | 4860 |
| agcgcgggcg | gcgcgcgcta | gccatgttcg | tcacagggtc | cccagtcctc | gcggagattg | 4920 |
| acgagatgtg | agaggcaata | ttcggagcag | ggtttactgt | tcctgaactg | gagccaccag | 4980 |
| caggaaaata | cagaccctg | actctgggat | cctgacctgg | aagatagtca | gggttgaggc | 5040 |
| aagcaaaagg | tacatgtaag | agaagagccc | acagcgtccc | tcaaatccct | ggagtcttga | 5100 |
| ctggggaagc | caggcccacc | ctggagagta | catacctgct | tgctgagatc | cggacggtga | 5160 |
| gtcactcttg | gcacggggaa | tccgcgttcc | aatgcaccgt | tcccggccgc | ggaggctgga | 5220 |
| tcggtcccgg | tgtcttctat | ggaggtcaaa | acagcgtgga | tggcgtctcc | aggcgatctg | 5280 |
| acggttcact | aaacgagctc | tgcttatata | gacctcccac | cgtacacgcc | taccgcccat | 5340 |
| ttgcgtcaac | ggggcggggt | tattacgaca | ttttggaaag | tcccgttgat | tttggtgctc | 5400 |
| gacctgcagg | gtaccaatat | tggctattgg | ccattgcata | cgttgtatct | atatcataat | 5460 |
| atgtacattt | atattggctc | atgtccaata | tgaccgccat | gttgacattg | attattgact | 5520 |
| agttattaat | agtaatcaat | tacggggtca | ttagttcata | gcccatatat | ggagttccgc | 5580 |
| gttacataac | ttacggtaaa | tggcccgcct | ggctgaccgc | ccaacgaccc | ccgcccattg | 5640 |
| acgtcaataa | tgacgtatgt | tcccatagta | acgccaatag | ggactttcca | ttgacgtcaa | 5700 |
| tgggtggagt | atttacggta | aactgcccac | ttggcagtac | atcaagtgta | tcatatgcca | 5760 |
| agtccgcccc | ctattgacgt | caatgacggt | aaatggcccg | cctggcatta | tgcccagtac | 5820 |
| atgaccttac | gggactttcc | tacttggcag | tacatctacg | tattagtcat | cgctattacc | 5880 |
| atggtgatgc | ggttttggca | gtacaccaat | gggcgtggat | agcggtttga | ctcacgggga | 5940 |
| tttccaagtc | tccaccccat | tgacgtcaat | gggagtttgt | tttggcacca | aaatcaacgg | 6000 |
| gactttccaa | aatgtcgtaa | taaccccgcc | ccgttgacgc | aaatgggcgg | taggcgtgta | 6060 |
| cggtgggagg | tctatataag | cagagctcgt | ttagtgaacc | gtcagatcgc | ctggagacgc | 6120 |
| catccacgct | gttttgacct | ccatagaaga | caccgggacc | gatccagcct | ccgcggccgg | 6180 |
| gaacggtgca | ttggaacgcg | gattcccgt | gccaagagtg | actcaccgtc | cggatctcag | 6240 |
| caagcaggta | tgtactctcc | agggtgggcc | tggcttcccc | agtcaagact | ccagggattt | 6300 |
| gagggacgct | gtgggctctt | ctcttacatg | taccttttgc | ttgcctcaac | cctgactatc | 6360 |
| ttccaggtca | ggatcccaga | gtcaggggtc | tgtattttcc | tgctggtggc | tccagttcag | 6420 |

```
gaacagtaaa ccctgctccg aatattgcct ctcacatctc gtcaatctcc gcgaggactg    6480
gggaccctgt gacgaacatg gctagcaagg ctgtgctgct tgccctgttg atggcaggct    6540
tggccctgca gccaggcact gccctgctgt gctactcctg caaagcccag gtgagcaacg    6600
aggactgcct gcaggtggag aactgcaccc agctggggga gcagtgctgg accgcgcgca    6660
tccgcgcagt tggcctcctg accgtcatca gcaaaggctg cagcttgaac tgcgtggatg    6720
actcacagga ctactacgtg ggcaagaaga acatcacgtg ctgtgacacc gacttgtgca    6780
acgccagcgg ggcccatgcc ctgcagccgg ctgccgccat ccttgcgctg ctccctgcac    6840
tcggcctgct gctctgggga cccggccagc tatagagatc tgggccctaa caaaacaaaa    6900
agatggggtt attccctaaa cttcatgggt tacgtaattg aagttgggg gacattgcca    6960 caagatcata ttgtacaaaa gatcaaacac tgttttagaa acttcctgt aaacaggcct    7020 attgattgga aagtatgtca aaggattgtg ggtcttttgg gctttgctgc tccatttaca    7080
caatgtggat atcctgcctt aatgcctttg tatgcatgta tacaagctaa acaggctttc    7140
actttctcgc caacttacaa ggcctttcta agtaaacagt acatgaacct ttaccccgtt    7200
gctcggcaac ggcctggtct gtgccaagtg tttgctgacg caaccccac tggctggggc    7260 ttggccatag gccatcagcg catgcgtgga acctttgtgg ctcctctgcc gatccatact    7320
gcggaactcc tagccgcttg ttttgctcgc agccggtctg gagcaaagct cataggaact    7380
gacaattctg tcgtcctctc gcggaaatat acatcgtttc gatctacgta tgatcttttt    7440
ccctctgcca aaattatgg ggacatcatg aagccccttg agcatctgac ttctggctaa    7500
taaaggaaat ttatttttcat tgcaatagtg tgttggaatt ttttgtgtct ctcactcgga    7560
agc                                                                  7563
```

<210> SEQ ID NO 27
<211> LENGTH: 6396
<212> TYPE: DNA
<213> ORGANISM: Artificial
<220> FEATURE:
<223> OTHER INFORMATION: Synthetic Construct

<400> SEQUENCE: 27

```
ggcgtaatgc tctgccagtg ttacaaccaa ttaaccaatt ctgattagaa aaactcatcg      60
agcatcaaat gaaactgcaa tttattcata tcaggattat caataccata ttttgaaaa    120 agccgtttct gtaatgaagg agaaaactca ccgaggcagt tccataggat ggcaagatcc    180
tggtatcggt ctgcgattcc gactcgtcca acatcaatac aacctattaa tttccctcg    240 tcaaaaataa ggttatcaag tgagaaatca ccatgagtga cgactgaatc cggtgagaat    300
ggcaaaagct tatgcatttc tttccagact tgttcaacag gccagccatt acgctcgtca    360
tcaaaatcac tcgcatcaac caaaccgtta ttcattcgtg attgcgcctg agcgagacga    420
aatacgcgat cgctgttaaa aggacaatta caaacaggaa tcaaatgcaa ccggcgcagg    480
aacactgcca gcgcatcaac aatatttca cctgaatcag gatattcttc taatacctgg    540
aatgctgttt tcccggggat cgcagtggtg agtaaccatg catcatcagg agtacggata    600
aaatgcttga tggtcggaag aggcataaat tccgtcagcc agtttagtct gaccatctca    660
tctgtaacat cattggcaac gctacctttg ccatgtttca gaaacaactc tggcgcatcg    720
ggcttcccat acaatcgata gattgtcgca cctgattgcc cgacattatc gcgagcccat    780
ttatacccat ataaatcagc atccatgttg gaatttaatc gcggcctcga gcaagacgtt    840
tcccgttgaa tatggctcat aacaccccctt gtattactgt ttatgtaagc agacaggtcg    900
```

```
acaatattgg ctattggcca ttgcatacgt tgtatctata tcataatatg tacatttata    960
ttggctcatg tccaatatga ccgccatgtt gacattgatt attgactagt tattaatagt   1020
aatcaattac ggggtcatta gttcatagcc catatatgga gttccgcgtt acataactta   1080
cggtaaatgg cccgcctggc tgaccgccca acgaccccg cccattgacg tcaataatga    1140
cgtatgttcc catagtaacg ccaataggga cttcccattg acgtcaatgg gtggagtatt   1200
tacggtaaac tgcccacttg gcagtacatc aagtgtatca tatgccaagt ccgcccccta   1260
ttgacgtcaa tgacggtaaa tggcccgcct ggcattatgc ccagtacatg accttacggg   1320
actttcctac ttggcagtac atctacgtat tagtcatcgc tattaccatg gtgatgcggt   1380
tttggcagta caccaatggg cgtggatagc ggtttgactc acggggattt ccaagtctcc   1440
accccattga cgtcaatggg agtttgtttt ggcaccaaaa tcaacgggac tttccaaaat   1500
gtcgtaataa ccccgccccg ttgacgcaaa tgggcggtag gcgtgtacgg tgggaggtct   1560
atataagcag agctcgttta gtgaaccgtc agatcgcctg gagacgccat ccacgctgtt   1620
ttgacctcca tagaagacac cgggaccgat ccagcctccg cggccgggaa cggtgcattg   1680
gaacgcggat tccccgtgcc aagagtgact caccgtccgg atctcagcaa gcaggtatgt   1740
actctccagg gtgggcctgg cttccccagt caagactcca gggatttgag gacgctgtg    1800
ggctcttctc ttacatgtac cttttgcttg cctcaaccct gactatcttc caggtcagga   1860
tcccagagtc aggggtctgt attttcctgc tggtggctcc agttcaggaa cagtaaaccc   1920
tgctccgaat attgcctctc acatctcgtc aatctccgcg aggactgggg accctgtgac   1980
gaacatggct agcgcgcgcc gcccgcgctg gctgtgcgct ggggcgctgg tgctggcggg   2040
tggcttcttt ctcctcggct tcctcttcgg gtggtttata aaatcctcca atgaagctac   2100
taacattact ccaaagcata atatgaaagc attttttggat gaattgaaag ctgagaacat   2160
caagaagttc ttatataatt ttacacagat accacattta gcaggaacag aacaaaactt   2220
tcagcttgca aagcaaattc aatcccagtg gaaagaattt ggcctggatt ctgttgagct   2280
ggcacattat gatgtcctgt tgtcctaccc aaataagact catcccaact acatctcaat   2340
aattaatgaa gatggaaatg agattttcaa cacatcatta tttgaaccac ctcctccagg   2400
atatgaaaat gtttcggata ttgtaccacc tttcagtgct ttctctcctc aaggaatgcc   2460
agagggcgat ctagtgtatg ttaactatgc acgaactgaa gacttcttta aattggaacg   2520
ggacatgaaa atcaattgct ctgggaaaat tgtaattgcc agatatggga agttttcag    2580
aggaaataag gttaaaaatg cccagctggc aggggccaaa ggagtcattc tctactccga   2640
ccctgctgac tactttgctc ctggggtgaa gtcctatcca gatggttgga tcttcctgg    2700
aggtggtgtc cagcgtggaa atatcctaaa tctgaatggt gcaggagacc ctctcacacc   2760
aggttaccca gcaaatgaat atgcttatag gcgtggaatt gcagaggctg ttggtcttcc   2820
aagtattcct gttcatccaa ttggatacta tgatgcacag aagctcctag aaaaaatggg   2880
tggctcagca ccaccagata gcagctggag aggaagtctc aaagtgccct acaatgttgg   2940
acctggcttt actggaaact tttctacaca aaagtcaag atgcacatcc actctaccaa    3000
tgaagtgaca agaatttaca atgtgatagg tactctcaga ggagcagtgg aaccagacag   3060
atatgtcatt ctgggaggtc accgggactc atgggtgttt ggtggtattg accctcagag   3120
tggagcagct gttgttcatg aaattgtgag gagctttgga acactgaaaa aggaagggtg   3180
gagacctaga agaacaattt tgtttgcaag ctgggatgca gaagaatttg gtcttcttgg   3240
```

```
ttctactgag tgggcagagg agaattcaag actccttcaa gagcgtggcg tggcttatat    3300
taatgctgac tcatctatag aaggaaacta cactctgaga gttgattgta caccgctgat    3360
gtacagcttg gtacacaacc taacaaaaga gctgaaaagc cctgatgaag ctttgaagg     3420
caaatctctt tatgaaagtt ggactaaaaa aagtccttcc ccagagttca gtggcatgcc    3480
caggataagc aaattgggat ctggaaatga ttttgaggtg ttcttccaac gacttggaat    3540
tgcttcaggc agagcacggt atactaaaaa ttgggaaaca aacaaattca gcggctatcc    3600
actgtatcac agtgtctatg aaacatatga gttggtggaa aagttttatg atccaatgtt    3660
taaatatcac ctcactgtgg cccaggttcg aggaggatg  gtgtttgagc tggccaattc    3720
catagtgctc ccttttgatt gtcgagatta tgctgtagtt ttaagaaagt atgctgacaa    3780
aatctacagt atttctatga aacatccaca ggaaatgaag acatacagtg tatcatttga    3840
ttcactttt tctgcagtaa agaattttac agaaattgct ccaagttca gtgagagact      3900
ccaggacttt gacaaaagca acccaatagt attaagaatg atgaatgatc aactcatgtt    3960
tctggaaaga gcatttattg atccattagg gttaccagac aggcctttt  ataggcatgt    4020
catctatgct ccaagcagcc acaacaagta tgcaggggag tcattcccag gaatttatga    4080
tgctctgttt gatattgaaa gcaaagtgga cccttccaag gctgggggag aagtgaagag    4140
acagatttat gttgcagcct tcacagtgca ggcagctgca gagactttga gtgaagtagc    4200
cggatccgaa ggtaggggtt cattattgac ctgtggagat gtcgaagaaa cccaggacc    4260
cgcaagcaag gctgtgctgc ttgccctgtt gatggcaggc ttggccctgc agccaggcac    4320
tgccctgctg tgctactcct gcaaagccca ggtgagcaac gaggactgcc tgcaggtgga    4380
gaactgcacc cagctggggg agcagtgctg gaccgcgcgc atccgcgcag ttggcctcct    4440
gaccgtcatc agcaaaggct gcagcttgaa ctgcgtggat gactcacagg actactacgt    4500
gggcaagaag aacatcacgt gctgtgacac cgacttgtgc aacgccagcg ggcccatgc    4560
cctgcagccg gctgccgcca tccttgcgct gctccctgca ctcggcctgc tgctctgggg    4620
acccggccag ctatagagat ctgggcccta acaaaacaaa agatggggt  tattccctaa    4680
acttcatggg ttacgtaatt ggaagttggg ggacattgcc acaagatcat attgtacaaa    4740
agatcaaaca ctgttttaga aaacttcctg taaacaggcc tattgattgg aaagtatgtc    4800
aaaggattgt gggtctttg  ggctttgctg ctccatttac acaatgtgga tatcctgcct    4860
taatgccttt gtatgcatgt atacaagcta acaggctt t  cactttctcg ccaacttaca   4920
aggcctttct aagtaaacag tacatgaacc tttaccccgt tgctcggcaa cggcctggtc    4980
tgtgccaagt gtttgctgac gcaaccccca ctggctgggg cttggccata ggccatcagc    5040
gcatgcgtgg aaccttttgtg gctcctctgc cgatccatac tgcggaactc ctagccgctt    5100
gttttgctcg cagccggtct ggagcaaagc tcataggaac tgacaattct gtcgtcctct    5160
cgcggaaata tacatcgttt cgatctacgt atgatctttt tccctctgcc aaaaattatg    5220
gggacatcat gaagccccttt gagcatctga cttctggcta taaaggaaa  tttattttca    5280
ttgcaatagt gtgttggaat ttttttgtgtc tctcactcgg aaggaattct gcattaatga    5340
atcggccaac gcgcgggag  aggcggtttg cgtattgggc gctcttccgc ttcctcgctc    5400
actgactcgc tgcgctcggt cgttcggctg cggcgagcgg tatcagctca ctcaaaggcg    5460
gtaatacggt tatccacaga atcaggggat aacgcaggaa agaacatgtg agcaaaaggc    5520
cagcaaaagg ccaggaaccg taaaaaggcc gcgttgctgg cgtttttcca taggctccgc    5580
ccccctgacg agcatcacaa aaatcgacgc tcaagtcaga ggtggcgaaa cccgacagga    5640
```

```
ctataaagat accaggcgtt tccccctgga agctccctcg tgcgctctcc tgttccgacc    5700
ctgccgctta ccggatacct gtccgccttt ctcccttcgg aagcgtggc gctttctcat    5760 agctcacgct gtaggtatct cagttcggtg taggtcgttc gctccaagct gggctgtgtg    5820
cacgaacccc ccgttcagcc cgaccgctgc gccttatccg gtaactatcg tcttgagtcc    5880
aacccggtaa gacacgactt atcgccactg gcagcagcca ctggtaacag gattagcaga    5940
gcgaggtatg taggcggtgc tacagagttc ttgaagtggt ggcctaacta cggctacact    6000
agaagaacag tatttggtat ctgcgctctg ctgaagccag ttaccttcgg aaaaagagtt    6060
ggtagctctt gatccggcaa acaaaccacc gctggtagcg tggtttttt tgtttgcaag    6120 cagcagatta cgcgcagaaa aaaggatctc aagaagatc ctttgatctt ttctacgggg    6180
tctgacgctc agtggaacga aaactcacgt taagggattt tggtcatgag attatcaaaa    6240
aggatcttca cctagatcct tttaaattaa aaatgaagtt ttaaatcaat ctaaagtata    6300
tatgagtaaa cttggtctga cagttaccaa tgcttaatca gtgaggcacc tatctcagcg    6360
atctgtctat ttcgttcatc catagttgcc tgactc                              6396
```

<210> SEQ ID NO 28
<211> LENGTH: 6405
<212> TYPE: DNA
<213> ORGANISM: Artificial
<220> FEATURE:
<223> OTHER INFORMATION: Synthetic Construct

<400> SEQUENCE: 28

```
ggcgtaatgc tctgccagtg ttacaaccaa ttaaccaatt ctgattagaa aaactcatcg      60
agcatcaaat gaaactgcaa tttattcata tcaggattat caataccata tttttgaaaa    120
agccgtttct gtaatgaagg agaaaactca ccgaggcagt tccataggat ggcaagatcc    180
tggtatcggt ctgcgattcc gactcgtcca acatcaatac aacctattaa tttcccctcg    240 tcaaaataa ggttatcaag tgagaaatca ccatgagtga cgactgaatc cggtgagaat    300
ggcaaaagct tatgcatttc tttccagact tgttcaacag gccagccatt acgctcgtca    360
tcaaaatcac tcgcatcaac caaaccgtta ttcattcgtg attgcgcctg agcgagacga    420
aatacgcgat cgctgttaaa aggacaatta caaacaggaa tcaaatgcaa ccggcgcagg    480
aacactgcca gcgcatcaac aatatttca cctgaatcag gatattcttc taatacctgg    540
aatgctgttt tcccggggat cgcagtggtg agtaaccatg catcatcagg agtacggata    600
aaatgcttga tggtcggaag aggcataaat tccgtcagcc agtttagtct gaccatctca    660
tctgtaacat cattggcaac gctacctttg ccatgtttca gaaacaactc tggcgcatcg    720
ggcttcccat acaatcgata gattgtcgca cctgattgcc cgacattatc gcgagcccat    780
ttatacccat ataaatcagc atccatgttg gaatttaatc gcggcctcga gcaagacgtt    840
tcccgttgaa tatggctcat aacacccctt gtattactgt ttatgtaagc agacaggtcg    900
acaatattgg ctattggcca ttgcatacgt tgtatctata tcataatatg tacatttata    960
ttggctcatg tccaatatga ccgccatgtt gacattgatt attgactagt tattaatagt   1020
aatcaattac gggtcatta gttcatagcc catatatgga gttccgcgtt acataactta   1080
cggtaaatgg cccgcctggc tgaccgccca acgacccccg cccattgacg tcaataatga   1140
cgtatgttcc catagtaacg ccaatagga ctttccattg acgtcaatgg gtggagtatt   1200
tacggtaaac tgcccacttg gcagtacatc aagtgtatca tatgccaagt ccgcccccta   1260
```

```
ttgacgtcaa tgacggtaaa tggcccgcct ggcattatgc ccagtacatg accttacggg    1320
actttcctac ttggcagtac atctacgtat tagtcatcgc tattaccatg gtgatgcggt    1380
tttggcagta caccaatggg cgtggatagc ggtttgactc acggggattt ccaagtctcc    1440
accccattga cgtcaatggg agtttgtttt ggcaccaaaa tcaacgggac tttccaaaat    1500
gtcgtaataa ccccgccccg ttgacgcaaa tgggcggtag gcgtgtacgg tgggaggtct    1560
atataagcag agctcgttta gtgaaccgtc agatcgcctg gagacgccat ccacgctgtt    1620
ttgacctcca tagaagacac cgggaccgat ccagcctccg cggccgggaa cggtgcattg    1680
gaacgcggat tccccgtgcc aagagtgact caccgtccgg atctcagcaa gcaggtatgt    1740
actctccagg gtgggcctgg cttccccagt caagactcca gggatttgag ggacgctgtg    1800
ggctcttctc ttacatgtac cttttgcttg cctcaaccct gactatcttc caggtcagga    1860
tcccagagtc aggggtctgt attttcctgc tggtggctcc agttcaggaa cagtaaaccc    1920
tgctccgaat attgcctctc acatctcgtc aatctccgcg aggactgggg accctgtgac    1980
gaacatggct agcaaggctg tgctgcttgc cctgttgatg gcaggcttgg ccctgcagcc    2040
aggcactgcc ctgctgtgct actcctgcaa agcccaggtg agcaacgagg actgcctgca    2100
ggtggagaac tgcacccagc tgggggagca gtgctgacc gcgcgcatcc gcgcagttgg    2160
cctcctgacc gtcatcagca aaggctgcag cttgaactgc gtggatgact cacaggacta    2220
ctacgtgggc aagaagaaca tcacgtgctg tgacaccgac ttgtgcaacg ccagcggggc    2280
ccatgccctg cagccggctg ccgccatcct tgcgctgctc cctgcactcg gcctgctgct    2340
ctggggaccc ggccagctag gatcccagac cctgaacttt gatctgctga aactggcagg    2400
cgatgtggaa agcaacccag gcccaatggc aagcgcgcgc cgcccgcgct ggctgtgcgc    2460
tggggcgctg gtgctggcgg gtggcttctt tctcctcggc ttcctcttcg ggtggttat    2520 aaaatcctcc aatgaagcta ctaacattac tccaaagcat aatatgaaag cattttggga    2580
tgaattgaaa gctgagaaca tcaagaagtt cttatataat tttacacaga taccacattt    2640
agcaggaaca gaacaaaact ttcagcttgc aaagcaaatt caatcccagt ggaaagaatt    2700
tggcctggat tctgttgagc tggcacatta tgatgtcctg ttgtcctacc caataagac    2760 tcatcccaac tacatctcaa taattaatga agatggaaat gagattttca acacatcatt    2820
atttgaacca cctcctccag gatatgaaaa tgtttcggat attgtaccac ctttcagtgc    2880
tttctctcct caaggaatgc cagagggcga tctagtgtat gttaactatg cacgaactga    2940
agacttcttt aaattggaac gggacatgaa aatcaattgc tctgggaaaa ttgtaattgc    3000
cagatatggg aaagttttca gaggaaataa ggttaaaaat gcccagctgg caggggccaa    3060
aggagtcatt ctctactccg accctgctga ctactttgct cctggggtga agtcctatcc    3120
agatggttgg aatcttcctg gaggtggtgt ccagcgtgga aatatcctaa atctgaatgg    3180
tgcaggagac cctctcacac caggttaccc agcaaatgaa tatgcttata ggcgtggaat    3240
tgcagaggct gttggtcttc caagtattcc tgttcatcca attggatact atgatgcaca    3300
gaagctccta gaaaaaatgg gtggctcagc accaccagat agcagctgga gaggaagtct    3360
caaagtgccc tacaatgttg gacctggctt tactggaaac ttttctacac aaaaagtcaa    3420
gatgcacatc cactctacca atgaagtgac aagaatttac aatgtgatag gtactctcag    3480
aggagcagtg gaaccagaca gatatgtcat tctgggaggt caccgggact catgggtgtt    3540
tggtggtatt gaccctcaga gtggagcagc tgttgttcat gaaattgtga ggagctttgg    3600
aacactgaaa aaggaagggt ggagacctag aagaacaatt ttgtttgcaa gctgggatgc    3660
```

```
agaagaattt ggtcttcttg gttctactga gtgggcagag gagaattcaa gactccttca    3720
agagcgtggc gtggcttata ttaatgctga ctcatctata gaaggaaact acactctgag    3780
agttgattgt acaccgctga tgtacagctt ggtacacaac ctaacaaaag agctgaaaag    3840
ccctgatgaa ggctttgaag gcaaatctct ttatgaaagt tggactaaaa aaagtccttc    3900
cccagagttc agtggcatgc ccaggataag caaattggga tctggaaatg attttgaggt    3960
gttcttccaa cgacttggaa ttgcttcagg cagagcacgg tatactaaaa attgggaaac    4020
aaacaaattc agcggctatc cactgtatca cagtgtctat gaaacatatg agttggtgga    4080
aaagttttat gatccaatgt ttaaatatca cctcactgtg gcccaggttc gaggagggat    4140
ggtgtttgag ctggccaatt ccatagtgct ccctttttgat tgtcgagatt atgctgtagt    4200
tttaagaaag tatgctgaca aaatctacag tatttctatg aaacatccac aggaaatgaa    4260
gacatacagt gtatcatttg attcactttt ttctgcagta aagaatttta cagaaattgc    4320
ttccaagttc agtgagagac tccaggactt gacaaaagc aacccaatag tattaagaat    4380
gatgaatgat caactcatgt ttctggaaag agcatttatt gatccattag gttaccaga    4440 caggcctttt tataggcatg tcatctatgc tccaagcagc cacaacaagt atgcagggga    4500
gtcattccca ggaatttatg atgctctgtt tgatattgaa agcaaagtgg acccttccaa    4560
ggcctgggga gaagtgaaga cagatttta tgttgcagcc ttcacagtgc aggcagctgc    4620
agagactttg agtgaagtag cctaaagatc tgggccctaa caaacaaaa agatggggtt    4680 attccctaaa cttcatgggt tacgtaattg gaagttgggg gacattgcca caagatcata    4740
ttgtacaaaa gatcaaacac tgttttagaa aacttcctgt aaacaggcct attgattgga    4800
aagtatgtca aaggattgtg ggtcttttgg gctttgctgc tccatttaca caatgtggat    4860
atcctgcctt aatgcctttg tatgcatgta tacaagctaa acaggctttc actttctcgc    4920
caacttacaa ggccttttcta agtaaacagt acatgaacct ttaccccgtt gctcggcaac    4980
ggcctggtct gtgccaagtg tttgctgacg caaccccccac tggctgggggc ttggccatag    5040 gccatcagcg catgcgtgga acctttgtgg ctcctctgcc gatccatact gcggaactcc    5100
tagccgcttg ttttgctcgc agccggtctg gagcaaagct cataggaact gacaattctg    5160
tcgtcctctc gcggaaatat acatcgtttc gatctacgta tgatcttttt ccctctgcca    5220
aaaattatgg ggacatcatg aagcccttg agcatctgac ttctggctaa taaggaaat    5280 ttattttcat tgcaatagtg tgttggaatt ttttgtgtct ctcactcgga aggaattctg    5340
cattaatgaa tcggccaacg cgcggggaga ggcggtttgc gtattgggcg ctcttccgct    5400
tcctcgctca ctgactcgct gcgctcggtc gttcggctgc ggcgagcggt atcagctcac    5460
tcaaaggcgg taatacggtt atccacagaa tcagggggata acgcaggaaa gaacatgtga    5520
gcaaaaggcc agcaaaaggc caggaaccgt aaaaaggccg cgttgctggc gttttccat    5580 aggctccgcc cccctgacga gcatcacaaa aatcgacgct caagtcagag gtggcgaaac    5640
ccgacaggac tataaagata ccaggcgttt ccccctggaa gctccctcgt gcgctctcct    5700
gttccgaccc tgccgcttac cggatacctg tccgcctttc tcccttcggg aagcgtggcg    5760
ctttctcata gctcacgctg taggtatctc agttcggtgt aggtcgttcg ctccaagctg    5820
ggctgtgtgc acgaaccccc cgttcagccc gaccgctgcg ccttatccgg taactatcgt    5880
cttgagtcca acccggtaag acacgactta tcgccactgg cagcagccac tggtaacagg    5940
attagcagag cgaggtatgt aggcggtgct acagagttct tgaagtggtg gcctaactac    6000
```

```
ggctacacta aagaacagt atttggtatc tgcgctctgc tgaagccagt taccttcgga    6060
aaaagagttg gtagctcttg atccggcaaa caaaccaccg ctggtagcgg tggtttttt    6120 gtttgcaagc agcagattac gcgcagaaaa aaaggatctc aagaagatcc tttgatcttt    6180
tctacggggt ctgacgctca gtggaacgaa aactcacgtt aagggatttt ggtcatgaga    6240
ttatcaaaaa ggatcttcac ctagatcctt ttaaattaaa aatgaagttt taaatcaatc    6300
taaagtatat atgagtaaac ttggtctgac agttaccaat gcttaatcag tgaggcacct    6360
atctcagcga tctgtctatt tcgttcatcc atagttgcct gactc                   6405

<210> SEQ ID NO 29
<211> LENGTH: 6750
<212> TYPE: DNA
<213> ORGANISM: Artificial
<220> FEATURE:
<223> OTHER INFORMATION: Synthetic Construct

<400> SEQUENCE: 29
ggcgtaatgc tctgccagtg ttacaaccaa ttaaccaatt ctgattagaa aaactcatcg      60
agcatcaaat gaaactgcaa tttattcata tcaggattat caataccata ttttgaaaa     120 agccgtttct gtaatgaagg agaaaactca ccgaggcagt tccataggat ggcaagatcc    180
tggtatcggt ctgcgattcc gactcgtcca acatcaatac aacctattaa ttccccctcg    240
tcaaaaataa ggttatcaag tgagaaatca ccatgagtga cgactgaatc cggtgagaat    300
ggcaaaagct tatgcatttc tttccagact tgttcaacag gccagccatt acgctcgtca    360
tcaaaatcac tcgcatcaac caaaccgtta ttcattcgtg attgcgcctg agcgagacga    420
aatacgcgat cgctgttaaa aggacaatta caaacaggaa tcaaatgcaa ccggcgcagg    480
aacactgcca gcgcatcaac aatattttca cctgaatcag gatattcttc taatacctgg    540
aatgctgttt tcccggggat cgcagtggtg agtaaccatg catcatcagg agtacggata    600
aaatgcttga tggtcggaag aggcataaat tccgtcagcc agtttagtct gaccatctca    660
tctgtaacat cattggcaac gctacctttg ccatgtttca gaaacaactc tggcgcatcg    720
ggcttcccat acaatcgata gattgtcgca cctgattgcc cgacattatc gcgagcccat    780
ttatacccat ataaatcagc atccatgttg gaatttaatc gcggcctcga gcaagacgtt    840
tcccgttgaa tatggctcat aacaccccct tgtattactg tttatgtaag cagacaggtcg    900 acaatattgg ctattggcca ttgcatacgt tgtatctata tcataatatg tacatttata    960
ttggctcatg tccaatatga ccgccatgtt gacattgatt attgactagt tattaatagt   1020
aatcaattac ggggtcatta gttcatagcc catatatgga gttccgcgtt acataactta   1080
cggtaaatgg cccgcctggc tgaccgccca acgacccccg cccattgacg tcaataatga   1140
cgtatgttcc catagtaacg ccaatagggactttccattg acgtcaatgg gtggagtatt    1200
tacggtaaac tgcccacttg gcagtacatc aagtgtatca tatgccaagt ccgcccccta   1260 tgacgtcaa tgacggtaaa tggcccgcct ggcattatgc ccagtacatg accttacggg    1320
actttcctac ttggcagtac atctacgtat tagtcatcgc tattaccatg gtgatgcggt    1380
tttggcagta caccaatggg cgtggatagc ggtttgactc acggggattt ccaagtctcc    1440 acccccattga cgtcaatggg agtttgtttt ggcaccaaaa tcaacgggac tttccaaaat    1500
gtcgtaataa ccccgccccg ttgacgcaaa tgggcggtag gcgtgtacgg tgggaggtct    1560
atataagcag agctcgttta gtgaaccgtc agatcgcctg gagacgccat ccacgctgtt    1620
ttgacctcca tagaagacac cgggaccgat ccagcctccg cggccgggaa cggtgcattg    1680
```

```
gaacgcggat tccccgtgcc aagagtgact caccgtccgg atctcagcaa gcaggtatgt   1740
actctccagg gtgggcctgg cttccccagt caagactcca gggatttgag ggacgctgtg   1800
ggctcttctc ttacatgtac cttttgcttg cctcaaccct gactatcttc caggtcagga   1860
tcccagagtc aggggtctgt attttcctgc tggtggctcc agttcaggaa cagtaaaccc   1920
tgctccgaat attgcctctc acatctcgtc aatctccgcg aggactgggg accctgtgac   1980
gaacatggct agcattgtgg gaggctggga gtgcgagaag cattcccaac cctggcaggt   2040
gcttgtggcc tctcgtggca gggcagtctg cggcggtgtt ctggtgcacc cccagtgggt   2100
cctcacagct gcccactgca tcaggaacaa aagcgtgatc ttgctgggtc ggcacagctt   2160
gtttcatcct gaagacacag gccaggtatt tcaggtcagc cacagcttcc cacacccgct   2220
ctacgatatg agcctcctga agaatcgatt cctcaggcca ggtgatgact ccagccacga   2280
cctcatgctg ctccgcctgt cagagcctgc cgagctcacg gatgctgtga aggtcatgga   2340
cctgcccacc caggagccag cactggggac cacctgctac gcctcaggct ggggcagcat   2400
tgaaccagag gagttcttga ccccaaagaa acttcagtgt gtggacctcc atgttatttc   2460
caatgacgtg tgtgcgcaag ttcaccctca gaaggtgacc aagttcatgc tgtgtgctgg   2520
acgctggaca gggggcaaaa gcacctgctc gggtgattct gggggcccac ttgtctgtaa   2580
tggtgtgctt caaggtatca cgtcatgggg cagtgaacca tgtgccctgc ccgaaaggcc   2640
ttccctgtac accaaggtgg tgcattaccg gaagtggatc aaggacacca tcgtggccaa   2700
ccccggatcc cagaccctga actttgatct gctgaaactg gcaggcgatg tggaaagcaa   2760
cccaggccca atggcaagcg cgcgccgccc gcgctggctg tgcgctgggg cgctggtgct   2820
ggcgggtggc ttcttttctcc tcggcttcct cttcgggtgg tttataaaat cctccaatga   2880
agctactaac attactccaa agcataatat gaaagcattt ttggatgaat tgaaagctga   2940
gaacatcaag aagttcttat ataatttttac acagatacca catttagcag gaacagaaca   3000
aaactttcag cttgcaaagc aaattcaatc ccagtggaaa gaatttggcc tggattctgt   3060
tgagctggca cattatgatg tcctgttgtc ctacccaaat aagactcatc ccaactacat   3120
ctcaataatt aatgaagatg gaaatgagat tttcaacaca tcattatttg aaccacctcc   3180
tccaggatat gaaaatgttt cggatattgt accacctttc agtgctttct ctcctcaagg   3240
aatgccagag ggcgatctag tgtatgttaa ctatgcacga actgaagact tctttaaatt   3300
ggaacgggac atgaaaatca attgctctgg gaaaattgta attgccagat atgggaaagt   3360
tttcagagga aataaggtta aaaatgccca gctggcaggg gccaaaggag tcattctcta   3420
ctccgaccct gctgactact ttgctcctgg ggtgaagtcc tatccagatg ttggaatct    3480 tcctggaggt ggtgtccagc gtggaaatat cctaaatctg aatggtgcag agaccctct    3540 cacaccaggt tacccagcaa atgaatatgc ttataggcgt ggaattgcag aggctgttgg   3600
tcttccaagt attcctgttc atccaattgg atactatgat gcacagaagc tcctagaaaa   3660
aatgggtggc tcagcaccac cagatagcag ctggagagga agtctcaaag tgccctacaa   3720
tgttggacct ggctttactg gaaactttc tacacaaaaa gtcaagatgc acatccactc   3780
taccaatgaa gtgacaagaa tttacaatgt gataggtact ctcagaggag cagtggaacc   3840
agacagatat gtcattctgg gaggtcaccg ggactcatgg gtgtttggtg gtattgaccc   3900
tcagagtgga gcagctgttg ttcatgaaat tgtgaggagc tttggaacac tgaaaaagga   3960
agggtggaga cctagaagaa caattttgtt tgcaagctgg gatgcagaag aatttggtct   4020
```

```
tcttggttct actgagtggg cagaggagaa ttcaagactc cttcaagagc gtggcgtggc   4080
ttatattaat gctgactcat ctatagaagg aaactacact ctgagagttg attgtacacc   4140
gctgatgtac agcttggtac acaacctaac aaaagagctg aaaagccctg atgaaggctt   4200
tgaaggcaaa tctctttatg aaagttggac taaaaaaagt ccttccccag agttcagtgg   4260
catgcccagg ataagcaaat tgggatctgg aaatgatttt gaggtgttct ccaacgact   4320 tggaattgct tcaggcagag cacggtatac taaaaattgg gaaacaaaca aattcagcgg   4380
ctatccactg tatcacagtg tctatgaaac atatgagttg gtggaaaagt tttatgatcc   4440
aatgtttaaa tatcacctca ctgtggccca ggttcgagga gggatggtgt ttgagctggc   4500
caattccata gtgctccctt ttgattgtcg agattatgct gtagttttaa gaaagtatgc   4560
tgacaaaatc tacagtattt ctatgaaaca tccacaggaa atgaagacat acagtgtatc   4620
atttgattca cttttttctg cagtaaagaa ttttacagaa attgcttcca gttcagtga   4680 gagactccag gactttgaca aaagcaaccc aatagtatta agaatgatga atgatcaact   4740
catgtttctg gaaagagcat ttattgatcc attagggtta ccagacaggc cttttttatag   4800 gcatgtcatc tatgctccaa gcagccacaa caagtatgca ggggagtcat tcccaggaat   4860
ttatgatgct ctgtttgata ttgaaagcaa agtggaccct tccaaggcct ggggagaagt   4920
gaagagacag atttatgttg cagccttcac agtgcaggca gctgcagaga ctttgagtga   4980
agtagcctaa agatctgggc cctaacaaaa caaaaagatg gggttattcc ctaaacttca   5040
tgggttacgt aattggaagt tgggggacat tgccacaaga tcatattgta caaaagatca   5100
aacactgttt tagaaaactt cctgtaaaca ggcctattga ttggaaagta tgtcaaagga   5160
ttgtgggtct tttgggcttt gctgctccat ttacacaatg tggatatcct gccttaatgc   5220
ctttgtatgc atgtatacaa gctaaacagg ctttcacttt ctcgccaact tacaaggcct   5280
ttctaagtaa acagtacatg aacctttacc ccgttgctcg gcaacggcct ggtctgtgcc   5340
aagtgtttgc tgacgcaacc cccactggct ggggcttggc cataggccat cagcgcatgc   5400
gtggaacctt tgtggctcct ctgccgatcc atactgcgga actcctagcc gcttgttttg   5460
ctcgcagccg gtctggagca aagctcatag gaactgacaa ttctgtcgtc ctctcgcgga   5520
aatatacatc gtttcgatct acgtatgatc ttttttccctc tgccaaaaat tatggggaca   5580
tcatgaagcc ccttgagcat ctgacttctg gctaataaag gaaatttatt ttcattgcaa   5640
tagtgtgttg gaattttttg tgtctctcac tcggaaggaa ttctgcatta atgaatcggc   5700
caacgcgcgg ggagaggcgg tttgcgtatt gggcgctctt ccgcttcctc gctcactgac   5760
tcgctgcgct cggtcgttcg gctgcggcga gcggtatcag ctcactcaaa ggcggtaata   5820
cggttatcca cagaatcagg ggataacgca ggaaagaaca tgtgagcaaa aggccagcaa   5880
aaggccagga accgtaaaaa ggccgcgttg ctggcgtttt tccataggct ccgcccccct   5940
gacgagcatc acaaaaatcg acgctcaagt cagaggtggc gaaacccgac aggactataa   6000
agataccagg cgtttccccc tggaagctcc ctcgtgcgct ctcctgttcc gaccctgccg   6060
cttaccggat acctgtccgc ctttctccct tcgggaagcg tggcgctttc tcatagctca   6120
cgctgtaggt atctcagttc ggtgtaggtc gttcgctcca agctgggctg tgtgcacgaa   6180
ccccccgttc agcccgaccg ctgcgcctta tccggtaact atcgtcttga gtccaacccg   6240
gtaagacacg acttatcgcc actggcagca gccactggta acaggattag cagagcgagg   6300
tatgtaggcg gtgctacaga gttcttgaag tggtggccta actacggcta cactagaaga   6360
acagtatttg gtatctgcgc tctgctgaag ccagttacct tcggaaaaag agttggtagc   6420
```

| | |
|---|---|
| tcttgatccg gcaaacaaac caccgctggt agcggtggtt ttttttgtttg caagcagcag | 6480 |
| attacgcgca gaaaaaaagg atctcaagaa gatcctttga tctttttctac ggggtctgac | 6540 |
| gctcagtgga acgaaaactc acgttaaggg attttggtca tgagattatc aaaaaggatc | 6600 |
| ttcacctaga tccttttaaa ttaaaaatga agttttaaat caatctaaag tatatatgag | 6660 |
| taaacttggt ctgacagtta ccaatgctta atcagtgagg cacctatctc agcgatctgt | 6720 |
| ctatttcgtt catccatagt tgcctgactc | 6750 |

<210> SEQ ID NO 30
<211> LENGTH: 6908
<212> TYPE: DNA
<213> ORGANISM: Artificial
<220> FEATURE:
<223> OTHER INFORMATION: Synthetic Construct

<400> SEQUENCE: 30

| | |
|---|---|
| ggcgtaatgc tctgccagtg ttacaaccaa ttaaccaatt ctgattagaa aaactcatcg | 60 |
| agcatcaaat gaaactgcaa tttattcata tcaggattat caataccata tttttgaaaa | 120 |
| agccgtttct gtaatgaagg agaaaactca ccgaggcagt tccataggat ggcaagatcc | 180 |
| tggtatcggt ctgcgattcc gactcgtcca acatcaatac aacctattaa tttcccctcg | 240 |
| tcaaaaataa ggttatcaag tgagaaatca ccatgagtga cgactgaatc cggtgagaat | 300 |
| ggcaaaagct tatgcatttc tttccagact tgttcaacag gccagccatt acgctcgtca | 360 |
| tcaaaatcac tcgcatcaac caaaccgtta ttcattcgtg attgcgcctg agcgagacga | 420 |
| aatacgcgat cgctgttaaa aggacaatta caaacaggaa tcgaatgcaa ccggcgcagg | 480 |
| aacactgcca gcgcatcaac aatattttca cctgaatcag gatattcttc taatacctgg | 540 |
| aatgctgttt tcccggggat cgcagtggtg agtaaccatg catcatcagg agtacggata | 600 |
| aaatgcttga tggtcggaag aggcataaat tccgtcagcc agtttagtct gaccatctca | 660 |
| tctgtaacat cattggcaac gctacctttg ccatgtttca gaaacaactc tggcgcatcg | 720 |
| ggcttcccat acaatcgata gattgtcgca cctgattgcc cgacattatc gcgagcccat | 780 |
| ttatacccat ataaatcagc atccatgttg gaatttaatc gcggcctcga gcaagacgtt | 840 |
| tcccgttgaa tatggctcat aacacccctt gtattactgt ttatgtaagc agacaggtcg | 900 |
| acaatattgg ctattggcca ttgcatacgt tgtatctata tcataatatg tacatttata | 960 |
| ttggctcatg tccaatatga ccgccatgtt gacattgatt attgactagt tattaatagt | 1020 |
| aatcaattac ggggtcatta gttcatagcc catatatgga gttccgcgtt acataactta | 1080 |
| cggtaaatgg cccgcctggc tgaccgccca acgacccccg cccattgacg tcaataatga | 1140 |
| cgtatgttcc catagtaacg ccaatagggg ctttccattg acgtcaatgg gtggagtatt | 1200 |
| tacggtaaac tgcccacttg gcagtacatc aagtgtatca tatgccaagt ccgccccccta | 1260 |
| ttgacgtcaa tgacggtaaa tggcccgcct ggcattatgc ccagtacatg accttacggg | 1320 |
| actttcctac ttggcagtac atctacgtat tagtcatcgc tattaccatg gtgatgcggt | 1380 |
| tttggcagta caccaatggg cgtggatagc ggtttgactc acggggattt ccaagtctcc | 1440 |
| accccattga cgtcaatggg agtttgtttt ggcaccaaaa tcaacgggac tttccaaaat | 1500 |
| gtcgtaataa cccgccccg ttgacgcaaa tgggcggtag gcgtgtacgg tgggaggtct | 1560 |
| atataagcag agctcgttta gtgaaccgtc agatcgcctg gagacgccat ccacgctgtt | 1620 |
| ttgacctcca tagaagacac cgggaccgat ccagcctccg cggccgggaa cggtgcattg | 1680 |

```
gaacgcggat tccccgtgcc aagagtgact caccgtccgg atctcagcaa gcaggtatgt   1740
actctccagg gtgggcctgg cttcccagt caagactcca gggatttgag ggacgctgtg    1800
ggctcttctc ttacatgtac cttttgcttg cctcaaccct gactatcttc caggtcagga   1860
tcccagagtc aggggtctgt attttcctgc tggtggctcc agttcaggaa cagtaaaccc   1920
tgctccgaat attgcctctc acatctcgtc aatctccgcg aggactgggg accctgtgac   1980
gaacatggct agcgcgcgcc gcccgcgctg gctgtgcgct ggggcgctgg tgctggcggg   2040
tggcttcttt ctcctcggct tcctcttcgg gtggtttata aaatcctcca atgaagctac   2100
taacattact ccaaagcata atatgaaagc attttttggat gaattgaaag ctgagaacat  2160
caagaagttc ttatataatt ttacacagat accacattta gcaggaacag aacaaaactt   2220
tcagcttgca aagcaaattc aatcccagtg gaaagaattt ggcctggatt ctgttgagct   2280
ggcacattat gatgtcctgt tgtcctaccc aaataagact catcccaact acatctcaat   2340
aattaatgaa gatggaaatg agattttcaa cacatcatta tttgaaccac ctcctccagg   2400
atatgaaaat gtttcggata ttgtaccacc tttcagtgct ttctctcctc aaggaatgcc   2460
agagggcgat ctagtgtatg ttaactatgc acgaactgaa gacttcttta aattggaacg   2520
ggacatgaaa atcaattgct ctgggaaaat tgtaattgcc agatatggga agttttcag    2580
aggaaataag gttaaaaatg cccagctggc aggggccaaa ggagtcattc tctactccga   2640
ccctgctgac tactttgctc tgggggtgaa gtcctatcca gatggttgga atcttcctgg   2700
aggtggtgtc cagcgtggaa atatcctaaa tctgaatggt gcaggagacc ctctcacacc   2760
aggttaccca gcaaatgaat atgcttatag gcgtggaatt gcagaggctg ttggtcttcc   2820
aagtattcct gttcatccaa ttggatacta tgatgcacag aagctcctag aaaaaatggg   2880
tggctcagca ccaccagata gcagctggag aggaagtctc aaagtgccct acaatgttgg   2940
acctggcttt actggaaact tttctacaca aaaagtcaag atgcacatcc actctaccaa   3000
tgaagtgaca agaatttaca atgtgatagg tactctcaga ggagcagtgg aaccagacag   3060
atatgtcatt ctgggaggtc accgggactc atgggtgttt ggtggtattg accctcagag   3120
tggagcagct gttgttcatg aaattgtgag gagcttgga acactgaaaa aggaagggtg    3180
gagacctaga agaacaattt tgtttgcaag ctgggatgca aagaatttg gtcttcttgg    3240
ttctactgag tgggcagagg agaattcaag actccttcaa gagcgtggcg tggcttatat   3300
taatgctgac tcatctatag aaggaaacta cactctgaga gttgattgta caccgctgat   3360
gtacagcttg gtacacaacc taacaaaaga gctgaaaagc cctgatgaag ctttgaagg    3420
caaatctctt tatgaaagtt ggactaaaaa aagtccttcc ccagagttca gtggcatgcc   3480
caggataagc aaattgggat ctggaaatga ttttgaggtg ttcttccaac gacttggaat   3540
tgcttcaggc agagcacggt atactaaaaa ttgggaaaca aacaaattca gcggctatcc   3600
actgtatcac agtgtctatg aaacatatga gttggtggaa aagttttatg atccaatgtt   3660
taaatatcac ctcactgtgg cccaggttcg aggagggatg gtgtttgagc tggccaattc   3720
catagtgctc ccttttgatt gtcgagatta tgctgtagtt ttaagaaagt atgctgacaa   3780
aatctacagt atttctatga aacatccaca ggaaatgaag acatacagtg tatcatttga   3840
ttcacttttt tctgcagtaa agaattttac agaaattgct tccaagttca gtgagagact   3900
ccaggacttt gacaaaagca acccaatagt attaagaatg atgaatgatc aactcatgtt   3960
tctggaaaga gcatttattg atccattagg gttaccagac aggcctttt ataggcatgt    4020
catctatgct ccaagcagcc acaacaagta tgcaggggag tcattcccag gaatttatga   4080
```

```
tgctctgttt gatattgaaa gcaaagtgga cccttccaag gcctgggag aagtgaagag    4140
acagatttat gttgcagcct tcacagtgca ggcagctgca gagactttga gtgaagtagc    4200
ctaaagatct gacccctaa cgttactggc cgaagccgct tggaataagg ccggtgtgcg    4260
tttgtctata tgttattttc caccatattg ccgtcttttg gcaatgtgag ggcccggaaa    4320
cctggccctg tcttcttgac gagcattcct aggggtcttt ccctctcgc caaggaatg     4380
caaggtctgt tgaatgtcgt gaaggaagca gttcctctgg aagcttcttg aagacaaaca    4440
acgtctgtag cgaccctttg caggcagcgg aaccccccac ctggcgacag gtgcctctgc    4500
ggccaaaagc cacgtgtata agatacacct gcaaaggcgg cacaacccca gtgccacgtt    4560
gtgagttgga tagttgtgga aagagtcaaa tggctctcct caagcgtatt caacaagggg    4620
ctgaaggatg cccagaaggt accccattgt atgggatctg atctgggcc tcggtgcaca    4680
tgctttacat gtgtttagtc gaggttaaaa aacgtctagg cccccgaac cacggggacg     4740
tggttttcct ttgaaaaaca cgatgataat atggccagca aggctgtgct gcttgccctg    4800
ttgatggcag gcttggccct gcagccaggc actgccctgc tgtgctactc ctgcaaagcc    4860
caggtgagca acgaggactg cctgcaggtg gagaactgca cccagctggg ggagcagtgc    4920
tggaccgcgc gcatccgcgc agttggcctc ctgaccgtca tcagcaaagg ctgcagcttg    4980
aactgcgtgg atgactcaca ggactactac gtgggcaaga gaacatcac gtgctgtgac     5040
accgacttgt gcaacgccag cggggcccat gccctgcagc cggctgccgc catccttgcg    5100
ctgctccctg cactcggcct gctgctctgg ggacccggcc agctataggg atctgggccc    5160
taacaaaaca aaagatggg gttattccct aaacttcatg ggttacgtaa ttggaagttg     5220
ggggacattg ccacaagatc atattgtaca aagatcaaa cactgtttta gaaaacttcc     5280
tgtaaacagg cctattgatt ggaaagtatg tcaaggatt gtgggtcttt tgggctttgc     5340
tgctccattt acacaatgtg gatatcctgc cttaatgcct ttgtatgcat gtatacaagc    5400
taaacaggct ttcactttct cgccaactta caaggccttt ctaagtaaac agtacatgaa    5460
cctttacccc gttgctcggc aacggctgg tctgtgccaa gtgtttgctg acgcaacccc     5520
cactggctgg ggcttggcca taggccatca gcgcatgcgt ggaacctttg tggctcctct    5580
gccgatccat actgcggaac tcctagccgc ttgttttgct cgcagccggt ctggagcaaa    5640
gctcatagga actgacaatt ctgtcgtcct ctcgcggaaa tatacatcgt ttcgatctac    5700
gtatgatctt ttccctctg ccaaaaatta tggggacatc atgaagcccc ttgagcatct     5760
gacttctggc taataaagga aatttatttt cattgcaata gtgtgttgga attttttgtg    5820
tctctcactc ggaaggaatt ctgcattaat gaatcggcca acgcgcgggg agaggcggtt    5880
tgcgtattgg gcgctcttcc gcttcctcgc tcactgactc gctgcgctcg gtcgttcggc    5940
tgcggcgagc ggtatcagct cactcaaagg cggtaatacg ttatccaca gaatcagggg     6000
ataacgcagg aaagaacatg tgagcaaaag gccagcaaaa ggccaggaac cgtaaaaagg    6060
ccgcgttgct ggcgtttttc cataggctcc gcccccctga cgagcatcac aaaaatcgac    6120
gctcaagtca gaggtggcga aacccgacag gactataaag ataccaggcg tttccccctg    6180
gaagctccct cgtgcgctct cctgttccga cctgccgct taccggatac ctgtccgcct     6240
ttctcccttc gggaagcgtg gcgctttctc atagctcacg ctgtaggtat ctcagttcgg    6300
tgtaggtcgt tcgctccaag ctgggctgtg tgcacgaacc cccgttcag cccgaccgct     6360
gcgccttatc cggtaactat cgtcttgagt ccaacccggt aagacacgac ttatcgccac    6420
```

```
tggcagcagc cactggtaac aggattagca gagcgaggta tgtaggcggt gctacagagt    6480
tcttgaagtg gtggcctaac tacggctaca ctagaagaac agtatttggt atctgcgctc    6540
tgctgaagcc agttaccttc ggaaaaagag ttggtagctc ttgatccggc aaacaaacca    6600
ccgctggtag cggtggtttt tttgtttgca agcagcagat tacgcgcaga aaaaaggat    6660 ctcaagaaga tcctttgatc ttttctacgg ggtctgacgc tcagtggaac gaaaactcac    6720
gttaagggat tttggtcatg agattatcaa aaaggatctt cacctagatc cttttaaatt    6780
aaaaatgaag ttttaaatca atctaaagta tatatgagta aacttggtct gacagttacc    6840
aatgcttaat cagtgaggca cctatctcag cgatctgtct atttcgttca tccatagttg    6900
cctgactc                                                             6908

<210> SEQ ID NO 31
<211> LENGTH: 6914
<212> TYPE: DNA
<213> ORGANISM: Artificial
<220> FEATURE:
<223> OTHER INFORMATION: Synthetic Construct

<400> SEQUENCE: 31
ggcgtaatgc tctgccagtg ttacaaccaa ttaaccaatt ctgattagaa aaactcatcg      60
agcatcaaat gaaactgcaa tttattcata tcaggattat caataccata tttttgaaaa    120
agccgtttct gtaatgaagg agaaaactca ccgaggcagt tccataggat ggcaagatcc    180
tggtatcggt ctgcgattcc gactcgtcca acatcaatac aacctattaa tttcccctcg    240
tcaaaaataa ggttatcaag tgagaaatca ccatgagtga cgactgaatc cggtgagaat    300
ggcaaaagct tatgcatttc tttccagact tgttcaacag gccagccatt acgctcgtca    360
tcaaaatcac tcgcatcaac caaaccgtta ttcattcgtg attgcgcctg agcgagacga    420
aatacgcgat cgctgttaaa aggacaatta caaacaggaa tcaaatgcaa ccggcgcagg    480
aacactgcca gcgcatcaac aatatttca cctgaatcag gatattcttc taatacctgg    540
aatgctgttt tcccggggat cgcagtggtg agtaaccatg catcatcagg agtacggata    600
aaatgcttga tggtcggaag aggcataaat tccgtcagcc agtttagtct gaccatctca    660
tctgtaacat cattggcaac gctacctttg ccatgtttca gaaacaactc tggcgcatcg    720
ggcttcccat acaatcgata gattgtcgca cctgattgcc cgacattatc gcgagcccat    780
ttatacccat ataaatcagc atccatgttg gaatttaatc gcggcctcga gcaagacgtt    840
tcccgttgaa tatggctcat aacacccctt gtattactgt ttatgtaagc agacaggtcg    900
acaatattgg ctattggcca ttgcatacgt tgtatctata tcataatatg tacatttata    960
ttggctcatg tccaatatga ccgccatgtt gacattgatt attgactagt tattaatagt   1020
aatcaattac ggggtcatta gttcatagcc catatatgga gttccgcgtt acataactta   1080
cggtaaatgg cccgcctggc tgaccgccca acgacccccg cccattgacg tcaataatga   1140
cgtatgttcc catagtaacg ccaatagggg ctttccattg acgtcaatgg gtggagtatt   1200
tacggtaaac tgcccacttg gcagtacatc aagtgtatca tatgccaagt ccgccccta    1260 ttgacgtcaa tgacggtaaa tggcccgcct ggcattatgc ccagtacatg accttacggg   1320
actttcctac ttggcagtac atctacgtat tagtcatcgc tattaccatg gtgatgcggt   1380
tttggcagta caccaatggg cgtggatagc ggtttgactc acggggattt ccaagtctcc   1440
accccattga cgtcaatggg agtttgtttt ggcaccaaaa tcaacgggac tttccaaaat   1500
gtcgtaataa ccccgccccg ttgacgcaaa tgggcggtag gcgtgtacgg tgggaggtct   1560
```

```
atataagcag agctcgttta gtgaaccgtc agatcgcctg gagacgccat ccacgctgtt    1620
ttgacctcca tagaagacac cgggaccgat ccagcctccg cggccgggaa cggtgcattg    1680
gaacgcggat tccccgtgcc aagagtgact caccgtccgg atctcagcaa gcaggtatgt    1740
actctccagg gtgggcctgg cttccccagt caagactcca gggatttgag ggacgctgtg    1800
ggctcttctc ttacatgtac cttttgcttg cctcaaccct gactatcttc caggtcagga    1860
tcccagagtc aggggtctgt attttcctgc tggtggctcc agttcaggaa cagtaaaccc    1920
tgctccgaat attgcctctc acatctcgtc aatctccgcg aggactgggg accctgtgac    1980
gaacatggct agcaaggctg tgctgcttgc cctgttgatg gcaggcttgg ccctgcagcc    2040
aggcactgcc ctgctgtgct actcctgcaa agcccaggtg agcaacgagg actgcctgca    2100
ggtggagaac tgcacccagc tgggggagca gtgctgacc gcgcgcatcc gcgcagttgg     2160
cctcctgacc gtcatcagca aggctgcag cttgaactgc gtggatgact cacaggacta     2220
ctacgtgggc aagaagaaca tcacgtgctg tgacaccgac ttgtgcaacg ccagcggggc    2280
ccatgccctg cagccggctg ccgccatcct tgcgctgctc cctgcactcg gcctgctgct    2340
ctggggaccc ggccagctat agagatctga ccccctaacg ttactggccg aagccgcttg    2400
gaataaggcc ggtgtgcgtt tgtctatatg ttattttcca ccatattgcc gtcttttggc    2460
aatgtgaggg cccggaaacc tggccctgtc ttcttgacga gcattcctag ggtctttcc     2520
cctctcgcca aggaatgca aggtctgttg aatgtcgtga aggaagcagt tcctctggaa     2580
gcttcttgaa gacaaacaac gtctgtagcg accctttgca ggcagcggaa ccccccacct    2640
ggcgacaggt gcctctgcgg ccaaaagcca cgtgtataag atacacctgc aaaggcggca    2700
caacccagt gccacgttgt gagttggata ttgtggaaa gagtcaaatg gctctcctca     2760
agcgtattca acaaggggct gaaggatgcc cagaaggtac cccattgtat gggatctgat    2820
ctggggcctc ggtgcacatg ctttacatgt gtttagtcga ggttaaaaaa cgtctaggcc    2880
ccccgaacca cggggacgtg gttttccttt gaaaaacacg atgataatat ggccacaacc    2940
atggcgcgcc gcccgcgctg gctgtgcgct ggggcgctgg tgctggcggg tggcttcttt    3000
ctcctcggct tcctcttcgg gtggtttata aaatcctcca atgaagctac taacattact    3060
ccaaagcata atatgaaagc atttttggat gaattgaaag ctgagaacat caagaagttc    3120
ttatataatt ttcacagat accacattta gcaggaacga aacaaaactt tcagcttgca    3180
aagcaaattc aatcccagtg gaaagaattt ggcctggatt ctgttgagct ggcacattat    3240
gatgtcctgt tgtcctaccc aaataagact catcccaact acatctcaat aattaatgaa    3300
gatggaaatg agattttcaa cacatcatta tttgaaccac ctcctccagg atatgaaaat    3360
gtttcggata ttgtaccacc tttcagtgct ttctctcctc aaggaatgcc agagggcgat    3420
ctagtgtatg ttaactatgc acgaactgaa gacttcttta aattggaacg ggacatgaaa    3480
atcaattgct ctgggaaaat tgtaattgcc agatatggga agttttcag aggaaataag     3540
gttaaaaatg cccagctggc aggggccaaa ggagtcattc tctactccga ccctgctgac    3600
tactttgctc ctgggtgaa gtcctatcca gatggttgga tcttcctgg aggtggtgtc      3660
cagcgtggaa atatcctaaa tctgaatggt gcaggagacc ctctcacacc aggttaccca    3720
gcaaatgaat atgcttatag gcgtggaatt gcagaggctg ttggtcttcc aagtattcct    3780
gttcatccaa ttggatacta tgatgcacag aagctcctag aaaaaatggg tggctcagca    3840
ccaccagata gcagctggag aggaagtctc aaagtgccct acaatgttgg acctggcttt    3900
```

-continued

| | |
|---|---|
| actggaaact tttctacaca aaaagtcaag atgcacatcc actctaccaa tgaagtgaca | 3960 |
| agaatttaca atgtgatagg tactctcaga ggagcagtgg aaccagacag atatgtcatt | 4020 |
| ctgggaggtc accgggactc atgggtgttt ggtggtattg accctcagag tggagcagct | 4080 |
| gttgttcatg aaattgtgag gagctttgga acactgaaaa aggaagggtg agacctaga | 4140 |
| agaacaattt tgtttgcaag ctgggatgca gaagaatttg gtcttcttgg ttctactgag | 4200 |
| tgggcagagg agaattcaag actccttcaa gagcgtggcg tggcttatat taatgctgac | 4260 |
| tcatctatag aaggaaacta cactctgaga gttgattgta caccgctgat gtacagcttg | 4320 |
| gtacacaacc taacaaaaga gctgaaaagc cctgatgaag ctttgaaagg caaatctctt | 4380 |
| tatgaaagtt ggactaaaaa aagtccttcc ccagagttca gtggcatgcc caggataagc | 4440 |
| aaattgggat ctggaaatga ttttgaggtg ttcttccaac gacttggaat tgcttcaggc | 4500 |
| agagcacggt atactaaaaa ttgggaaaca aacaaattca gcggctatcc actgtatcac | 4560 |
| agtgtctatg aaacatatga gttggtggaa aagttttatg atccaatgtt taaatatcac | 4620 |
| ctcactgtgg cccaggttcg aggagggatg gtgtttgagc tggccaattc catagtgctc | 4680 |
| ccttttgatt gtcgagatta tgctgtagtt ttaagaaagt atgctgacaa aatctacagt | 4740 |
| atttctatga aacatccaca ggaaatgaag acatacagtg tatcatttga ttcactttt | 4800 |
| tctgcagtaa agaattttac agaaattgct tccaagttca gtgagagact ccaggacttt | 4860 |
| gacaaaagca acccaatagt attaagaatg atgaatgatc aactcatgtt tctggaagaa | 4920 |
| gcatttattg atccattagg gttaccagac aggcctttt ataggcatgt catctatgct | 4980 |
| ccaagcagcc acaacaagta tgcaggggag tcattcccag gaattatga tgctctgttt | 5040 |
| gatattgaaa gcaaagtgga cccttccaag gcctggggag aagtgaagag acagatttat | 5100 |
| gttgcagcct tcagtgtgca ggcagctgca gagactttga gtgaagtagc ctaaagatct | 5160 |
| gggccctaac aaaacaaaaa gatggggtta ttccctaaac ttcatggggtt acgtaattgg | 5220 |
| aagttggggg acattgccac aagatcatat tgtacaaaag atcaaacact gttttagaaa | 5280 |
| acttcctgta aacaggccta ttgattggaa agtatgtcaa aggattgtgg gtcttttggg | 5340 |
| cttgctgct ccatttacac aatgtggata tcctgcctta atgcctttgt atgcatgtat | 5400 |
| acaagctaaa caggctttca cttttctcgcc aacttacaag gccttctaa gtaaacagta | 5460 |
| catgaacctt taccccgttg ctcggcaacg gcctggtctg tgccaagtgt ttgctgacgc | 5520 |
| aacccccact ggctggggct tggccatagg ccatcagcgc atgcgtggaa cctttgtggc | 5580 |
| tcctctgccg atccatactg cggaactcct agccgcttgt tttgctcgca gccggtctgg | 5640 |
| agcaaagctc ataggaactg acaattctgt cgtcctctcg cggaaatata catcgtttcg | 5700 |
| atctacgtat gatcttttc cctctgccaa aaattatggg gacatcatga agcccttga | 5760 |
| gcatctgact tctggctaat aaaggaaatt tattttcatt gcaatagtgt gttggaattt | 5820 |
| tttgtgtctc tcactcggaa ggaattctgc attaatgaat cggccaacgc gcggggagag | 5880 |
| gcggtttgcg tattgggcgc tcttccgctt cctcgctcac tgactcgctg cgctcggtcg | 5940 |
| ttcggctgcg gcgagcggta tcagctcact caaaggcggt aatacggtta tccacagaat | 6000 |
| caggggataa cgcaggaaag aacatgtgag caaaaggcca gcaaaggcc aggaaccgta | 6060 |
| aaaaggccgc gttgctggcg tttttccata ggctccgccc cctgacgag catcacaaaa | 6120 |
| atcgacgctc aagtcagagg tggcgaaacc cgacaggact ataaagatac caggcgtttc | 6180 |
| ccctggaag ctccctcgtg cgctctcctg ttccgaccct gccgcttacc ggatacctgt | 6240 |
| ccgcctttct cccttcggga agcgtggcgc tttctcatag ctcacgctgt aggtatctca | 6300 |

```
gttcggtgta ggtcgttcgc tccaagctgg gctgtgtgca cgaacccccc gttcagcccg      6360
accgctgcgc cttatccggt aactatcgtc ttgagtccaa cccggtaaga cacgacttat      6420
cgccactggc agcagccact ggtaacagga ttagcagagc gaggtatgta ggcggtgcta      6480
cagagttctt gaagtggtgg cctaactacg gctacactag aagaacagta tttggtatct      6540
gcgctctgct gaagccagtt accttcggaa aaagagttgg tagctcttga tccggcaaac      6600
aaaccaccgc tggtagcggt ggtttttttg tttgcaagca gcagattacg cgcagaaaaa      6660
aaggatctca agaagatcct ttgatctttt ctacggggtc tgacgctcag tggaacgaaa      6720
actcacgtta agggattttg gtcatgagat tatcaaaaag gatcttcacc tagatccttt      6780
taaattaaaa atgaagtttt aaatcaatct aaagtatata tgagtaaact tggtctgaca      6840
gttaccaatg cttaatcagt gaggcaccta tctcagcgat ctgtctattt cgttcatcca      6900
tagttgcctg actc                                                       6914

<210> SEQ ID NO 32
<211> LENGTH: 5411
<212> TYPE: DNA
<213> ORGANISM: Artificial
<220> FEATURE:
<223> OTHER INFORMATION: Synthetic Construct

<400> SEQUENCE: 32
ggcgtaatgc tctgccagtg ttacaaccaa ttaaccaatt ctgattagaa aaactcatcg        60
agcatcaaat gaaactgcaa tttattcata tcaggattat caataccata tttttgaaaa       120
agccgtttct gtaatgaagg agaaaactca ccgaggcagt tccataggat ggcaagatcc       180
tggtatcggt ctgcgattcc gactcgtcca acatcaatac aacctattaa tttcccctcg       240
tcaaaaataa ggttatcaag tgagaaatca ccatgagtga cgactgaatc cggtgagaat       300
ggcaaaagct tatgcatttc tttccagact tgttcaacag gccagccatt acgctcgtca       360
tcaaaatcac tcgcatcaac caaaccgtta ttcattcgtg attgcgcctg agcgagacga       420
aatacgcgat cgctgttaaa aggacaatta caaacaggaa tcaaatgcaa ccggcgcagg       480
aacactgcca gcgcatcaac aatatttttca cctgaatcag gatattcttc taatacctgg       540
aatgctgttt tcccggggat cgcagtggtg agtaaccatg catcatcagg agtacggata       600
aaatgcttga tggtcggaag aggcataaat tccgtcagcc agtttagtct gaccatctca       660
tctgtaacat cattggcaac gctacctttg ccatgtttca gaaacaactc tggcgcatcg       720
ggcttcccat acaatcgata gattgtcgca cctgattgcc cgacattatc gcgagcccat       780
ttatacccat ataaatcagc atccatgttg gaatttaatc gcggcctcga gcaagacgtt       840
tcccgttgaa tatggctcat aacacccctt gtattactgt ttatgtaagc agacaggtcg       900
acaatattgg ctattggcca ttgcatacgt tgtatctata tcataatatg tacatttata       960
ttggctcatg tccaatatga ccgccatgtt gacattgatt attgactagt tattaatagt      1020
aatcaattac ggggtcatta gttcatagcc catatatgga gttccgcgtt acataactta      1080
cggtaaatgg cccgcctggc tgaccgccca acgacccccg cccattgacg tcaataatga      1140
cgtatgttcc catagtaacg ccaataggga ctttccattg acgtcaatgg gtggagtatt      1200
tacggtaaac tgcccacttg gcagtacatc aagtgtatca tatgccaagt ccgcccccta      1260
ttgacgtcaa tgacggtaaa tggcccgcct ggcattatgc ccagtacatg accttacggg      1320
actttcctac ttggcagtac atctacgtat tagtcatcgc tattaccatg gtgatgcggt      1380
```

```
tttggcagta caccaatggg cgtggatagc ggtttgactc acggggattt ccaagtctcc   1440
accccattga cgtcaatggg agtttgtttt ggcaccaaaa tcaacgggac tttccaaaat   1500
gtcgtaataa ccccgccccg ttgacgcaaa tgggcggtag gcgtgtacgg tgggaggtct   1560
atataagcag agctcgttta gtgaaccgtc agatcgcctg gagacgccat ccacgctgtt   1620
ttgacctcca tagaagacac cgggaccgat ccagcctccg cggccgggaa cggtgcattg   1680
gaacgcggat tccccgtgcc aagagtgact caccgtccgg atctcagcaa gcaggtatgt   1740
actctccagg gtgggcctgg cttccccagt caagactcca gggatttgag gacgctgtg    1800
ggctcttctc ttacatgtac cttttgcttg cctcaaccct gactatcttc caggtcagga   1860
tcccagagtc aggggtctgt attttcctgc tggtggctcc agttcaggaa cagtaaaccc   1920
tgctccgaat attgcctctc acatctcgtc aatctccgcg aggactgggg accctgtgac   1980
gaacatggct agcaaggctg tgctgcttgc cctgttgatg gcaggcttgg ccctgcagcc   2040
aggcactgcc ctgctgtgct actcctgcaa agcccaggtg agcaacgagg actgcctgca   2100
ggtggagaac tgcacccagc tggggagca gtgctgacc gcgcgcatcc gcgcagttgg     2160
cctcctgacc gtcatcagca aaggctgcag cttgaactgc gtggatgact cacaggacta   2220
ctacgtgggc aagaagaaca tcacgtgctg tgacaccgac ttgtgcaacg ccagcggggc   2280
ccatgccctg cagccggctg ccgccatcct tgcgctgctc cctgcactcg gcctgctgct   2340
ctggggaccc ggccagctat agagatctga cccctaacg ttactggccg aagccgcttg    2400
gaataaggcc ggtgtgcgtt tgtctatatg ttatttcca ccatattgcc gtcttttggc     2460
aatgtgaggg cccggaaacc tggccctgtc ttcttgacga gcattcctag ggtctttcc    2520
cctctcgcca aaggaatgca aggtctgttg aatgtcgtga aggaagcagt tcctctggaa   2580
gcttcttgaa gacaaacaac gtctgtagcg acccttttgca ggcagcggaa ccccccacct  2640
ggcgacaggt gcctctgcgg ccaaaagcca cgtgtataag atacacctgc aaaggcggca   2700
caaccccagt gccacgttgt gagttggata ttgtgaaa gagtcaaatg gctctcctca     2760
agcgtattca acaaggggct gaaggatgcc cagaaggtac cccattgtat gggatctgat   2820
ctggggcctc ggtgcacatg ctttacatgt gtttagtcga ggttaaaaaa cgtctaggcc   2880
ccccgaacca cggggacgtg gttttccttt gaaaaacacg atgataatat ggccagcatt   2940
gtgggaggct gggagtgcga gaagcattcc caacccggc aggtgcttgt ggcctctcgt    3000
ggcagggcag tctgcggcgg tgttctggtg cacccccagt gggtcctcac agctgcccac   3060
tgcatcagga acaaaagcgt gatcttgctg ggtcggcaca gcttgtttca tcctgaagac   3120
acaggccagg tatttcaggt cagccacagc ttcccacacc cgctctacga tatgagcctc   3180
ctgaagaatc gattcctcag gccaggtgat gactccagcc acgacctcat gctgctccgc   3240
ctgtcagagc ctgccgagct cacggatgct gtgaaggtca tggacctgcc cacccaggag   3300
ccagcactgg ggaccacctg ctacgcctca ggctggggca gcattgaacc agaggagttc   3360
ttgaccccaa agaaacttca gtgtgtggac ctccatgtta tttccaatga cgtgtgtgcg   3420
caagttcacc ctcagaaggt gaccaagttc atgctgtgtg ctggacgctg acagggggc    3480
aaaagcacct gctcgggtga ttctgggggc ccacttgtct gtaatggtgt gcttcaaggt   3540
atcacgtcat ggggcagtga accatgtgcc ctgcccgaaa ggccttccct gtacaccaag   3600
gtggtgcatt accggaagtg gatcaaggac accatcgtgg ccaaccctg aggatctggg    3660
ccctaacaaa acaaaaagat ggggttattc cctaaacttc atgggttacg taattggaag   3720
ttgggggaca ttgccacaag atcatattgt acaaaagatc aaacactgtt ttagaaaact   3780
```

```
tcctgtaaac aggcctattg attggaaagt atgtcaaagg attgtgggtc ttttgggctt    3840
tgctgctcca tttacacaat gtggatatcc tgccttaatg cctttgtatg catgtataca    3900
agctaaacag gctttcactt tctcgccaac ttacaaggcc tttctaagta aacagtacat    3960
gaacctttac cccgttgctc ggcaacggcc tggtctgtgc caagtgtttg ctgacgcaac    4020
ccccactggc tggggcttgg ccataggcca tcagcgcatg cgtggaacct tgtggctcc     4080
tctgccgatc catactgcgg aactcctagc cgcttgtttt gctcgcagcc ggtctggagc    4140
aaagctcata ggaactgaca attctgtcgt cctctcgcgg aaatatacat cgtttcgatc    4200
tacgtatgat cttttccct ctgccaaaaa ttatggggac atcatgaagc cccttgagca     4260
tctgacttct ggctaataaa ggaaatttat tttcattgca atagtgtgtt ggaatttttt    4320
gtgtctctca ctcggaagga attctgcatt aatgaatcgg ccaacgcgcg gggagaggcg    4380
gtttgcgtat tgggcgctct tccgcttcct cgctcactga ctcgctgcgc tcggtcgttc    4440
ggctgcggcg agcggtatca gctcactcaa aggcggtaat acggttatcc acagaatcag    4500
gggataacgc aggaaagaac atgtgagcaa aaggccagca aaaggccagg aaccgtaaaa    4560
aggccgcgtt gctggcgttt ttccataggc tccgccccc tgacgagcat cacaaaaatc     4620
gacgctcaag tcagaggtgg cgaaacccga caggactata agataccag gcgtttcccc     4680
ctggaagctc cctcgtgcgc tctcctgttc cgaccctgcc gcttaccgga tacctgtccg    4740
cctttctccc ttcgggaagc gtggcgcttt ctcatagctc acgctgtagg tatctcagtt    4800
cggtgtaggt cgttcgctcc aagctgggct gtgtgcacga accccccgtt cagcccgacc    4860
gctgcgcctt atccggtaac tatcgtcttg agtccaaccc ggtaagacac gacttatcgc    4920
cactggcagc agccactggt aacaggatta gcagagcgag gtatgtaggc ggtgctacag    4980
agttcttgaa gtggtggcct aactacggct acactagaag aacagtattt ggtatctgcg    5040
ctctgctgaa gccagttacc ttcggaaaaa gagttggtag ctcttgatcc ggcaaacaaa    5100
ccaccgctgg tagcggtggt ttttttgttt gcaagcagca gattacgcgc agaaaaaaag    5160
gatctcaaga agatcctttg atcttttcta cggggtctga cgctcagtgg aacgaaaact    5220
cacgttaagg gattttggtc atgagattat caaaaaggat cttcacctag atccttttaa    5280
attaaaaatg aagttttaaa tcaatctaaa gtatatatga gtaaacttgg tctgacagtt    5340
accaatgctt aatcagtgag gcacctatct cagcgatctg tctatttcgt tcatccatag    5400
ttgcctgact c                                                         5411
```

<210> SEQ ID NO 33
<211> LENGTH: 7694
<212> TYPE: DNA
<213> ORGANISM: Artificial
<220> FEATURE:
<223> OTHER INFORMATION: Synthetic Construct

<400> SEQUENCE: 33

```
ggcgtaatgc tctgccagtg ttacaaccaa ttaaccaatt ctgattagaa aaactcatcg     60
agcatcaaat gaaactgcaa ttattcata tcaggattat caataccata tttttgaaaa     120
agccgtttct gtaatgaagg agaaaactca ccgaggcagt tccataggat ggcaagatcc    180
tggtatcggt ctgcgattcc gactcgtcca acatcaatac aacctattaa tttcccctcg    240
tcaaaaataa ggttatcaag tgagaaatca ccatgagtga cgactgaatc cggtgagaat    300
ggcaaaagct tatgcatttc tttccagact tgttcaacag gccagccatt acgctcgtca    360
```

| | |
|---|---|
| tcaaaatcac tcgcatcaac caaaccgtta ttcattcgtg attgcgcctg agcgagacga | 420 |
| aatacgcgat cgctgttaaa aggacaatta caaacaggaa tcaaatgcaa ccggcgcagg | 480 |
| aacactgcca gcgcatcaac aatattttca cctgaatcag gatattcttc taatacctgg | 540 |
| aatgctgttt tcccggggat cgcagtggtg agtaaccatg catcatcagg agtacggata | 600 |
| aaatgcttga tggtcggaag aggcataaat tccgtcagcc agtttagtct gaccatctca | 660 |
| tctgtaacat cattggcaac gctacctttg ccatgtttca gaaacaactc tggcgcatcg | 720 |
| ggcttcccat acaatcgata gattgtcgca cctgattgcc cgacattatc gcgagcccat | 780 |
| ttatacccat ataaatcagc atccatgttg gaatttaatc gcggcctcga gcaagacgtt | 840 |
| tcccgttgaa tatggctcat aacacccctt gtattactgt ttatgtaagc agacaggtcg | 900 |
| acaatattgg ctattggcca ttgcatacgt tgtatctata tcataatatg tacatttata | 960 |
| ttggctcatg tccaatatga ccgccatgtt gacattgatt attgactagt tattaatagt | 1020 |
| aatcaattac ggggtcatta gttcatagcc catatatgga gttccgcgtt acataactta | 1080 |
| cggtaaatgg cccgcctggc tgaccgccca acgaccccg cccattgacg tcaataatga | 1140 |
| cgtatgttcc catagtaacg ccaatagggg ctttccattg acgtcaatgg gtggagtatt | 1200 |
| tacggtaaac tgcccacttg gcagtacatc aagtgtatca tatgccaagt ccgcccccta | 1260 |
| ttgacgtcaa tgacggtaaa tggcccgcct ggcattatgc ccagtacatg accttacggg | 1320 |
| actttcctac ttggcagtac atctacgtat tagtcatcgc tattaccatg gtgatgcggt | 1380 |
| tttggcagta caccaatggg cgtggatagc ggtttgactc acggggattt ccaagtctcc | 1440 |
| accccattga cgtcaatggg agtttgtttt ggcaccaaaa tcaacgggac tttccaaaat | 1500 |
| gtcgtaataa ccccgccccg ttgacgcaaa tgggcggtag gcgtgtacgg tgggaggtct | 1560 |
| atataagcag agctcgttta gtgaaccgtc agatcgcctg gagacgccat ccacgctgtt | 1620 |
| ttgacctcca tagaagacac cgggaccgat ccagcctccg cggccgggaa cggtgcattg | 1680 |
| gaacgcggat tccccgtgcc aagagtgact caccgtccgg atctcagcaa gcaggtatgt | 1740 |
| actctccagg gtgggcctgg cttccccagt caagactcca gggatttgag gacgctgtg | 1800 |
| ggctcttctc ttacatgtac cttttgcttg cctcaaccct gactatcttc caggtcagga | 1860 |
| tcccagagtc aggggtctgt attttcctgc tggtggctcc agttcaggaa cagtaaaccc | 1920 |
| tgctccgaat attgcctctc acatctcgtc aatctccgcg aggactgggg accctgtgac | 1980 |
| gaacatggct agcattgtgg gaggctggga gtgcgagaag cattcccaac cctggcaggt | 2040 |
| gcttgtggcc tctcgtggca gggcagtctg cggcggtgtt ctggtgcacc cccagtgggt | 2100 |
| cctcacagct gcccactgca tcaggaacaa aagcgtgatc ttgctgggtc ggcacagctt | 2160 |
| gtttcatcct gaagacacag gccaggtatt tcaggtcagc cacagcttcc cacacccgct | 2220 |
| ctacgatatg agcctcctga agaatcgatt cctcaggcca ggtgatgact ccagccacga | 2280 |
| cctcatgctg ctccgcctgt cagagcctgc cgagctcacg gatgctgtga aggtcatgga | 2340 |
| cctgcccacc caggagccag cactggggac cacctgctac gcctcaggct ggggcagcat | 2400 |
| tgaaccagag gagttcttga ccccaaagaa acttcagtgt gtggacctcc atgttatttc | 2460 |
| caatgacgtg tgtgcgcaag ttcaccctca gaaggtgacc aagttcatgc tgtgtgctgg | 2520 |
| acgctggaca gggggcaaaa gcacctgctc gggtgattct gggggcccac ttgtctgtaa | 2580 |
| tggtgtgctt caaggtatca cgtcatgggg cagtgaacca tgtgccctgc ccgaaaggcc | 2640 |
| ttccctgtac accaaggtgg tgcattaccg gaagtggatc aaggacacca tcgtggccaa | 2700 |
| ccccggatcc cagaccctga actttgatct gctgaaactg gcaggcgatg tggaaagcaa | 2760 |

```
cccaggccca atggcaagcg cgcgccgccc gcgctggctg tgcgctgggg cgctggtgct    2820
ggcgggtggc ttctttctcc tcggcttcct cttcgggtgg tttataaaat cctccaatga    2880
agctactaac attactccaa agcataatat gaaagcattt ttggatgaat gaaagctga     2940
gaacatcaag aagttcttat ataattttac acagatacca catttagcag gaacagaaca    3000
aaactttcag cttgcaaagc aaattcaatc ccagtggaaa gaatttggcc tggattctgt    3060
tgagctggca cattatgatg tcctgttgtc ctacccaaat aagactcatc ccaactacat    3120
ctcaataatt aatgaagatg gaaatgagat tttcaacaca tcattatttg aaccacctcc    3180
tccaggatat gaaaatgttt cggatattgt accacctttc agtgctttct ctcctcaagg    3240
aatgccagag ggcgatctag tgtatgttaa ctatgcacga actgaagact tctttaaatt    3300
ggaacgggac atgaaaatca attgctctgg gaaaattgta attgccagat atgggaaagt    3360
tttcagagga aataaggtta aaaatgccca gctggcaggg gccaaaggag tcattctcta    3420
ctccgaccct gctgactact tgctcctgg ggtgaagtcc tatccagatg gttggaatct     3480
tcctggaggt ggtgtccagc gtggaaatat cctaaatctg aatggtgcag gagaccctct    3540
cacaccaggt tacccagcaa atgaatatgc ttataggcgt ggaattgcag aggctgttgg    3600
tcttccaagt attcctgttc atccaattgg atactatgat gcacagaagc tcctagaaaa    3660
aatgggtggc tcagcaccac cagatagcag ctggagagga agtctcaaag tgccctacaa    3720
tgttggacct ggctttactg gaaactttc tacacaaaaa gtcaagatgc acatccactc     3780
taccaatgaa gtgacaagaa tttacaatgt gataggtact ctcagaggag cagtggaacc    3840
agacagatat gtcattctgg gaggtcaccg ggactcatgg gtgtttggtg gtattgaccc    3900
tcagagtgga gcagctgttg ttcatgaaat tgtgaggagc tttggaacac tgaaaaagga    3960
agggtggaga cctagaagaa caattttgtt tgcaagctgg gatgcagaag aatttggtct    4020
tcttggttct actgagtggg cagaggagaa ttcaagactc cttcaagagc gtggcgtggc    4080
ttatattaat gctgactcat ctatagaagg aaactacact ctgagagttg attgtacacc    4140
gctgatgtac agcttggtac acaacctaac aaaagagctg aaaagccctg atgaaggctt    4200
tgaaggcaaa tctctttatg aaagttggac taaaaaaagt ccttccccag agttcagtgg    4260
catgcccagg ataagcaaat gggatctgg aaatgatttt gaggtgttct ccaacgact     4320
tggaattgct tcaggcagag cacggtatac taaaaattgg gaaacaaaca aattcagcgg    4380
ctatccactg tatcacagtg tctatgaaac atatgagttg gtggaaaagt tttatgatcc    4440
aatgttaaa tatcacctca ctgtggccca ggttcgagga gggatggtgt ttgagctggc     4500
caattccata gtgctcccctt ttgattgtcg agattatgct gtagttttaa gaaagtatgc   4560
tgacaaaatc tacagtattt ctatgaaaca tccacaggaa atgaagacat acagtgtatc    4620
atttgattca cttttttctg cagtaaagaa ttttacagaa attgcttcca gttcagtga     4680
gagactccag gactttgaca aaagcaaccc aatagtatta agaatgatga atgatcaact    4740
catgtttctg gaaagagcat ttattgatcc attagggtta ccagacaggc ttttttatag    4800
gcatgtcatc tatgctccaa gcagccacaa caagtatgca ggggagtcat tcccaggaat    4860
ttatgatgct ctgtttgata ttgaaagcaa agtggaccct tccaaggcct ggggagaagt    4920
gaagagacag atttatgttg cagccttcac agtgcaggca gctgcagaga ctttgagtga    4980
agtagcctaa agatctgacc ccctaacgtt actggccgaa gccgcttgga ataaggccga    5040
tgtgcgtttg tctatatgtt attttccacc atattgccgt cttttggcaa tgtgagggcc    5100
```

-continued

```
cggaaacctg gccctgtctt cttgacgagc attcctaggg gtctttcccc tctcgccaaa      5160
ggaatgcaag gtctgttgaa tgtcgtgaag gaagcagttc ctctggaagc ttcttgaaga      5220
caaacaacgt ctgtagcgac cctttgcagg cagcggaacc ccccacctgg cgacaggtgc      5280
ctctgcggcc aaaagccacg tgtataagat acacctgcaa aggcggcaca acccccagtgc    5340 cacgttgtga gttggatagt tgtggaaaga gtcaaatggc tctcctcaag cgtattcaac      5400
aaggggctga aggatgccca gaaggtaccc cattgtatgg gatctgatct ggggcctcgg      5460
tgcacatgct ttacatgtgt ttagtcgagg ttaaaaaacg tctaggcccc ccgaaccacg      5520
gggacgtggt tttcctttga aaaacacgat gataatatgg ccagcaaggc tgtgctgctt      5580
gccctgttga tggcaggctt ggccctgcag ccaggcactg ccctgctgtg ctactcctgc      5640
aaagcccagg tgagcaacga ggactgcctg caggtggaga actgcaccca gctgggggag      5700
cagtgctgga ccgcgcgcat ccgcgcagtt ggcctcctga ccgtcatcag caaaggctgc      5760
agcttgaact gcgtggatga ctcacaggac tactacgtgg gcaagaagaa catcacgtgc      5820
tgtgacaccg acttgtgcaa cgccagcggg gcccatgccc tgcagccggc tgccgccatc      5880
cttgcgctgc tccctgcact cggcctgctg ctctggggac ccggccagct atagggatct      5940
gggccctaac aaaacaaaaa gatggggtta ttccctaaac ttcatgggtt acgtaattgg      6000
aagttggggg acattgccac aagatcatat tgtacaaaag atcaaacact gttttagaaa      6060
acttcctgta aacaggccta ttgattggaa agtatgtcaa aggattgtgg gtcttttggg      6120
ctttgctgct ccatttacac aatgtggata tcctgcctta atgcctttgt atgcatgtat      6180
acaagctaaa caggctttca ctttctcgcc aacttacaag gcctttctaa gtaaacagta      6240
catgaacctt taccccgttg ctcggcaacg gcctggtctg tgccaagtgt tgctgacgc       6300 aaccccact ggctggggct tggccatagg ccatcagcgc atgcgtggaa cctttgtggc       6360
tcctctgccg atccatactg cggaactcct agccgcttgt tttgctcgca gccggtctgg      6420
agcaaagctc ataggaactg acaattctgt cgtcctctcg cggaaatata catcgtttcg      6480
atctacgtat gatctttttc cctctgccaa aaattatggg gacatcatga agccccttga      6540
gcatctgact tctggctaat aaaggaaatt tattttcatt gcaatagtgt gttggaattt      6600
tttgtgtctc tcactcggaa ggaattctgc attaatgaat cggccaacgc gcggggagag      6660
gcggtttgcg tattgggcgc tcttccgctt cctcgctcac tgactcgctg cgctcggtcg      6720
ttcggctgcg gcgagcggta tcagctcact caaaggcggt aatacggtta tccacagaat      6780
caggggataa cgcaggaaag aacatgtgag caaaaggcca gcaaaaggcc aggaaccgta      6840
aaaaggccgc gttgctggcg ttttccata ggctccgccc cctgacgag catcacaaaa        6900 atcgacgctc aagtcagagg tggcgaaacc cgacaggact ataaagatac caggcgtttc     6960 ccctggaag ctccctcgtg cgctctcctg ttccgaccct gccgcttacc ggatacctgt        7020
ccgcctttct cccttcggga agcgtggcgc tttctcatag ctcacgctgt aggtatctca     7080
gttcggtgta ggtcgttcgc tccaagctgg gctgtgtgca cgaaccccc gttcagcccg      7140 accgctgcgc cttatccggt aactatcgtc ttgagtccaa cccggtaaga cacgacttat      7200
cgccactggc agcagccact ggtaacagga ttagcagagc gaggtatgta ggcggtgcta      7260
cagagttctt gaagtggtgg cctaactacg gctacactag aagaacagta tttggtatct     7320
gcgctctgct gaagccagtt accttcggaa aaagagttgg tagctcttga tccggcaaac      7380
aaaccaccgc tggtagcgt ggttttttg tttgcaagca gcagattacg cgcagaaaaa        7440
aaggatctca agaagatcct ttgatctttt ctacggggtc tgacgctcag tggaacgaaa      7500
```

```
actcacgtta agggattttg gtcatgagat tatcaaaaag gatcttcacc tagatccttt    7560
taaattaaaa atgaagtttt aaatcaatct aaagtatata tgagtaaact tggtctgaca    7620
gttaccaatg cttaatcagt gaggcaccta tctcagcgat ctgtctattt cgttcatcca    7680
tagttgcctg actc                                                     7694

<210> SEQ ID NO 34
<211> LENGTH: 7182
<212> TYPE: DNA
<213> ORGANISM: Artificial
<220> FEATURE:
<223> OTHER INFORMATION: Synthetic Construct

<400> SEQUENCE: 34
ggcgtaatgc tctgccagtg ttacaaccaa ttaaccaatt ctgattagaa aaactcatcg      60
agcatcaaat gaaactgcaa tttattcata tcaggattat caataccata tttttgaaaa    120
agccgtttct gtaatgaagg agaaaactca ccgaggcagt tccataggat ggcaagatcc    180
tggtatcggt ctgcgattcc gactcgtcca acatcaatac aacctattaa tttcccctcg    240
tcaaaaataa ggttatcaag tgagaaatca ccatgagtga cgactgaatc cggtgagaat    300
ggcaaaagct tatgcatttc tttccagact tgttcaacag gccagccatt acgctcgtca    360
tcaaaatcac tcgcatcaac caaaccgtta ttcattcgtg attgcgcctg agcgagacga    420
aatacgcgat cgctgttaaa aggacaatta caaacaggaa tcaaatgcaa ccggcgcagg    480
aacactgcca gcgcatcaac aatattttca cctgaatcag gatattcttc taatacctgg    540
aatgctgttt tcccggggat cgcagtggtg agtaaccatg catcatcagg agtacggata    600
aaatgcttga tggtcggaag aggcataaat tccgtcagcc agtttagtct gaccatctca    660
tctgtaacat cattggcaac gctacctttg ccatgtttca gaaacaactc tggcgcatcg    720
ggcttcccat acaatcgata gattgtcgca cctgattgcc cgacattatc gcgagcccat    780
ttatacccat ataaatcagc atccatgttg gaatttaatc gcggcctcga gcaagacgtt    840
tcccgttgaa tatggctcat aacacccctt gtattactgt ttatgtaagc agacaggtcg    900
acaatattgg ctattggcca ttgcatacgt tgtatctata tcataatatg tacatttata    960
ttggctcatg tccaatatga ccgccatgtt gacattgatt attgactagt tattaatagt   1020
aatcaattac gggtcatta gttcatagcc catatatgga gttccgcgtt acataactta   1080
cggtaaatgg cccgcctggc tgaccgccca acgacccccg cccattgacg tcaataatga   1140
cgtatgttcc catagtaacg ccaatagggaa ctttccattg acgtcaatgg gtggagtatt   1200
tacggtaaac tgcccacttg gcagtacatc aagtgtatca tatgccaagt ccgccccccta   1260 ttgacgtcaa tgacggtaaa tggcccgcct ggcattatgc ccagtacatg accttacggg   1320
actttcctac ttggcagtac atctacgtat tagtcatcgc tattaccatg gtgatgcggt   1380
tttggcagta caccaatggg cgtggatagc ggtttgactc acggggattt ccaagtctcc   1440
accccattga cgtcaatggg agtttgtttt ggcaccaaaa tcaacgggac tttccaaaat   1500
gtcgtaataa ccccgcccg ttgacgcaaa tgggcggtag gcgtgtacgg tgggaggtct   1560
atataagcag agctcgttta gtgaaccgtc agatcgcctg gagacgccat ccacgctgtt   1620
ttgacctcca tagaagacac cgggaccgat ccagcctccg cggccgggaa cggtgcattg   1680
gaacgcggat tccccgtgcc aagagtgact caccgtccgg atctcagcaa gcaggtatgt   1740
actctccagg gtgggcctgg cttccccagt caagactcca gggatttgag gacgctgtg   1800
```

```
ggctcttctc ttacatgtac cttttgcttg cctcaaccct gactatcttc caggtcagga      1860
tcccagagtc aggggtctgt attttcctgc tggtggctcc agttcaggaa cagtaaaccc      1920
tgctccgaat attgcctctc acatctcgtc aatctccgcg aggactgggg accctgtgac      1980
gaacatggct agcattgtgg gaggctggga gtgcgagaag cattcccaac cctggcaggt      2040
gcttgtggcc tctcgtggca gggcagtctg cggcggtgtt ctggtgcacc cccagtgggt      2100
cctcacagct gcccactgca tcaggaacaa aagcgtgatc ttgctgggtc ggcacagctt      2160
gtttcatcct gaagacacag gccaggtatt tcaggtcagc cacagcttcc cacacccgct      2220
ctacgatatg agcctcctga gaatcgatt cctcaggcca ggtgatgact ccagccacga      2280
cctcatgctg ctccgcctgt cagagcctgc cgagctcacg gatgctgtga aggtcatgga      2340
cctgcccacc caggagccag cactggggac cacctgctac gcctcaggct ggggcagcat      2400
tgaaccagag gagttcttga ccccaaagaa acttcagtgt gtggacctcc atgttatttc      2460
caatgacgtg tgtgcgcaag ttcaccctca gaaggtgacc aagttcatgc tgtgtgctgg      2520
acgctggaca gggggcaaaa gcacctgctc gggtgattct gggggcccac ttgtctgtaa      2580
tggtgtgctt caaggtatca cgtcatgggg cagtgaacca tgtgccctgc ccgaaaggcc      2640
ttccctgtac accaaggtgg tgcattaccg gaagtggatc aaggacacca tcgtggccaa      2700
ccccggatcc cagaccctga ctttgatct gctgaaactg gcaggcgatg tggaaagcaa      2760
cccaggccca atggcaagcg cgcgccgccc gcgctggctg tgcgctgggg cgctggtgct      2820
ggcgggtggc ttcttctctc tcggcttcct cttcgggtgg tttataaaat cctccaatga      2880
agctactaac attactccaa agcataatat gaaagcattt ttggatgaat tgaaagctga      2940
gaacatcaag aagttcttat ataatttac acagatacca catttagcag gaacagaaca      3000
aaactttcag cttgcaaagc aaattcaatc ccagtggaaa gaatttggcc tggattctgt      3060
tgagctggca cattatgatg tcctgttgtc ctacccaaat aagactcatc caactacat      3120 ctcaataatt aatgaagatg gaaatgagat tttcaacaca tcattatttg aaccacctcc      3180
tccaggatat gaaaatgttt cggatattgt accacctttc agtgctttct ctcctcaagg      3240
aatgccagag ggcgatctag tgtatgttaa ctatgcacga actgaagact tctttaaatt      3300
ggaacgggac atgaaaatca attgctctgg gaaaattgta attgccagat atgggaaagt      3360
tttcagagga aataaggtta aaaatgccca gctggcaggg gccaaaggag tcattctcta      3420
ctccgaccct gctgactact ttgctcctgg ggtgaagtcc tatccagatg ttggaatct      3480 tcctggaggt ggtgtccagc gtggaaatat cctaaatctg aatggtgcag agaccctct      3540 cacaccaggt tacccagcaa atgaatatgc ttataggcgt ggaattgcag aggctgttgg      3600
tcttccaagt attcctgttc atccaattgg atactatgat gcacagaagc tcctagaaaa      3660
aatgggtggc tcagcaccac cagatagcag ctggagagga agtctcaaag tgccctacaa      3720
tgttggacct ggctttactg gaaacttttc tacacaaaaa gtcaagatgc acatccactc      3780
taccaatgaa gtgacaagaa tttacaatgt gataggtact ctcagaggag cagtggaacc      3840
agacagatat gtcattctgg gaggtcaccg ggactcatgg gtgtttggtg gtattgaccc      3900
tcagagtgga gcagctgttg ttcatgaaat tgtgaggagc tttggaacac tgaaaaagga      3960
agggtggaga cctagaagaa caattttgtt tgcaagctgg gatgcagaag aatttggtct      4020
tcttggttct actgagtggg cagaggagaa ttcaagactc cttcaagagc gtggcgtggc      4080
ttatattaat gctgactcat ctatagaagg aaactacact ctgagagttg attgtacacc      4140
gctgatgtac agcttggtac acaacctaac aaaagagctg aaaagccctg atgaaggctt      4200
```

```
tgaaggcaaa tctctttatg aaagttggac taaaaaaagt ccttccccag agttcagtgg   4260
catgcccagg ataagcaaat tgggatctgg aaatgatttt gaggtgttct tccaacgact   4320
tggaattgct tcaggcagag cacggtatac taaaaattgg gaaacaaaca aattcagcgg   4380
ctatccactg tatcacagtg tctatgaaac atatgagttg gtggaaaagt tttatgatcc   4440
aatgtttaaa tatcacctca ctgtggccca ggttcgagga gggatggtgt ttgagctggc   4500
caattccata gtgctcccTt ttgattgtcg agattatgct gtagttttaa gaagtatgc    4560
tgacaaaatc tacagtattt ctatgaaaca tccacaggaa atgaagacat acagtgtatc   4620
atttgattca cttttttctg cagtaaagaa ttttacagaa attgcttcca agttcagtga   4680
gagactccag gactttgaca aaagcaaccc aatagtatta agaatgatga atgatcaact   4740
catgtttctg gaaagagcat ttattgatcc attagggtta ccagacaggc cttttttatag  4800
gcatgtcatc tatgctccaa gcagccacaa caagtatgca ggggagtcat tcccaggaat   4860
ttatgatgct ctgtttgata ttgaaagcaa agtggaccct tccaaggcct ggggagaagt   4920
gaagagacag atttatgttg cagccttcac agtgcaggca gctgcagaga ctttgagtga   4980
agtagccgga tccgaaggta gggcttcatt attgacctgt ggagatgtcg aagaaaaccc   5040
aggacccgca agcaaggctg tgctgcttgc cctgttgatg gcaggcttgg ccctgcagcc   5100
aggcactgcc ctgctgtgct actcctgcaa agcccaggtg agcaacgagg actgcctgca   5160
ggtggagaac tgcacccagc tgggggagca gtgctggacc gcgcgcatcc gcgcagttgg   5220
cctcctgacc gtcatcagca aaggctgcag cttgaactgc gtggatgact cacaggacta   5280
ctacgtgggc aagaagaaca tcacgtgctg tgacaccgac ttgtgcaacg ccagcggggc   5340
ccatgccctg cagccggctg ccgccatcct tgcgctgctc cctgcactcg gcctgctgct   5400
ctggggaccc ggccagctat agagatctgg gccctaacaa aacaaaaaga tggggttatt   5460
ccctaaactt catgggttac gtaattggaa gttggggggac attgccacaa gatcatattg   5520
tacaaaagat caaacactgt tttagaaaac ttcctgtaaa caggcctatt gattggaaag   5580
tatgtcaaag gattgtgggt cttttgggct ttgctgctcc atttacacaa tgtggatatc   5640
ctgccttaat gcctttgtat gcatgtatac aagctaaaca ggctttcact ttctcgccaa   5700
cttacaaggc cttctaagt aaacagtaca tgaacctta ccccgttgct cggcaacggc     5760
ctggtctgtg ccaagtgttt gctgacgcaa cccccactgg ctggggcttg ccataggcc    5820
atcagcgcat gcgtggaacc tttgtggctc ctctgccgat ccatactgcg gaactcctag   5880
ccgcttgttt tgctcgcagc cggtctggag caaagctcat aggaactgac aattctgtcg   5940
tcctctcgcg gaaatataca tcgtttcgat ctacgtatga tcttttttccc tctgccaaaa   6000
attatgggga catcatgaag ccccttgagc atctgacttc tggctaataa ggaaatttta   6060
ttttcattgc aatagtgtgt tggaattttt tgtgtctctc actcggaagg aattctgcat   6120
taatgaatcg gccaacgcgc ggggagaggc ggtttgcgta ttgggcgctc ttccgcttcc   6180
tcgctcactg actcgctgcg ctcggtcgtt cggctgcggc gagcggtatc agctcactca   6240
aaggcggtaa tacggttatc cacagaatca ggggataacg caggaaagaa catgtgagca   6300
aaaggccagc aaaaggccag gaaccgtaaa aaggccgcgt tgctggcgtt tttccatagg   6360
ctccgccccc ctgacgagca tcacaaaaat cgacgctcaa gtcagaggtg gcgaaacccg   6420
acaggactat aaagatacca ggcgtttccc cctggaagct ccctcgtgcg ctctcctgtt   6480
ccgaccctgc cgcttaccgg atacctgtcc gcctttctcc cttcgggaag cgtggcgctt   6540
```

| | |
|---|---|
| tctcatagct cacgctgtag gtatctcagt tcggtgtagg tcgttcgctc caagctgggc | 6600 |
| tgtgtgcacg aacccccgt tcagcccgac cgctgcgcct tatccggtaa ctatcgtctt | 6660 |
| gagtccaacc cggtaagaca cgacttatcg ccactggcag cagccactgg taacaggatt | 6720 |
| agcagagcga ggtatgtagg cggtgctaca gagttcttga agtggtggcc taactacggc | 6780 |
| tacactagaa gaacagtatt tggtatctgc gctctgctga agccagttac cttcggaaaa | 6840 |
| agagttggta gctcttgatc cggcaaacaa accaccgctg gtagcggtgg ttttttgtt | 6900 |
| tgcaagcagc agattacgcg cagaaaaaaa ggatctcaag aagatccttt gatcttttct | 6960 |
| acggggtctg acgctcagtg gaacgaaaac tcacgttaag ggattttggt catgagatta | 7020 |
| tcaaaaagga tcttcaccta gatccttttta aattaaaaat gaagttttaa atcaatctaa | 7080 |
| agtatatatg agtaaacttg gtctgacagt taccaatgct taatcagtga ggcacctatc | 7140 |
| tcagcgatct gtctatttcg ttcatccata gttgcctgac tc | 7182 |

<210> SEQ ID NO 35
<211> LENGTH: 7182
<212> TYPE: DNA
<213> ORGANISM: Artificial
<220> FEATURE:
<223> OTHER INFORMATION: Synthetic Construct

<400> SEQUENCE: 35

| | |
|---|---|
| ggcgtaatgc tctgccagtg ttacaaccaa ttaaccaatt ctgattagaa aaactcatcg | 60 |
| agcatcaaat gaaactgcaa tttattcata tcaggattat caataccata ttttgaaaa | 120 |
| agccgtttct gtaatgaagg agaaaactca ccgaggcagt tccataggat ggcaagatcc | 180 |
| tggtatcggt ctgcgattcc gactcgtcca acatcaatac aacctattaa tttcccctcg | 240 |
| tcaaaaataa ggttatcaag tgagaaatca ccatgagtga cgactgaatc cggtgagaat | 300 |
| ggcaaaagct tatgcatttc tttccagact tgttcaacag gccagccatt acgctcgtca | 360 |
| tcaaaatcac tcgcatcaac caaaccgtta ttcattcgtg attgcgcctg agcgagacga | 420 |
| aatacgcgat cgctgttaaa aggacaatta caaacaggaa tcaaatgcaa ccggcgcagg | 480 |
| aacactgcca gcgcatcaac aatattttca cctgaatcag gatattcttc taatacctgg | 540 |
| aatgctgttt tcccggggat cgcagtggtg agtaaccatg catcatcagg agtacggata | 600 |
| aaatgcttga tggtcggaag aggcataaat tccgtcagcc agtttagtct gaccatctca | 660 |
| tctgtaacat cattggcaac gctacctttg ccatgtttca gaaacaactc tggcgcatcg | 720 |
| ggcttcccat acaatcgata gattgtcgca cctgattgcc cgacattatc gcgagcccat | 780 |
| ttataccat ataaatcagc atccatgttg gaatttaatc gcggcctcga gcaagacgtt | 840 |
| tcccgttgaa tatggctcat aacaccctt gtattactgt ttatgtaagc agacaggtcg | 900 |
| acaatattgg ctattggcca ttgcatacgt tgtatctata tcataatatg tacatttata | 960 |
| ttggctcatg tccaatatga ccgccatgtt gacattgatt attgactagt tattaatagt | 1020 |
| aatcaattac ggggtcatta gttcatagcc catatatgga gttccgcgtt acataactta | 1080 |
| cggtaaatgg cccgcctggc tgaccgccca acgacccccg cccattgacg tcaataatga | 1140 |
| cgtatgttcc catagtaacg ccaatagggA ctttccattg acgtcaatgg gtggagtatt | 1200 |
| tacggtaaac tgcccacttg gcagtacatc aagtgtatca tatgccaagt ccgcccccta | 1260 |
| ttgacgtcaa tgacggtaaa tggcccgcct ggcattatgc ccagtacatg accttacggg | 1320 |
| actttcctac ttggcagtac atctacgtat tagtcatcgc tattaccatg gtgatgcggt | 1380 |
| tttggcagta caccaatggg cgtggatagc ggtttgactc acggggattt ccaagtctcc | 1440 |

```
acccattga cgtcaatggg agtttgtttt ggcaccaaaa tcaacgggac tttccaaaat    1500
gtcgtaataa ccccgccccg ttgacgcaaa tgggcggtag gcgtgtacgg tgggaggtct    1560
atataagcag agctcgttta gtgaaccgtc agatcgcctg gagacgccat ccacgctgtt    1620
ttgacctcca tagaagacac cgggaccgat ccagcctccg cggccgggaa cggtgcattg    1680
gaacgcggat tccccgtgcc aagagtgact caccgtccgg atctcagcaa gcaggtatgt    1740
actctccagg gtgggcctgg cttcccccagt caagactcca gggatttgag ggacgctgtg    1800
ggctcttctc ttacatgtac cttttgcttg cctcaaccct gactatcttc caggtcagga    1860
tcccagagtc aggggtctgt attttcctgc tggtggctcc agttcaggaa cagtaaaccc    1920
tgctccgaat attgcctctc acatctcgtc aatctccgcg aggactgggg accctgtgac    1980
gaacatggct agcattgtgg gaggctggga gtgcgagaag cattcccaac cctggcaggt    2040
gcttgtggcc tctcgtggca gggcagtctg cggcggtgtt ctggtgcacc cccagtgggt    2100
cctcacagct gcccactgca tcaggaacaa aagcgtgatc ttgctgggtc ggcacagctt    2160
gtttcatcct gaagacacag gccaggtatt tcaggtcagc cacagcttcc cacacccgct    2220
ctacgatatg agcctcctga gaatcgatt cctcaggcca ggtgatgact ccagccacga    2280
cctcatgctg ctccgcctgt cagagcctgc cgagctcacg gatgctgtga aggtcatgga    2340
cctgcccacc caggagccag cactggggac cacctgctac gcctcaggct ggggcagcat    2400
tgaaccagag gagttcttga ccccaaagaa acttcagtgt gtggacctcc atgttatttc    2460
caatgacgtg tgtgcgcaag ttcaccctca gaaggtgacc aagttcatgc tgtgtgctgg    2520
acgctggaca gggggcaaaa gcacctgctc gggtgattct gggggcccac ttgtctgtaa    2580
tggtgtgctt caaggtatca cgtcatgggg cagtgaacca tgtgccctgc ccgaaaggcc    2640
ttccctgtac accaaggtgg tgcattaccg gaagtggatc aaggacacca tcgtggccaa    2700
ccccggatcc gaaggtaggg gttcattatt gacctgtgga gatgtcgaag aaaacccagg    2760
acccgctagc aaggctgtgc tgcttgccct gttgatggca ggcttggccc tgcagccagg    2820
cactgccctg ctgtgctact cctgcaaagc ccaggtgagc aacgaggact gcctgcaggt    2880
ggagaactgc acccagctgg gggagcagtg ctggaccgcg cgcatccgcg cagttggcct    2940
cctgaccgtc atcagcaaag gctgcagctt gaactgcgtg gatgactcac aggactacta    3000
cgtgggcaag aagaacatca cgtgctgtga caccgacttg tgcaacgcca gcggggccca    3060
tgccctgcag ccggctgccg ccatccttgc gctgctccct gcactcggcc tgctgctctg    3120
gggacccggc cagctaggat cccagaccct gaactttgat ctgctgaaac tggcaggcga    3180
tgtggaaagc aacccaggcc caatggcaag cgcgcgccgc ccgcgctggc tgtgcgctgg    3240
ggcgctggtc ctggcgggtg gcttctttct cctcggcttc ctcttcgggt ggtttataaa    3300
atcctccaat gaagctacta acattactcc aaagcataat atgaaagcat ttttggatga    3360
attgaaagct gagaacatca agaagttctt atataatttt acacagatac cacatttagc    3420
aggaacagaa caaaactttc agcttgcaaa gcaaattcaa tcccagtgga agaatttgg    3480 cctggattct gttgagctgg cacattatga tgtcctgttg tcctacccaa ataagactca    3540
tcccaactac atctcaataa ttaatgaaga tggaaatgag attttcaaca catcattatt    3600
tgaaccacct cctccaggat atgaaaatgt ttcggatatt gtaccacctt tcagtgcttt    3660
ctctcctcaa ggaatgccag agggcgatct agtgtatgtt aactatgcac gaactgaaga    3720
cttctttaaa ttggaacggg acatgaaaat caattgctct gggaaaattg taattgccag    3780
```

```
atatgggaaa gttttcagag gaaataaggt taaaaatgcc cagctggcag gggccaaagg    3840
agtcattctc tactccgacc ctgctgacta ctttgctcct ggggtgaagt cctatccaga    3900
tggttggaat cttcctggag gtggtgtcca gcgtggaaat atcctaaatc tgaatggtgc    3960
aggagaccct ctcacaccag gttacccagc aaatgaatat gcttataggc gtggaattgc    4020
agaggctgtt ggtcttccaa gtattcctgt tcatccaatt ggatactatg atgcacagaa    4080
gctcctagaa aaaatggggtg ctcagcacc accagatagc agctggagag gaagtctcaa    4140
agtgccctac aatgttggac ctggctttac tggaaacttt tctacacaaa aagtcaagat    4200
gcacatccac tctaccaatg aagtgacaag aatttacaat gtgataggta ctctcagagg    4260
agcagtggaa ccagacagat atgtcattct gggaggtcac cgggactcat gggtgtttgg    4320
tggtattgac cctcagagtg gagcagctgt tgttcatgaa attgtgagga gctttggaac    4380
actgaaaaag gaagggtgga gacctagaag aacaattttg tttgcaagct gggatgcaga    4440
agaatttggt cttcttggtt ctactgagtg ggcagaggag aattcaagac tccttcaaga    4500
gcgtggcgtg gcttatatta atgctgactc atctatagaa ggaaactaca ctctgagagt    4560
tgattgtaca ccgctgatgt acagcttggt acacaaccta acaaaagagc tgaaaagccc    4620
tgatgaaggc tttgaaggca atctctttta tgaaagttgg actaaaaaaa gtccttcccc    4680
agagttcagt ggcatgccca ggataagcaa attgggatct ggaaatgatt ttgaggtgtt    4740
cttccaacga cttggaattg cttcaggcag agcacggtat actaaaaatt gggaaacaaa    4800
caaattcagc ggctatccac tgtatcacag tgtctatgaa acatatgagt tggtggaaaa    4860
gttttatgat ccaatgttta aatatcacct cactgtggcc caggttcgag agggatggt    4920 gtttgagctg gccaattcca tagtgctccc ttttgattgt cgagattatg ctgtagtttt    4980
aagaaagtat gctgacaaaa tctacagtat ttctatgaaa catccacagg aaatgaagac    5040
atacagtgta tcatttgatt cacttttttc tgcagtaaag aattttacag aaattgcttc    5100
caagttcagt gagagactcc aggactttga caaaagcaac ccaatagtat taagaatgat    5160
gaatgatcaa ctcatgtttc tggaaagagc atttattgat ccattagggt taccagacag    5220 gccttttttat aggcatgtca tctatgctcc aagcagccac aacaagtatg caggggagtc    5280
attcccagga atttatgatg ctctgtttga tattgaaagc aaagtggacc cttccaaggc    5340
ctggggagaa gtgaagagac agatttatgt tgcagccttc acagtgcagg cagctgcaga    5400
gactttgagt gaagtagcct aaagatctgg gccctaacaa aacaaaaaga tggggttatt    5460
ccctaaactt catgggttac gtaattggaa gttgggggac attgccacaa gatcatattg    5520
tacaaaagat caaacactgt tttagaaaac ttcctgtaaa caggcctatt gattggaaag    5580
tatgtcaaag gattgtgggt cttttgggct tgctgctcc atttacacaa tgtggatatc    5640
ctgccttaat gcctttgtat gcatgtatac aagctaaaca ggctttcact ttctcgccaa    5700
cttacaaggc ctttctaagt aaacagtaca tgaaccttta ccccgttgct cggcaacggc    5760
ctggtctgtg ccaagtgttt gctgacgcaa cccccactgg ctggggcttg ccataggcc    5820 atcagcgcat gcgtggaacc tttgtggctc ctctgccgat ccatactgcg gaactcctag    5880
ccgcttgttt tgctcgcagc cggtctggag caaagctcat aggaactgac aattctgtcg    5940
tcctctcgcg gaaatataca tcgtttcgat ctacgtatga tcttttccc tctgccaaaa    6000 attatgggga catcatgaag ccccttgagc atctgacttc tggctaataa aggaaattta    6060
ttttcattgc aatagtgtgt tggaattttt tgtgtctctc actcggaagg aattctgcat    6120
taatgaatcg gccaacgcgc ggggagaggc ggtttgcgta ttgggcgctc ttccgcttcc    6180
```

```
tcgctcactg actcgctgcg ctcggtcgtt cggctgcggc gagcggtatc agctcactca    6240
aaggcggtaa tacggttatc cacagaatca ggggataacg caggaaagaa catgtgagca    6300
aaaggccagc aaaaggccag gaaccgtaaa aaggccgcgt tgctggcgtt tttccatagg    6360
ctccgccccc ctgacgagca tcacaaaaat cgacgctcaa gtcagaggtg gcgaaacccg    6420
acaggactat aaagatacca ggcgtttccc cctggaagct ccctcgtgcg ctctcctgtt    6480
ccgaccctgc cgcttaccgg atacctgtcc gcctttctcc cttcgggaag cgtggcgctt    6540
tctcatagct cacgctgtag gtatctcagt tcggtgtagg tcgttcgctc caagctgggc    6600
tgtgtgcacg aaccccccgt tcagcccgac cgctgcgcct tatccggtaa ctatcgtctt    6660
gagtccaacc cggtaagaca cgacttatcg ccactggcag cagccactgg taacaggatt    6720
agcagagcga ggtatgtagg cggtgctaca gagttcttga agtggtggcc taactacggc    6780
tacactagaa gaacagtatt tggtatctgc gctctgctga agccagttac cttcggaaaa    6840
agagttggta gctcttgatc cggcaaacaa accaccgctg gtagcggtgg tttttttgtt    6900
tgcaagcagc agattacgcg cagaaaaaaa ggatctcaag aagatccttt gatcttttct    6960
acggggtctg acgctcagtg gaacgaaaac tcacgttaag ggattttggt catgagatta    7020
tcaaaaagga tcttcaccta gatcctttta aattaaaaat gaagttttaa atcaatctaa    7080
agtatatatg agtaaacttg gtctgacagt taccaatgct taatcagtga ggcacctatc    7140
tcagcgatct gtctatttcg ttcatccata gttgcctgac tc                       7182
```

<210> SEQ ID NO 36
<211> LENGTH: 7694
<212> TYPE: DNA
<213> ORGANISM: Artificial
<220> FEATURE:
<223> OTHER INFORMATION: Synthetic Construct

<400> SEQUENCE: 36

```
ggcgtaatgc tctgccagtg ttacaaccaa ttaaccaatt ctgattagaa aaactcatcg      60
agcatcaaat gaaactgcaa tttattcata tcaggattat caataccata ttttgaaaa    120 agccgtttct gtaatgaagg agaaaactca ccgaggcagt tccataggat ggcaagatcc    180
tggtatcggt ctgcgattcc gactcgtcca acatcaatac aacctattaa tttcccctcg    240
tcaaaaataa ggttatcaag tgagaaatca ccatgagtga cgactgaatc cggtgagaat    300
ggcaaaagct tatgcatttc tttccagact tgttcaacag gccagccatt acgctcgtca    360
tcaaaatcac tcgcatcaac caaaccgtta ttcattcgtg attgcgcctg agcgagacga    420
aatacgcgat cgctgttaaa aggacaatta caaacaggaa tcaaatgcaa ccggcgcagg    480
aacactgcca gcgcatcaac aatatttttca cctgaatcag gatattcttc taatacctgg    540
aatgctgttt tcccggggat cgcagtggtg agtaaccatg catcatcagg agtacggata    600
aaatgcttga tggtcggaag aggcataaat tccgtcagcc agtttagtct gaccatctca    660
tctgtaacat cattggcaac gctacctttg ccatgtttca gaaacaactc tggcgcatcg    720
ggcttcccat acaatcgata gattgtcgca cctgattgcc cgacattatc gcgagcccat    780
ttatacccat ataaatcagc atccatgttg gaatttaatc gcggcctcga gcaagacgtt    840
tcccgttgaa tatggctcat aacaccccttt gtattactgt ttatgtaagc agacaggtcg    900
acaatattgg ctattggcca ttgcatacgt tgtatctata tcataatatg tacatttata    960
ttggctcatg tccaatatga ccgccatgtt gacattgatt attgactagt tattaatagt   1020
```

```
aatcaattac ggggtcatta gttcatagcc catatatgga gttccgcgtt acataactta    1080
cggtaaatgg cccgcctggc tgaccgccca acgaccccg cccattgacg tcaataatga     1140
cgtatgttcc catagtaacg ccaataggga cttTccattg acgtcaatgg gtggagtatt    1200
tacggtaaac tgcccacttg gcagtacatc aagtgtatca tatgccaagt ccgcccccta    1260
ttgacgtcaa tgacggtaaa tggcccgcct ggcattatgc ccagtacatg accttacggg    1320
actttcctac ttggcagtac atctacgtat tagtcatcgc tattaccatg gtgatgcggt    1380
tttggcagta caccaatggg cgtggatagc ggtttgactc acggggattt ccaagtctcc    1440
accccattga cgtcaatggg agtttgtttt ggcaccaaaa tcaacgggac tttccaaaat    1500
gtcgtaataa ccccgccccg ttgacgcaaa tgggcggtag gcgtgtacgg tgggaggtct    1560
atataagcag agctcgttta gtgaaccgtc agatcgcctg gagacgccat ccacgctgtt    1620
ttgacctcca tagaagacac cgggaccgat ccagcctccg cggccgggaa cggtgcattg    1680
gaacgcggat tccccgtgcc aagagtgact caccgtccgg atctcagcaa gcaggtatgt    1740
actctccagg gtgggcctgg cttccccagt caagactcca gggatttgag gacgctgtg     1800
ggctcttctc ttacatgtac cttttgcttg cctcaaccct gactatcttc caggtcagga    1860
tcccagagtc aggggtctgt attttcctgc tggtggctcc agttcaggaa cagtaaaccc    1920
tgctccgaat attgcctctc acatctcgtc aatctccgcg aggactgggg accctgtgac    1980
gaacatggct agcaaggctg tgctgcttgc cctgttgatg gcaggcttgg ccctgcagcc    2040
aggcactgcc ctgctgtgct actcctgcaa gcccaggtg agcaacgagg actgcctgca     2100
ggtggagaac tgcacccagc tgggggagca gtgctggacc gcgcgcatcc gcgcagttgg    2160
cctcctgacc gtcatcagca aggctgcag cttgaactgc gtggatgact cacaggacta     2220
ctacgtgggc aagaagaaca tcacgtgctg tgacaccgac ttgtgcaacg ccagcggggc    2280
ccatgccctg cagccggctg ccgccatcct tgcgctgctc cctgcactcg gcctgctgct    2340
ctggggaccc ggccagctag gatcccagac cctgaacttt gatctgctga aactggcagg    2400
cgatgtggaa agcaacccag gcccaatggc aagcgcgcgc cgcccgcgct ggctgtgcgc    2460
tggggcgctg gtgctggcgg gtggcttctt tctcctcggc ttcctcttcg ggtggttat    2520
aaaatcctcc aatgaagcta ctaacattac tccaaagcat aatatgaaag cattttttga    2580
tgaattgaaa gctgagaaca tcaagaagtt cttatataat tttacacaga taccacattt    2640
agcaggaaca gaacaaaact ttcagcttgc aaagcaaatt caatcccagt ggaaagaatt    2700
tggcctggat tctgttgagc tggcacatta tgatgtcctg ttgtcctacc aaataagac     2760
tcatcccaac tacatctcaa taattaatga agatggaaat gagattttca acacatcatt    2820
atttgaacca cctcctccag gatatgaaaa tgtttcggat attgtaccac ctttcagtgc    2880
tttctctcct caaggaatgc cagagggcga tctagtgtat gttaactatg cacgaactga    2940
agacttcttt aaattggaac gggacatgaa aatcaattgc tctgggaaaa ttgtaattgc    3000
cagatatggg aaagttttca gaggaaataa ggttaaaaat gcccagctgg caggggccaa    3060
aggagtcatt ctctactccg accctgctga ctactttgct cctgggtga agtcctatcc      3120
agatggttgg aatcttcctg gaggtggtgt ccagcgtgga aatatcctaa atctgaatgg    3180
tgcaggagac cctctcacac caggttaccc agcaaatgaa tatgcttata ggcgtggaat    3240
tgcagaggct gttggtcttc caagtattcc tgttcatcca attggatact atgatgcaca    3300
gaagctccta gaaaaatgg gtggctcagc accaccagat agcagctgga gaggaagtct     3360
caaagtgccc tacaatgttg gacctggctt tactggaaac ttttctacac aaaaagtcaa    3420
```

```
gatgcacatc cactctacca atgaagtgac aagaatttac aatgtgatag gtactctcag   3480
aggagcagtg gaaccagaca gatatgtcat tctgggaggt caccgggact catgggtgtt   3540
tggtggtatt gaccctcaga gtggagcagc tgttgttcat gaaattgtga ggagctttgg   3600
aacactgaaa aaggaagggt ggagacctag aagaacaatt ttgtttgcaa gctgggatgc   3660
agaagaattt ggtcttcttg gttctactga gtgggcagag gagaattcaa gactccttca   3720
agagcgtggc gtggcttata ttaatgctga ctcatctata gaaggaaact acactctgag   3780
agttgattgt acaccgctga tgtacagctt ggtacacaac ctaacaaaag agctgaaaag   3840
ccctgatgaa ggctttgaag gcaaatctct ttatgaaagt tggactaaaa aaagtccttc   3900
cccagagttc agtggcatgc ccaggataag caaattggga tctggaaatg attttgaggt   3960
gttcttccaa cgacttggaa ttgcttcagg cagagcacgg tatactaaaa attgggaaac   4020
aaacaaattc agcggctatc cactgtatca cagtgtctat gaaacatatg agttggtgga   4080
aaagttttat gatccaatgt ttaaatatca cctcactgtg gcccaggttc gaggagggat   4140
ggtgtttgag ctggccaatt ccatagtgct cccttttgat tgtcgagatt atgctgtagt   4200
tttaagaaag tatgctgaca aaatctacag tatttctatg aaacatccac aggaaatgaa   4260
gacatacagt gtatcatttg attcactttt ttctgcagta aagaatttta cagaaattgc   4320
ttccaagttc agtgagagac tccaggactt tgacaaaagc aacccaatag tattaagaat   4380
gatgaatgat caactcatgt ttctggaaag agcatttatt gatccattag ggttaccaga   4440
caggcctttt tataggcatg tcatctatgc tccaagcagc cacaacaagt atgcagggga   4500
gtcattccca ggaatttatg atgctctgtt tgatattgaa agcaaagtgg acccttccaa   4560
ggcctgggga gaagtgaaga gacagattta tgttgcagcc ttcacagtgc aggcagctgc   4620
agagactttg agtgaagtag cctaaagatc tgaccccta cgttactgg ccgaagccgc   4680 ttggaataag gccggtgtgc gtttgtctat atgttatttt ccaccatatt gccgtctttt   4740
ggcaatgtga gggcccggaa acctggccct gtcttcttga cgagcattcc tagggtctt   4800 tcccctctcg ccaaaggaat gcaaggtctg ttgaatgtcg tgaaggaagc agttcctctg   4860
gaagcttctt gaagacaaac aacgtctgta gcgacccttt gcaggcagcg gaaccccca   4920 cctggcgaca ggtgcctctg cggccaaaag ccacgtgtat aagatacacc tgcaaaggcg   4980
gcacaacccc agtgccacgt tgtgagttgg atagttgtgg aaagagtcaa atggctctcc   5040
tcaagcgtat tcaacaaggg gctgaaggat gcccagaagg tacccattg tatgggatct   5100 gatctgggc ctcggtgcac atgctttaca tgtgtttagt cgaggttaaa aaacgtctag   5160 gcccccgaa ccacggggac gtggttttcc tttgaaaaac acgatgataa tatggccagc   5220
attgtgggag gctgggagtg cgagaagcat tcccaaccct ggcaggtgct tgtggcctct   5280
cgtggcaggg cagtctgcgg cggtgttctg gtgcaccccc agtgggtcct cacagctgcc   5340
cactgcatca ggaacaaaag cgtgatcttg ctggtcggc acagcttgtt tcatcctgaa   5400
gacacaggcc aggtatttca ggtcagccac agcttccac acccgctcta cgatatgagc   5460
ctcctgaaga atcgattcct caggccaggt gatgactcca gccacgacct catgctgctc   5520
cgcctgtcag agcctgccga gctcacggat gctgtgaagg tcatggacct gcccacccag   5580
gagccagcac tggggaccac ctgctacgcc tcaggctggg gcagcattga accagaggag   5640
ttcttgaccc caaagaaact tcagtgtgtg gacctccatg ttatttccaa tgacgtgtgt   5700
gcgcaagttc accctcagaa ggtgaccaag ttcatgctgt gtgctggacg ctggacaggg   5760
```

| ggcaaaagca cctgctcggg tgattctggg ggcccacttg tctgtaatgg tgtgcttcaa | 5820 |
| ggtatcacgt catggggcag tgaaccatgt gccctgcccg aaaggccttc cctgtacacc | 5880 |
| aaggtggtgc attaccggaa gtggatcaag gacaccatcg tggccaaccc ctgaggatct | 5940 |
| gggccctaac aaaacaaaaa gatggggtta ttccctaaac ttcatgggtt acgtaattgg | 6000 |
| aagttggggg acattgccac aagatcatat tgtacaaaag atcaaacact gttttagaaa | 6060 |
| acttcctgta aacaggccta ttgattggaa agtatgtcaa aggattgtgg gtcttttggg | 6120 |
| cttttgctgct ccatttacac aatgtggata tcctgcctta atgcctttgt atgcatgtat | 6180 |
| acaagctaaa caggctttca ctttctcgcc aacttacaag gcctttctaa gtaaacagta | 6240 |
| catgaacctt taccccgttg ctcggcaacg gcctggtctg tgccaagtgt ttgctgacgc | 6300 |
| aacccccact ggctgggct tggccatagg ccatcagcgc atgcgtggaa cctttgtggc | 6360 |
| tcctctgccg atccatactg cggaactcct agccgcttgt tttgctcgca gccggtctgg | 6420 |
| agcaaagctc ataggaactg acaattctgt cgtcctctcg cggaaatata catcgtttcg | 6480 |
| atctacgtat gatcttttc cctctgccaa aaattatggg gacatcatga agcccttga | 6540 |
| gcatctgact tctggctaat aaaggaaatt tattttcatt gcaatagtgt gttggaattt | 6600 |
| tttgtgtctc tcactcggaa ggaattctgc attaatgaat cggccaacgc gcggggagag | 6660 |
| gcggtttgcg tattgggcgc tcttccgctt cctcgctcac tgactcgctg cgctcggtcg | 6720 |
| ttcggctgcg gcgagcggta tcagctcact caaaggcggt aatacggtta tccacagaat | 6780 |
| caggggataa cgcaggaaag aacatgtgag caaaaggcca gcaaaaggcc aggaaccgta | 6840 |
| aaaaggccgc gttgctggcg ttttccata ggctccgccc ccctgacgag catcacaaaa | 6900 |
| atcgacgctc aagtcagagg tggcgaaacc cgacaggact ataaagatac caggcgtttc | 6960 |
| cccctggaag ctccctcgtg cgctctcctg ttccgaccct gccgcttacc ggatacctgt | 7020 |
| ccgcctttct cccttcggga agcgtggcgc tttctcatag ctcacgctgt aggtatctca | 7080 |
| gttcggtgta ggtcgttcgc tccaagctgg gctgtgtgca cgaacccccc gttcagcccg | 7140 |
| accgctgcgc cttatccggt aactatcgtc ttgagtccaa cccggtaaga cacgacttat | 7200 |
| cgccactggc agcagccact ggtaacagga ttagcagagc gaggtatgta ggcggtgcta | 7260 |
| cagagttctt gaagtggtgg cctaactacg gctacactag aagaacagta tttggtatct | 7320 |
| gcgctctgct gaagccagtt accttcggaa aaagagttgg tagctcttga tccggcaaac | 7380 |
| aaaccaccgc tggtagcggt ggtttttttg tttgcaagca gcagattacg cgcagaaaaa | 7440 |
| aaggatctca agaagatcct ttgatctttt ctacggggtc tgacgctcag tggaacgaaa | 7500 |
| actcacgtta agggattttg gtcatgagat tatcaaaaag gatcttcacc tagatccttt | 7560 |
| taaattaaaa atgaagtttt aaatcaatct aaagtatata tgagtaaact tggtctgaca | 7620 |
| gttaccaatg cttaatcagt gaggcaccta tctcagcgat ctgtctattt cgttcatcca | 7680 |
| tagttgcctg actc | 7694 |

<210> SEQ ID NO 37
<211> LENGTH: 8461
<212> TYPE: DNA
<213> ORGANISM: Artificial
<220> FEATURE:
<223> OTHER INFORMATION: Synthetic Construct

<400> SEQUENCE: 37

| catcatcaat aatataccct attttggatt gaagccaata tgataatgag ggggtggagt | 60 |
| ttgtgacgtg gcgcggggcg tgggaacggg gcgggtgacg tagtagtgtg gcggaagtgt | 120 |

-continued

```
gatgttgcaa gtgtggcgga acacatgtaa gcgacggatg tggcaaaagt gacgttttg      180
gtgtgcgccg gtgtacacag gaagtgacaa ttttcgcgcg gttttaggcg gatgttgtag      240
taaatttggg cgtaaccgag taagatttgg ccattttcgc gggaaaactg aataagagga      300
agtgaaatct gaataatttt gtgttactca tagcgcgtaa tactgtaata gtaatcaatt      360
acggggtcat tagttcatag cccatatatg gagttccgcg ttacataact acggtaaat      420
ggcccgcctg gctgaccgcc caacgacccc cgcccattga cgtcaataat gacgtatgtt      480
cccatagtaa cgccaatagg gactttccat tgacgtcaat gggtggagta tttacggtaa      540
actgcccact tggcagtaca tcaagtgtat catatgccaa gtacgccccc tattgacgtc      600
aatgacggta atggcccgc ctggcattat gcccagtaca tgaccttatg gactttcct      660
acttggcagt acatctacgt attagtcatc gctattacca tggtgatgcg gttttggcag      720
tacatcaatg ggcgtggata gcggtttgac tcacgggat ttccaagtct ccaccccatt      780
gacgtcaatg ggagtttgtt ttggcaccaa aatcaacggg actttccaaa atgtcgtaac      840
aactccgccc cattgacgca aatgggcggt aggcgtgtac ggtgggaggt ctatataagc      900
agagctggtt tagtgaaccg tcagatccgc tagagatcca ccatggctag cggtgccccg      960
acgttgcccc ctgcctggca gccctttctc aaggaccacc gcatctctac attcaagaac     1020
tggcccttct tggagggctg cgcctgcgcc ccggagcgga tggccgaggc tggcttcatc     1080
cactgcccca ctgagaacga gccagacttg gcccagtgtt tcttctgctt caaggagctg     1140
gaaggctggg agccagatga cgaccccata gaggaacata aaaagcattc gtccggttgc     1200
gctttccttt ctgtcaagaa gcagtttgaa gaattaaccc ttggtgaatt tttgaaactg     1260
gacagagaaa gagccaagaa caaaattgca aaggaaacca acaataagaa gaaagaattt     1320
gaggaaactg cggagaaagt gcgccgtgcc atcgagcagc tggctgccat ggattagaga     1380
tctgaccccc taacgttact ggccgaagcc gcttggaata aggccggtgt gcgtttgtct     1440
atatgttatt ttccaccata ttgccgtctt ttggcaatgt gagggcccgg aaacctggcc     1500
ctgtcttctt gacgagcatt cctagggtt tttcccctct cgccaaagga atgcaaggtc     1560
tgttgaatgt cgtgaaggaa gcagttcctc tggaagcttc ttgaagacaa acaacgtctg     1620
tagcgaccct ttgcaggcag cggaaccccc cacctggcga caggtgcctc tgcggccaaa     1680
agccacgtgt ataagataca cctgcaaagg cggcacaacc ccagtgccac gttgtgagtt     1740
ggatagttgt ggaaagagtc aaatggctct cctcaagcgt attcaacaag gggctgaagg     1800
atgcccagaa ggtaccccat tgtatgggat ctgatctggg gcctcggtgc acatgcttta     1860
catgtgttta gtcgaggtta aaaaacgtct aggccccccg aaccacgggg acgtggtttt     1920
cctttgaaaa acacgataat atggcggccg ctcgagccta agcttctaga taagatatcc     1980
gatccaccgg atctagataa ctgatcataa tcagccatac cacatttgta gaggttttac     2040
ttgctttaaa aaacctccca cacctccccc tgaacctgaa acataaaatg aatgcaattg     2100
ttgttgttaa cttgtttatt gcagcttata atggttacaa ataaagcaat agcatcacaa     2160
atttcacaaa taaagcattt ttttcactgc attctagttg tggtttgtcc aaactcatca     2220
atgtatctta acgcggatct gggcgtggtt aagggtggga agaatatat aaggtggggg     2280
tcttatgtag ttttgtatct gttttgcagc agccgccgcc gccatgagca ccaactcgtt     2340
tgatggaagc attgtgagct catatttgac aacgcgcatg ccccatgggc cggggtgcg      2400
tcagaatgtg atgggctcca gcattgatgg tcgccccgtc ctgcccgcaa actctactac     2460
```

```
cttgacctac gagaccgtgt ctggaacgcc gttggagact gcagcctccg ccgccgcttc    2520
agccgctgca gccaccgccc gcgggattgt gactgacttt gctttcctga gcccgcttgc    2580
aagcagtgca gcttcccgtt catccgcccg cgatgacaag ttgacggctc ttttggcaca    2640
attggattct ttgaccgggg aacttaatgt cgtttctcag cagctgttgg atctgcgcca    2700
gcaggtttct gccctgaagg cttcctcccc tcccaatgcg gtttaaaaca taaataaaaa    2760
accagactct gtttggattt ggatcaagca agtgtcttgc tgtctttatt tagggttttt    2820
gcgcgcgcgg taggcccggg accagcggtc tcggtcgttg agggtcctgt gtattttttc    2880
caggacgtgg taaaggtgac tctggatgtt cagatacatg gcataagcc cgtctctggg     2940 gtggaggtag caccactgca gagcttcatg ctgcggggtg gtgttgtaga tgatccagtc    3000
gtagcaggag cgctgggcgt ggtgcctaaa aatgtctttc agtagcaagc tgattgccag    3060
gggcaggccc ttggtgtaag tgtttacaaa gcggttaagc tgggatgggt gcatacgtgg    3120
ggatatgaga tgcatcttgg actgtatttt taggttggct atgttccag ccatatccct      3180 ccggggattc atgttgtgca gaaccaccag cacagtgtat ccggtgcact tgggaaattt    3240
gtcatgtagc ttagaaggaa atgcgtggaa gaacttggag acgcccttgt gacctccaag    3300
attttccatg cattcgtcca taatgatggc aatgggccca cggcggcgg cctgggcgaa     3360 gatatttctg ggatcactaa cgtcatagtt gtgttccagg atgagatcgt cataggccat    3420
ttttacaaag cgcgggcgga gggtgccaga ctgcggtata atggttccat ccggcccagg    3480
ggcgtagtta ccctcacaga tttgcatttc ccacgctttg agttcagatg ggggatcat     3540 gtctacctgc ggggcgatga agaaaacggt ttccggggta ggggagatca gctgggaaga    3600
aagcaggttc ctgagcagct gcgacttacc gcagccggtg ggcccgtaaa tcacacctat    3660
taccggctgc aactggtagt taagagagct gcagctgccg tcatccctga gcagggggc     3720 cacttcgtta agcatgtccc tgactcgcat gttttccctg accaaatccg ccagaaggcg    3780
ctcgccgccc agcgatagca gttcttgcaa ggaagcaaag tttttcaacg gtttgagacc    3840
gtccgccgta ggcatgcttt tgagcgtttg accaagcagt tccaggcggt cccacagctc    3900
ggtcacctgc tctacggcat ctcgatccag catatctcct cgtttcgcgg gttggggcgg    3960 cttttcgctgt acggcagtag tcggtgctcg tccagacggg ccagggtcat gtcttttccac    4020 gggcgcaggg tcctcgtcag cgtagtctgg gtcacggtga aggggtgcgc tccgggctgc    4080
gcgctggcca gggtgcgctt gaggctggtc ctgctggtgc tgaagcgctg ccggtcttcg    4140
ccctgcgcgt cggccaggta gcatttgacc atggtgtcat agtccagccc ctccgcggcg    4200
tggcccttgg cgcgcagctt gcccttggag gaggcgccgc acgagggca gtgcagactt     4260 ttgagggcgt agagcttggg cgcgagaaat accgattccg gggagtaggc atccgcgccg    4320
caggccccgc agacggtctc gcattccacg agccaggtga gctctggccg ttcggggtca    4380
aaaaccaggt ttccccatg cttttttgatg cgtttcttac ctctggtttc catgagccgg     4440
tgtccacgct cggtgacgaa aaggctgtcc gtgtccccgt atacagactt gagagggagt    4500
ttaaacgaat tcaatagctt gttgcatggg cggcgatata aaatgcaagg tgctgctcaa    4560
aaaatcaggc aaagcctcgc gcaaaaaaga aagcacatcg tagtcatgct catgcagata    4620
aaggcaggta agctccggaa ccaccacaga aaaagacacc attttctctc caaacatgtc    4680
tgcgggtttc tgcataaaca caaaataaaa taacaaaaaa acatttaaac attagaagcc    4740
tgtcttacaa caggaaaaac aacccttata agcataagac ggactacggc catgccggcg    4800
tgaccgtaaa aaaactggtc accgtgatta aaaagcacca ccgacagctc ctcggtcatg    4860
```

-continued

```
tccggagtca taatgtaaga ctcggtaaac acatcaggtt gattcacatc ggtcagtgct   4920
aaaaagcgac cgaaatagcc cggggaata catacccgca ggcgtagaga caacattaca    4980
gcccccatag gaggtataac aaaattaata ggagagaaaa acacataaac acctgaaaaa   5040
ccctcctgcc taggcaaaat agcaccctcc cgctccagaa caacatacag cgcttccaca   5100
gcggcagcca taacagtcag ccttaccagt aaaaagaaa acctattaaa aaaacaccac    5160
tcgacacggc accagctcaa tcagtcacag tgtaaaaaag gccaagtgc agagcgagta    5220 tataggac taaaaatga cgtaacggtt aaagtccaca aaaacaccc agaaaccgc        5280 acgcgaacct acgcccagaa acgaaagcca aaaacccac aacttcctca aatcgtcact    5340
tccgttttcc cacgttacgt cacttcccat tttaagaaaa ctacaattcc caacacatac   5400
aagttactcc gccctaaaac ctacgtcacc cgccccgttc ccacgcccg cgccacgtca    5460 caaactccac cccctcatta tcatattggc ttcaatccaa aataaggtat attattgatg   5520
atgttaatta acatgcatgg atccatatgc ggtgtgaaat accgcacaga tgcgtaagga   5580
gaaaataccg catcaggcgc tcttccgctt cctcgctcac tgactcgctg cgctcggtcg   5640
ttcggctgcg gcgagcggta tcagctcact caaaggcggt aatacggtta ccacagaat    5700 caggggataa cgcaggaaag aacatgtgag caaaaggcca gcaaaaggcc aggaaccgta   5760
aaaaggccgc gttgctggcg ttttccata ggctccgccc ccctgacgag catcacaaaa    5820
atcgacgctc aagtcagagg tggcgaaacc cgacaggact ataaagatac caggcgtttc   5880
cccctggaag ctccctcgtg cgctctcctg ttccgaccct gccgcttacc ggatacctgt   5940
ccgcctttct cccttcggga agcgtggcgc tttctcatag ctcacgctgt aggtatctca   6000
gttcggtgta ggtcgttcgc tccaagctgg gctgtgtgca cgaaccccc gttcagcccg    6060 accgctgcgc cttatccggt aactatcgtc ttgagtccaa cccggtaaga cacgacttat   6120
cgccactggc agcagccact ggtaacagga ttagcagagc gaggtatgta ggcggtgcta   6180
cagagttctt gaagtggtgg cctaactacg gctacactag aaggacagta tttggtatct   6240
gcgctctgct gaagccagtt accttcggaa aaagagttgg tagctcttga tccggcaaac   6300
aaaccaccgc tggtagcggt ggtttttttg tttgcaagca gcagattacg cgcagaaaaa   6360
aaggatctca agaagatcct ttgatctttt ctacggggtc tgacgctcag tggaacgaaa   6420
actcacgtta agggattttg gtcatgagat tatcaaaaag gatcttcacc tagatccttt   6480
taaattaaaa atgaagtttt aaatcaatct aaagtatata tgagtaaact tggtctgaca   6540
gttaccaatg cttaatcagt gaggcaccta tctcagcgat ctgtctattt cgttcatcca   6600
tagttgcctg actccccgtc gtgtagataa ctacgatacg ggagggctta ccatctggcc   6660
ccagtgctgc aatgataccg cgagacccac gctcaccggc tccagattta tcagcaataa   6720
accagccagc cggaagggcc gagcgcagaa gtggtcctgc aactttatcc gcctccatcc   6780
agtctattaa ttgttgccgg gaagctagag taagtagttc gccagttaat agtttgcgca   6840
acgttgttgc cattgctgca gccatgagat tatcaaaaag gatcttcacc tagatccttt   6900
tcacgtagaa agccagtccg cagaaacggt gctgaccccg gatgaatgtc agctactggg   6960
ctatctggac aagggaaaac gcaagcgcaa agagaaagca ggtagcttgc agtgggctta   7020
catggcgata gctagactgg gcggttttat ggacagcaag cgaaccggaa ttgccagctg   7080
gggcgccctc tggtaaggtt gggaagccct gcaaagtaaa ctggatggct tcttgccgc    7140 caaggatctg atggcgcagg ggatcaagct ctgatcaaga gacaggatga ggatcgtttc   7200
```

```
gcatgattga acaagatgga ttgcacgcag gttctccggc cgcttgggtg gagaggctat    7260
tcggctatga ctgggcacaa cagacaatcg gctgctctga tgccgccgtg ttccggctgt    7320
cagcgcaggg gcgcccggtt cttttttgtca agaccgacct gtccggtgcc ctgaatgaac    7380
tgcaagacga ggcagcgcgg ctatcgtggc tggccacgac gggcgttcct tgcgcagctg    7440
tgctcgacgt tgtcactgaa gcgggaaggg actggctgct attgggcgaa gtgccggggc    7500
aggatctcct gtcatctcac cttgctcctg ccgagaaagt atccatcatg gctgatgcaa    7560
tgcggcggct gcatacgctt gatccggcta cctgcccatt cgaccaccaa gcgaaacatc    7620
gcatcgagcg agcacgtact cggatggaag ccggtcttgt cgatcaggat gatctggacg    7680
aagagcatca ggggctcgcg ccagccgaac tgttcgccag gctcaaggcg agcatgcccg    7740
acggcgagga tctcgtcgtg acccatggcg atgcctgctt gccgaatatc atggtggaaa    7800
atggccgctt ttctggattc atcgactgtg gccggctggg tgtggcggac cgctatcagg    7860
acatagcgtt ggctacccgt gatattgctg aagagcttgg cggcgaatgg gctgaccgct    7920
tcctcgtgct ttacggtatc gccgctcccg attcgcagcg catcgccttc tatcgccttc    7980
ttgacgagtt cttctgaatt ttgttaaaat ttttgttaaa tcagctcatt ttttaaccaa    8040
taggccgaaa tcggcaccat cccttataaa tcaaaagaat agaccgagat agggttgagt    8100
gttgttccag tttggaacaa gagtccacta ttaaagaacg tggactccaa cgtcaaaggg    8160
cgaaaaaccg tctatcaggg cgatggccca ctacgtgaac catcaccccta atcaagtttt    8220 ttgtggtcga ggtgccgtaa agcactaaat cggaacccta agggagcccc cgatttaga    8280 gcttgacggg gaaagccggc gaacgtggcg agaaaggaag ggaagaaagc gaaaggagcg    8340
ggcgctaggg cgctggcaag tgtagcggtc acgctgcgcg taaccaccac acccgcgcgc    8400
ttaatgcgcc gctacagggc gcgtccattc gccattcagg atcgaattaa ttcttaatta    8460
a                                                                    8461
```

<210> SEQ ID NO 38
<211> LENGTH: 956
<212> TYPE: PRT
<213> ORGANISM: Artificial
<220> FEATURE:
<223> OTHER INFORMATION: Synthetic Construct

<400> SEQUENCE: 38

```
Met Ala Ser Glu Leu Ala Ala Leu Cys Arg Trp Gly Leu Leu Leu Ala
1               5                   10                  15

Leu Leu Pro Pro Gly Ala Ala Ser Thr Gln Val Cys Thr Gly Thr Asp
            20                  25                  30

Met Lys Leu Arg Leu Pro Ala Ser Pro Glu Thr His Leu Asp Met Leu
        35                  40                  45

Arg His Leu Tyr Gln Gly Cys Gln Val Val Gln Gly Asn Leu Glu Leu
    50                  55                  60

Thr Tyr Leu Pro Thr Asn Ala Ser Leu Ser Phe Leu Gln Asp Ile Gln
65                  70                  75                  80

Glu Val Gln Gly Tyr Val Leu Ile Ala His Asn Gln Val Arg Gln Val
                85                  90                  95

Pro Leu Gln Arg Leu Arg Ile Val Arg Gly Thr Gln Leu Phe Glu Asp
            100                 105                 110

Asn Tyr Ala Leu Ala Val Leu Asp Asn Gly Asp Pro Leu Asp Ser Val
        115                 120                 125

Ala Pro Ala Ala Gly Ala Thr Pro Gly Gly Leu Gln Glu Leu Gln Leu
```

```
            130                 135                 140
Arg Ser Leu Thr Glu Ile Leu Lys Gly Gly Val Leu Ile Arg Arg Ser
145                 150                 155                 160

Pro Gln Leu Cys His Gln Asp Thr Val Leu Trp Glu Asp Val Phe Arg
                165                 170                 175

Lys Asn Asn Gln Leu Ala Leu Val Leu Met Asp Thr Asn Arg Ser Arg
                180                 185                 190

Ala Cys His Pro Cys Ala Pro Met Cys Lys Ala Asn His Cys Trp Gly
            195                 200                 205

Glu Ser Ser Gln Asp Cys Gln Thr Leu Thr Arg Thr Ile Cys Thr Ser
        210                 215                 220

Ala Cys Ala Arg Cys Lys Ala Pro Leu Pro Thr Asp Cys Cys His Glu
225                 230                 235                 240

Gln Cys Ala Ala Gly Cys Thr Gly Pro Lys His Ser Asp Cys Leu Ala
                245                 250                 255

Cys Leu His Phe Asn His Ser Gly Ile Cys Glu Leu His Cys Pro Ala
                260                 265                 270

Leu Val Thr Tyr Asn Thr Asp Thr Phe Glu Ser Met Pro Asn Pro Glu
            275                 280                 285

Gly Arg Tyr Thr Phe Gly Ala Ser Cys Val Thr Ala Cys Pro Tyr Asn
        290                 295                 300

Tyr Leu Ser Thr Asp Val Gly Ser Cys Thr Leu Val Cys Pro Leu His
305                 310                 315                 320

Asn Gln Glu Val Thr Ala Glu Asp Gly Thr Gln Arg Cys Glu Lys Cys
                325                 330                 335

Ser Lys Pro Cys Ala Arg Val Cys Tyr Gly Leu Gly Met Glu His Leu
                340                 345                 350

Arg Glu Ala Arg Ala Ile Thr Ser Ala Asn Val Gln Asp Phe Val Gly
            355                 360                 365

Cys Lys Lys Ile Phe Gly Ser Leu Ala Phe Leu Pro Glu Ser Phe Asp
        370                 375                 380

Gly Asp Pro Ala Ser Gly Thr Ala Pro Leu Gln Pro Glu Gln Leu Gln
385                 390                 395                 400

Val Phe Glu Thr Leu Glu Glu Ile Thr Gly Tyr Leu Tyr Ile Ser Ala
                405                 410                 415

Trp Pro Asp Ser Phe Pro Asn Leu Ser Val Phe Gln Asn Leu Arg Val
                420                 425                 430

Ile Arg Gly Arg Ile Leu His Asn Gly Ala Tyr Ser Leu Thr Leu Gln
            435                 440                 445

Gly Leu Gly Ile Ser Trp Leu Gly Leu Arg Ser Leu Gln Glu Leu Gly
        450                 455                 460

Ser Gly Leu Ala Leu Val His Arg Asn Ala Arg Leu Cys Phe Val His
465                 470                 475                 480

Thr Val Pro Trp Asp Gln Leu Phe Arg Asn Pro His Gln Ala Leu Leu
                485                 490                 495

His Ser Gly Asn Arg Pro Glu Glu Asp Cys Val Gly Glu Gly Phe Val
                500                 505                 510

Cys Tyr Ser Leu Cys Ala His Gly His Cys Trp Gly Pro Gly Pro Thr
            515                 520                 525

Gln Cys Val Asn Cys Ser His Phe Leu Arg Gly Gln Glu Cys Val Glu
        530                 535                 540

Glu Cys Arg Val Leu Gln Gly Leu Pro Arg Glu Tyr Val Asn Ala Arg
545                 550                 555                 560
```

```
His Cys Leu Pro Cys His Pro Glu Cys Gln Pro Gln Asn Gly Ser Val
            565                 570                 575
Thr Cys Phe Gly Pro Glu Ala Asp Gln Cys Val Ala Cys Ala His Tyr
            580                 585                 590
Lys Asp Pro Pro Phe Cys Val Ala Arg Cys Pro Ser Gly Val Lys Pro
            595                 600                 605
Asp Leu Ser Tyr Met Pro Ile Trp Lys Phe Pro Asp Glu Glu Gly Ala
            610                 615                 620
Cys Gln Pro Cys Pro Ile Asn Cys Thr His Ser Cys Val Asp Leu Asp
625                 630                 635                 640
Asp Lys Gly Cys Pro Ala Glu Gln Arg Ala Ser Pro Leu Thr Ser Ile
            645                 650                 655
Ile Ser Ala Val Val Gly Ile Leu Leu Val Val Val Leu Gly Val Val
            660                 665                 670
Phe Gly Ile Leu Ile Lys Arg Arg Gln Gln Lys Ile Arg Lys Tyr Thr
            675                 680                 685
Met Arg Arg Asn Glu Asp Leu Gly Pro Ser Ser Pro Met Asp Ser Thr
            690                 695                 700
Phe Tyr Arg Ser Leu Leu Glu Asp Glu Met Gly Glu Leu Val Asp
705                 710                 715                 720
Ala Glu Glu Tyr Leu Val Pro Gln Gln Gly Phe Phe Cys Pro Asp Pro
            725                 730                 735
Thr Pro Gly Thr Gly Ser Thr Ala His Arg Arg His Arg Ser Ser Ser
            740                 745                 750
Ala Arg Asn Gly Gly Gly Asp Leu Thr Leu Gly Met Glu Pro Ser Gly
            755                 760                 765
Glu Gly Pro Pro Arg Ser Pro Arg Ala Pro Ser Glu Gly Thr Gly Ser
            770                 775                 780
Asp Val Phe Asp Gly Asp Leu Ala Val Gly Val Thr Lys Gly Leu Gln
785                 790                 795                 800
Ser Leu Ser Pro Gln Asp Leu Ser Pro Leu Gln Arg Tyr Ser Glu Asp
            805                 810                 815
Pro Thr Leu Pro Leu Pro Ser Glu Thr Asp Gly Lys Val Ala Pro Leu
            820                 825                 830
Ser Cys Ser Pro Gln Pro Glu Phe Val Asn Gln Ser Asp Val Gln Pro
            835                 840                 845
Lys Ser Pro Leu Thr Pro Glu Gly Pro Ser Pro Ala Arg Pro Thr
            850                 855                 860
Gly Ala Thr Leu Glu Arg Ala Lys Thr Leu Ser Pro Gly Lys Asn Gly
865                 870                 875                 880
Val Val Lys Asp Val Phe Thr Phe Gly Gly Ala Val Glu Asn Pro Glu
            885                 890                 895
Phe Leu Ala Pro Arg Glu Gly Thr Ala Ser Pro Pro His Pro Ser Pro
            900                 905                 910
Ala Phe Ser Pro Ala Phe Asp Asn Leu Phe Phe Trp Asp Gln Asn Ser
            915                 920                 925
Ser Glu Gln Gly Pro Pro Ser Asn Phe Glu Gly Thr Pro Thr Ala
            930                 935                 940
Glu Asn Pro Glu Phe Leu Gly Leu Asp Val Pro Val
945                 950                 955

<210> SEQ ID NO 39
<211> LENGTH: 2871
```

<212> TYPE: DNA
<213> ORGANISM: Artificial
<220> FEATURE:
<223> OTHER INFORMATION: Synthetic Construct

<400> SEQUENCE: 39

| | | | | | |
|---|---|---|---|---|---|
| atggctagcg | agctggccgc | cctgtgtaga | tggggactgc | tgctggctct | gctgcctcct | 60 |
| ggagccgctt | ctacacaggt | ctgcaccggc | accgacatga | agctgagact | gcccgccagc | 120 |
| cccgagacac | acctggacat | gctgcggcac | ctgtaccagg | ctgccaggt | ggtccagggg | 180 |
| aatctggaac | tgacctacct | gccccaccaa | gccagcctga | gcttcctgca | ggacatccag | 240 |
| gaagtgcagg | gctacgtcct | gatcgcccac | aaccaggtcc | gccaggtgcc | cctgcagcgg | 300 |
| ctgagaatcg | tgcggggcac | ccagctgttc | gaggacaact | acgccctggc | cgtgctggac | 360 |
| aacggcgacc | tctggatagc | gtggcccct | gctgctgggg | ctacacctgg | cggactgcag | 420 |
| gaactgcagc | tgcggagcct | gaccgagatc | ctgaagggcg | gcgtgctgat | caggcggagc | 480 |
| cctcagctgt | gccaccagga | caccgtgctg | tgggaggacg | tgttccggaa | gaacaaccag | 540 |
| ctggccctcg | tgctgatgga | caccaacaga | gccgggcct | gccacccctg | cgccccatg | 600 |
| tgcaaggcca | atcactgctg | gggagagagc | agccaggact | gccagaccct | gacccggacc | 660 |
| atctgcacca | gcgcctgcgc | cagatgcaag | gccccctgc | ctaccgactg | ctgccacgaa | 720 |
| cagtgcgccg | ctggctgcac | cggcccaag | cacagcgatt | gcctggcctg | cctgcacttc | 780 |
| aaccacagcg | gcatctgcga | gctgcactgc | cctgccctgg | tgacatacaa | caccgacacc | 840 |
| ttcgagagca | tgcccaaccc | cgagggccgg | tacaccttcg | cgccagctg | tgtgaccgcc | 900 |
| tgccccctaca | actacctgag | caccgacgtg | ggcagctgca | ccctggtgtg | cccctgcac | 960 |
| aaccaggaag | tgaccgccga | ggacggcacc | cagagatgcg | agaagtgcag | caagccttgc | 1020 |
| gccagagtgt | gctacggcct | gggcatggaa | cacctgagag | aggccagagc | catcaccagc | 1080 |
| gccaacgtgc | aggacttcgt | gggctgcaag | aagatttcg | gctccctggc | cttcctgccc | 1140 |
| gagagcttcg | acggcgatcc | tgcctctggc | accgcccctc | tgcagcctga | gcagctgcag | 1200 |
| gtcttcgaga | cactggaaga | gatcaccggc | tacctgtaca | tcagcgcctg | gcccgacagc | 1260 |
| ttccccaacc | tgagcgtgtt | ccagaacctg | agagtgatcc | ggggcagaat | cctgcacaac | 1320 |
| ggcgcctaca | gcctgaccct | gcagggcctg | ggaatcagct | ggctgggcct | gcggagcctg | 1380 |
| caggaactgg | gatctggcct | ggctctggtg | caccggaacg | cccggctgtg | cttcgtgcac | 1440 |
| accgtgccct | gggaccagct | gttcagaaac | ccccaccagg | ctctgctgca | cagcggcaac | 1500 |
| cggcccgaag | aggattgcgt | gggcgagggc | ttcgtgtgct | actccctgtg | cgcccacggc | 1560 |
| cactgttggg | gacctggccc | tacccagtgc | gtgaactgca | gccacttcct | gcggggccaa | 1620 |
| gaatgcgtga | agagtgccg | ggtgctgcag | ggactgcccc | gggaatacgt | gaacgccaga | 1680 |
| cactgcctgc | cttgccaccc | cgagtgccag | ccccagaatg | gcagcgtgac | ctgcttcgga | 1740 |
| cccgaggccg | atcagtgtgt | ggcctgcgcc | cactacaagg | accccccatt | ctgcgtggcc | 1800 |
| agatgcccca | gcggcgtgaa | gcccgacctg | agctacatgc | ccatctggaa | gttccccgac | 1860 |
| gaggaaggcg | cctgccagcc | ttgccccatc | aactgcaccc | acagctgcgt | ggacctggac | 1920 |
| gacaagggct | gccctgccga | gcagagagcc | agccccctga | ccagcatcat | cagcgccgtg | 1980 |
| gtgggaatcc | tgctggtggt | ggtgctgggc | gtggtgttcg | gcatcctgat | caagcggcgg | 2040 |
| cagcagaaga | tccggaagta | caccatgcgg | cggaacgagg | acctgggccc | ctctagcccc | 2100 |
| atggacagca | ccttctaccg | gtccctgctg | gaagatgagg | acatgggcga | gctggtggac | 2160 |

-continued

```
gccgaggaat acctggtgcc tcagcagggc ttcttctgcc ccgaccctac ccctggcacc   2220
ggctctaccg cccacagacg gcacagaagc agcagcgcca gaaacggcgg aggcgacctg   2280
accctgggaa tggaacctag cggcgaggga cctcccagaa gccctagagc ccctagcgag   2340
ggcaccggca gcgacgtgtt cgatggcgat ctggccgtgg gcgtgaccaa gggactgcag   2400
agcctgagcc cccaggacct gtccccctg cagagataca gcgaggaccc caccctgccc   2460
ctgcccagcg agacagatgg caaggtggcc cccctgagct gcagccctca gcccgagttc   2520
gtgaaccaga gcgacgtgca gcccaagtcc cccctgacac ccgagggacc tccaagccct   2580
gccagaccta ccggcgccac cctggaaaga gccaagaccc tgagccccgg caagaacggc   2640
gtggtgaaag acgtgttcac cttcggaggc gccgtggaaa accccgagtt cctggccccc   2700
agagagggca cagccagccc tccacacccc agcccagcct tctcccccgc cttcgacaac   2760
ctgttcttct gggaccagaa cagcagcgag cagggcccac cccccagcaa tttcgagggc   2820
acccccaccg ccgagaatcc tgagttcctg ggcctggacg tgcccgtgtg a            2871
```

<210> SEQ ID NO 40
<211> LENGTH: 471
<212> TYPE: PRT
<213> ORGANISM: Artificial
<220> FEATURE:
<223> OTHER INFORMATION: Synthetic Construct

<400> SEQUENCE: 40

```
Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr Tyr Met His Trp Val Arg Gln Ala Pro Gly Gln Gly Leu
    50                  55                  60

Glu Trp Met Gly Trp Ile Asn Pro Asp Ser Gly Gly Thr Asn Tyr Ala
65                  70                  75                  80

Gln Lys Phe Gln Gly Arg Val Thr Met Thr Arg Asp Thr Ser Ile Ser
                85                  90                  95

Thr Ala Tyr Met Glu Leu Asn Arg Leu Arg Ser Asp Asp Thr Ala Val
            100                 105                 110

Tyr Tyr Cys Ala Arg Asp Gln Pro Leu Gly Tyr Cys Thr Asn Gly Val
        115                 120                 125

Cys Ser Tyr Phe Asp Tyr Trp Gly Gln Gly Thr Leu Val Thr Val Ser
    130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Asn Phe Gly Thr Gln
    210                 215                 220

Thr Tyr Thr Cys Asn Val Asp His Lys Pro Ser Asn Thr Lys Val Asp
225                 230                 235                 240
```

```
Lys Thr Val Glu Arg Lys Cys Cys Val Glu Cys Pro Pro Cys Pro Ala
                245                 250                 255

Pro Pro Val Ala Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Gln Phe Asn Trp Tyr Val Asp
    290                 295                 300

Gly Val Glu Val His Asn Ala Lys Thr Lys Pro Arg Glu Glu Gln Phe
305                 310                 315                 320

Asn Ser Thr Phe Arg Val Val Ser Val Leu Thr Val Val His Gln Asp
                325                 330                 335

Trp Leu Asn Gly Lys Glu Tyr Lys Cys Lys Val Ser Asn Lys Gly Leu
            340                 345                 350

Pro Ala Pro Ile Glu Lys Thr Ile Ser Lys Thr Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Met Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 41
<211> LENGTH: 234
<212> TYPE: PRT
<213> ORGANISM: Artificial
<220> FEATURE:
<223> OTHER INFORMATION: Synthetic Construct

<400> SEQUENCE: 41

Met Arg Leu Pro Ala Gln Leu Leu Gly Leu Leu Leu Leu Trp Phe Pro
1               5                   10                  15

Gly Ser Arg Cys Asp Ile Gln Met Thr Gln Ser Pro Ser Ser Val Ser
            20                  25                  30

Ala Ser Val Gly Asp Arg Val Thr Ile Thr Cys Arg Ala Ser Gln Gly
        35                  40                  45

Ile Tyr Ser Trp Leu Ala Trp Tyr Gln Gln Lys Pro Gly Lys Ala Pro
    50                  55                  60

Asn Leu Leu Ile Tyr Thr Ala Ser Thr Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Ala Asn
            100                 105                 110

Ile Phe Pro Leu Thr Phe Gly Gly Gly Thr Lys Val Glu Ile Lys Arg
        115                 120                 125
```

Thr Val Ala Ala Pro Ser Val Phe Ile Phe Pro Pro Ser Asp Glu Gln
            130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
                195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 42
<211> LENGTH: 451
<212> TYPE: PRT
<213> ORGANISM: Artificial
<220> FEATURE:
<223> OTHER INFORMATION: Synthetic Construct

<400> SEQUENCE: 42

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Arg Gly Ala Thr Leu Tyr Tyr Tyr Tyr Gly Met
                100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

```
Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 43
<211> LENGTH: 214
<212> TYPE: PRT
<213> ORGANISM: Artificial
<220> FEATURE:
<223> OTHER INFORMATION: Synthetic Construct

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asp Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Phe
                85                  90                  95

Thr Phe Gly Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 44
<211> LENGTH: 24
<212> TYPE: DNA
<213> ORGANISM: Artificial
<220> FEATURE:
<223> OTHER INFORMATION: Synthetic Construct

<400> SEQUENCE: 44
tcgtcgtttt gtcgttttgt cgtt                                              24

<210> SEQ ID NO 45
<211> LENGTH: 21
<212> TYPE: DNA
<213> ORGANISM: Artificial
<220> FEATURE:
<223> OTHER INFORMATION: Synthetic Construct

<400> SEQUENCE: 45
tcgtcgtttt cggtgctttt t                                                 21

<210> SEQ ID NO 46
<211> LENGTH: 21
<212> TYPE: DNA
<213> ORGANISM: Artificial
<220> FEATURE:
<223> OTHER INFORMATION: Synthetic Construct

<400> SEQUENCE: 46
tcgtcgtttt cggtcgtttt t                                                 21

<210> SEQ ID NO 47
<211> LENGTH: 239
<212> TYPE: PRT
<213> ORGANISM: Artificial
<220> FEATURE:
<223> OTHER INFORMATION: Synthetic Construct

<400> SEQUENCE: 47

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110
```

```
Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
            210                 215                 220

Val Thr Ala Ala Gly Ile Thr Leu Gly Met Asp Glu Leu Tyr Lys
225                 230                 235

<210> SEQ ID NO 48
<211> LENGTH: 185
<212> TYPE: PRT
<213> ORGANISM: Orthohepadnavirus hepatitis B virus

<400> SEQUENCE: 48

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
            130                 135                 140

Glu Thr Thr Val Val Arg Arg Gly Arg Gly Arg Ser Pro Arg Arg
145                 150                 155                 160

Arg Thr Pro Ser Pro Arg Arg Arg Ser Gln Ser Pro Arg Arg Arg
                165                 170                 175

Arg Ser Gln Ser Arg Glu Ser Gln Cys
            180                 185

<210> SEQ ID NO 49
<211> LENGTH: 226
<212> TYPE: PRT
<213> ORGANISM: Orthohepadnavirus hepatitis B virus

<400> SEQUENCE: 49

Met Glu Asn Ile Thr Ser Gly Phe Leu Gly Pro Leu Leu Val Leu Gln
1               5                   10                  15
```

```
Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ser Pro Val Cys
        35                  40                  45

Leu Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Thr Thr Thr Ser Thr Gly Pro Cys Lys Thr Cys Thr Thr Pro Ala
        115                 120                 125

Gln Gly Asn Ser Met Phe Pro Ser Cys Cys Cys Thr Lys Pro Thr Asp
    130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
            165                 170                 175

Val Pro Phe Val Gln Trp Phe Val Gly Leu Ser Pro Thr Val Trp Leu
        180                 185                 190

Ser Ala Ile Trp Met Met Trp Tyr Trp Gly Pro Ser Leu Tyr Ser Ile
    195                 200                 205

Val Ser Pro Phe Ile Pro Leu Leu Pro Ile Phe Phe Cys Leu Trp Val
    210                 215                 220

Tyr Ile
225

<210> SEQ ID NO 50
<211> LENGTH: 737
<212> TYPE: PRT
<213> ORGANISM: Artificial
<220> FEATURE:
<223> OTHER INFORMATION: Synthetic Construct

<400> SEQUENCE: 50

Met Ala Ser Glu Thr Asp Thr Leu Leu Leu Trp Val Leu Leu Leu Trp
1               5                   10                  15

Val Pro Gly Ser Thr Gly Asp Ala Ala His His His His His His Lys
            20                  25                  30

Ser Ser Ser Glu Ala Thr Asn Ile Thr Pro Lys His Asn Met Lys Ala
        35                  40                  45

Phe Leu Asp Glu Leu Lys Ala Glu Asn Ile Lys Lys Phe Leu His Asn
    50                  55                  60

Phe Thr Gln Ile Pro His Leu Ala Gly Thr Glu Gln Asn Phe Gln Leu
65                  70                  75                  80

Ala Lys Gln Ile Gln Ser Gln Trp Lys Glu Phe Gly Leu Asp Ser Val
            85                  90                  95

Glu Leu Thr His Tyr Asp Val Leu Leu Ser Tyr Pro Asn Lys Thr His
        100                 105                 110

Pro Asn Tyr Ile Ser Ile Ile Asn Glu Asp Gly Asn Glu Ile Phe Asn
    115                 120                 125

Thr Ser Leu Phe Glu Pro Pro Pro Ala Gly Tyr Glu Asn Val Ser Asp
    130                 135                 140
```

-continued

```
Ile Val Pro Pro Phe Ser Ala Phe Ser Pro Gln Gly Met Pro Glu Gly
145                 150                 155                 160

Asp Leu Val Tyr Val Asn Tyr Ala Arg Thr Glu Asp Phe Phe Lys Leu
            165                 170                 175

Glu Arg Asp Met Lys Ile Asn Cys Ser Gly Lys Ile Val Ile Ala Arg
                180                 185                 190

Tyr Gly Lys Val Phe Arg Gly Asn Lys Val Lys Asn Ala Gln Leu Ala
        195                 200                 205

Gly Ala Thr Gly Val Ile Leu Tyr Ser Asp Pro Ala Asp Tyr Phe Ala
    210                 215                 220

Pro Gly Val Lys Ser Tyr Pro Asp Gly Trp Asn Leu Pro Gly Gly Gly
225                 230                 235                 240

Val Gln Arg Gly Asn Ile Leu Asn Leu Asn Gly Ala Gly Asp Pro Leu
                245                 250                 255

Thr Pro Gly Tyr Pro Ala Asn Glu Tyr Ala Tyr Arg Arg Gly Ile Ala
            260                 265                 270

Glu Ala Val Gly Leu Pro Ser Ile Pro Val His Pro Ile Gly Tyr Tyr
        275                 280                 285

Asp Ala Gln Lys Leu Leu Glu Lys Met Gly Gly Ser Ala Ser Pro Asp
    290                 295                 300

Ser Ser Trp Arg Gly Ser Leu Lys Val Pro Tyr Asn Val Gly Pro Gly
305                 310                 315                 320

Phe Thr Gly Asn Phe Ser Thr Gln Lys Val Lys Met His Ile His Ser
                325                 330                 335

Thr Ser Glu Val Thr Arg Ile Tyr Asn Val Ile Gly Thr Leu Arg Gly
            340                 345                 350

Ala Val Glu Pro Asp Arg Tyr Val Ile Leu Gly Gly His Arg Asp Ser
        355                 360                 365

Trp Val Phe Gly Gly Ile Asp Pro Gln Ser Gly Ala Ala Val Val His
    370                 375                 380

Glu Ile Val Arg Ser Phe Gly Thr Leu Lys Lys Glu Gly Trp Arg Pro
385                 390                 395                 400

Arg Arg Thr Ile Leu Phe Ala Ser Trp Asp Ala Glu Glu Phe Gly Leu
                405                 410                 415

Leu Gly Ser Thr Glu Trp Ala Glu Glu Asn Ser Arg Leu Leu Gln Glu
            420                 425                 430

Arg Gly Val Ala Tyr Ile Asn Ala Asp Ser Ser Ile Glu Gly Asn Tyr
        435                 440                 445

Thr Leu Arg Val Asp Cys Thr Pro Leu Met Tyr Ser Leu Val Tyr Asn
    450                 455                 460

Leu Thr Lys Glu Leu Glu Ser Pro Asp Glu Gly Phe Glu Gly Lys Ser
465                 470                 475                 480

Leu Tyr Glu Ser Trp Thr Lys Ser Pro Ser Pro Glu Phe Ser Gly Met
                485                 490                 495

Pro Arg Ile Ser Lys Leu Gly Ser Gly Asn Asp Phe Glu Val Phe Phe
            500                 505                 510

Gln Arg Leu Gly Ile Ala Ser Gly Arg Ala Arg Tyr Thr Lys Asn Trp
        515                 520                 525

Glu Thr Asn Lys Phe Ser Ser Tyr Pro Leu Tyr His Ser Val Tyr Glu
    530                 535                 540

Thr Tyr Glu Leu Val Glu Lys Phe Tyr Asp Pro Met Phe Lys Tyr His
545                 550                 555                 560

Leu Thr Val Ala Gln Val Arg Gly Gly Met Val Phe Glu Leu Ala Asn
```

```
                    565                 570                 575

Ser Val Val Leu Pro Phe Asp Cys Arg Asp Tyr Ala Val Val Leu Arg
            580                 585                 590

Lys Tyr Ala Asp Lys Ile Tyr Asn Ile Ser Met Lys His Pro Gln Glu
            595                 600                 605

Met Lys Thr Tyr Ser Val Ser Phe Asp Ser Leu Phe Ser Ala Val Lys
            610                 615                 620

Asn Phe Thr Glu Ile Ala Ser Lys Phe Ser Glu Arg Leu Arg Asp Phe
625                 630                 635                 640

Asp Lys Ser Asn Pro Ile Leu Leu Arg Met Met Asn Asp Gln Leu Met
                645                 650                 655

Phe Leu Glu Arg Ala Phe Ile Asp Pro Leu Gly Leu Pro Asp Arg Pro
            660                 665                 670

Phe Tyr Arg His Val Ile Tyr Ala Pro Ser Ser His Asn Lys Tyr Ala
            675                 680                 685

Gly Glu Ser Phe Pro Gly Ile Tyr Asp Ala Leu Phe Asp Ile Glu Ser
            690                 695                 700

Lys Val Asp Pro Ser Gln Ala Trp Gly Glu Val Lys Arg Gln Ile Ser
705                 710                 715                 720

Ile Ala Thr Phe Thr Val Gln Ala Ala Glu Thr Leu Ser Glu Val
                725                 730                 735
Ala
```

<210> SEQ ID NO 51
<211> LENGTH: 9
<212> TYPE: PRT
<213> ORGANISM: Artificial
<220> FEATURE:
<223> OTHER INFORMATION: Synthetic Construct

<400> SEQUENCE: 51

```
Thr Tyr Val Pro Ala Asn Ala Ser Leu
1               5
```

<210> SEQ ID NO 52
<211> LENGTH: 15
<212> TYPE: PRT
<213> ORGANISM: Artificial
<220> FEATURE:
<223> OTHER INFORMATION: Synthetic Construct

<400> SEQUENCE: 52

```
Asp Met Val Leu Trp Lys Asp Val Phe Arg Lys Asn Asn Gln Leu
1               5                   10                  15
```

<210> SEQ ID NO 53
<211> LENGTH: 9
<212> TYPE: PRT
<213> ORGANISM: Artificial
<220> FEATURE:
<223> OTHER INFORMATION: Synthetic Construct

<400> SEQUENCE: 53

```
Ser Tyr Val Asn Thr Asn Met Gly Leu
1               5
```

<210> SEQ ID NO 54
<211> LENGTH: 957
<212> TYPE: PRT
<213> ORGANISM: Artificial
<220> FEATURE:

<223> OTHER INFORMATION: Synthetic Construct

<400> SEQUENCE: 54

```
Met Ala Ser Glu Leu Ala Ala Trp Cys Arg Trp Gly Phe Leu Leu Ala
1               5                   10                  15

Leu Leu Pro Pro Gly Ile Ala Gly Thr Gln Val Cys Thr Gly Thr Asp
            20                  25                  30

Met Lys Leu Arg Leu Pro Ala Ser Pro Glu Thr His Leu Asp Met Leu
        35                  40                  45

Arg His Leu Tyr Gln Gly Cys Gln Val Val Gln Gly Asn Leu Glu Leu
    50                  55                  60

Thr Tyr Val Pro Ala Asn Ala Ser Leu Ser Phe Leu Gln Asp Ile Gln
65                  70                  75                  80

Glu Val Gln Gly Tyr Met Leu Ile Ala His Asn Gln Val Lys Arg Val
                85                  90                  95

Pro Leu Gln Arg Leu Arg Ile Val Arg Gly Thr Gln Leu Phe Glu Asp
            100                 105                 110

Lys Tyr Ala Leu Ala Val Leu Asp Asn Arg Asp Pro Gln Asp Asn Val
        115                 120                 125

Ala Ala Ser Thr Pro Gly Arg Thr Pro Glu Gly Leu Arg Glu Leu Gln
    130                 135                 140

Leu Arg Ser Leu Thr Glu Ile Leu Lys Gly Gly Val Leu Ile Arg Gly
145                 150                 155                 160

Asn Pro Gln Leu Cys Tyr Gln Asp Met Val Leu Trp Lys Asp Val Phe
                165                 170                 175

Arg Lys Asn Asn Gln Leu Ala Pro Val Asp Ile Asp Thr Asn Arg Ser
            180                 185                 190

Arg Ala Cys Pro Pro Cys Ala Pro Ala Cys Lys Asp Asn His Cys Trp
        195                 200                 205

Gly Glu Ser Pro Glu Asp Cys Gln Ile Leu Thr Gly Thr Ile Cys Thr
    210                 215                 220

Ser Gly Cys Ala Arg Cys Lys Gly Arg Leu Pro Thr Asp Cys Cys His
225                 230                 235                 240

Glu Gln Cys Ala Ala Gly Cys Thr Gly Pro Lys His Ser Asp Cys Leu
                245                 250                 255

Ala Cys Leu His Phe Asn His Ser Gly Ile Cys Glu Leu His Cys Pro
            260                 265                 270

Ala Leu Val Thr Tyr Asn Thr Asp Thr Phe Glu Ser Met His Asn Pro
        275                 280                 285

Glu Gly Arg Tyr Thr Phe Gly Ala Ser Cys Val Thr Thr Cys Pro Tyr
    290                 295                 300

Asn Tyr Leu Ser Thr Glu Val Gly Ser Cys Thr Leu Val Cys Pro Pro
305                 310                 315                 320

Asn Asn Gln Glu Val Thr Ala Glu Asp Gly Thr Gln Arg Cys Glu Lys
                325                 330                 335

Cys Ser Lys Pro Cys Ala Arg Val Cys Tyr Gly Leu Gly Met Glu His
            340                 345                 350

Leu Arg Gly Ala Arg Ala Ile Thr Ser Asp Asn Val Gln Glu Phe Asp
        355                 360                 365

Gly Cys Lys Lys Ile Phe Gly Ser Leu Ala Phe Leu Pro Glu Ser Phe
    370                 375                 380

Asp Gly Asp Pro Ser Ser Gly Ile Ala Pro Leu Arg Pro Glu Gln Leu
385                 390                 395                 400
```

```
Gln Val Phe Glu Thr Leu Glu Glu Ile Thr Gly Tyr Leu Tyr Ile Ser
                405                 410                 415
Ala Trp Pro Asp Ser Leu Arg Asp Leu Ser Val Phe Gln Asn Leu Arg
            420                 425                 430
Ile Ile Arg Gly Arg Ile Leu His Asp Gly Ala Tyr Ser Leu Thr Leu
        435                 440                 445
Gln Gly Leu Gly Ile His Ser Leu Gly Leu Arg Ser Leu Arg Glu Leu
    450                 455                 460
Gly Ser Gly Leu Ala Leu Ile His Arg Asn Ala His Leu Cys Phe Val
465                 470                 475                 480
His Thr Val Pro Trp Asp Gln Leu Phe Arg Asn Pro His Gln Ala Leu
                485                 490                 495
Leu His Ser Gly Asn Arg Pro Glu Glu Asp Cys Gly Leu Glu Gly Leu
            500                 505                 510
Val Cys Asn Ser Leu Cys Ala His Gly His Cys Trp Gly Pro Gly Pro
        515                 520                 525
Thr Gln Cys Val Asn Cys Ser His Phe Leu Arg Gly Gln Glu Cys Val
    530                 535                 540
Glu Glu Cys Arg Val Trp Lys Gly Leu Pro Arg Glu Tyr Val Ser Asp
545                 550                 555                 560
Lys Arg Cys Leu Pro Cys His Pro Glu Cys Gln Pro Gln Asn Ser Ser
                565                 570                 575
Glu Thr Cys Phe Gly Ser Glu Ala Asp Gln Cys Ala Ala Cys Ala His
            580                 585                 590
Tyr Lys Asp Ser Ser Ser Cys Val Ala Arg Cys Pro Ser Gly Val Lys
        595                 600                 605
Pro Asp Leu Ser Tyr Met Pro Ile Trp Lys Tyr Pro Asp Glu Glu Gly
    610                 615                 620
Ile Cys Gln Pro Cys Pro Ile Asn Cys Thr His Ser Cys Val Asp Leu
625                 630                 635                 640
Asp Glu Arg Gly Cys Pro Ala Glu Gln Arg Ala Ser Pro Val Thr Phe
                645                 650                 655
Ile Ile Ala Thr Val Val Gly Val Leu Leu Phe Leu Ile Leu Val Val
            660                 665                 670
Val Val Gly Ile Leu Ile Lys Arg Arg Arg Gln Lys Ile Arg Lys Tyr
        675                 680                 685
Thr Met Arg Arg Asn Glu Asp Leu Gly Pro Ser Ser Pro Met Asp Ser
    690                 695                 700
Thr Phe Tyr Arg Ser Leu Leu Glu Asp Asp Met Gly Asp Leu Val
705                 710                 715                 720
Asp Ala Glu Glu Tyr Leu Val Pro Gln Gln Gly Phe Phe Ser Pro Asp
                725                 730                 735
Pro Thr Pro Gly Thr Gly Ser Thr Ala His Arg Arg His Arg Ser Ser
            740                 745                 750
Ser Thr Arg Ser Gly Gly Gly Glu Leu Thr Leu Gly Leu Glu Pro Ser
        755                 760                 765
Glu Glu Gly Pro Pro Arg Ser Pro Leu Ala Pro Ser Glu Gly Ala Gly
    770                 775                 780
Ser Asp Val Phe Asp Gly Asp Leu Ala Met Gly Val Thr Lys Gly Leu
785                 790                 795                 800
Gln Ser Leu Ser Pro His Asp Leu Ser Pro Leu Gln Arg Tyr Ser Glu
                805                 810                 815
Asp Pro Thr Leu Pro Leu Pro Pro Glu Thr Asp Gly Tyr Val Ala Pro
```

```
              820                 825                 830
Leu Ala Cys Ser Pro Gln Pro Glu Phe Val Asn Gln Ser Glu Val Gln
            835                 840                 845

Pro Gln Pro Pro Leu Thr Pro Glu Gly Pro Leu Pro Pro Val Arg Pro
        850                 855                 860

Ala Gly Ala Thr Leu Glu Arg Pro Lys Thr Leu Ser Pro Gly Lys Asn
865                 870                 875                 880

Gly Val Val Lys Asp Val Phe Ala Phe Gly Gly Ala Val Glu Asn Pro
                885                 890                 895

Glu Phe Leu Val Pro Arg Glu Gly Thr Ala Ser Pro Pro His Pro Ser
            900                 905                 910

Pro Ala Phe Ser Pro Ala Phe Asp Asn Leu Phe Phe Trp Asp Gln Asn
        915                 920                 925

Ser Ser Glu Gln Gly Pro Pro Ser Asn Phe Glu Gly Thr Pro Thr
    930                 935                 940

Ala Glu Asn Pro Glu Phe Leu Gly Leu Asp Val Pro Val
945                 950                 955

<210> SEQ ID NO 55
<211> LENGTH: 739
<212> TYPE: PRT
<213> ORGANISM: Artificial
<220> FEATURE:
<223> OTHER INFORMATION: Synthetic Construct

<400> SEQUENCE: 55

Met Ala Ser Ala Arg Arg Pro Arg Trp Leu Cys Ala Gly Ala Leu Val
1               5                   10                  15

Leu Ala Gly Gly Phe Phe Leu Leu Gly Phe Leu Phe Gly Trp Phe Ile
                20                  25                  30

Lys Ser Ser Ser Glu Ala Thr Asn Ile Thr Pro Lys His Asn Met Lys
            35                  40                  45

Ala Phe Leu Asp Glu Leu Lys Ala Glu Asn Ile Lys Lys Phe Leu His
        50                  55                  60

Asn Phe Thr Gln Ile Pro His Leu Ala Gly Thr Glu Gln Asn Phe Gln
65                  70                  75                  80

Leu Ala Lys Gln Ile Gln Ser Gln Trp Lys Glu Phe Gly Leu Asp Ser
                85                  90                  95

Val Glu Leu Thr His Tyr Asp Val Leu Leu Ser Tyr Pro Asn Lys Thr
                100                 105                 110

His Pro Asn Tyr Ile Ser Ile Ile Asn Glu Asp Gly Asn Glu Ile Phe
            115                 120                 125

Asn Thr Ser Leu Phe Glu Pro Pro Ala Gly Tyr Glu Asn Val Ser
        130                 135                 140

Asp Ile Val Pro Pro Phe Ser Ala Phe Ser Pro Gln Gly Met Pro Glu
145                 150                 155                 160

Gly Asp Leu Val Tyr Val Asn Tyr Ala Arg Thr Glu Asp Phe Phe Lys
                165                 170                 175

Leu Glu Arg Asp Met Lys Ile Asn Cys Ser Gly Lys Ile Val Ile Ala
                180                 185                 190

Arg Tyr Gly Lys Val Phe Arg Gly Asn Lys Val Lys Asn Ala Gln Leu
            195                 200                 205

Ala Gly Ala Thr Gly Val Ile Leu Tyr Ser Asp Pro Ala Asp Tyr Phe
        210                 215                 220

Ala Pro Gly Val Lys Ser Tyr Pro Asp Gly Trp Asn Leu Pro Gly Gly
```

-continued

```
             225                 230                 235                 240
        Gly Val Gln Arg Gly Asn Ile Leu Asn Leu Asn Gly Ala Gly Asp Pro
                        245                 250                 255
        Leu Thr Pro Gly Tyr Pro Ala Asn Glu Tyr Ala Tyr Arg Arg Gly Ile
                        260                 265                 270
        Ala Glu Ala Val Gly Leu Pro Ser Ile Pro Val His Pro Ile Gly Tyr
                        275                 280                 285
        Tyr Asp Ala Gln Lys Leu Leu Glu Lys Met Gly Gly Ser Ala Ser Pro
                        290                 295                 300
        Asp Ser Ser Trp Arg Gly Ser Leu Lys Val Pro Tyr Asn Val Gly Pro
        305                 310                 315                 320
        Gly Phe Thr Gly Asn Phe Ser Thr Gln Lys Val Lys Met His Ile His
                        325                 330                 335
        Ser Thr Ser Glu Val Thr Arg Ile Tyr Asn Val Ile Gly Thr Leu Arg
                        340                 345                 350
        Gly Ala Val Glu Pro Asp Arg Tyr Val Ile Leu Gly Gly His Arg Asp
                        355                 360                 365
        Ser Trp Val Phe Gly Gly Ile Asp Pro Gln Ser Gly Ala Ala Val Val
                        370                 375                 380
        His Glu Ile Val Arg Ser Phe Gly Thr Leu Lys Lys Glu Gly Trp Arg
        385                 390                 395                 400
        Pro Arg Arg Thr Ile Leu Phe Ala Ser Trp Asp Ala Glu Glu Phe Gly
                        405                 410                 415
        Leu Leu Gly Ser Thr Glu Trp Ala Glu Glu Asn Ser Arg Leu Leu Gln
                        420                 425                 430
        Glu Arg Gly Val Ala Tyr Ile Asn Ala Asp Ser Ser Ile Glu Gly Asn
                        435                 440                 445
        Tyr Thr Leu Arg Val Asp Cys Thr Pro Leu Met Tyr Ser Leu Val Tyr
                        450                 455                 460
        Asn Leu Thr Lys Glu Leu Glu Ser Pro Asp Glu Gly Phe Glu Gly Lys
        465                 470                 475                 480
        Ser Leu Tyr Glu Ser Trp Thr Lys Lys Ser Pro Ser Pro Glu Phe Ser
                        485                 490                 495
        Gly Met Pro Arg Ile Ser Lys Leu Gly Ser Gly Asn Asp Phe Glu Val
                        500                 505                 510
        Phe Phe Gln Arg Leu Gly Ile Ala Ser Gly Arg Ala Arg Tyr Thr Lys
                        515                 520                 525
        Asn Trp Glu Thr Asn Lys Phe Ser Ser Tyr Pro Leu Tyr His Ser Val
        530                 535                 540
        Tyr Glu Thr Tyr Glu Leu Val Glu Lys Phe Tyr Asp Pro Met Phe Lys
        545                 550                 555                 560
        Tyr His Leu Thr Val Ala Gln Val Arg Gly Gly Met Val Phe Glu Leu
                        565                 570                 575
        Ala Asn Ser Val Val Leu Pro Phe Asp Cys Arg Asp Tyr Ala Val Val
                        580                 585                 590
        Leu Arg Lys Tyr Ala Asp Lys Ile Tyr Asn Ile Ser Met Lys His Pro
                        595                 600                 605
        Gln Glu Met Lys Thr Tyr Ser Val Ser Phe Asp Ser Leu Phe Ser Ala
                        610                 615                 620
        Val Lys Asn Phe Thr Glu Ile Ala Ser Lys Phe Ser Glu Arg Leu Arg
        625                 630                 635                 640
        Asp Phe Asp Lys Ser Asn Pro Ile Leu Leu Arg Met Met Asn Asp Gln
                        645                 650                 655
```

```
Leu Met Phe Leu Glu Arg Ala Phe Ile Asp Pro Leu Gly Leu Pro Asp
            660                 665                 670

Arg Pro Phe Tyr Arg His Val Ile Tyr Ala Pro Ser Ser His Asn Lys
        675                 680                 685

Tyr Ala Gly Glu Ser Phe Pro Gly Ile Tyr Asp Ala Leu Phe Asp Ile
    690                 695                 700

Glu Ser Lys Val Asp Pro Ser Gln Ala Trp Gly Val Lys Arg Gln
705                 710                 715                 720

Ile Ser Ile Ala Thr Phe Thr Val Gln Ala Ala Glu Thr Leu Ser
            725                 730                 735

Glu Val Ala
```

<210> SEQ ID NO 56
<211> LENGTH: 2217
<212> TYPE: DNA
<213> ORGANISM: Artificial
<220> FEATURE:
<223> OTHER INFORMATION: Synthetic Construct

<400> SEQUENCE: 56

```
atggctagcg ctagaaggcc cagatggctg tgcgctggcg ccctggtgct ggctggcgga    60
ttcttcctgc tgggcttcct gttcggctgg ttcatcaagt cctccagcga ggccaccaac   120
atcacccca gcacaacat gaaggccttt ctggacgagc tgaaggccga gaatatcaag    180
aagttcctgc acaacttcac ccagatcccc acctggccg caccgagca gaacttccag    240
ctggccaagc agatccagtc ccagtggaaa gagttcggcc tggactccgt ggaactgacc    300
cactacgacg tgctgctgtc ctaccccaac aagacccacc caactacat ctccatcatc    360
aacgaggacg gcaacgaaat cttcaacacc tccctgttcg agcccccacc agccggctac    420
gagaacgtgt ccgacatcgt gccccattc tccgcattca gtccacaagg catgcccgag    480
ggcgacctgt gtacgtgaa ctacgccagg accgaggact cttcaagct ggaaagggac    540
atgaagatca actgctccgg caagatcgtg atcgccagat acggcaaggt gttcaggggc    600
aacaaagtga agaacgctca gctggctggg gccaccggcg tgatcctgta ctctgacccc    660
gccgactact tcgccccagg cgtgaagtcc taccccgacg gctggaacct gccaggtggc    720
ggagtgcaga ggggcaacat cctgaacctg aacggcgctg cgaccccct gaccccagga    780
taccccgcca acgagtacgc ctacagaaga ggaatcgccg aggccgtggg cctgccctct    840
atcccagtgc accccatcgg ctactacgac gcccagaaac tgctggaaaa gatgggcggc    900
tccgcctccc ccgactcctc ttggagaggc tccctgaagg tgccctacaa cgtgggccca    960
ggcttcaccg caacttctc cacccagaaa gtgaagatgc acatccactc cacctccgaa   1020
gtgaccagga tctacaacgt gatcggcacc ctgagaggcg ccgtggaacc cgacagatac   1080
gtgatcctgg cggccacag ggacagctgg gtgttcggcg catcgaccc acagtctggc   1140
gccgctgtgg tgcacgagat cgtgcggtcc ttcggaaccc tgaagaaaga gggatggcgc   1200
cccagaagga caatcctgtt cgcctcctgg gacgccgagg aattcggcct gctgggatcc   1260
accgagtggg ccgaggaaaa ctccaggctg ctgcaggaaa ggggcgtcgc ctacatcaac   1320
gccgactcct ccatcgaggg caactacacc ctgagggtgg actgcacccc cctgatgtac   1380
tcccctggtgt acaacctgac caaagagctg gaatccccg acgagggctt cgagggcaag   1440
tccctgtacg agtcctggac caagaagtcc ccatcccccg agttctccgg catgcccagg   1500
atctccaagc tgggctccgg caacgacttc gaggtgttct tccagaggct gggaatcgcc   1560
```

```
tccggcaggg ccagatacac caagaactgg gagacaaaca agttctcctc ctaccccctg    1620
taccactccg tgtacgaaac ctacgagctg gtggaaaagt tctacgaccc catgttcaag    1680
taccacctga ccgtggccca ggtccgcgga ggcatggtgt tcgagctggc caactccgtg    1740
gtgctgccct tcgactgcag agactatgct gtggtgctga ggaagtacgc cgacaaaatc    1800
tacaacatct ccatgaagca ccccaggaa atgaagacct actccgtgtc cttcgactcc     1860
ctgttctccg ccgtgaagaa tttcaccgag atcgcctcca gttctccga gaggctgagg     1920 gacttcgaca gtccaaccc catcctgctg aggatgatga cgaccagct gatgttcctg      1980 gaaagggcct tcatcgaccc cctgggcctg ccagacaggc ccttctacag gcacgtgatc    2040
tacgccccat cctcccacaa caaatacgcc ggcgagtcct ccccggcat ctacgatgcc    2100 ctgttcgaca tcgagtccaa ggtggacccc tcccaggctt ggggcgaagt gaagaggcag    2160
atcagtatcg ccacattcac agtgcaggcc gctgccgaaa ccctgtccga ggtggcc      2217
```

<210> SEQ ID NO 57
<211> LENGTH: 20
<212> TYPE: PRT
<213> ORGANISM: Foot-and-mouth disease virus

<400> SEQUENCE: 57

Gln Thr Leu Asn Phe Asp Leu Leu Lys Leu Ala Gly Asp Val Glu Ser
1               5                   10                  15

Asn Pro Gly Pro
            20

<210> SEQ ID NO 58
<211> LENGTH: 18
<212> TYPE: PRT
<213> ORGANISM: Thosea Asigna Virus

<400> SEQUENCE: 58

Glu Gly Arg Gly Ser Leu Leu Thr Cys Gly Asp Val Glu Glu Asn Pro
1               5                   10                  15

Gly Pro

<210> SEQ ID NO 59
<211> LENGTH: 20
<212> TYPE: PRT
<213> ORGANISM: Encephalomyocarditis virus

<400> SEQUENCE: 59

His Tyr Ala Gly Tyr Phe Ala Asp Leu Leu Ile His Asp Ile Glu Thr
1               5                   10                  15

Asn Pro Gly Pro
            20

<210> SEQ ID NO 60
<211> LENGTH: 20
<212> TYPE: PRT
<213> ORGANISM: Equine Rhinitis A Virus

<400> SEQUENCE: 60

Gln Cys Thr Asn Tyr Ala Leu Leu Lys Leu Ala Gly Asp Val Glu Ser
1               5                   10                  15

Asn Pro Gly Pro
            20

```
<210> SEQ ID NO 61
<211> LENGTH: 19
<212> TYPE: PRT
<213> ORGANISM: Porcine Teschovirus

<400> SEQUENCE: 61

Ala Thr Asn Phe Ser Leu Leu Lys Gln Ala Gly Asp Val Glu Glu Asn
1               5                   10                  15

Pro Gly Pro

<210> SEQ ID NO 62
<211> LENGTH: 568
<212> TYPE: RNA
<213> ORGANISM: Encephalomyocarditis virus

<400> SEQUENCE: 62
uaacguuacu ggccgaagcc gcuuggaaua aggccggugu gcguuugucu auauguuauu      60
uuccaccaua uugccgucuu uuggcaaugu gagggcccgg aaaccuggcc cugucuucuu    120
gacgagcauu ccuagggguc uuucccucu cgccaaagga augcaagguc uguugaaugu     180
cgugaaggaa gcaguuccuc uggaagcuuc uugaagacaa acaacgucug uagcgacccu    240
uugcaggcag cggaaccccc caccuggcga caggugccuc ugcggccaaa agccacgugu    300
auaagauaca ccugcaaagg cggcacaacc ccagugccac guugugaguu ggauaguugu    360
ggaaagaguc aaauggcucu ccucaagcgu auucaacaag gggcugaagg augcccagaa    420 gguacccccau uguaugggau cugaucuggg gccucggugc acaugcuuua cauguguuua    480
gucgagguua aaaaacgucu aggcccccg aaccacgggg acgugguuuu ccuuugaaaa    540
acacgaugau aauauggcca caaccaug                                        568
```

PROSTATE-ASSOCIATED ANTIGENS AND VACCINE-BASED IMMUNOTHERAPY REGIMENS

CROSS-REFERENCE TO RELATED APPLICATIONS

This application is a division of application Ser. No. 13/875,162 filed on May 1, 2013, now allowed, which claims benefit of U.S. Provisional Application No. 61/642,844 filed on May 4, 2012. Both application Ser. No. 13/875,162 and U.S. Provisional Application No. 61/642,844 are incorporated herein by reference in their entirety.

REFERENCE TO SEQUENCE LISTING

This application is being filed along with a sequence listing in electronic format. The sequence listing is provided as a file in .txt format entitled "PC71854B_SEQ LISTING_ST25.TXT", created on Jan. 5, 2016 and having a size of 260 KB. The sequence listing contained in the .txt file is part of the specification and is herein incorporated by reference in its entity.

FIELD OF THE INVENTION

The present invention relates generally to immunotherapy and specifically to vaccines and methods for treating or preventing neoplastic disorders.

BACKGROUND OF THE INVENTION

Cancer is a leading cause of mortality worldwide. Traditional regimens of cancer management have been successful in the management of a selective group of circulating and solid cancers. However, many tumors are resistant to traditional approaches. In recent years, immunotherapy for the treatment of cancers has been explored, which involves the generation of an active systemic tumor-specific immune response of host origin by administering a vaccine composition at a site distant from the tumor. Various types of vaccines have been proposed, including those containing isolated tumor-associated antigens.

Prostate cancer is the second most commonly diagnosed cancer and the fourth leading cause of cancer-related death in men in the developed countries worldwide. Various prostate-associated antigens (PAA), such as prostate-specific antigen (PSA), prostate-specific membrane antigen (PSMA), and prostate stem cell antigen (PSCA) have been shown to be overexpressed by prostate cancer cells as compared to normal counterparts. These antigens, therefore, represent possible targets for inducing specific immune responses against cancers expressing the antigens via the use of vaccine-based immunotherapy. (see e.g. Marrari, A., M. lero, et al. (2007). "Vaccination therapy in prostate cancer." Cancer Immunol Immunother 56(4): 429-45.)

PSCA is a 123-amino acid membrane protein. The amino acid sequence of the full length human PSCA consists of amino acids 4-123 of SEQ ID NO:21. PSCA has high tissue specificity and is expressed on more than 85% of prostate cancer specimens, with expression levels increasing with higher Gleason scores and androgen independence. It is expressed in 80-100% of bone metastasis of prostate cancer patients.

PSA is a kallikrein-like serine protease that is produced exclusively by the columnar epithelial cells lining the acini and ducts of the prostate gland. PSA mRNA is translated as an inactive 261-amino acid preproPSA precursor. PreproPSA has 24 additional residues that constitute the pre-region (the signal polypeptide) and the propolypeptide. Release of the propolypeptide results in the 237-amino acid, mature extracellular form, which is enzymatically active. The amino acid sequence of the human full length PSA is provided in SEQ ID NO: 15. PSA is organ-specific and, as a result, it is produced by the epithelial cells of benign prostatic hyperplastic (BPH) tissue, primary prostate cancer tissue, and metastatic prostate cancer tissue.

PSMA, also known as Folate hydrolase 1 (FOLH1), is composed of 750 amino acids. The amino acid sequence of the human full length PSMA is provided in SEQ ID NO:1. PSMA includes a cytoplasmic domain (amino acids 1-19), a transmembrane domain (amino acids 20-43), and an extracellular domain (amino acids 44-750). PSMA is a type II dimeric transmembrane protein expressed on the surface of prostate cancer cells and on neovasculature. It is also expressed on normal prostate cells, brain, salivary gland and biliary tree. However, in prostate cancer cells it was found to be expressed at 1000-fold higher levels than normal tissues. It is abundantly expressed on neovasculature of a variety of other solid tumors such as colon, breast, liver, bladder, pancreas, lung, renal cancers as well as melanoma and sarcomas. Thus, PSMA is considered a target not only specific for prostate cancer cells but also a pan-carcinoma target for other cancers. The expression of PSMA appears to be a universal feature of prostate carcinomas and its increased expression correlates with tumor aggressiveness. PSMA expression is highest in high-grade tumors, metastatic lesions and androgen-independent disease.

While a large number of tumor-associated antigens have been identified and many of these antigens have been explored as protein-based or DNA-based vaccines for the treatment or prevention of cancers, most clinical trials so far have failed to produce a therapeutic product. One of the challenges in developing cancer vaccines resides in the fact that the cancer antigens are usually self-derived and, therefore, poorly immunogenic because the immune system is self-regulated not to recognize self-proteins. Accordingly, a need exists for a method to enhance the immunogenicity or therapeutic effect of cancer vaccines.

Numerous approaches have been explored for enhancing the immunogenicity or enhancing anti-tumor efficacy of cancer vaccines. One of such approach involves the use of various immune modulators, such as TLR agonists, TNFR agonists, CTLA-4 inhibitors, and protein kinase inhibitors.

Toll-like receptors (TLRs) are type 1 membrane receptors that are expressed on hematopoietic and non-hematopoietic cells. At least 11 members have been identified in the TLR family. These receptors are characterized by their capacity to recognize pathogen-associated molecular patterns (PAMP) expressed by pathogenic organisms. It has been found that triggering of TLR elicits profound inflammatory responses through enhanced cytokine production, chemokine receptor expression (CCR2, CCR5 and CCR7), and costimulatory molecule expression. As such, these receptors in the innate immune systems exert control over the polarity of the ensuing acquired immune response. Among the TLRs, TLR9 has been extensively investigated for its functions in immune responses. Stimulation of the TLR9 receptor directs antigen-presenting cells (APCs) towards priming potent, $T_H1$-dominated T-cell responses, by increasing the production of pro-inflammatory cytokines and the presentation of co-stimulatory molecules to T cells. CpG oligonucleotides, ligands for TLR9, were found to be a class of potent immunostimulatory factors. CpG therapy has been tested against a wide variety of tumor models in mice, and has consistently been shown to promote tumor inhibition or regression.

Cytotoxic T-Lymphocyte Antigen 4 (CTLA-4) is a member of the immunoglobulin superfamily and is expressed on the surface of Helper T cells. CTLA-4 is a negative regulator of CD28 dependent T cell activation, and acts as an inhibitory checkpoint for the adaptive immune response. Similar to the T-cell costimulatory protein CD28, CTLA-4 binds to CD80 and CD86 on antigen-presenting cells. CTLA-4 transmits an inhibitory signal to T cells, whereas CD28 transmits a stimulatory signal. Human antibodies against human CTLA-4 have been described as immunostimulation modulators in a number of disease conditions, such as treating or preventing viral and bacterial infection and for treating cancer (WO 01/14424 and WO 00/37504). Various preclinical studies have shown that CTLA-4 blockade by monoclonal antibodies enhances the host immune response against immunogenic tumors, and can even reject established tumors. Two fully human anti-human CTLA-4 monoclonal antibodies (mAbs), ipilimumab (MDX-010) and Tremelimumab (also known as CP-675206), have been investigated in clinical trials in the treatment of various types of solid tumors.

The tumor necrosis factor (TNF) superfamily is a group of cytokines that engage specific cognate cell surface receptors, the TNF receptor (TNFR) superfamily. Members of the tumor necrosis factor superfamily act through ligand-mediated trimerization, causing recruitment of several intracellular adaptors to activate multiple signal transduction pathways, such as apoptosis, NF-kB pathway, JNK pathway, as well as immune and inflammatory responses. Examples of the TNF Superfamily include CD40 ligands, OX40 ligands, 4-1BB ligands, CD27, CD30 ligand (CD153), TNF-alpha, TNF-beta, RANK ligands, LT-alpha, LT-beta, GITR ligands, and LIGHT. The TNFR Superfamily includes, for example, CD40, OX40, 4-1BB, CD70 (CD27 ligand), CD30, TNFR2, RANK, LT-beta R, HVEM, GITR, TROY, and RELT. CD40 is found on the surface of B lymphocytes, dendritic cells, follicular dendritic cells, hematopoietic progenitor cells, epithelial cells, and carcinomas. CD40 binds to a ligand (CD40-L), which is a glycoprotein and expressed on activated T cells, mostly CD4+ but also some CD8+ as well as basophils/mast cells. Because of the role of CD40 in innate and adaptive immune responses, CD40 agonists, including various CD40 agonistic antibodies, such as the fully human agonist CD40 monoclonal antibody CP870893, have been explored for usage as vaccine adjuvants and in therapies.

Protein kinases are a family of enzymes that catalyze the phosphorylation of specific residues in proteins. Protein kinases are key elements in signal transduction pathways responsible for transducing extracellular signals, including the action of cytokines on their receptors, to the nuclei, triggering various biological events. The many roles of protein kinases in normal cell physiology include cell cycle control and cell growth, differentiation, apoptosis, cell mobility and mitogenesis. Kinases such as c-Src, c-Abl, mitogen activated protein (MAP) kinase, phosphotidylinositol-3-kinase (PI3K) AKT, and the epidermal growth factor (EGF) receptor are commonly activated in cancer cells, and are known to contribute to tumorigenesis. Logically, a number of kinase inhibitors are currently being developed for anti-cancer therapy, in particular tyrosine kinase inhibitors (TKIs): cyclin-dependent kinase inhibitors, aurora kinase inhibitors, cell cycle checkpoint inhibitors, epidermal growth factor receptor (EGFR) inhibitors, FMS-like tyrosine kinase inhibitors, platelet-derived growth factor receptor (PDGFR) inhibitors, kinase insert domain inhibitors, inhibitors targeting the PI3K/Akt/mTOR pathway, inhibitors targeting the Ras-Raf-MEK-ERK (ERK) pathway, vascular endothelial growth factor receptor (VEGFR) kinase inhibitors, c-kit inhibitors and serine/threonine kinase inhibitors. A number of kinase inhibitors have been investigated in clinical investigation for use in anti-cancer therapies, which includes, for example, MK0457, VX-680, ZD6474, MLN8054, AZD2171, SNS-032, PTK787/ZK222584, Sorafenib (BAY43-9006), SU5416, SU6668 AMG706, Zactima (ZD6474), MP-412, Dasatinib, CEP-701, (Lestaurtinib), XL647, XL999, Tykerb, (Lapatinib), MLN518, (formerly known as CT53518), PKC412, ST1571, AMN107, AEE 788, OSI-930, OSI-817, Sunitinib malate (Sutent; SU11248), Vatalanib (PTK787/ZK 222584), SNS-032, SNS-314 and Axitinib (AG-013736). Gefitinib and Erlotinib are two orally available EGFR-TKIs.

The immune modulators that have been explored are typically administered systemically to the patients, for example, by oral administration, intravenous injection or infusion, or intramuscular injection. One major factor that limits the effective use of some of the immune modulators is toxicity caused by high systemic exposure to the administered agents. For example, with respect to CD40 agonists, it has been reported that 0.3 mg/kg is the maximum tolerated dose for an exemplified agonistic CD40 antibody and that higher doses may elicit side effects including venous thromboembolism, grade 3 headache, cytokine release resulting in toxic effects such as chills and the like, and transient liver toxicity. (Vanderheide et al., J Clin. Oncol. 25(7): 876-8833 (March 2007). In a clinical trial to investigate combinations of intravenous Tremelimumab (an anti-CTLA-4 antibody) plus oral sunitinib in patients with metastatic renal cell carcinoma, rapid onset of renal failure was observed and, as a result, further investigation of Tremelimumab at doses higher than 6 mg/kg plus sunitinib at 37.5 mg daily was not recommended. See: Brian I. Rini et al.: Phase 1 Dose-Escalation Trial of Tremelimumab Plus Sunitinib in Patients With Metastatic Renal Cell Carcinoma. Cancer 117(4)158-767 (2011)]. Therefore, there is a need for vaccine-based immunotherapy regimens where the immune modulators are administered at effective doses which do not elicit severe adverse side effects such as liver toxicity or renal failure.

SUMMARY OF THE INVENTION

In some aspects, the present disclosure provides isolated immunogenic PSMA polypeptides and immunogenic PSA polypeptides, which are useful, for example, for eliciting an immune response in vivo (e.g. in an animal, including humans) or in vitro, generating antibodies, or for use as a component in vaccines for treating cancers, including prostate cancer. In one aspect, the present disclosure provides isolated immunogenic PSMA polypeptides which have at least 90% identity to amino acids 15-750 of the human PSMA of SEQ ID NO:1 and comprise the amino acids of at least 10, 11, 12, 13, 14, 15, 16, 17, 18, or 19 of the conserved T cell epitopes of the human PSMA at corresponding positions.

In other aspects, the present disclosure provides nucleic acid molecules that encode immunogenic PAA polypeptides. In some embodiments, the present disclosure provides isolated nucleic acid molecules, or degenerate variants thereof, which comprise a nucleotide sequence encoding an immunogenic PSMA polypeptide, or a functional variant of said polypeptide, provided by the present disclosure.

In some other aspects, the present disclosure provides multi-antigen nucleic acid constructs that each encode two or more immunogenic PAA polypeptides.

The disclosure also provides vectors containing one or more nucleic acid molecules of the invention. The vectors are useful for cloning or expressing the immunogenic PAA polypeptides encoded by the nucleic acid molecules, or for delivering the nucleic acid molecules in a composition, such as a vaccine, to a host cell or to a host animal, such as a human.

In some further aspects, the present disclosure provides compositions comprising one or more immunogenic PAA polypeptides, isolated nucleic acid molecules encoding immunogenic PAA polypeptides, or vectors or plasmids containing nucleic acid molecules encoding immunogenic PAA polypeptides. In some embodiments, the composition is an immunogenic composition useful for eliciting an immune response against a PAA in a mammal, such as a mouse, dog, monkey, or human. In some embodiments, the composition is a vaccine composition useful for immunization of a mammal, such as a human, for inhibiting abnormal cell proliferation, for providing protection against the development of cancer (used as a prophylactic), or for treatment of disorders (used as a therapeutic) associated with PAA over-expression, such as cancer, particularly prostate cancer.

In still other aspects, the present disclosure provides methods of using the immunogenic PAA polypeptides, isolated nucleic acid molecules, and compositions comprising an immunogenic PAA polypeptide or isolated nucleic acid molecules described herein above. In some embodiments, the present disclosure provides a method of eliciting an immune response against a PAA in a mammal, particularly a human, comprising administering to the mammal an effective amount of a polypeptide provided by the invention that is immunogenic against the target PAA, an effective amount of an isolated nucleic acid molecule encoding such an immunogenic polypeptide, or a composition comprising such an immunogenic PAA polypeptide or an isolated nucleic acid molecule encoding such an immunogenic PAA polypeptide. The polypeptide or nucleic acid vaccines may be used together with one or more adjuvants.

In yet other aspects, the present disclosure provides vaccine-based immunotherapy regimens (or "VBIR") that involve co-administration of a vaccine delivering various tumor associated antigens (TAAs) for inducing TAA specific immune responses to treat a variety of cancers in combination with at least one immune-suppressive-cell inhibitor and at least one immune-effector-cell enhancer. Specifically, in some aspects, the disclosure provides a method of enhancing the immunogenicity or therapeutic effect of a vaccine for the treatment of a neoplastic disorder in a mammal, comprising administering to the mammal receiving the vaccine an effective amount of at least one immune-suppressive-cell inhibitor and at least one immune-effector-cell enhancer. In a further aspect, the disclosure provides a method of treating a neoplastic disorder in a mammal, comprising administering to the mammal a vaccine, at least one immune-suppressive-cell inhibitor, and at least one immune-effector-cell enhancer.

BRIEF DESCRIPTION OF THE DRAWINGS

FIG. 2. Amino acid alignment of five viral 2A cassettes, which are FMDV 2A (SEQ ID NO:57), TAV 2A (SEQ ID NO:58), EMCV 2A (SEQ ID NO:59), ERAV 2A (SEQ ID NO:60), and PTV 2A (SEQ ID NO:61). The skipped glycine-proline bonds are indicated by asterisks.

FIG. 3. Sequence of the preferred EMCV IRES (SEQ ID NO:62). The translation initiation site is indicated by the asterisk. The minimal IRES element excludes the underlined first 5 codons of the EMCV L protein.

FIG. 5A) and full length human PSCA (FIG. 5B) in HEK293 cells transfected with dual antigen vaccine constructs as measured by western blotting with PSMA and PSCA specific monoclonal antibodies.

FIGS. 16A-16C. Graphs depicting results of a representative study that evaluates the immunogenicity of the dual antigen vaccines by IFN-γ ELISPOT assay, in which T cell responses to (a) individual PSMA peptides (FIG. 16A), (b) three different PSMA peptide pools (FIG. 16B), and (c) a PSCA peptide (FIG. 16C) were assessed.

FIGS. 27A, 27B. Graphs depicting results of a representative study that evaluates the T cell immune response of human PSMA modified antigen (amino acids 15-750) versus full-length human PSMA antigen (amino acids 1-750) in Pasteur (HLA-A2/DR1) transgenic mice by IFN-γ ELISPOT assay using (a) PSMA derived HLA-A2-restricted peptides (FIG. 27A) or (b) SK-Mel5 cells transduced with Ad-hPSMA or purified hPSMA full-length protein (FIG. 27B).

FIGS. 31A and 31B. Graphs depicting results of a representative study that evaluates the immunomodulatory activity of anti-murine CTLA-4 monoclonal antibody (clone 9H10) on the quality of the immune responses induced by a rat Her-2 DNA vaccine using an intracellular cytokine staining assay, in which (a) cytokine positive CD8 T cells (FIG. 31A) and (b) cytokine positive CD4 T cells (FIG. 31B) were measured.

FIGS. 33A-33D. Graphs depicting results from a representative study that evaluates the effect of sunitinib malate (Sutent) on the anti-tumor efficacy of a cancer vaccine (rHER2), in which individual tumor growth rates were measured in mice treated with (a) the control agents (FIG. 33A), (b) sunitinib malate and the control vaccine (FIG. 33B), (c) the vehicle and the cancer vaccine (FIG. 33C), or (d) sunitinib malate and the cancer vaccine (FIG. 33D).

FIG. 35A) and Treg containing CD25+CD4+ cells (FIG. 35B) in the periphery blood of the groups of mice from the study described FIGS. 33A-33D.

FIG. 36A), (b) myeloid derived suppressor cells (Gr1+CD11b+; FIG. 36B), and (c) PD-1+CD8 T cells (FIG. 36C) isolated from tumors of the mice.

DETAILED DESCRIPTION OF THE INVENTION

A. Definitions

Figure 1:
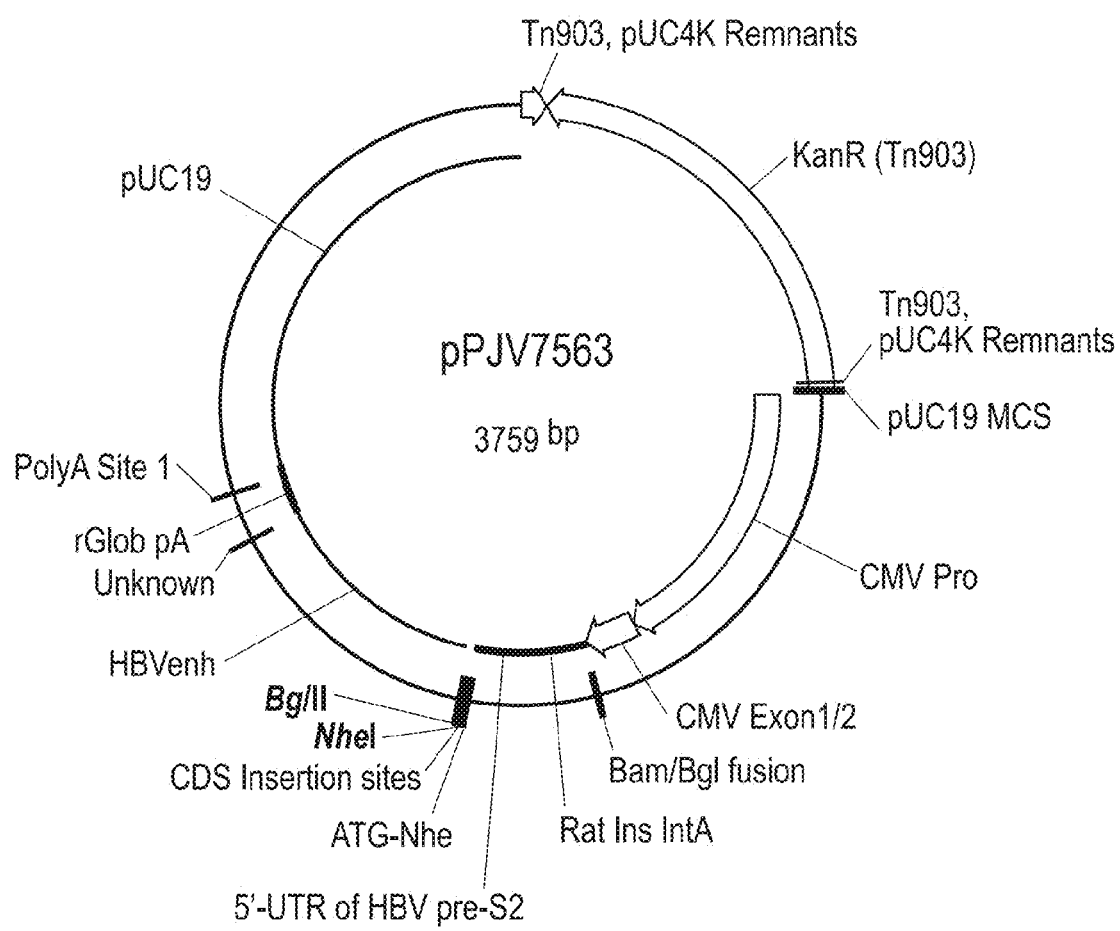
FIG. 1. Schematic illustration of PJV7563 vector.
Figure 4:
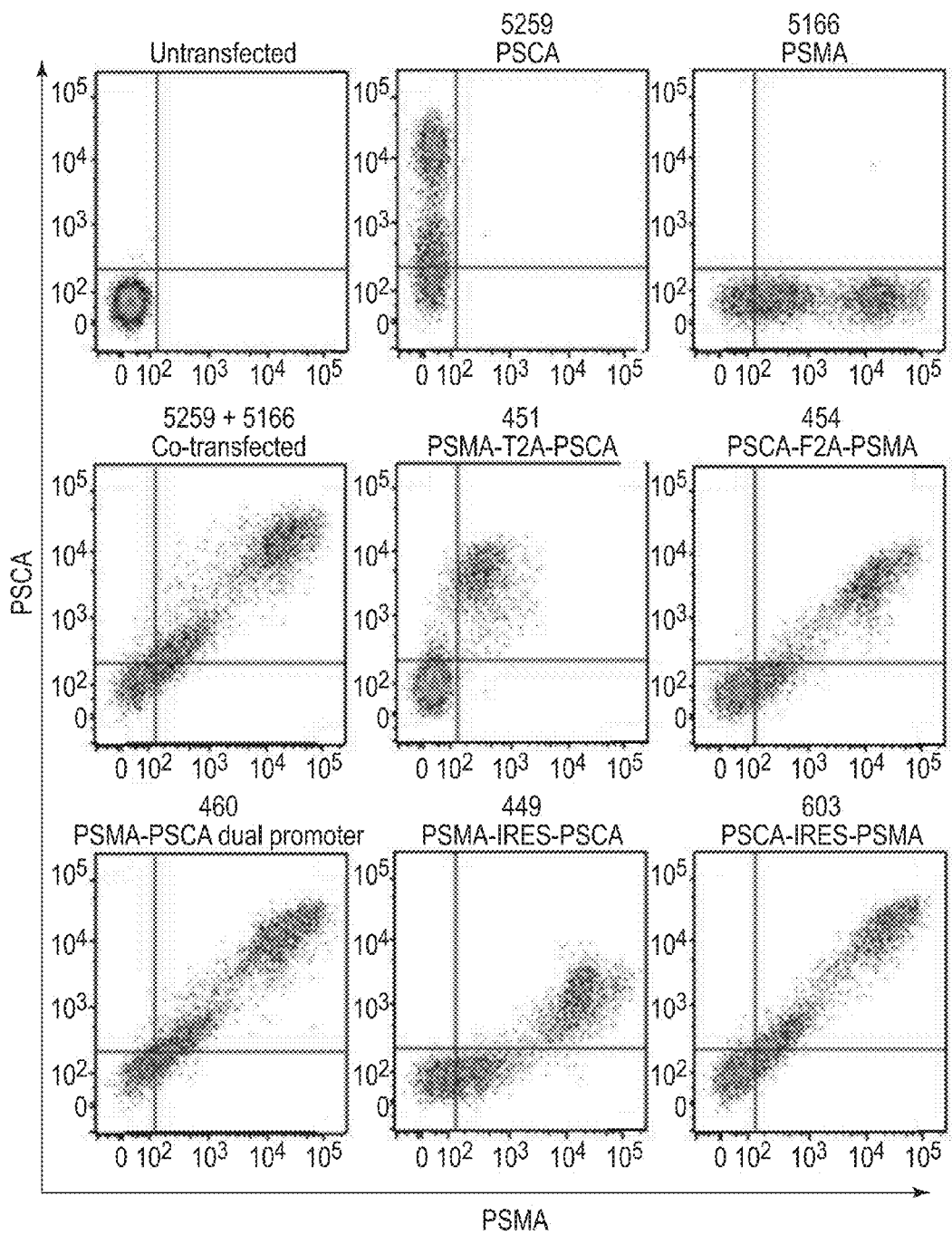
FIG. 4. Dot plots showing expression of the human PSMA modified antigen (amino acids 15-750) and full length human PSCA on the surface of HEK293 cells transfected with dual antigen vaccine constructs as measured by flow cytometry.
Figure 5A:
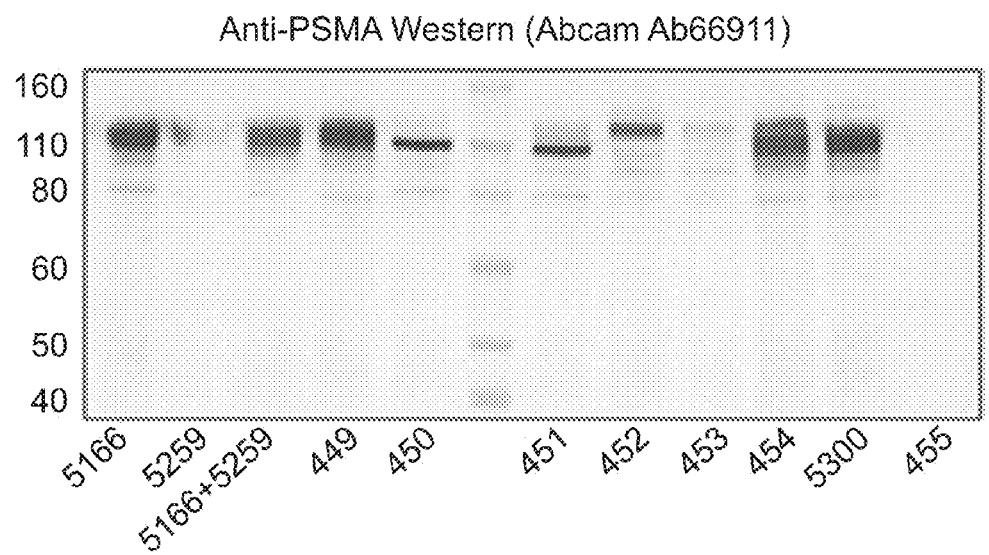
FIGS. 5A and 5B. Image of Western blots showing expression of the human PSMA modified antigen (amino acids 15-750.
Figure 5B:
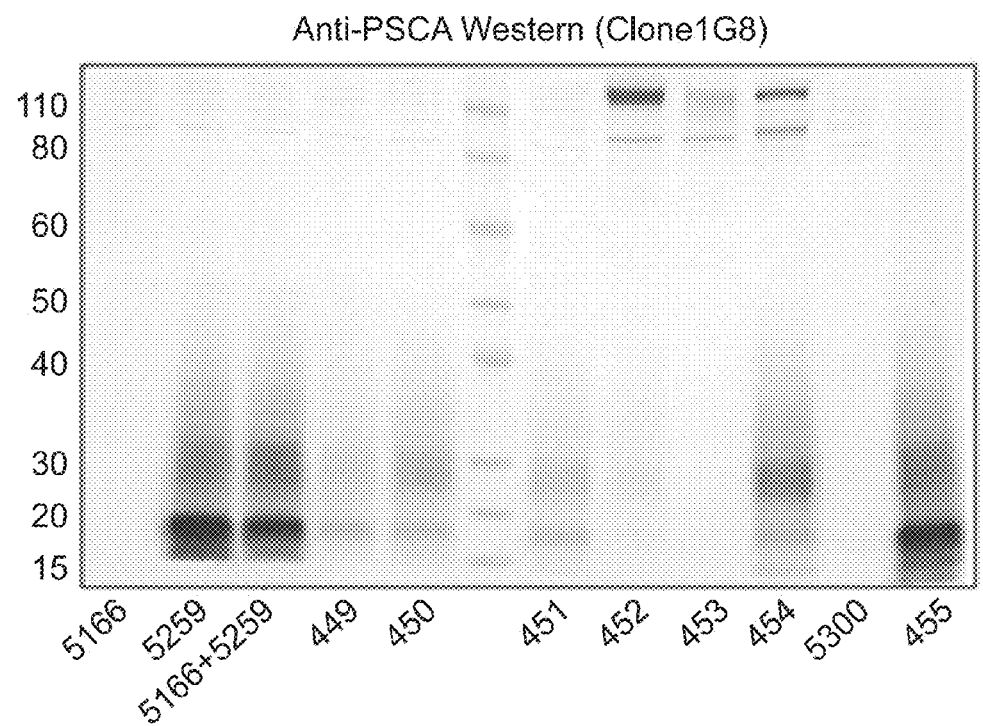
Figure 6:
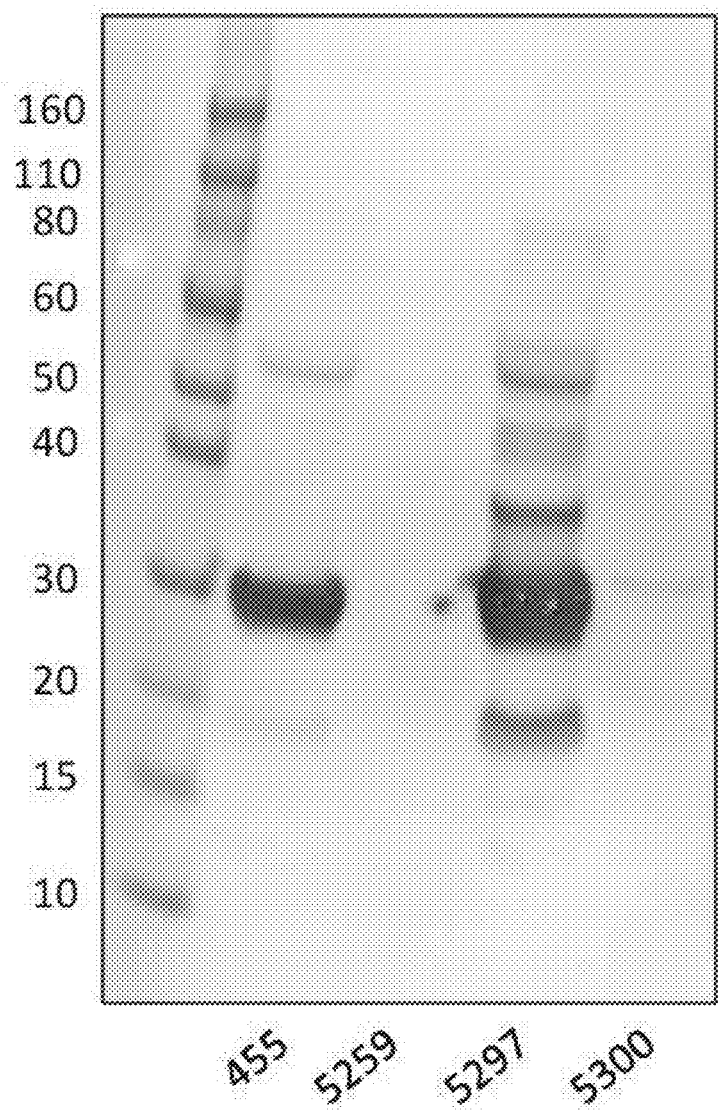
FIG. 6. Image of Western blots showing expression of human PSA cytosolic antigen (amino acids 25-261) in HEK293 cells transfected with dual antigen vaccine constructs as measured by western blotting with a PSA specific monoclonal antibody. Lane 5300 exhibited a faint band about 2 kD larger than PSA, consistent with a C-terminal fusion of the 2A peptide.

The term "adjuvant" refers to a substance that is capable of enhancing, accelerating, or prolonging an immune response when given with a vaccine immunogen.

The term "agonist" refers to is a substance which promotes (induces, causes, enhances or increases) the activity of another molecule or a receptor. The term agonist encompasses substances which bind receptor (e.g., an antibody, a homolog of a natural ligand from another species) and substances which promote receptor function without binding thereto (e.g., by activating an associated protein).

The term "antagonist" or "inhibitor" refers to a substance that partially or fully blocks, inhibits, or neutralizes a biological activity of another molecule or receptor.

The term "co-administration" refers to administration of two or more agents to the same subject during a treatment period. The two or more agents may be encompassed in a single formulation and thus be administered simultaneously. Alternatively, the two or more agents may be in separate physical formulations and administered separately, either sequentially or simultaneously to the subject. The term "administered simultaneously" or "simultaneous administration" means that the administration of the first agent and that of a second agent overlap in time with each other, while the term "administered sequentially" or "sequential administration" means that the administration of the first agent and that of a second agent does not overlap in time with each other.

The term "conserved T cell epitope" refers to one of the following amino acid sequences of the human PSMA protein as set forth in SEQ ID NO. 1:
  amino acids 168-176 (GMPEGDLVY),
  amino acids 347-356 (HSTNGVTRIY),
  amino acids 557-566 (ETYELVEKFY),
  amino acids 207-215 (KVFRGNKVK),
  amino acids 431-440 (STEWAEENSR),
  amino acids 4-12 (LLHETDSAV),
  amino acids 27-35 (VLAGGFFLL),
  amino acids 168-177 (GMPEGDLVYV),
  amino acids 441-450 (LLQERGVAYI),
  amino acids 469-477 (LMYSLVHNL),
  amino acids 711-719 (ALFDIESKV),
  amino acids 663-671 (MNDQVMFL),
  amino acids 178-186 (NYARTEDFF),
  amino acids, 227-235 (LYSDPADYF),
  amino acids 624-632 (TYSVSFDSL),
  amino acids 334-348 (TGNFSTQKVKMHIHS),
  amino acids 459-473 (NYTLRVDCTPLMYSL),
  amino acids 687-701(YRHVIYAPSSHNKYA), and
  amino acids 730-744 (RQIYVAAFTVQAAAE).

The term "cytosolic" means that after a nucleotide sequence encoding a particular polypeptide is expressed by a host cell, the expressed polypeptide is retained inside the host cell.

The terms "degenerate variant" refers to DNA sequences that have substitutions of bases but encode the same polypeptide.

The term "effective amount" refers to an amount administered to a mammal that is sufficient to cause a desired effect in the mammal.

The term "fragment" of a given polypeptide refers to a polypeptide that is shorter than the given polypeptide and shares 100% identity with the sequence of the given polypeptide.

The term "identical" or percent "identity," in the context of two or more nucleic acid or polypeptide sequences, refers to two or more sequences or subsequences that are the same or have a specified percentage of amino acid residues or nucleotides that are the same, when compared and aligned for maximum correspondence.

The term "immune-effector-cell enhancer" or "IEC enhancer" refers to a substance capable of increasing or enhancing the number, quality, or function of one or more types of immune effector cells of a mammal. Examples of immune effector cells include cytolytic CD8 T cells, CD40 T cells, NK cells, and B cells.

The term "immune modulator" refers to a substance capable of altering (e.g., inhibiting, decreasing, increasing, enhancing or stimulating) the working of any component of the innate, humoral or cellular immune system of a mammal. Thus, the term "immune modulator" encompasses the "immune-effector-cell enhancer" as defined herein and the "immune-suppressive-cell inhibitor" as defined herein, as well as substance that affects other components of the immune system of a mammal.

The term "immune response" refers to any detectable response to a particular substance (such as an antigen or immunogen) by the immune system of a host vertebrate animal, including, but not limited to, innate immune responses (e.g., activation of Toll receptor signaling cascade), cell-mediated immune responses (e.g., responses mediated by T cells, such as antigen-specific T cells, and non-specific cells of the immune system), and humoral immune responses (e.g., responses mediated by B cells, such as generation and secretion of antibodies into the plasma, lymph, and/or tissue fluids). Examples of immune responses include an alteration (e.g., increase) in Toll-like receptor activation, lymphokine (e.g., cytokine (e.g., Th1, Th2 or Th17 type cytokines) or chemokine) expression or secretion, macrophage activation, dendritic cell activation, T cell (e.g., CD4+ or CD8+ T cell) activation, NK cell activation, B cell activation (e.g., antibody generation and/or secretion), binding of an immunogen (e.g., antigen (e.g., immunogenic polypolypeptide)) to an MHC molecule, induction of a cytotoxic T lymphocyte ("CTL") response, induction of a B cell response (e.g., antibody production), and, expansion (e.g., growth of a population of cells) of cells of the immune system (e.g., T cells and B cells), and increased processing and presentation of antigen by antigen presenting cells. The term "immune response" also encompasses any detectable response to a particular substance (such as an antigen or immunogen) by one or more components of the immune system of a vertebrate animal in vitro.

The term "immunogenic" refers to the ability of a substance to cause, elicit, stimulate, or induce an immune response, or to improve, enhance, increase or prolong a pre-existing immune response, against a particular antigen, whether alone or when linked to a carrier, in the presence or absence of an adjuvant.

The term "immunogenic PSA polypeptide" refers to a polypeptide that is immunogenic against human PSA protein or against cells expressing human PSA protein.

The term "immunogenic PSCA polypeptide" refers to a polypeptide that is immunogenic against human PSCA protein or against cells expressing human PSCA protein.

The term "immunogenic PSMA polypeptide" refers to a polypeptide that is immunogenic against human PSMA protein or against cells expressing human PSMA protein.

The term "immunogenic PAA polypeptide" refers to an "immunogenic PSA polypeptide," an "immunogenic PSCA polypeptide," or an "immunogenic PSMA polypeptide" as defined herein above.

The term "immunogenic PSA nucleic acid molecule" refers to a nucleic acid molecule that encodes an immunogenic PSA polypeptide as defined herein.

The term "immunogenic PSCA nucleic acid molecule" refers to a nucleic acid molecule that encodes an "immunogenic PSCA polypeptide" as defined herein.

The term "immunogenic PSMA nucleic acid molecule" refers to a nucleic acid molecule that encodes an "immunogenic PSMA polypeptide" as defined herein.

The term "immunogenic PAA nucleic acid molecule" refers to a nucleic acid molecule that encodes an "immunogenic PSA polypeptide," an "immunogenic PSCA polypeptide," or an "immunogenic PSMA polypeptide" as defined herein above.

The term "immune-suppressive-cell inhibitor" or "ISC inhibitor" refers to a substance capable of reducing or suppressing the number or function of immune suppressive cells of a mammal. Examples of immune suppressive cells include regulatory T cells ("T regs"), myeloid-derived suppressor cells, and tumor-associated macrophages.

The term "intradermal administration," or "administered intradermally," in the context of administering a substance, such as a therapeutic agent or an immune modulator, to a mammal including a human, refers to the delivery of the substance into the dermis layer of the skin of the mammal. The skin of a mammal is composed of three layers—the epidermis, dermis, and subcutaneous layer. The epidermis is the relatively thin, tough, outer layer of the skin. Most of the cells in the epidermis are keratinocytes. The dermis, the skin's next layer, is a thick layer of fibrous and elastic tissue (made mostly of collagen, elastin, and fibrillin) that gives the skin its flexibility and strength. The dermis contains nerve endings, sweat glands and oil (sebaceous) glands, hair follicles, and blood vessels. The dermis varies in thickness depending on the location of the skin. In humans it is about 0.3 mm on the eyelid and about 3.0 mm on the back. The subcutaneous layer is made up of fat and connective tissue that houses larger blood vessels and nerves. The thickness of this layer varies throughout the body and from person to person. The term "intradermal administration" refers to delivery of a substance to the inside of the dermis layer. In contrast; "subcutaneous administration" refers to the administration of a substance into the subcutaneous layer and "topical administration" refers to the administration of a substance onto the surface of the skin.

The term "local administration" or "administered locally" encompasses "topical administration," "intradermal administration," and "subcutaneous administration," each as defined herein above. This term also encompasses "intratumoral administration," which refers to administration of a substance to the inside of a tumor. Local administration is intended to allow for high local concentrations around the site of administration for a period of time until systemic biodistribution has been achieved with of the administered substance, while "systemic administration" is intended for the administered substance to be absorbed into the blood and attain systemic exposure rapidly by being distributed through the circulatory system to organs or tissues throughout the body.

The term "mammal" refers to any animal species of the Mammalia class. Examples of mammals include: humans; non-human primates such as monkeys; laboratory animals such as rats, mice, guinea pigs; domestic animals such as cats, dogs, rabbits, cattle, sheep, goats, horses, and pigs; and captive wild animals such as lions, tigers, elephants, and the like.

The term "membrane-bound" means that after a nucleotide sequence encoding a particular polypeptide is expressed by a host cell, the expressed polypeptide is bound to, attached to, or otherwise associated with, the membrane of the cell.

The term "neoplastic disorder" refers to a condition in which cells proliferate at an abnormally high and uncontrolled rate, the rate exceeding and uncoordinated with that of the surrounding normal tissues. It usually results in a solid lesion or lump known as "tumor." This term encompasses benign and malignant neoplastic disorders. The term "malignant neoplastic disorder", which is used interchangeably with the term "cancer" in the present disclosure, refers to a neoplastic disorder characterized by the ability of the tumor cells to spread to other locations in the body (known as "metastasis"). The term "benign neoplastic disorder" refers to a neoplastic disorder in which the tumor cells lack the ability to metastasize.

The term "operably linked" refers to a juxtaposition wherein the components so described are in a relationship permitting them to function in their intended manner. A control sequence "operably linked" to a transgene is ligated in such a way that expression of the transgene is achieved under conditions compatible with the control sequences.

The term "ortholog" refers to genes in different species that are similar to each other and originated from a common ancestor.

The term "pharmaceutically acceptable excipient" refers to a substance in an immunogenic or vaccine composition, other than the active ingredients (e.g., the antigen, antigen-coding nucleic acid, immune modulator, or adjuvant) that is compatible with the active ingredients and does not cause significant untoward effect in subjects to whom it is administered.

The terms "peptide," "polypeptide," and "protein" are used interchangeably herein, and refer to a polymeric form of amino acids of any length, which can include coded and non-coded amino acids, chemically, or biochemically modified or derivatized amino acids, and polypeptides having modified polypeptide backbones.

The term "preventing" or "prevent" refers to (a) keeping a disorder from occurring or (b) delaying the onset of a disorder or onset of symptoms of a disorder.

The term "prostate-associated-antigen" (or PAA) refers to the TAA (as defined herein) that is specifically expressed on prostate tumor cells or expressed at a higher frequency or density by tumor cells than by non-tumor cells of the same tissue type. Examples of PAA include PSA, PSCA, and PSMA.

The term "secreted" in the context of a polypeptide means that after a nucleotide sequence encoding the polypeptide is expressed by a host cell, the expressed polypeptide is secreted outside of the host cell.

The term "suboptimal dose" when used to describe the amount of an immune modulator, such as a protein kinase inhibitor, refers to a dose of the immune modulator that is below the minimum amount required to produce the desired therapeutic effect for the disease being treated when the immune modulator is administered alone to a patient.

The term "treating," "treatment," or "treat" refers to abrogating a disorder, reducing the severity of a disorder, or reducing the severity or occurrence frequency of a symptom of a disorder.

The term "tumor-associated antigen" or "TAA" refers to an antigen which is specifically expressed by tumor cells or expressed at a higher frequency or density by tumor cells than by non-tumor cells of the same tissue type. Tumor-associated antigens may be antigens not normally expressed by the host; they may be mutated, truncated, misfolded, or otherwise abnormal manifestations of molecules normally expressed by the host; they may be identical to molecules normally expressed but expressed at abnormally high levels; or they may be expressed in a context or milieu that is abnormal. Tumor-associated antigens may be, for example, proteins or protein fragments, complex carbohydrates, gangliosides, haptens, nucleic acids, or any combination of these or other biological molecules.

The term "vaccine" refers to an immunogenic composition for administration to a mammal for eliciting an immune response against a particular antigen.

The term "variant" of a given polypeptide refers to a polypeptide that shares less than 100% but more than 80% identity to the amino acid sequence of that given polypeptide and exhibits at least some of the immunogenic activity of that given polypeptide.

The term "vector" refers to a nucleic acid molecule capable of transporting or transferring a foreign nucleic acid molecule. The term encompasses both expression vectors and transcription vectors. The term "expression vector" refers to a vector capable of expressing the insert in the target cell, and generally contain control sequences, such as enhancer, promoter, and terminator sequences, that drive expression of the insert. The term "transcription vector" refers to a vector capable of being transcribed but not translated. Transcription vectors are used to amplify their insert. The foreign nucleic acid molecule is referred to as "insert" or "transgene." A vector generally consists of an insert and a larger sequence that serves as the backbone of the vector. Based on the structure or origin of vectors, major types of vectors include plasmid vectors, cosmid vectors, phage vectors such as lambda phage, viral vectors such as adenovirus (Ad) vectors, and artificial chromosomes.

B. Immunogenic Prostate-Associated-Antigen (PAA) Polypeptides

In some aspects, the present disclosure provides isolated immunogenic PSA polypeptides and PSMA polypeptides, which are useful, for example, for eliciting an immune response in vivo (e.g. in an animal, including humans) or in vitro, activating effector T cells, or generating antibodies specific for PSA and PSMA, respectively, or for use as a component in vaccines for treating cancer, particularly prostate cancer. These polypeptides can be prepared by methods known in the art in light of the present disclosure. The capability of the polypeptides to elicit an immune response can be measured in in vitro assays or in vivo assays. In vitro assays for determining the capability of a polypeptide or DNA construct to elicit immune responses are known in the art. One example of such in vitro assays is to measure the capability of the polypeptide or nucleic acid expressing an polypeptide to stimulate T cell response as described in U.S. Pat. No. 7,387,882, the disclosure of which is incorporated in this application. The assay method comprises the steps of: (1) contacting antigen presenting cells in culture with an antigen thereby the antigen can be taken up and processed by the antigen presenting cells, producing one or more processed antigens; (2) contacting the antigen presenting cells with T cells under conditions sufficient for the T cells to respond to one or more of the processed antigens; (3) determining whether the T cells respond to one or more of the processed antigens. The T cells used may be $CD8^+$ T cells or $CD4^+$ T cells. T cell response may be determined by measuring the release of one of more of cytokines, such as interferon-gamma and interleukin-2, lysis of the antigen presenting cells (tumor cells), and production of antibodies by B cells.

B-1. Immunogenic PSMA Polypeptides

In one aspect, the present disclosure provides isolated immunogenic PSMA polypeptides which have at least 90% identity to amino acids 15-750 of the human PSMA of SEQ ID NO:1 and comprise the amino acids of at least 10, 11, 12, 13, 14, 15, 16, 17, 18, or 19 of the conserved T cell epitopes of the human PSMA at corresponding positions.

In some embodiments, the immunogenic PSMA polypeptides comprise at least 15, 16, 17, 18, or 19 of the conserved T cell epitopes of the human PSMA.

In some embodiments, the present disclosure provides an immunogenic PSMA polypeptide consisting of the amino acid sequence of SEQ ID NO:9, or an immunogenic PSMA polypeptide having 93%-99%, 94%-98%, or 94%-97% identity to the amino acid sequence of SEQ ID NO:9.

Examples of some particular immunogenic PSMA polypeptides include:

1) a polypeptide consisting of amino acids 15-750 of SEQ ID NO: 1;
2) a polypeptide comprising the amino acids 4-739 of SEQ ID NO: 3;
3) a polypeptide comprising the amino acids 4-739 of SEQ ID NO:5;
4) a polypeptide comprising the amino acids 4-739 of SEQ ID NO:7;
2) a polypeptide comprising the amino acid sequence of SEQ ID NO:3;
3) a polypeptide comprising the amino acid sequence of SEQ ID NO:5; and
4) a polypeptide comprising the amino acid sequence of SEQ ID NO:7.

In other embodiments, the present disclosure provides an immunogenic PSMA polypeptide selected from the group consisting of:

1) a polypeptide consisting of the amino acid sequence of SEQ ID NO:11
2) a polypeptide consisting of the amino acid sequence of SEQ ID NO:13; and
3) a polypeptide comprising the amino acid sequence of SEQ ID NO:13.

In some other embodiments, the present disclosure provides isolated immunogenic PSMA polypeptides that are variants of any of the following polypeptides:

2) a polypeptide comprising the amino acids 4-739 of SEQ ID NO: 3;
3) a polypeptide comprising the amino acids 4-739 of SEQ ID NO: 5; and 4) a polypeptide comprising the amino acids 4-739 of SEQ ID NO: 7, wherein the amino acid sequence of the variant has 93%-99% identity to the sequence of SEQ ID NO:1 and share at least 80%, at least 85%, at least 90%, at least 95%, or at least 99% identity with the amino acid sequence of SEQ ID NO: 3, 5, or 7.

The variants of a given PAA polypeptide can be obtained by deleting, inserting, or substituting one or more amino acids in the parent immunogenic PAA polypeptide. An example for the production of such variants is the conservative substitution of individual amino acids of the polypeptides, that is, by substituting one amino acid for another having similar properties.

An immunogenic PSMA polypeptide of the invention may be constructed by conserving some or all of the conserved T cell epitopes of the human PSMA of SEQ ID NO:1 while substituting certain amino acids in the remaining regions of the human PSMA with amino acids found in one or more orthologs of human PSMA at corresponding positions. Sequences of various PSMA orthologs that may be utilized to make the immunogenic PSMA polypeptides are available from the GeneBank database. These orthologs along with their NCBI ID numbers are provided in Table 18. Substitutions of amino acids of human PSMA with amino acids from one or more of the orthologs may be conservative substitutions or non-conservative substitutions, or both, and may be selected based on a number of factors known in the art, including the divergence needed to be achieved, MHC binding, the presence of ortholog amino acids at the site of substitution, surface exposure, and maintaining the 3-D structure of the protein for optimal processing and presentation.

B-2. Immunogenic PSA Polypeptides

In another aspect, the present disclosure provides isolated immunogenic PSA polypeptides. In one embodiment, the isolated immunogenic PSA polypeptide is a polypeptide consisting of the amino acid sequence of SEQ ID NO:15 or amino acids 4-263 of SEQ ID NO: 15, or a variant thereof. In another embodiment, the isolated immunogenic PSA polypeptide is a polypeptide consisting of the amino acid sequence of SEQ ID NO:17 or amino acids 4-240 of SEQ ID NO: 17, or a variant thereof. In a further embodiment, the isolated immunogenic PSA polypeptide is a polypeptide consisting of the amino acid sequence of SEQ ID NO:19 or amino acids 4-281 of SEQ ID NO: 19, or a variant thereof.

C. Nucleic Acid Molecules Encoding Immunogenic PAA Polypeptides

In some aspects, the present disclosure provides nucleic acid molecules that encode immunogenic PAA polypeptides. The nucleic acid molecules can be deoxyribonucleotides (DNA) or ribonucleotides (RNA). Thus, a nucleic acid molecule can comprise a nucleotide sequence disclosed herein wherein thymidine (T) can also be uracil (U), which reflects the differences between the chemical structures of DNA and RNA. The nucleic acid molecules can be modified forms, single or double stranded forms, or linear or circular forms. The nucleic acid molecules can be prepared using methods known in the art light of the present disclosure.

C-1. Nucleic Acid Molecules Encoding Immunogenic PSMA Polypeptides

In one aspect, the present disclosure provides isolated nucleic acid molecules, or degenerate variants thereof, which comprise a nucleotide sequence encoding an immunogenic PSMA polypeptide, including the immunogenic PSMA polypeptides provided by the present disclosure or a functional variant thereof.

In some embodiments, the nucleotide sequence encodes a membrane-bound immunogenic PSMA polypeptide. In some particular embodiments, the isolated nucleic acid molecule comprises a nucleotide sequence, or a degenerate variant thereof, selected from the group consisting of:

1) a nucleotide sequence encoding the amino acid sequence of SEQ ID NO:9;
2) a nucleotide sequence encoding amino acids 4-739 of SEQ ID NO:3;
3) a nucleotide sequence encoding amino acids 4-739 of SEQ ID NO:5; and
4) a nucleotide sequence encoding amino acids 4-739 of SEQ ID NO:7.

In some other particular embodiments, the nucleotide sequence encodes a variant of an immunogenic PSMA polypeptide of SEQ ID NO:3, SEQ ID NO:5, SEQ ID NO:7, or SEQ ID NO:9, wherein the variant has an amino acid sequence that has (a) 93% to 99% identity with the amino acid sequence of SEQ ID NO:1 and (b) at least 80%, at least 85%, at least 90%, at least 95%, or at least 99% identity with the amino acid sequence of SEQ ID NO: 3, 5, or 7.

In still some other particular embodiments, the isolated nucleic acid molecule comprises a nucleotide sequence, or a degenerate variant thereof, selected from the group consisting of:

1) a nucleotide sequence comprising nucleotides 10-2217 of SEQ ID NO:4;
2) a nucleotide sequence comprising nucleotides 10-2217 of SEQ ID NO:6;
3) a nucleotide sequence comprising nucleotides 10-2217 of SEQ ID NO:8; and
4) a nucleotide sequence comprising nucleotides 10-2217 of SEQ ID NO:10.

C-2. Nucleic Acid Molecules Encoding Immunogenic PSA Polypeptides

In another aspect, the present disclosure provides isolated nucleic acid molecules, or degenerate variants thereof, which encode an immunogenic PSA polypeptide, including the immunogenic PSA polypeptides provided by the present disclosure.

In some embodiments, the isolated nucleic acid molecule comprises or consists of a nucleotide sequence encoding a cytosolic immunogenic PSA polypeptide. In one embodiment, the nucleotide sequence encodes a cytosolic immunogenic PSA polypeptide consisting of consecutive amino acid residues 4-240 of SEQ ID NO:17. In another embodiment, the nucleotide sequence encodes a cytosolic immunogenic PSA polypeptide comprising the amino acid sequence of SEQ ID NO:17. In still another embodiment, the nucleotide sequence encodes a cytosolic immunogenic PSA polypeptide consisting of the amino acid sequence of SEQ ID NO:17. In yet another embodiment, the nucleotide sequence encodes a functional variant of any of said cytosolic immunogenic polypeptides provided herein above.

In some other embodiments, the isolated nucleic acid molecule comprises a nucleotide sequence encoding a membrane-bound immunogenic PSA polypeptide. In one embodiment, the nucleotide sequence encodes a membrane-bound immunogenic PSA polypeptide comprising consecutive amino acid residues 4-281 of SEQ ID NO:19. In another embodiment, the nucleotide sequence encodes a membrane-bound immunogenic PSA polypeptide comprising the amino acid sequence of SEQ ID NO:19. In still another embodiment, the nucleotide sequence encodes a membrane-bound immunogenic PSA polypeptide consisting of the amino acid sequence of SEQ ID NO:19. In yet other embodiments, the nucleotide sequence encodes a functional variant of any of said membrane-bound immunogenic PSA polypeptides provided herein above.

Examples of particular nucleic acid molecules provided by the present disclosure include:

1) a nucleic acid molecule consisting of the nucleotide sequence of SEQ ID NO: 18;

2) a nucleic acid molecule comprising the nucleotide sequence of SEQ ID NO; 18;

3) a nucleic acid molecule consisting of the nucleotide sequence of SEQ ID NO; 20;

4) a nucleic acid molecule comprising the nucleotide sequence of SEQ ID NO: 20; and 5) a degenerate variant of any of the nucleic acid molecules 1)-4) above.

C-3. Nucleic Acid Molecules Encoding Two or More Immunogenic PAA Polypeptides

In another aspect, the present disclosure provides a nucleic acid molecule that encodes more than one immunogenic PAA polypeptide, for example at least two, at least three, or at least four immunogenic PAA polypeptides. Such nucleic acid molecules are also be referred to as "multi-antigen constructs," "multi-antigen vaccine," "multi-antigen plasmid," and the like, in the present disclosure. Thus, in some aspects, one nucleic acid molecule carries two coding nucleotide sequences wherein each of the coding nucleotide sequences expresses an individual immunogenic PAA polypeptide. Such a nucleic acid molecule is also referred to as "dual antigen construct," "dual antigen vaccine," or "dual antigen plasmid," etc., in this disclosure. In some other aspects, one nucleic acid molecule carries three coding nucleotide sequences wherein each of the coding nucleotide sequences expresses an individual immunogenic PAA polypeptide. Such a nucleic acid molecule is also referred to as "triple antigen construct," "triple antigen vaccine," or "triple antigen plasmid" in this disclosure. The individual PAA polypeptides encoded by a multi-antigen construct may be immunogenic against the same antigen, such as PSMA, PSA, or PSCA. The individual PAA polypeptides encoded by a multi-antigen construct may be immunogenic against different antigens, for example, one PAA polypeptide being a PSMA polypeptide and another one a PSA polypeptide. Specifically, one multi-antigen construct may encode two or more immunogenic PAA polypeptides in any one of the following combinations:

1) at least one immunogenic PSMA polypeptide and at least one immunogenic PSA polypeptide;

2) at least one immunogenic PSMA polypeptide and at least one immunogenic PSCA polypeptide;

3) at least one immunogenic PSA polypeptide and at least one immunogenic PSCA polypeptide; and 4) at least one immunogenic PSMA polypeptide, at least one immunogenic PSA polypeptide, and at least one immunogenic PSCA polypeptide.

The immunogenic PSMA polypeptides encoded by a multi-antigen construct may be either cytosolic, secreted, or membrane-bound, but preferably membrane-bound. Similarly, the immunogenic PSA polypeptide encoded by a multi-antigen construct may be either cytosolic, secreted, or membrane-bound, but preferably cytosolic. The immunogenic PSCA polypeptide encoded by a multi-antigen construct is preferably the full length human PSCA protein, the amino acid sequence of which is set forth in SEQ ID No:21.

In some embodiments, the present disclosure provides a multi-antigen construct that encodes at least one membrane-bound immunogenic PSMA polypeptide and at least one membrane-bound immunogenic PSA polypeptide.

In some other embodiments, the present disclosure provides a multi-antigen construct that encodes at least one membrane-bound immunogenic PSMA polypeptide, at least one cytosolic immunogenic PSA polypeptide, and at least one immunogenic PSCA polypeptide, wherein the at least one cytosolic immunogenic PSA polypeptide comprises amino acids 4-240 of SEQ ID NO:17, wherein the at least one immunogenic PSCA polypeptide is the full length human PSCA protein of SEQ ID NO:21, and wherein the at least one immunogenic PSMA polypeptide is selected from the group consisting of:

1) a polypeptide comprising amino acids 15-750 of SEQ ID NO: 1;

2) a polypeptide comprising the amino acid sequence of SEQ ID NO:3;

3) a polypeptide comprising the amino acid sequence of SEQ ID NO:5;

4) a polypeptide comprising the amino acid sequence of SEQ ID NO:7;

5) a polypeptide comprising the amino acids 4-739 of SEQ ID NO:9;

6) a polypeptide comprising the amino acids 4-739 of SEQ ID NO:3;

7) a polypeptide comprising the amino acids 4-739 of SEQ ID NO:5;

8) a polypeptide comprising the amino acids 4-739 of SEQ ID NO:7; and 9) polypeptide comprising the amino acid sequence of SEQ ID NO: 9.

In some particular embodiments, the present disclosure provides a multi-antigen construct comprising at least one nucleotide sequence encoding an immunogenic PSMA polypeptide, at least one nucleotide sequence encoding an immunogenic PSA polypeptide, and at least one nucleotide sequence encoding an immunogenic PSCA polypeptide, wherein the nucleotide sequence encoding the immunogenic PSA polypeptide is selected from the nucleotide sequence of SEQ ID NO: 18 or SEQ ID NO: 20, wherein the nucleotide sequence encoding the immunogenic PSCA polypeptide is set forth in SEQ ID NO:22, and wherein the nucleotide sequence encoding the immunogenic PSMA polypeptide is selected from the group consisting of:

1) the nucleotide sequence of SEQ ID NO:2;

2) the nucleotide sequence of SEQ ID NO:4;

3) the nucleotide sequence of SEQ ID NO:6;

4) the nucleotide sequence of SEQ ID NO:8;

5) the nucleotide sequence of SEQ ID NO:10;

6) a nucleotide sequence comprising nucleotides 10-2217 of SEQ ID NO:4;

7) a nucleotide sequence comprising nucleotides 10-2217 of SEQ ID NO:6;

8) a nucleotide sequence comprising nucleotides 10-2217 of SEQ ID NO:8; and 9) a nucleotide sequence comprising nucleotides 10-2217 of SEQ ID NO:10.

Examples of specific multi-antigen constructs provided by the present disclosure include the nucleic acid molecules that comprise a nucleotide sequence set forth in SEQ ID NOs:23-36.

Multi-antigen constructs provided by the present disclosure can be prepared using various techniques known in the art in light of the disclosure. For example, a multi-antigen construct can be constructed by incorporating multiple independent promoters into a single plasmid (Huang, Y., Z. Chen, et al. (2008). "Design, construction, and characterization of a dual-promoter multigenic DNA vaccine directed against an HIV-1 subtype C/B' recombinant." J Acquir Immune Defic Syndr 47(4): 403-411; Xu, K., Z. Y. Ling, et al. (2011). "Broad humoral and cellular immunity elicited by a bivalent DNA vaccine encoding HA and NP genes from an H5N1 virus." Viral Immunol 24(1): 45-56). The plasmid can be engineered to carry multiple expression cassettes, each consisting of a) a eukaryotic promoter for initiating RNA polymerase dependent transcription, with or without an enhancer element, b) a gene encoding a target antigen, and c) a transcription terminator sequence. Upon delivery of the plasmid to the transfected cell nucleus, transcription will be initiated from each promoter, resulting in the production of separate mRNAs, each encoding one of the target antigens. The mRNAs will be independently translated, thereby producing the desired antigens.

Multi-antigen constructs provided by the present disclosure can also be constructed using a single vector through the use of viral 2A-like polypeptides (Szymczak, A. L. and D. A. Vignali (2005). "Development of 2A peptide-based strategies in the design of multicistronic vectors." Expert Opin Biol Ther 5(5): 627-638; de Felipe, P., G. A. Luke, et al. (2006). "E unum pluribus: multiple proteins from a self-processing polyprotein." Trends Biotechnol 24(2): 68-75; Luke, G. A., P. de Felipe, et al. (2008). "Occurrence, function and evolutionary origins of '2A-like' sequences in virus genomes." J Gen Virol 89 (Pt 4): 1036-1042; Ibrahimi, A., G. Vande Velde, et al. (2009). "Highly efficient multicistronic lentiviral vectors with peptide 2A sequences." Hum Gene Ther 20(8): 845-860; Kim, J. H., S. R. Lee, et al. (2011). "High cleavage efficiency of a 2A peptide derived from porcine teschovirus-1 in human cell lines, zebrafish and mice." PLoS One 6(4): e18556). These polypeptides, also called cleavage cassettes or CHYSELs (cis-acting hydrolase elements), are approximately 20 amino acids long with a highly conserved carboxy terminal D-V/I-EXNPGP motif (FIG. 2). The cassettes are rare in nature, most commonly found in viruses such as Foot-and-mouth disease virus (FMDV), Equine rhinitis A virus (ERAV), Encephalomyocarditis virus (EMCV), Porcine teschovirus (PTV), and Thosea asigna virus (TAV) (Luke, G. A., P. de Felipe, et al. (2008). "Occurrence, function and evolutionary origins of '2A-like' sequences in virus genomes." J Gen Virol 89 (Pt 4): 1036-1042). With a 2A-based multi-antigen expression strategy, genes encoding multiple target antigens can be linked together in a single open reading frame, separated by 2A cassettes. The entire open reading frame can be cloned into a vector with a single promoter and terminator. Upon delivery of the constructs to a host cell, mRNA encoding the multiple antigens will be transcribed and translated as a single polyprotein. During translation of the 2A cassettes, ribosomes skip the bond between the C-terminal glycine and proline. The ribosomal skipping acts like a cotranslational autocatalytic "cleavage" that releases upstream from downstream proteins. The incorporation of a 2A cassette between two protein antigens results in the addition of ~20 amino acids onto the C-terminus of the upstream polypeptide and 1 amino acid (proline) to the N-terminus of downstream protein. In an adaptation of this methodology, protease cleavage sites can be incorporated at the N terminus of the 2A cassette such that ubiquitous proteases will cleave the cassette from the upstream protein (Fang, J., S. Yi, et al. (2007). "An antibody delivery system for regulated expression of therapeutic levels of monoclonal antibodies in vivo." Mol Ther 15(6): 1153-1159).

Another strategy for constructing the multi-antigen constructs provided by the present disclosure involves the use of an internal ribosomal entry site, or IRES. Internal ribosomal entry sites are RNA elements (FIG. 3) found in the 5' untranslated regions of certain RNA molecules (Bonnal, S., C. Boutonnet, et al. (2003). "IRESdb: the Internal Ribosome Entry Site database." Nucleic Acids Res 31(1): 427-428). They attract eukaryotic ribosomes to the RNA to facilitate translation of downstream open reading frames. Unlike normal cellular 7-methylguanosine cap-dependent translation, IRES-mediated translation can initiate at AUG codons far within an RNA molecule. The highly efficient process can be exploited for use in multi-cistronic expression vectors (Bochkov, Y. A. and A. C. Palmenberg (2006). "Translational efficiency of EMCV IRES in bicistronic vectors is dependent upon IRES sequence and gene location." Biotechniques 41(3): 283-284, 286, 288). Typically, two transgenes are inserted into a vector between a promoter and transcription terminator as two separate open reading frames separated by an IRES. Upon delivery of the constructs to a host cell, a single long transcript encoding both transgenes will be transcribed. The first ORF will be translated in the traditional cap-dependent manner, terminating at a stop codon upstream of the IRES. The second ORF will be translated in a cap-independent manner using the IRES. In this way, two independent proteins can be produced from a single mRNA transcribed from a vector with a single expression cassette.

Although the multi-antigen expression strategies are described here in the context of a DNA vaccine construct, the principles apply similarly in the context of viral vector genetic vaccines.

D. Vectors Containing a Nucleic Acid Molecule Encoding an Immunogenic PAA Polypeptide Another aspect of the invention relates to vectors containing one or more nucleic acid molecules of the invention. The vectors are useful for cloning or expressing the immunogenic PAA polypeptides encoded by the nucleic acid molecules, or for delivering the nucleic acid molecule in a composition, such as a vaccine, to a host cell or to a host animal, such as a human. A wide variety of vectors may be prepared to contain and express a nucleic acid molecule of the invention, such as plasmid vectors, cosmid vectors, phage vectors, and viral vectors.

In some embodiments, the disclosure provides a plasmid-based vector containing a nucleic acid molecule of the invention. Representative examples of suitable plasmid vectors include pBR325, pUC18, pSKF, pET23D, and pGB-2. Other representative examples of plasmid vectors, as well as method of constructing such vectors, are described in U.S. Pat. Nos. 5,580,859, 5,589,466, 5,688,688, 5,814,482 and 5,580,859.

In other embodiments, the present invention provides vectors that are constructed from viruses, such as retroviruses, alphaviruses, adenoviruses. Representative examples of retroviral vectors are described in more detail in EP 0,415,731; PCT Publication Nos. WO 90/07936; WO 91/0285, WO 9311230; WO 9310218, WO 9403622; WO 9325698; WO 9325234; and U.S. Pat. Nos. 5,219,740, 5,716,613, 5,851,529, 5,591,624, 5,716,826, 5,716,832, and 5,817,491. Representative examples of vectors that can be generated from alphaviruses are described in U.S. Pat. Nos. 5,091,309 and 5,217,879, 5,843,723, and 5,789,245. In some particular embodiments, the present disclosure provides adenoviral vectors derived from non-human primate adenoviruses, such as simian adenoviruses. Examples of such adenoviral vectors, as well as their preparation, are described in PCT application publication WO2005/071093 and WO 2010/086189, and include non-replicating vectors such as ChAd3, ChAd4, ChAd5, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd63, ChAd68, ChAd82, ChAd55, ChAd73, ChAd83, ChAd146, ChAd147, PanAd1, Pan Ad2, and Pan Ad3, and replication-competent vectors such as Ad4 and Ad7 vectors. It is preferred that in constructing the adenoviral vectors from the simian adenoviruses one or more of the early genes from the genomic region of the virus selected from E1A, E1B, E2A, E2B, E3, and E4 are either deleted or rendered non-functional by deletion or mutation. In a particular embodiment, the vector is constructed from ChAd3 or ChAd68. Suitable vectors can also be generated from other viruses such as: pox viruses, such as canary pox virus or vaccinia virus (Fisher-Hoch et al., PNAS 86:317-321, 1989; Flexner et al., Ann. N.Y. Acad. Sci. 569:86-103, 1989; Flexner et al., Vaccine 8:17-21, 1990; U.S. Pat. Nos. 4,603,112, 4,769,330 and 5,017,487; WO 89/01973); adeno-associated vectors (see, e.g., U.S. Pat. No. 5,872,005); SV40 (Mulligan et al., Nature 277:108-114, 1979); herpes (Kit, Adv. Exp. Med. Biol. 215:219-236, 1989; U.S. Pat. No. 5,288,641); and lentivirus such as HIV (Poznansky, J. Virol. 65:532-536, 1991).

Methods of constructing vectors are well known in the art. Expression vectors typically include one or more control elements that are operatively linked to the nucleic acid sequence to be expressed. The term "control elements" refers collectively to promoter regions, polyadenylation signals, transcription termination sequences, upstream regulatory domains, origins of replication, internal ribosome entry sites ("IRES"), enhancers, and the like, which collectively provide for the replication, transcription, and translation of a coding sequence in a recipient cell. Not all of these control elements need always be present so long as the selected coding sequence is capable of being replicated, transcribed, and translated in an appropriate host cell. The control elements are selected based on a number of factors known to those skilled in that art, such as the specific host cells and source or structures of other vector components, For enhancing the expression of an immunogenic PAA polypeptide, a Kozak sequence can be provided upstream of the sequence encoding the immunogenic PAA polypeptide. For vertebrates, a known Kozak sequence is (GCC)NC-CATGG, wherein N is A or G and GCC is less conserved. Exemplary Kozak sequences that can be used include ACCAUGG and ACCATGG.

E. Compositions Comprising an Immunogenic PAA Polypeptide (Polypeptide Compositions)

In another aspect, the present disclosure provides compositions comprising one or more isolated immunogenic PAA polypeptides provided by the present disclosure ("polypeptide composition"). In some embodiments, the polypeptide composition is an immunogenic composition useful for eliciting an immune response against a PAA protein in a mammal, such as a mouse, dog, nonhuman primates or human. In some other embodiments, the polypeptide composition is a vaccine composition useful for immunization of a mammal, such as a human, for inhibiting abnormal cell proliferation, for providing protection against the development of cancer (used as a prophylactic), or for treatment of disorders (used as a therapeutic) associated with PAA over expression, such as cancers, particularly prostate cancer.

A polypeptide composition provided by the present disclosure may contain a single type of immunogenic PAA polypeptide, such an immunogenic PSMA polypeptide, an immunogenic PSA polypeptide, or an immunogenic PSCA polypeptide. A composition may also contain a combination of two or more different types of immunogenic PAA polypeptides. For example, a polypeptide composition may contain immunogenic PAA polypeptides in any of the following combinations:

1) an immunogenic PSMA polypeptide and an immunogenic PSA polypeptide;

2) an immunogenic PSMA polypeptide and a PSCA polypeptide; or 3) an immunogenic PSMA polypeptide, an immunogenic PSA polypeptide, and a PSCA polypeptide.

An immunogenic composition or vaccine composition provided by the present disclosure may further comprise a pharmaceutically acceptable excipient. Pharmaceutically acceptable excipients for immunogenic or vaccine compositions are known in the art. Examples of suitable excipients include biocompatible oils, such as rape seed oil, sunflower oil, peanut oil, cotton seed oil, jojoba oil, squalan, squalene, physiological saline solution, preservatives and osmotic pressure controlling agents, carrier gases, pH-controlling agents, organic solvents, hydrophobic agents, enzyme inhibitors, water absorbing polymers, surfactants, absorption promoters, pH modifiers, and anti-oxidative agents.

The immunogenic PAA polypeptide in a composition, particularly an immunogenic composition or a vaccine composition, may be linked to, conjugated to, or otherwise incorporated into a carrier for administration to a recipient. The term "carrier" refers to a substance or structure that an immunogenic polypeptide can be attached to or otherwise associated with for delivery of the immunogenic polypeptide to the recipient (e.g., patient). The carrier itself may be immunogenic. Examples of carriers include immunogenic polypeptides, immune CpG islands, limpet hemocyanin (KLH), tetanus toxoid (TT), cholera toxin subunit B (CTB), bacteria or bacterial ghosts, liposome, chitosome, virosomes, microspheres, dendritic cells, or their like. One or more immunogenic PAA polypeptide molecules may be linked to a single carrier molecule. Methods for linking an immunogenic polypeptide to a carrier are known in the art, A vaccine composition or immunogenic composition provided by the present disclosure may be used in conjunction with one or more immune modulators or adjuvants. The immune modulators or adjuvants may be formulated separately from the vaccine composition, or they may be part of the same vaccine composition formulation. Thus, in one embodiment, the vaccine composition further comprises one or more immune modulators or adjuvants. Examples of immune modulators and adjuvants are provided herein below.

The polypeptide compositions, including the immunogenic and vaccine compositions, can be prepared in any suitable dosage forms, such as liquid forms (e.g., solutions, suspensions, or emulsions) and solid forms (e.g., capsules, tablets, or powder), and by methods known to one skilled in the art.

F. Compositions Comprising an Immunogenic PAA Nucleic Acid Molecule (Nucleic Acid Compositions)

The present disclosure also provides a composition comprising an isolated nucleic acid molecule or vector provided by the present disclosure (herein "nucleic acid composition'). The nucleic acid compositions are useful for eliciting an immune response against a PAA protein in vitro or in vivo in a mammal, including a human.

In some particular embodiments, the nucleic acid composition is a DNA vaccine composition for administration to humans for inhibiting abnormal cell proliferation, providing protection against the development of cancer (used as a prophylactic), or for treatment of cancer (used as a therapeutic) associated with PAA over-expression, or for eliciting an immune response to a particular human PAA, such as PSMA, PSA, and PSCA. The nucleic acid molecule in the composition may be a "naked" nucleic acid molecule, i.e. simply in the form of an isolated DNA free from elements that promote transfection or expression. Alternatively, the nucleic acid molecule in the composition can be incorporated into a vector.

A nucleic acid composition provided by the present disclosure may comprise individual isolated nucleic acid molecules that each encode only one type of immunogenic PAA polypeptide, such as an immunogenic PSMA polypeptide, an immunogenic PSA polypeptide, or an immunogenic PSCA polypeptide.

A nucleic acid composition may comprise a multi-antigen construct provided by the present disclosure that encodes two or more types of immunogenic PAA polypeptides. A multi-antigen construct may encode two or more immunogenic PAA polypeptides in any of the following combinations:

1) an immunogenic PSMA polypeptide and an immunogenic PSA polypeptide;
2) an immunogenic PSMA polypeptide and an immunogenic PSCA polypeptide;
3) an immunogenic PSA polypeptide and an immunogenic PSCA polypeptide; and
4) an immunogenic PSMA polypeptide, an immunogenic PSA polypeptide, and an immunogenic PSCA polypeptide.

The nucleic acid compositions, including the DNA vaccine compositions, may further comprise a pharmaceutically acceptable excipient. Examples of suitable pharmaceutically acceptable excipients for nucleic acid compositions, including DNA vaccine compositions, are well known to those skilled in the art and include sugars, etc. Such excipients may be aqueous or non aqueous solutions, suspensions, and emulsions. Examples of non-aqueous excipients include propylene glycol, polyethylene glycol, vegetable oils such as olive oil, and injectable organic esters such as ethyl oleate. Examples of aqueous excipient include water, alcoholic/ aqueous solutions, emulsions or suspensions, including saline and buffered media. Suitable excipients also include agents that assist in cellular uptake of the polynucleotide molecule. Examples of such agents are (i) chemicals that modify cellular permeability, such as bupivacaine, (ii) liposomes or viral particles for encapsulation of the polynucleotide, or (iii) cationic lipids or silica, gold, or tungsten microparticles which associate themselves with the polynucleotides. Anionic and neutral liposomes are well-known in the art (see, e.g., Liposomes: A Practical Approach, RPC New Ed, IRL press (1990), for a detailed description of methods for making liposomes) and are useful for delivering a large range of products, including polynucleotides. Cationic lipids are also known in the art and are commonly used for gene delivery. Such lipids include Lipofectin™ also known as DOTMA (N—[1-(2,3-dioleyloxy) propyls N,N, N-trimethylammonium chloride), DOTAP (1,2-bis (oleyloxy)-3 (trimethylammonio) propane), DDAB (dimethyl-dioctadecyl-ammonium bromide), DOGS (dioctadecylami-dologlycyl spermine) and cholesterol derivatives such as DCChol (3 beta-(N—(N',N'-dimethyl aminomethane)-carbamoyl) cholesterol). A description of these cationic lipids can be found in EP 187,702, WO 90/11092, U.S. Pat. No. 5,283,185, WO 91/15501, WO 95/26356, and U.S. Pat. No. 5,527,928. A particular useful cationic lipid formulation that may be used with the nucleic vaccine provided by the disclosure is VAXFECTIN, which is a commixture of a cationic lipid (GAP-DMORIE) and a neutral phospholipid (DPyPE) which, when combined in an aqueous vehicle, self-assemble to form liposomes. Cationic lipids for gene delivery are preferably used in association with a neutral lipid such as DOPE (dioleyl phosphatidylethanolamine), as described in WO 90/11092 as an example. In addition, a DNA vaccine can also be formulated with a nonionic block copolymer such as CRL1005.

G. Uses of the Immunogenic PAA Polypeptides, Nucleic Acid Molecules, and Compositions In other aspects, the present disclosure provides methods of using the immunogenic PAA polypeptides, isolated nucleic acid molecules, and compositions comprising an immunogenic PAA polypeptide or isolated nucleic acid molecule described herein above.

In one aspect, the present disclosure provides a method of eliciting an immune response against a PAA in a mammal, particularly a human, comprising administering to the mammal an effective amount of (1) an immunogenic PAA polypeptide provided by the disclosure that is immunogenic against the target PAA, (2) an isolated nucleic acid molecule encoding such an immunogenic PAA polypeptide, (3) a composition comprising such an immunogenic PAA polypeptide, or (4) a composition comprising an isolated nucleic acid molecule encoding such an immunogenic PAA polypeptide.

In some embodiments, the disclosure provides a method of eliciting an immune response against PSMA in a human, comprising administering to the human an effective amount of an immunogenic PSMA composition provided by the present disclosure, wherein the immunogenic PSMA composition is selected from: (1) an immunogenic PSMA polypeptide, (2) an isolated nucleic acid molecule encoding an immunogenic PSMA polypeptide, (3) a composition comprising an immunogenic PSMA polypeptide, or (4) a composition comprising an isolated nucleic acid molecule encoding an immunogenic PSMA polypeptide.

In some other embodiments, the disclosure provides a method of eliciting an immune response against PSA in a human, comprising administering to the human an effective amount of an immunogenic PSA composition provided by the present disclosure, wherein the immunogenic PSA composition is selected from: (1) an immunogenic PSA polypeptide, (2) an isolated nucleic acid molecule encoding an immunogenic PSA polypeptide, (3) a composition comprising an immunogenic PSA polypeptide, or (4) a composition comprising an isolated nucleic acid molecule encoding an immunogenic PSA polypeptide.

In another aspect, the present disclosure provides a method of inhibiting abnormal cell proliferation in a human, wherein the abnormal cell proliferation is associated with over-expression of a PAA. The method comprises administering to the human an effective amount of immunogenic PAA composition provided by the present disclosure that is immunogenic against the over-expressed PAA. The immunogenic PAA composition may be (1) an immunogenic PAA polypeptide, (2) an isolated nucleic acid molecule encoding one or more immunogenic PAA polypeptides, (3) a composition comprising an immunogenic PAA polypeptide, or (4) a composition comprising an isolated nucleic acid molecule encoding one or more immunogenic PAA polypeptides. In some embodiments, the method is for inhibiting abnormal cell proliferation in prostate in a human. In a particular embodiment, the present disclosure provide a method of inhibiting abnormal cell proliferation in prostate over-expressing PSMA, comprising administering to the human effective amount of (1) an immunogenic PSMA polypeptide, (2) an isolated nucleic acid molecule encoding one or more immunogenic PSMA polypeptides, (3) a composition comprising an immunogenic PSMA polypeptide, or (4) a composition comprising an isolated nucleic acid molecule encoding one or more immunogenic PSMA polypeptide.

In another aspect, the present disclosure provides a method of treating cancer in a human wherein cancer is associated with over-expression of a PAA. The method comprises administering to the human an effective amount of immunogenic PAA composition capable of eliciting an immune response against the over-expressed PAA. The immunogenic PAA composition may be (1) an immunogenic PAA polypeptide, (2) an isolated nucleic acid molecule encoding one or more immunogenic PAA polypeptides, (3) a composition comprising an immunogenic PAA polypeptide, or (4) a composition comprising an isolated nucleic acid molecule encoding one or more immunogenic PAA polypeptides. Examples of cancers that may be treated with the method include breast cancer, stomach cancer, ovarian cancer, lung cancer, bladder cancer, colorectal cancer, renal cancer, pancreatic cancer and prostate cancer.

In some embodiments, the disclosure provides a method of treating prostate cancer in a human, comprising administering to the human an effective amount of a nucleic acid composition provided herein above. The nucleic acids in the composition may encode only one particular immunogenic PAA polypeptide, such an immunogenic PSMA polypeptide, an immunogenic PSA polypeptide, or an immunogenic PSCA polypeptide. The nucleic acids in the composition may also encode two or more different immunogenic PAA polypeptides, such as: (1) an immunogenic PSMA polypeptide and an immunogenic PSA polypeptide; (2) an immunogenic PSMA polypeptide and an immunogenic PSCA polypeptide; (3) an immunogenic PSA polypeptide and an immunogenic PSCA polypeptide; (4) an immunogenic PSMA polypeptide, an immunogenic PSA polypeptide, and an immunogenic PSCA polypeptide. Each individual nucleic acid molecule in the composition may encode only one particular immunogenic PAA polypeptide, such as a PSMA polypeptide, a PSA polypeptide, or a PSCA polypeptide. Alternatively, an individual nucleic acid molecule in the composition may be a multi-antigen constructs encoding two different types of immunogenic PAA polypeptides, such as: (1) an immunogenic PSMA polypeptide and an immunogenic PSA polypeptide; (2) an immunogenic PSMA polypeptide and an immunogenic PSCA polypeptide; (3) an immunogenic PSCA polypeptide and an immunogenic PSA polypeptide; or (4) an immunogenic PSMA polypeptide, an immunogenic PSA polypeptide, and an immunogenic PSCA polypeptide. In some particular embodiments, the nucleic acid composition comprises a multi-antigen construct that encode at least (4) an immunogenic PSMA polypeptide, an immunogenic PSA polypeptide, and an immunogenic PSCA polypeptide. The immunogenic PSCA polypeptide contained in vaccine compositions or expressed by a nucleic acid in vaccine compositions for the treatment of prostate cancer in human is preferably the human full length PSCA protein.

The polypeptide and nucleic acid compositions can be administered to an animal, including human, by a number of methods known in the art. Examples of suitable methods include: (1) intramuscular, intradermal, intraepidermal, intravenous, intraarterial, subcutaneous, or intraperitoneal administration, (2) oral administration, and (3) topical application (such as ocular, intranasal, and intravaginal application). One particular method of intradermal or intraepidermal administration of a nucleic acid vaccine composition that may be used is gene gun delivery using the Particle Mediated Epidermal Delivery (PMED™) vaccine delivery device marketed by PowderMed. PMED is a needle-free method of administering vaccines to animals or humans. The PMED system involves the precipitation of DNA onto microscopic gold particles that are then propelled by helium gas into the epidermis. The DNA-coated gold particles are delivered to the APCs and keratinocytes of the epidermis, and once inside the nuclei of these cells, the DNA elutes off the gold and becomes transcriptionally active, producing encoded protein. This protein is then presented by the APCs to the lymphocytes to induce a T-cell-mediated immune response. Another particular method for intramuscular administration of a nucleic acid vaccine provided by the present disclosure is electroporation. Electroporation uses controlled electrical pulses to create temporary pores in the cell membrane, which facilitates cellular uptake of the nucleic acid vaccine injected into the muscle. Where a CpG is used in combination with a nucleic acid vaccine, it is preferred that the CpG and nucleic acid vaccine are co-formulated in one formulation and the formulation is administered intramuscularly by electroporation.

The effective amount of the immunogenic PAA polypeptide or nucleic acid encoding an immunogenic PAA polypeptide in the composition to be administered in a given method provided by the present disclosure can be readily determined by a person skilled in the art and will depend on a number of factors. In a method of treating cancer, such as prostate cancer, factors that may be considered in determining the effective amount of the immunogenic PAA polypeptide or nucleic acid include, but not limited: (1) the subject to be treated, including the subject's immune status and health, (2) the severity or stage of the cancer to be treated, (3) the specific immunogenic PAA polypeptides used or expressed, (4) the degree of protection or treatment desired, (5) the administration method and schedule, and (6) other therapeutic agents (such as adjuvants or immune modulators) used. In the case of nucleic acid vaccine compositions, including the multi-antigen vaccine compositions, the method of formulation and delivery are among the key factors for determining the dose of the nucleic acid required to elicit an effective immune response. For example, the effective amounts of the nucleic acid may be in the range of 2 µg/dose-10 mg/dose when the nucleic acid vaccine composition is formulated as an aqueous solution and administered by hypodermic needle injection or pneumatic injection, whereas only 16 ng/dose-16 µg/dose may be required when the nucleic acid is prepared as coated gold beads and delivered using a gene gun technology. The dose range for a nucleic acid vaccine by electroporation is generally in the range of 0.5-10 mg/dose. In the case where the nucleic acid vaccine is administered together with a CpG by electroporation in a co-formulation, the dose of the nucleic acid vaccine may be in the range of 0.5-5 mg/dose and the dose of CpG is typically in the range of 0.05 mg-5 mg/dose, such as 0.05, 0.2, 0.6, or 1.2 mg/dose per person.

The nucleic acid or polypeptide vaccine composition of the present invention can be used in a prime-boost strategy to induce robust and long-lasting immune response. Priming and boosting vaccination protocols based on repeated injections of the same immunogenic construct are well known. In general, the first dose may not produce protective immunity, but only "primes" the immune system. A protective immune response develops after the second or third dose (the "boosts). The boosts are performed according to conventional techniques, and can be further optimized empirically in terms of schedule of administration, route of administration, choice of adjuvant, dose, and potential sequence when administered with another vaccine. In one embodiment, the nucleic acid or polypeptide vaccines of the present invention are used in a conventional homologous prime-boost strategy, in which the same vaccine is administered to the animal in multiple doses. In another embodiment, the nucleic acid or polypeptide vaccine compositions are used in a heterologous prime-boost vaccination, in which different types of vaccines containing the same antigens are administered at predetermined time intervals. For example, a nucleic acid construct may be administered in the form of a plasmid in the initial dose ("prime") and as part of a vector in the subsequent doses ("boosts"), or vice versa.

For the treatment of prostate cancer, the polypeptide or nucleic acid vaccines of the present invention may be used together with prostate cancer vaccines based on other antigens, such as prostatic acid phosphatase-based antigens and androgen receptor.

The polypeptide or nucleic acid vaccine composition of the present invention may be used together with one or more adjuvants. Examples of suitable adjuvants include: (1) oil-in-water emulsion formulations (with or without other specific immunostimulating agents such as muramyl polypeptides or bacterial cell wall components), such as for example (a) MF59™ (PCT Publication No. WO 90/14837; Chapter 10 in *Vaccine design: the subunit and adjuvant approach*, eds. Powell & Newman, Plenum Press 1995), containing 5% Squalene, 0.5% Tween 80 (polyoxyethylene sorbitan monooleate), and 0.5% Span 85 (sorbitan trioleate) formulated into submicron particles using a microfluidizer, (b) SAF, containing 10% Squalene, 0.4% Tween 80, 5% pluronic-blocked polymer L121, and thr-MDP either microfluidized into a submicron emulsion or vortexed to generate a larger particle size emulsion, and (c) RIBI™ adjuvant system (RAS) (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS); (2) saponin adjuvants, such as QS21, STIMULON™ (Cambridge Bioscience, Worcester, Mass.), Abisco® (Isconova, Sweden), or Iscomatrix® (Commonwealth Serum Laboratories, Australia); (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (PCT Publication No. WO 99/44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL), optionally in the substantial absence of alum when used with pneumococcal saccharides (e.g. GB-2220221, EP-A-0689454, WO 00/56358); (6) combinations of 3dMPL with, for example, QS21 and/or oil-in-water emulsions (e.g. EP-A-0835318, EP-A-0735898, EP-A-0761231); (7) oligonucleotides comprising CpG motifs, i.e. containing at least one CG dinucleotide, where the cytosine is unmethylated (e.g., Krieg, *Vaccine* (2000) 19:618-622; Krieg, *Curr Opin Mol Ther* (2001) 3:15-24; WO 98/40100, WO 98/55495, WO 98/37919 and WO 98/52581); (8) a polyoxyethylene ether or a polyoxyethylene ester (e.g. WO 99/52549); (9) a polyoxyethylene sorbitan ester surfactant in combination with an octoxynol (e.g., WO 01/21207) or a polyoxyethylene alkyl ether or ester surfactant in combination with at least one additional non-ionic surfactant such as an octoxynol (e.g., WO 01/21152); (10) a saponin and an immunostimulatory oligonucleotide (e.g. a CpG oligonucleotide) (e.g., WO 00/62800); (11) metal salt including aluminum salts (such as alum, aluminum phosphate, aluminum hydroxide); (12) a saponin and an oil-in-water emulsion (e.g. WO 99/11241); (13) a saponin (e.g. QS21)+3dMPL+IM2 (optionally+a sterol)(e.g. WO 98/57659); (14) other substances that act as immunostimulating agents to enhance the efficacy of the composition, such as Muramyl polypeptides including N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), (15) ligands for toll-like receptors (TLR), natural or synthesized (e.g. Kanzler et al., *Nature Med.* 13:1552-1559 (2007)), including TLR3 ligands such as polyI:C and similar compounds such as Hiltonol and Ampligen.

The polypeptide or nucleic acid vaccine compositions of the present invention may be used together with one or more immune modulators. Examples of suitable immune modulators include protein tyrosine kinase inhibitors (such as afatinib, axitinib, cediranib, erlotinib, gefitinib, grandinin, lapatinib, lestaurtinib, neratinib, pazopanib, quizartinib, regorafenib, semaxanib, sorafenib, sunitinib, tivozanib, toceranib, bosutinib and vandetanib), CD40 agonists (such as CD40 agonist antibody), OX40 agonists (such as OX40 agonist antibody), CTLA-4 inhibitors (such as antiCTLA-4 antibody Ipilimumab and Tremelimumab), TLR agonists, 4-1BB agonists, Tim-1 antagonists, LAGE-3 antagonists and PD-L1 & PD-1 antagonists.

H. Vaccine-Based Immunotherapy Regimens (VBIR)

In a further aspect, the present disclosure provides a method of enhancing the immunogenicity or therapeutic effect of a vaccine for the treatment of a neoplastic disorder in a mammal, particularly a human. The method comprises administering to the mammal receiving the vaccine for the treatment of a neoplastic disorder (1) an effective amount of at least one immune-suppressive-cell inhibitor (ISC inhibitor) and (2) an effective amount of at least one immune-effector-cell enhancer (IEC enhancer). The method may be used in combination with a vaccine in any form or formulation, for example, a subunit vaccine, a protein-based vaccine, a peptide-based vaccine, or a nucleic acid-based vaccines such as a DNA-based vaccine, a RNA-based vaccine, a plasmid-based vaccine, or a vector-based vaccine. In addition, the method is not limited to any particular types of vaccines or any particular types of cancer. Rather, the method may be used in combination with any vaccine intended for the treatment of neoplastic disorder, including benign, pre-malignant, and malignant neoplastic disorders. For example, the method may be used in combination a vaccine that is intended for the treatment of any of the following neoplastic disorders: carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyosarcoma, and osteosarcoma; other tumors including melanoma, xenoderma pigmentosum, keratoactanthoma, seminoma, thyroid follicular cancer, and teratocarcinoma; melanoma, unresectable stage III or IV malignant melanoma, squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, bone cancer, bone tumors, adult malignant fibrous histiocytoma of bone; childhood malignant fibrous histiocytoma of bone, sarcoma, pediatric sarcoma, sinonasal natural killer, neoplasms, plasma cell neoplasm; myelodysplastic syndromes; neuroblastoma; testicular germ cell tumor, intraocular melanoma, myelodysplastic syndromes; myelodysplastic/myeloproliferative diseases, synovial sarcoma, chronic myeloid leukemia, acute lymphoblastic leukemia, philadelphia chromosome positive acute lymphoblastic leukemia (Ph+ALL), multiple myeloma, acute myelogenous leukemia, chronic lymphocytic leukemia, and mastocytosis.

In some embodiments, present disclosure provides a method of enhancing the immunogenicity or therapeutic effect of a vaccine for the treatment of prostate cancer in a human. The vaccine administered may be capable of eliciting an immune response against any human PAA, such as PSMA, PSA, or PSCA. In some particular embodiments, the vaccine administered comprises a nucleic acid molecule encoding an antigen capable of eliciting immunogenicity against a human PAA, such as PSMA, PSA, or PSCA. Examples of specific nucleic acid molecules that may be contained in the vaccine include the following provided by the present disclosure:

1) a nucleic acid molecule encoding an immunogenic PSMA polypeptide, an immunogenic PSA polypeptide, or an immunogenic PSCA polypeptide;

2) a nucleic acid molecule encoding two immunogenic PAA polypeptides provided by the present disclosure, such as a) an immunogenic PSMA polypeptide and an immunogenic PSA polypeptide; b) an immunogenic PSMA polypeptide and an immunogenic PSCA polypeptide; or c) an immunogenic PSA polypeptide and an immunogenic PSCA polypeptide; and 3) a nucleic acid molecule encoding three immunogenic PAA polypeptides, which are an immunogenic PSMA polypeptide, an immunogenic PSA polypeptide, and an immunogenic PSCA polypeptide.

In another further aspect, the present disclosure provides a method of treating a neoplastic disorder in a mammal, particularly a human. The method comprises administering to the mammal (1) an effective amount of a vaccine capable of eliciting an immune response against a TAA associated with the neoplastic disorder, (2) an effective amount of at least one immune-suppressive-cell inhibitor (ISC inhibitor), and (3) an effective amount of at least one immune-effector-cell enhancer (IEC enhancer). Any vaccine that is capable of eliciting an immune response against a particular TAA may be used in the method. Many TAAs are known in the art. In addition to the prostate-associated antigens, the following are examples of TAAs that are known in the art: CEA, MUC-1, Ep-CAM, 5T4, hCG-b, K-ras, and TERT for colorectal cancer; CEA, Muc-1, p53, mesothelin, Survivin, and NY-ESO-1 for ovarian cancer; Muc-1, 5T4, WT-1, TERT, CEA, EGF-R and MAGE-A3 for non-small cell lung cancer; 5T4 for renal cell carcinoma; and Muc-1, mesothelin, K-Ras, Annexin A2, TERT, and CEA for pancreatic cancer. New TAAs continue to be identified. A vaccine that is capable of eliciting an immune response against any of the known or new TAAs can be used in the method. In addition, the vaccine administered may be in any form or formulation, for example, subunit vaccines, protein-based vaccine, peptide based vaccines, or nucleic acid-based vaccines such DNA-based vaccines, RNA-based vaccines, plasmid-based vaccines, or vector-based vaccines.

In some embodiments, the present disclosure provides a method of treating a prostate cancer in a human, the method comprising administering to the human a vaccine capable of eliciting an immune response against any human PAA, such as PSMA, PSA, or PSCA. In some particular embodiments, the vaccine administered comprises a nucleic acid molecule encoding an antigen capable of eliciting immunogenicity against a human PAA, such as PSMA, PSA, or PSCA. Examples of specific nucleic acid molecules that may be contained in the vaccine include the following provided by the present disclosure:

1) a nucleic acid molecule encoding an immunogenic PSMA polypeptide, an immunogenic PSA polypeptide, or an immunogenic PSCA polypeptide;

2) a nucleic acid molecule encoding two immunogenic PAA polypeptides provided by the present disclosure, such as a) an immunogenic PSMA polypeptide and an immunogenic PSA polypeptide; b) an immunogenic PSMA polypeptide and an immunogenic PSCA polypeptide; or c) an immunogenic PSA polypeptide and an immunogenic PSCA polypeptide; and 3) a nucleic acid molecule encoding three immunogenic PAA polypeptides, which are an immunogenic PSMA polypeptide, an immunogenic PSA polypeptide, and an immunogenic PSMA polypeptide.

The method of treating a neoplastic disorder in a mammal and the method of enhancing the immunogenicity or therapeutic effect of a vaccine for the treatment of a neoplastic disorder in a mammal described herein above are alternatively referred to as "vaccine-based immunotherapy regimens" (or "VBIR").

In the vaccine-based immunotherapy regimens, the IEC enhancers and ISC inhibitors may be administered by any suitable methods and routes, including (1) systemic administration such as intravenous, intramuscular, or oral administration, and (2) local administration such intradermal and subcutaneous administration. Where appropriate or suitable, local administration is generally preferred over systemic administration. Local administration of any IEC enhancer and ISC inhibitor can be carried out at any location of the body of the mammal that is suitable for local administration of pharmaceuticals; however, it is more preferable that these immune modulators are administered locally at close proximity to the vaccine draining lymph node.

Two or more specific IEC enhancers from a single class of IEC enhancers (for examples, two CTLA-agonists) may be administered in combination with the ISC inhibitors. In addition, two or more specific IEC enhancers from two or more different classes of IEC enhancers (for example, one CTLA-4 antagonist and one TLR agonist) may be administered together. Similarly, two or more specific ISC inhibitors from a single class of ISC inhibitors (for examples, two or more protein kinase inhibitors) may be administered in combination with the IEC enhancers. In addition, two or more specific ISC inhibitors from two or more different classes of ISC inhibitors (for example, one protein kinase inhibitor and one COX-2 inhibitor) may be administered together.

In the vaccine-based immunotherapy regimens the vaccine may be administered simultaneously or sequentially with any or all of the immune modulators (i.e., ISC inhibitors and IEC enhancers) used. Similarly, when two or more immune modulators are used, they may be administered simultaneously or sequentially with respect to each other. In some embodiments, a vaccine is administered simultaneously (e.g., in a mixture) with respect to one immune modulator, but sequentially with respect to one or more additional immune modulators. Co-administration of the vaccine and the immune modulators in the vaccine-based immunotherapy regimen can include cases in which the vaccine and at least one immune modulator are administered so that each is present at the administration site, such as vaccine draining lymph node, at the same time, even though the antigen and the immune modulators are not administered simultaneously. Co-administration of the vaccine and the immune modulators also can include cases in which the vaccine or the immune modulator is cleared from the administration site, but at least one cellular effect of the cleared vaccine or immune modulator persists at the administration site, such as vaccine draining lymph node, at least until one or more additional immune modulators are administered to the administration site. In cases where a nucleic acid vaccine is administered in combination with a CpG, the vaccine and CpG may be contained in a single formulation and administered together by any suitable method. In some embodiments, the nucleic acid vaccine and CpG in a co-formulation (mixture) is administered by intramuscular injection in combination with electroporation.

Any ISC inhibitors may be used in the vaccine-based immunotherapy regimens. Examples of classes of SIC inhibitors include protein kinase inhibitors, cyclooxygenase-2 (COX-2) inhibitors, phosphodiesterase type 5 (PDE5) inhibitors, and DNA crosslinkers. Examples COX-2 inhibitors include celecoxib and rofecoxib. Examples of PDE5 inhibitors include avanafil, lodenafil, mirodenafil, sildenafil, tadalafil, vardenafil, udenafil, and zaprinast. An example of DNA crosslinkers is cyclophosphamide. Examples of specific protein kinase inhibitors are described in details below.

The term "protein kinase inhibitor" refers to any substance that acts as a selective or non-selective inhibitor of a protein kinase. The term "protein kinases" refers to the enzymes that catalyze the transfer of the terminal phosphate of adenosine triphosphate to tyrosine, serine or threonine residues in protein substrates. Protein kinases include receptor tyrosine kinases and non-receptor tyrosine kinases. Examples of receptor tyrosine kinases include EGFR (e.g., EGFR/HER1/ErbB1, HER2/Neu/ErbB2, HER3/ErbB3, HER4/ErbB4), INSR (insulin receptor), IGF-IR, IGF-II1R, IRR (insulin receptor-related receptor), PDGFR (e.g., PDGFRA, PDGFRB), c-KIT/SCFR, VEGFR-1/FLT-1, VEGFR-2/FLK-1/KDR, VEGFR-3/FLT-4, FLT-3/FLK-2, CSF-1R, FGFR 1-4, CCK4, TRK A-C, MET, RON, EPHA 1-8, EPHB 1-6, AXL, MER, TYRO3, TIE, TEK, RYK, DDR 1-2, RET, c-ROS, LTK (leukocyte tyrosine kinase), ALK (anaplastic lymphoma kinase), ROR 1-2, MUSK, AATYK 1-3, and RTK 106. Examples of non-receptor tyrosine kinases include BCR-ABL, Src, Frk, Btk, Csk, Abl, Zap70, Fes/Fps, Fak, Jak, Ack, and LIMK. In the vaccine-based immunotherapy regimen provided by the present disclosure, the protein kinase inhibitors are administered to the mammal at a suboptimal dose. The term "suboptimal dose" refers to the dose amount that is below the minimum effective dose when the tyrosine kinase inhibitor is administered in a monotherapy (i.e., where the protein kinase inhibitor is administered alone without any other therapeutic agents) for the target neoplastic disorder.

Examples of specific protein kinase inhibitors suitable for use in the vaccine-based immunotherapy regimen include Lapatinib, AZD 2171, ET18OCH 3, Indirubin-3'-oxime, NSC-154020, PD 169316, Quercetin, Roscovitine, Triciribine, ZD 1839, 5-Iodotubercidin, Adaphostin, Aloisine, Alsterpaullone, Aminogenistein, API-2, Apigenin, Arctigenin, ARRY-334543, Axitinib (AG-013736), AY-22989, AZD 2171, Bisindolylmaleimide IX, CCI-779, Chelerythrine, DMPQ, DRB, Edelfosine, ENMD-981693, Erbstatin analog, Erlotinib, Fasudil, Gefitinib (ZD1839), H-7, H-8, H-89, HA-100, HA-1004, HA-1077, HA-1100, Hydroxyfasudil, Kenpaullone, KN-62, KY12420, LFM-A13, Luteolin, LY294002, LY-294002, Mallotoxin, ML-9, MLN608, NSC-226080, NSC-231634, NSC-664704, NSC-680410, NU6102, Olomoucine, Oxindole I, PD 153035, PD 98059, Phloridzin, Piceatannol, Picropodophyllin, PKI, PP1, PP2, PTK787/ZK222584, PTK787/ZK-222584, Purvalanol A, Rapamune, Rapamycin, Ro 31-8220, Rottlerin, SB202190, SB203580, Sirolimus, SL327, SP600125, Staurosporine, STI-571, SU1498, SU4312, SU5416, SU5416 (Semaxanib), SU6656, SU6668, syk inhibitor, TBB, TCN, Tyrphostin AG 1024, Tyrphostin AG 490, Tyrphostin AG 825, Tyrphostin AG 957, U0126, W-7, Wortmannin, Y-27632, Zactima (ZD6474), ZM 252868. gefitinib (Iressa®), sunitinib malate (Sutent®; SU11248), erlotinib (Tarceva®; OSI-1774), lapatinib (GW572016; GW2016), canertinib (CI 1033), semaxinib (SU5416), vatalanib (PTK787/ZK222584), sorafenib (BAY 43-9006), imatinib (Gleevec®; STI571), dasatinib (BMS-354825), leflunomide (SU101), vandetanib (Zactima®; ZD6474), and nilotinib. Additional protein kinase inhibitors suitable for use in the present invention are described in, e.g., U.S. Pat. Nos. 5,618,829, 5,639,757, 5,728,868, 5,804,396, 6,100,254, 6,127,374, 6,245,759, 6,306,874, 6,313,138, 6,316,444, 6,329,380, 6,344,459, 6,420,382, 6,479,512, 6,498,165, 6,544,988, 6,562,818, 6,586,423, 6,586,424, 6,740,665, 6,794,393, 6,875,767, 6,927,293, and 6,958,340.

In some embodiments, the protein kinase inhibitor is a multi-kinase inhibitor, which is an inhibitor that acts on more than one specific kinase. Examples of multi-kinase inhibitors include imatinib, sorafenib, lapatinib, BIRB-796, and AZD-1152, AMG706, Zactima (ZD6474), MP-412, sorafenib (BAY 43-9006), dasatinib, CEP-701 (lestaurtinib), XL647, XL999, Tykerb (lapatinib), MLN518, (formerly known as CT53518), PKC412, ST1571, AEE 788, OSI-930, OSI-817, sunitinib malate (Sutent), axitinib (AG-013736), erlotinib, gefitinib, axitinib, bosutinib, temsirolismus and nilotinib (AMN107). In some particular embodiments, the tyrosine kinase inhibitor is sunitinib, sorafenib, or a pharmaceutically acceptable salt or derivative (such as a malate or a tosylate) of sunitinib or sorafenib.

Sunitinib malate, which is marketed by Pfizer Inc. under the trade name SUTENT, is described chemically as butanedioic acid, hydroxy-, (2S)-, compound with N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (1:1). The compound, its synthesis, and particular polymorphs are described in U.S. Pat. No. 6,573,293, U.S. Patent Publication Nos. 2003-0229229, 2003-0069298 and 2005-0059824, and in J. M. Manley, M. J. Kalman, B. G. Conway, C. C. Ball, J. L Havens and R. Vaidyanathan, "Early Amidation Approach to 3-[(4-amido)pyrrol-2-yl]-2-indolinones," J. Org. Chew. 68, 6447-6450 (2003). Formulations of sunitinib and its L-malate salt are described in PCT Publication No. WO 2004/024127. Sunitinib malate has been approved in the U.S. for the treatment of gastrointestinal stromal tumor, advanced renal cell carcinoma, and progressive, well-differentiated pancreatic neuroendocrine tumors in patients with unresectable locally advanced or metastatic disease. The recommended dose of sunitinib malate for gastrointestinal stromal tumor (GIST) and advanced renal cell carcinoma (RCC) for humans is 50 mg taken orally once daily, on a schedule of 4 weeks on treatment followed by 2 weeks off (Schedule 4/2). The recommended dose of sunitinib malate for pancreatic neuroendocrine tumors (pNET) is 37.5 mg taken orally once daily.

In the vaccine-based immunotherapy regimen, sunitinib malate may be administered orally in a single dose or multiple doses. Typically, sunitinib malate is delivered for two, three, four or more consecutive weekly doses followed by a "off" period of about 1 or 2 weeks, or more where no sunitinib malate is delivered. In one embodiment, the doses are delivered for about 4 weeks, with 2 weeks off. In another embodiment, the sunitinib malate is delivered for two weeks, with 1 week off. However, it may also be delivered without a "off" period for the entire treatment period. The effective amount of sunitinib malate administered orally to a human in the vaccine-based immunotherapy regimen is typically below 40 mg per person per dose. For example, it may be administered orally at 37.5, 31.25, 25, 18.75, 12.5, 6.25 mg per person per day. In some embodiments, sunitinib malate is administered orally in the range of 1-25 mg per person per dose. In some other embodiments, sunitinib malate is administered orally in the range of 6.25, 12.5, or 18.75 mg per person per dose. Other dosage regimens and variations are foreseeable, and will be determined through physician guidance.

Sorafenib tosylate, which is marketed under the trade name NEXAVAR, is also a multi-kinase inhibitor. Its chemical name is 4-(4-{3-[4-Chloro-3-(trifluoromethyl)phenyl]ureido}phenoxy)-N-methylpyrid-ine-2-carboxamide. It is approved in the U.S. for the treatment of primary kidney cancer (advanced renal cell carcinoma) and advanced primary liver cancer (hepatocellular carcinoma). The recommended daily dose is 400 mg taken orally twice daily. In the vaccine-based immunotherapy regimen provided by the present disclosure, the effective amount of sorafenib tosylate administered orally is typically below 400 mg per person per day. In some embodiments, the effective amount of sorafenib tosylate administered orally is in the range of 10-300 mg per person per day. In some other embodiments, the effective amount of sorafenib tosylate administered orally is between 10-200 mg per person per day, such as 10, 20, 60, 80, 100, 120, 140, 160, 180, or 200 mg per person per day.

Axitinib, which is marketed under the trade name INLYTA, is a selective inhibitor of VEGF receptors 1, 2, and 3. Its chemical name is (N-Methyl-2-[3-((E)-2-pyridin-2-ylvinyl)-1H-indazol-6-ylsulfanyl]-benzamide. It is approved for the treatment of advanced renal cell carcinoma after failure of one prior systemic therapy. The starting dose is 5 mg orally twice daily. Dose adjustments can be made based on individual safety and tolerability. In the vaccine-based immunotherapy regimen provided by the present disclosure, the effective amount of axitinib administered orally is typically below 5 mg twice daily. In some other embodiments, the effective amount of axitinib administered orally is between 1-5 mg twice daily. In some other embodiments, the effective amount of axitinib administered orally is between 1, 2, 3, 4, or 5 mg twice daily.

In the vaccine-based immunotherapy regimens any IEC enhancers may be used. They may be small molecules or large molecules (such as protein, polypeptide, DNA, RNA, and antibody). Examples of IEC enhancers that may be used include TNFR agonists, CTLA-4 antagonists, TLR agonists, programmed cell death protein 1 (PD-1) antagonists (such as BMS-936558), anti-PD-1 antibody CT-011), and programmed cell death protein 1 ligand 1 (PD-L1) antagonists (such as BMS-936559), lymphocyte-activation gene 3 (LAG3) antagonists, and T cell Immunoglobulin- and mucin-domain-containing molecule-3 (TIM-3) antagonists. Examples of specific TNFR agonists, CTLA-4 antagonists, and TLR agonists are provided in details herein below.

TNFR Agonists.

Examples of TNFR agonists include agonists of OX40, 4-1BB (such as BMS-663513), GITR (such as TRX518), and CD40. Examples of specific CD40 agonists are described in details herein below.

CD40 agonists are substances that bind to a CD40 receptor on a cell and is capable of increasing one or more CD40 or CD40L associated activities. Thus, CD40 "agonists" encompass CD40 "ligands".

Examples of CD40 agonists include CD40 agonistic antibodies, fragments CD40 agonistic antibodies, CD40 ligands (CD40L), and fragments and derivatives of CD40L such as oligomeric (e.g., bivalent, trimeric CD40L), fusion proteins containing and variants thereof.

CD40 ligands for use in the present invention include any peptide, polypeptide or protein, or a nucleic acid encoding a peptide, polypeptide or protein that can bind to and activate one or more CD40 receptors on a cell. Suitable CD40 ligands are described, for example, in U.S. Pat. Nos. 6,482, 411, 6,410,711; U.S. Pat. No. 6,391,637; and U.S. Pat. No. 5,981,724, all of which patents and application and the CD40L sequences disclosed therein are incorporated by reference in their entirety herein. Although human CD40 ligands will be preferred for use in human therapy, CD40 ligands from any species may be used in the invention. For use in other animal species, such as in veterinary embodiments, a species of CD40 ligand matched to the animal being treated will be preferred. In certain embodiments, the CD40 ligand is a gp39 peptide or protein oligomer, including naturally forming gp39 peptide, polypeptide or protein oligomers, as well as gp39 peptides, polypeptides, proteins (and encoding nucleic acids) that comprise an oligomerization sequence. While oligomers such as dimers, trimers and tetramers are preferred in certain aspects of the invention, in other aspects of the invention larger oligomeric structures are contemplated for use, so long as the oligomeric structure retains the ability to bind to and activate one or more CD40 receptor(s).

In certain other embodiments, the CD40 agonist is an anti-CD40 antibody, or antigen-binding fragment thereof. The antibody can be a human, humanized or part-human chimeric anti-CD40 antibody. Examples of specific anti- CD40 monoclonal antibodies include the G28-5, mAb89, EA-5 or S2C6 monoclonal antibody, and CP870893. In a particular embodiment, the anti-CD40 agonist antibody is CP870893 or dacetuzumab (SGN-40).

CP-870,893 is a fully human agonistic CD40 monoclonal antibody (mAb) that has been investigated clinically as an anti-tumor therapy. The structure and preparation of CP870,893 is disclosed in WO2003041070 (where the antibody is identified by the internal identified "21.4.1"). The amino acid sequences of the heavy chain and light chain of CP-870,893 are set forth in SEQ ID NO: 40 and SEQ ID NO: 41, respectively. In clinical trials, CP870,893 was administered by intravenous infusion at doses generally in the ranges of 0.05-0.25 mg/kg per infusion. In a phase I clinical study, the maximum tolerated dose (MTD) of CP-870893 was estimated to be 0.2 mg/kg and the dose-limiting toxicities included grade 3 CRS and grade 3 urticaria. [Jens Ruter et al.: Immune modulation with weekly dosing of an agonist CD40 antibody in a phase I study of patients with advanced solid tumors. Cancer Biology & Therapy 10:10, 983-993; Nov. 15, 2010.]. In the vaccine-based immunotherapy regimen provided by the present disclosure, CP-870,893 can be administered intradermally, subcutaneously, or topically. It is preferred that it is administered intradermally. The effective amount of CP870893 to be administered in the regimen is generally below 0.2 mg/kg, typically in the range of 0.01 mg-0.15 mg/kg, or 0.05-0.1 mg/kg.

Dacetuzumab (also known as SGN-40 or huS2C6; CAS number 88-486-59-9) is another anti-CD40 agonist antibody that has been investigated in clinical trials for indolent lymphomas, diffuse large B cell lymphomas and Multiple Myeloma. In the clinical trials, dacetuzumab was administered intravenously at weekly doses ranging from 2 mg/kg to 16 mg/kg. In the vaccine-based immunotherapy regimen provided by the present disclosure, dacetuzumab can be administered intradermally, subcutaneously, or topically. It is preferred that it is administered intradermally. The effective amount of dacetuzumab to be administered in the vaccine-based immunotherapy regimen is generally below 16 mg/kg, typically in the range of 0.2 mg-14 mg/kg, or 0.5-8 mg/kg, or 1-5 mg/kg.

CTLA-4 Inhibitors.

Suitable anti-CTLA-4 antagonist agents for use in the vaccine-based immunotherapy regimen provided by the disclosure include, without limitation, anti-CTLA-4 antibodies (such as human anti-CTLA-4 antibodies, mouse anti-CTLA-4 antibodies, mammalian anti-CTLA-4 antibodies, humanized anti-CTLA-4 antibodies, monoclonal anti-CTLA-4 antibodies, polyclonal anti-CTLA-4 antibodies, chimeric anti-CTLA-4 antibodies, anti-CTLA-4 domain antibodies), fragments of anti-CTLA-4 antibodies (such as (single chain anti-CTLA-4 fragments, heavy chain anti-CTLA-4 fragments, and light chain anti-CTLA-4 fragments), and inhibitors of CTLA-4 that agonize the co-stimulatory pathway. In some embodiments, the CTLA-4 inhibitor is Ipilimumab or Tremelimumab.

Ipilimumab (also known as MEX-010 or MDX-101), marketed as YERVOY, is a human anti-human CTLA-4 antibody. Ipilimumab can also be referred to by its CAS Registry No. 477202-00-9, and is disclosed as antibody 10D1 in PCT Publication No. WO 01/14424, incorporated herein by reference in its entirety and for all purposes. Examples of pharmaceutical composition comprising Ipilimumab are provided in PCT Publication No. WO 2007/67959. Ipilimumab is approved in the U.S. for the treatment of unresectable or metastatic melanoma. The recommended dose of Ipilimumab as monotherapy is 3 mg/kg by intravenous administration every 3 weeks for a total of 4 doses. In the methods provided by the present invention, Ipilimumab is administered locally, particularly intradermally or subcutaneously. The effective amount of Ipilimumab administered locally is typically in the range of 5-200 mg/dose per person. In some embodiments, the effective amount of Ipilimumab is in the range of 10-150 mg/dose per person per dose. In some particular embodiments, the effective amount of Ipilimumab is about 10, 25, 50, 75, 100, 125, 150, 175, or 200 mg/dose per person.

Tremelimumab (also known as CP-675,206) is a fully human IgG2 monoclonal antibody and has the CAS number 745013-59-6. Tremelimumab is disclosed as antibody 11.2.1 in U.S. Pat. No. 6,682,736, incorporated herein by reference in its entirety and for all purposes. The amino acid sequences of the heavy chain and light chain of Tremelimumab are set forth in SEQ IND NOs:42 and 43, respectively. Tremelimumab has been investigated in clinical trials for the treatment of various tumors, including melanoma and breast cancer; in which Tremelimumab was administered intravenously either as single dose or multiple doses every 4 or 12 weeks at the dose range of 0.01 and 15 mg/kg. In the regimens provided by the present invention, Tremelimumab is administered locally, particularly intradermally or subcutaneously. The effective amount of Tremelimumab administered intradermally or subcutaneously is typically in the range of 5-200 mg/dose per person. In some embodiments, the effective amount of Tremelimumab is in the range of 10-150 mg/dose per person per dose. In some particular embodiments, the effective amount of Tremelimumab is about 10, 25, 50, 75, 100, 125, 150, 175, or 200 mg/dose per person.

Toll-Like Receptor (TLR) Agonists.

The term "toll-like receptor agonist" or "TLR agonist" refers to a compound that acts as an agonist of a toll-like receptor (TLR). This includes agonists of TLR1, TLR2, TLR3, TLR4, TLR5, TLR6, TLR7, TLR8, TLR9, TLR10, and TLR11 or a combination thereof. Unless otherwise indicated, reference to a TLR agonist compound can include the compound in any pharmaceutically acceptable form, including any isomer (e.g., diastereomer or enantiomer), salt, solvate, polymorph, and the like. In particular, if a compound is optically active, reference to the compound can include each of the compound's enantiomers as well as racemic mixtures of the enantiomers. Also, a compound may be identified as an agonist of one or more particular TLRs (e.g., a TLR7 agonist, a TLR8 agonist, or a TLR7/8 agonist).

The TLR agonism for a particular compound may be assessed in any suitable manner known in the art. Regardless of the particular assay employed, a compound can be identified as an agonist of a particular TLR if performing the assay with a compound results in at least a threshold increase of some biological activity mediated by the particular TLR. Conversely, a compound may be identified as not acting as an agonist of a specified TLR if, when used to perform an assay designed to detect biological activity mediated by the specified TLR, the compound fails to elicit a threshold increase in the biological activity. Unless otherwise indicated, an increase in biological activity refers to an increase in the same biological activity over that observed in an appropriate control. An assay may or may not be performed in conjunction with the appropriate control. With experience, one skilled in the art may develop sufficient familiarity with a particular assay (e.g., the range of values observed in an appropriate control under specific assay conditions) that performing a control may not always be necessary to determine the TLR agonism of a compound in a particular assay.

Certain TLR agonists useful in the method of the present invention are small organic molecules, as opposed to large biological molecules such as proteins, peptides, and the like. Examples of small molecule TLR agonists include those disclosed in, for example, U.S. Pat. Nos. 4,689,338; 4,929, 624; 4,988,815; 5,037,986; 5,175,296; 5,238,944; 5,266, 575; 5,268,376; 5,346,905; 5,352,784; 5,367,076; 5,389, 640; 5,395,937; 5,446,153; 5,482,936; 5,693,811; 5,741, 908; 5,756,747; 5,939,090; 6,039,969; 6,083,505; 6,110, 929; 6,194,425; 6,245,776; 6,331,539; 6,376,669; 6,451, 810; 6,525,064; 6,545,016; 6,545,017; 6,558,951; and 6,573,273. Examples of specific small molecule TLR agonists useful in the methods provided by the present invention include 4-amino-alpha, alpha,2-trimethyl-IH-imidazo[4,5-c] qumolin-I-ethanol, N-(2-{2-[4-amino-2-(2-methoxyethyl)-IH-imidazo[4,5-c]quinolin-I-yl]ethoxy-}ethyl)-N-methyl-morpholine-4-carboxamide, I~(2~amino-2-methylpropyl)-2-(ethoxymethyl-)-IH-imidazo[4,5-c]quinolin-4-arnine, N-[4-(4-amino-2-ethyl-IH-imidazo[4,5-c]quinolin-I-yl)butyl]methanesulfonamide, N-[4-(4-amino-2-propyl-IH-imidazo[4,5-c]quinolin-I-yl)butyl]methanesulfonamide, and imiquimod. Some TLR agonists particularly useful in the methods or regimen provided by the present disclosure are discussed in review article: Folkert Steinhagen, et al.: TLR-based immune adjuvants. Vaccine 29 (2011): 3341-3355.

In some embodiments, the TLR agonists are TLR9 agonists, particularly CpG oligonucleotides (or CpG.ODN). A CpG oligonucleotide is a short nucleic acid molecule containing a cytosine followed by a guanine linked by a phosphate bond in which the pyrimidine ring of the cytosine is unmethylated. A CpG motif is a pattern of bases that include an unmethylated central CpG surrounded by at least one base flanking (on the 3' and the 5' side of) the central CpG. CpG oligonucleotides include both D and K oligonucleotides. The entire CpG oligonucleotide can be unmethylated or portions may be unmethylated. Examples of CpG oligonucleotides useful in the methods provided by the present disclosure include those disclosed in U.S. Pat. Nos. 6,194,388, 6,207,646, 6,214,806, 628,371, 6,239,116, and 6,339,068.

The CpG oligonucleotides can encompass various chemical modifications and substitutions, in comparison to natural RNA and DNA, involving a phosphodiester internucleoside bridge, a beta-D-ribose (deoxyhbose) unit and/or a natural nucleoside base (adenine, guanine, cytosine, thymine, uracil). Examples of chemical modifications are known to the skilled person and are described, for example in Uhlmann E. et al. (1990), Chem. Rev. 90:543; "Protocols for Oligonucleotides and Analogs", Synthesis and Properties and Synthesis and Analytical Techniques, S. Agrawal, Ed., Humana Press, Totowa, USA 1993; Crooke, S T. et al. (1996) Annu. Rev. Pharmacol. Toxicol. 36:107-129; and Hunziker J. et al., (1995), Mod. Synth. Methods 7:331-417. Specifically, a CpG oligonucleotide can contain a modified cytosine. A modified cytosine is a naturally occurring or non-naturally occurring pyrimidine base analog of cytosine which can replace this base without impairing the immunostimulatory activity of the oligonucleotide. Modified cytosines include but are not limited to 5-substituted cytosines (e.g. 5-methyl-cytosine, 5-fluorocytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g. N4-ethyl-cytosine), 5-aza-cytosine, 2-mercapto-cytosine, isocytosine, pseudo-isocytosine, cytosine analogs with condensed ring systems (e.g. N,N'-propylene cytosine or phenoxazine), and uracil and its derivatives (e.g. 5-fluoro-uracil, 5-bromo-uracil, 5-bromovinyl-uracil, 4-thio-uracil, 5-hydroxy-uracil, 5-propynyl-uracil). Some of the preferred cytosines include 5-methyl-cytosine, 5-fluoro-cytosine, 5-hydroxy-cytosine, 5-hydroxymethyl-cytosine, and N4-ethyl-cytosine.

A CpG oligonucleotide can also contain a modified guanine. A modified guanine is a naturally occurring or non-naturally occurring purine base analog of guanine which can replace this base without impairing the immunostimulatory activity of the oligonucleotide. Modified guanines include but are not limited to 7-deeazaguanine, 7-deaza-7-substituted guanine, hypoxanthine, N2-substituted guanines (e.g. N2-methyl-guanine), 5-amino-3-methyl-3H,6H-thiazolo[4, 5-d]pyhmidine-2,7-dione, 2,6-diaminopuhne, 2-aminopuhne, purine, indole, adenine, substituted adenines (e.g. N6-methyl-adenine, 8-oxo-adenine), 8-substituted guanine (e.g. 8-hydroxyguanine and 8-bromoguanine), and 6-thioguanine. In some embodiments of the disclosure, the guanine base is substituted by a universal base (e.g. 4-methyl-indole, 5-nitro-indole, and K-base), an aromatic ring system (e.g. benzimidazole or dichloro-benzimidazole, 1-methyl-1H-[1,2,4]triazole-3-carboxylic acid amide) or a hydrogen atom.

In certain aspects, the CpG oligonucleotides include modified backbones. It has been demonstrated that modification of the nucleic acid backbone provides enhanced activity of nucleic acids when administered in vivo. Secondary structures, such as stem loops, can stabilize nucleic acids against degradation. Alternatively, nucleic acid stabilization can be accomplished via phosphate backbone modifications. A preferred stabilized nucleic acid has at least a partial phosphorothioate modified backbone. Phosphorothioates may be synthesized using automated techniques employing either phosphoramidate or H-phosphonate chemistries. Aryl- and alkyl-phosphonates can be made, e.g. as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described (Uhlmann, E. and Peyman, A. (1990) Chem. Rev. 90:544; Goodchild, J. (1990) Bioconjugate Chem. 1:165). 2'-O-methyl nucleic acids with CpG motifs also cause immune activation, as do ethoxy-modified CpG nucleic acids. In fact, no backbone modifications have been found that completely abolish the CpG effect, although it is greatly reduced by replacing the C with a 5-methyl C. Constructs having phosphorothioate linkages provide maximal activity and protect the nucleic acid from degradation by intracellular exo- and endo-nucleases. Other modified oligonucleotides include phosphodiester modified oligonucleotides, combinations of phosphodiester and phosphorothioate oligonucleotides, methylphosphonate, methylphosphorothioate, phosphorordithioate, p-ethoxy, and combinations thereof. Each of these combinations and their particular effects on immune cells is discussed in more detail with respect to CpG nucleic acids in PCT Publication Nos. WO 96/02555 and WO 98/18810 and in U.S. Pat. Nos. 6,194,388 and 6,239,116.

The CpG oligonucleotides may have one or two accessible 5' ends. It is possible to create modified oligonucleotides having two such 5' ends, for instance, by attaching two oligonucleotides through a 3'-3' linkage to generate an oligonucleotide having one or two accessible 5' ends. The 3'-3'-linkage may be a phosphodiester, phosphorothioate or any other modified internucleoside bridge. Methods for accomplishing such linkages are known in the art. For instance, such linkages have been described in Seliger, H. et al., Oligonucleotide analogs with terminal 3'-3'- and 5'-5'-internucleotidic linkages as antisense inhibitors of viral gene expression, Nucleosides and Nucleotides (1991), 10(1-3), 469-77 and Jiang, et al., Pseudo-cyclic oligonucleotides: in vitro and in vivo properties, Bioorganic and Medicinal Chemistry (1999), 7(12), 2727-2735.

Additionally, 3'-3'-linked oligonucleotides where the linkage between the 3'-terminal nucleosides is not a phosphodiester, phosphorothioate or other modified bridge, can be prepared using an additional spacer, such as tri- or tetraethyleneglycol phosphate moiety (Durand, M. et al., Triple-helix formation by an oligonucleotide containing one (dA) 12 and two (dT)12 sequences bridged by two hexaethylene glycol chains, Biochemistry (1992), 31 (38), 9197-204, U.S. Pat. Nos. 5,658,738 and 5,668,265). Alternatively, the non-nucleotidic linker may be derived from ethanediol, propanediol, or from an abasic deoxyhbose (dSpacer) unit (Fontanel, Marie Laurence et al., Nucleic Acids Research (1994), 22(11), 2022-7) using standard phosphoramidite chemistry. The non-nucleotidic linkers can be incorporated once or multiple times, or combined with each other allowing for any desirable distance between the 3'-ends of the two oligonucleotides to be linked.

A phosphodiester internucleoside bridge located at the 3' and/or the 5' end of a nucleoside can be replaced by a modified internucleoside bridge, wherein the modified internucleoside bridge is for example selected from phosphorothioate, phosphorodithioate, NRiR$_2$-phosphoramidate, boranophosphate, a-hydroxybenzyl phosphonate, phosphate-$(C_1$-$C_{21})$—O-alkyl ester, phosphate-$[(C_6$-$C_{21})$aryl-$(C_1$-$C_{21})$—O-alkyl]ester, $(C1$-$C_8)$alkylphosphonate and/or $(C_6$—$Cl_2)$arylphosphonate bridges, $(C_7$-$C_{12})$-a-hydroxymethyl-aryl (e.g. disclosed in PCT Publication No. WO 95/01363), wherein $(C_6$-$C_{12})$aryl, $(C_6$-$C_{20})$aryl and $(C_6$-$C_{14})$ aryl are optionally substituted by halogen, alkyl, alkoxy, nitro, cyano, and where Ri and R$_2$ are, independently of each other, hydrogen, $(C_1$-$Cl_8)$-alkyl, $(C_6$-$C_{20})$-aryl, $(C_6$-$C_{14})$-aryl, $(C_1$-$C_8)$-alkyl, preferably hydrogen, $(C_1$-$C_8)$-alkyl, preferably $(C_1$-$C_4)$-alkyl and/or methoxyethyl, or R$_1$ and R$_2$ form, together with the nitrogen atom carrying them, a 5 to 6-membered heterocyclic ring which can additionally contain a further heteroatom selected from the group O, S and N.

The replacement of a phosphodiester bridge located at the 3' and/or the 5' end of a nucleoside by a dephospho bridge (dephospho bridges are described, for example, in Uhlmann E. and Peyman A. in "Methods in Molecular Biology", Vol. 20, "Protocols for Oligonucleotides and Analogs", S. Agrawal, Ed., Humana Press, Totowa 1993, Chapter 16, pp. 355 if), wherein a dephospho bridge is for example selected from the dephospho bridges formacetal, 3'-thioformacetal, methylhydroxylamine, oxime, methylenedimethyl-hydrazo, dimethylenesulfone and/or silyl groups.

The CpG oligonucleotides for use in the methods or regimen provided by the disclosure may optionally have chimeric backbones. A chimeric backbone is one that comprises more than one type of linkage. In one embodiment, the chimeric backbone can be represented by the formula: 5' Y1 N1ZN2Y2 3'. Y1 and Y2 are nucleic acid molecules having between 1 and 10 nucleotides. Y1 and Y2 each include at least one modified internucleotide linkage. Since at least 2 nucleotides of the chimeric oligonucleotides include backbone modifications these nucleic acids are an example of one type of "stabilized immunostimulatory nucleic acids".

With respect to the chimeric oligonucleotides, Y1 and Y2 are considered independent of one another. This means that each of Y1 and Y2 may or may not have different sequences and different backbone linkages from one another in the same molecule. In some embodiments, Y1 and/or Y2 have between 3 and 8 nucleotides. N1 and N2 are nucleic acid molecules having between 0 and 5 nucleotides as long as N1ZN2 has at least 6 nucleotides in total. The nucleotides of N1ZN2 have a phosphodiester backbone and do not include nucleic acids having a modified backbone. Z is an immunostimulatory nucleic acid motif, preferably selected from those recited herein.

The center nucleotides (N1ZN2) of the formula Y1 N1ZN2Y2 have phosphodiester internucleotide linkages and Y1 and Y2 have at least one, but may have more than one or even may have all modified internucleotide linkages. In preferred embodiments, Y1 and/or Y2 have at least two or between two and five modified internucleotide linkages or Y1 has five modified internucleotide linkages and Y2 has two modified internucleotide linkages. The modified internucleotide linkage, in some embodiments, is a phosphorothioate modified linkage, a phosphorodithioate linkage or a p-ethoxy modified linkage.

Examples of particular CpG oligonucleotides useful in the methods provided by the present disclosure include:

```
5' TCGTCGTTTTGTCGTTTTGTCGTT3';    (CpG 7909)

5' TCGTCGTTTTTCGGTGCTTTT3';       (CpG 24555)
and

5' TCGTCGTTTTTCGGTCGTTTT3'.       (CpG 10103)
```

CpG7909, a synthetic 24mer single stranded, has been extensively investigated for the treatment of cancer as a monotherapy and in combination with chemotherapeutic agents, as well as adjuvant as an adjuvant for vaccines against cancer and infectious diseases. It was reported that a single intravenous dose of CpG 7909 was well tolerated with no clinical effects and no significant toxicity up to 1.05 mg/kg, while a single dose subcutaneous CpG 7909 had a maximum tolerated dose (MTD) of 0.45 mg/kg with dose limiting toxicity of myalgia and constitutional effects. [See Zent, Clive S, et al: Phase I clinical trial of CpG oligonucleotide 7909 (PF-03512676) in patients with previously treated chronic lymphocytic leukemia. Leukemia and Lymphoma, 53(2):211-217(7)(2012). In the regimens provided by the present disclosure, CpG7909 may be administered by injection into the muscle or any other suitable methods. It is preferred that it is administered locally in proximity to the vaccine draining lymph node, particularly by intradermal or subcutaneous administration. For use with a nucleic acid vaccine, such as a DNA vaccine, a CpG may be preferably co-formulated with the vaccine in a single formulation and administered by intramuscular injection coupled with electroporation. The effective amount of CpG7909 by intramuscular, intradermal, or subcutaneous administration is typically in the range of 10 μg/dose-10 mg/dose. In some embodiments, the effective amount of CpG7909 is in the range of 0.05 mg-14 mg/dose. In some particular embodiments, the effective amount of CpG7909 is about 0.05, 0.1, 0.2, 0.3, 0.4, 0.5, 05 1 mg/dose. Other CpG oligonucleotides, including CpG 24555 and CpG 10103, may be administered in similar manner and dose levels.

In some particular embodiments, the present disclosure provides a method of enhancing the immunogenicity or therapeutic effect of a vaccine for the treatment of a neoplastic disorder in a human, comprising administering the human (1) an effective amount of at least one ISC inhibitor and (2) an effective amount of at least one IEC enhancer, wherein the at least one ISC inhibitor is protein kinase inhibitor selected from sorafenib tosylate, sunitinib malate, axitinib, erlotinib, gefitinib, axitinib, bosutinib, temsirolismus, or nilotinib and wherein the at least one IEC enhancer is selected from a CTLA-4 inhibitor, a TLR agonist, or a CD40 agonist. In some preferred embodiments, regimen comprises administering to the human (1) an effective amount of at least one ISC inhibitor and (2) effective amount of at least one IEC enhancer, wherein the at least one ISC inhibitor is a protein kinase inhibitor selected from axitinib, sorafenib tosylate, or sunitinib malate and wherein the wherein the at least one IEC enhancer is a CTLA-4 inhibitor selected from Ipilimumab or Tremelimumab. In some further preferred embodiments, the regimen comprises administering to the human (1) an effective amount of at least one ISC inhibitor and (2) an effective amount of at least two IEC enhancers, wherein the at least one ISC inhibitor is a protein kinase inhibitor selected from sunitinib or axitinib and wherein the at least two IEC enhancers are Tremelimumab and a TLR agonist selected from CpG7909, CpG2455, or CpG 10103.

In some other embodiments, the present disclosure provides a method of treating prostate cancer in a human, comprising administering to the human (1) an effective amount of a vaccine capable of eliciting an immune response against a human PAA, (2) an effective amount of at least one ISC inhibitor, and (3) an effective amount of at least one IEC enhancer, wherein the at least one ISC inhibitor is a protein kinase inhibitor selected from sorafenib tosylate, sunitinib malate, axitinib, erlotinib, gefitinib, axitinib, bosutinib, temsirolismus, or nilotinib, and wherein the at least one IEC enhancer is selected from a CTLA-4 inhibitor, a TLR agonist, or a CD40 agonist. In some preferred embodiments, the method comprises administering to the human (1) an effective amount of a vaccine capable of eliciting an immune response against a human PAA, (2) an effective amount of at least one ISC inhibitor, and (3) an effective amount of at least one IEC enhancer, wherein the at least one ISC inhibitor is a protein kinase inhibitor selected from sorafenib tosylate, sunitinib malate, or axitinib and wherein the at least one IEC enhancer is a CTLA-4 inhibitor selected from Ipilimumab or Tremelimumab.

In some further specific embodiments, the method comprises administering to the human (1) an effective amount of at least one ISC inhibitor and (2) an effective amount of at least two IEC enhancers, wherein the at least one ISC inhibitor is a protein kinase inhibitor selected from sunitinib or axitinib and wherein the at least two IEC enhancers are Tremelimumab and a TLR agonist selected from CpG7909, CpG2455, or CpG10103.

Additional Therapeutic Agents.

The vaccine-based immunotherapy regimen provided by the present disclosure may further comprise an additional therapeutic agent. A wide variety of cancer therapeutic agents may be used, including chemotherapeutic agents and hormone therapeutic agents. One of ordinary skill in the art will recognize the presence and development of other cancer therapies which can be used in VBIR provided by the present disclosure, and will not be restricted to those forms of therapy set forth herein.

The term "chemotherapeutic agent" refers to a chemical or biological substance that can cause death of cancer cells, or interfere with growth, division, repair, and/or function of cancer cells. Examples of chemotherapeutic agents include those that are disclosed in WO2006/088639, WO2006/129163, and US 20060153808, the disclosures of which are incorporated herein by reference. Examples of particular chemotherapeutic agents include: (1) alkylating agents, such as chlorambucil (LEUKERAN), cyclophosphamide (CYTOXAN), ifosfamide (IFEX), mechlorethamine hydrochloride (MUSTARGEN), thiotepa (THIOPLEX), streptozotocin (ZANOSAR), carmustine (BICNU, GLIADEL WAFER), lomustine (CEENU), and dacarbazine (DTIC-DOME); (2) alkaloids or plant vinca alkaloids, including cytotoxic antibiotics, such as doxorubicin (ADRIAMYCIN), epirubicin (ELLENCE, PHARMORUBICIN), daunorubicin (CERUBIDINE, DAUNOXOME), nemorubicin, idarubicin (IDAMYCIN PFS, ZAVEDOS), mitoxantrone (DHAD, NOVANTRONE). dactinomycin (actinomycin D, COSMEGEN), plicamycin (MITHRACIN), mitomycin (MUTAMYCIN), and bleomycin (BLENOXANE), vinorelbine tartrate (NAVELBINE)), vinblastine (VELBAN), vincristine (ONCOVIN), and vindesine (ELDISINE); (3) antimetabolites, such as capecitabine (XELODA), cytarabine (CYTOSAR-U), fludarabine (FLUDARA), gemcitabine (GEMZAR), hydroxyurea (HYDRA), methotrexate (FOLEX, MEXATE, TREXALL), nelarabine (ARRANON), trimetrexate (NEUTREXIN), and pemetrexed (ALIMTA); (4) Pyrimidine antagonists, such as 5-fluorouracil (5-FU); capecitabine (XELODA), raltitrexed (TOMUDEX), tegafur-uracil (UFTORAL), and gemcitabine (GEMZAR); (5) taxanes, such as docetaxel (TAXOTERE), paclitaxel (TAXOL); (6) platinum drugs, such as cisplatin (PLATINOL) and carboplatin (PARAPLATIN), and oxaliplatin (ELOXATIN); (7) topoisomerase inhibitors, such as irinotecan (CAMPTOSAR), topotecan (HYCAMTIN), etoposide (ETOPOPHOS, VEPESSID, TOPOSAR), and teniposide (VUMON); (8) epipodophyllotoxins (podophyllotoxin derivatives), such as etoposide (ETOPOPHOS, VEPESSID, TOPOSAR); (9) folic acid derivatives, such as leucovorin (WELLCOVORIN); (10) nitrosoureas, such as carmustine (BiCNU), lomustine (CeeNU); (11) inhibitors of receptor tyrosine kinase, including epidermal growth factor receptor (EGFR), vascular endothelial growth factor (VEGF), insulin receptor, insulin-like growth factor receptor (IGFR), hepatocyte growth factor receptor (HGFR), and platelet-derived growth factor receptor (PDGFR), such as gefitinib (IRESSA), erlotinib (TARCEVA), bortezomib (VELCADE), imatinib mesylate (GLEEVEC), genefitinib, lapatinib, sorafenib, thalidomide, sunitinib (SUTENT), axitinib, rituximab (RITUXAN, MABTHERA), trastuzumab (HERCEPTIN), cetuximab (ERBITUX), bevacizumab (AVASTIN), and ranibizumab (LUCENTIS), lym-1 (ONCOLYM), antibodies to insulin-like growth factor-1 receptor (IGF-1R) that are disclosed in WO2002/053596); (12) angiogenesis inhibitors, such as bevacizumab (AVASTIN), suramin (GERMANIN), angiostatin, SU5416, thalidomide, and matrix metalloproteinase inhibitors (such as batimastat and marimastat), and those that are disclosed in WO2002055106; and (13) proteasome inhibitors, such as bortezomib (VELCADE).

The term "hormone therapeutic agent" refers to a chemical or biological substance that inhibits or eliminates the production of a hormone, or inhibits or counteracts the effect of a hormone on the growth and/or survival of cancer cells. Examples of such agents suitable for the VBIR include those disclosed in US20070117809. Examples of particular hormone therapeutic agents include tamoxifen (NOLVADEX), toremifene (Fareston), fulvestrant (FASLODEX), anastrozole (ARIMIDEX), exemestane (AROMASIN), letrozole (FEMARA), megestrol acetate (MEGACE), goserelin (ZOLADEX), leuprolide (LUPRON), abiraterone, and MDV3100.

The VBIR provided by this disclosure may also be used in combination with other therapies, including (1) surgical methods that remove all or part of the organs or glands which participate in the production of the hormone, such as the ovaries, the testicles, the adrenal gland, and the pituitary gland, and (2) radiation treatment, in which the organs or glands of the patient are subjected to radiation in an amount sufficient to inhibit or eliminate the production of the targeted hormone.

I. EXAMPLES

The following examples are provided to illustrate certain embodiments of the invention. They should not be construed to limit the scope of the invention in any way. From the above discussion and these examples, one skilled in the art can ascertain the essential characteristics of the invention, and without departing from the spirit and scope thereof, can make various changes and modifications of the invention to adapt it to various usage and conditions.

Example 1

Antigens in Cytosolic, Secreted, and Membrane-Bound Formats Derived from the Human PSMA Protein Example 1 illustrates the construction of three immunogenic PSMA polypeptides referred to an "human PSMA cytosolic antigen," "human PSMA secreted antigen," and "human PSMA membrane-bound antigen," respectively, and biological properties of these polypeptides.

1A. Design of Immunogenic PSMA Polypeptides

DNA constructs encoding immunogenic PSMA polypeptides in cytosolic, secreted, and modified formats were constructed based on the native human PSMA protein sequence and tested for their ability to induce anti-tumor effector immune responses. The structure and preparation of each of the human PSMA antigen formats are provided as follows.

1A1. Human PSMA Cytosolic Antigen.

An immunogenic PSMA polypeptide in cytosolic form was designed to retain the immunogenic polypeptide inside the cell once it is expressed. The cytoplasmic domain (amino acids 1-19) and the transmembrane domain (amino acids 20-43) of the human PSMA were removed, resulting in a cytosolic PSMA polypeptide that consists of amino acids 44-750 (extracellular domain or ECD) of the human PSMA of SEQ ID NO: 1. The optimal Kozak sequence "MAS" may be added to the N-terminus of the polypeptide for enhancing the expression.

1A2. Human PSMA Secreted Antigen.

An immunogenic PSMA polypeptide in secreted form was designed to secret the polypeptide outside of the cell once it is expressed. The secreted polypeptide is made with amino acids 44-750 (ECD) of the human PSMA of SEQ ID NO:1 and the Ig Kappa secretory element that has the amino acid sequence ETDTLLLWVLLLWVPGSTGD and a two-amino acid linker (AA) in the N-terminal in order to maximize the secretion of the PSMA antigen once it is expressed.

1A3. Human PSMA Membrane-Bound Antigen.

An immunogenic PSMA membrane-bound polypeptide was designed to stabilize the polypeptide on the cell surface. The first 14 amino acids of the human PSMA protein were removed and the resultant immunogenic polypeptide consists of amino adds 15-750 of the human PSMA protein of SEQ ID NO:1. The immunogenic polypeptide that consists of amino adds 15-750 of the native human PSMA protein of SES ID NO: 1 and share 100% sequence identity with the native human PSMA protein is also referred to as "human PSMA modified," "hPSMA modified," or "hPSMAmod" antigen in the present disclosure.

1B. Preparation of DNA Plasmids for Expressing the PSMA Antigens

DNA constructs encoding the PSMA cytosolic, PSMA secreted, and PSMA modified antigens were cloned individually into PJV7563 vector that was suitable for in vivo testing in animals (FIG. 1). Both strands of the DNA in the PJV7563 vectors were sequenced to confirm the design integrity.

A large scale plasmid DNA preparation (Qiagen/CsCl) was produced from a sequence confirmed clone. The quality of the plasmid DNA was confirmed by high 260/280 ratio, high super coiled/nicked DNA ratio, low endotoxin levels (<10 U/mg DNA) and negative bio burden.

1C. Expression of PSMA Constructs in Mammalian Cells

The expression of the PSMA cytosolic, secreted, and modified antigens was determined by FACS. Mammalian 293 cells were transfected with the PJV7563 PMED vectors encoding the various immunogenic PSMA polypeptides. Three days later, the 293 cells were stained with mouse anti-PSMA antibody, followed with a fluorescent conjugated (FITC) rat anti-mouse secondary antibody. The data below, which were reported as mean fluorescent intensity (MFI) over negative controls, confirmed that human PSMA modified antigen is expressed on the cell surface.

| Samples | Average mean fluorescent intensity |
|---|---|
| Untransfected 293 cells | 231 |
| 293 cells transfected with full length human PSMA (SEQ ID NO: 1) | 6425 |
| 293 cells transfected with human PSMA modified antigen (SEQ ID NO: 9) | 12270 |

1D. Formulations of PSMA Plasmids onto Gold Particles (for ND10/X15)

Particle Mediated Epidermal Delivery technology (PMED) is a needle-free method of administering vaccines to animals or to patients. The PMED system involves the precipitation of DNA onto microscopic gold particles that are then propelled by helium gas into the epidermis. The ND10, a single use device, uses pressurized helium from an internal cylinder to deliver gold particles and the x15, a repeater delivery device, uses an external helium tank which is connected to the x15 via high pressure hose to deliver the gold particles. Both of these devices were used in studies to deliver the PSMA DNA plasmids. The gold particle was usually 1-3 µm in diameter and the particles were formulated to contain 2 µg of PSMA plasmids per 1 mg of gold particles. (Sharpe, M. et al.: P. Protection of mice from H5N1 influenza challenge by prophylactic DNA vaccination using particle mediated epidermal delivery. Vaccine, 2007, 25(34): 6392-98: Roberts L K, et al.: Clinical safety and efficacy of a powdered Hepatitis B nucleic acid vaccine delivered to the epidermis by a commercial prototype device. Vaccine, 2005; 23(40):4867-78).

1E. Transgenic Mice Used for In Vivo Studies

Two human HLA transgenic mouse models were used to evaluate the presentation of various PSMA antigens by different HLAs and a human PSMA transgenic mouse model was used to assess the breaking of immune tolerance to human PSMA. The first HLA transgenic mouse model utilizes the HLA A2/DR1 mice (from the Pasteur Institute, Paris, France; also referred to as "Pasteur mice"). Pasteur mice are knock out for murine β-2-microglobulin and do not express functional H-2b molecules; therefore this model is believed to represent the presentation of antigen in the human HLA A2 and DR1 context (Pajot, A., M.-L. Michel, N. Faxilleau, V. Pancre, C. Auriault, D. M. Ojcius, F. A. Lemonnier, and Y.-C. Lone. A mouse model of human adaptive immune functions: HLA-A2.1-/HLA-DR1-transgenic H-2 class I-/class II-knockout mice. Eur. J. Immunol. 2004, 34:3060-69). The second HLA transgenic mouse model uses mice that are knock in with human HLA A24 that is covalently linked to the human β-2-microglobulin at the H2bk locus. These mice lack murine β-2-microglobulin and do not express functional H-2b molecules. This model allows evaluation of antigen presentation in the context of human HLA A24.

1F. Immunogenicity of the Human PSMA Proteins in Cytosolic, Secreted and Modified Formats Study Design.

Eight-to-10 week-old transgenic mice were immunized using PMED method with various PSMA DNA constructs in a prime/boost/boost regimen, two weeks apart between each vaccination. Alternatively, mice were primed with adenovirus vectors encoding the PSMA antigen at $1 \times 10^9$ viral particles in 50 μl (PBS) by intramuscular injection. The adenovirus vector (pShuttle-CMV vector from Stratagene) was modified to contain NheI and BglII restriction sites within the multiple cloning site. The DNA encoding human PSMA modified was then restriction digested with NheI and BglII, ligated into this vector and sequence confirmed. The pShuttle human PSMA modified vector was then recombined with the pAdEasy-1 vector and virus was propagated according to the AdEasy system (Stratagene). Twenty-days later, they were boosted with PMED as described above. In each of the regimens used, antigen specific T cell response was measured 7 days after the last immunization in an interferon-gamma (IFNγ) ELISPOT assay. The ELISPOT assay is similar to the sandwich enzyme-linked immunosorbent assay (ELISA). Briefly, a capture antibody specific to IFNγ BD Bioscience, #51-2525kc) is coated onto a polyvinylidene fluoride (PVDF) membrane in a microplate overnight at 4° C. The plate is blocked with serum/protein to prevent nonspecific binding to the antibody. After blocking, effector cells (such as splenocytes isolated from PSMA immunized mice) and targets (such as PSMA peptides from peptide library, target cells pulsed with peptides or tumor cells expressing the relevant antigens) or mitogen (which will stimulate splenocytes non-specifically to produce IFNγ are added to the wells and incubated overnight at 37° C. in a 5% $CO_2$ incubator. Cytokine secreted by effector cells are captured by the coating antibody on the surface of the PVDF membrane. After removing the cells and culture media, 100 μl of a biotinylated polyclonal anti-mouse IFNγ antibody (0.5 mg/ml-BD Bioscience, #51-1818kz) was added to each of the wells for detection. The spots are visualized by adding streptavidin-horseradish peroxidase (HRP, BD Bioscience, #557630) and the precipitate substrate, 3-amino-9-ethylcarbazole (AEC), to yield a red color spot. Each spot represents a single cytokine producing T cell. In general, in the studies disclosed here the ELISpot assay was set up as follows: $5 \times 10^5$ splenocytes from PSMA immunized mice were cultured (1) in the presence of PSMA specific peptides derived from a PSMA peptide library (see Table 16) made of 15-amino acid peptides overlapping by 11 amino acids, (2) with known HLA A2.1 restricted PSMA specific peptides, or (3) with tumor cells. To measure the recognition of endogenous antigen presentation, splenocytes were cultured with a human HLA A2 prostate cancer cells (i.e. LNCaP, available from ATCC) that naturally express PSMA or cultured with HLA A2 tumor cells transduced with adenovirus encoding and thus expressing the human PSMA modified antigen. In addition, human PSMA ECD protein was added to the ELISpot assay to measure specifically CD4 IFNγ producing cells. For controls where appropriate, HLA A2 restricted HER-2 specific peptide p168-175 or tumor cells not expressing PSMA or irrelevant protein such as BSA were used as a negative control in the IFNγ ELISpot assay. Data results are given in normalized format for the number of spot forming cells (SFC) that secrete IFNγ in $1 \times 10^6$ splenocytes. At least three studies were performed for each of the PSMA antigen peptides tested.

Results.

Data from the ELISpot assay with splenocytes of Pasteur mice cultured with peptides derived from a PSMA peptide library are presented in Table 1. A positive response is defined as having SFC >100. As shown in Table 1, the immunogenic PMSA polypeptides made with all three antigen formats, the human PSMA cytosolic, secreted, and modified antigens described in Example 1A above, are capable of inducing T cell responses. The human PSMA modified antigen format induced the best breadth and magnitude of T cell responses.

TABLE 1

T cell response induced by the human PSMA cytosolic, secreted, and modified antigens in Pasteur mice

| aa sequence coverage of target peptide pools from PSMA peptide library | IFN-γ SFC/1 × 10$^6$ splenocytes (SD) | | |
|---|---|---|---|
| | PSMA cytosolic | PSMA modified | PSMA secreted |
| 13-35 | 1(14) | 809(78) | 44(6) |
| 97-117 | 1(1) | 96(17) | 0 |
| 109-131 | 8(9) | 923(21) | 179(24) |
| 121-243 | 21(4) | 1329(109) | 320(28) |
| 145-167 | 23(4) | 1499(1) | 312(14) |
| 169-191 | 497(4) | 248(14) | 183(13) |
| 181-203 | 43(21) | 70(20) | 19(10) |
| 205-227 | 5(1) | 112(0) | 9(13) |
| 217-239 | 44(13) | 1627(38) | 351(10) |
| 265-287 | 23(4) | 527(100) | 10(6) |
| 277-299 | 39(1) | 1143(86) | 151(4) |
| 289-311 | 27(1) | 429(4) | 28(11) |
| 409-431 | 14(9) | 281(18) | 12(9) |
| 421-443 | 4(0) | 676(45) | 48(14) |
| 433-455 | 339(18) | 713(64) | 119(21) |
| 481-503 | 22 | 288(9) | 1(1) |
| 577-599 | 227(27) | 131(16) | 33(16) |
| 589-611 | 187(13) | 27(10) | 6(9) |
| 613-635 | 418(6) | 437(1) | 55(1) |
| 637-659 | 222(31) | 49(10) | 95(16) |
| 649-671 | 203(21) | 1625(33) | 420(11) |
| 661-683 | 102(14) | 1633(140) | 366(48) |
| 697-719 | 179(4) | 1357(58) | 342(6) |
| 709-731 | 40(11) | 1162(59) | 223(4) |
| 721-743 | 56(6) | 1409(103) | 344(23) |
| 733-750 | 50(11) | 1512(51) | 365(27) |

( ) = standard deviation

Data from the ELISpot assay on T cell responses induced by various PSMA vaccine formats in Pasteur mice (which that recognized HLA A2.1 restricted PSMA peptide pulsed target cells as well as PSMA+HLA A2.1 LNCaP tumor cells) are presented in Table 2. PC3, which is a human prostate cancer cell line that does not express PSMA, was used here as a negative control. A positive response is defined as having SFC >50. As shown in Table 2, the various PSMA constructs tested are capable of inducing T cells that recognize known HLA A2 restricted PSMA epitopes as well as PSMA protein and human prostate cancer cells LNCaP. However, the PSMA modified construct was shown to induce the best breadth and magnitude T cell response.

TABLE 2

T cell responses induced by the human PSMA cytosolic, secreted, and modified antigens in Pasteur mice that recognized HLA A2.1 restricted PSMA peptide pulsed target cells as well as PSMA+ HLA A2.1 LNCaP tumor cells.

| HLA A2.1 restricted peptides | PSMA cytosolic | PSMA modified | PSMA secreted |
|---|---|---|---|
| Target peptide or protein | IFN-γ SFC/1 × 10⁶ splenocytes | | |
| PSMA p663 | 1554(4) | 1524.9(45) | 444(23) |
| PSMA p275 | 14(10) | 304(21) | 3(1) |
| PSMA p662 | 41(15) | 925.1(77) | 455(25) |
| PSMA p627 | 1(1) | 222(14) | 9(8) |
| PSA p64 | 0 | 2(4) | 1(1) |
| Protein or tumor cells | IFN-γ SFC/1 × 10⁶ splenocytes | | |
| PSMA ECD protein | 45(11) | 731(16) | 13(5) |
| LNCap | 4(2) | 96(12) | 5(3) |
| PC3 | 0 | 1(1) | 1(1) |

( ) = standard deviation

1G. Humoral Immune Response Measured in Pasteur Mice or Nonhuman Primates

1G1. Sandwich ELISA Assay.

The standard sandwich ELISA assay was done using an automated Biotek system. The plates were coated with 25 μl of native PSMA protein at a 1.0 μg/ml in PBS overnight, the plates were washed and blocked with 35 μl/well of 5% FBS 1×PBS-T 0.05% and incubated for 1 hour at RT on a shaker at 600 RPM. The blocking media was decanted and serial dilute vaccinated mouse serum with half log dilutions in 5% FBS 1×PBS-T 0.05% starting at 1:100 or 1:500 were made and 25μ samples of the diluted serum were added to each well of the 96 well plates and incubated for 1 hour at RT on a shaker at 600 RPM. The plates were washed 3 times with 75 ul/well in 1×PBS-T 0.05% using the Biotek ELx405, and 25 μl/well of 1:30,000 diluted anti-mouse IgG HRP (AbCam cat# ab20043) secondary antibody (diluted in 1× PBS-T 0.05%) was added to each well of the 96 well plates and incubated for 1 hour at RT on a shaker at 600 RPM. Plates were washed 5× with 75 ul/well in 1×PBS-T 0.05% using the Biotek Elx405. TMB Substrate was diluted at 1:10 and 25 μl was added to each well and incubated at RT for 30 minutes. The reaction was stopped by adding 12.5 μl/well of 1M H2SO4. Plates were read using the Spectramax Plus at 450 nm wavelength. Data were reported as titers and these could be reported as first positive (average and both values above 5% FBS PBS+3 time Standard Deviation) and/or as calculated titers at OD of 0.5 or 1.0. Serum from irrelevant vaccinated mice were used as negative controls.

TABLE 3

Induction of anti-PSMA antibody response by human PSMA antigens as measured by an ELISA assay.

| Antigen format | ELISA (OD = 1) Average (+/−SD) | N | # of positive |
|---|---|---|---|
| PSMA cytosolic | 499 (0) | 4 | 0/4 |
| PSMA modified | 1067 (518) | 4 | 4/4 |
| PSMA secreted | 959 (920) | 4 | 1/4 |

Results.

Data presented in Table 3 shows that the human PSMA cytosolic antigen did not induce any anti-PSMA responses, while the human PSMA modified antigen consistently induced good anti-PSMA antibody responses in all mice.

Data presented in Table 5 shows that antibodies induced by the human PSMA antigens reacted to multiple peptide epitopes in the PSMA library. Serum from the individual mice in each group was pooled in equal amounts and tested at a 1:500 dilution in an ELISA assay. A negative control group of mice vaccinated with anti-diphtheria (CRM) toxoid was tested in parallel. Each well of the 96 well ELISA plate was coated with 0.03 μg of a single15aa peptide derived from the PSMA peptide library. An OD value above 0.10 is considered positive.

1G2. FACS Cell Binding Assay.

Various prostate cancer cell lines were used for this assay. LNCaP (ATCC) was used as human prostate cancer cells expressing PSMA and PC3 (ATCC) was used as negative human prostate cancer cells that do not expressing PSMA. In some assays, a TRAMP-C2 cell line engineered to stably express the human native full length PSMA and the parental TRAMP-C2 cell line that does not express PSMA (negative control) were used for the cell binding assay. The cell binding assay was performed as follows: LNCaP and PC3 cells (or TRAMP-C2PSMA and TRAMP C2) were plated in separate wells at 2×10⁵ cells/well (50 μL) in a 96 well plate. Sera from PSMA vaccinated mice, as described in 1f, were diluted 1:50 with FACS buffer (PBS pH 7.4, 1% FBS, 25 mM HEPES, and 1 mM EDTA). Fifty μL of diluted J591-A antibody (mouse anti-human PSMA antibody, clone J591-A from ATCC) were added to the diluted test sera or FACS buffer (unstained samples) to achieve the appropriate cell numbers per well in the staining plate. All was mixed by pipetting and then kept on ice for 20 min. The cells were washed twice with FACS buffer; each wash was by centrifugation at 1200RPM at 5° C. for 5 minutes. Fifty μL of secondary staining solution were added containing a 1:200 dilution of PE-labeled goat anti-mouse Ig (Sigma, cat P9670-5) and 0.25 μl of Live/Dead Aqua stain (Invitrogen, cat. # L34957) to each of the cell containing wells and kept on ice for 20 min. Cells were washed twice as described earlier. Washed cell pellets were resuspended in 125 uL FACS buffer and then 75 uL 4% paraformaldehyde solution were added to each well to fix the cells. Samples were kept on ice and protected from light for at least 15 min. Samples were run on FACS Canto II. Ten thousand live cell events were recorded for each sample. Control samples for each cell type were 1) unstained cells, 2) cells with secondary antibody only, 3) Cells with J591 plus secondary antibody, and 4) cells with naïve serum plus secondary antibody. Data were reported as mean fluorescent intensity (MFI) over negative controls.

Results of FACS Cell Binding Assay.

Table 4 shows that antibodies induced by both human PSMA secreted and modified antigens are capable of binding to human PSMA positive prostate cancer cells (LNCaP) and not to PSMA negative prostate cancer cells (PC3). The PSMA modified antigen consistently induced good anti-PSMA antibody response in all mice.

TABLE 4

Binding of anti-PSMA antibodies to human prostate cancer cells as measured by FACS.

| Antigen Format | Fold over background Average (+/−SD) | N | # of positive |
|---|---|---|---|
| PSMA cytosolic | 1.40 (0.12) | 4 | 0/4 |
| PSMA modified | 6.01 (0.38) | 4 | 4/4 |
| PSMA secreted | 5.50 (4.10) | 4 | 3/4 |
| background (PC3) | 1.36 (0.04) | 4 | NA |

TABLE 5

Antibodies induced by PSMA vaccine reacted to multiple peptides in the PSMA library. Based on this result, four B cell epitopes of PSMA were identified, 1: aa 138-147, 2: aa 119-123, 3: aa 103-106, 4: aa 649-659.

| | | ELISA O.D. results | |
|---|---|---|---|
| Target peptide or protein | | PSMA vaccinated serum | CRM-197 vaccinated serum |
| Peptides from PSMA library (no. of first aa) | 93 | 0.21 | 0.05 |
| | 101 | 0.27 | 0.05 |
| | 133 | 0.58 | 0.05 |
| | 137 | 0.89 | 0.05 |
| | 141 | 0.12 | 0.05 |
| | 645 | 0.17 | 0.05 |
| PSMA protein | | 3.87 | 0.05 |

1 G3. Antibody-Dependent Cell-Mediated Cytotoxicity (ADCC) Assay

Study Design.

An Indian rhesus macaque was immunized with a nucleic acid encoding a human PSMA modified antigen delivered by adenovirus (1e11 V.P. injected intramuscularly) followed by 2 PMED immunizations (8 actuations/immunization, 4 actuations per each right and left side of the lower abdomen) with 8 and 6 week intervals respectively. The animal also received intradermal injections of 3 mg of CpG (PF-03512676) in proximity to each inguinal draining lymph node at the time of the second PMED immunization. The antibody dependent cell-mediated cytotoxicity was determined from the plasma collected from the blood before any immunizations (pre-immune plasma) and 8 days after the last PMED immunization (immune plasma).

Antibody-Dependent Cell-Mediated Cytotoxicity Assay.

Antibody-dependent cell-mediated cytotoxicity was determined using the standard chromium 51 release assay. Human prostate cancer cell lines LNCaP and PC3 were used as target cells. Freshly isolated human PBMC cells were used as effector cells. Effectors to target cells were set at 30:1. Briefly, for one labeling reaction, $1.5 \times 10^6$ target cells in 200 ul were incubated with 200 µCi $^{51}$Cr (37° C., 5% $CO_2$ for 1 hour). Cells were washed three times and the cell concentration was adjusted to $2 \times 10^5$ cells/ml. Control monoclonal antibodies (mAb) or test plasma (1:50) were made at 2× concentration and 175 ul of each of the (depending on the size of the assay) mAb/plasma dilution were added to 175 ul of target cells. The mixture was incubated for 30 minutes at 4° C. in an Eppendorf tube. Cells were washed once to free unbound antibodies. At this time, 100 ul of freshly isolated effector cells were added to each well of the 96 well plate along with 100 ul of monoclonal antibodies or test plasma bound target cells and incubated at 37° C. and 5% $CO_2$ for 4 hrs. Samples were tested in duplicates. 100 µl 2N HCl were added to the target wells for maximum release and 100 µl of media were added to the target wells for spontaneous release. Specific lysis was calculated as follows: Percent release=(ER−SR)/(MR−SR)×100 where ER (effectors+target cells release) was experimental release, SR (target cells alone incubated with media) was spontaneous release, and MR (target cells alone incubated with 2N HCl) was maximum release. Percent specific lysis was calculated by subtracting irrelevant target (PC3) release from antigen specific target (LNCaP) release.

TABLE 6

Antibody dependent cytotoxicity activity measured in plasma from human PSMA modified vaccinated animal.

| | Percent specific lysis at E:T of 30:1 (based on type of antibodies and targets used in an ADCC assay) | | | | |
|---|---|---|---|---|---|
| Targets | Herceptin | Rituxan | Pre-immune plasma (naive) | Post-immune plasma | None |
| LNCaP | 56.14 | 8.99 | 0 | 49.9 | 0 |
| PC3 | 8.04 | 0 | 0 | 0 | 0 |

Results.

The data from the antibody dependent cytotoxicity assay are presented in Table 6. LNCaP, a human prostate PSMA+ cancer cell line coated with immune plasma derived from the hPSMA immunized animal, was lysed by effector cells while PC3, a human prostate PSMA-cancer cell line coated with the same immune serum, was not lysed by effector cells. Similarly, LNCaP coated with pre-immune plasma was not lysed by effector cells. Herceptin, a monoclonal antibody against HER-2 was used as a positive control since LNCaP cells are known to express HER-2 (Li, Cozzi et al. 2004). Rituxan, a monoclonal against B cell antigen (CD20) was used as a negative control antibody since LNCaP cells do not express CD20. Both monoclonal antibodies are reported to have ADCC activities (Dall'Ozzo, Tartas et al. 2004; Collins, O'Donovan et al. 2011).

Example 2

Construction of PSMA Shuffled Antigens

This example illustrates the construction and certain biological properties of various immunogenic PSMA polypeptides that are variants of the human PSMA modified antigen (SEQ ID NO:9) as described in Example 1.

2A. Design of PSMA Shuffled Antigens

Various immunogenic PSMA polypeptides that are variants of the human PSMA modified antigen (SEQ ID NO:9) as described in Example 1 were designed. These variants were created by introducing mutations selected from orthologs of the human PSMA into the human PSMA modified antigen sequence. These variants are referred to, interchangeably, as "PSMA shuffled antigens" or "shuffled PSMA modified antigens" in the disclosure. The principle and procedure used in creating these variants are provided below.

A computational algorithm was written to select point mutations for the shuffled variant. First, a multiple sequence alignment of PSMA and 12 orthologs (Appendix 2a) was assembled using NCBI's PSI-BLAST. The output from PSI-BLAST included propensities for each residue at each PSMA position among the orthologs. The perl script then used these propensities to select point mutations as follows:

1) Among all positions, the most commonly observed residue is selected that does not match the identity in the native human PSMA.

2) Verify that this mutation position does not overlap with identified Class I or II human PSMA epitopes to ensure that the point mutation is not within a conserved T cell epitope as defined herein above (Table 19).

3) Calculate similarity of mutation to the human residue via the BLOSUM62 matrix to verify that the BLOSUM62 similarity score for the residue substitution is within the range of 0-1 (inclusive).

This iterative procedure is followed until a certain percent sequence identity (below 100) is reached with respect to the human PSMA.

To serve as the input to this algorithm, the PSMA orthologs were assembled to construct a position-specific probability matrix using PSI-BLAST from NCBI. Additionally, the identified epitope regions of PSMA were listed in a file which was also provided to the shuffle algorithm. The non-shuffling regions were also extended to the cytosolic and transmembrane regions of the protein to avoid membrane-bound functionality problems. The orthologous PSMA protein sequences, BLOSUM62 matrix, and PSI-BLAST program were downloaded from the NCBI site.

The shuffling script was then run using these input data and produced a variant of human PSMA with 94% sequence identity with the original human PSMA. Additionally, three mutations to improve HLA-A2 binding were introduced based on their performance in the Epitoptimizer algorithm (Houghton, Engelhorn et al. 2007). These mutations are M664L (epitope: 663-671), I676V (epitope: 668-676), and N76L (epitope: 75-83). The resultant antigen is referred to as "shuffled PSMA modified antigen 1," "shuffled PSMA modified 1," or "PSMA shuffled antigen 1".

Results based on epitopes with consensus rank <1% and IC50 by neural Network (single best method)<500 showed that predicted epitopes from HLA A2.1, HLA A3, HLA A11, HLA A24, and HLA B7 were highly conserved in this shuffled antigen. Two additional variants of the human PSMA modified antigen described in Example 1 were designed 'with higher sequence identities and a more restrictive BLOSUM score cutoff of 1 to remove all non-conservative substitutions. These two variants are also referred to as "shuffled PSMA modified antigen 2" and "shuffled PSMA modified antigen 3," respectively. Percent identities of shuffled PSMA modified antigens 1-3 with respect to the human PSMA modified construct (e.g., amino acids 15-750 of the human PSMA) are approximately 93.6%, 94.9%, and 96.4%, respectively.

The shuffled PSMA modified antigen 1 has the amino acid sequence of SEQ ID NO:3 and has the following mutations relative to the human PSMA modified antigen:
N47S, T53S, K55Q, M58V, L65M, N76L, S98A, Q99E, K122E, N132D, V154I, I157V, F161Y, D191E, M192L, V201L, V225I, I258V, G282E, I283L, R320K, L362I, S380A, E408K, L417I, H475Y, K482Q, M509V, S513N, E542K, M583L, N589D, R598Q, S613N, I614L, S615A, Q620E, M622L, S647N, E648Q, S656N, I659L, V660L, L661V, M664L, I676V The shuffled PSMA modified antigen 2 has the amino acid sequence of SEQ ID NO:5 and has the following mutations relative to the human PSMA modified antigen:
Mutations:
N47S, K55Q, M58V, Q91E, S98A, A111S, K122E, N132D, V154I, I157V, F161Y, V201L, V225I, I258V, S312A, R320K, K324Q, R363K, S380A, E408K, H475Y, K482Q, Y494F, E495D, K499E, M509L, N540D, E542K, N544S, M583I, I591V, R598Q, R605K, S613N, S647N, E648Q, S656N, V660L The shuffled PSMA modified antigen 3 has the amino acid sequence of SEQ ID NO:7 and has the following mutations relative to the human PSMA modified antigen:
Mutations:
T339A, V342L, M344L, T349N, N350T, E351K, S401T, E408K, M470L, Y471H, H475Y, F506L, M509L, A531S, N540D, E542K, N544S, G548S, V555I, E563V, V603A, R605K, K606N, Y607H, D609E, K610N, I611L 2B. Immune Responses Measured Post Vaccination in Pasteur Mice Study Design.

Eight- to 10-week old Pasteur mice were immunized using PMED method with the various plasmid DNAs expressing shuffled PSMA modified antigens in a prime/boost/boost regimen, two weeks apart between each vaccination as described in Example 1F. Antigen specific T and B cell responses were measured 7 days after the last immunization in an interferon-gamma (IFNγ) ELISPOT assay and sandwich ELISA respectively.

TABLE 7

T cell responses induced by various shuffled PSMA modified antigens to peptide pools in PSMA peptide library

| Amino acid sequence coverage of target peptide pools from PSMA peptide library | IFN-γ SFC/1 × 10⁶ splenocytes (SD) | | | |
|---|---|---|---|---|
| | Human PSMA modified antigen | Shuffled PSMA modified antigen1 | Shuffled PSMA modified antigen 2 | Shuffled PSMA modified antigen 3 |
| 13-35 | 608 (31) | 135 (4) | 539 (33) | 339 (16) |
| 109-131 | 132 (14) | 97 (21) | 49 (13) | 360 (40) |
| 121-243 | 275 (7) | 146 (17) | 104 (17) | 542 (119) |
| 145-167 | 218 (6) | 158 (8) | 98 (8) | 505 (16) |
| 157-179 | 212 (14) | 293 (24) | 800 (0)* | 800 (0)* |
| 169-191 | 50 (11) | 52 (14) | 814 (23) | 804 (65) |
| 181-203 | 415 (33) | 8 (0) | 243 (18) | 103 (1) |
| 205-227 | 125 (7) | 1 (1) | 17 (7) | 7 (4) |
| 217-239 | 883 (47) | 302 (0) | 467 (52) | 538 (14) |
| 229-251 | 565 (24) | 188 (23) | 150 (17) | 460 (122) |
| 265-287 | 418 (8) | 2 (0) | 154 (25) | 168 (23) |
| 277-299 | 908 (79) | 132 (3) | 574 (25) | 670 (74) |
| 289-311 | 417 (27) | 20 (8) | 260 (3) | 374 (51) |
| 409-431 | 377 (7) | 61 (10) | 38 (3) | 48 (11) |
| 421-443 | 720 (34) | 110 (9) | 720 (17) | 38 (17) |
| 433-455 | 974 (51) | 211 (16) | 800 (0)* | 771 (52) |
| 481-503 | 400 (59) | 0 (0) | 116 (6) | 100 (34) |
| 589-611 | 60 (14) | 245 (30) | 679 (35) | 364 (11) |
| 601-623 | 70 (9) | 79 (13) | 344 (20) | 27 (1) |
| 613-635 | 629 (41) | 102 (11) | 772 (93) | 634 (9) |
| 637-659 | 226 (17) | 292 (0) | 539 (16) | 420 (198) |
| 649-671 | 530 (74) | 319 (16) | 614 (20) | 644 (65) |
| 661-683 | 507 (52) | 248 (9) | 330 (3) | 661 (16) |

Results.

ELISpot data presented in Table 7 demonstrates that overall the shuffled PSMA modified antigens are capable of inducing T cell responses in breadth and magnitude very similar to the human PSMA modified antigen. SFC >100 is considered positive. The "*" symbol represents too numerous to accurately count.

TABLE 8

T cell responses induced by shuffled PSMA modified antigens to HLA A2 targets and PSMA protein.

| | IFN-γ SFC/1 × $10^6$ splenocytes(SD) | | | |
|---|---|---|---|---|
| IFNγ ELISPOT targetstargets | Human PSMA modified antigen | Shuffled PSMA modified antigen 1 | Shuffled PSMA modified antigen 2 | Shuffled PSMA modified antigen 3 |
| PSMA p168 | 261 (21) | 337 (16) | 800+ (0) | 800+ (0) |
| PSMA p275 | 540 (66) | 2 (2) | 181 (17) | 134 (17) |
| PSMA p663 | 441 (46) | 152 (10) | 219 (6) | 600 (48) |
| HER-2 p106 | 1 (1) | 1 (1) | 1 (1) | 1 (1) |
| PSMA ECD protein | 839 (70) | 165 (31) | 569 (44) | 319 (6) |
| BSA protein | 1 (1) | 1 (1) | 1 (1) | 2 (0) |
| LNCaP | 229 (45) | 40 (3) | 137 (23) | 45 (6) |
| MeWo | 3 (1) | 1 (1) | 2 (2) | 1 (1) |
| MeWo-Ad-hPSMA | 365 (33) | 31 (10) | 341 (46) | 415 (128) |

As shown in Table 8, all the shuffled PSMA antigens are capable of inducing T cells that recognized known HLA A2 restricted PSMA epitopes as well as human HLA A2 tumor cells transduced with adenovirus bearing the PSMA transgene to express PSMA. The tumor cells that did not express PSMA served as negative controls and were not recognized. SFC>50 is considered positive.

TABLE 9

T cell responses induced by shuffled PSMA modified antigens to specific to CD4 T cells.

| aa sequence | IFN-γ SFC/1 × $10^6$ CD8 depleted splenocytes(SD) | | | |
|---|---|---|---|---|
| coverage of target peptide pools from PSMA peptide library | Human PSMA modified antigen | Shuffled PSMA modified antigen 1 | Shuffled PSMA modified antigen 2 | Shuffled PSMA modified antigen 3 |
| 17-31 | 396 (51) | 49 (33) | 294 (3) | 209 (13) |
| 281-295 | 528 (6) | 51 (1) | 592 (9) | 461 (24) |
| 285-299 | 512 (34) | 55 (18) | 529 (38) | 471 (38) |
| 429-443 | 552 (51) | 51 (1) | 524 (17) | 0 |
| 581-595 | 11 (1) | 0 | 199 (24) | 0 |

ELISpot data shown in Table 9 were obtained with splenocytes that were depleted of CD8; therefore the data represents T cell responses to specific to CD4 T cells. The data show that the CD4 response elicited by shuffled PSMA modified antigen 2 is very similar to that induced by the human PSMA modified antigen. SFC>50 is considered positive.

TABLE 10

Induction of anti-PSMA antibody response as measured by an ELISA assay

| Antigen | ELISA (OD = 0.5) | # of positive |
|---|---|---|
| Human PSMA modified antigen | 1159 (802) | 7/7 |
| Shuffled PSMA modified antigen 1 | 899 (1016) | 4/7 |
| Shuffled PSMA modified antigen 2 | 4898 (3636) | 6/6 |
| Shuffled PSMA modified antigen 3 | 1482 (3092) | 1/5 |

Data in Table 10 demonstrates that all the shuffled PSMA modified antigens are capable of inducing anti-human PSMA antibody responses. Shuffled PSMA modified antigen 2 and the human PSMA modified antigen induced consistent antibody responses in all mice.

TABLE 11

T cell responses in HLA A24 mice induced by the human PSMA modified antigen and shuffled PSMA modified antigen 2.

| Amino acid sequence | IFN-γ SFC/1 × $10^6$ splenocytes (SD) | |
|---|---|---|
| coverage of target peptide pools from PSMA peptide library | Human PSMA modified antigen | Shuffled PSMA modified antigen 2 |
| 217-231 | 280 (10) | 271 (7) |
| 233-247 | 219 (2) | 0 |
| 237-251 | 197 (1) | 228 (1) |
| 249-263 | 203 (1) | 28 (1) |
| 273-287 | 57 (2) | 323 (3) |
| 277-291 | 194 (24) | 337 (18) |
| 293-307 | 147 (6) | 379 (11) |
| 309-323 | 17 (1) | 441 (14) |
| 401-415 | 256 (1) | 292 (3) |
| 429-443 | 255 (7) | 0 |
| 433-447 | 59 (1) | 179 (6) |
| 481-495 | 167 (11) | 475 (21) |
| 557-571 | 194 (14) | 297 (1) |
| 601-615 | 500 (35) | 166 (10) |
| 605-619 | 500 (28) | 143 (7) |
| 613-627 | 218 (4) | 0 |
| 697-711 | 0 | 141 (8) |
| 729-743 | 0 | 140 (1) |
| 733-747 | 0 | 271 (3) |
| 737-750 | 0 | 401 (8) |

ELISpot data in Table 11 demonstrates that overall the T cell response induced by shuffled PSMA modified antigen 2 in HLA A24 mice is very similar in breadth and magnitude to the human PSMA modified antigen. SFC >100 is considered positive.

2C. Breaking of Immune Tolerance to Human PSMA by Shuffled PSMA Modified Antigens Study Design.

The human PSMA transgenic mouse model uses mice that were made using the minimal rat probasin promoter driving the expression of PSMA specifically in the prostate gland (Zhang, Thomas et al. 2000) Endocrinology 141(12): 4698-4710. These mice were made in the C57BL/6 background. RT-PCR and immune histochemistry staining data confirmed the expression of PSMA in the ventral and dorsolateral roots of the prostate gland in these PSMA transgenic mice. The endogenous expression of human PSMA protein in these mice is expected to generate immune tolerance.

Results.

As shown in Table 12, only 20% of the PSMA transgenic mice were able to mount a T cell response to human PSMA using the human PSMA modified antigen. However, 67% of the PSMA transgenic mice were able to mount a PSMA specific T cell response using the shuffled PSMA modified antigen 2. The data suggests that the inclusion of non-self amino acid sequences in the shuffled PSMA modified antigen 2 improved the breaking tolerance to the self human PSMA antigen. SFC>50 is considered positive.

TABLE 12

T cell responses in human PSMA transgenic mice to known PSMA epitope (PADYFAPGVKSYPDG; Durso R J, *Clin Cancer Res.* 2007 Jul. 1; 13(13): 3999-400).

| Antigen | IFN-γ SFC/1 × 10⁶ splenocytes (SD) | | | | | | | | | | # of positive |
|---|---|---|---|---|---|---|---|---|---|---|---|
| Human PSMA modified antigen | 7 (3) | 126 (20) | 1 (2) | 3 (1) | 10 (5) | 22 (5) | 30 (3) | 12 (0) | 7 (2) | 404 (4) | 2/10 |
| Shuffled PSMA modified antigen 2 | 474 (52) | 104 (18) | 7 (3) | 111 (8) | 12 (2) | 21 (2) | 139 (12) | 246 (9) | 226 (11) | NA | 6/9 |

Example 3

Design of Various Immunogenic PSA Polypeptides

Example 3 illustrates the construction and certain biological properties of immunogenic PSA polypeptides in cytosolic, secreted, and membrane-bound forms.

3A. Construction of Various PSA Antigen Forms

Similar to what was described in Example 1 for the three different immunogenic PSMA polypeptide forms (e.g., the cytosolic, membrane-bound, and secreted forms), immunogenic PSA polypeptides in the three forms were also designed based on the human PSA sequence. An immunogenic PSA polypeptide in cytosolic form, which consists of amino acids 25-261 of the native human PSA, is constructed by deleting the secretory signal and the pro domain (amino acids 1-24). The amino acid sequence of this cytosolic immunogenic PSA polypeptide is provided in SEQ ID NO: 17. The secreted form of the PSA polypeptide is the native full length human PSA (amino acids 1-261). An immunogenic PSA polypeptide in membrane-bound form is constructed by linking the immunogenic PSA polypeptide cytosolic form (amino acids 25-261 of the native human PSA) to the human PSMA transmembrane domain (amino acids 15-54 of the human PSMA).

3B. Immune Responses in Pasteur and HLA A24 Mice Study Design.

Eight to 10 week old HLA A2 Pasteur mice or HLA A24 mice were immunized with DNA expressing the various PSA antigens using PMED provided in Example 3A in a prime/boost/boost regimen with two week intervals between each vaccination as described in Example 1. The antigen specific T and B cell responses were measured 7 days after the last immunization in an interferon-gamma (IFNγ) ELISPOT assay and sandwich ELISA.

TABLE 13

Induction of T cell responses in Pasteur mice and HLA A24 mice vaccinated with PSA polypeptides

| Amino acid sequence coverage of target | IFN-γ SFC/1 × 10⁶ splenocytes (SD) | | |
|---|---|---|---|
| peptide pools from PSA peptide library | PSA cytosolic | PSA membrane-bound | PSA secreted |
| T cell response detected in HLA A2 Pasteur mice | | | |
| 25-47 | 12 (0) | 134 (6) | 27 (1) |
| 49-71 | 150 (0) | 23 (1) | 151 (10) |
| 61-83 | 904 (17) | 27 (7) | 452 (14) |
| 73-95 | 128 (25) | 8 (6) | 78 (14) |
| 85-107 | 17 (7) | 205 (18) | 11 (1) |
| 97-117 | 26 (3) | 378 (25) | 13 (1) |
| 217-239 | 16 (8) | 234 (8) | 6 (6) |
| 229-251 | 96 (34) | 844 (6) | 35 (12) |
| T cell response detected in HLA A24 mice | | | |
| 145-167 | 357 (2) | Not determined | Not determined |

Results.

Table 13 shows ELISpot data derived from splenocytes isolated from HLA A2 Pasteur mice or HLA A24 mice cultured with peptides derived from the PSA peptide library. T cell responses can be detected in both HLA A2 and HLA A24 mice. SFC>100 is considered positive.

TABLE 14

The induction of T cell responses by PSA antigens in Pasteur mice to PSA+ HLA A2.1+ SKmel5 human cancer cells

| HLA A2.1+ human cancer cells or protein | IFN-γ SFC/1 × 10⁶ splenocytes (SD) | | |
|---|---|---|---|
|  | PSA cytosolic | PSA membrane-bound | PSA secreted |
| SKmel5-Ad-eGFP | 7.7 (9.6) | 1.2 (1.4) | 2.9 (2.7) |
| SKmel5-Ad-PSA | 112.0 (169.3) | 546.1 (379.6) | 18.7 (18.5) |
| PSA protein | 108.8 (161.0) | 536.9 (380.9) | 20.6 (21) |

ELISpot data shown in table 14 indicates that immunogenic PSA polypeptides in both cytosolic and membrane-bound forms are capable of inducing T cells that recognize human tumor cells transduced with adenovirus to express the cytosolic PSA antigen (SKmel5-Ad-PSA) but not cells transduced with adenovirus to express eGFP (SKmel5-Ad-eGFP). These two antigens also elicited response to PSA protein. The PSA secreted antigen failed to induce T cells to both SKmel5-Ad-PSA or PSA protein. SFC>50 is considered positive.

TABLE 15

The induction of anti-PSA antibody response as measured by a sandwich ELISA assay

| Antigen Forms | ELISA (OD = 1.0) Average (SD) | # of positive |
|---|---|---|
| PSA cytosolic | 99 (0) | 0/6 |
| PSA membrane-bound | 4838 (835) | 6/6 |
| PSA secreted | 1151 2410) | 2/6 |

Data in Table 15 demonstrates that immunogenic PSA polypeptides in both secreted and membrane-bound forms are capable of inducing anti-PSA antibody responses.

TABLE 16

Human PSMA Peptide Library peptide pools and corresponding amino acid sequences

| PSMA peptide pool (aa no.) | aa sequences of individual peptides |
|---|---|
| 1-23 | MWNLLHETDSAVATA<br>LHETDSAVATARRPR<br>DSAVATARRPRWLCA |
| 13-35 | ATARRPRWLCAGALV<br>RPRWLCAGALVLAGG<br>LCAGALVLAGGFFLL |
| 25-47 | ALVLAGGFFLLGFLF<br>AGGFFLLGFLFGWFI<br>FLLGFLFGWFIKSSN |
| 37-59 | FLFGWFIKSSNEATN<br>WFIKSSNEATNITPK<br>SSNEATNITPKHNMK |
| 49-71 | ATNITPKHNMKAFLD<br>TPKHNMKAFLDELKA<br>NMKAFLDELKAENIK |
| 61-83 | FLDELKAENIKKFLY<br>LKAENIKKFLYNFTQ<br>NIKKFLYNFTQIPHL |
| 73-95 | FLYNFTQIPHLAGTE<br>FTQIPHLAGTEQNFQ<br>PHLAGTEQNFQLAKQ |
| 85-107 | GTEQNFQLAKQIQSQ<br>NFQLAKQIQSQWKEF<br>AKQIQSQWKEFGLDS |
| 97-117 | QSQWKEFGLDSVELA<br>KEFGLDSVELAHYDV<br>LDSVELAHYDVLLSY |
| 109-131 | ELAHYDVLLSYPNKT<br>YDVLLSYPNKTHPNY<br>LSYPNKTHPNYISII |
| 121-243 | NKTHPNYISIINEDG<br>PNYISIINEDGNEIF<br>SIINEDGNEIFNTSL |
| 133-155 | EDGNEIFNTSLFEPP<br>EIFNTSLFEPPPPGY<br>TSLFEPPPPGYENVS |
| 145-167 | EPPPPGYENVSDIVP<br>PGYENVSDIVPPFSA<br>NVSDIVPPFSAFSPQ |
| 157-179 | IVPPFSAFSPQGMPE<br>FSAFSPQGMPEGDLV<br>SPQGMPEGDLVYVNY |

TABLE 16-continued

Human PSMA Peptide Library peptide pools and corresponding amino acid sequences

| PSMA peptide pool (aa no.) | aa sequences of individual peptides |
|---|---|
| 169-191 | MPEGDLVYVNYARTE<br>DLVYVNYARTEDFFK<br>VNYARTEDFFKLERD |
| 181-203 | RTEDFFKLERDMKIN<br>FFKLERDMKINCSGK<br>ERDMKINCSGKIVIA |
| 193-215 | KINCSGKIVIARYGK<br>SGKIVIARYGKVFRG<br>VIARYGKVFRGNKVK |
| 205-227 | YGKVFRGNKVKNAQL<br>FRGNKVKNAQLAGAK<br>KVKNAQLAGAKGVIL |
| 217-239 | AQLAGAKGVILYSDP<br>GAKGVILYSDPADYF<br>VILYSDPADYFAPGV |
| 229-251 | SDPADYFAPGVKSYP<br>DYFAPGVKSYPDGWN<br>PGVKSYPDGWNLPGG |
| 241-263 | SYPDGWNLPGGGVQR<br>GWNLPGGGVQRGNIL<br>PGGGVQRGNILNLNG |
| 253-275 | VQRGNILNLNGAGDP<br>NILNLNGAGDPLTPG<br>LNGAGDPLTPGYPAN |
| 265-287 | GDPLTPGYPANEYAY<br>TPGYPANEYAYRRGI<br>PANEYAYRRGIAEAV |
| 277-299 | YAYRRGIAEAVGLPS<br>RGIAEAVGLPSIPVH<br>EAVGLPSIPVHPIGY |
| 289-311 | LPSIPVHPIGYYDAQ<br>PVHPIGYYDAQKLLE<br>IGYYDAQKLLEKMGG |
| 301-323 | DAQKLLEKMGGSAPP<br>LLEKMGGSAPPDSSW<br>MGGSAPPDSSWRGSL |
| 313-335 | APPDSSWRGSLKVPY<br>SSWRGSLKVPYNVGP<br>GSLKVPYNVGPGFTG |
| 325-347 | VPYNVGPGFTGNFST<br>VGPGFTGNFSTQKVK<br>FTGNFSTQKVKMHIH |
| 337-359 | FSTQKVKMHIHSTNE<br>KVKMHIHSTNEVTRI<br>HIHSTNEVTRIYNVI |
| 349-371 | TNEVTRIYNVIGTLR<br>TRIYNVIGTLRGAVE<br>NVIGTLRGAVEPDRY |
| 361-383 | TLRGAVEPDRYVILG<br>AVEPDRYVILGGHRD<br>DRYVILGGHRDSWVF |
| 373-395 | ILGGHRDSWVFGGID<br>HRDSWVFGGIDPQSG<br>WVFGGIDPQSGAAVV |

TABLE 16-continued

Human PSMA Peptide Library peptide pools and corresponding amino acid sequences

| PSMA peptide pool (aa no.) | aa sequences of individual peptides |
|---|---|
| 385-407 | GIDPQSGAAVVHEIV<br>QSGAAVVHEIVRSFG<br>AVVHEIVRSFGTLKK |
| 397-419 | EIVRSFGTLKKEGWR<br>SFGTLKKEGWRPRRT<br>LKKEGWRPRRTILFA |
| 409-431 | GWRPRRTILFASWDA<br>RRTILFASWDAEEFG<br>LFASWDAEEFGLLGS |
| 421-443 | WDAEEFGLLGSTEWA<br>EFGLLGSTEWAEENS<br>LGSTEWAEENSRLLQ |
| 433-455 | EWAEENSRLLQERGV<br>ENSRLLQERGVAYIN<br>LLQERGVAYINADSS |
| 445-467 | RGVAYINADSSIEGN<br>YINADSSIEGNYTLR<br>DSSIEGNYTLRVDCT |
| 457-479 | EGNYTLRVDCTPLMY<br>TLRVDCTPLMYSLVH<br>DCTPLMYSLVHNLTK |
| 469-491 | LMYSLVHNLTKELKS<br>LVHNLTKELKSPDEG<br>LTKELKSPDEGFEGK |
| 481-503 | LKSPDEGFEGKSLYE<br>DEGFEGKSLYESWTK<br>EGKSLYESWTKKSPS |
| 493-515 | LYESWTKKSPSPEFS<br>WTKKSPSPEFSGMPR<br>SPSPEFSGMPRISKL |
| 505-527 | EFSGMPRISKLGSGN<br>MPRISKLGSGNDFEV<br>SKLGSGNDFEVFFQR |
| 517-539 | SGNDFEVFFQRLGIA<br>FEVFFQRLGIASGRA<br>FQRLGIASGRARYTK |
| 529-551 | GIASGRARYTKNWET<br>GRARYTKNWETNKFS<br>YTKNWETNKFSGYPL |
| 541-563 | WETNKFSGYPLYHSV<br>KFSGYPLYHSVYETY<br>YPLYHSVYETYELVE |
| 553-575 | HSVYETYELVEKFYD<br>ETYELVEKFYDPMFK<br>LVEKFYDPMFKYHLT |
| 565-587 | FYDPMFKYHLTVAQV<br>MFKYHLTVAQVRGGM<br>HLTVAQVRGGMVFEL |
| 577-599 | AQVRGGMVFELANSI<br>GGMVFELANSIVLPF<br>FELANSIVLPFDCRD |
| 589-611 | NSIVLPFDCRDYAVV<br>LPFDCRDYAVVLRKY<br>CRDYAVVLRKYADKI |

TABLE 16-continued

Human PSMA Peptide Library peptide pools and corresponding amino acid sequences

| PSMA peptide pool (aa no.) | aa sequences of individual peptides |
|---|---|
| 601-623 | AVVLRKYADKIYSIS<br>RKYADKIYSISMKHP<br>DKIYSISMKHPQEMK |
| 613-635 | SISMKHPQEMKTYSV<br>KHPQEMKTYSVSFDS<br>EMKTYSVSFDSLFSA |
| 625-647 | YSVSFDSLFSAVKNF<br>FDSLFSAVKNFTEIA<br>FSAVKNFTEIASKFS |
| 637-659 | KNFTEIASKFSERLQ<br>EIASKFSERLQDFDK<br>KFSERLQDFDKSNPI |
| 649-671 | RLQDFDKSNPIVLRM<br>FDKSNPIVLRMMNDQ<br>NPIVLRMMNDQLMFL |
| 661-683 | LRMMNDQLMFLERAF<br>NDQLMFLERAFIDPL<br>MFLERAFIDPLGLPD |
| 673-695 | RAFIDPLGLPDRPFY<br>DPLGLPDRPFYRHVI<br>LPDRPFYRHVIYAPS |
| 685-707 | PFYRHVIYAPSSHNK<br>HVIYAPSSHNKYAGE<br>APSSHNKYAGESFPG |
| 697-719 | HNKYAGESFPGIYDA<br>AGESFPGIYDALFDI<br>FPGIYDALFDIESKV |
| 709-731 | YDALFDIESKVDPSK<br>FDIESKVDPSKAWGE<br>SKVDPSKAWGEVKRQ |
| 721-743 | PSKAWGEVKRQIYVA<br>WGEVKRQIYVAAFTV<br>KRQIYVAAFTVQAAA |
| 733-750 | YVAAFTVQAAAETLS<br>FTVQAAAETLSEVA |

TABLE 17

Human PSA Peptide Library

| PSA peptide pool (aa no.) | aa sequences of individual peptides |
|---|---|
| 1-23 | MWVPVVFLTLSVTWI<br>VVFLTLSVTWIGAAP<br>TLSVTWIGAAPLILS |
| 13-35 | TWIGAAPLILSRIVG<br>AAPLILSRIVGGWEC<br>ILSRIVGGWECEKHS |
| 25-47 | IVGGWECEKHSQPWQ<br>WECEKHSQPWQVLVA<br>KHSQPWQVLVASRGR |
| 37-59 | PWQVLVASRGRAVCG<br>LVASRGRAVCGGVLV<br>RGRAVCGGVLVHPQW |

TABLE 17-continued

Human PSA Peptide Library

| PSA peptide pool (aa no.) | aa sequences of individual peptides |
|---|---|
| 49-71 | VCGGVLVHPQWVLTA<br>VLVHPQWVLTAAHCI<br>PQWVLTAAHCIRNKS |
| 61-83 | LTAAHCIRNKSVILL<br>HCIRNKSVILLGRHS<br>NKSVILLGRHSLFHP |
| 73-95 | ILLGRHSLFHPEDTG<br>RHSLFHPEDTGQVFQ<br>FHPEDTGQVFQVSHS |
| 85-107 | DTGQVFQVSHSFPHP<br>VFQVSHSFPHPLYDM<br>SHSFPHPLYDMSLLK |
| 97-117 | PHPLYDMSLLKNRFL<br>YDMSLLKNRFLRPGD<br>LLKNRFLRPGDDSSH |
| 109-131 | RFLRPGDDSSHDLML<br>PGDDSSHDLMLLRLS<br>SSHDLMLLRLSEPAE |
| 121-243 | LMLLRLSEPAELTDA<br>RLSEPAELTDAVKVM<br>PAELTDAVKVMDLPT |
| 133-155 | TDAVKVMDLPTQEPA<br>KVMDLPTQEPALGTT<br>LPTQEPALGTTCYAS |
| 145-167 | EPALGTTCYASGWGS<br>GTTCYASGWGSIEPE<br>YASGWGSIEPEEFLT |
| 157-179 | WGSIEPEEFLTPKKL<br>EPEEFLTPKKLQCVD<br>FLTPKKLQCVDLHVI |
| 169-191 | KKLQCVDLHVISNDV<br>CVDLHVISNDVCAQV<br>HVISNDVCAQVHPQK |
| 181-203 | NDVCAQVHPQKVTKF<br>AQVHPQKVTKFMLCA<br>PQKVTKFMLCAGRWT |
| 193-215 | TKFMLCAGRWTGGKS<br>LCAGRWTGGKSTCSG<br>RWTGGKSTCSGDSGG |
| 205-227 | GKSTCSGDSGGPLVC<br>CSGDSGGPLVCNGVL<br>SGGPLVCNGVLQGIT |
| 217-239 | LVCNGVLQGITSWGS<br>GVLQGITSWGSEPCA<br>GITSWGSEPCALPER |
| 229-251 | WGSEPCALPERPSLY<br>PCALPERPSLYTKVV<br>PERPSLYTKVVHYRK |
| 241-263 | SLYTKVVHYRKWIKD<br>KVVHYRKWIKDTIVA<br>YRKWIKDTIVANP |

TABLE 18

PSMA Orthologs

| PSMA species | NCBI ID | % ID with human |
|---|---|---|
| human | 2897946 | 100 |
| chimpanzee | 114639743 | 99 |
| macaque | 109108238 | 97 |
| dog | 73987958 | 93 |
| horse | 149719573 | 92 |
| pig | 47523822 | 90 |
| cow | 156120365 | 89 |
| rat | 149069047 | 84 |
| mouse | 20138153 | 84 |
| opossum | 126327828 | 80 |
| chicken | 118085215 | 78 |
| platypus | 149635150 | 76 |
| zebra fish | 41053648 | 69 |

TABLE 19

Conserved T Cell Epitopes in the Human PSMA as Set Forth in SEQ ID NO: 1.

| Amino acid Start | Amino acid End | Sequence |
|---|---|---|
| 168 | 176 | GMPEGDLVY |
| 347 | 356 | HSTNGVTRIY |
| 557 | 566 | ETYELVEKFY |
| 207 | 215 | KVFRGNKVK |
| 431 | 440 | STEWAEENSR |
| 4 | 12 | LLHETDSAV |
| 27 | 35 | VLAGGFFLL |
| 168 | 177 | GMPEGDLVYV |
| 441 | 450 | LLQERGVAYI |
| 469 | 477 | LMYSLVHNL |
| 711 | 719 | ALFDIESKV |
| 663 | 671 | MNDQVMFL |
| 178 | 186 | NYARTEDFF |
| 227 | 235 | LYSDPADYF |
| 624 | 632 | TYSVSFDSL |
| 334 | 348 | TGNFSTQKVKMHIHS |
| 459 | 473 | NYTLRVDCTPLMYSL |
| 687 | 701 | YRHVIYAPSSHNKYA |
| 730 | 744 | RQIYVAAFTVQAAAE |

Example 4

Construction of Multi-Antigen Vaccine Constructs

In this Example, several strategies for expressing multiple antigens from single component DNA vaccine construct are described. These multi-antigen DNA vaccine constructs share the same general plasmid backbone as pPJV7563. Although the multi-antigen expression strategies are described here in the context of a DNA vaccine, the principles will apply similarly in the context of viral vector genetic vaccines (such as adenovirus vectors). Unless otherwise specified, the genes included in the multi-antigen constructs encode the human PSMA modified antigen (noted as PSMA), full length human PSCA (noted as PSCA), and the human PSA cytosolic antigen (noted as PSA), as described in the examples herein above.

Example 4A

Dual Antigen Constructs

4A1. Construction of Dual Antigen Constructs Utilizing Multiple Promoters

General Strategy.

One strategy for creating multivalent nucleic acid vaccine constructs is to incorporate multiple independent promoters into a single plasmid (Huang, Y., Z. Chen, et al. (2008). "Design, construction, and characterization of a dual-promoter multigenic DNA vaccine directed against an HIV-1 subtype C/B' recombinant." J Acquir Immune Defic Syndr 47(4): 403-411; Xu, K., Z. Y. Ling, et al. (2011). "Broad humoral and cellular immunity elicited by a bivalent DNA vaccine encoding HA and NP genes from an H5N1 virus." Viral Immunol 24(1): 45-56). The plasmid can be engineered to carry multiple expression cassettes, each consisting of a) a eukaryotic promoter for initiating RNA polymerase dependent transcription, with or without an enhancer element, b) a gene encoding a target antigen, and c) a transcription terminator sequence. Upon delivery of the plasmid to the transfected cell nucleus, transcription will be initiated from each promoter, resulting in the production of separate mRNAs, each encoding one of the target antigens. The mRNAs will be independently translated, thereby producing the desired antigens.

Plasmid 460 (PSMA/PSCA Dual Promoter).

Plasmid 460 was constructed using the techniques of site-directed mutagenesis, PCR, and restriction fragment insertion. First, a Kpn I restriction site was introduced upstream of the CMV promoter in plasmid 5259 using site-directed mutagenesis with MD5 and MD6 primers according to manufacturer's protocol (Quickchange kit, Agilent Technologies, Santa Clara, Calif.). Second, an expression cassette consisting of a minimal CMV promoter, human PSMA, and rabbit B globulin transcription terminator was amplified by PCR from plasmid 5166 using primers that carried Kpn I restriction sites (MD7 and MD8). The PCR amplicon was digested with Kpn I and inserted into the newly introduced Kpn I site of calf intestinal alkaline phosphatase (CIP)-treated plasmid 5259.

4A2. Construction of Dual Antigen Constructs Utilizing 2A Peptides

General Strategy.

Multiple protein antigens can also be expressed from a single vector through the use of viral 2A-like peptides (Szymczak, A. L. and D. A. Vignali (2005). "Development of 2A peptide-based strategies in the design of multicistronic vectors." Expert Opin Biol Ther 5(5): 627-638; de Felipe, P., G. A. Luke, et al. (2006). "E unum pluribus: multiple proteins from a self-processing polyprotein." Trends Biotechnol 24(2): 68-75; Luke, G. A., P. de Felipe, et al. (2008). "Occurrence, function and evolutionary origins of '2A-like' sequences in virus genomes." J Gen Virol 89 (Pt 4): 1036-1042; Ibrahimi, A., G. Vande Velde, et al. (2009). "Highly efficient multicistronic lentiviral vectors with peptide 2A sequences." Hum Gene Ther 20(8): 845-860; Kim, J. H., S. R. Lee, et al. (2011). "High cleavage efficiency of a 2A peptide derived from porcine teschovirus-1 in human cell lines, zebrafish and mice." PLoS One 6(4): e18556). These peptides, also called cleavage cassettes or CHYSELs (cis-acting hydrolase elements), are approximately 20 amino acids long with a highly conserved carboxy terminal D-V/I-EXNPGP motif (FIG. 2). The cassettes are rare in nature, most commonly found in viruses such as Foot-and-mouth disease virus (FMDV), Equine rhinitis A virus (ERAV), Encephalomyocarditis virus (EMCV), Porcine teschovirus (PTV), and Thosea asigna virus (TAV) (Luke, G. A., P. de Felipe, et al. (2008). "Occurrence, function and evolutionary origins of '2A-like' sequences in virus genomes." J Gen Virol 89 (Pt 4): 1036-1042). With a 2A-based multi-antigen expression strategy, genes encoding multiple target antigens can be linked together in a single open reading frame, separated by 2A cassettes. The entire open reading frame can be cloned into a vector with a single promoter and terminator. Upon delivery of the genetic vaccine to a cell, mRNA encoding the multiple antigens will be transcribed and translated as a single polyprotein. During translation of the 2A cassettes, ribosomes skip the bond between the C-terminal glycine and proline. The ribosomal skipping acts like a cotranslational autocatalytic "cleavage" that releases upstream from downstream proteins. The incorporation of a 2A cassette between two protein antigens results in the addition of ~20 amino acids onto the C-terminus of the upstream polypeptide and 1 amino acid (proline) to the N-terminus of downstream protein. In an adaptation of this methodology, protease cleavage sites can be incorporated at the N terminus of the 2A cassette such that ubiquitous proteases will cleave the cassette from the upstream protein (Fang, J., S. Yi, et al. (2007). "An antibody delivery system for regulated expression of therapeutic levels of monoclonal antibodies in vivo." Mol Ther 15(6): 1153-1159).

Plasmid 451 (PSMA-T2A-PSCA).

Plasmid 451 was constructed using the techniques of overlapping PCR and restriction fragment exchange. First, the gene encoding human PSMA amino acids 15-750 was amplified by PCR using plasmid 5166 as a template with primers 119 and 117. The gene encoding full-length human PSCA was amplified by PCR using plasmid 5259 as a template with primers 118 and 120. PCR resulted in the addition of overlapping TAV 2A (T2A) sequences at the 3' end of PSMA and 5' end of PSCA. The amplicons were mixed together and amplified by PCR with primers 119 and 120. The PSMA-T2A-PSCA amplicon was digested with Nhe I and Bgl II and inserted into similarly digested plasmid 5166. A glycine-serine linker was included between PSMA and the T2A cassette to promote high cleavage efficiency.

Plasmid 454 (PSCA-F2A-PSMA).

Plasmid 454 was created using the techniques of PCR and restriction fragment exchange. First, the gene encoding full-length human PSCA was amplified by PCR using plasmid 5259 as a template with primers 42 and 132. The amplicon was digested with BamH I and inserted into similarly digested, CIP-treated plasmid 5300. A glycine-serine linker was included between PSCA and the FMDV 2A (F2A) cassette to promote high cleavage efficiency.

Plasmid 5300 (PSA-F2A-PSMA)

Plasmid 5300 was constructed using the techniques of overlapping PCR and restriction fragment exchange. First, the gene encoding PSA amino acids 25-261 was amplified by PCR from plasmid 5297 with primers MD1 and MD2. The gene encoding human PSMA amino acids 15-750 was amplified by PCR from plasmid 5166 with primers MD3 and MD4. PCR resulted in the addition of overlapping F2A sequences at the 3' end of PSA and 5' end of PSMA. The amplicons were mixed together and extended by PCR. The PSA-F2A-PSMA amplicon was digested with Nhe I and Bgl II and inserted into similarly digested plasmid pPJV7563.

4A3. Dual Antigen Constructs Utilizing Internal Ribosomal Entry Sites

General Strategy:

A third strategy for expressing multiple protein antigens from a single plasmid or vector involves the use of an internal ribosomal entry site, or IRES. Internal ribosomal entry sites are RNA elements (FIG. 3) found in the 5' untranslated regions of certain RNA molecules (Bonnal, S., C. Boutonnet, et al. (2003). "IRESdb: the Internal Ribosome Entry Site database." Nucleic Acids Res 31(1): 427-428). They attract eukaryotic ribosomes to the RNA to facilitate translation of downstream open reading frames. Unlike normal cellular 7-methylguanosine cap-dependent translation, IRES-mediated translation can initiate at AUG codons far within an RNA molecule. The highly efficient process can be exploited for use in multi-cistronic expression vectors (Bochkov, Y. A. and A. C. Palmenberg (2006). "Translational efficiency of EMCV IRES in bicistronic vectors is dependent upon IRES sequence and gene location." Biotechniques 41(3): 283-284, 286, 288). Typically, two transgenes are inserted into a vector between a promoter and transcription terminator as two separate open reading frames separated by an IRES. Upon delivery of the genetic vaccine to the cell, a single long transcript encoding both transgenes will be transcribed. The first ORF will be translated in the traditional cap-dependent manner, terminating at a stop codon upstream of the IRES. The second ORF will be translated in a cap-independent manner using the IRES. In this way, two independent proteins can be produced from a single mRNA transcribed from a vector with a single expression cassette.

Plasmid 449 (PSMA-mIRES-PSCA).

Plasmid 449 was constructed using the techniques of overlapping PCR and restriction fragment exchange. First, the gene encoding full length human PSCA was amplified by PCR from plasmid 5259 with primers 124 and 123. The minimal EMCV IRES was amplified by PCR from pShuttle-IRES with primers 101 and 125. The overlapping amplicons were mixed together and amplified by PCR with primers 101 and 123. The IRES-PSCA amplicon was digested with Bgl II and BamH I and inserted into Bgl II-digested, CIP-treated plasmid 5166. In order to fix a spontaneous mutation within the IRES, the IRES containing Avr II to Kpn I sequence was replaced with an equivalent fragment from pShuttle-IRES.

Plasmid 603 (PSCA-pIRES-PSMA).

Plasmid 603 was constructed using the techniques of PCR and seamless cloning. The gene encoding full length human PSCA attached at its 3' end to a preferred EMCV IRES was amplified from plasmid 455 by PCR with primers SD546 and SD547. The gene encoding human PSMA amino acids 15-750 was amplified by PCR from plasmid 5166 using primers SD548 and SD550. The two overlapping PCR amplicons were inserted into Nhe I and Bgl II-digested pPJV7563 by seamless cloning according to manufacturer's instructions (Invitrogen, Carlsbad, Calif.).

Plasmid 455 (PSCA-mIRES-PSA).

Plasmid 455 was constructed using the techniques of overlapping PCR and restriction fragment exchange. First, the gene encoding human PSA amino acids 25-261 was amplified by PCR from plasmid 5297 with primers 115 and 114. The minimal EMCV IRES was amplified by PCR from pShuttle-IRES with primers 101 and 116. The overlapping amplicons were mixed together and amplified by PCR with primers 101 and 114. The IRES-PSA amplicon was digested with Bgl II and BamH I and inserted into Bgl II-digested, CIP-treated plasmid 5259. In order to fix a spontaneous mutation within this clone, the Bgl II to BstE II sequence was replaced with an equivalent fragment from a fresh overlapping PCR reaction.

Example 4B

Triple Antigen DNA Constructs

General Strategy.

Figure 7A:
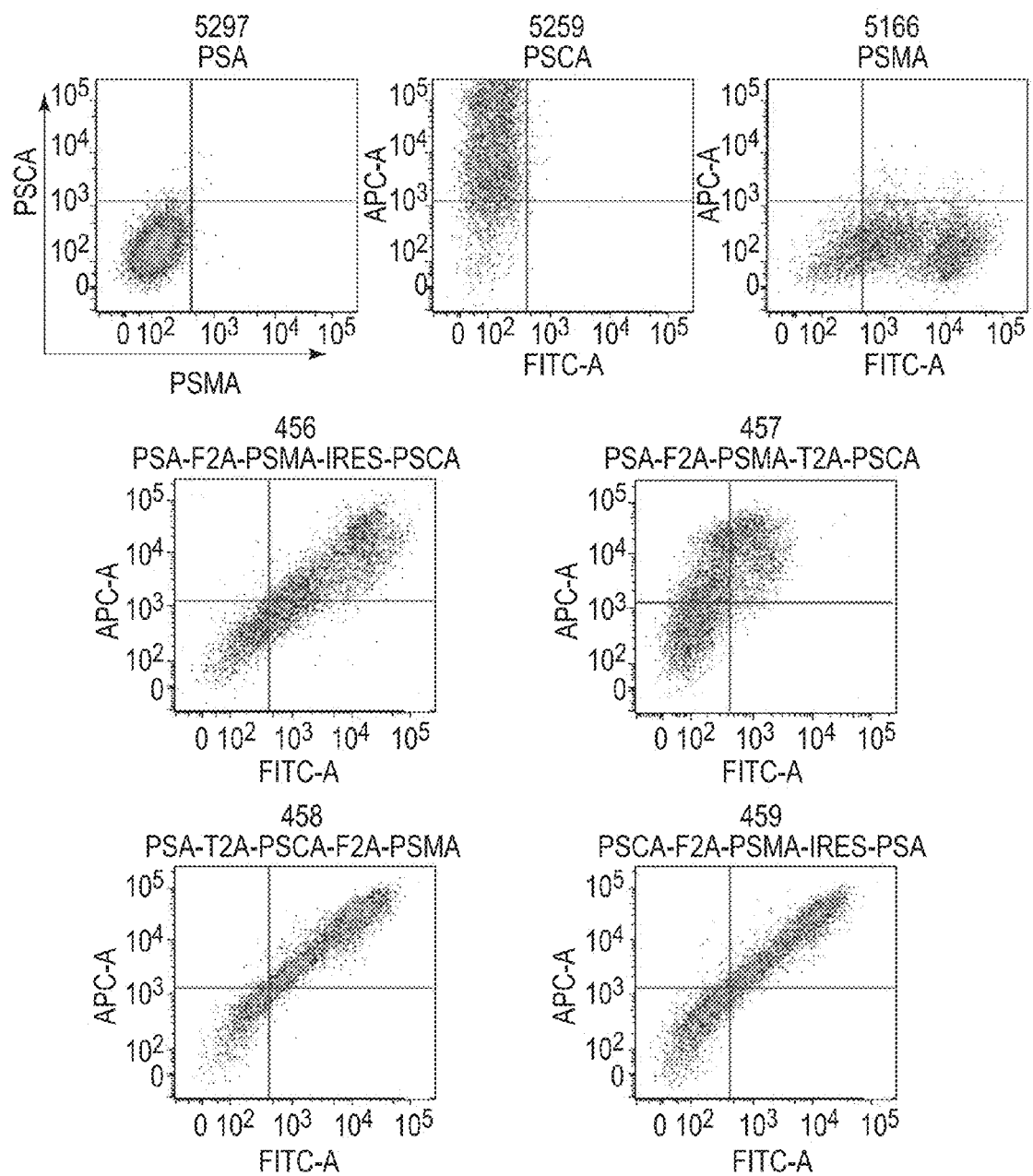
FIGS. 7A, 7B. Dot plots showing expression of human PSMA modified antigen (amino acids 15-750) and full length human PSCA on the surface of HEK293 cells transfected with either single promoter triple antigen constructs (FIG. 7A) or dual promoter triple antigen vaccine constructs (FIG. 7B) as measured by flow cytometry.
Figure 7B:
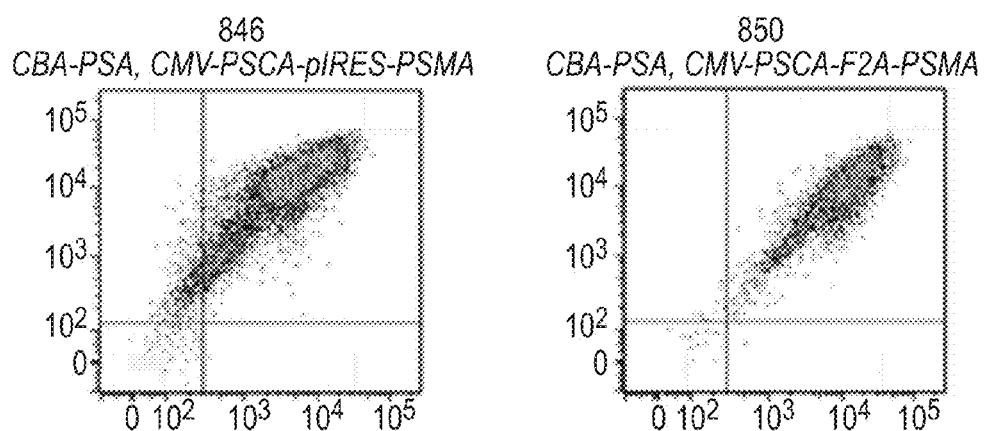
Figure 8A:
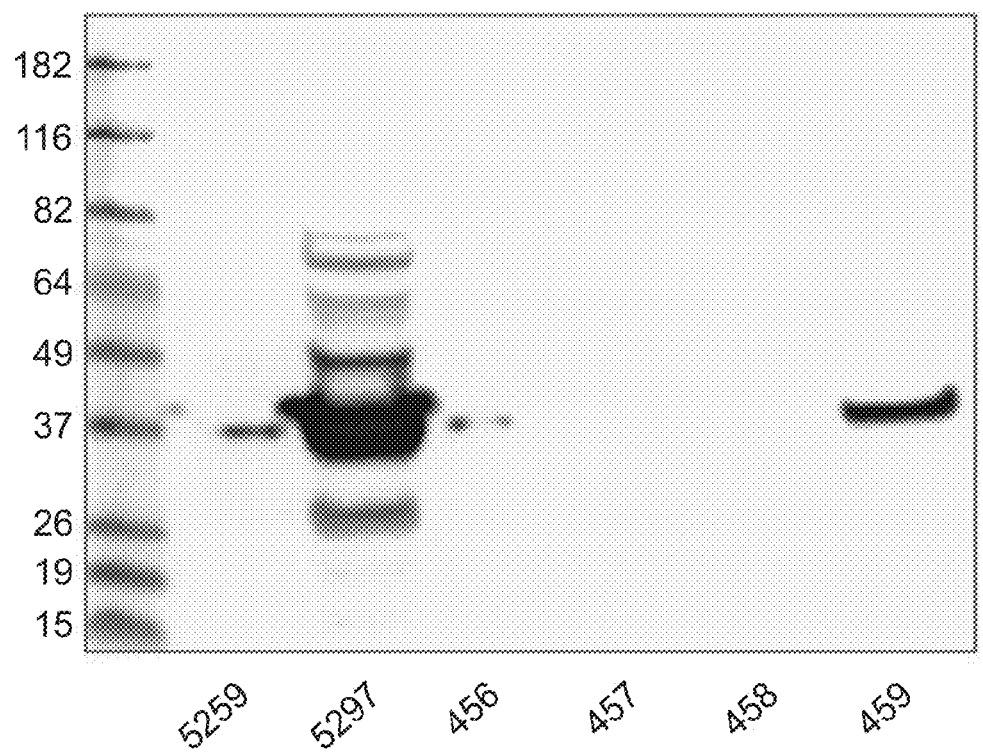
FIGS. 8A, 8B. Images of Western blots showing expression of human PSA in HEK293 cells transfected with either single promoter triple antigen constructs (FIG. 8A) or dual promoter triple antigen vaccine constructs (FIG. 8B) as measured by western blotting with a PSA specific monoclonal antibody. The bands in lanes 5259 and 456 are spillover from lane 5297. Although not visible in the scanned gel, lanes 456, 457, and 458 exhibited a band about 2 kD larger than PSA.
Figure 8B:
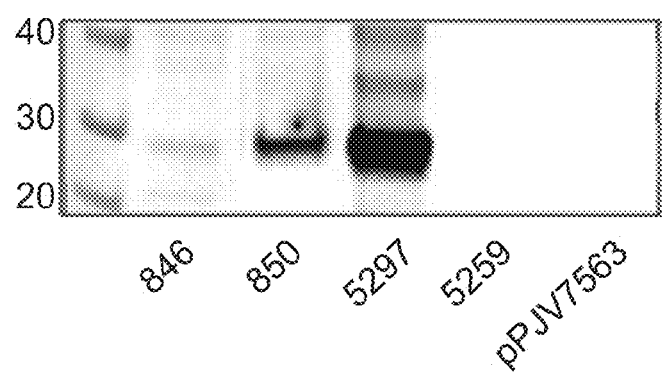
Figure 9A:
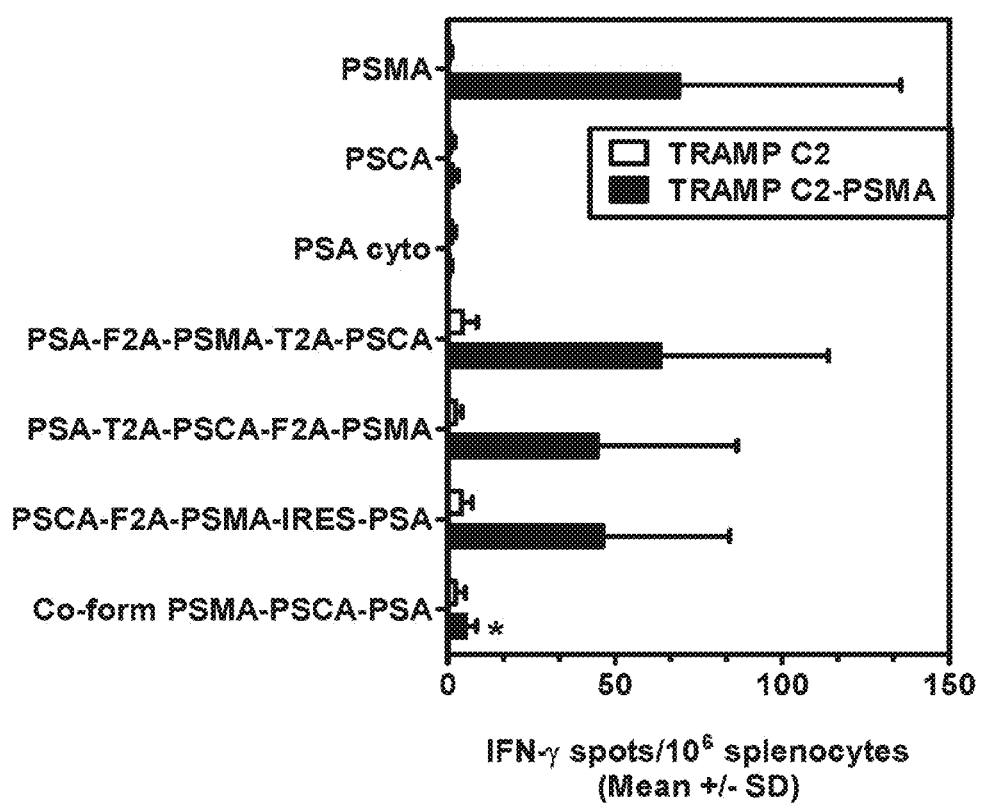
FIGS. 9A-9D. Graphs depicting results of a representative study that evaluates the immunogenicity of the triple antigen vaccines by IFN-γ ELISPOT assay, in which recognition of endogenous prostate antigens was assessed by examining T cell responses to (a) TRAMP C2 cells expressing PSMA (FIG. 9A), (b) TRAMP C2 cells expressing PSCA (FIG. 9B), (c) TRAMP C2 cells expressing PSA (FIG. 9C), and (d) TRAMP C2 cells expressing PSMA, PSA, and PSCA (FIG. 9D).
Figure 9B:
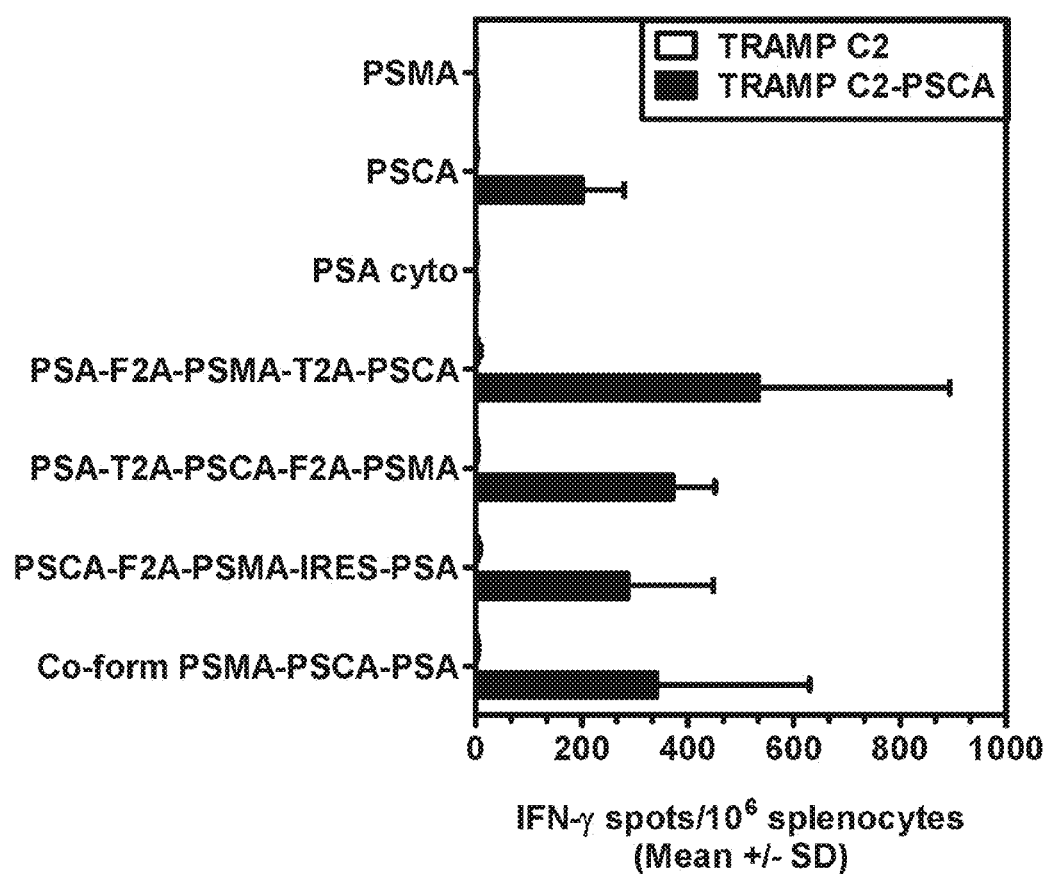
Figure 9C:
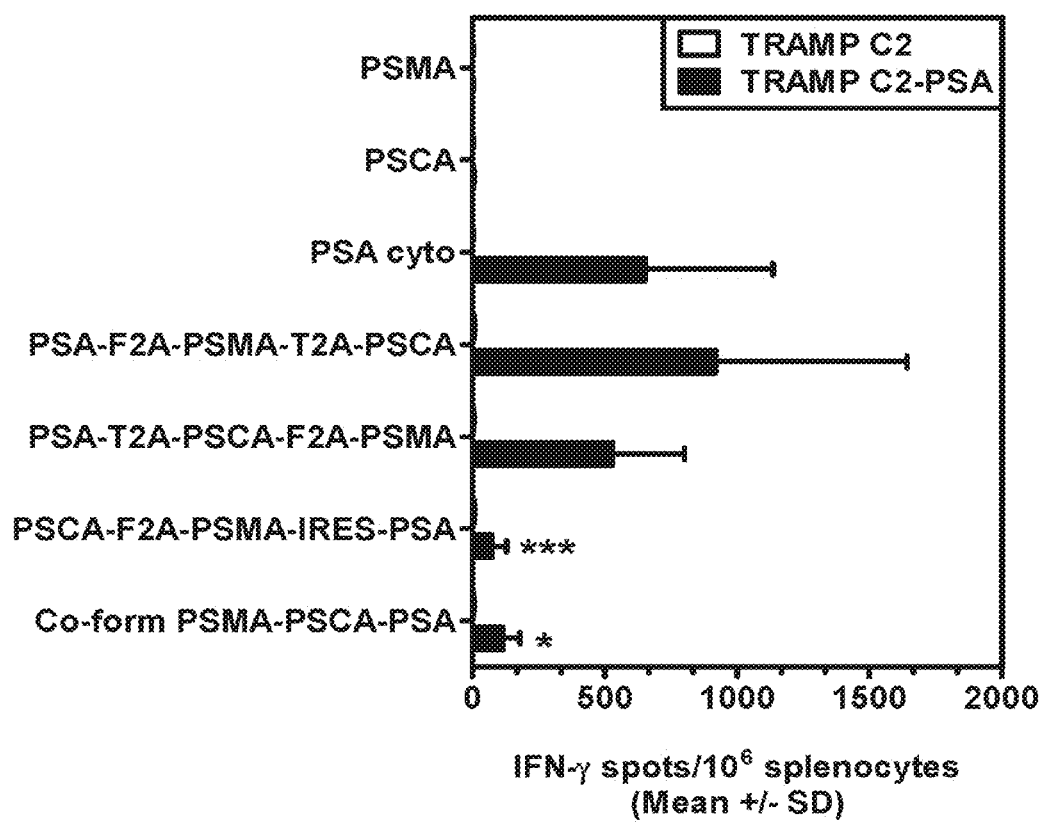
Figure 9D:
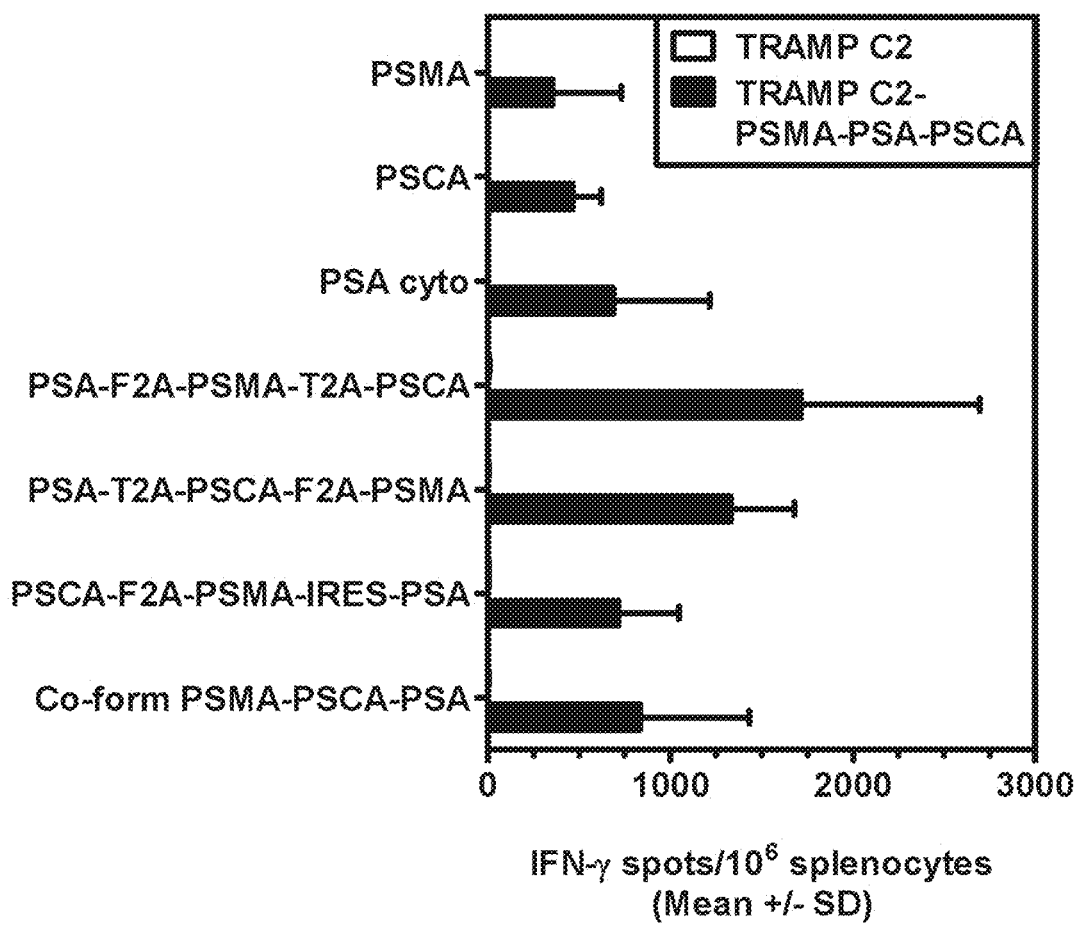
Figure 10A:
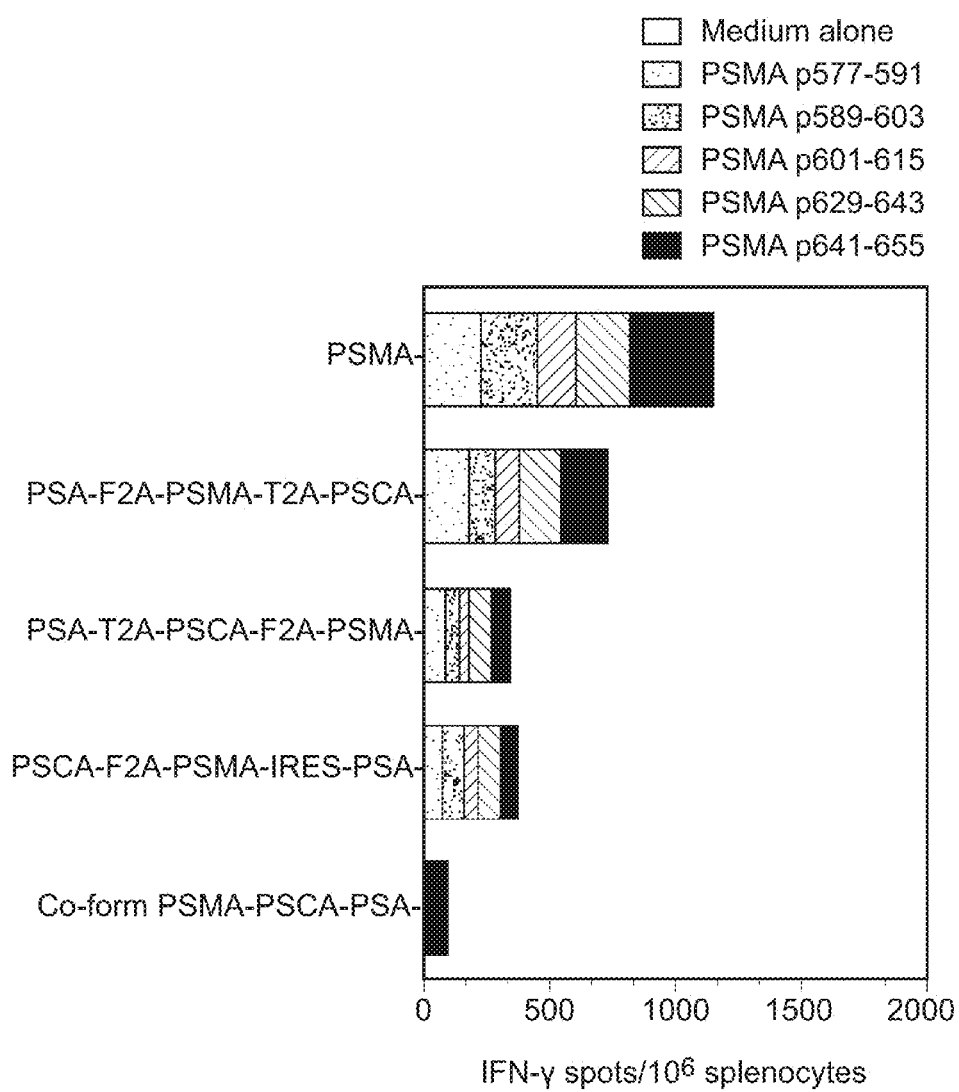
FIGS. 10A-10D. Graphs depicting results of a representative study that evaluates the immunogenicity of the triple antigen vaccines by IFN-γ ELISPOT assay, in which T cell responses to (a) individual PSMA peptides (FIG. 10A), (b) three PSMA peptide pools (FIG. 10B), (c) a PSCA peptide (FIG. 10C), and (d) PSA peptides (FIG. 10D) were assessed.
Figure 10B:
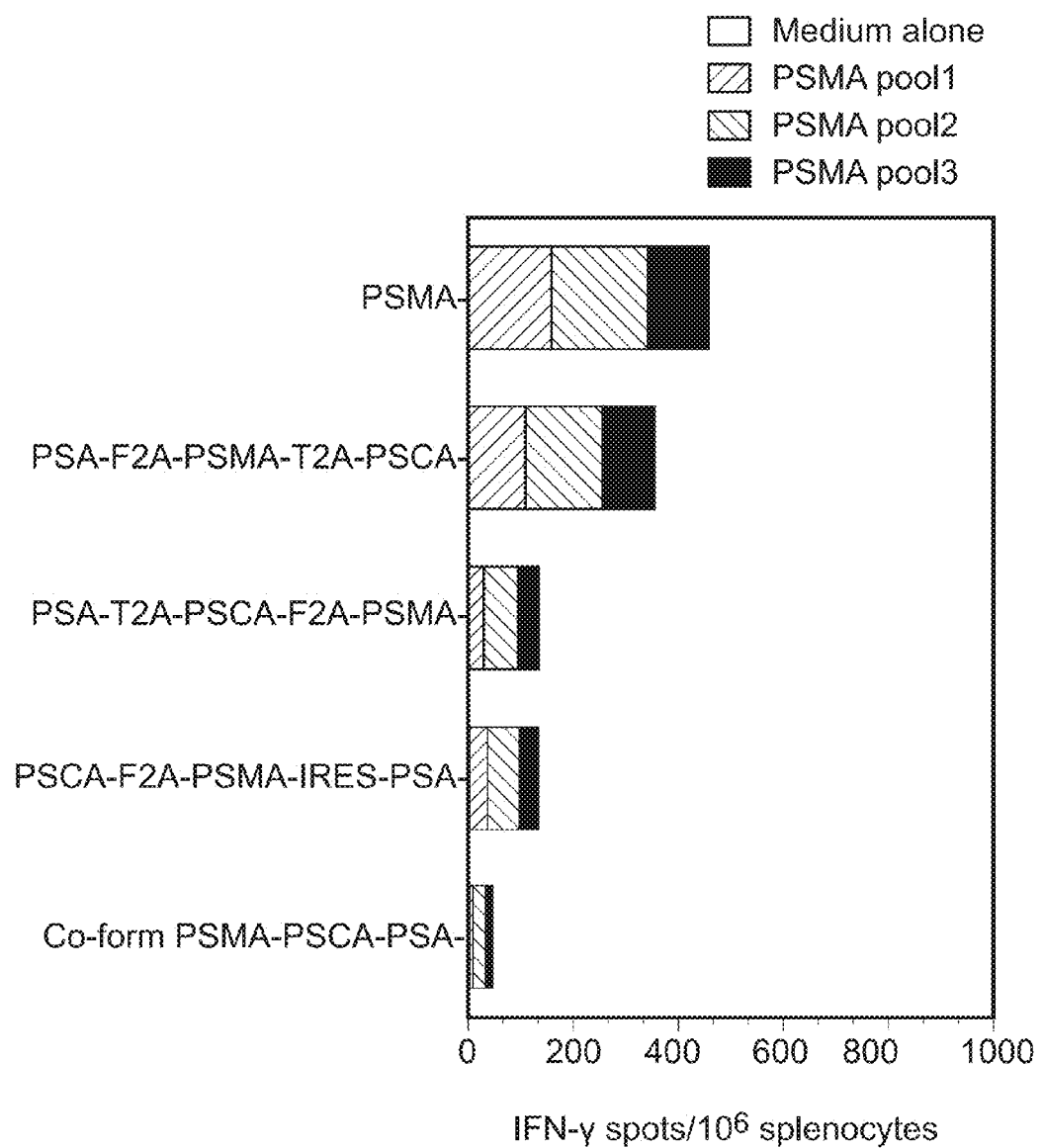
Figure 10C:
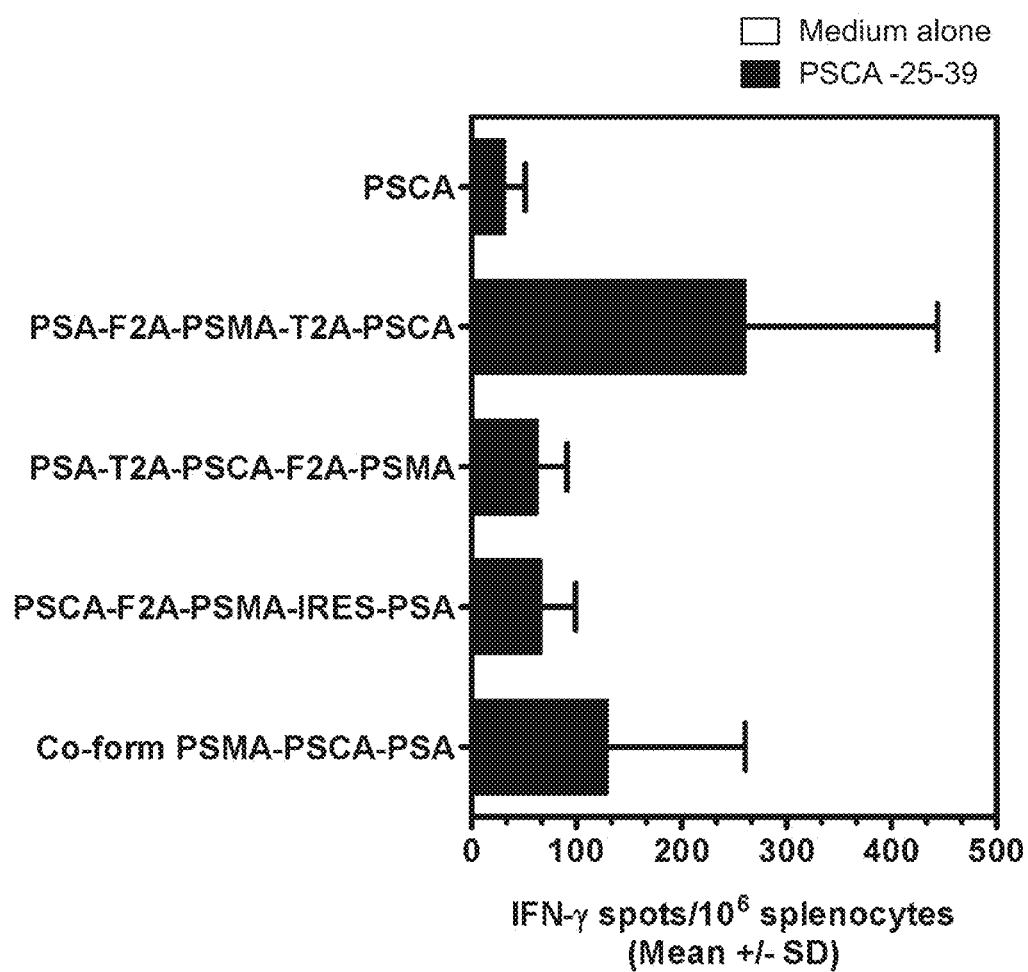
Figure 10D:
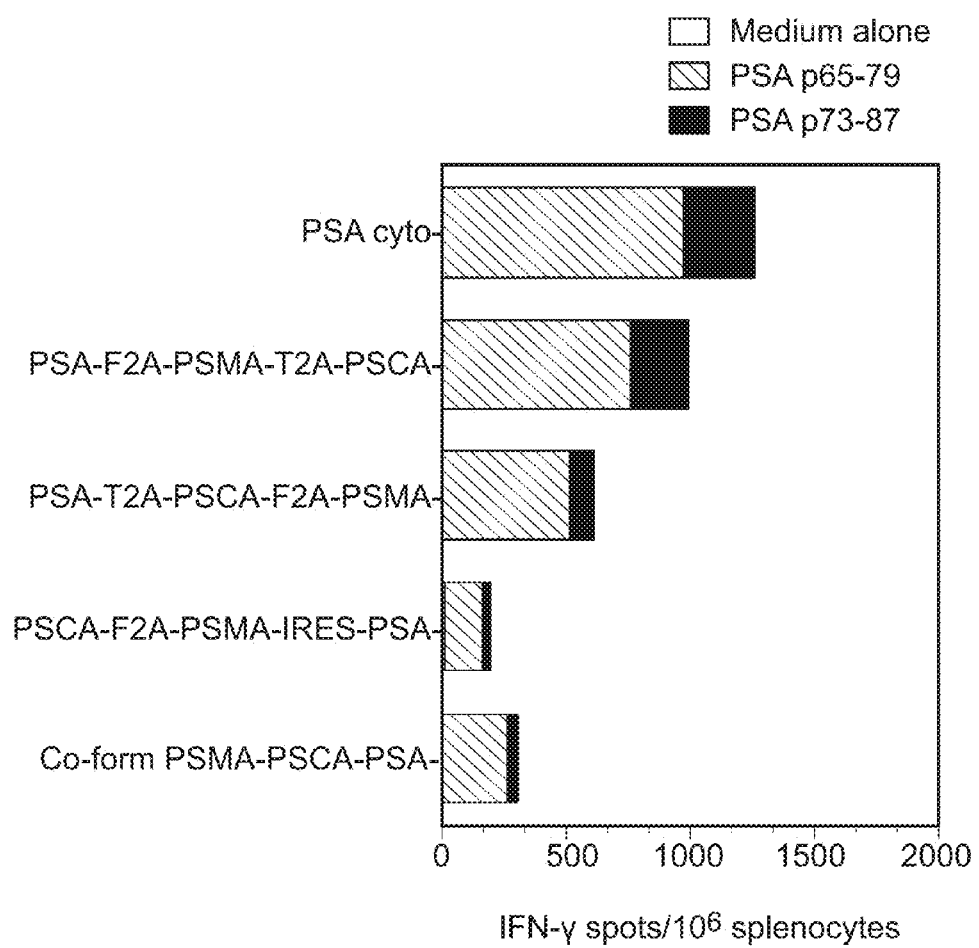

The abilities of the dual antigen expression vectors to direct the expression of PSMA, PSCA, and/or PSA were characterized in transfected HEK293 cells (FIGS. 4, 5A, 5B, and 6). A number of dual antigen expression cassettes, including PSA-F2A-PSMA, PSMA-mIRES-PSCA, PSMA-T2A-PSCA, PSA-T2A-PSCA, PSCA-F2A-PSMA, PSCA-pIRES-PSMA, and PSMA-mIRES-PSA, were selected for incorporation in various combinations into triple antigen expression vectors. In all cases, the vectors were based on the parental pPJV7563 plasmid backbone. Four vectors (plasmids 456, 457, 458, and 459) utilized a single full CMV promoter with a rabbit B globulin transcription terminator to drive expression of all three antigens. Two other vectors (plasmids 846 and 850) incorporated a dual promoter strategy in combination with either an IRES or 2A to drive expression of the three antigens. Vectors with multiple 2A cassettes were engineered to carry different cassettes to minimize the likelihood of recombination between the first and second cassette during plasmid/vector amplification. Antigen expression was demonstrated by flow cytometry (FIGS. 7A and 7B) and western blotting (FIGS. 8A and 8B).

Plasmid 456 (PSA-F2A-PSMA-mIRES-PSCA).

Plasmid 456 was constructed by restriction fragment exchange. Plasmid 5300 was digested with Nhe I and Hpa I and the ~1.8 kb insert was ligated into similarly digested plasmid 449.

Plasmid 457 (PSA-F2A-PSMA-T2A-PSCA).

Plasmid 457 was constructed by restriction fragment exchange. Plasmid 5300 was digested with Nhe I and Hpa I and the ~1.8 kb insert was ligated into similarly digested plasmid 451.

Plasmid 458 (PSA-T2A-PSCA-F2A-PSMA).

Plasmid 458 was constructed using the techniques of PCR and restriction fragment exchange. The gene encoding human PSA amino acids 25-261 was amplified by PCR from plasmid 5297 with primers 119 and 139, resulting in the addition of a T2A sequence and Nhe I restriction site at the 3' end. The amplicon was digested with Nhe I and inserted into similarly digested plasmid 454.

Plasmid 459 (PSCA-F2A-PSMA-mIRES-PSA).

Plasmid 459 was constructed by restriction fragment exchange. Plasmid 454 was digested with Nhe I and Bgl II and the PSCA-F2A-PSMA containing insert was ligated into similarly digested plasmid 455.

Plasmid 846 (CBA-PSA, CMV-PSCA-pIRES-PSMA).

Plasmid 846 was constructed using the techniques of PCR and seamless cloning. First, an expression cassette was synthesized that consisted of 1) the promoter and 5' untranslated region from the chicken beta actin (CBA) gene, 2) a hybrid chicken beta actin/rabbit beta globin intron, 3) the gene encoding human PSA amino acids 25-261, and 4) the bovine growth hormone terminator. This PSA expression cassette was amplified by PCR from plasmid 796 with primers 3SalICBA and 5SalIBGH. The amplicon was cloned into the SalI site of plasmid 603 using a GeneArt Seamless Cloning and Assembly Kit (Invitrogen, Carlsbad, Calif.). Upon delivery of this plasmid into a cell, PSA expression will be driven off the CBA promoter while PSCA and PSMA expression will be driven off the CMV promoter.

Plasmid 850 (CBA-PSA, CMV-PSCA-F2A-PSMA).

Plasmid 850 was constructed using the techniques of PCR and seamless cloning. First, the CBA promoter-driven PSA expression cassette was amplified by PCR from plasmid 796 with primers 3SalICBA and 5SalIBGH. The amplicon was cloned into the SalI site of plasmid 454 using GeneArt Seamless Cloning. Upon delivery of this plasmid into a cell, PSA expression will be driven off the CBA promoter while PSCA and PSMA expression will be driven off the CMV promoter.

TABLE 20

List of Plasmids Expressing Multiple-Antigens

| 1st Antigen | Expression strategy | 2nd Antigen | Expression strategy | 3rd Antigen | Plasmid ID # |
|---|---|---|---|---|---|
| PSMA | | | | | 5166 |
| PSCA | | | | | 5259 |
| PSA | | | | | 5297 |

TABLE 20-continued

List of Plasmids Expressing Multiple-Antigens

| 1st Antigen | Expression strategy | 2nd Antigen | Expression strategy | 3rd Antigen | Plasmid ID # |
|---|---|---|---|---|---|
| PSMA | 2 promoters | PSCA | | | 460 |
| PSMA | T2A | PSCA | | | 451 |
| PSCA | F2A | PSMA | | | 454 |
| PSA | F2A | PSMA | | | 5300 |
| PSMA | IRES | PSCA | | | 449 |
| PSCA | IRES | PSMA | | | 603 |
| PSCA | IRES | PSA | | | 455 |
| PSA | F2A | PSMA | mIRES | PSCA | 456 |
| PSA | F2A | PSMA | T2A | PSCA | 457 |
| PSA | T2A | PSCA | F2A | PSMA | 458 |
| PSCA | F2A | PSMA | mIRES | PSA | 459 |
| PSA | 2 promoters | PSCA | pIRES | PSMA | 796 |
| PSA | 2 promoters | PSCA | pIRES | PSMA | 846 |
| PSA | 2 promoters | PSCA | F2A | PSMA | 850 |

TABLE 21

List of Primers Used in the Construction of the Multi-antigen Plasmids

| Primer | Sequence (5' to 3') | Strand |
|---|---|---|
| 42 | CGTTGACGCAAATGGGCGGTAGG | Sense |
| 101 | TCAGAGATCTGACCCCCTAACGTTACTGGC | Sense |
| 114 | TATAGGATCCTCAGGGGTTGGCCACGATG | Antisense |
| 115 | GAAAAACACGATGATAATATGGCCAGCATTGTGGGAGGCTGGGAGTG | Sense |
| 116 | CCACAATGCTGGCCATATTATCATCGTGTTTTTCAAAGGAAAACCACGTCC | Antisense |
| 117 | CATCTCCACAGGTCAATAATGAACCCCTACCTTCGGATCCGGCTACTTCACTCAAAGTC | Antisense |
| 118 | GTTCATTATTGACCTGTGGAGATGTCGAAGAAAACCCAGGACCCGCAAGCAAGGCTGTGCTGCTTGCCCTG | Sense |
| 119 | TTGCCTCTCACATCTCGTCAATCTCCGCGAGGAC | Sense |
| 120 | GATCTTTTGTACAATATGATCTTGTGGCAATGTCCC | Antisense |
| 123 | TATAGGATCCCTATAGCTGGCCGGGTCC | Antisense |
| 124 | CACGATGATAATATGGCCAGCAAGGCTGTGCTGCTTGCC | Sense |
| 125 | CACAGCCTTGCTGGCCATATTATCATCGTGTTTTTCAAAGGAAAACCACGTCC | Antisense |
| 132 | TATAGGATCCTAGCTGGCCGGGTCCCCAGAG | Antisense |
| 139 | ATATGCTAGCGGGTCCTGGGTTTTCTTCGACATCTCCACAGGTCAATAATGAACCCCTACCTTCGGATCCGGGGTTGGCCACGATGGTGTCC | Antisense |
| SD546 | CTGTGACGAACATGGCTAGCAAGG | Sense |
| SD547 | ATTATCATCGTGTTTTTCAAAGGAAAACC | Antisense |
| SD548 | AAACACGATGATAATATGGCCACAACCATGGCGCGCCGCCCGC | Sense |
| SD550 | TTTTGTTAGGGCCCAGATCTTTAGGC | Antisense |
| MD1 | GACGAACATGGCTAGCATTGTGGGAGGCTG | Sense |
| MD2 | CCACATCGCCTGCCAGTTTCAGCAGATCAAAGTTCAGGGTCTGGGATCCGGGGTTGGCCACGATGGTGTC | Antisense |

TABLE 21-continued

List of Primers Used in the Construction of the Multi-antigen Plasmids

| Primer | Sequence (5' to 3') | Strand |
|---|---|---|
| MD3 | GATCTGCTGAAACTGGCAGGCGATGTGGAAAGCAACCCAGGCCCAATGGCAAGCGCGCGCCGCCCGCGCTG | Sense |
| MD4 | GTTAGGGCCCAGATCTTTAGGCTACTTCACTCAAAGTC | Antisense |
| MD5 | CTTGTATTACTGTTTATGTAAGCAGACAGGGTACCAATATTGGCTATTGGCCATTGCATAC | Sense |
| MD6 | GTATGCAATGGCCAATAGCCAATATTGGTACCCTGTCTGCTTACATAAACAGTAATACAAG | Antisense |
| MD7 | CATGCATGGGTACCAATCTTCCGAGTGAGAGACACAAAAAATTCC | Sense |
| MD8 | GATCGATCGGTACCCTGCAGGTCGAGCACCAAAATCAACGGG | Antisense |
| 5SalIBGH | GTTTATGTAAGCAGACAGGTCGACCCATAGAGCCCACCGCATCCCCAGC | Antisense |
| 3SalICBA | TGGCCAATAGCCAATATTGTCGACTGGGTCGAGGTGAGCCCCACGTTCTG | Sense |

Example 4C

Triple Antigen Adenovirus Constructs

General Strategy.

As with DNA plasmids, viral vaccine vectors can be engineered to deliver multiple prostate cancer antigens. The three multi-antigen expression strategies described above for DNA vaccines—dual promoters, 2A peptides, and internal ribosome entry sites—were incorporated in various combinations to create triple antigen adenovirus vectors. Briefly, the multi-antigen expression cassettes were cloned into a pShuttle-CMV plasmid modified to carry two copies of the tetracycline operator sequence (TetO2). Recombinant adenovirus serotype 5 vectors were created using the AdEasy Vector System according to manufacturer's protocols (Agilent Technologies, Inc., Santa Clara, Calif.). Viruses were amplified in HEK293 cells and purified by double cesium chloride banding according to standard protocols. Prior to in vivo studies, viral stocks were thoroughly characterized for viral particle concentration, infectivity titer, sterility, endotoxin, genomic and transgene integrity, transgene identity and expression.

Adenovirus-733 (PSA-F2A-PSMA-T2A-PSCA).

Ad-733 is the viral equivalent of plasmid 457. Expression of the three antigens is driven off a single CMV promoter with a tetracycline operator for repressing transgene expression during large scale production in Tet repressor expressing HEK293 lines. Multi-antigen expression strategies include two different 2A sequences.

Adenovirus-734 (PSA-T2A-PSCA-F2A-PSMA).

Ad-734 is the viral equivalent of plasmid 458. Expression of the three antigens is driven off a single CMV promoter with a tetracycline operator for repressing transgene expression during large scale production in Tet repressor expressing HEK293 lines. Multi-antigen expression strategies include two different 2A sequences.

Adenovirus-735 (PSCA-F2A-PSMA-mIRES-PSA).

Ad-735 is the viral equivalent of plasmid 459. Expression of the three antigens is driven off a single CMV promoter with a tetracycline operator for repressing transgene expression during large scale production in Tet repressor expressing HEK293 lines. Multi-antigen expression strategies include a 2A sequence and an IRES.

Adenovirus-796 (CBA-PSA, CMV-PSCA-pIRES-PSMA).

Ad-796 is the viral equivalent of plasmid 846. Expression of PSA is driven off the chicken beta actin promoter while PSCA and PSMA expression is driven off the CMV-TetO2 promoter. Multi-antigen expression strategies include two promoters and an IRES.

Adenovirus-809 (CBA-PSA, CMV-PSCA-F2A-PSMA).

Ad-809 is the viral equivalent of plasmid 850. Expression of PSA is driven off the chicken beta actin promoter while PSCA and PSMA expression is driven off the CMV-TetO2 promoter. Multi-antigen expression strategies include two promoters and a 2A sequence.

Example 5

Immunogenicity of Triple Antigen DNA Vaccines

Example 5 illustrates the capability of triple antigen nucleic acid vaccine constructs expressing PSMA, PSCA and PSA to elicit antigen-specific T and B cell responses to all three encoded prostate antigens.

Cellular Immune Response Study.

Immunogenicity of triple antigen constructs containing PSMA, PSCA and PSA, as described in Example 5, was studied in C57BL/6 mice according to the procedure described below.

Female C57BL/6 mice were primed on day 0 and boosted on days 14, 28 and 49 with DNA vaccine constructs encoding human-PSMA, PSCA and PSA antigens by PMED administration. In total, four different triple antigen vaccination strategies were evaluated, which included three DNA vaccines that co-expressed the target proteins and one co-formulation approach. For co-expression, single DNA plasmids encoding all three prostate antigens linked by 2A peptides or internal ribosome entry sites (IRES) were used as follows: PSA-F2A-PSMA-T2A-PSCA (plasmid ID#457), PSA-T2A-PSCA-F2A-PSMA (plasmid ID#458) and PSCA-F2A-PSMA-IRES-PSA (plasmid ID#459). For the co-formulation approach, three different DNA plasmids, each individually encoding PSMA, PSCA or PSA, were co-formulated onto a single gold particle for PMED delivery. With the exception of co-formulation, the DNA elements that control co-expression (2A and IRES) differ in length, transgene expression efficiency and the presence of foreign genetic material attached to the target transgenes. As controls, C57BL/6 mice were vaccinated with DNA expressing a single prostate antigen, either PSMA, PSCA or PSA. For the co-expressed triple or single antigen DNA vaccines, a dose 2 μg of DNA vaccine plasmid was given per PMED administration, whereas 1 μg of each of the co-formulated triple antigen DNA vaccines (a total of 3 μg) was administered per PMED administration. Cellular immune responses against the triple and single antigen vaccines were measured by collecting the spleens from each animal on day 56, seven days after the final PMED vaccination. Splenocytes were isolated and subjected to an IFN-γ ELISPOT assay to measure the PSMA, PSCA and PSA-specific T cell responses. Briefly, $2\times10^5$ splenocytes from individual animals were plated per well with $5\times10^4$ per well of TRAMP-C2 (transgenic adenocarcinoma mouse prostate) cells stably expressing a single human prostate antigen or PSMA, PSCA and PSA together, or with individual or pools of human PSMA, PSCA and PSA-specific peptides at 10 μg/ml (see Table 22 for peptides and peptide pool composition), or medium alone as a control. Each condition was performed in triplicate. The plates were incubated for 20 h at 37° C. and 5% $CO_2$, washed and developed after incubation as per the manufacturer's instructions. The number of IFN-γ spot forming cells (SFC) was counted by a Cellular Technology Ltd. (CTL) reader. The results are presented in FIGS. 9 and 10, which show the average number of PSMA, PSCA or PSA-specific SFCs+/−the standard deviation of five mice per group, normalized to $1\times10^6$ splenocytes.

TABLE 22

The 15mer PSMA, PSCA and PSA peptides that were tested in the ELISPOT assay. The amino acid position of the N and C-terminal end of each peptide is indicated.

| Prostate antigen | Peptides | Tested individually or pool |
|---|---|---|
| PSMA | 577-591 | Individual |
| PSMA | 589-603 | Individual |
| PSMA | 601-615 | Individual |
| PSMA | 629-643 | Individual |
| PSMA | 641-655 | Individual |
| PSMA | 77-91 | Pool 1 |
|  | 91-111 |  |
|  | 153-167 |  |
|  | 229-243 |  |
|  | 365-379 |  |
| PSMA | 401-415 | Pool 2 |
|  | 429-443 |  |
|  | 521-535 |  |
|  | 613-627 |  |
| PSMA | 657-671 | Pool 3 |
|  | 685-699 |  |
|  | 701-715 |  |
|  | 733-747 |  |
| PSCA | 25-39 | Individual |
| PSA | 65-79 | Individual |
| PSA | 73-87 | Individual |

Antibody Response Study.

Antibody responses against the triple and single antigen vaccines were measured by collecting the serum from each animal on day 56, seven days after the final PMED vaccination. Serum was subjected to enzyme-linked immunosorbent assays (ELISA) to determine the anti-PSMA and anti-PSCA antibody titers. In brief, ELISA plates were coated with 1 μg/ml of human PSMA or PSCA and incubated overnight at 4° C. Plates were then blocked and incubated at RT for 1 h with 1% bovine serum albumin (BSA). Each serum sample was serially diluted in duplicate starting at a 1:100 dilution and incubated for 1 h at RT. After washing, a horseradish-peroxidise (HRP)-conjugated goat anti-mouse polyclonal IgG antibody was incubated at RT for 1 h. After washing, the TMB Peroxidase EIA-Substrate was incubated at RT for 30 min. The colorimetric reaction was stopped by addition 1N sulfuric acid and the absorbance then read at 450 nm. Titration curves were plotted for each serum sample (sample dilution versus absorbance). The serum titer (subsequently transformed into reciprocal titer) was then taken as the most dilute serum sample tested with an optical density (OD) value of above the lower limit of detection (LLOD; background plus 3 standard deviations) or the serum dilution calculated to achieve an OD value of 1.0. The results are presented in FIGS. 11 and 12, which show the average titers+/−the standard deviation of five mice per group.

Serum was also subjected to a fluorescence-activated cell sorting (FACS) assay to measure antibody binding to either human PSMA or PSCA expressed on the cell surface of appropriate cell lines, thus determining whether antibodies generated by the multi-antigen vaccines were capable of recognizing native PSMA and PSCA conformations, respectively. LNCaP (human prostate adenocarcinoma) cells were utilized to measure antibody binding to native PSMA. PC3 (human prostate cancer) cells served as a control in the FACS assay, as these cells do not express human PSMA. MIA-PaCa-2 (human pancreatic carcinoma) cells transduced with an adenovirus expressing human PSCA (Ad-PSCA) were utilized to measure antibody binding to native PSCA. Untransduced MIA-PaCa-2 cells served as the control. In brief, to measure anti-PSMA antibody binding, $2\times10^5$ LNCaP or PC3 cells were incubated with a 1:100 dilution of mouse serum or 15 μg/ml of the control mouse-anti-human PSMA monoclonal antibody (mAb) (clone J591-A) for 20 min at 4° C. To measure anti-PSCA antibody binding, $2\times10^5$ Ad-PSCA transduced and untransduced MIA-PaCa-2 cells were incubated with a 1:30 dilution of mouse serum or 4 μg/ml of the control mouse anti-human PSCA mAb (clone 7F5) for 20 min at 4° C. Subsequently, cells were washed and incubated with a secondary Phycoerythrin (PE)-conjugated goat-anti-mouse IgG antibody and a live/dead dye for an additional 20 min at 4° C. After the incubation, cells were washed and resuspended in 1.5% paraformaldehyde, and 10,000 live cells were acquired on a FACS Canto II. The results are presented in FIGS. 13 and 14, which show the average fold change in mean fluorescence intensity (MFI) of the mouse serum over the secondary anti-mouse antibody alone+/−the standard deviation of five mice per group. Antibody titers were not measured because PSA was expressed as a cytoplasmic protein by the multi-antigen vaccines investigated in this study.

Results:

FIGS. 9A-9D show the results of a representative study that evaluates the cellular immune responses of the triple antigen vaccines by IFN-γ ELISPOT assay. Briefly, 5 mice per group were primed on day 0 and boosted with PMED on days 14, 28 and 49. On day 56, seven days after the last PMED vaccination, recognition of the endogenous prostate antigens was assessed by examining T cell responses to (A) TRAMP C2-PSMA, (B) TRAMP C2-PSCA, (C) TRAMP C2-PSA, and (D) TRAMP C2-PSMA-PSA-PSCA cells by IFN-γ ELISPOT assay. The TRAMP C2 cells served as a background control for the assay. For IFN-γ T cell responses to endogenous PSMA, a significant response to TRAMP C2-PSMA was observed following the single PSMA PMED vaccination, which was consistent with responses seen in other studies. Similar PSMA-specific IFN-γ T cell response to TRAMP C2-PSMA was detected following the triple antigen vaccinations. In contrast, complete ablation of the response was observed following co-formulated PSMA, PSCA and PSA vaccination (* indicates p<0.05 by two-way ANOVA). For IFN-γ T cell responses to endogenous PSCA, no significant difference in response to the TRAMP C2-PSCA cells was observed when comparing the single PSCA vaccine to the four different triple antigen vaccines. For IFN-γ T cell responses to endogenous PSA, a significant decrease in the response magnitude to TRAMP C2-PSA was detected when comparing the immunogenicity of the single PSA vaccine to either PSCA-F2A-PSMA-IRES-PSA (*** indicates p<0.001 by two-way ANOVA) or the co-formulated vaccine (* indicates p<0.05 by two-way ANOVA). When examining the response to TRAMP C2-PSMA-PSCA-PSA, the highest magnitude IFN-γ T cell response was observed following the PSA-F2A-PSMA-T2A-PSCA vaccine. Taken together, these data demonstrate recognition of endogenous PSMA, PSCA and PSA and generation of antigen-specific T cell responses to all three prostate antigens using a co-expression DNA vaccination strategy, especially with the PSA-F2A-PSMA-T2A-PSCA vaccine construct. However, the co-formulation DNA vaccination strategy resulted in a loss of antigen-specific IFN-γ T cell responses to PSMA and PSA.

FIGS. 10A-10D show the results of a representative study that evaluates the immunogenicity of the triple antigen vaccines by IFN-γ ELISPOT assay. Briefly, 5 mice per group were primed on day 0 and boosted with PMED on days 14, 28 and 49. On day 56, T cell responses to (A) PSMA peptides, (B) PSMA peptide pools, (C) PSCA peptides and (D) PSA peptides (see Table 22) were assessed by IFN-γ ELISPOT assay. Medium alone served as a background control for the assay. For IFN-γ T cell responses to both the individual and pools of PSMA peptides, compared to the single PSMA vaccine, the highest magnitude response was observed following administration of the PSA-F2A-PSMA-T2A-PSCA triple antigen vaccine. Similarly, the highest magnitude IFN-γ T cell response to PSCA and PSA-specific peptides was detected following administration of the PSA-F2A-PSMA-T2A-PSCA vaccine. The co-formulated PSMA, PSCA and PSA vaccine resulted in low to no T cell responses to the PSMA-specific peptides and low magnitude responses to the PSCA and PSA-specific peptides. These data also demonstrate generation of T cell responses to PSMA, PSCA and PSA when co-expressed from the same vaccine construct. There was consistent and robust IFN-γ T cell responses to all three prostate antigens following PSA-F2A-PSMA-T2A-PSCA vaccination, and significant decreases in the magnitude of IFN-γ T cell responses to the prostate antigens following PSA-T2A-PSCA-F2A-PSMA, PSMA-F2A-PSMA-IRES-PSA and co-formulated PSMA, PSCA and PSA vaccinations.

Figure 11:
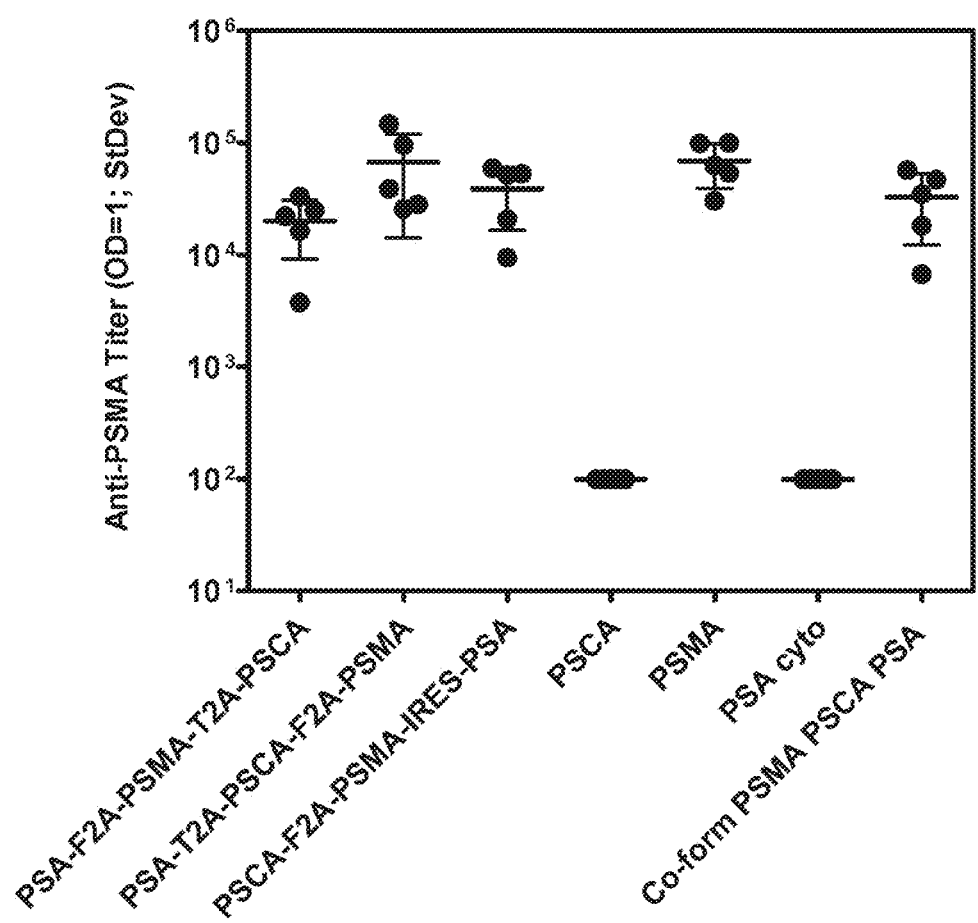
FIG. 11. Graph depicting results of a representative study that evaluates the immunogenicity of the triple antigen vaccines by anti-PSMA antibody titers.

FIG. 11 shows the results of a representative study that evaluates the immunogenicity of the triple antigen vaccines by anti-PSMA antibody titers. Briefly, 5 mice per group were primed on day 0 and boosted with PMED on days 14, 28 and 49. On day 56, serum anti-PSMA antibody titers were assessed by ELISA. All animals vaccinated with PSMA generated significant anti-PSMA antibody titers. There were no significant differences between titers, although vaccination with PSA-F2A-PSMA-T2A-PSCA resulted in slightly lower titers compared to the other groups vaccinated with PSMA. These data demonstrate the generation of anti-PSMA-specific antibodies following triple antigen vaccination, using both co-expression and co-formulation vaccine strategies.

Figure 12:
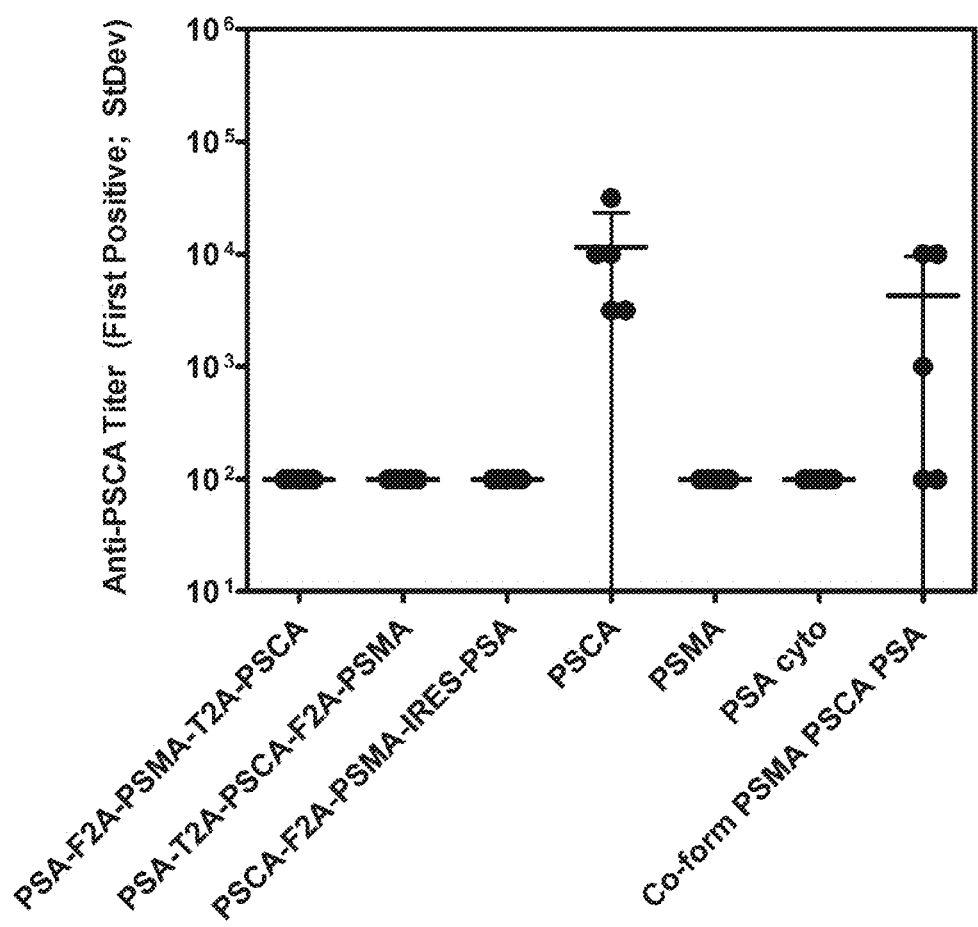
FIG. 12. Graph depicting results of a representative study that evaluates the immunogenicity of the triple antigen vaccines by anti-PSCA antibody titers.

FIG. 12 shows the results of a representative study that evaluates the immunogenicity of the triple antigen vaccines by anti-PSCA antibody titers. Briefly, 5 mice per group were primed on day 0 and boosted with PMED on days 14, 28 and 49. On day 56, serum anti-PSCA antibody titers were assessed by ELISA. Antibody titers were detected in mice vaccinated with PSCA alone and co-formulated PSMA, PSCA and PSA. These results indicate that co-formulation of PSMA, PSCA and PSA elicits a detectable anti-PSCA antibody titer compared to the co-expressed DNA vaccination strategies.

Figure 13:
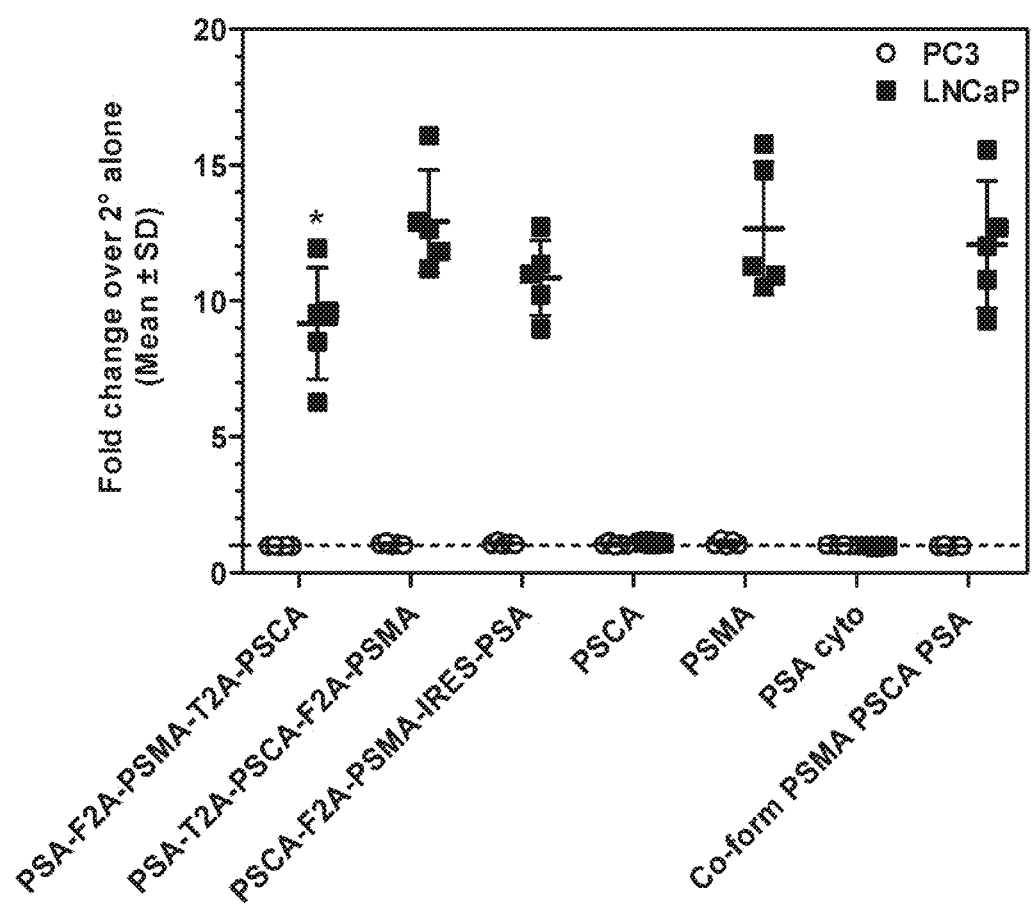
FIG. 13. Graph depicting results of a representative study that evaluates the immunogenicity of the triple antigen vaccines by anti-PSMA antibody cell-surface binding.

FIG. 13 shows the results of a representative study that evaluates the immunogenicity of the triple antigen vaccines by anti-PSMA antibody cell-surface binding. Briefly, 5 mice per group were primed on day 0 and boosted with PMED on days 14, 28 and 49. On day 56, recognition of cell-surface native PSMA was assessed by serum antibody binding to LNCaP and PC3 cells. The PC3 cells served as a background control for the assay. PSA-F2A-PSMA-T2A-PSCA vaccination resulted in anti-PSMA antibodies with a significantly lower binding capacity to LNCaP cells compared to mice vaccinated with PSA-T2A-PSCA-F2A-PSMA and PSMA alone (* indicates p-value <0.05 by one-way ANOVA). All other PSMA vaccinated groups showed no significant difference in anti-PSMA antibody binding. The fold-change over secondary antibody alone for the J591-A mAb was 45.3 (data not shown). Overall, these data demonstrate generation of anti-PSMA-specific antibodies that recognize native PSMA following triple antigen vaccination, using both co-expression and co-formulation DNA vaccination strategies.

Figure 14:
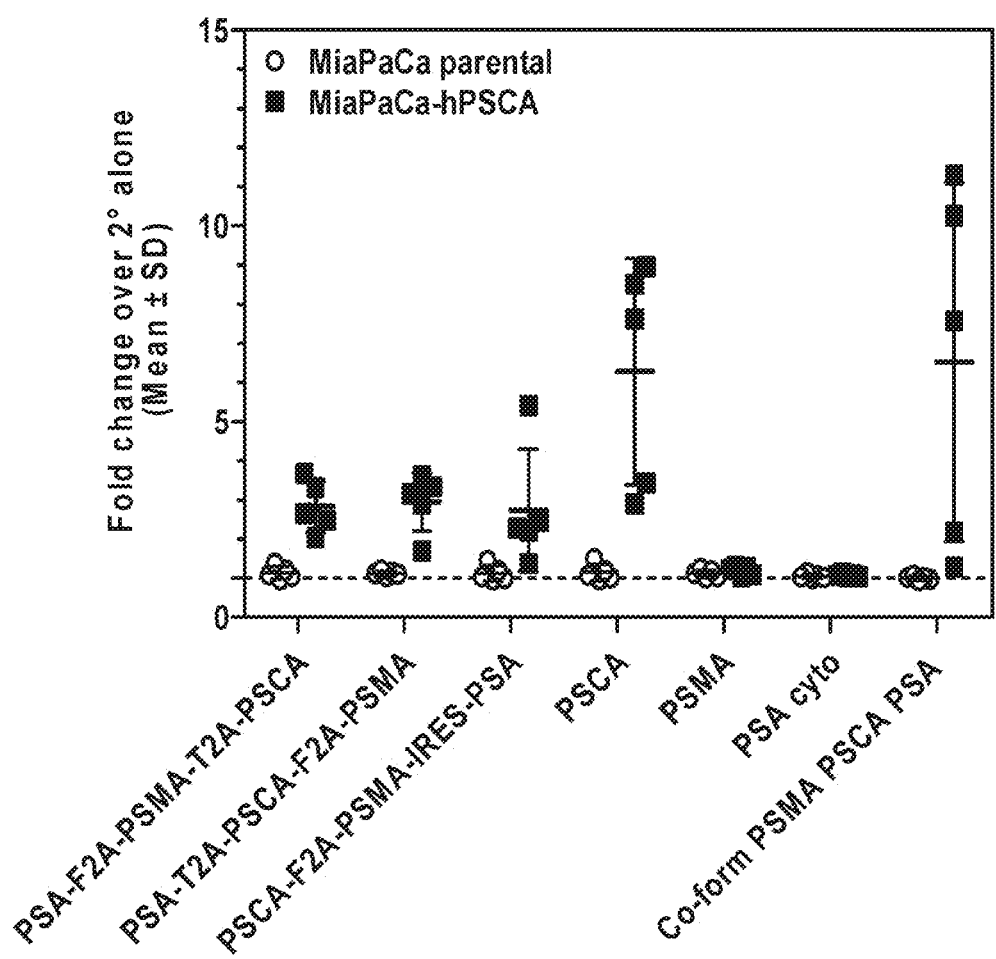
FIG. 14. Graph depicting results of a representative study that evaluates the immunogenicity of the triple antigen vaccines by anti-PSCA antibody cell-surface binding.

FIG. 14 shows the results of a representative study that evaluates the immunogenicity of the triple antigen vaccines by anti-PSCA antibody cell-surface binding. Briefly, 5 mice per group were primed on day 0 and boosted with PMED on days 14, 28 and 49. On day 56, recognition of cell-surface native PSCA was assessed by serum antibody binding to Ad-PSCA transduced and untransduced MIA-PaCa-2 cells. The untransduced, parental cells served as a background control for the assay. With the exception of the single PSMA and single PSA cyto vaccines, all vaccine regimens with PSCA resulted in significant anti-PSCA antibody binding to Ad-PSCA transduced MIA-PaCa-2 cells compared to the parental cells. There were no significant differences in the anti-PSCA antibody binding to Ad-PSCA transduced MIA-PaCa-2 cells between the PSCA-vaccinated groups (one-way ANOVA, p-value >0.05). The fold change over secondary antibody alone for the 7F5 mAb was 18.7 (data not shown). Overall, these data demonstrate the generation of anti-PSCA-specific antibodies that recognize native PSCA following triple antigen vaccination, using both co-expression and co-formulation DNA vaccination strategies.

Example 6

Immunogenicity of Dual Antigen Vaccines

The following examples are provided to illustrate the capability of dual antigen vaccines expressing two prostate antigens to elicit antigen-specific T and B cell responses to the two encoded prostate antigens.

6A. Immunogenicity of Dual Antigen Vaccines Containing PSMA and PSCA in C57BL/6:
Study Procedure.
Cellular Immune Response Study.
Female C57BL/6 mice were primed on day 0 and boosted on days 14, 28, 42 and 70 with human PSMA and PSCA expressing DNA by PMED epidermal injection. In total, five different dual antigen DNA vaccination strategies were evaluated, which included four DNA vaccines that co-expressed the antigens and one co-formulation approach. For co-expression, single DNA vaccine plasmids encoding two prostate antigens, PSMA and PSCA, linked by a dual promoter, 2A peptides or IRES were administered. These included PSMA-PSCA dual promoter (plasmid ID#460), PSMA-T2A-PSCA (plasmid ID#451), PSCA-F2A-PSMA (plasmid ID#454) and PSCA-IRES-PSMA (plasmid ID#603). For co-formulation, two different DNA plasmids, each individually encoding PSMA and PSCA, were co-formulated onto a single gold particle for PMED delivery. With the exception of co-formulation, the DNA elements that control co-expression (dual promoter, 2A and IRES) differ in length, transgene expression efficiency and the presence of foreign genetic material attached to the target transgenes. As controls, C57BL/6 mice were vaccinated with DNA expressing a single prostate antigen, PSMA or PSCA. For the co-expressed dual or single antigen DNA vaccines, a total dose of 2 µg of DNA vaccine was given per PMED administration, whereas 2 µg of each DNA vaccine plasmid (total of 4 µg of DNA per administration) was given for the co-formulation. Cellular immune responses of the dual and single antigen vaccines were measured by collecting the spleens from each animal on day 77, seven days after the final PMED vaccination. Splenocytes were isolated and subjected to an IFN-γ ELISPOT assay to measure the PSMA and PSCA-specific T cell responses. Briefly, $2 \times 10^5$ splenocytes from individual animals were plated per well with $5 \times 10^4$ per well of TRAMP-C2 cells expressing a single endogenous human prostate antigen or PSMA, PSCA and PSA together, or with individual or pools of human PSMA and PSCA-specific peptides at 10 µg/ml (see Table 22 for peptides and peptide pool composition), or medium alone as a control. Each condition was performed in triplicate. The plates were incubated for 20 h at 37° C. and 5% $CO_2$, washed and developed after incubation as per the manufacturer's instructions. The number of IFN-γ SFC was counted by a CTL reader. The results are presented in FIGS. 15 and 16, which show the average number of PSMA or PSCA-specific SFCs+/−the standard deviation of five mice per group, normalized to $1 \times 10^6$ splenocytes.

Antibody Response Study.

Antibody responses against the dual and single antigen vaccines were measured by collecting the serum from each animal on day 77, seven days after the final PMED vaccination. The anti-PSMA and anti-PSCA antibody titers in the serum was determined using ELISA as described in Example 5. The results are presented in FIGS. 17 and 18, which show the average titers+/−the standard deviation of five mice per group.

Figure 19:
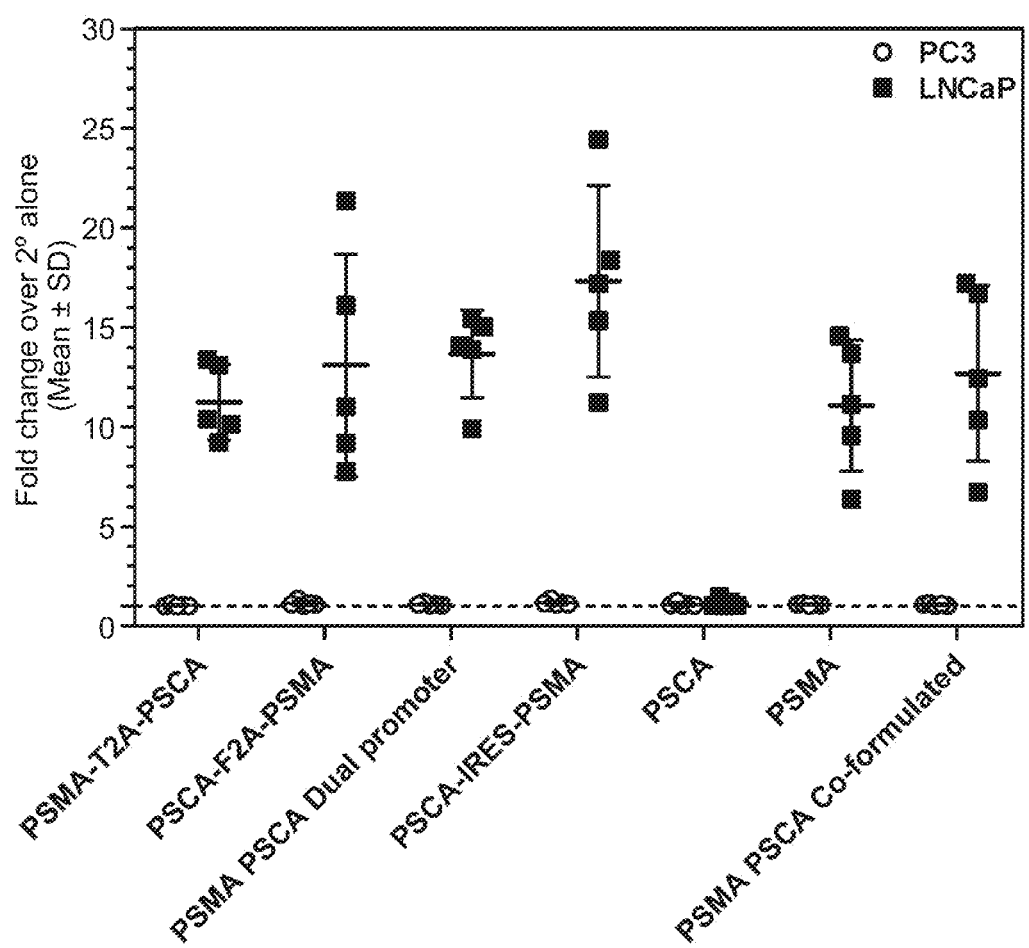
FIG. 19. Graph depicting results of a representative study that evaluates the immunogenicity of the dual antigen vaccines by anti-PSMA antibody cell-surface binding.
Figure 20:
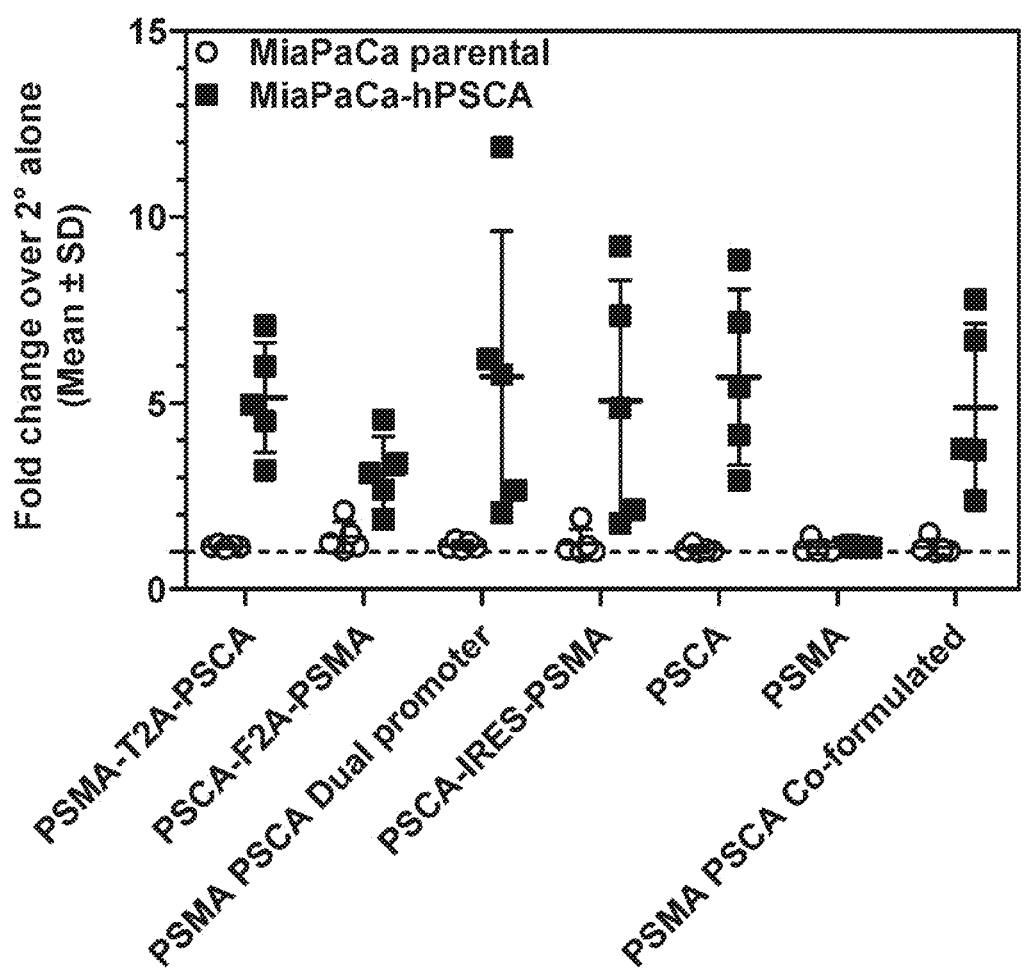
FIG. 20. Graph depicting results of a representative study that evaluates the immunogenicity of the dual antigen vaccines by anti-PSCA antibody cell-surface binding.
Figure 21A:
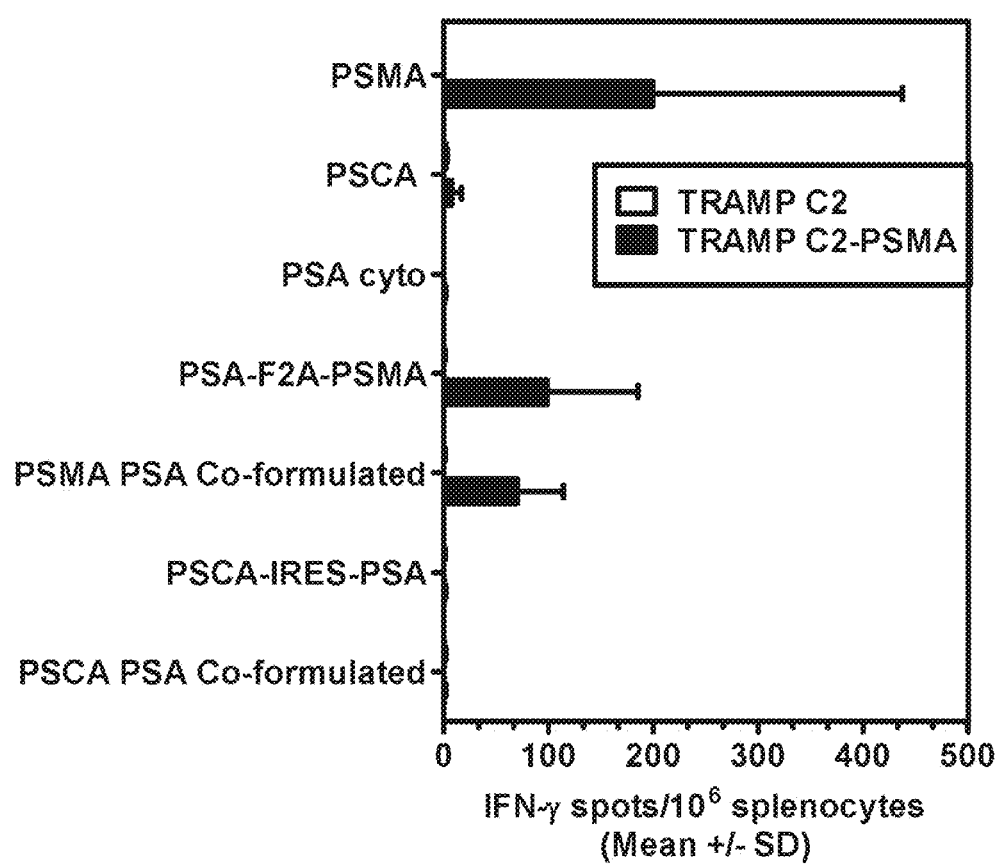
FIGS. 21A-21D. Graphs depicting results of a representative study that evaluates the immunogenicity of the dual antigen vaccines by IFN-γ ELISPOT assay, in which recognition of endogenous PSMA, PSCA, and PSA was assessed by examining T cell responses to (a) TRAMP C2 cells expressing PSMA (FIG. 21A), (b) TRAMP C2 cells expressing PSCA (FIG. 21B), (c) TRAMP C2 cells expressing PSA (FIG. 21C), and (d) TRAMP C2 cells expressing PSMA, PSA, and PSCA (FIG. 21D).
Figure 21B:
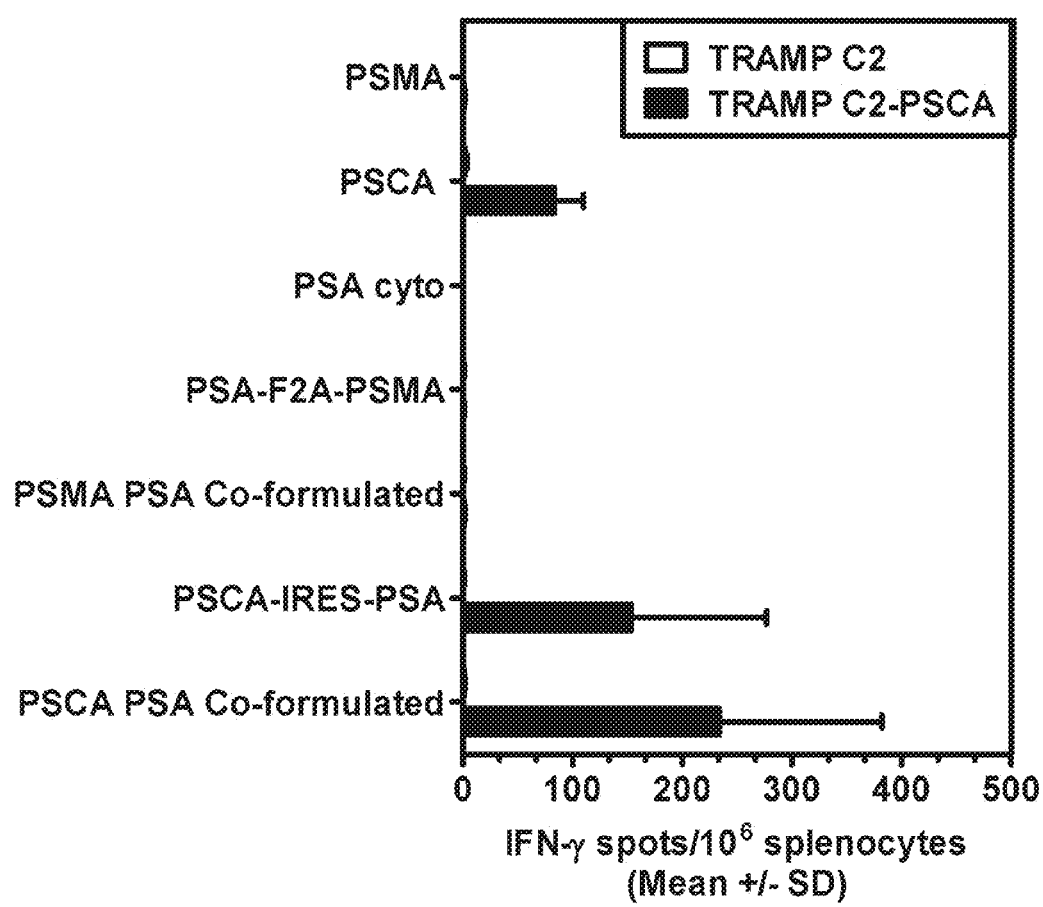
Figure 21C:
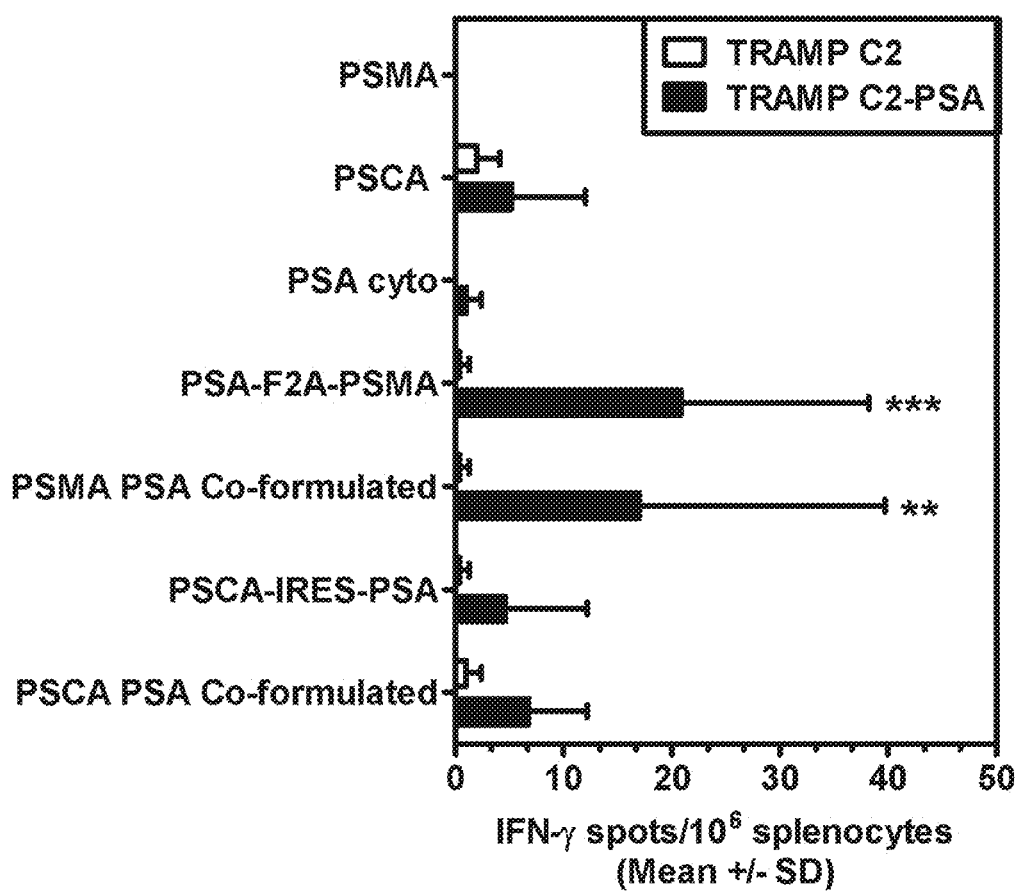
Figure 21D:
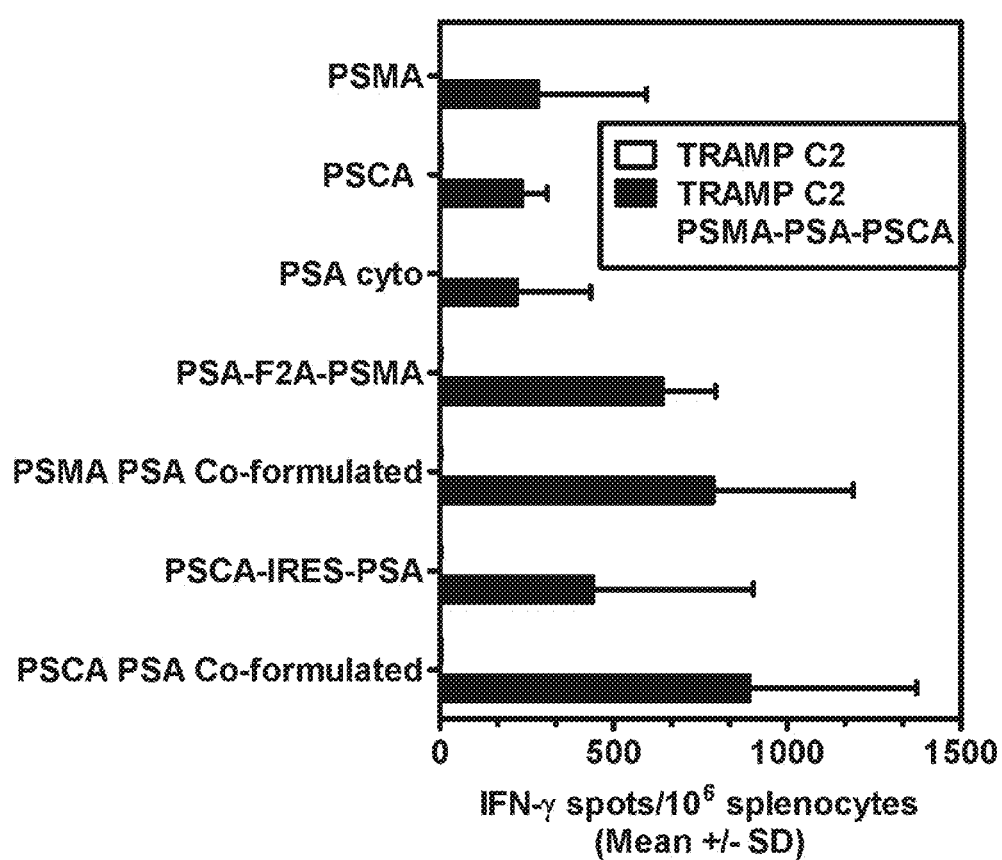

Serum was also subjected to a FACS assay to measure antibody binding to either human PSMA or PSCA expressed on the cell surface of appropriate cell lines, thus determining whether antibodies generated by the multi-antigen vaccines were capable of recognizing native PSMA and PSCA conformations, respectively. Antibody binding to cell-surface native PSA was not measured because PSA was expressed as a cytoplasmic protein by the multi-antigen vaccines investigated in this study. The FACS assay was conducted according to procedure as described in Example 5. The results presented in FIGS. 19 and 20, show the average fold-change in MFI of the mouse serum over the secondary anti-mouse antibody alone+/−the standard deviation of five mice per group. Antibody titers and binding to cell-surface native PSA were not measured because PSA was expressed as a cytoplasmic protein by the multi-antigen vaccines investigated in this study.

Results.

Figure 15A:
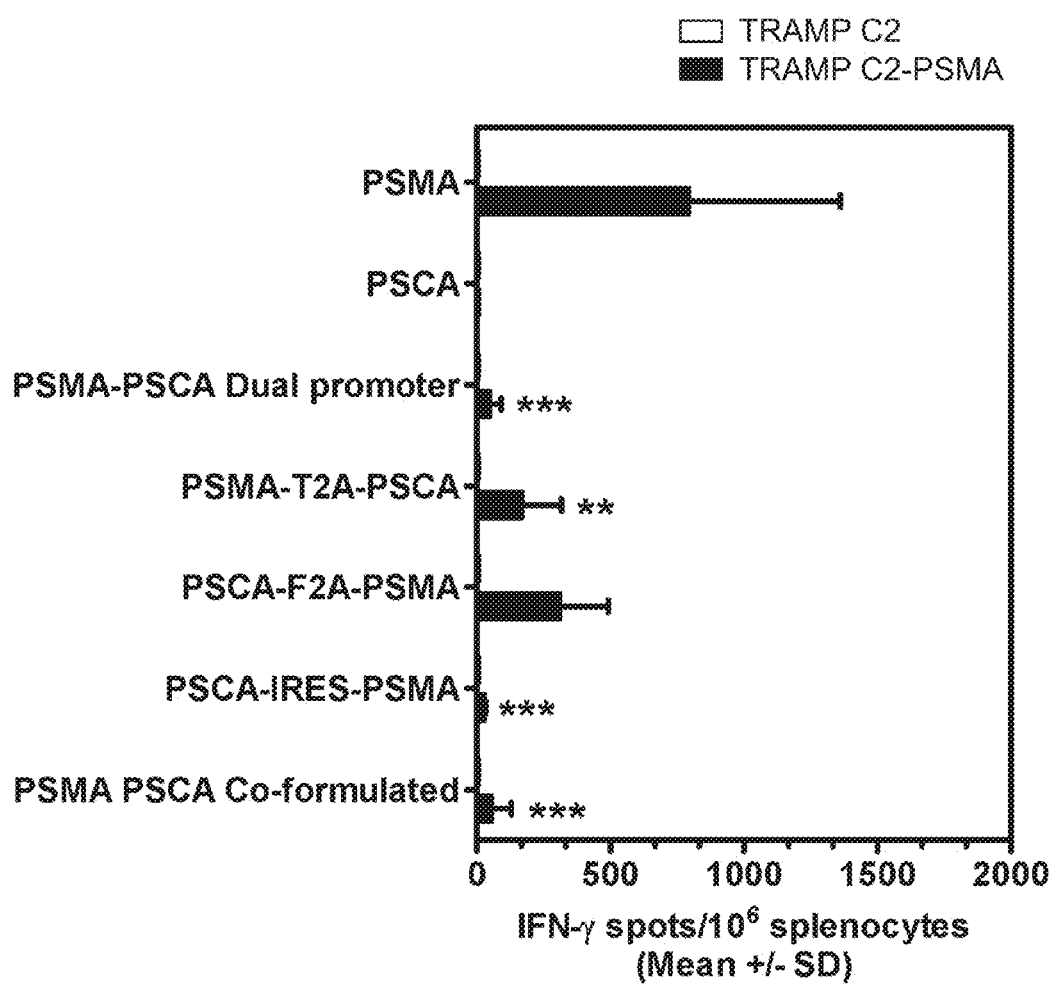
FIGS. 15A-15C. Graphs depicting results of a representative study that evaluates the immunogenicity of the dual antigen vaccines by IFN-γ ELISPOT assay, in which recognition of endogenous prostate antigens was assessed by examining T cell responses to (a) TRAMP C2 cells expressing PSMA (FIG. 15A), (b) TRAMP C2 cells expressing PSCA (FIG. 15B), and (c) TRAMP C2 cells expressing PSMA, PSA, and PSCA (FIG. 15C).
Figure 15B:
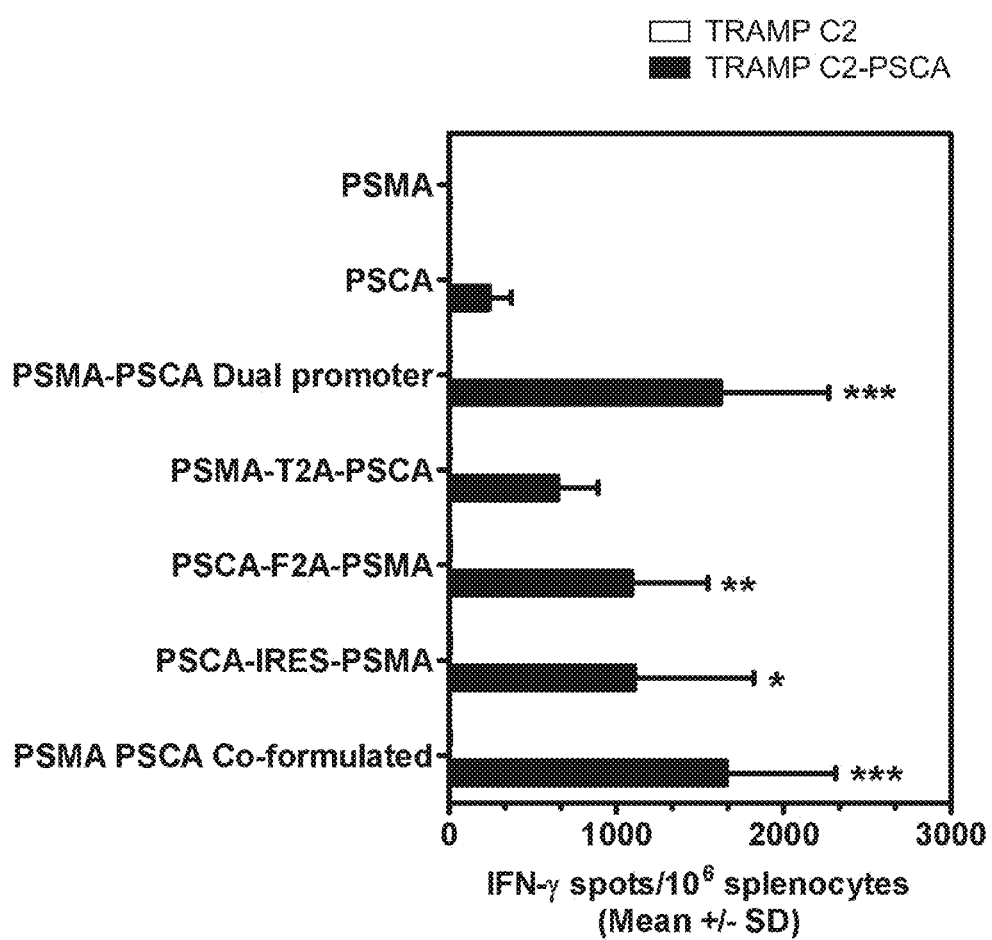
Figure 15C:
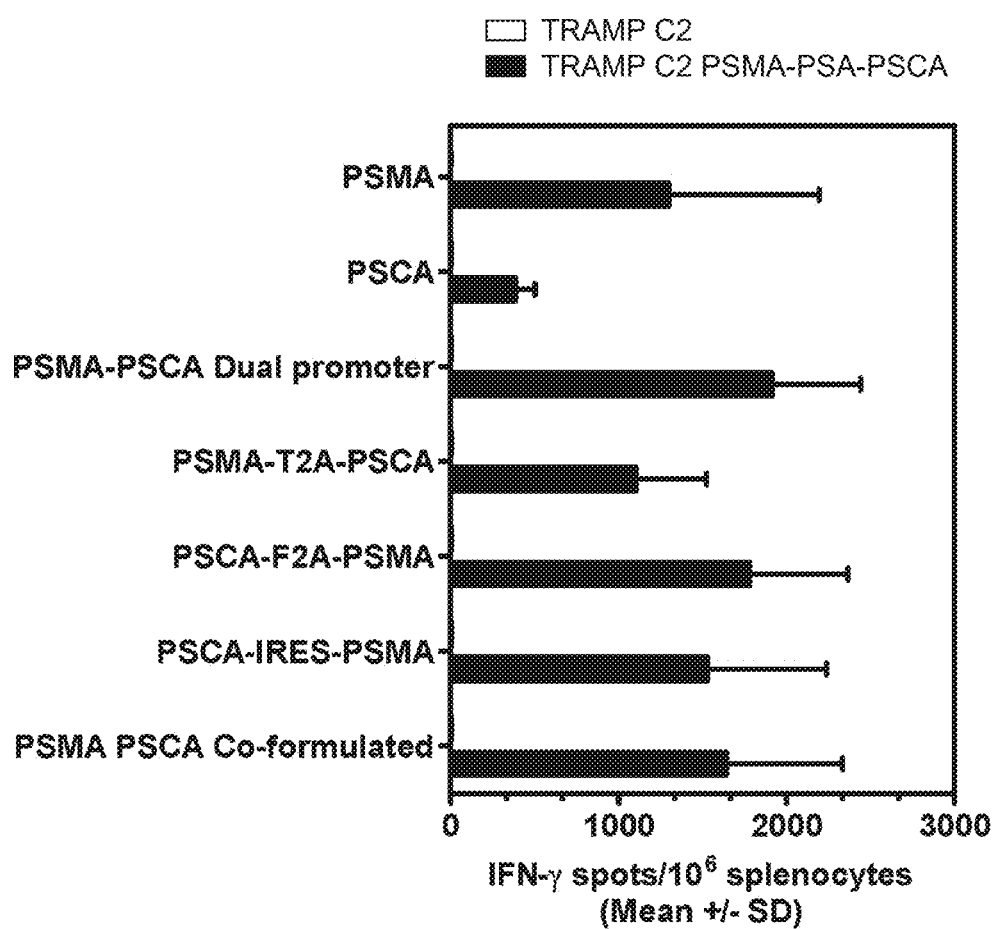

FIGS. 15A-15C show the results of a representative study that evaluates the immunogenicity of the dual antigen vaccines by IFN-γ ELISPOT assay. Briefly, 5 mice per group were primed on day 0 and boosted with PMED on days 14, 28, 42 and 70. On day 77, recognition of endogenous PSMA and PSCA was assessed by examining T cell responses to (A) TRAMP C2-PSMA, (B) TRAMP C2-PSCA and (C) TRAMP C2-PSMA-PSA-PSCA cells by IFN-γ ELISPOT assay. The TRAMP C2 cells served as a background control for the assay. For IFN-γ T cell responses to endogenous PSMA, the magnitude of the response TRAMP C2-PSMA was significantly decreased following vaccination with PSMA-PSCA dual promoter, PSMA-T2A-PSCA, PSCA-IRES-PSMA and co-formulated PSMA PSCA compared to vaccination with PSMA alone ( and * indicate p-values <0.01 and <0.001, respectively, by two-way ANOVA). However, the PSCA-F2A-PSMA vaccine construct elicited a similar magnitude IFN-γ T cell response to the TRAMP C2-PSMA cells as the single PSMA vaccine. For IFN-γ T cell responses to endogenous PSCA, significantly increased responses were observed following vaccination with several of the dual antigen vaccines, including PSMA-PSCA dual promoter, PSCA-F2A-PSMA, PSCA-IRES-PSMA and co-formulated PSMA PSCA compared to the PSCA vaccine alone (*,  and * indicate p-values of <0.05, 0.01 and 0.001, respectively, by two-way ANOVA). The PSCA-T2A-PSMA vaccine construct elicited a similar magnitude IFN-γ T cell response to the TRAMP C2-PSCA cells as the single PSCA vaccine. Comparing the IFN-γ T cell responses to TRAMP C2-PSMA-PSA-PSCA, there were no significant differences between the groups vaccinated with different dual antigen vaccines. Taken together, these data demonstrate generation of PSMA and PSCA-specific T cell responses following dual antigen vaccination, using both co-expression and co-formulation DNA vaccination strategies.

Figure 16B:
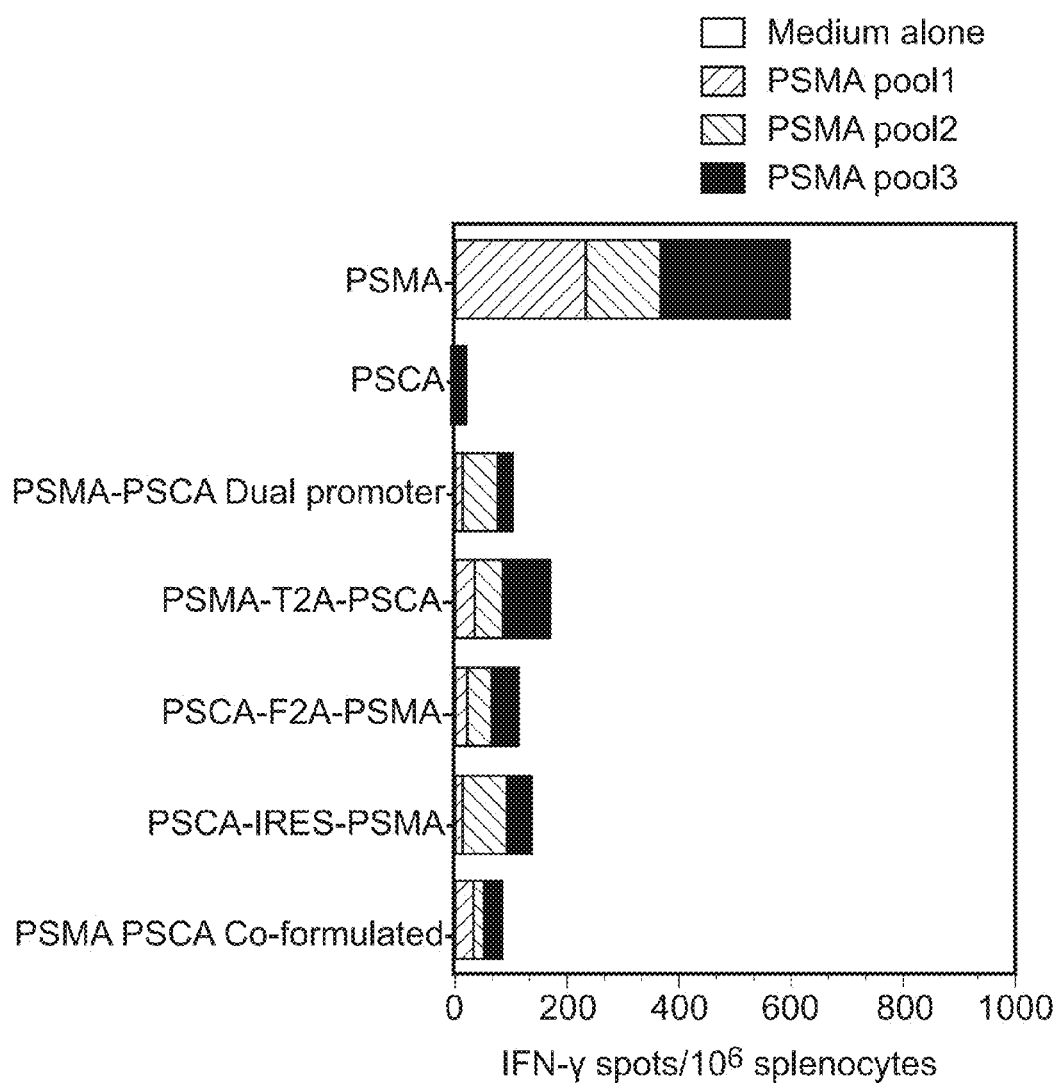
Figure 16C:
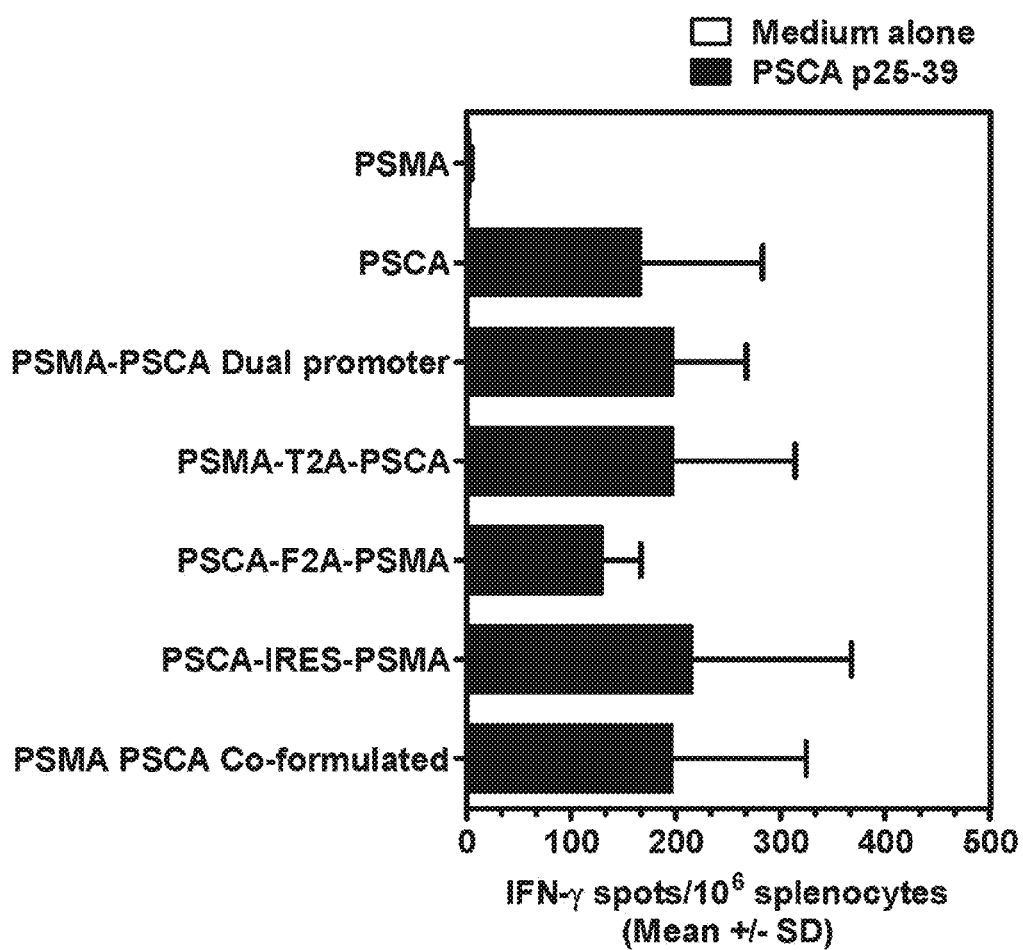

FIGS. 16A-16C show the results of a representative study that evaluates the immunogenicity of the dual antigen vaccines by IFN-γ ELISPOT assay. Briefly, 5 mice per group were primed on day 0 and boosted with PMED on days 14, 28, 42 and 70. On day 77, T cell responses to (A) PSMA peptides, (B) PSMA peptide pools and (C) PSCA peptides (see Table 22) were assessed by IFN-γ ELISPOT assay. Medium alone served as a background control for the assay. For IFN-γ T cell responses to both the individual and pools of PSMA peptides, the highest magnitude responses compared to the single PSMA vaccine were observed following the PSMA-T2A-PSCA and PSCA-F2A-PSMA dual antigen vaccinations. A significant reduction in the IFN-γ T cell response to the individual PSMA peptides was observed following vaccination with PSMA-PSCA dual promoter, PSCA-IRES-PSMA and co-formulated PSMA PSCA. The IFN-γ T cell response to the PSCA-specific peptide was similar between the groups vaccinated with the different dual antigen vaccines. These data also demonstrate generation of T cell responses to both PSMA and PSCA when co-expressed on the same DNA vaccine construct, or delivered as a co-formulation.

Figure 17:
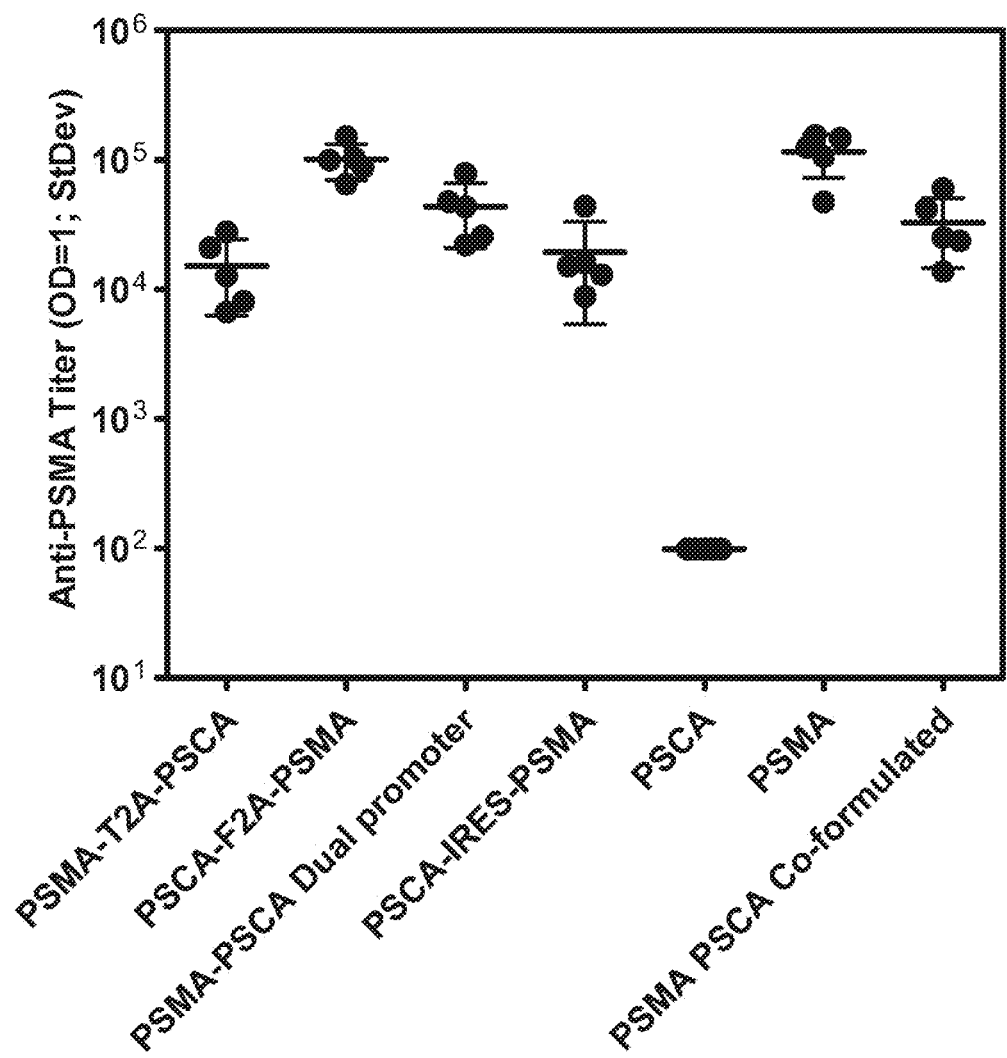
FIG. 17. Graph depicting results of a representative study that evaluates the immunogenicity of the dual antigen vaccines by anti-PSMA antibody titers.

FIG. 17 shows the results of a representative study that evaluates the immunogenicity of the dual antigen vaccines by anti-PSMA antibody titers. Briefly, 5 mice per group were primed on day 0 and boosted with PMED on days 14, 28, 42 and 70. On day 77, serum anti-PSMA antibody titers were assessed by ELISA. All animals vaccinated with PSMA generated significant anti-PSMA antibody titers. Mice vaccinated with the dual vaccine construct, PSCA-F2A-PSMA, and the single PSMA vaccine generated significantly higher antibody titers compared to all other groups of mice vaccinated with PSMA (one-way ANOVA, p-value <0.05). Vaccination with PSMA-PSCA dual promoter and co-formulated PSMA and PSCA resulted in higher antibody titers compared to mice that received the PSMA-T2A-PSCA vaccine. Taken together, these data demonstrate generation of anti-PSMA-specific antibodies following dual antigen DNA vaccination with PSMA and PSCA, using both co-expression and co-formulation vaccination strategies.

Figure 18:
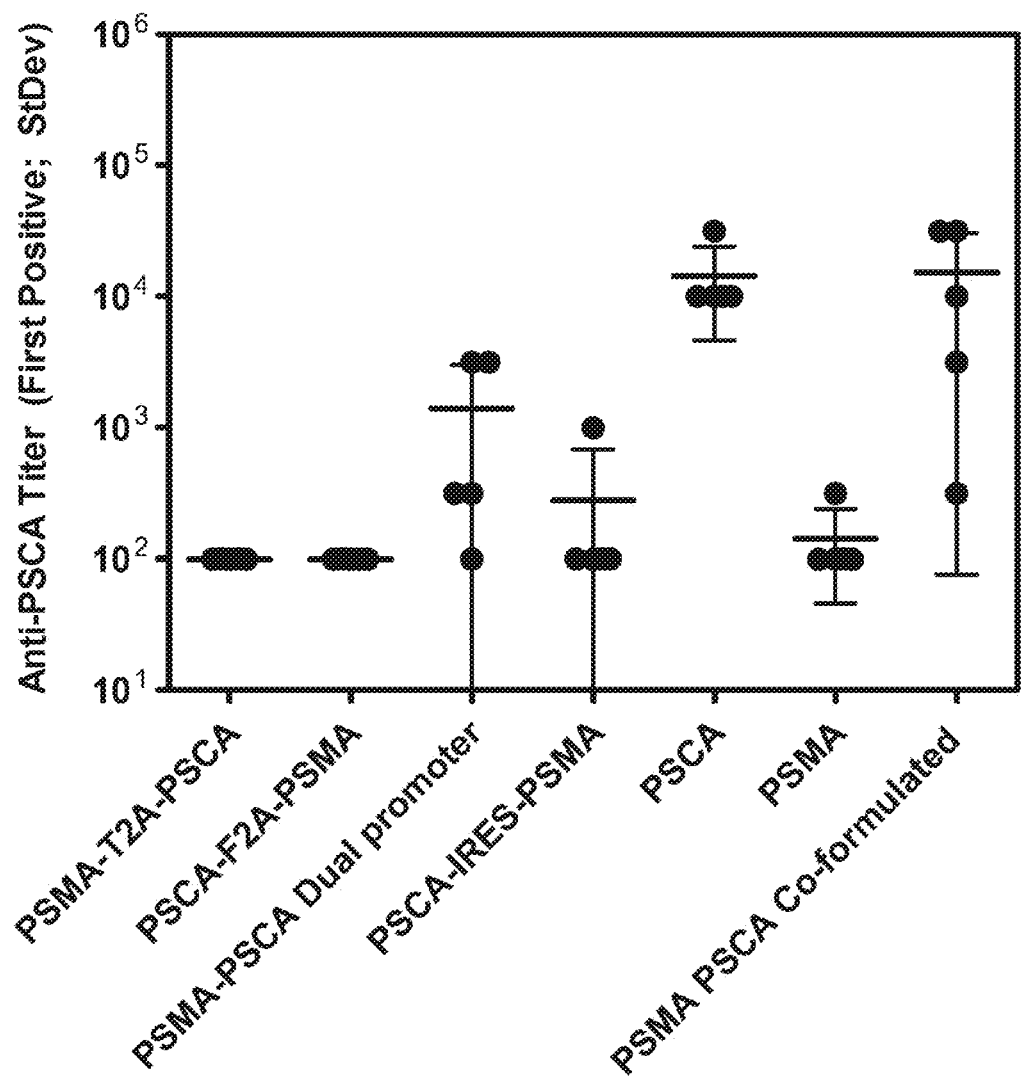
FIG. 18. Graph depicting results of a representative study that evaluates the immunogenicity of the dual antigen vaccines by anti-PSCA antibody titers.

FIG. 18 shows the results of a representative study that evaluates the immunogenicity of the dual antigen vaccines by anti-PSCA antibody titers. Briefly, 5 mice per group were primed on day 0 and boosted with PMED on days 14, 28, 42 and 70. On day 77, serum anti-PSCA antibody titers were assessed by ELISA. Mice vaccinated with the co-formulated PSMA and PSCA, and the single PSCA vaccine generated significantly higher antibody titers compared to all other groups of mice vaccinated with PSCA (one-way ANOVA). Vaccination with PSMA-PSCA dual promoter resulted in higher antibody titers compared to vaccination with PSMA-T2A-PSCA, PSCA-F2A-PSMA and PSCA-IRES-PSMA. These results indicate that co-expression or co-formulation of PSMA and PSCA elicits anti-PSCA antibodies.

FIG. 19 shows the results of a representative study that evaluates the immunogenicity of the dual antigen vaccines by anti-PSMA antibody cell-surface binding. Briefly, 5 mice per group were primed on day 0 and boosted with PMED on days 14, 28, 42 and 70. On day 77, recognition of cell-surface native PSMA was assessed by serum antibody binding to LNCaP and PC3 cells. The PC3 cells served as a background control for the assay. With the exception of the single PSCA vaccine, all vaccine regimens with PSMA resulted in significant anti-PSMA antibody binding to LNCaP cells compared to the control PC3 cells. There were no significant differences in the anti-PSMA antibody binding to LNCaP cells between the PSMA-vaccinated groups (one-way ANOVA, p-value >0.05). The fold change over secondary antibody alone for the J591-A mAb was 45.3 (data not shown). These data demonstrate generation of anti-PSMA-specific antibodies that recognized native PSMA following dual antigen DNA vaccination, using both co-expression and co-formulation vaccination strategies.

FIG. 20 shows the results of a representative study that evaluates the immunogenicity of the dual antigen vaccines by anti-PSCA antibody cell-surface binding. Briefly, 5 mice per group were primed on day 0 and boosted with PMED on days 14, 28, 42 and 70. On day 77, recognition of cell-surface native PSCA was assessed by serum antibody binding to Ad-PSCA transduced and untransduced MIA-PaCa-2 cells. The untransduced, parental cells served as a background control for the assay. With the exception of the single PSMA vaccine, all vaccine regimens with PSCA resulted in significant anti-PSCA antibody binding to Ad-PSCA transduced MIA-PaCa-2 cells compared to the control cells. There were no significant differences in the anti-PSCA antibody binding to Ad-PSCA transduced MIA-PaCa-2 cells between the PSCA-vaccinated groups (one-way ANOVA, p-value >0.05). The fold change over secondary antibody alone for the 7F5 mAb was 18.7 (data not shown). Overall, these data demonstrate generation of anti-PSCA-specific antibodies that recognized native PSCA following dual antigen DNA vaccination, using both co-expression and co-formulation vaccination strategies.

6B. Immunogenicity of Dual Antigen Vaccines Containing Either PSMA and PSA or PSCA and PSA in C57BL/6

Study Procedure.

Cellular Immune Response Study.

Female C57BL/6 mice were primed on day 0 and boosted on days 14 and 28 with human PSMA, PSCA and PSA expressing DNA by PMED epidermal injection. In total, four different dual antigen vaccines strategies were evaluated, which included two co-expression approaches and two co-formulation strategies. For co-expression, a single DNA plasmid encoding two prostate antigens, PSMA and PSA linked a 2A peptide (plasmid ID#5300) or PSCA and PSA linked by IRES (plasmid ID#455) were administered. For co-formulation, plasmids individually encoding PSMA, PSCA or PSA were co-formulated onto a single gold particle for PMED delivery. Specifically, these included PSMA and PSA co-formulated and PSCA and PSA co-formulated. As controls, C57BL/6 mice were vaccinated with DNA expressing a single prostate antigen, PSMA, PSCA or PSA. For the co-expressed dual or single antigen vaccines, a dose 2 μg of DNA was given per PMED administration, whereas 2 μg of each DNA vaccine plasmid (total of 4 μg of DNA per administration) was given for the co-formulation. Cellular immune responses of the dual and single antigen vaccines were measured by collecting the spleens from each animal on day 35. Splenocytes were isolated and subjected to an IFN-γ ELISPOT assay to measure the PSMA, PSCA and PSA-specific T cell responses. Briefly, $2 \times 10^5$ splenocytes from individual animals were plated per well with $5 \times 10^4$ per well of TRAMP-C2 cells expressing a single endogenous human prostate antigen or PSMA, PSCA and PSA together, or with individual or pools of human PSMA, PSCA and PSA-specific peptides at 10 μg/ml (see Table 22 for peptides and peptide pool composition), or medium alone as a control. Each condition was performed in triplicate. The plates were incubated for 20 h at 37° C. and 5% $CO_2$, washed and developed after incubation as per manufacturer's instructions. The number of IFN-γ SFC was counted by a CTL reader. The results are presented in FIGS. 21 and 22, which show the average number of PSMA, PSCA and PSA-specific SFCs+/−the standard deviation of five mice per group, normalized to $1 \times 10^6$ splenocytes.

Antibody Response Study.

Female C57BL/6 mice were primed on day 0 and boosted on days 14, 28 and 49 with human PSMA, PSCA and PSA expressing DNA by PMED. Antibody responses against the dual and single antigen vaccines were measured by collecting the serum from each animal on day 56, seven days after the final PMED vaccination. The anti-PSMA and anti-PSCA antibody titers in the serum was determined using ELISA assay as described in Example 5. The results are presented in FIGS. 23 and 24, which show the average titers+/−the standard deviation of five mice per group.

Serum was also subjected to a FACS assay to measure antibody binding to either human PSMA or PSCA expressed on the cell surface of appropriate cell lines, thus determining whether antibodies generated by the multi-antigen vaccines were capable of recognizing native PSMA and PSCA conformations, respectively. Antibody binding to cell-surface native PSA was not measured because PSA was expressed as a cytoplasmic protein by the multi-antigen vaccines investigated in this study. The FACS assay was conducted according to the procedure as described in Example 5. The results are presented in FIGS. 25 and 26, which show the average fold change in MFI of the mouse serum over the secondary anti-mouse antibody alone+/−the standard deviation of five mice per group. Antibody titers and binding to cell-surface native PSA were not measured because PSA was expressed as a cytoplasmic protein by the multi-antigen vaccines investigated in this study.

Results.

FIGS. 21A-21D show the results of a representative study that evaluates the immunogenicity of the dual antigen vaccines by IFN-γ ELISPOT assay. Briefly, 5 mice per group were primed on day 0 and boosted with PMED on days 14 and 28. On day 35, recognition of endogenous PSMA, PSCA and PSA was assessed by examining T cell responses to (A) TRAMP C2-PSMA, (B) TRAMP C2-PSCA, (C) TRAMP C2-PSA and (D) TRAMP C2-PSMA-PSA-PSCA cells by IFN-γ ELISPOT assay. The TRAMP C2 cells served as a background control for the assay. For IFN-γ T cell responses to endogenously expressed PSMA on cells, no significant differences were observed between responses to TRAMP C2-PSMA following vaccination with dual antigens containing PSMA (PSA-F2A-PSMA and co-formulated PSMA and PSA) and PSMA alone. Likewise, for IFN-γ T cell responses to endogenous PSCA, there were no observed differences in response magnitude to TRAMP C2-PSCA between the dual PSCA-IRES-PSA and co-formulated PSCA and PSA vaccines compared to the single PSCA vaccine. For IFN-γ T cell responses to endogenous PSA, a significant increase in the response magnitude to TRAMP C2-PSA was detected when comparing the immunogenicity of the single PSA vaccine to either PSA-F2A-PSMA (* indicates p<0.001 by two-way ANOVA) and co-formulated PSMA and PSA ( indicates p<0.01 by two-way ANOVA). There were no observed differences in response magnitude to TRAMP C2-PSA when comparing animals that received the dual PSCA and PSA vaccines to the single PSA vaccine. When examining the IFN-γ T cell response to TRAMP C2-PSMA-PSA-PSCA, there were no significant differences in the response between the groups vaccinated with different dual antigen vaccines. Taken together, these data demonstrate the generation of PSMA and PSA-specific T cell responses, as well as PSCA and PSA-specific T cell responses following dual antigen DNA vaccination, using both co-expression and co-formulation vaccine strategies.

Figure 22:
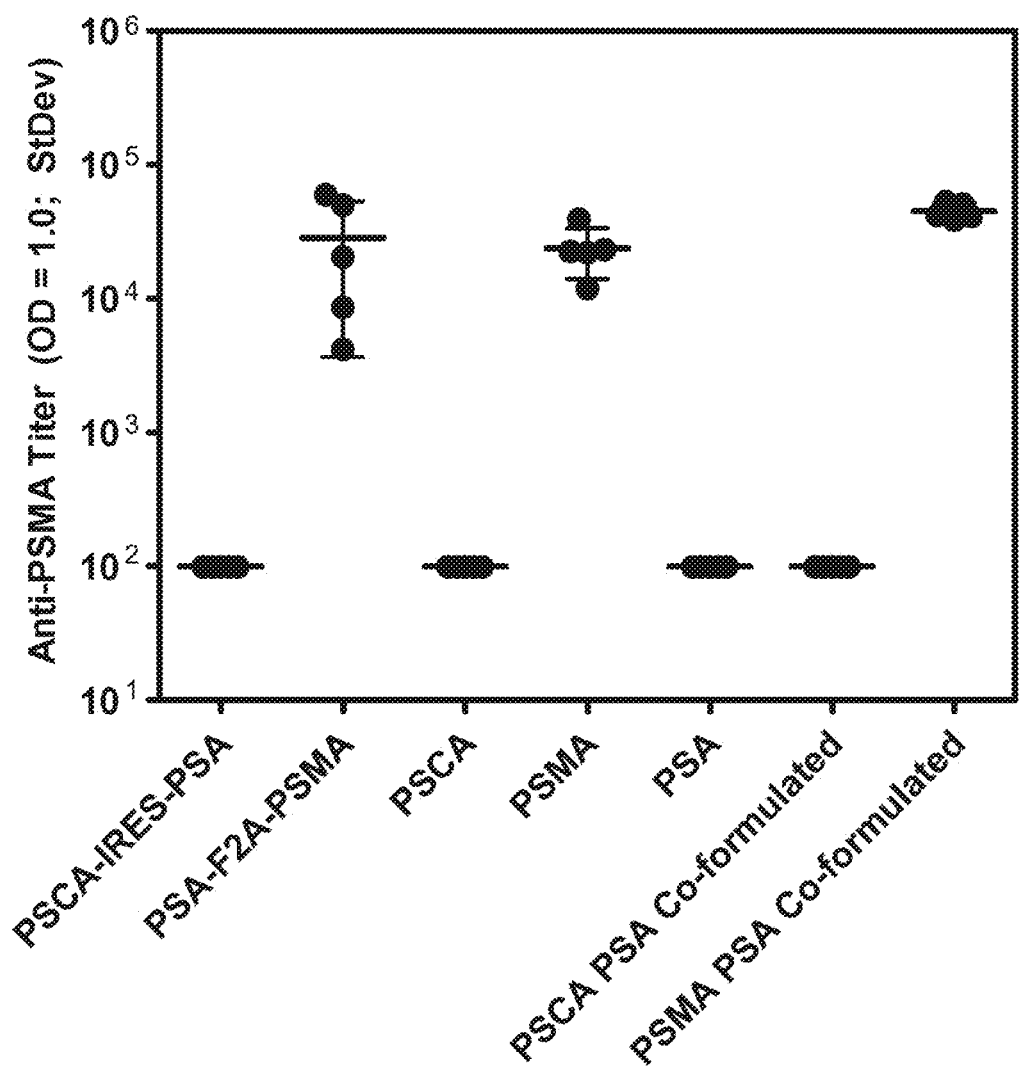
FIG. 22. Graph depicting results of a representative study that evaluates the immunogenicity of the dual antigen vaccines by anti-PSMA antibody titers.

FIG. 22 shows the results of a representative study that evaluates the immunogenicity of the dual antigen vaccines by anti-PSMA antibody titers. Briefly, 5 mice per group were primed on day 0 and boosted with PMED on days 14, 28 and 49. On day 56, serum anti-PSMA antibody titers were assessed by ELISA. All animals vaccinated with PSMA generated significant anti-PSMA antibody titers. There was no significant difference in the antibody titers between mice vaccinated with PSA-F2A-PSMA, co-formulated PSMA and PSA, and PSMA alone (one-way ANOVA, p-value >0.05). Taken together, these data demonstrate the generation of anti-PSMA-specific antibodies following dual antigen DNA vaccination with PSMA and PSA, using both co-expression and co-formulation vaccine strategies.

Figure 23:
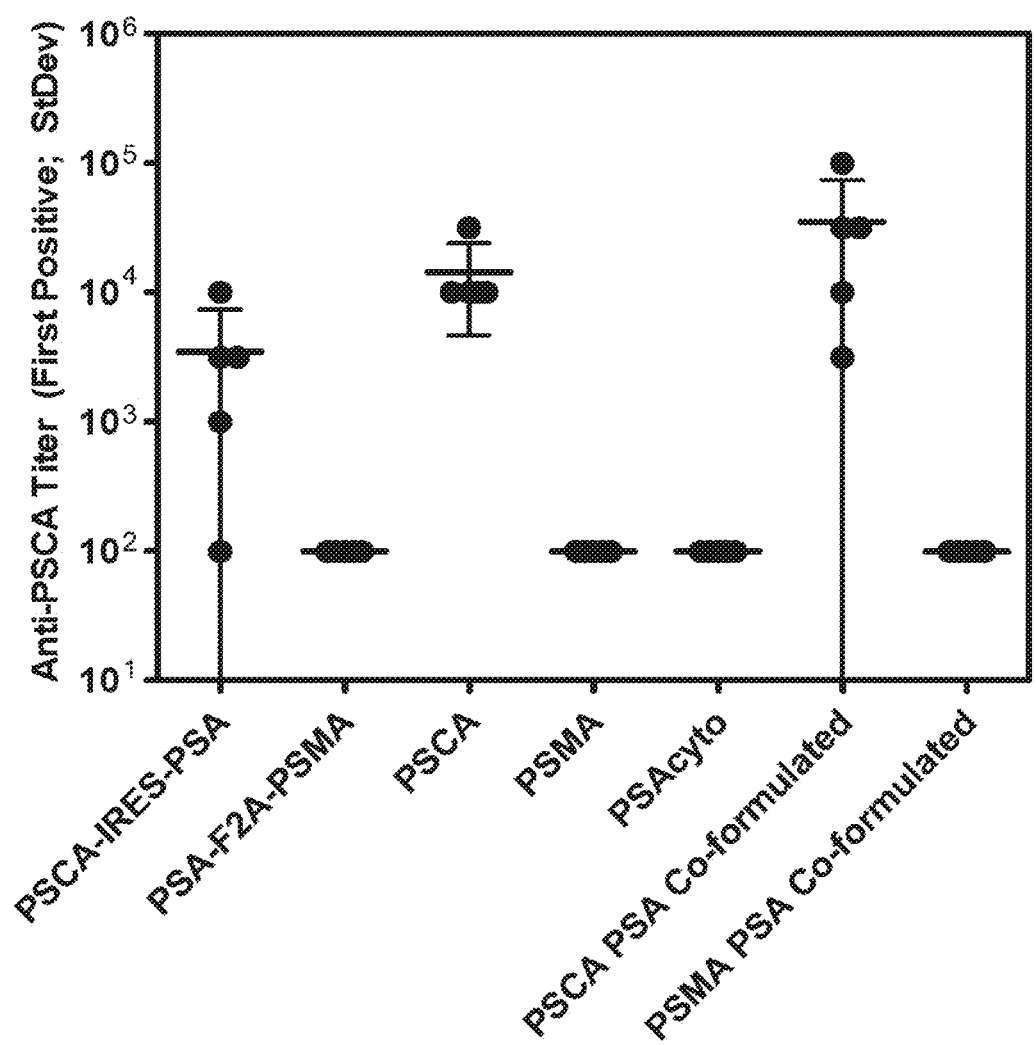
FIG. 23. Graph depicting results of a representative study that evaluates the immunogenicity of the dual antigen vaccines by anti-PSCA antibody titers.

FIG. 23 shows the results of a representative study that evaluates the immunogenicity of the dual antigen vaccines by anti-PSCA antibody titers. Briefly, 5 mice per group were primed on day 0 and boosted with PMED on days 14, 28 and 49. On day 56, serum anti-PSCA antibody titers were assessed by ELISA. All animals vaccinated with PSCA generated significant anti-PSCA antibody titers. There was no significant difference in the antibody titers between mice vaccinated with PSCA-IRES-PSA, co-formulated PSCA and PSA, and PSCA alone (one-way ANOVA, p-value >0.05), although the antibody titers generated following PSCA-IRES-PSA vaccination trended lower than the other groups vaccinated with PSCA. These results indicate that co-expression or co-formulation of PSCA and PSA elicits anti-PSCA antibodies.

Figure 24:
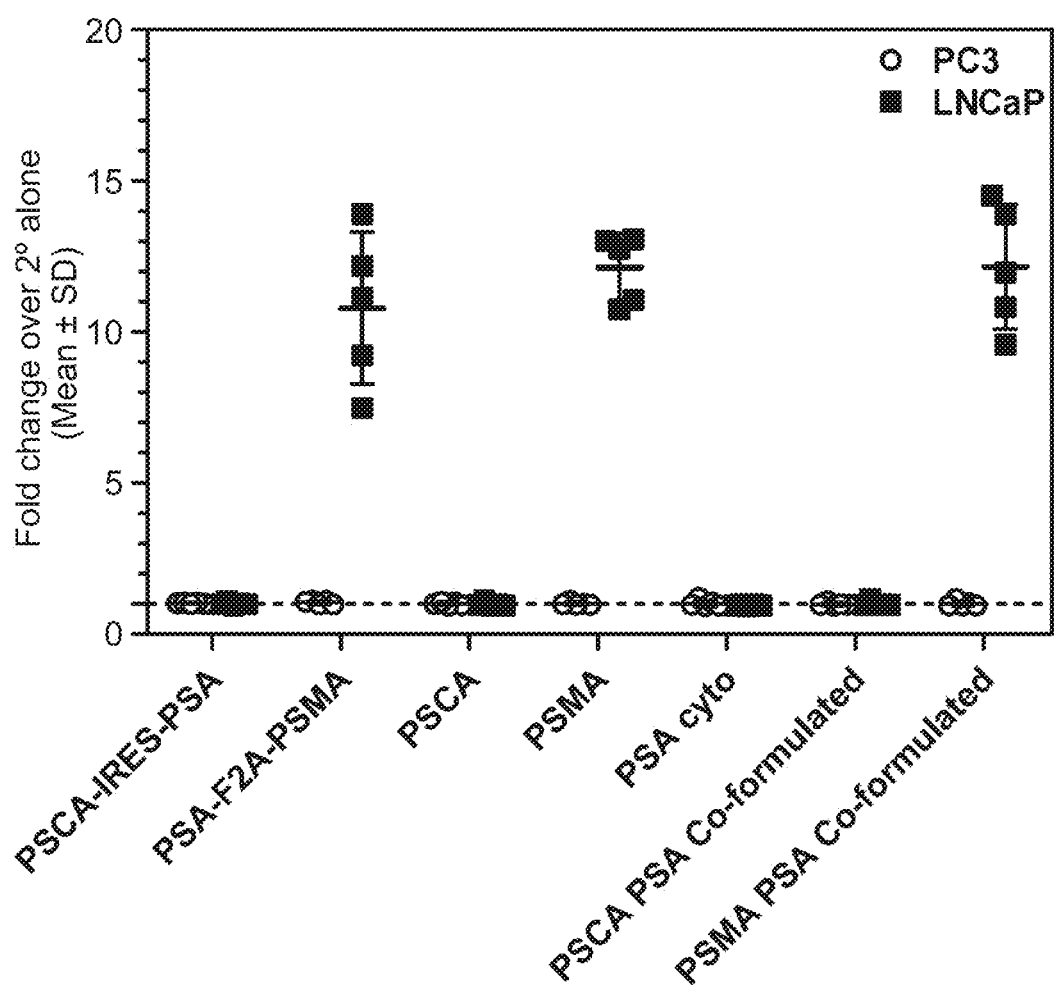
FIG. 24. Graph depicting results of a representative study that evaluates the immunogenicity of the dual antigen vaccines by anti-PSMA antibody cell-surface binding.

FIG. 24 shows the results of a representative study that evaluates the immunogenicity of the dual antigen vaccines by anti-PSMA antibody cell-surface binding. Briefly, 5 mice per group were primed on day 0 and boosted with PMED on days 14, 28 and 49. On day 56, recognition of cell-surface native PSMA was assessed by serum antibody binding to LNCaP and PC3 cells. The PC3 cells served as a background control for the assay. There were no significant differences in the anti-PSMA antibody binding to LNCaP cells between the PSMA-vaccinated groups (one-way ANOVA, p-value >0.05). The fold change over secondary antibody alone for the J591-A mAb was 45.3 (data not shown). Overall, these data demonstrate the generation of anti-PSMA-specific antibodies that recognized native PSMA following dual antigen vaccination, using both co-expression and co-formulation vaccine strategies.

Figure 25:
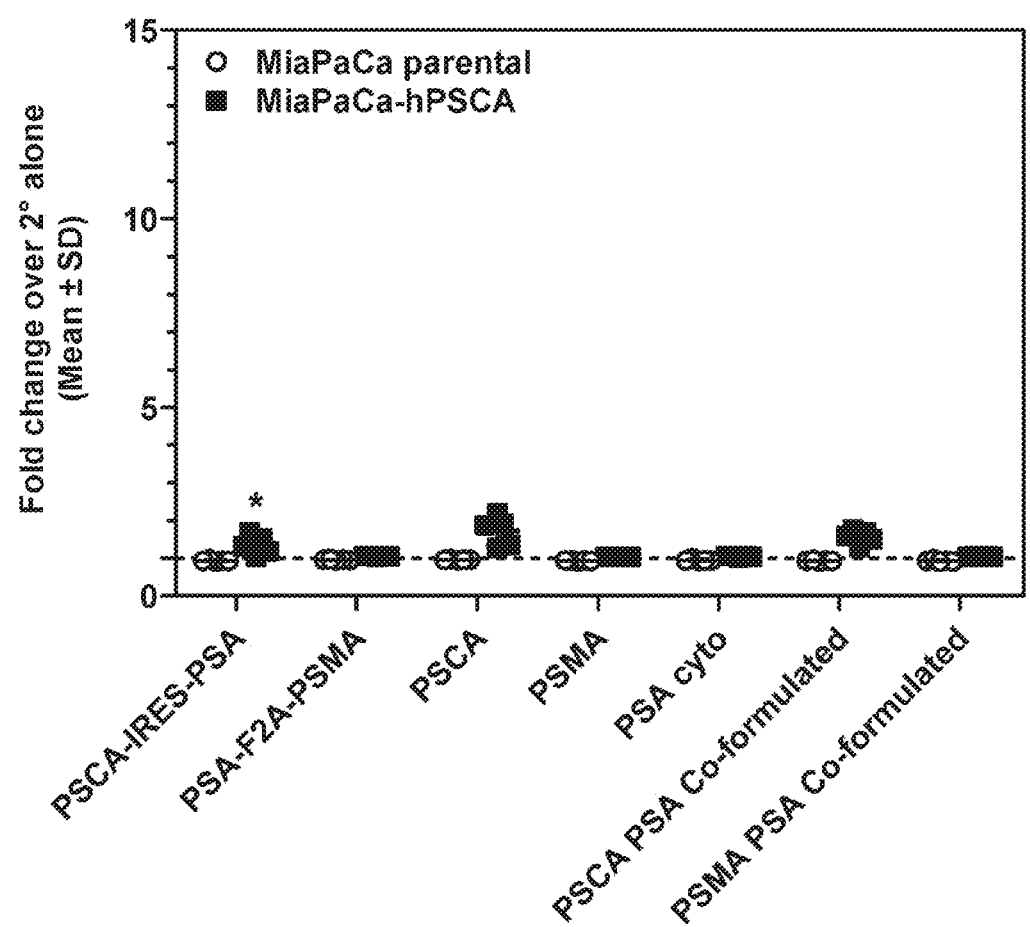
FIG. 25. Graph depicting results of a representative study that evaluates the immunogenicity of the dual antigen vaccines by anti-PSCA antibody cell-surface binding.

FIG. 25 shows the results of a representative study that evaluates the immunogenicity of the dual antigen vaccines by anti-PSCA antibody cell-surface binding. Briefly, 5 mice per group were primed on day 0 and boosted with PMED on days 14, 28 and 49. On day 56, recognition of cell-surface native PSCA was assessed by serum antibody binding to Ad-PSCA transduced and untransduced MIA-PaCa-2 cells. The untransduced, parental cells served as a background control for the assay. All groups of mice vaccinated with PSCA demonstrated very low anti-PSCA antibody binding to Ad-PSCA transduced MIA-PaCa-2 cells. PSCA-IRES-PSA vaccination resulted in significantly decreased binding to Ad-PSCA transduced MIA-PaCa-2 cells compared to mice vaccinated with PSCA alone (* indicates p<0.05 by one-way ANOVA). Taken together, these data demonstrate that co-expression or co-formulation of PSCA and PSA results in very low recognition of native PSCA by anti-PSCA-specific antibodies.

Example 7

Immunogenicity of the Human Psma Modified Antigen

Study Design.

The immune responses induced by DNA vaccination using a construct encoding an immunogenic PSMA polypeptide (the "human PSMA modified antigen" or "hPSMA modified") consisting 15-750 amino acids (aa) of the native human PSMA protein of SEQ ID NO: 1 were compared with those induced by the native human full-length PSMA protein (hPSMA full length). Groups of female C57BL/6 mice or female Pasteur (HLA-A2/DR1) transgenic mice were primed on day 0 and boosted on days 14, 28 by PMED administration with a 2 μg dose of a DNA vaccine encoding either hPSMA full-length or hPSMA modified protein. Mice were bled and sacrificed on day 35 (7 days after the third vaccination) and T cell immune responses against the hPSMA full-length protein were determined in splenocytes by IFN-γ ELISPOT assay. For C57BL/6 mice, single cell suspensions of 5×10$^5$ splenocytes from individual animals were plated per well with 10 μg purified hPSMA protein, 5×10$^4$ TRAMP-C2 cells alone, or TRAMP-C2 cells expressing hPSMA or a PSMA-PSA-PSCA fusion protein. For Pasteur (HLA-A2/DR1) transgenic mice, single cell suspensions of 5×10$^5$ splenocytes from individual animals were plated per well with 5×10$^4$ K562 cells expressing human HLA-A2 that had been pulsed with known HLA-A2-restricted CD8+ T cell epitopes derived from the human PSMA protein sequence (Table 23). Responses in Pasteur mice were also determined using 10 μg/ml purified PSMA protein or 5×10⁴ SK-Mel5 cells that had been transduced with Adenoviral vectors expressing a control protein (Ad-eGFP) or the full-length human PSMA protein (Ad-hPSMA). Each condition was performed in triplicate. The plates were incubated for 20 h at 37° C. and 5% $CO_2$, washed and developed after incubation as per the manufacturer's instruction. The number of IFN-γ SFC was counted by a CTL reader. The results are presented in FIGS. 19 and 20, which show the average number of PSMA-specific SFC/million splenocytes+/−the standard deviation per group.

ELISA Assay.

Antibody responses induced by the modified and full-length PSMA vaccines were measured in serum from each animal collected on day 35. Serum from was subjected to ELISA to determine the anti-PSMA antibody titers in the serum was determined using the ELISA assay as described in Example 5. The results are presented in FIG. 26, which shows the average titers+/−the standard deviation of the number of mice per group.

FACS Assay.

Serum was also subjected to a FACS assay to measure antibody binding to either human PSMA expressed on the cell surface of appropriate cell lines, thus determining whether antibodies generated by the modified and full-length PSMA vaccines were capable of recognizing native PSMA conformation. The FACS assay was conducted according to the procedure as described in Example 5. The results are presented in FIG. 29, which show the average fold change in MFI of the mouse serum over the secondary anti-mouse antibody alone+/−the standard deviation of the number of mice per group.

TABLE 23

HLA-A2 restricted peptide epitopes tested in the assays conducted for the Pasteur (HLA-A2/DR1) transgenic mice. Peptides were tested individually at a concentration of 10 μg/ml. The amino acid position of the N and C-terminal end of each peptide is indicated.

| Prostate antigen | Peptides | Purpose |
| --- | --- | --- |
| hHer2 | 106-114 | HLA-A2-restricted control peptide derived from the human Her2 protein |
| PSMA | 168-177 | HLA-A2-restricted PSMA test peptide |
| PSMA | 663-671 | HLA-A2-restricted PSMA test peptide |
| PSMA | 275-289 | HLA-A2-restricted PSMA test peptide |

Results.

Figure 26:
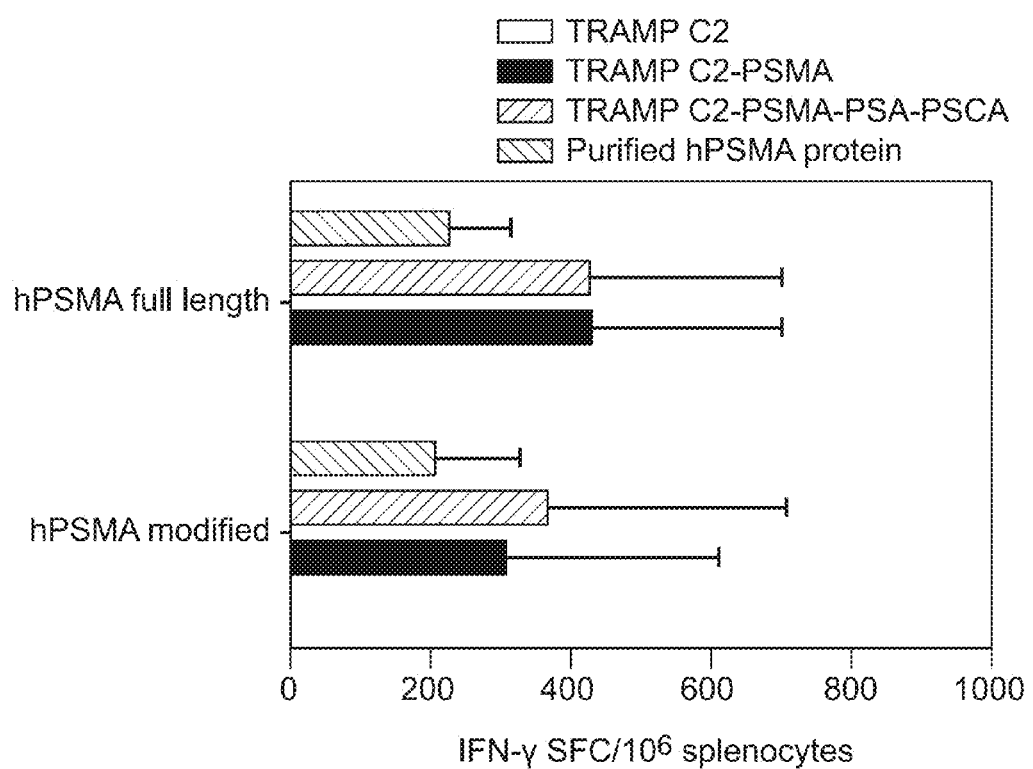
FIG. 26. Graph depicting results of a representative study that evaluates the T cell immune response elicited by human PSMA modified antigen (amino acids 15-750) versus full-length human PSMA (amino acids 1-750) in C57BL/6 mice.

FIG. 26 shows the results of a representative study to evaluate the T cell immune response elicited by the human PSMA modified (aa 15-750) versus full-length human PSMA (aa 1-750) in C57BL/6 mice determined by IFN-γ ELISPOT assay. Five (5) mice per group were primed on day 0 and boosted PMED with DNA vaccines expressing hPSMA modified or hPSMA full-length proteins on days 14 and 28. On day 35, the response elicited against the hPSMA full-length protein were compared by determining T cell responses to TRAMP C2-PSMA or purified human PSMA ECD protein (referred to Purified hPSMA protein in FIG. 26) by IFNγ ELISPOT assay. TRAMP C2 cells served as a background control for the assay. The magnitude of the IFN-γ T cell responses elicited to TRAMP C2-PSMA or purified hPSMA protein were not significantly different (two-way ANOVA, p-value >0.05) between groups. These results indicate that the DNA vaccines expressing hPSMA modified and hPSMA full-length proteins elicit equivalent T cell immune responses in C57BL/6 mice.

FIGS. 27A and 27B show the results of a representative study to evaluate the T cell immune response of human PSMA modified antigen (aa 15-750) versus full-length human PSMA antigen (aa 1-750) in Pasteur (HLA-A2/DR1) transgenic mice by IFN-γ ELISPOT assay. Ten (10) mice per group were primed on day 0 and boosted PMED with DNA vaccines encoding hPSMA modified or hPSMA full-length protein on days 14 and 28. On day 35, the T cell response elicited against the hPSMA full-length protein was determined by IFN-ELISPOT assay using (A) PSMA derived HLA-A2-restricted peptides representing known CD8+ epitopes and (B) SK-Mel5 cells transduced with Ad-hPSMA or purified hPSMA full-length protein. The hHER2 106 peptide and SK-Mel5 Ad-eGFP served as negative controls in the assays. The hPSMA modified vaccine elicited the highest magnitude of IFN-γ T cell immune responses to the HLA-A2-restricted CD8+ T cell epitopes, although the difference between groups was not significant (two-way ANOVA, p-value >0.05). Similarly, the hPSMA modified vaccine elicited the highest magnitude of immune response against the SK-Mel5 cells transduced with Ad-hPSMA and significantly (two-way ANOVA, p-value >0.05) higher frequencies of IFN-γ SFC to the purified hPSMA protein. These results demonstrate that the DNA vaccine expressing the hPSMA modified protein is more potent in inducing T cell responses to the hPSMA protein than the hPSMA full-length protein in Pasteur (HLA-A2/DR1) transgenic mice.

Figure 28:
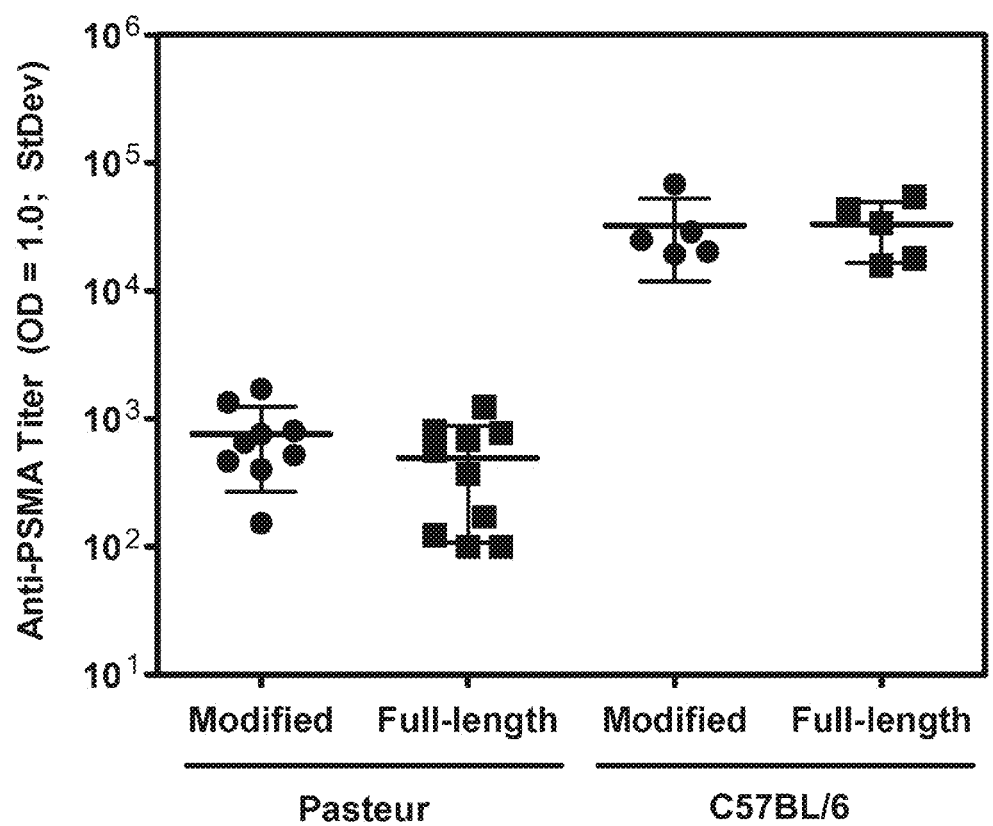
FIG. 28. Graph depicting results of a representative study that evaluates the immunogenicity of the human modified and full-length PSMA vaccines by anti-PSMA antibody titers.

FIG. 28 shows the results of a representative study that evaluates the immunogenicity of the human modified and full-length PSMA vaccines by anti-PSMA antibody titers. Briefly, mice were primed on day 0 and boosted with PMED on days 14 and 28. Nine Pasteur mice were vaccinated with modified PSMA, 10 Pasteur mice were vaccinated with full-length PSMA, and 5 C57BL/6 mice per group were vaccinated with either modified or full-length PSMA. On day 35, serum anti-PSMA antibody titers were assessed by ELISA. As expected, C57BL/6 mice generated significantly greater anti-PSMA antibody titers compared to Pasteur mice (one-way ANOVA). Comparing antibody titers between the same strains of mice, there was no significant difference in the antibody titers between mice vaccinated with modified and full-length PSMA (one-way ANOVA, p-value >0.05). Overall, these results demonstrate that vaccination with the full-length version of human PSMA generates an equivalent anti-PSMA antibody titer compared to the human modified PSMA vaccine.

Figure 29:
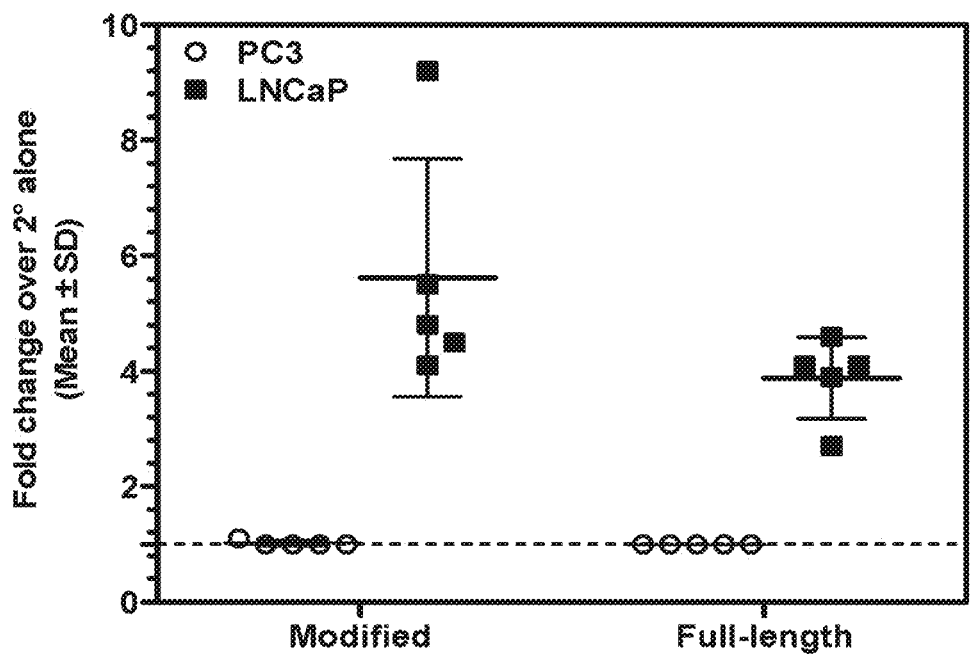
FIG. 29. Graph depicting results of a representative study that evaluates the immunogenicity of the human modified and full-length PSMA vaccines by anti-PSMA antibody cell-surface binding.

FIG. 29 shows the results of a representative study that evaluates the immunogenicity of the human modified and full-length PSMA vaccines by anti-PSMA antibody cell-surface binding. Briefly, 5 C57BL/6 mice per group were primed on day 0 and boosted with PMED on days 14 and 28. On day 35, recognition of cell-surface native PSMA was assessed by serum antibody binding to LNCaP and PC3 cells. The PC3 cells served as a background control for the assay. There were no significant differences in the anti-PSMA antibody binding to LNCaP cells between mice vaccinated with modified or full-length PSMA (one-way ANOVA, p-value >0.05). The fold change over secondary antibody alone for the J591-A mAb was 14.3 (data not shown). Overall, these data demonstrate that it is feasible to generate anti-PSMA-specific antibodies that recognized native PSMA following either modified or full-length PSMA vaccination.

Example 8

Effect of Anti-CTLA-4 Antibody on Vaccine-Induced Immune Response

The effect of local administration of anti-CTLA-4 monoclonal antibody (CP-675, 206) on the immune responses induced by a human PSMA nucleic acid molecule provided by the invention was investigated in a monkey study, in which the immune response was assessed by measuring PSMA specific T cell responses using an IFNγ ELISPOT assay.

Animal Treatment and Sample Collection.

Three groups of male Indian rhesus macaques, five to six (#1 to 5 or 6) per each test group, were immunized with a nucleic acid (SEQ ID NO: 10) that encodes a human PSMA modified antigen (SEQ ID NO: 9) delivered by adenovirus (1e11 V.P. injected intramuscularly) followed by 2 DNA immunizations (8 actuations/immunization, 4 actuations per each right and left side of the lower abdomen) by PMED with 6 and 9 week intervals respectively. Animals in Groups 2 and 3 additionally received bilateral intradermal injections of 3 mg of CpG (PF-03512676) subsequently after the PMED immunization in proximity to each inguinal draining lymph node. Group 2 also received intravenous injections of anti-CTLA-4 monoclonal antibody (CP-675, 206) at 10 mg/kg and group 3 received intradermal injections of anti-CTLA-4 monoclonal antibody (CP-675, 206) at 5 mg/kg in proximity to each left and right inguinal vaccine draining lymph node at the time of the second PMED immunization.

Peripheral blood samples were collected from each animal sixteen days after the last PMED immunization. Peripheral blood mononuclear cells (PBMCs) were isolated from the samples and were subjected to an IFNγ ELISPOT assay to measure the PSMA specific T cell responses. Briefly, 4e5 PBMCs from individual animals were plated per well with pools of PSMA specific peptides each at 2 ug/ml hPSMA ECD protein at 10 ug/ml, rhesus PSMA ECD protein at 10 ug/ml or nonspecific control peptides (human HER2 peptide pool) each at 2 ug/ml in IFNγ ELISPOT plates. The composition of each of the PSMA specific peptide pools is provided in Table 24A. The plates were incubated for 16 hrs at 37° C. and 5% CO2 and washed and developed after incubation as per manufacturer's instruction. The number of IFNγ spot forming cells (SFC) were counted by CTL reader. Each condition was performed in duplicates. The results are presented in Table 24B, which shows the average number of the PSMA specific SFC from the triplicates subtracting the average number of SFC from the nonspecific control peptides normalized to 1e6 PBMCs. A indicates that the count is not accurate because the numbers of spots were too numerous to count.

IFNγ ELISPOT Assay Procedure.

A capture antibody specific to IFNγ (BD Bioscience, #51-2525kc) is coated onto a polyvinylidene fluoride (PVDF) membrane in a microplate overnight at 4° C. The plate is blocked with serum/protein to prevent nonspecific binding to the antibody. After blocking, effector cells (such as splenocytes isolated from immunized mice or PBMCs isolated from rhesus macaques) and targets (such as PSMA peptides from peptide library, target cells pulsed with antigen specific peptides or tumor cells expressing the relevant antigens) are added to the wells and incubated overnight at 37° C. in a 5% $CO_2$ incubator. Cytokine secreted by effector cells are captured by the coating antibody on the surface of the PVDF membrane. After removing the cells and culture media, 100 μl of a biotinylated polyclonal anti-humanIFNγ antibody was added to each of the wells for detection. The spots are visualized by adding streptavidin-horseradish peroxidase and the precipitate substrate, 3-amino-9-ethylcarbazole (AEC), to yield a red color spot as per manufacturer's (Mabtech) protocol. Each spot represents a single cytokine producing T cell.

Results.

Table 24B. shows the results of a representative IFNγ ELISPOT assay that evaluates and compares the T cell responses induced by the vaccine without (group 1) or with anti-CTLA-4 monoclonal antibody (CP-675, 206) given either systemically by intravenous injections (group 2) or locally by intradermal injections in proximity to the vaccine draining lymph node (group 3). As shown in Table 1B, PSMA vaccine induced measurable IFNγ T cell responses to multiple PSMA specific peptides and proteins in the absence of CpG (PF-03512676) and anti-CTLA-4 monoclonal antibody (CP-675, 206). The responses were modestly enhanced by the addition of CpG (PF-03512676) and systemic delivery of the anti-CTLA-4 antibody (CP-675, 206; group 2). However, a more potent and significant enhancement of the response to multiple PSMA peptides and PSMA protein was observed when the anti-CTLA-4 monoclonal antibody (CP-675, 206) was delivered locally by intradermal injections in proximity to the vaccine draining lymph node (group 3).

TABLE 24A

PSMA peptide pools: Each peptide pool (i.e., P1, P2, P3, H1, H2, R1, and R2) is composed of 15mer peptides from either human PSMA protein (hPMSA protein) or rhesus PSMA protein (rPMSA protein) sequences as indicated below. The amino acid position of the N and C-terminal end of each peptide is indicated.

| P1 | P2 | P3 | H1 | H2 | R1 | R2 |
|---|---|---|---|---|---|---|
| h 1-15 | h 249-263 | h 449-463 | h 33-47 | h 465-479 | r 33-47 | r 465-479 |
| h 5-19 | h 253-267 | h 453-467 | h 37-51 | h 469-483 | r 37-51 | r 469-483 |
| h 9-23 | h 257-271 | h 457-471 | h 41-55 | h 473-487 | r 41-55 | r 473-487 |
| h 13-27 | h 261-275 | h 485-499 | h 45-59 | h 477-491 | r 45-59 | r 477-491 |
| h 17-31 | h 265-279 | h 489-503 | h 61-75 | h 481-495 | r 61-75 | r 481-495 |
| h 21-35 | h 269-283 | h 493-507 | h 65-79 | h 537-551 | r 65-79 | r 537-551 |
| h 25-39 | h 273-287 | h 497-511 | h 69-83 | h 541-555 | r 69-83 | r 541-555 |
| h 29-43 | h 277-291 | h 501-515 | h 73-87 | h 545-559 | r 73-87 | r 545-559 |
| h 49-63 | h 281-295 | h 505-519 | h 97-111 | h 577-591 | r 97-111 | r 577-591 |
| h 53-67 | h 285-299 | h 509-523 | h 101-115 | h 581-595 | r 101-115 | r 581-595 |
| h 57-71 | h 289-303 | h 513-527 | h 105-119 | h 585-599 | r 105-119 | r 585-599 |
| h 77-91 | h 293-307 | h 517-531 | h 109-123 | h 589-603 | r 109-123 | r 589-603 |
| h 81-95 | h 297-311 | h 521-535 | h 137-151 | h 601-615 | r 137-151 | r 601-615 |
| h 85-99 | h 317-331 | h 525-539 | h 141-155 | h 605-619 | r 141-155 | r 605-619 |
| h 89-103 | h 321-335 | h 529-543 | h 145-159 | h 609-623 | r 145-159 | r 609-623 |

TABLE 24A-continued

PSMA peptide pools: Each peptide pool (i.e., P1, P2, P3, H1, H2, R1, and R2)
is composed of 15mer peptides from either human PSMA protein (hPMSA
protein) or rhesus PSMA protein (rPMSA protein) sequences as indicated below.
The amino acid position of the N and C-terminal end of each peptide is indicated.

| P1 | P2 | P3 | H1 | H2 | R1 | R2 |
|---|---|---|---|---|---|---|
| h 93-107 | h 325-339 | h 533-547 | h 149-163 | h 613-627 | r 149-163 | r 613-627 |
| h 113-127 | h 329-343 | h 549-563 | h 209-223 | h 637-651 | r 209-223 | r 637-651 |
| h 117-131 | h 333-347 | h 553-567 | h 213-227 | h 641-655 | r 213-227 | r 641-655 |
| h 121-135 | h 353-367 | h 557-571 | h 217-231 | h 645-659 | r 217-231 | r 645-659 |
| h 125-139 | h 357-371 | h 561-575 | h 221-235 | h 649-663 | r 221-235 | r 649-663 |
| h 129-143 | h 361-375 | h 565-579 | h 301-315 | h 653-667 | r 301-315 | r 653-667 |
| h 133-147 | h 365-379 | h 569-583 | h 305-319 | h 657-671 | r 305-319 | r 657-671 |
| h 153-167 | h 369-383 | h 573-587 | h 309-323 | h 709-723 | r 309-323 | r 709-723 |
| h 157-171 | h 373-387 | h 593-607 | h 313-327 | h 713-727 | r 313-327 | r 713-727 |
| h 161-175 | h 377-391 | h 597-611 | h 337-351 | h 717-731 | r 337-351 | r 717-731 |
| h 165-179 | h 381-395 | h 617-631 | h 341-355 | h 721-735 | r 341-355 | r 721-735 |
| h 169-183 | h 385-399 | h 621-635 | h 345-359 | h 725-739 | r 345-359 | r 725-739 |
| h 173-187 | h 389-403 | h 625-639 | h 349-363 | h 729-743 | r 349-363 | r 729-743 |
| h 177-191 | h 393-407 | h 629-643 | h 461-475 | h 733-747 | r 461-475 | r 733-747 |
| h 181-195 | h 397-411 | h 633-647 | | | | |
| h 185-199 | h 401-415 | h 661-675 | | | | |
| h 189-203 | h 405-419 | h 665-679 | | | | |
| h 193-207 | h 409-423 | h 669-683 | | | | |
| h 197-211 | h 413-427 | h 673-687 | | | | |
| h 201-215 | h 417-431 | h 677-691 | | | | |
| h 205-219 | h 421-435 | h 681-695 | | | | |
| h 225-239 | h 425-439 | h 685-699 | | | | |
| h 229-243 | h 429-443 | h 689-703 | | | | |
| h 233-247 | h 433-447 | h 693-707 | | | | |
| h 237-251 | h 437-451 | h 697-711 | | | | |
| h 241-255 | h 441-455 | h 701-715 | | | | |
| h 245-259 | h 445-459 | h 705-719 | | | | |
| | | h 737-750 | | | | |

TABLE 24B

T cell responses induced by the vaccine without (Group 1) or with anti-
CTLA-4 antibody Tremelimumab (CP-675, 206) given systemically by
intravenous injections (Group 2) or local intradermal injections (Group 3).

| Group | animal ID | P1 | P2 | P3 | H1 | H2 | hPSMA protein | R1 | R2 | rPSMA protein |
|---|---|---|---|---|---|---|---|---|---|---|
| 1. | #1 | 7.5 | 62.5 | 0.0 | 210.0 | 172.5 | 455.0 | 3.8 | 1.3 | 0.0 |
| no | #2 | 11.3 | 48.8 | 0.0 | 17.5 | 146.3 | 111.3 | 0.0 | 3.8 | 0.0 |
| immune | #3 | 12.5 | 342.5 | 13.8 | 115.0 | 517.5 | 705.0 | 12.5 | 40.0 | 138.8 |
| modulator | #4 | 6.3 | 23.8 | 0.0 | 211.3 | 38.8 | 45.0 | 5.0 | 7.5 | 7.5 |
| | #5 | 0.0 | 16.3 | 0.0 | 0.0 | 52.5 | 45.0 | 0.0 | 0.0 | 0.0 |
| | #6 | 6.3 | 442.5 | 21.3 | 42.5 | 238.5 | 736.3 | 11.3 | 8.8 | 93.8 |
| 2. | #1 | 23.8 | 57.5 | 1.3 | 71.3 | 292.5 | 278.8 | 6.3 | 6.3 | 0.0 |
| with | #2 | 0.0 | 61.3 | 0.0 | 2.5 | 108.8 | 78.8 | 0.0 | 6.3 | 3.8 |
| aCTLA4 | #3 | 58.8 | 41.3 | 7.5 | 1063.8 | 82.5 | 1197.5 | 22.5 | 7.5 | 1.3 |
| (IV) | #4 | 25.0 | 318.8 | 27.5 | 147.5 | 983.8 | 1046.3 | 26.3 | 86.3 | 2.5 |
| | #5 | 15.0 | 312.5 | 5.0 | 402.5 | 573.8 | 707.5 | 97.5 | 25.0 | 20.0 |
| 3. | #1 | 48.8 | 1236.3^ | 38.8 | 405.0 | 1236.3^ | 1236.8^ | 218.8 | 490.0 | 1120.0 |
| with | #2 | 113.8 | 946.3 | 17.5 | 293.8 | 1247.5^ | 1247.5^ | 162.5 | 86.3 | 5.0 |
| aCTLA4 | #3 | 16.3 | 1248.8^ | 6.3 | 465.0 | 1248.8^ | 1248.8^ | 187.5 | 295.0 | 11.3 |
| (ID) | #4 | 6.3 | 828.8 | 6.3 | 1006.3 | 1247.5^ | 1247.5^ | 142.5 | 30.0 | 17.5 |
| | #5 | 152.5 | 566.3 | 18.8 | 757.5 | 1173.8 | 1242.5^ | 287.5 | 57.5 | 110.0 |

Example 9

Systemic Exposure of CTLA-4 Antibody after Administration in Monkeys

The blood levels of anti-CTLA-4 antibody Tremelimumab (CP675206) were investigated in Indian Rhesus macaques after the antibody was administered by intradermal or intravenous injections.

Animal Treatment and Sample Collection.

Three animals per treatment group were injected with the anti-CTLA-4 antibody Tremelimumab at 10 mg/kg, either with a single intravenous injection into the saphenous vein or multiple 0.2 ml intradermal bilateral injections in the upper thigh in proximity to the inguinal draining lymph nodes. Blood samples were collected at 0, 1, 2, 4, 8, 12, 24, and 48 hrs post injection into 2.0 ml vaccutainer tubes containing lithium heparin as the anticoagulant. Plasma was collected from the supernatant in the vaccutainer tubes after centrifugation at 1500×g at 4° C. for 10 min. The levels of Tremelimumab in the plasma was measured by a quantitative ELISA assay according to the procedure provided below.

Tremelimumab Quantitative ELISA Assay Procedure.

The 384-well high bind assay plates (VWR-Greiner Bio-One Cat#82051-264) were coated with 25 μl/well of CD-152 (CTLA-4; Ancell Immunology Research Products Cat#501-020) at 1.0 μg/ml in 100 mM carbonate-bicarbonate coating buffer and incubated overnight at 4° C. Plates were washed ×6 with 1×PBS-Tween (0.01M PBS pH 7.4/0.05% Tween 20) and blocked using 40 μL/well of 5% FBS/1×PBS-Tween and incubated shaking at 600 rpm RT for 1 hour. Standards were prepared by making the following dilutions of Tremelimumab: 200, 67, 22, 7.4, 2.5, 0.82, 0.27, 0.09 and 0.03 ng/mL. The samples were diluted to 1:100, 1:1,000 and 1:10,000. The diluent consisted of 1% naive cynomolgus macaque sera and 5% FBS in 1×PBS-Tween (0.01M PBS pH 7.4/0.05% Tween 20). 25 μL/well of each standard, sample and diluent control were transferred in duplicate into the plate and incubated shaking at 600 rpm RT for 1 hour. After washing ×6 with 1×PBS-Tween, 25 μL/well of secondary antibody (goat anti-human IgG HRP, Southern Biotech Cat#9042-05) at a 1:5,000 dilution with 1×PBS-Tween was added and then incubated shaking at 600 rpm room temperature for 1 hour. After washing ×6 with 1×PBS-Tween, 25 μL/well of TMB Peroxidase EIA-Substrate (solution A+B) (Bio-Rad Cat#172-1067) were added and the plates were incubated at RT for 4 minutes. The colorimetric reaction was stopped by addition of 12.5 μL/well 1N Sulfuric acid and the absorbance then read at 450 nm. The amount of Tremelimumab in each sample was quantified using the standard curve with 0.27 to 67 ng/mL used as the quantitative range.

Results.

Figure 30:
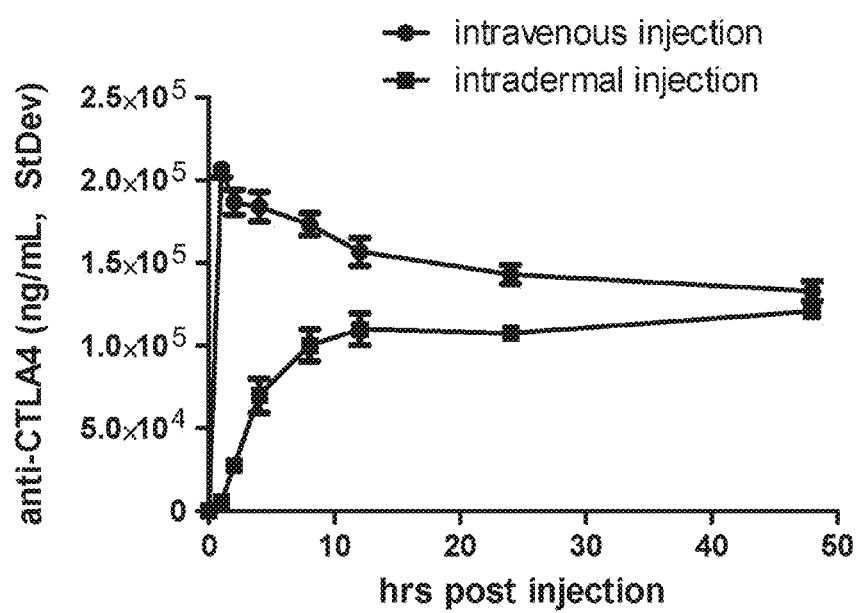
FIG. 30. Graph depicting results of a representative study that evaluates the blood anti-CTLA-4 monoclonal antibody levels measured by competitive ELISA in Indian Rhesus macaques injected with anti-CTLA-4 (CP-675, 206) at 10 mg/kg.

The plasma anti-CTLA-4 levels from a representative study are presented in FIG. 30. As shown, intradermal injection of the anti-CTLA-4 antibody Tremelimumab displays a slower release kinetics of the antibody in the blood and a lower systemic exposure ($AUC_{0-24}$=4.9×10$^6$ ng·hr/ml) profile than intravenous injections ($AUC_{0-24}$=7.2×10$^6$ ng·hr/ml).

Example 10

Effect of Anti-CTLA-4 Antibody on Vaccine-Induced Immune Responses in Mice

Study Procedure.

Female BALB/c mice, 6 per group, were primed and boosted with rHer-2 expressing DNA by PMED separated by a four week interval. 150 μg of the monoclonal antibody specific to mouse CTLA-4 (clone 9H10, Bioxcell or #BE0131) or isotype control monoclonal antibodies (Bioxcell #BE0091) was administered on the days of PMED actuation and 100 μg on the days after PMED by local intradermal or systemic intraperitoneal injections as indicated in the legends. The polyfunctional (multi-cytokine positive) T cell immune responses were measured from splenocytes isolated from individual mice 7 days after the last PMED immunizations by ICS assay. After a 5 hr stimulation with a vaccine specific epitope peptide (rHer-2 specific antigen specific CD8 (p66), CD4 (p169) epitope or irrelevant peptide HBV (core antigen p87)) at 10 μg/ml, the splenocytes were first stained for CD4, CD3 and CD8 which was followed by permeabilization and staining for IFNα, TNFα and IL-2 expression that was analyzed by flow cytometry. The total number of antigen specific single, double or triple cytokine positive T cells per total spleen of each animal is calculated by subtracting the responses to the irrelevant peptide HBV from the vaccine specific responses and normalized by the total number of splenocytes isolated per spleen.

Results.

FIGS. 31A and 31B show the results of a representative study that evaluates the immunomodulatory activity of anti-CTLA-4 monoclonal antibody (clone 9H10) on the quality of the vaccine induced immune responses by intracellular cytokine staining assay. Seven days after the last PMED, significant increases in antigen specific single and double cytokine positive CD8 T cell responses by the local intradermal delivery of anti-CTLA-4 and double and triple cytokine positive CD8 T cell responses by the systemic delivery was observed. Additionally, significant increases in antigen specific single cytokine positive CD4 T cells by intradermal delivery and double cytokine positive cells by systemic delivery of anti-CTLA-4 was observed (*indicates $P<0.05$ by Student's T-test).

Example 11

Synergistic Effect of Sunitinib in Combination with an Anti-Cancer Vaccine

Study Procedure.

The Anti-tumor efficacy of sunitinib malate in combination with an anti-cancer DNA vaccine was investigated in BALB/neuT transgenic female mice. Heterozygote BALB/neuT transgenic female mice that express rat Her-2 (rHer-2) tumor associate antigen were implanted subcutaneously with 1e6 TUBO cells expressing rHer-2 which are derived from the spontaneous mammary tumors of BALB/neuT mice. After 7 days post tumor cell implantation, the mice were dosed once a day orally with either vehicle or sunitinib malate at doses as indicated in the legends. Three days after the initiation of sunitinib malate therapy, the mice were immunized with regimens comprised of either (a) control vaccine that expresses an antigen that is not expressed in the tumor or the mouse or (b) DNA cancer vaccine construct that expresses a rat Her-2 antigen of SEQ ID NO: 54 (rHER2) which is expressed in the tumor and the mouse. The tumor growth rate was analyzed by measuring the long (a) and short diameter (b) of the subcutaneous TUBO tumors twice a week and calculating the volume as $a \times b^2 \times 0.5$ mm$^3$. The average and standard error of the mean of the tumor volumes from 10 mice per each treatment group are plotted against the days after tumor implantation.

Results.

Figure 32:
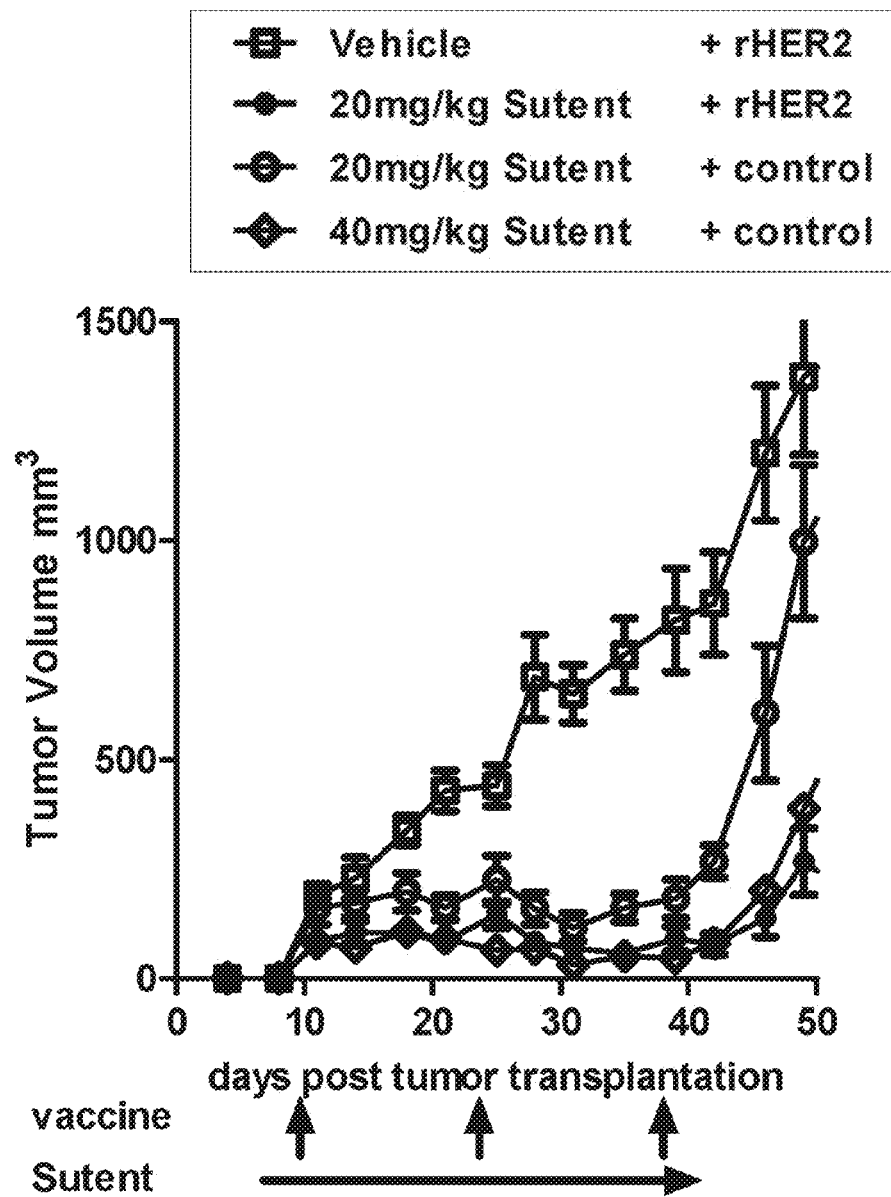
FIG. 32. Graph depicting results of a representative study that evaluates the effect of sunitinib malate (Sutent) on the anti-tumor efficacy of a cancer vaccine (rHER2) in mice, in which the subcutaneous tumor growth rate was measured.

FIG. 32 shows the results of a representative study that evaluates and compares the subcutaneous tumor growth rate upon treatment with sunitinib malate as a monotherapy or in combination with the DNA cancer vaccine. While the tumors from mice that received the DNA cancer vaccine (rHER2: intramuscular injection of 1e9 V.P. of rHer-2 expressing adenovirus followed by two biweekly actuations of rHer-2 expressing DNA by PMED) continued to grow rapidly, the tumors from mice that received sunitinib malate at either 20 mg/kg or 40 mg/kg doses with control vaccines (control: intramuscular injection of 1e9 V.P. of eGFP expressing adenovirus followed by two biweekly, actuations of HBV core antigen expressing DNA by PMED) significantly decreased the tumor growth rate, with 20 mg/kg displaying suboptimal efficacy compared to the 40 mg/kg dose. However when the cancer vaccine was co-administered with the suboptimal dose of sunitinib malate at 20 mg/kg, the tumors grew at a much slower growth rate than in mice treated with the same dose of sunitinib malate co-administered with a control vaccine and similar to that of mice treated with sunitinib malate at a higher dose. Cancer vaccine provides additional therapeutic benefit to mice that received suboptimal doses of sunitinib malate.

FIGS. 33A-33D show the individual tumor growth rates of mice from a representative study that evaluates and compares the anti-tumor efficacy of sunitinib malate at 20 mg/kg with control (control) or the DNA cancer vaccine (rHER2). Briefly, after 7 days post tumor cell implantation, ten mice per treatment group were daily orally dosed with either vehicle or 20 mg/kg sunitinib malate (Sutent) for 34 days. Three days after the initiation of Sutent dosing, a series of immunizations, primed by Adenovirus followed by PMED, were initiated that continued after the discontinuation of Sutent therapy. Specifically the mice were immunized with either control vaccine comprised of an intramuscular injection of 1e9 V.P. of eGFP expressing adenovirus subsequently followed by two biweekly, two 9 days and four weekly actuations of DNA expressing HBV core and surface antigens by PMED or cancer vaccine comprised of rHer-2 expressing adenovirus and DNA instead. The tumors of the animals that received vehicle with the control vaccine became measurable around day 7 and continued growing reaching 2000 mm$^3$ after 50 days post tumor implant. The tumor growth of the animals that received Sutent with control vaccine was significantly impaired until Sutent therapy was discontinued. The tumors displayed a rapid growth rate immediately after the discontinuation of Sutent, the majority reaching 2000 mm$^3$ after 50 days post tumor implant. The tumor growth rate of animals that only received the cancer vaccinations was modestly slower than the animals that did not receive cancer vaccine or Sutent. The combination of cancer vaccine with Sutent not only suppressed the tumor growth during Sutent therapy (FIG. 33) but also significantly impaired the progression of the tumor in 60% of the animals after discontinuation of Sutent treatment.

Figure 34:
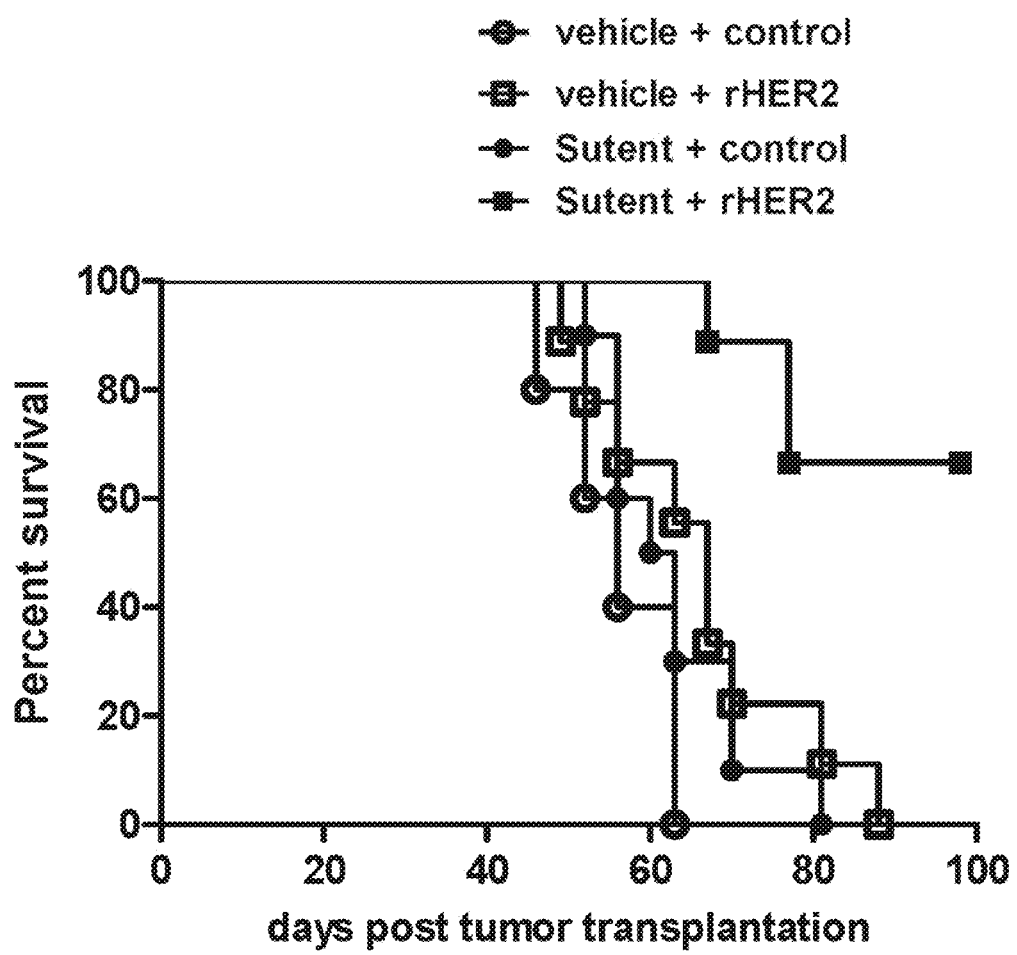
FIG. 34. Graph showing the Kaplan-Meier survival curves of the groups of mice from the study described in FIGS. 33A-33D that evaluates the effect of sunitinib malate (Sutent) on the anti-tumor efficacy of a cancer vaccine (rHER2).
Figure 35A:
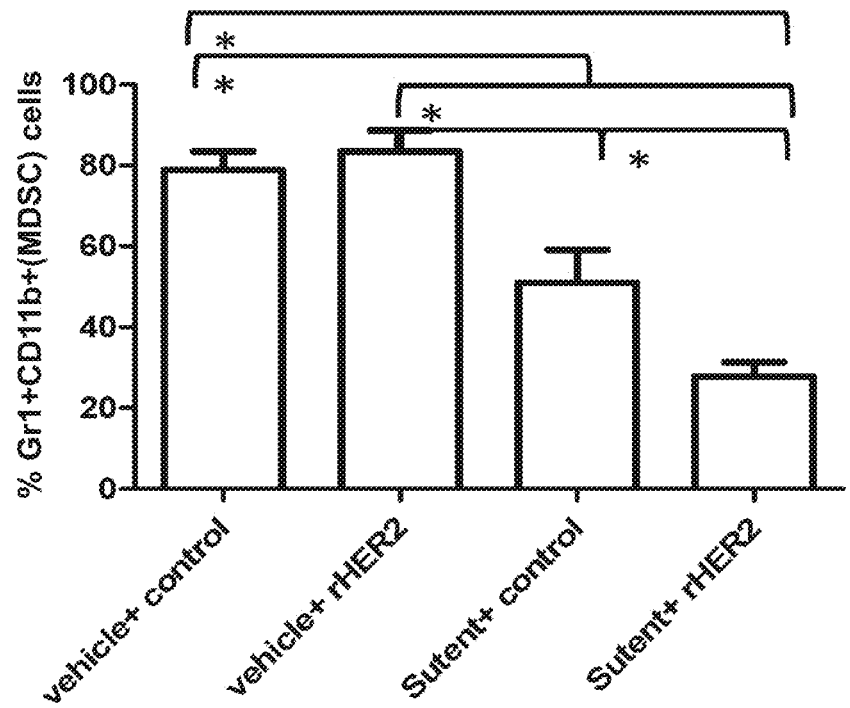
FIGS. 35A, 35B. Graphs showing changes in myeloid derived suppressor cells (Gr1+CD11b+.
Figure 35B:
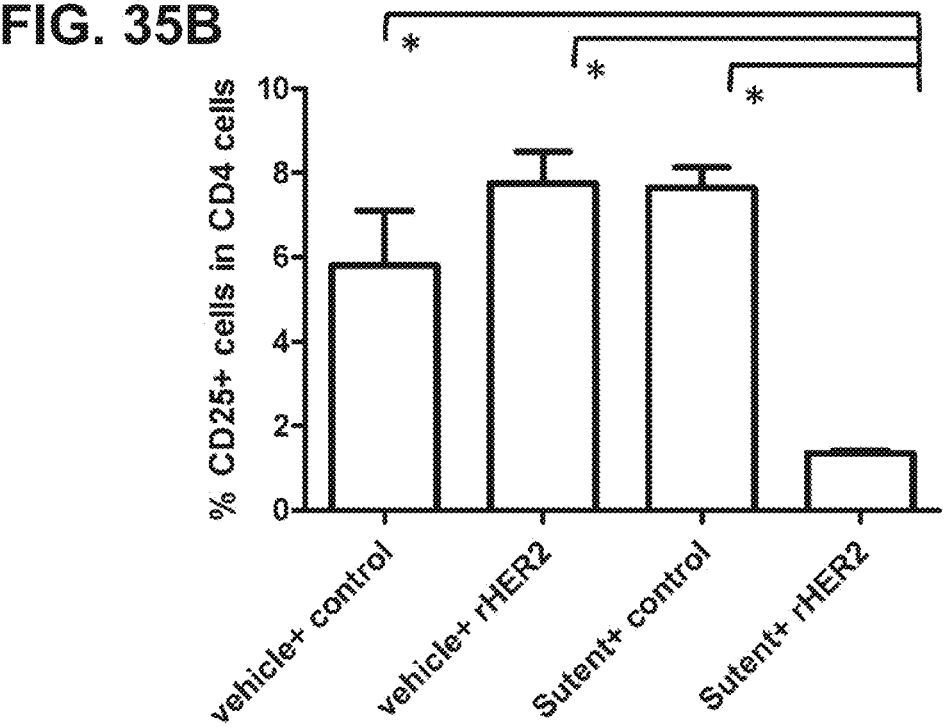

FIG. 34 shows the Kaplan-Meier survival curve of the groups of mice from the study described in FIGS. 33A-33D FIG. 2B that evaluates the anti-tumor efficacy of Sutent with the control (control) or cancer vaccine (rHER2). The mice were sacrificed when the tumor volume reached 2000 mm$^3$ according to IAUCUC guidelines. Only mice treated with Sutent (at 20 mg/kg) and cancer vaccine displayed a significantly prolonged survival compared to mice either treated with vehicle and control vaccine, cancer vaccine without Sutent or Sutent without cancer vaccine (*P<0.01 by Log-rank Test).

FIGS. 35A-35D show the percentage of myeloid derived suppressor cells (Gr1+CD11b+) and Treg containing CD25+ CD4+ cells in the periphery blood from the groups of mice from the study described in FIGS. 33A-33D. Briefly, PBMCs were stained and analyzed by flow cytometry for the expression of Gr1, CD11b, CD3, CD4, and CD25 from submandibular bleeds of five mice from each group on d27 (20 days post the initiation of Sutent or vehicle treatment). The mean and standard error of the mean of each treatment group is shown. A statistically significant reduction of % myeloid derived suppressor cells was observed in mice that were treated by Sutent with either control or cancer vaccine compared to mice that did not receive Sutent nor cancer vaccine (vehicle+control). However significantly lower myeloid derived suppressor cells were observed in mice treated with the combination of Sutent with cancer vaccine (Sutent+rHER2) compared to mice that were treated with cancer vaccine without Sutent (vehicle+rHER2) or Sutent without cancer vaccine (Sutent+control). A statistically significant reduction of Treg containing CD25+CD4+ T cells in the CD4 population was observed by Sutent with cancer vaccine. These mice had significantly lower % of Treg containing CD25+CD4+ T cells in the CD4 population than mice that were treated with cancer vaccine without Sutent or Sutent without cancer vaccine in their blood. * indicates P<0.05 by Student's T-test.

Figure 36A:
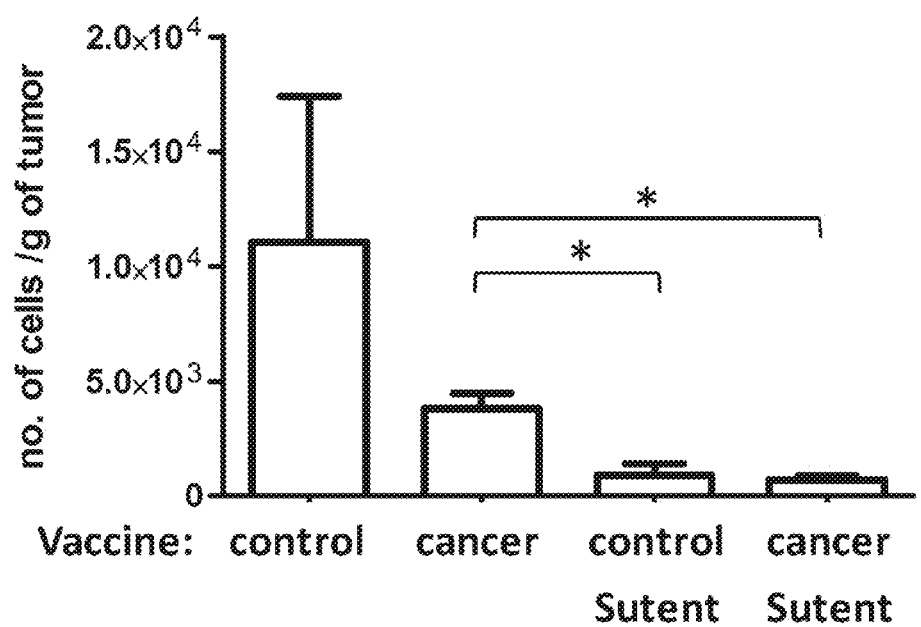
FIGS. 36A-36C. Graphs depicting results of a representative study in a mouse tumor model that evaluates the effect of sunitinib malate (Sutent) on the total number of (a) Tregs (CD4+CD25+Foxp3+.
Figure 36B:
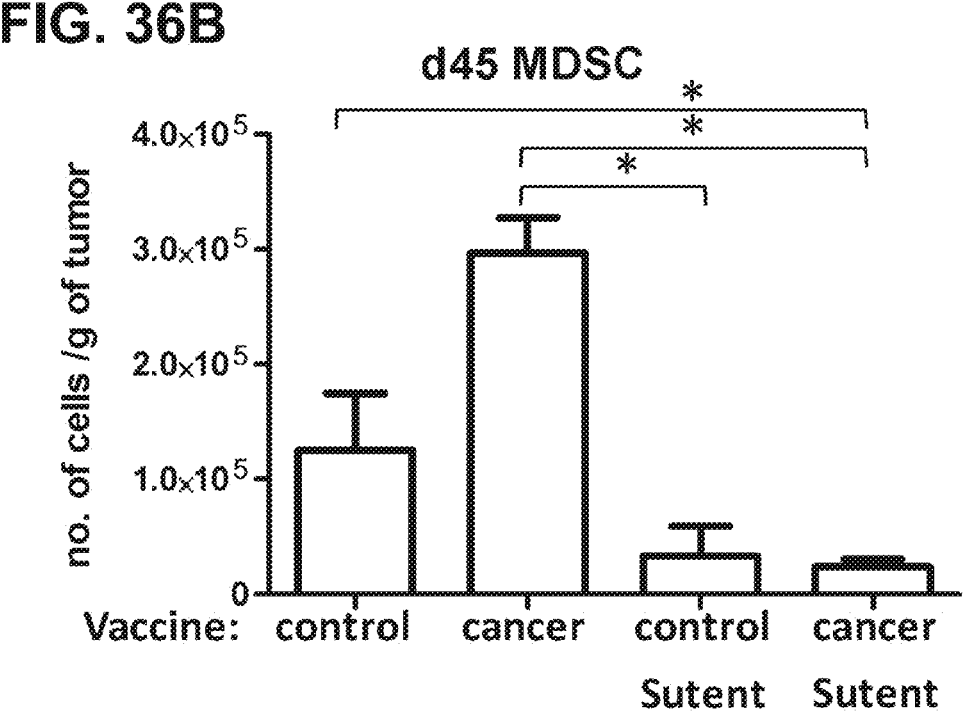
Figure 36C:
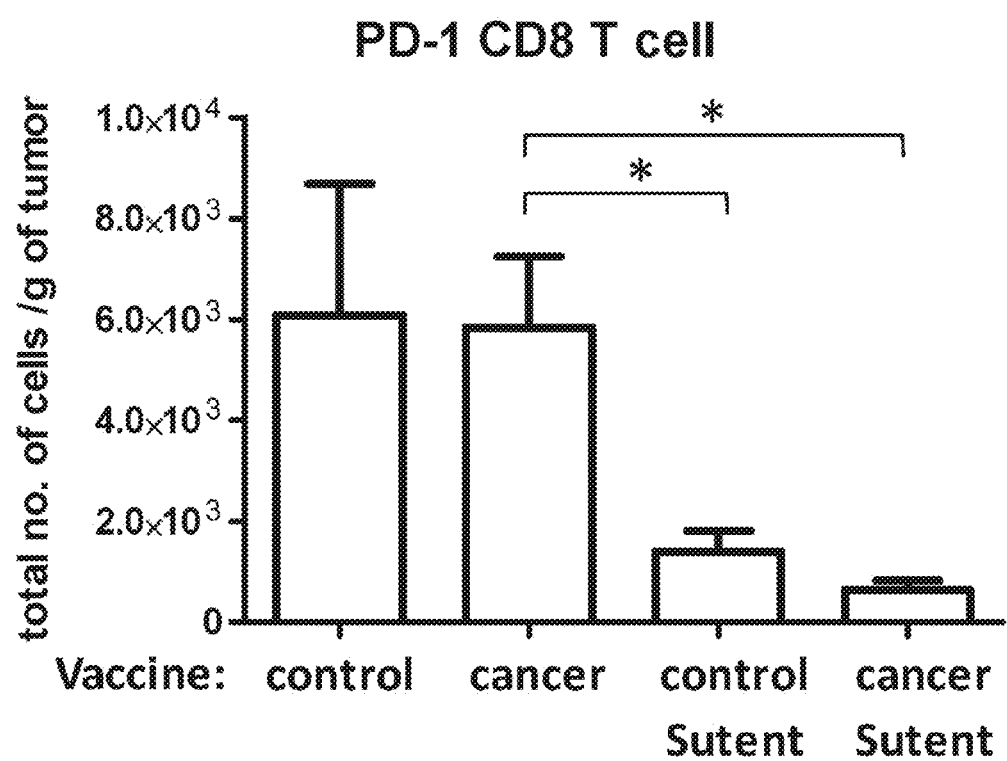

FIGS. 36A-36C show the total number of myeloid derived suppressor cells (Gr1+CD11b+), Tregs (CD4+ CD25+Foxp3+) and PD-1+CD8 T cells isolated from tumors of mice. Briefly, the mice were given a single daily oral dose of either vehicle or Sutent at 20 mg/kg three days after implantation with TUBO cells for 28 days. The same mice were immunized with either control vaccine comprised of an intramuscular injection of 1e9 V.P. of eGFP expressing adenovirus subsequently followed by two biweekly administrations of DNA expressing HBV core antigen delivered by PMED or cancer vaccine comprised of rHer-2 expressing adenovirus and DNA. An intradermal injection of 50 µg of CpG (PF-03512676) was given with the PMED administrations in proximity to the right side inguinal draining lymph node. Seven days after the second PMED and CpG administration, individual tumors were isolated, from 6 mice per treatment group. The single cell suspension prepared from the isolated subcutaneous tumors were stained by antibodies specific for Gr1, Cd11 b, CD3, CD8, CD25, FoxP3, and PD-1 and analyzed by flow cytometry. The mean and standard error of the mean of the total number of specific cells as indicated in the figures per µg of tumor from each treatment group is plotted. (*indicates P<0.05 by Student's T-test) While there was no significant difference in the frequency of immune suppressive Tregs or MDSC found in the tumor when mice were given cancer vaccine (A and B) compared to mice that received control vaccine (A and B), a significant reduction was observed when the mice were treated with Sutent (A and B) compared to mice that received cancer vaccine only. A reduction of PD-1+CD8 T cells was also observed in mice that were treated with Sutent (C) compared to mice that received cancer vaccine (C) only. Taken together, these data demonstrate that agents that reduce Tregs, MDSCs or CD8+PD-1+Tcells in combination with the vaccine would be beneficial in reducing tumor burden in tumor bearing animals.

Example 12

Anti-Cancer Efficacy of Vaccine in Combination with Sunitinib and Anti-CTLA-4 Antibody The anti-tumor efficacy of a cancer vaccine in combination with sunitinib and anti-CTLA-4 monoclonal antibody (clone 9D9) was investigated in subcutaneous TUBO tumor bearing BALB/neuT mice.

Study Procedure.

Briefly, ten mice per each group were daily orally dosed with either vehicle or sunitinib malate at 20 mg/kg starting at day 10 post tumor implant until day 64. Vaccination with DNA constructs that either encode no antigen (control vaccine) or a rat Her-2 antigen of SEQ Id NO: 54 (cancer vaccine) as adenovirus vectors initiated on day 13 subsequently followed by two weekly immunizations, two biweekly immunizations, and seven weekly immunizations of respective antigens (HBV antigens or rHer-2) by DNA. The groups of mice (closed circle and open triangle) that were treated with anti-murine CTLA-4 monoclonal antibody were intraperitoneally injected with 250 μg of the antibody on day 20, 27, 41, 55, 62, 69, 76, 83, 90, and 97 right after the PMED injections.

Results.

Figure 37:
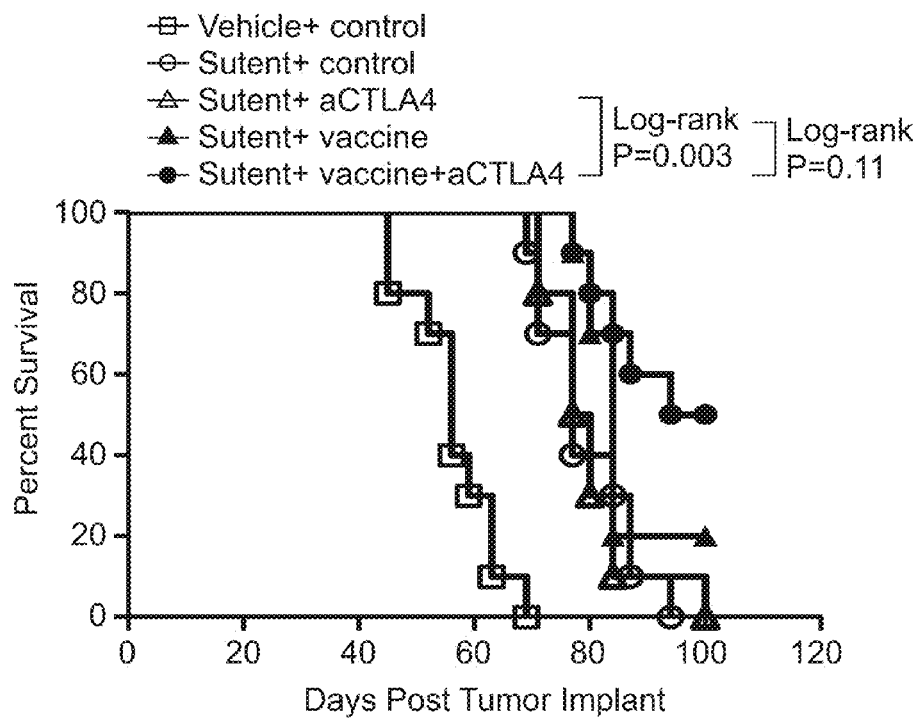
FIG. 37. Graph showing the Kaplan-Meier survival curves of the groups of mice from a representative study evaluating the effect of sunitinib malate (Sutent) and an anti-murine CTLA-4 monoclonal antibody (clone 9D9) on the anti-tumor efficacy of a cancer vaccine (vaccine) in subcutaneous TUBO tumor bearing BALB/neuT mice.

FIG. 37 shows the Kaplan-Meier survival curve of the groups of mice from a representative study evaluating the anti-tumor efficacy of sunitinib and anti-murine CTLA-4 monoclonal antibody (clone 9D9) in combination with a cancer vaccine. Increased survival time was observed in mice treated with Sutent with control vaccine (open circle), anti-murine CTLA-4 monoclonal antibody (open triangle) or cancer vaccine (closed triangle). A further increase of survival was observed in mice treated with Sutent and cancer vaccine in combination with anti-murine CTLA-4 (closed circle). P values were calculated by log-rank test.

Example 13

Systemic Exposure of Sunitinib and Anti-Cancer Efficacy of Anti-Cancer Vaccine in Combination with Low Dose Sunitinib Sunitinib Systemic Exposure Study.

The kinetics of blood sunitinib was investigated in BALB/neuT mice with subcutaneous TUBO tumors. Briefly, 20 mice per each treatment group were given Sutent orally, at 20 mg/kg once a day (SID) or at 10 mg/kg twice a day (BID) with 6 hr intervals, 6 days after tumor implantation. Submandibular blood from 2-3 mice was collected into lithium heparin tubes at several time points after Sutent dosing as indicated (0, 2, 4, 6, 8, 10, 12, and 24 hr). The plasma supernatant was recovered from the tubes after centrifugation at ×1000 g for 15 min. and the sunitinib levels from the plasma samples were measured by LC/MS/MS. The mean and standard error of the mean of each group at each time point is plotted.

Figure 38:
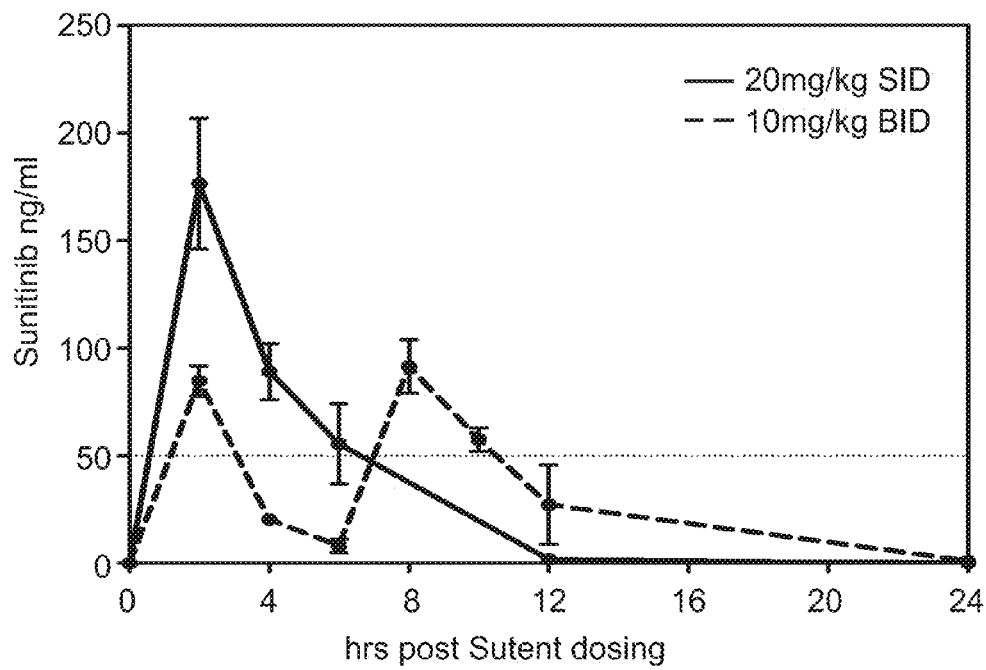
FIG. 38. Graph showing kinetics of the blood sunitinib levels of BALB/neuT mice with subcutaneous TUBO tumors.

Results are presented in FIG. 38. The mean and standard error of the mean of each group at each time point is plotted. The dotted horizontal line marks the minimum sunitinib blood level, 50 ng/ml, that is necessary to effectively inhibit tumor growth in monotherapy (Mendel, D., et al.: "In vivo antitumor activity of SU11248, a novel tyrosine kinase inhibitor targeting vascular endothelial growth factor and platelet-derived growth factor receptors: determination of a pharmacokinetic/pharmacodynamic relationship". Clinical Cancer Research, 203, 9:327-337). As shown, the blood suntinib levels in the mice that received either 20 mg/kg SID or 10 mg/kg BID only maintain the target effective dose of 50 ng/ml that effectively inhibits tumor growth transiently within 24 hr. The blood levels in 20 mg/kg SID group peaked above 50 ng/ml at 2 hrs, dropped to 50 ng/ml at 6 hrs and cleared the blood by 12 hrs post Sutent dosing he levels in the group that received 10 mg/kg BID peaked above 50 ng/ml at 2 hrs but rapidly dropped below 50 ng/ml by 4 hrs that peaked again 2 hrs after the second dose. The levels rapidly dropped to 50 ng/ml by 4 hrs and cleared the blood by 18 hrs after the second dose. Despite the bi-daily dosing regimen, the animals that received 10 mg/kg, remained to display lower duration of exposure at target concentration than the 20 mg/kg single daily dosing regimen.

Anti-Tumor Efficacy Study.

Anti-tumor efficacy of long term administration of low dose sunitinib in combination with an anti-cancer vaccine was investigated in BALB/neuT mice with subcutaneous TUBO tumors. Briefly, the mice were given sunitinib malate (Sutent) for 31 days at 20 mg/kg SID or for 104 days at 10 mg/kg BID and received either control vaccine or cancer vaccine. The control vaccine, which delivers no antigen, and the cancer vaccine, which delivers a rat her-2 antigen (rHer-2) of SEQ ID NO: 54, was given by adenovirus on day 9 subsequently followed by five biweekly administrations of the DNA by PMED delivering HBV antigens or rHer-2 respectively.

Figure 39:
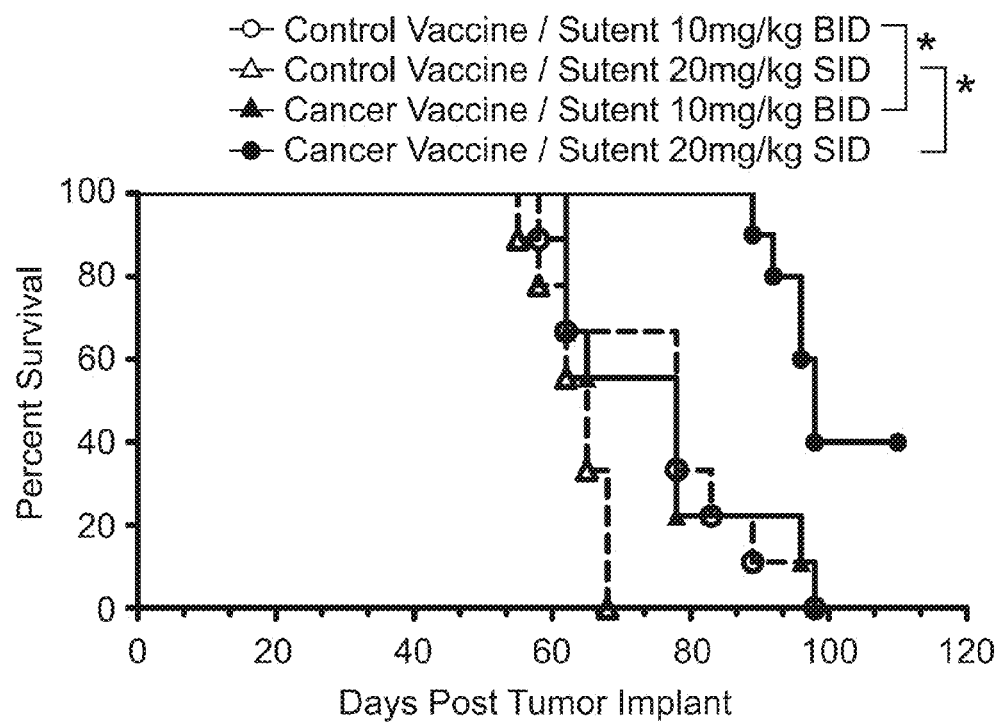
FIG. 39. Graph showing the Kaplan-Meier survival curves of the groups of mice from a representative study that evaluates the effect of sunitinib malate (Sutent) on the anti-tumor efficacy of a cancer vaccine in BALB/neuT mice with subcutaneous TUBO tumors.

The results are presented in FIG. 39. While the cancer vaccine improved the survival of mice given Sutent at 20 m/kg, there was even significant improvement of the survival of mice given Sutent at 10 mg/kg (*P=0.05 by Log rank test).

Example 14

Effect of CpG or CD40 Agonist on the Immune Responses Induced by Cancer Vaccine

Immunogenicity Studies in BALB/c Mice

The effect of local administration of immune modulators on the magnitude and quality of antigen specific immune responses induced by a cancer was investigated in BALB/c mice, in which the immune response was assessed by measuring rHER2 specific T cell responses using the IFNγ ELISPOT assay or intracellular cytokine staining assay. Briefly, 4 to 6 female BALB/c mice per group as indicated were immunized with DNA plasmid expression constructs encoding rHER2 antigen sequences (SEQ ID NO:54) by PMED delivery system. The immune modulators, CpG7909 (PF-03512676) and anti-CD40 monoclonal agonistic antibody, were administered locally by intradermal injections in proximity to the vaccine draining inguinal lymph node subsequently after the PMED actuations. Antigen specific T cell responses were measured by IFNγ ELISPOT or intracellular cytokine staining assay according to the procedure described below.

Intracellular Cytokine Staining (ICS) Assay

The rHer-2 specific polyfunctional (multi-cytokine positive) T cell immune responses were measured from splenocytes or PBMCs isolated from individual animals by ICS assay. Typically 1e6 splenocytes were incubated with Brefeldin A at 1 μg/ml and peptide stimulant (rHer-2 specific CD8 p66, rHer-2 specific CD4 p169 or irrelevant HBV p87) at 10 μg/ml for 5 hr at 37° C. in a 5% $CO_2$ incubator. After the stimulation, the splenocytes were washed and blocked with Fcγ block (anti-mouse CD16/CD32) for 10 min. at 4° C. followed by a 20 min staining with Live/dead aqua stain, anti-mouse CD3ePE-Cy7, anti-mouse CD8a Pacific blue, and anti-mouse CD45R/B220 PerCP-Cy5.5. The cells were washed, fixed with 4% paraformaldehyde overnight at 4° C., permeabilized with BD fix/perm solution for 30 min at RT and incubated with anti-mouse IFNγ APC, anti-mouse TNFα Alexa488 and anti-mouse IL-2 PE for 30 min at RT. The cells were washed and 20,000 CD4 or CD8 T cells were acquired for analysis by flow cytometry. The total number of antigen specific single, double or triple cytokine positive T cells per total spleen of each animal is calculated by subtracting the rHer-2 specific responses to the irrelevant peptide HBV from the vaccine specific responses and normalized to the total number of splenocytes isolated from the spleen.

IFNγ ELISPOT Assay Results

Figure 40:
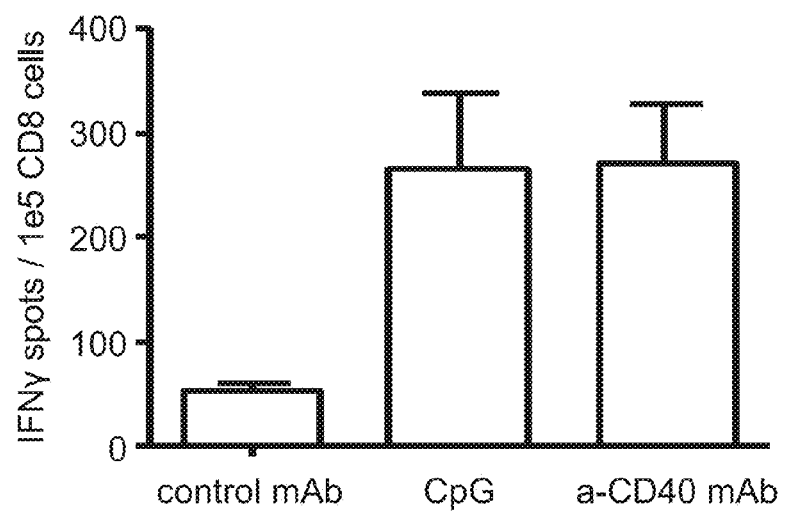
FIG. 40. Graph depicting the IFNγ ELISPOT results from a representative study evaluating the effect of CpG7909 and an anti-CD40 antibody (Bioxcell #BE0016-2) on the antigen specific T cell responses induced by a cancer vaccine (rHER2).

FIG. 40 shows the IFNγ ELISPOT results from groups of mice from a representative study evaluating the magnitude of antigen specific T cell responses induced by the rHER2 vaccine when given with the immune modulators as indicated. Briefly, each mouse per treatment group (n=4) was immunized with DNA plasmid expression constructs encoding rHER2 antigen sequences (SEQ ID NO:54) by PMED immediately followed by either 100 ug of control rat IgG monoclonal antibody (Bioxcell #BE0089: control mAb) or 50 μg CpG7909 or 100 ug of anti-CD40 monoclonal antibody (Bioxcell #BE0016-2: a-CD40 mAb) as indicated. The antigen specific immune responses were measured by IFNγ ELISPOT assay from 5e5 splenocytes mixed with control or rHer-2 specific p66 peptides at 10 μg/ml concentration, 7 days after the PMED actuation. The number of total IFNγ secreting cells from splenocytes containing 1e5 CD8 T cells were calculated from the ELISPOT results from individual animals and the % of CD8 T cells in splenocytes and mean and standard mean of error of each group are plotted. As shown, both CpG7909 and the anti-CD40 monoclonal antibody both significantly enhanced the magnitude of antigen specific immune responses induced by rHer-2 DNA compared to mice that received control antibodies.

Intracellular Cytokine Staining (ICS) Assay Results.

Figure 41A:
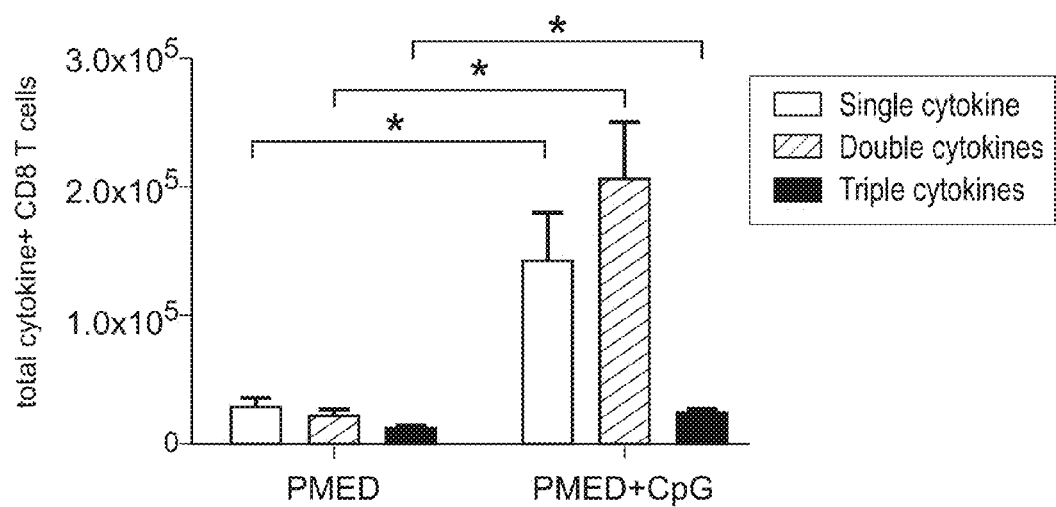
FIGS. 41A, 41B. Graphs depicting results of a representative study that evaluates the immunomodulatory activity of CpG7909 on the quality of the immune responses induced by a cancer vaccine (PMED) using intracellular cytokine staining assay, in which cytokine positive CD8 T cells (FIG. 41A) and cytokine positive CD4 T cells (FIG. 41B) were measured.
Figure 41B:
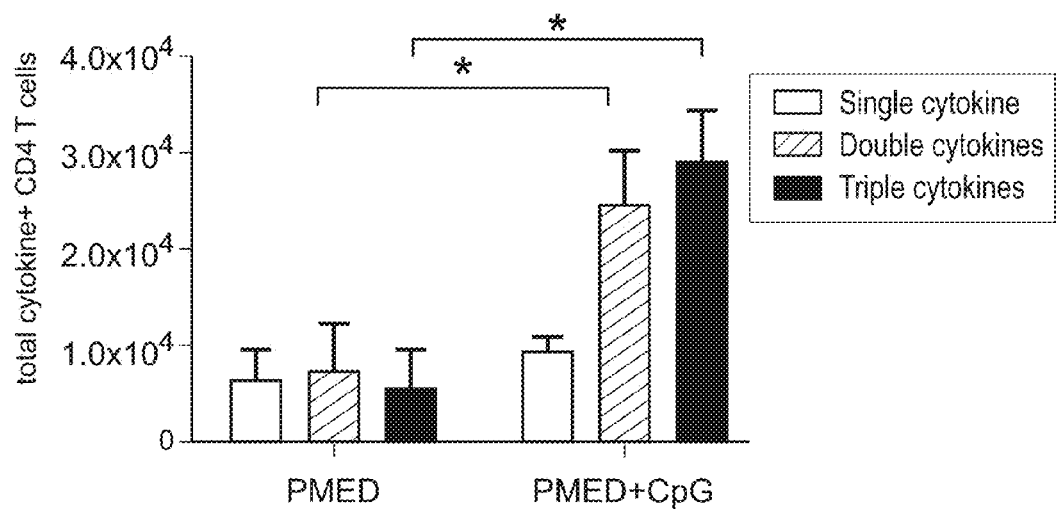

FIGS. 41A and 41B show the results of a representative study that evaluates the immunomodulatory activity of CpG 7909 on the quality of the vaccine induced immune responses by intracellular cytokine staining assay. Briefly, each animal was immunized twice with the DNA plasmid expression constructs encoding rHER2 antigen sequences (SEQ ID NO:54) delivered by PMED with a 4-week interval. The mice in each group (n=5) were given intradermal injections of either PBS (PMED group) or 50 μg of CpG 7909 (PMED+CpG group) in proximity to the right side vaccine draining inguinal node immediately following both DNA immunizations by PMED. Seven days after the last immunization by PMED, an ICS assay was performed on the splenocytes isolated from each individual mice to detect antigen specific polyfunctional CD8 or CD4 T cells that secrete IFNγ, TNFα and/or IL-2. A significant increase in rHer-2 specific multi-cytokine positive CD8 and CD4 T cell responses were detected from mice treated with the local delivery of CpG 7909 compared to PBS. An increase in the single cytokine positive CD8 population was observed in the animals that received local delivery of CpG7909 administration compared to PBS (*indicates P<0.05 by Student's T-test).

Figure 42A:
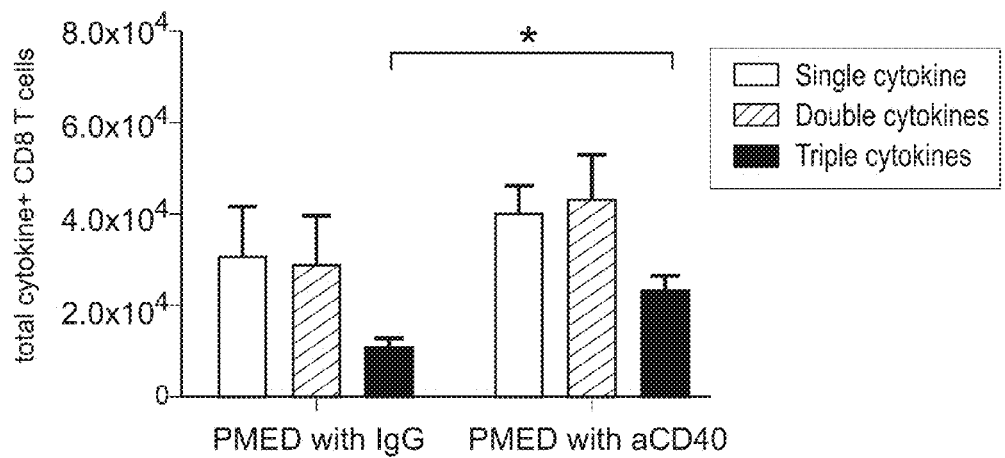
FIGS. 42A, 42B. Graphs depicting results of a representative study that evaluates the immunomodulatory activity of an agonistic anti-murine CD40 monoclonal antibody on the quality of the immune responses induced by a cancer vaccine (PMED) using intracellular cytokine staining assay, in which cytokine positive CD8 T cells (FIG. 42A) and cytokine positive CD4 T cells (FIG. 42B) were measured.
Figure 42B:
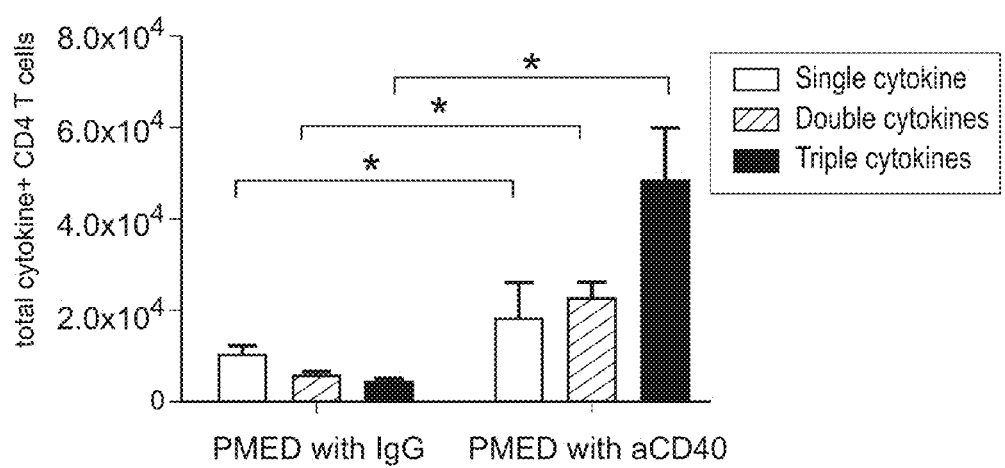

FIGS. 42A and 42B show the results of a representative study that evaluates the immunomodulatory activity of an agonistic anti-CD40 monoclonal antibody on the quality of the vaccine induced immune responses by intracellular cytokine staining assay. Briefly, each animal was immunized twice by DNA plasmid expression constructs encoding rHER2 antigen sequences (SEQ ID NO:54) delivered by PMED with a 4 week interval. The mice in each group (n=6) were given 100 μg of intradermal injections of either isotype IgG control (PMED with IgG) or anti-CD40 monoclonal antibody (PMED with aCD40) in proximity to the right side vaccine draining inguinal node, one day after the first immunization was administered by PMED. Seven days after the last PMED, an ICS assay was performed on the splenocytes isolated from each individual mice to detect rHer-2 specific polyfunctional CD8 or CD4 T cells that secrete IFNγ, TNFα and/or IL-2. A significant increase in the rHer-2 specific triple-cytokine positive CD8 and CD4 T cell responses were detected from mice treated with the local delivery of anti-CD40 monoclonal antibody compared to isotype IgG control. There were also significant increases in rHer-2 specific single and double cytokine positive CD4 T cells by anti-CD40 monoclonal antibody given locally (*indicates P<0.05 by Student's T-test).

Example 15

Anti-Cancer Efficacy of Cancer Vaccine in Combination with Low Dose Sunitinib

Anti-tumor efficacy of anti-cancer vaccine in combination with low dose sunitinib was investigated in BALB/neuT mice with spontaneous mammary pad tumors.

Animal Treatment.

Figure 43:
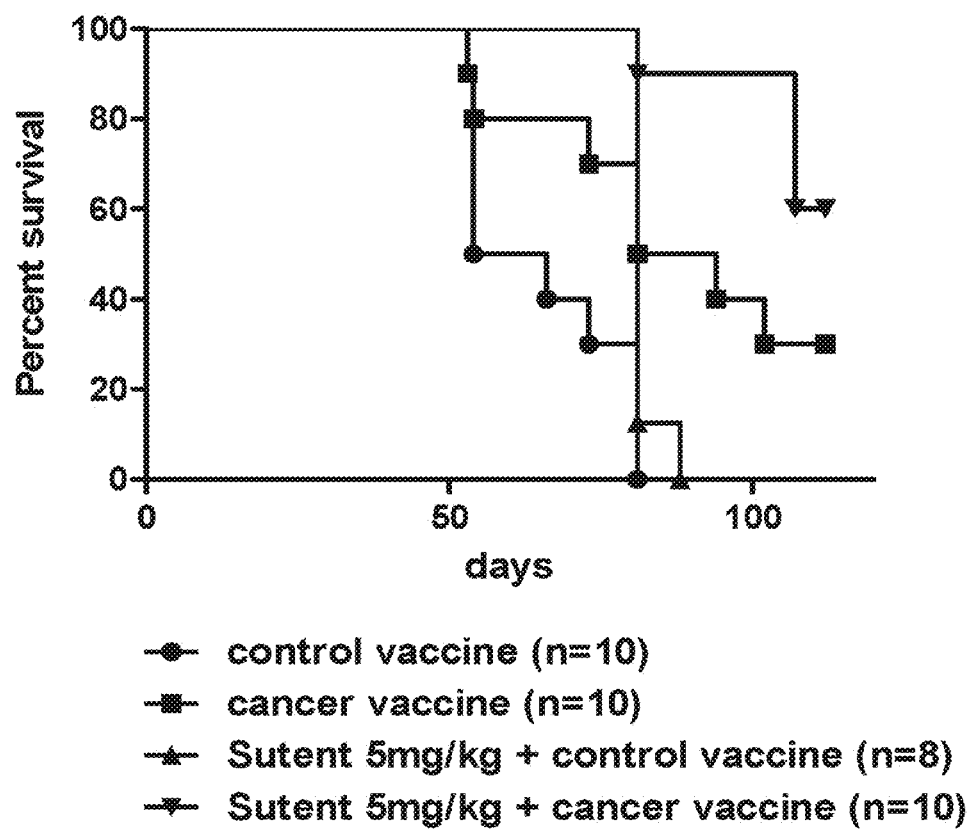
FIG. 43. Graph showing the Kaplan-Meier survival curves of the groups of mice from a representative study that evaluates the effect of low dose sunitinib malate (Sutent) on the anti-tumor efficacy of a cancer vaccine in spontaneous mammary tumor bearing BALB/neuT mice.

Briefly, 13-14 weeks old female mice were orally given sunitinib malate (Sutent) at 5 mg/kg for 112 days twice a day. The control vaccine, which delivers no antigen, and cancer vaccine which delivers a rat Her-2 antigen of SEQ ID NO: 54 (rHer-2), were given by adenovirus injections on day 3 as a prime followed by 7 biweekly administrations by PMED of DNA delivering HBV antigens (control vaccine) or rHer-2 (cancer vaccine) respectively. The survival end point was determined when all ten mammary pads became tumor positive or when the volume of any of the mammary tumors reach 2000 mm$^3$. The results are presented in FIG. 43.

Results.

Compared to previously published pharmacokinetic profile of Sutent (Mendel, D., Laird, D., et al.: "In vivo antitumor activity of SU11248, a novel tyrosine kinase inhibitor targeting vascular endothelial growth factor and platelet-derived growth factor receptors: determination of a pharmacokinetic/pharmacodynamic relationship". Clinical Cancer Research, 203, 9:327-337) and previous data (FIG. 38), the $C_{Max}$ of Sutent in mice dosed twice a day at 5 mg/kg is expected to be significantly lower than the minimum blood levels necessary to achieve efficient anti-tumor efficacy in mice and man. The data shows a quick and temporary improvement in the survival of the mice treated with low dose Sutent monotherapy. However when given with the cancer vaccine, a more persistent and significant improvement of survival was observed (P<0.0001 by Log rank test).

Example 16

Enhancement of Vaccine-Induced Immune Responses by Local Administration of CpG

The immune enhancement of local administration of CpG (PF-03512676) on the immune responses induced by a human PSMA nucleic acid provided by the invention was investigated in a monkey study, in which the immune response was assessed by measuring PSMA specific T cell responses using an IFNγ ELISPOT assay.

Animal Treatment and Sample Collection.

Six groups of Chinese cynomolgus macaques, six (#1 to 6) per each test group, were immunized with a plasmid DNA encoding the human PSMA modified antigen (amino acids 15-750 of SEQ ID NO:1) delivered by electroporation. Briefly, all animals received bilateral intramuscular injections of 5 mg of plasmid DNA followed by electroporation (DNA EP) on day 0. Subsequently right after the electroporation, group 2 received bilateral intramuscular injections of 2 mg of CpG mixed with 1 mg Alum in proximity to the DNA injection sites. Group 3 and 4 received bilateral intramuscular injections of 2 mg of CpG delivered without alum in proximity to the DNA injection sites either on day 0 or day 3, respectively. Group 5 received 2 mg of bilateral intradermal injections of CpG delivered in proximity to the vaccine draining inguinal nodes on day 3. Group 6 received bilateral injections of 200 μg of CpG mixed with the DNA solution which was co-electroporated into the muscle on day 0.

IFNγ ELISPOT Assay Procedure.

Peripheral blood samples were collected from each animal fifteen days after the DNA immunization. Peripheral blood mononuclear cells (PBMCs) were isolated from the blood samples and were subjected to an IFNγ ELISPOT assay to measure the PSMA specific T cell responses. Briefly, 4e5 PBMCs from individual animals were plated per well with pools of PSMA specific peptides or nonspecific control peptides (human HER2 peptide pool) each at 2 ug/ml in IFNγ ELISPOT plates. The composition of each of the PSMA specific peptide pool is provided in Table 1A. The plates were incubated for 16 hrs at 37° C. and 5% CO2 and washed and developed after incubation as per manufacturer's instruction. The number of IFNγ spot forming cells (SFC) were counted by CTL reader. Each condition was performed in duplicates. The result of a representative experiment is presented in Table 1B. The reported PSMA specific response is calculated by subtracting the average number of the SFC to the nonspecific control peptides (human HER2 peptide pool) from the average number of SFC to the PSMA peptide pools and normalized to the SFC observed with 1e6 PBMCs. ^ indicates that the count is not accurate because the numbers of spots were too numerous to count. ND indicates not determined.

Results.

Table 28 shows the result of a representative IFNγ ELISPOT assay that evaluates and compares the IFNγ T cell responses induced by the vaccine without (group 1) or with CpG (PF-03512676) given locally by intramuscular (groups 2, 3, 4, and 5) or intradermal injections (group 6). There results in Table 1B is plotted in FIG. 1. As shown in Table 1B and FIG. 1, the PSMA specific IFNγ T cell responses were detected to multiple PSMA specific peptide pools in the absence of CpG (PF-03512676) in all six animals (group 1). The total response to the PSMA peptides measured were modestly higher in a few animals that additionally received CpG (PF-03512676) either by intramuscular (group 4: 3/6) or intradermal (group 5: 2/6) injections 3 days after DNA electroporation. However, when CpG was delivered subsequently right after electroporation on the same day (groups 2 and 3), there were several animals that failed to produce high responses (group 2: 4/6 and group 3: 3/6) whether mixed or not mixed with Alum. However higher net responses were detected in 4/6 animals when a ten-fold lower dose of CpG was co-electroporated with the DNA solution into the muscle (group 6) with a statistically higher response (P<0.05) to peptide pools H1 and R1 compared to animals that did not receive CpG (group 1). The data shows that low dose of CpG can effectively enhance IFNγ T cell responses induced by a DNA vaccine when co-electroporated into the muscle.

TABLE 28

PSMA specific IFNγ T cell responses induced by the DNA vaccine without (Group 1) or with CpG (Groups 2, 3, 4, 5 and 6) is measured by IFNγ ELISPOT assay from PBMCS, 15 days after DNA electroporation

| Group | Animal ID | P1 | P2 | P3 | H1 | H2 | R1 | R2 |
|---|---|---|---|---|---|---|---|---|
| 1 | #1 | 36 | 31 | 1 | 126 | 183 | 5 | 14 |
|  | #2 | 6 | 3 | 13 | 61 | 524 | 6 | 141 |
|  | #3 | 11 | 4 | 8 | 108 | 1049 | 3 | 56 |
|  | #4 | 10 | 0 | 13 | 20 | 151 | 13 | 10 |
|  | #5 | 8 | 6 | 11 | 39 | 469 | 14 | 18 |
|  | #6 | 26 | 5 | 0 | 145 | 356 | 8 | 30 |
| 2 | #1 | 3 | 10 | 0 | 15 | 35 | 0 | 0 |
|  | #2 | 0 | 0 | 8 | 4 | 6 | 13 | 0 |
|  | #3 | 3 | 0 | 0 | 0 | 10 | 11 | 0 |
|  | #4 | 6 | 209 | 4 | 111 | 414 | 23 | 9 |
|  | #5 | 15 | 5 | 30 | 171 | 104 | 68 | 6 |
|  | #6 | 0 | 0 | 0 | 9 | 9 | 6 | 8 |
| 3 | #1 | 14 | 19 | 8 | 123 | 1066 | 10 | 60 |
|  | #2 | 14 | 16 | 20 | 384 | 393 | 104 | 8 |
|  | #3 | 0 | 0 | 15 | 0 | 6 | 0 | 0 |
|  | #4 | 0 | 0 | 0 | 33 | 21 | 0 | 4 |
|  | #5 | 4 | 91 | 1 | 875 | ^1235 | 233 | 109 |
|  | #6 | 0 | 0 | 0 | 0 | 3 | 0 | 0 |
| 4 | #1 | 0 | 33 | 15 | 1025 | ^1209 | 280 | 90 |
|  | #2 | 0 | 313 | 3 | 23 | 656 | 6 | 31 |
|  | #3 | 61 | 120 | 61 | 428 | 1190 | 143 | 53 |
|  | #4 | 0 | 0 | 8 | 599 | 870 | 34 | 111 |
|  | #5 | 0 | 1 | 8 | 19 | 226 | 10 | 36 |
|  | #6 | 111 | 55 | 39 | 231 | 613 | 121 | 99 |
| 5 | #1 | 21 | 9 | 0 | 355 | 1131 | 73 | 5 |
|  | #2 | 0 | 0 | 0 | 118 | 233 | 0 | 0 |
|  | #3 | 0 | 0 | 0 | 18 | 129 | 0 | 0 |
|  | #4 | 0 | 28 | 78 | 68 | 294 | 58 | 8 |
|  | #5 | 25 | 0 | 28 | 329 | 1125 | 134 | 5 |
|  | #6 | 0 | 0 | 0 | 23 | 39 | 4 | 0 |
| 6 | #1 | 0 | 0 | 13 | 650 | 1096 | 270 | 5 |
|  | #2 | 34 | 1 | 74 | 124 | 474 | 29 | 15 |
|  | #3 | 0 | 3 | 14 | 684 | 1074 | 126 | 64 |
|  | #4 | 8 | 9 | 0 | 136 | 321 | 49 | 1 |
|  | #5 | 13 | 23 | 35 | ND | ^1235 | 333 | 195 |
|  | #6 | 0 | 0 | 0 | 421 | ^1201 | 138 | 29 |

Example 17

Enhancement of Vaccine-Induced Immune Responses by Local Administration of Anti-CTLA-4 Antibody The effect of low dose subcutaneous administration of anti-CTLA-4 monoclonal antibody (CP-675, 206) on the immune responses induced by a rhesus PSMA nucleic acid was investigated in a monkey study, in which the immune response was assessed by measuring PSMA specific T cell responses using an IFNγ ELISPOT assay. The rhesus PSMA nucleic acid used in the study has the sequence as set forth in SEQ ID NO: 56) and encodes an immunogenic PSMA polypeptide of SEQ ID NO: 55.

Animal Treatment and Sample Collection.

Five groups of male Indian rhesus macaques, seven (#1 to 7) per each test group, were immunized with an adenovirus encoding a rhesus PSMA modified polypeptide delivered by bilateral intramuscular injections (2× 5e10 V.P.). Immediately following the adenovirus injections, group 1 received vehicle, and groups 2 to 4 received bilateral subcutaneous injections of anti-CTLA-4 antibody (CP-675, 206) at doses 2× 25 mg, 2× 16.7 mg and 2× 8.4 mg respectively in proximity to the vaccine draining lymph node.

Nine days after the immunization, peripheral blood mononuclear cells (PBMCs) were isolated from each animal and were subjected to an IFNγ ELISPOT assay to measure the rhesus PSMA specific T cell responses. Briefly, 4e5 PBMCs from individual animals were plated per well with pools of rhesus PSMA specific peptides (P1, P2, P3 or R1+R2 defined in table 24A) or nonspecific control peptides (human HER2 peptide pool) each at 2 ug/ml in IFNγ ELISPOT plates. The plates were incubated for 16 hrs at 37° C. and 5% CO2 and washed and developed after incubation as per manufacturer's instruction. The number of IFNγ spot forming cells (SFC) were counted by CTL reader. Each condition was performed in duplicates. The average of the duplicates from the background adjusted SFC of the rhesus PSMA specific peptide pools was normalized to the response in 1e6 PBMCs. The individual and sum responses to the peptide pools from each individual animal are presented in Table 29.

IFNγ ELISPOT Assay Procedure.

A capture antibody specific to IFNγ BD Bioscience, #51-2525kc) is coated onto a polyvinylidene fluoride (PVDF) membrane in a microplate overnight at 4° C. The plate is blocked with serum/protein to prevent nonspecific binding to the antibody. After blocking, effector cells (such as splenocytes isolated from immunized mice or PBMCs isolated from rhesus macaques) and targets (such as PSMA peptides from peptide library, target cells pulsed with antigen specific peptides or tumor cells expressing the relevant antigens) are added to the wells and incubated overnight at 37° C. in a 5% $CO_2$ incubator. Cytokine secreted by effector cells are captured by the coating antibody on the surface of the PVDF membrane. After removing the cells and culture media, 100 µl of a biotinylated polyclonal anti-human IFNγ antibody was added to each of the wells for detection. The spots are visualized by adding streptavidin-horseradish peroxidase and the precipitate substrate, 3-amino-9-ethylcarbazole (AEC), to yield a red color spot as per manufacturer's (Mabtech) protocol. Each spot represents a single cytokine producing T cell.

Results.

Table 29. shows the results of a representative IFNγ ELISPOT assay that compares the T cell responses induced by the vaccine without (group 1) or with (groups 2-4) anti-CTLA-4 monoclonal antibody (CP-675, 206) given locally by subcutaneous injections in proximity to the vaccine draining lymph node. The vaccine generated an immune response (group 1) that was significantly enhanced by the local administration of the anti-CTLA-4 antibody (CP-675, 206) at a dose of 50 mg (group 2, P=0.001 by Student's T-test using underestimated values). The response was also significantly enhanced by low doses of anti-CTLA-4 antibody at 33.4 mg (group 3: P=0.004 by Student T-test using underestimated values) and 16.7 mg (group 4: P=0.05 by Student T-test) respectively. The data suggests that low doses of anti-CTLA-4 delivered by subcutaneous injection can significantly enhance the vaccine induced immune responses.

TABLE 29

IFNγ T cell responses induced by the vaccine without (Group 1) or with subcutaneous injections of anti-CTLA-4 antibody (CP-675, 206).

| Group | aCTLA4 dose, mg | animal ID | P1 | P2 | P3 | R1 + R2 | Sum |
|---|---|---|---|---|---|---|---|
| 1 | NA | 1 | 21 | 0 | 0 | 108 | 129 |
|   |    | 2 | 59 | 480 | 28 | 353 | 920 |
|   |    | 3 | 133 | 29 | 359 | 305 | 826 |
|   |    | 4 | 0 | 28 | 1 | 35 | 64 |
|   |    | 5 | 41 | 6 | 30 | 99 | 176 |
|   |    | 6 | 1 | 0 | 849 | 169 | 1019 |
|   |    | 7 | 0 | 0 | 0 | 23 | 23 |
| 2 | 50.0 | 1 | ^1105 | 704 | ^1116 | ^1116 | ^4041 |
|   |    | 2 | 371 | 26 | 661 | 779 | 1837 |
|   |    | 3 | 393 | 559 | 216 | 198 | 1366 |
|   |    | 4 | ^1100 | ^1100 | 406 | 1078 | ^3684 |
|   |    | 5 | 778 | 325 | 554 | 419 | 2076 |
|   |    | 6 | ^1079 | ^1079 | 844 | ^1079 | ^4081 |
|   |    | 7 | 423 | 103 | 535 | 398 | 1459 |
| 3 | 33.4 | 1 | ^425 | ^425 | ^425 | ^425 | ^1700 |
|   |    | 2 | ^580 | ^580 | ^580 | ^580 | ^2320 |
|   |    | 3 | TNTC | TNTC | TNTC | TNTC | TNTC |
|   |    | 4 | 321 | 778 | 370 | 409 | 1878 |
|   |    | 5 | 331 | 466 | 311 | 446 | 1554 |
|   |    | 6 | 545 | 121 | ^631 | ^1194 | ^2491 |
|   |    | 7 | 446 | 299 | ^1078 | ^1060 | ^2883 |
| 4 | 16.7 | 1 | ^964 | 296 | ^964 | ^964 | ^3188 |
|   |    | 2 | 76 | 76 | 76 | 76 | 304 |
|   |    | 3 | ^984 | ^984 | ^984 | ^984 | ^3936 |
|   |    | 4 | 260 | 489 | 648 | ^1109 | ^2506 |
|   |    | 5 | 119 | 45 | 28 | 140 | 332 |
|   |    | 6 | 55 | 76 | 43 | 198 | 372 |
|   |    | 7 | 146 | 726 | 141 | 400 | 1413 |

^ indicates that the count is underestimated due to the high spot numbers.
TNTC means too numerous to count.

Example 18

Immunomodulation of Myeloid Derived Suppressor Cells by Low Dose Sunitinib

The following example is provided to illustrate the immunomodulatory effects of low dose sunitinib on Myeloid Derived Suppressor Cells (MDSC) in vivo, in a non-tumor mouse model.

Study Procedures.

To generate MDSC enriched splenocytes, TUBO cells ($1\times10^6$) were implanted into the flanks of 5 BALB/neuT mice, and left for approx. 20-30 days until tumor volume reached between 1000-1500 mm$^3$. Mice were then sacrificed, spleens removed and the MDSC enriched splenocytes recovered. Splenocytes were labeled for 10 minutes with 5 μM CFSE, washed with PBS and counted. Labeled cells were subsequently resuspended at $5 \times 10^7$ splenocytes/ml in PBS solution and adoptively transferred via an i.v. tail vein injection into naïve BALB/c recipient mice. Three days prior to adoptive transfer, the recipient mice began bi-daily dosing with vehicle or sunitinib malate (Sutent) at 5 mg/kg, 10 mg/kg and 20 mg/kg. Following adoptive transfer, recipient mice continued to receive bi-daily dosing of Vehicle or sunitinib for two further days, after which point the mice were sacrificed, spleens removed, splenocytes recovered and processed for phenotypic analysis.

Splenocytes were counted and resuspended at $5 \times 10^6$ cells/ml in FACS staining buffer (PBS, 0.2% (w/v) bovine serum albumin, and 0.02% (w/v) Sodium Azide). For flow cytometry staining of splenocytes, $2.5 \times 10^6$ cells were first incubated with anti-bodies to CD16/CD32, 10 minutes at 4° C., to block Fc receptors and minimize non-specific binding. Splenocytes were then stained for 20 minutes at 4° C. with appropriate fluorophore conjugated antibodies (Biolegend) to murine cell surface markers. For T cells (anti-CD3 (Pacific Blue), clone 17A2) and for MDSC (anti-GR-1 (APC), clone RB6-8C5 and anti-CD11b (PerCp Cy5.5), clone M1/70). A live/dead stain was also included. Following antibody incubation, stained splenocytes were washed with 2 mls of FACS buffer, pelleted by centrifugation and resuspended in 0.2 ml of FACS buffer prior to data acquisition on a BD CANTO II flow cytometer. To monitor the effect of Sunitinib or Vehicle on the adoptively transferred MDSC survival, we calculated the percentage of CFSE+, CD3−,GR1+,CD11 b+ in the live, singlet gate. We then determined the number of adoptively transferred MDSC per spleen by calculating what actual cell number the percentage represented of total splenocytes count. Data was analyzed by FloJo and Graph pad software.

Results.

The data presented in Table 31 represents the mean number of adoptively transferred CSFE+,CD3−,GR1+, CD11b+ cells recovered per spleen (n=7/group), 2 days post adoptive transfer, from mice bi-daily dosed with either Vehicle or 5 mg/kg, 10 mg/kg and 20 mg/kg Sunitinib. The data demonstrates that Sunitinib, dosed bi-daily, in vivo, has an immunomodulatory effect on MDSCs, even when dosed as low as 5 mg/kg, resulting in a statistically significant reduction in the numbers recovered when compared to the vehicle treated control group.

Example 19

Immunogenicity of Triple Antigen Adenovirus and DNA Constructs

The following example is provided to illustrate the capability of triple antigen vaccine constructs (either in the form of adenovirus vector or DNA plasmid) expressing three antigens PSMA, PSCA and PSA provided by the invention to elicit specific T cell responses to all three encoded antigens in nonhuman primates.

In Vivo Study Procedures.

The T cell immunogenicity of five adenovirus vectors each expressing three antigens (PSMA, PSCA and PSA; Ad-733, Ad-734, Ad-735, Ad-796 and Ad-809) provided by the invention were compared to the mix of three adenovirus vectors each only expressing a single antigen (PSMA, PSA or PSCA), 9 days post prime. The response to single adenovirus expressing a single antigen (groups 1-3) was evaluated to demonstrate the specificity. Briefly, Indian rhesus macaques (n=6 for groups 1 and 3, n=7 for group 2 and n=8 for groups 4-9) were intramuscularly injected with a total of 1e11 V.P. followed by intradermal injections of anti-CTLA-4 at 10 mg/kg on the same day. Nine days after the injections, peripheral blood mononuclear cells (PBMCs) were isolated from each animal and were subjected to an IFNγ ELISPOT assay to measure the PSMA, PSA and PSCA specific T cell responses.

Thirteen weeks after the adenovirus and anti-CTLA-4 injections when the T cell responses have contracted, the monkeys received DNA (Group 1: PSMA, plasmid 5166; Group 2: PSA, plasmid 5297; Group 3: PSCA, plasmid 5259; Group 4: mix of PSMA, PSA and PSCA, plasmids 5166, 5259 and 5297; Group 4: plasmid 457; Group 6: plasmid 458; Group 7: plasmid 459; Group 8: plasmid 796 and Group 9: plasmid 809) boost vaccinations delivered by electroporation. In summary, each animal received a total 5 mg of plasmid DNA provided by the invention which delivers the same expression cassette encoded in the adenovirus used in the prime. Nine days after the boost vaccination, peripheral blood mononuclear cells (PBMCs) were isolated from each animal and were subjected to an IFNγ ELISPOT assay.

IFNγ ELISPOT Assay.

Briefly, 4e5 PBMCs from individual animals were plated per well with PSMA specific peptide pools P1, P2, P3 or H1 and H2 (Table 24A), PSA specific pool 1 or 2 (Table 25), PSCA specific pool (Table 26) or nonspecific control peptides (human HER2 peptide pool) each at 2 ug/ml in IFNγ ELISPOT plates. The plates were incubated for 16 hrs at 37° C. and 5% CO2 and washed and developed after incubation

TABLE 31

Mean number of CFSE+, CD3−, GR1+, CD11b+ MDSCs recovered from the spleen, 7 mice per group, and the corresponding standard error. Statistical significance was determined by one-way ANOVA using the Dunnett's multiple comparison test, comparing the Sunitinib dosed groups against the 0 mg/kg (vehicle) group.

| | Sunitinib Dose (mg/kg) | | | |
|---|---|---|---|---|
| | 0 (Vehicle) | 5 | 10 | 20 |
| MDSC #/spleen Mean +/− SEM | 17470 +/− 2017 | 10980 +/− 1082 | 4207 +/−338 | 4440 +/− 440 |
| Statistical significance, p < 0.5 [[?]] | NA | Yes | Yes | Yes | as per manufacturer's instruction. The number of IFNγ spot forming cells (SFC) were counted by CTL reader. Each condition was performed in duplicates. The average of the duplicates from the background adjusted SFC of the antigen specific peptide pools was normalized to the response in 1e6 PBMCs. The antigen specific responses in the tables present the sum of the responses to the corresponding antigen specific peptides or peptide pools.

Results:

Table 27 represents a study that evaluates the T cell immunogenicity of five different adenoviruses each expressing all three antigens in comparison to the mixture of three adenoviruses each expressing a single antigen in Indian rhesus macaques by IFNγ ELISPOT. The majority of animals that only received Ad-PSMA (group 1) injections induced specific responses to PSMA but not to PSA or PSCA (Student's T-test, P<0.03. One animal (#4) that induced responses to PSCA preferentially was removed from the statistical analysis). The animals that only received injections of Ad-PSA (group 2) induced specific responses to PSA but not to PSMA or PSCA (Student's T-test, P<0.02). The animals that only received injections of Ad-PSCA (group 3) induced specific responses to PSCA but not to PSMA or PSA (Student's T-test, P<0.03). All five triple-antigen expressing adenovirus vectors (groups 5-9) induced IFNγ T cell responses to all three antigens which the magnitude varied by animal. The magnitude of the responses to PSCA induced by the triple antigen expressing adenoviruses were similar to the mix of individual vectors (group 4). However the magnitude of responses to PSMA induced by Ad-809 (group 9) and responses to PSA induced by Ad-796 (group 8) were each significantly superior to the mix (Student's T-test, P=0.04 and P=0.02) respectively. These results indicate that vaccinating with an adenovirus expressing triple antigens can elicit equivalent or superior T cell immune responses to vaccinating with the mix of individual adenoviruses in nonhuman primates.

Table 28 shows the IFNγ ELISPOT results represents a study that evaluates the immunogenicity of the five different triple antigen expression cassettes provided in the invention delivered by an adenovirus prime in combination with anti-CTLA-4 followed by an electroporation boost of the corresponding plasmid DNA. The immune responses are compared to the mix of three constructs expressing a single antigen delivered similarly by an adenovirus prime with anti-CTLA-4 and DNA electroporation boost immunizations.

All of the animals that only received Ad-PSMA with anti-CTLA-4 followed by plasmid-PSMA (group 1) immunizations induced specific responses to PSMA but not to PSA or PSCA. Similarly all of the animals that only received Ad-PSA with anti-CTLA-4 followed by plasmid-PSA immunizations (group 2) induced specific responses to PSA but not to PSMA or PSCA and finally all of the animals that only received Ad-PSCA with anti-CTLA-4 followed by plasmid-PSCA (group 3) immunizations induced specific responses to PSCA but not to PSMA or PSA (Student's T-test, P<0.01).

All animals that have been immunized with either the triple-antigen expressing vectors (groups 5-9) or the mix (group 4) induced IFNγ T cell responses to all three antigens. The frequency of PSCA or PSA specific IFNγ T cells detected were similar in all of these groups (groups 4-9) respectively. However construct groups 7 and 9 that received triple antigen expression vector vaccinations produced significantly higher frequency of responses to PSMA than the mix of three single antigen expressing constructs (group 4).

These results indicate that adenovirus and DNA vaccines expressing triple antigens in one cassette can elicit equivalent or superior IFNγ T cell responses to the mix of adenoviruses and DNAs expressing the single antigens in nonhuman primates.

TABLE 25

PSA peptide pools: The amino acid position and sequence of fifteen amino acid peptides overlapping by thirteen amino acids from PSA peptide library is shown.

| PSA peptide pool 1 | | PSA peptide pool 2 | |
|---|---|---|---|
| amino acid no. | PSA peptide sequence | amino acid no. | PSA peptide sequence |
| 5-19 | VVFLTLSVTWIGAAP | 129-143 | PAELTDAVKVMDLPT |
| 9-23 | TLSVTWIGAAPLILS | 131-145 | ELTDAVKVMDLPTQE |
| 11-25 | SVTWIGAAPLILSRI | 133-147 | TDAVKVMDLPTQEPA |
| 13-27 | TWIGAAPLILSRIVG | 135-149 | AVKVMDLPTQEPALG |
| 15-29 | IGAAPLILSRIVGGW | 137-151 | KVMDLPTQEPALGTT |
| 17-31 | AAPLILSRIVGGWEC | 139-153 | MDLPTQEPALGTTCY |
| 19-33 | PLILSRIVGGWECEK | 141-155 | LPTQEPALGTTCYAS |
| 21-35 | ILSRIVGGWECEKHS | 143-157 | TQEPALGTTCYASGW |
| 23-37 | SRIVGGWECEKHSQP | 145-159 | EPALGTTCYASGWGS |
| 25-39 | IVGGWECEKHSQPWQ | 147-161 | ALGTTCYASGWGSIE |
| 27-41 | GGWECEKHSQPWQVL | 149-163 | GTTCYASGWGSIEPE |
| 29-43 | WECEKHSQPWQVLVA | 151-165 | TCYASGWGSIEPEEF |
| 31-45 | CEKHSQPWQVLVASR | 153-167 | YASGWGSIEPEEFLT |
| 33-47 | KHSQPWQVLVASRGR | 155-169 | SGWGSIEPEEFLTPK |
| 35-49 | SQPWQVLVASRGRAV | 157-171 | WGSIEPEEFLTPKKL |
| 37-51 | PWQVLVASRGRAVCG | 159-173 | SIEPEEFLTPKKLQC |
| 39-53 | QVLVASRGRAVCGGV | 161-175 | EPEEFLTPKKLQCVD |
| 41-55 | LVASRGRAVCGGVLV | 163-177 | EEFLTPKKLQCVDLH |
| 43-57 | ASRGRAVCGGVLVHP | 165-179 | FLTPKKLQCVDLHVI |
| 45-59 | RGRAVCGGVLVHPQW | 167-181 | TPKKLQCVDLHVISN |
| 47-61 | RAVCGGVLVHPQWVL | 169-183 | KKLQCVDLHVISNDV |
| 49-63 | VCGGVLVHPQWVLTA | 171-185 | LQCVDLHVISNDVCA |
| 51-65 | GGVLVHPQWVLTAAH | 173-187 | CVDLHVISNDVCAQV |
| 53-67 | VLVHPQWVLTAAHCI | 175-189 | DLHVISNDVCAQVHP |
| 55-69 | VHPQWVLTAAHCIRN | 177-191 | HVISNDVCAQVHPQK |
| 57-71 | PQWVLTAAHCIRNKS | 179-193 | ISNDVCAQVHPQKVT |
| 59-73 | WVLTAAHCIRNKSVI | 181-195 | NDVCAQVHPQKVTKF |
| 61-75 | LTAAHCIRNKSVILL | 183-197 | VCAQVHPQKVTKFML |
| 63-77 | AAHCIRNKSVILLGR | 185-199 | AQVHPQKVTKFMLCA |
| 65-79 | HCIRNKSVILLGRHS | 187-201 | VHPQKVTKFMLCAGR |
| 67-81 | IRNKSVILLGRHSLF | 189-203 | PQKVTKFMLCAGRWT |
| 69-83 | NKSVILLGRHSLFHP | 191-205 | KVTKFMLCAGRWTGG |

TABLE 25-continued

PSA peptide pools: The amino acid position and sequence of fifteen amino acid peptides overlapping by thirteen amino acids from PSA peptide library is shown.

| PSA peptide pool 1 | | PSA peptide pool 2 | |
|---|---|---|---|
| amino acid no. | PSA peptide sequence | amino acid no. | PSA peptide sequence |
| 71-85 | SVILLGRHSLFHPED | 193-207 | TKFMLCAGRWTGGKS |
| 73-87 | ILLGRHSLFHPEDTG | 195-209 | FMLCAGRWTGGKSTC |
| 75-89 | LGRHSLFHPEDTGQV | 197-211 | LCAGRWTGGKSTCSG |
| 77-91 | RHSLFHPEDTGQVFQ | 199-213 | AGRWTGGKSTCSGDS |
| 79-93 | SLFHPEDTGQVFQVS | 201-215 | RWTGGKSTCSGDSGG |
| 81-95 | FHPEDTGQVFQVSHS | 203-217 | TGGKSTCSGDSGGPL |
| 83-97 | PEDTGQVFQVSHSFP | 205-219 | GKSTCSGDSGGPLVC |
| 85-99 | DTGQVFQVSHSFPHP | 207-221 | STCSGDSGGPLVCNG |
| 87-101 | GQVFQVSHSFPHPLY | 209-223 | CSGDSGGPLVCNGVL |
| 89-103 | VFQVSHSFPHPLYDM | 211-225 | GDSGGPLVCNGVLQG |
| 91-105 | QVSHSFPHPLYDMSL | 213-227 | SGGPLVCNGVLQGIT |
| 93-107 | SHSFPHPLYDMSLLK | 215-229 | GPLVCNGVLQGITSW |
| 95-109 | SFPHPLYDMSLLKNR | 217-231 | LVCNGVLQGITSWGS |
| 97-111 | PHPLYDMSLLKNRFL | 219-233 | CNGVLQGITSWGSEP |
| 99-113 | PLYDMSLLKNRFLRP | 221-235 | GVLQGITSWGSEPCA |
| 101-115 | YDMSLLKNRFLRPGD | 223-237 | LQGITSWGSEPCALP |
| 103-117 | MSLLKNRFLRPGDDS | 225-239 | GITSWGSEPCALPER |
| 105-119 | LLKNRFLRPGDDSSH | 227-241 | TSWGSEPCALPERPS |
| 107-121 | KNRFLRPGDDSSHDL | 229-243 | WGSEPCALPERPSLY |
| 109-123 | RFLRPGDDSSHDLML | 231-245 | SEPCALPERPSLYTK |
| 111-125 | LRPGDDSSHDLMLLR | 233-247 | PCALPERPSLYTKVV |
| 113-127 | PGDDSSHDLMLLRLS | 235-249 | ALPERPSLYTKVVHY |
| 115-129 | DDSSHDLMLLRLSEP | 237-251 | PERPSLYTKVVHYRK |
| 117-131 | SSHDLMLLRLSEPAE | 239-253 | RPSLYTKVVHYRKWI |
| 119-133 | HDLMLLRLSEPAELT | 241-255 | SLYTKVVHYRKWIKD |
| 121-135 | LMLLRLSEPAELTDA | 243-257 | YTKVVHYRKWIKDTI |
| 123-137 | LLRLSEPAELTDAVK | 245-259 | KVVHYRKWIKDTIVA |
| 125-139 | RLSEPAELTDAVKVM | 247-261 | VHYRKWIKDTIVANP |
| 127-141 | SEPAELTDAVKVMDL | 249-261 | YRKWIKDTIVANP |
| | | 251-261 | KWIKDTIVANP |

TABLE 26

PSCA peptide pool: The amino acid position and sequence of fifteen amino acid peptides overlapping by thirteen amino acids from PSCA peptide library is shown.

| amino acid no. | PSCA peptide sequence |
|---|---|
| 1-15 | MKAVLLALLMAGLAL |
| 3-17 | AVLLALLMAGLALQP |
| 5-19 | LLALLMAGLALQPGT |
| 7-21 | ALLMAGLALQPGTAL |
| 9-23 | LMAGLALQPGTALLC |
| 11-25 | AGLALQPGTALLCYS |
| 13-27 | LALQPGTALLCYSCK |
| 15-29 | LQPGTALLCYSCKAQ |
| 17-31 | PGTALLCYSCKAQVS |
| 19-33 | TALLCYSCKAQVSNE |
| 21-35 | LLCYSCKAQVSNEDC |
| 23-37 | CYSCKAQVSNEDCLQ |
| 25-39 | SCKAQVSNEDCLQVE |
| 27-41 | KAQVSNEDCLQVENC |
| 29-43 | QVSNEDCLQVENCTQ |
| 31-45 | SNEDCLQVENCTQLG |
| 33-47 | EDCLQVENCTQLGEQ |
| 35-49 | CLQVENCTQLGEQCW |
| 37-51 | QVENCTQLGEQCWTA |
| 39-53 | ENCTQLGEQCWTARI |
| 41-55 | CTQLGEQCWTARIRA |
| 43-57 | QLGEQCWTARIRAVG |
| 45-59 | GEQCWTARIRAVGLL |
| 47-61 | QCWTARIRAVGLLTV |
| 49-63 | WTARIRAVGLLTVIS |
| 51-65 | ARIRAVGLLTVISKG |
| 53-67 | IRAVGLLTVISKGCS |
| 55-69 | AVGLLTVISKGCSLN |
| 57-71 | GLLTVISKGCSLNCV |
| 59-73 | LTVISKGCSLNCVDD |
| 61-75 | VISKGCSLNCVDDSQ |
| 63-77 | SKGCSLNCVDDSQDY |
| 65-79 | GCSLNCVDDSQDYYV |
| 67-81 | SLNCVDDSQDYYVGK |
| 69-83 | NCVDDSQDYYVGKKN |
| 71-85 | VDDSQDYYVGKKNIT |
| 73-87 | DSQDYYVGKKNITCC |

TABLE 26-continued

PSCA peptide pool: The amino acid position and sequence of fifteen amino acid peptides overlapping by thirteen amino acids from PSCA peptide library is shown.

| amino acid no. | PSCA peptide sequence |
|---|---|
| 75-89 | QDYYVGKKNITCCDT |
| 77-91 | YYVGKKNITCCDTDL |
| 79-93 | VGKKNITCCDTDLCN |
| 81-95 | KKNITCCDTDLCNAS |
| 83-97 | NITCCDTDLCNASGA |
| 85-99 | TCCDTDLCNASGAHA |
| 87-101 | CDTDLCNASGAHALQ |
| 89-103 | TDLCNASGAHALQPA |
| 91-105 | LCNASGAHALQPAAA |
| 93-107 | NASGAHALQPAAAIL |
| 95-109 | SGAHALQPAAAILAL |
| 97-111 | AHALQPAAAILALLP |
| 99-113 | ALQPAAAILALLPAL |
| 101-115 | QPAAAILALLPALGL |
| 103-117 | AAAILALLPALGLLL |
| 105-119 | AILALLPALGLLLWG |
| 107-121 | LALLPALGLLLWGPG |
| 109-123 | LLPALGLLLWGPGQL |
| 111-125 | PALGLLLWGPGQL |

TABLE 27

IFNγ T cell responses induced by the single antigen (Group 1: Ad-PSMA; Group 2: Ad-PSA; Group 3: Ad-PSCA; Group 4: mix of Ad-PSMA, Ad-PSA and Ad-PSCA) or triple antigen expressing adenovirus vectors (Group 4: Ad-733; Group 6: Ad-734; Group 7: Ad-735; Group 8: Ad-796 and Group 9: Ad-809) after adenovirus prime with anti-CTLA-4 analyzed by ELISPOT assay.

| Response to PSMA peptides | | animal ID | | | | | | | |
|---|---|---|---|---|---|---|---|---|---|
| | | 1 | 2 | 3 | 4 | 5 | 6 | 7 | 8 |
| Group No. | 1 | 2356 | 988 | 1505 | 335 | 501 | 2145 | NA | NA |
| | 2 | 342 | 1776 | 154 | 329 | 158 | 438 | 321 | NA |
| | 3 | 0 | 1276 | 40 | 126 | 20 | 0 | NA | NA |
| | 4 | 304 | 1198 | 774 | 2007 | 1277 | 1310 | 1159 | 2774 |
| | 5 | 943 | 2670 | 2757 | 780 | 1082 | 2251 | 1566 | 544 |
| | 6 | 472 | 2092 | 4248 | 1369 | 1760 | 2964 | 1447 | 263 |
| | 7 | 2161 | 2202 | 939 | 869 | 3513 | 1654 | 3424 | 900 |
| | 8 | 1166 | 799 | 2566 | 663 | 1043 | 497 | 1334 | 560 |
| | 9 | 1621 | 3247 | 2031 | 980 | 2942 | 1882 | 1918 | 3805 |

| Response to PSA peptides | | animal ID | | | | | | | |
|---|---|---|---|---|---|---|---|---|---|
| | | 1 | 2 | 3 | 4 | 5 | 6 | 7 | 8 |
| Group No. | 1 | 0 | 0 | 0 | 48 | 0 | 42 | NA | NA |
| | 2 | 1419 | 1426 | 298 | 1223 | 1346 | 1120 | 1694 | NA |
| | 3 | 6 | 462 | 91 | 0 | 77 | 0 | NA | NA |
| | 4 | 790 | 1093 | 1611 | 790 | 186 | 783 | 2016 | 1964 |
| | 5 | 101 | 510 | 955 | 665 | 336 | 1512 | 1052 | 119 |
| | 6 | 236 | 673 | 2155 | 724 | 504 | 1600 | 930 | 83 |
| | 7 | 0 | 1086 | 494 | 663 | 2265 | 117 | 1712 | 84 |
| | 8 | 1893 | 2060 | 1490 | 1759 | 2352 | 1700 | 2232 | 1326 |
| | 9 | 1193 | 1432 | 207 | 1738 | 1886 | 949 | 492 | 1940 |

| Response to PSCA peptides | | animal ID | | | | | | | |
|---|---|---|---|---|---|---|---|---|---|
| | | 1 | 2 | 3 | 4 | 5 | 6 | 7 | 8 |
| Group No. | 1 | 795 | 425 | 874 | 1069 | 219 | 203 | NA | NA |
| | 2 | 669 | 713 | 391 | 199 | 164 | 560 | 461 | NA |
| | 3 | 510 | 1234 | 1099 | 1115 | 1194 | 339 | NA | NA |
| | 4 | 778 | 528 | 680 | 1101 | 165 | 531 | 1175 | 1009 |
| | 5 | 378 | 1061 | 1161 | 143 | 71 | 756 | 766 | 204 |
| | 6 | 118 | 380 | 1190 | 403 | 829 | 1225 | 148 | 261 |
| | 7 | 615 | 1141 | 794 | 564 | 1175 | 490 | 856 | 204 |
| | 8 | 968 | 1136 | 745 | 290 | 550 | 976 | 955 | 841 |
| | 9 | 929 | 434 | 1150 | 745 | 1120 | 246 | 1195 | 970 |

TABLE 28

IFNγ T cell responses induced by the single antigen (Group 1: PSMA;
Group 2: PSA; Group 3: PSCA; Group 4: mix of PSMA, PSA and PSCA) or triple
antigen expressing vectors (Groups 5-9) after adenovirus prime with anti-CTLA-4
and DNA electroporation boost immunizations analyzed by ELISPOT assay.

| Response to PSMA | | animal ID | | | | | | | |
|---|---|---|---|---|---|---|---|---|---|
| peptides | | 1 | 2 | 3 | 4 | 5 | 6 | 7 | 8 |
| Group | 1 | 1327 | 1535 | 1643 | 535 | 1506 | 1267 | NA | NA |
| No. | 2 | 15 | 266 | 26 | 191 | 10 | 46 | 1305 | NA |
| | 3 | 0 | 445 | 5 | 75 | 4 | 6 | NA | NA |
| | 4 | 365 | 675 | 731 | 1134 | 244 | 714 | 999 | 1683 |
| | 5 | 270 | 1623 | 2254 | 626 | 860 | 2245 | 1453 | 1046 |
| | 6 | 541 | 1151 | 2923 | 1094 | 1061 | 1746 | 691 | 489 |
| | 7 | 1183 | 1183 | 1453 | 1649 | 2844 | 1470 | 2321 | 991 |
| | 8 | 486 | 69 | 399 | 216 | 351 | 758 | 416 | 1389 |
| | 9 | 1430 | 2631 | 2015 | 475 | 1368 | 1826 | 1851 | 3141 |

| Response to PSA | | animal ID | | | | | | | |
|---|---|---|---|---|---|---|---|---|---|
| peptides | | 1 | 2 | 3 | 4 | 5 | 6 | 7 | 8 |
| Group | 1 | 0 | 0 | 0 | 1 | 0 | 26 | NA | NA |
| No. | 2 | 1883 | 1236 | 1574 | 393 | 461 | 941 | 1565 | NA |
| | 3 | 33 | 30 | 9 | 13 | 8 | 11 | NA | NA |
| | 4 | 571 | 1129 | 1180 | 210 | 88 | 274 | 924 | 360 |
| | 5 | 50 | 1255 | 1344 | 628 | 210 | 638 | 948 | 1161 |
| | 6 | 88 | 228 | 1390 | 489 | 1006 | 908 | 683 | 51 |
| | 7 | 0 | 211 | 321 | 156 | 1509 | 56 | 199 | 85 |
| | 8 | 414 | 611 | 85 | 105 | 544 | 1080 | 331 | 1883 |
| | 9 | 434 | 821 | 556 | 343 | 1160 | 510 | 144 | 1115 |

| Response to PSCA | | animal ID | | | | | | | |
|---|---|---|---|---|---|---|---|---|---|
| peptides | | 1 | 2 | 3 | 4 | 5 | 6 | 7 | 8 |
| Group | 1 | 615 | 799 | 533 | 74 | 258 | 61 | NA | NA |
| No. | 2 | 194 | 170 | 133 | 133 | 8 | 66 | 405 | NA |
| | 3 | 819 | 1071 | 873 | 839 | 1045 | 724 | NA | NA |
| | 4 | 543 | 506 | 664 | 470 | 70 | 673 | 761 | 1235 |
| | 5 | 154 | 455 | 1218 | 109 | 218 | 1094 | 285 | 569 |
| | 6 | 56 | 293 | 603 | 506 | 745 | 911 | 63 | 165 |
| | 7 | 429 | 298 | 939 | 589 | 1226 | 263 | 803 | 451 |
| | 8 | 279 | 214 | 871 | 61 | 144 | 511 | 193 | 963 |
| | 9 | 379 | 191 | 1196 | 73 | 699 | 198 | 616 | 836 |

Example 20

Reduction of STAT3 Phosphorylation by Sunitinib

The following example is provided to illustrate the capability of sunitinib to directly inhibit the phosphorylation of STAT3 (signal transducer of activator of transcription 3), a key mediator of immune suppression in the spleen.

Study Procedure.

The acute effect of Sutent on the phosphorylation status of STAT3 in the spleen was investigated in a subcutaneous tumor mouse model to evaluate the direct immunomodulatory effects of the compound. Briefly, 10-12 week old female BALB/neuT mice were implanted with 1e6 TUBO cells subcutaneously in the right flank. After forty one days post tumor implant, Sutent was given by oral gavage at 20 mg/kg. At 0, 1, 3, 7 and 24 hrs post Sutent dosing, three animals per timepoint were sacrificed under IAUCUC guidelines and spleens were immediately snap frozen in liquid nitrogen to preserve the phosphorylation status. Spleens from female BALB/c mice were snap frozen to use as healthy mice controls.

STAT3 Assay Procedures.

Snap frozen spleens were homogenized at 100 mg tissue per 500 μL lysis buffer (70 mM NaCl, 50 mM β-glycerol phosphate, 10 mM HEPES, 1% Triton X-100, 100 mM $Na_3VO_4$, 100 mM PMSF, 1 mg/mL leupeptin) using a polytron tissue homogenizer. Resulting digests were centrifuged at 10,000 g for 15 minutes. The supernatant was isolated and protein concentrations were determined using BCA protein assay kit (Pierce, Rockford, Ill.). Forty micrograms of protein were added to each well of either a total STAT3 (eBioscience, cat no. 85-86101-11) or phosphor-STAT3 (eBioscience, cat no. 85-86102-11) ELISA Kit. Relative levels of either protein were compared with standards provided in the kit and with standards purchased independently (Signaling Technologies, cat no. 9333-S).

Results.

Table 29 shows the result of a representative STAT assay that evaluates the effect of Sutent on the phosphorylation status of STAT3 in the spleen. Both spleen extracts from healthy or tumor bearing mice exhibited similar levels of STAT3 protein by ELISA (Total STAT3). However, compared to healthy BALB/c, the extracts from tumor bearing mice had significantly higher levels of phosphorylated STAT3 (Student's T-test, $P<0.001$). The phosphorylation levels rapidly decreased to levels similar to healthy animals only 1 hr after Sutent treatment and maintained at lower levels than the untreated mice up to 7 hrs. At 24 hrs the phosphorylation levels of STAT3 completely recovered to levels before Sutent treatment. The phosphorylation kinetics mirrors the levels of circulating Sutent in the blood. The rapid response of STAT3 phosphorylation in the spleen reflecting the pharmacokinetic profile of Sutent suggests a direct immunomodulatory function of Sutent in tumor bearing animals.

TABLE. 29

The relative levels of phosphorylated STAT3 and total STAT3 from healthy BALB/c and tumor bearing BALB/neuT mice before or after Sutent treatment at multiple time points.

| Strain | Time Point, hrs | Phospho-STAT3 Individual values | Mean | SEM | Total STAT3 Individual values | Mean | SEM |
|---|---|---|---|---|---|---|---|
| Balb/c | 0 | 0.11 | 0.09 | 0.01 | 0.12 | 0.13 | 0.00 |
| | | 0.08 | | | 0.12 | | |
| | | 0.09 | | | 0.14 | | |
| Tumor bearing BALB/neuT | 0 | 1.08 | 1.31 | 0.12 | 0.08 | 0.09 | 0.01 |
| | | 1.38 | | | 0.11 | | |
| | | 1.46 | | | NA | | |
| | 1 | 0.26 | 0.23 | 0.02 | 0.12 | 0.09 | 0.01 |
| | | 0.25 | | | 0.08 | | |
| | | 0.19 | | | 0.08 | | |
| | 3 | 0.19 | 0.19 | 0.02 | 0.15 | 0.13 | 0.02 |
| | | 0.15 | | | 0.09 | | |
| | | 0.22 | | | 0.16 | | |
| | 7 | 0.19 | 0.27 | 0.04 | 0.10 | 0.08 | 0.01 |
| | | 0.31 | | | 0.07 | | |
| | | 0.29 | | | 0.08 | | |
| | 24 | 1.54 | 1.44 | 0.07 | 0.08 | 0.08 | 0.00 |
| | | 1.30 | | | 0.08 | | |
| | | 1.47 | | | 0.08 | | |

RAW SEQUENCE LISTING

SEQ ID NO: 1. AMINO ACID SEQUENCE OF THE FULL LENGTH HUMAN PSMA
MWNLLHETDSAVATARRPRWLCAGALVLAGGFFLLGFLFGWFIKSSNEATNITPKHN
MKAFLDELKAENIKKFLYNFTQIPHLAGTEQNFQLAKQIQSQWKEFGLDSVELAHYDV
LLSYPNKTHPNYISIINEDGNEIFNTSLFEPPPPGYENVSDIVPPFSAFSPQGMPEGDL
VYVNYARTEDFFKLERDMKINCSGKIVIARYGKVFRGNKVKNAQLAGAKGVILYSDPA
DYFAPGVKSYPDGWNLPGGGVQRGNILNLNGAGDPLTPGYPANEYAYRRGIAEAVG
LPSIPVHPIGYYDAQKLLEKMGGSAPPDSSWRGSLKVPYNVGPGFTGNFSTQKVKM
HIHSTNEVTRIYNVIGTLRGAVEPDRYVILGGHRDSWVFGGIDPQSGAAVVHEIVRSF
GTLKKEGWRPRRTILFASWDAEEFGLLGSTEWAEENSRLLQERGVAYINADSSIEGN
YTLRVDCTPLMYSLVHNLTKELKSPDEGFEGKSLYESWTKKSPSPEFSGMPRISKLG
SGNDFEVFFQRLGIASGRARYTKNWETNKFSGYPLYHSVYETYELVEKFYDPMFKYH
LTVAQVRGGMVFELANSIVLPFDCRDYAVVLRKYADKIYSISMKHPQEMKTYSVSFDS
LFSAVKNFTEIASKFSERLQDFDKSNPIVLRMMNDQLMFLERAFIDPLGLPDRPFYRH
VIYAPSSHNKYAGESFPGIYDALFDIESKVDPSKAWGEVKRQIYVAAFTVQAAAETLSE
VA

SEQ ID NO: 2. NUCLEOTIDE SEQUENCE ENCODING THE FULL LENGTH
HUMAN PSMA OF SEQ ID NO: 1
atgtggaatctccttcacgaaaccgactcggctgtggccaccgcgcgccgcccgcgctggctgtgcgctggggcgctgg
tgctggcgggtggcttctttctcctcggcttcctcttcgggtggtttataaaatcctccaatgaagctactaacattactccaaa
gcataatatgaaagcattttggatgaattgaaagctgagaacatcaagaagtcttatataattttacacagataccacatt
tagcaggaacagaacaaaactttcagcttgcaaagcaaattcaatcccagtggaaagaatttggcctggattctgttgag
ctagcacattatgatgtcctgttgtcctacccaaataagactcatcccaactacatctcaataattaatgaagatggaaatg
agattttcaacacatcattatttgaaccaccctcctccaggatatgaaaatgtttcggatattgtaccaccttcagtgcttctct
cctcaaggaatgccagagggcgatctagtgtatgttaactatgcacgaactgaagacttctttaaattggaacgggacat
gaaaatcaattgctctgggaaaattgtaattgccagatatggaaaggttttcagaggaaataaggttaaaaatgcccagc
tggcaggggccaaaggagtcattctctactccgaccctgctgactactttgctcctggggtgaagtcctatccagatggttg
gaatcttcctggaggtggtgtccagcgtggaaatatcctaaatctgaatggtgcaggagaccctctcacaccaggttacc
cagcaaatgaatatgcttataggcgtggaattgcagaggctgttggtcttccaagtattcctgttcatccaattggatactatg
atgcacagaagctcctagaaaaaatgggtggctcagcaccaccagatagcagctggagagggaagtctcaaagtgcc
ctacaatgttggacctggctttactggaaacttttctacacaaaaagtcagatgcacatccactctaccaatgaagtgac
aagaatttacaatgtgataggtactctcagaggagcagtggaaccagacagatatgtcattctgggaggtcaccgggac
tcatgggtgtttggtggtattgaccctcagagtggagcagctgttgttcatgaaattgtgaggagcttggaacactgaaaa
aggaagggtggagacctagaagaacaattttgtttgcaagctgggatgcagaagaatttggtcttcttggttctactgagtg
ggcagaggagaattcaagactcccttcaagagcgtggcgtggctttatattaatgctgactcatctatagaaggaaactaca
ctctgagagttgattgtacaccgctgatgtacagcttggtacacaacctaacaaaagagctgaaaagccctgatgaagg
ctttgaaggcaaatctctttatgaaagtggactaaaaaaagtccttcccagagttcagtggcatgccaggataagca
aattgggatctggaaatgattttgaggtgttcttccaacgacttggaattgcttcaggcagagcacggtatactaaaaattg
ggaaacaaacaaatcgcggctatccactgtatcacagtgtctatgaaacatatgagttggtggaaaagttttatgatcc
aatgtttaaatatcacctcactgtggcccaggttcgaggagggatggtgtttgagctagccaattccatagtgctccctttga
ttgtcgagattatgctgtagttttaagaaagtatgctgacaaaatctacagtatttctatgaaacatccacaggaaatgaag
acatacagtgtatcatttgattcactttttctgcagtaaagaattttacagaaattgcttccaagttcagtgagagactccagg
actttgacaaaagcaaaccaatagtattaagaatgatgaatgatcaactcatgtttctgaaagagcatttattgatccatta
gggttaccagacaggcctttttataggcatgtcatctatgctccaagcagccacaacaagtatgcaggggagtcattccc
aggaatttatgatgctctgtttgatattgaaagcaaagtgaccctccaaggcctggggagaagtgaagagacagattt
atgttgcagccttcacagtgcaggcagctgcagagactttgagtgaagtagcc SEQ ID NO: 3. AMINO ACID SEQUENCE OF PSMA SHUFFLED ANTIGEN 1
MASARRPRWLCAGALVLAGGFFLLGFLFGWFIKSSSEATNISPQHNVKAFLDEMKAE
NIKKFLYLFTQIPHLAGTEQNFQLAKQIQAEWKEFGLDSVELAHYDVLLSYPNETHPNY
ISIIDEDGNEIFNTSLFEPPPPGYENISDVVPPYSAFSPQGMPEGDLVYVNYARTEDFF
KLERELKINCSGKILIARYGKVFRGNKVKNAQLAGAKGIILYSDPADYFAPGVKSYPDG -continued

RAW SEQUENCE LISTING

WNLPGGGVQRGNVLNLNGAGDPLTPGYPANEYAYRRELAEAVGLPSIPVHPIGYYDA
QKLLEKMGGSAPPDSSWKGSLKVPYNVGPGFTGNFSTQKVKMHIHSTNEVTRIYNVI
GTIRGAVEPDRYVILGGHRDAWVFGGIDPQSGAAVVHEIVRSFGTLKKKGWRPRRTII
FASWDAEEFGLLGSTEWAEENSRLLQERGVAYINADSSIEGNYTLRVDCTPLMYSLV
YNLTKELQSPDEGFEGKSLYESWTKKSPSPEFSGVPRINKLGSGNDFEVFFQRLGIAS
GRARYTKNWKTNKFSGYPLYHSVYETYELVEKFYDPMFKYHLTVAQVRGGLVFELAD
SIVLPFDCQDYAVVLRKYADKIYNLAMKHPEELKTYSVSFDSLFSAVKNFTEIASKFNQ
RLQDFDKNNPLLVRMLNDQLMFLERAFVDPLGLPDRPFYRHVIYAPSSHNKYAGESF
PGIYDALFDIESKVDPSKAWGEVKRQIYVAAFTVQAAAETLSEVA

SEQ ID NO: 4. NUCLEOTIDE SEQUENCE ENCODING AMINO ACID SEQUENCE
OF PSMA SHUFFLED ANTIGEN 1 OF SEQ ID NO: 3
atggctagcgccagacggcccagatggctgtgcgccggagccctggtgctggccggaggattcttcctgctgggcttcct
gttcggctggttcatcaagagcagcagcgaggccaccaacatcagccccagcacaacgtgaaggcctttctggacg
agatgaaggccgagaacatcaagaagtttctgtacctgttcacccagatcccccacctggccggcaccgagcagaact
tccagctggccaagcagattcaggctgagtggaaagagttcggcctggacagcgtggagctggcccactacgacgtg
ctgctgtcctaccccaacgagacacaccccaactacatcagcatcatcgacgaggacggcaacgagattttcaacacc
agcctgttcgagccccctcccctggctacgagaacatctccgacgtggtgcccccctacagcgccttcagccctcagg
gaatgcctgaaggcgacctggtgtacgtgaactacgcccggaccgaggacttcttcaagctggaacgggagctgaag
atcaactgcagcggcaagatcctgatcgccagatacggcaaggtgttccggggcaacaaagtgaagaacgcacagc
tggctggagccaagggcatcatcctgtacagcgaccccgccgactacttcgcccctggcgtgaagtcctaccctgacgg
ctggaacctgcctggcggcggagtgcagcgggcaacgtgctgaacctgaacggagccggcgaccctctgacccca
ggctaccccgccaacgagtacgcctaccggcgggagctggccgaagccgtgggcctgccagcatccccgtgcacc
ccatcggctactacgacgcccagaaactgctggaaaagatgggcggcagccgccctcccgacagcagctggaagg
gcagcctgaaggtgccctacaacgtgggccctggcttcaccggcaacttcagcacccagaaagtgaagatgcacatc
cacagcaccaacgaagtgaccggatctacaacgtgatcggcaccatcagaggcgccgtggagcccgacagatac
gtgatcctgggcggccaccgggacgcctgggtgttcggcggcatcgaccccagagcggagccgccgtggtgcacg
agatcgtgcggagcttcggcacccctgaagaagaagggctggcggcccagacggaccatcatcttcgccagctgggac
gccgaggaattcggactgctgggctctaccgagtgggccgaggaaaacagcagactgctgcaggaacggggcgtcg
cctacatcaacgccgacagctccatcgagggcaactacaccctgcgggtggactgcacccccctgatgtacagcctgg
tgtacaacctgaccaaagagctgcagagccccgacgagggcttcgagggcaagccctgacgagagctggacca
agaagtccccagccccgagttcagcggcgtgccccggatcaacagctgggcagcggcaacgacttcgaggtgttc
ttccagaggctgggcattgccagcggcagagccggtacaccaagaactggaaaaccaacaagttctccggctaccc
cctgtaccacagcgtgtacgagacatacgaactggtggagaagttctacgacccatgttcaagtaccacctgaccgtg
gcccaggtccggggagggctggtgttcgaactggccgacagcatcgtgctgcccttcgactgccaggactatgctgtggt
gctgcggaagtacgccgacaaatctacaacctggccatgaagcaccccgaggaactgaaaacctacagcgtgtcct
tcgacagcctgttcagcgccgtgaagaacttcaccgagatcgccagcaagttcaaccagcggctgcaggacttcgaca
agaacaaccccctgctggtccggatgctgaacgaccagctgatgttcctggaacgggcttcgtggaccccctgggcct
gcctgaccggcccttctaccggcacgtgatctatgccccagcagccacaacaagtacgctggcgagagcttccccgg
catctacgatgccctgttcgacatcgagagcaaggtggaccccagcaaggcctgggcgaagtgaagcggcagatat
acgtggccgccttcacagtgcaggccgctgccgagacactgagcgaggtggcc SEQ ID NO: 5. AMINO ACID SEQUENCE OF PSMA SHUFFLED ANTIGEN 2
MASARRPRWLCAGALVLAGGFFLLGFLFGWFIKSSSEATNITPQHNVKAFLDELKAEN
IKKFLYNFTQIPHLAGTEQNFELAKQIQAQWKEFGLDSVELSHYDVLLSYPNETHPNYI
SIIDEDGNEIFNTSLFEPPPPGYENISDVVPPYSAFSPQGMPEGDLVYVNYARTEDFFK
LERDMKINCSGKILIARYGKVFRGNKVKNAQLAGAKGIILYSDPADYFAPGVKSYPDG
WNLPGGGVQRGNVLNLNGAGDPLTPGYPANEYAYRRGIAEAVGLPSIPVHPIGYYDA
QKLLEKMGGAAPPDSSWKGSLQVPYNVGPGFTGNFSTQKVKMHIHSTNEVTRIYNVI
GTLKGAVEPDRYVILGGHRDAWVFGGIDPQSGAAVVHEIVRSFGTLKKKGWRPRRTI
LFASWDAEEFGLLGSTEWAEENSRLLQERGVAYINADSSIEGNYTLRVDCTPLMYSL
VYNLTKELQSPDEGFEGKSLFDSWTEKSPSPEFSGLPRISKLGSGNDFEVFFQRLGIA
SGRARYTKDWKTSKFSGYPLYHSVYETYELVEKFYDPMFKYHLTVAQVRGGIVFELA
NSVVLPFDCQDYAVVLKKYADKIYNISMKHPQEMKTYSVSFDSLFSAVKNFTEIASKF
NQRLQDFDKNNPILLRMMNDQLMFLERAFIDPLGLPDRPFYRHVIYAPSSHNKYAGES
FPGIYDALFDIESKVDPSKAWGEVKRQIYVAAFTVQAAAETLSEVA SEQ ID NO: 6. NUCLEOTIDE SEQUENCE ENCODING AMINO ACID SEQUENCE
OF PSMA SHUFFLED ANTIGEN 2 OF SEQ ID NO: 5
atggctagcgccagacggcccagatggctgtgtgctggcgccctggtgctggctggcggcttttcctgctgggcttcctgtt
cggctggttcatcaagagcagcagcgaggccaccaacatcaccccccagcacaacgtgaaggcctttctggacgag
ctgaaggccgagaatatcaagaagttcctgtacaacttcacccagatcccccacctggccggcaccgagcagaacttc
gagctggccaagcagatccaggcccagtggaaagagttcggcctggacagcgtggaactgagccactacgacgtgc
tgctgagctaccccaacgagacacaccccaactacatcagcatcatcgacgaggacggcaacgagattttcaacacc
agcctgttcgagccccctccacccggctacgagaacatcagcgacgtggtgcccccctacagcgcattcagtccacag
ggaatgccgagggcgacctggtgtacgtgaactacgcccggaccgaggacttcttcaagctggaacgggacatgaa
gatcaactgcagcggcaagatcctgatcgccagatacggcaaggtgttccggggcaacaaagtgaagaacgcccag
ctggcaggcgccaagggcatcatcctgtacagcgaccccgccgactacttcgcccctggcgtgaagtcctaccccgac
ggctggaacctgcctggcggcggagtgcagaggggcaacgtgctgaacctgaacggcgctggcgaccctctgaccc
ctggctaccccgccaacgagtacgcctacagacggggaatcgccgaggccgtgggcctgcctagcatccctgtgcac
cccatcggctactacgacgcccagaaactgctggaaaagatgggcggagccgcccctcccgacagctcttggaagg
gcagcctgcaggtcccctacaacgtgggccctggcttcaccggcaacttcagcacccagaaagtgaagatgcacatcc
acagcaccaacgaagtgaccccggatctacaacgtgatcggcaccctgaagggcgccgtggaacccgacagatcgt
gatcctgggcggccaccgggacgcctgggtgttcggaggcatcgaccctcagagcggcgctgccgtggtgcacgaga
tcgtgcggagcttcggcacactgaagaagaagggctggcggcccagacggaccatcctgttcgccagctgggacgcc
gaggaattcggcctgctgggcagcaccgagtgggccgaggaaaacagcggctgctgcaggaacggggcgtcgcct
acatcaacgccgacagcagcatcgagggcaactacaccctgcgggtggactgcaccccctgatgtacagcctggtg

RAW SEQUENCE LISTING

```
tacaacctgaccaaagagctgcagagcccgacgagggcttcgagggcaagtccctgttcgactcctggaccgagaa
gtccccagccccgagttcagcggcctgcccagaatcagcaagctgggcagcggcaacgacttcgaggtgttcttcca
gcggctgggaatcgccagcggcagagcccggtacaccaaggactggaaaaccagcaagttctccggctaccccctg
taccacagcgtgtacgagacatacgagctggtggaaaagttctacgaccccatgttcaagtaccacctgaccgtggcc
aggtccgaggcggcatcgtgttcgaactggccaacagcgtggtgctgccattcgattgtcaggactacgccgtggtgctg
aagaagtacgccgacaaaatctacaacatcagcatgaagcaccccaggaaatgaaaacctacagcgtgtccttcg
acagcctgttcagccgccgtgaagaatttcaccgagatcgcctccaagttcagcgagcggctgcaggacttcgacaaga
acaacccatcctgctgcggatgatgaacgaccagctgatgttcctggaacgggccttcatcgaccccctgggcctgcc
cgaccggcccttttaccggcacgtgatctatgccccagcagccacaacaaatacgccggcgagagtttccccggcat
ctacgatgccctgttcgatatcgagagcaaggtggacccagcaaggcctggggcgaagtgaagcggcagatttacgt
ggccgcattcacagtgcaggctgctgccgagacactgagcgaggtggcc
```

SEQ ID NO: 7. AMINO ACID SEQUENCE OF PSMA SHUFFLED ANTIGEN 3
MASARRPRW

RAW SEQUENCE LISTING

SEQ ID NO: 10. NUCLEOTIDE SEQEUNCE ENCODING AMINO ACID SEQUENCE
OF THE MEMBRANE-BOUND PSMA ANTIGEN OF SEQ ID NO: 9
atggctagcgcgcgccgcccgcgctggctgtgcgctggggcgctggtgctggcgggtggcttctttctcctcggcttcctctt
cgggtggtttataaaatcctccaatgaagctactaacattactccaaagcataatatgaaagcattttttggatgaattgaaa
gctgagaacatcaagaagttcttatatataattttacacagataccacatttagcaggaacagaacaaaactttcagcttgca
aagcaaattcaatcccagtggaaagaatttggcctggattctgttgagctggcacattatgatgtcctgttgtcctacccaaa
taagactcatcccaactacatctcaataatttaatgaagatggaaatgagattttcaacacatcattatttgaaccacctcctc
caggatatgaaaatgtttcggatattgtaccacctttcagtgctttctctcctcaaggaatgccagagggcgatctagtgtat
gttaactatgcacgaactgaagacttctttaaattggaacgggacatgaaaatcaattgctctgggaaaattgtaattgcca
gatatgggaaagttttcagaggaaataaggttaaaaatgcccagctggcaggggccaaaggagtcattctctactccga
ccctgctgactactttgctcctggggtgaagtcctatccagatggttggaatcttcctggaggtggtgtccagcgtggaaata
tcctaaatctgaatggtgcaggagaccctctcacaccaggttacccagcaaatgaatatgcttataggcgtggaattgca
gaggctgttggtcttccaagtattcctgttcatccaattggatactatgatgcacagaagctcctagaaaaaatgggtggct
cagcaccaccagatagcagctggagaggaagtctcaaagtgccctacaatgttggacctggcttactggaaacttttct
acacaaaaagtcaagatgcacatccactctaccaatgaagtgacaagaatttacaatgtgataggtactctcagagga
gcagtggaaccagacagatatgtcattctgggaggtcaccgggactcatgggtgtttggtggtattgaccctcagagtgg
agcagctgttgttcatgaaattgtgaggagctttggaacactgaaaaaggaagggtggagacctagaagaacaattttgt
ttgcaagctgggatgcagaagaatttggtcttcttggttctactgagtgggcagaggagaattcaagactccttcaagagc
gtggcgtggcttatattaatgctgactcatctatagaaggaaactacactctgagagttgattgtacaccgctgatgtacag
cttggtacacaacctaacaaaagagctgaaaagccctgatgaaggcttgaaggcaaatctctttatgaaagttggacta
aaaaaagtccttccccagagttcagtggcatgcccaggataagcaaattgggatctggaaatgattttgaggtgttcttcc
aacgacttggaattgcttcaggcagagcacggtatactaaaaattgggaaacaaacaaattcagcggctatccactgta
tcacagtgtctatgaaacatatgagttggtggaaaagttttatgatccaatgtttaaatatcacctcactgtggcccaggttcg
aggagggatggtgtttgagctggccaattccatagtgctccctttttgattgtcgagattatgctgtagttttaagaaagtatgct
gacaaaatctacagtatttctatgaaacatccacaggaaatgaagacatacagtgtatcatttgattcactttttctgcagta
aagaattttacagaaattgcttccaagttcagtgagagactccaggactttgacaaaagcaacccaatagtattaagaat
gatgaatgatcaactcatgtttctggaaagagcatttattgatccattagggttaccagacaggccttttataggcatgtcat
ctatgctccaagcagccacaacaagtatgcagggagtcattcccaggaatttatgatgctctgtttgatattgaaagcaa
agtggaccctccaaggcctggggagaagtgaagagacagatttatgttgcagccttcacagtgcaggcagctgcaga
gactttgagtgaagtagcc SEQ ID NO: 11. AMINO ACID SEQUENCE OF A CYTOSOLIC PSMA ANTIGEN
MASKSSNEATNITPKHNMKAFLDELKAENIKKFLYNFTQIPHLAGTEQNFQLAKQIQSQ
WKEFGLDSVELAHYDVLLSYPNKTHPNYISIINEDGNEIFNTSLFEPPPPGYENVSDIVP
PFSAFSPQGMPEGDLVYVNYARTEDFFKLERDMKINCSGKIVIARYGKVFRGNKVKN
AQLAGAKGVILYSDPADYFAPGVKSYPDGWNLPGGGVQRGNILNLNGAGDPLTPGY
PANEYAYRRGIAEAVGLPSIPVHPIGYYDAQKLLEKMGGSAPPDSSWRGSLKVPYNV
GPGFTGNFSTQKVKMHIHSTNEVTRIYNVIGTLRGAVEPDRYVILGGHRDSWVFGGID
PQSGAAVVHEIVRSFGTLKKEGWRPRRTILFASWDAEEFGLLGSTEWAEENSRLLQE
RGVAYINADSSIEGNYTLRVDCTPLMYSLVHNLTKELKSPDEGFEGKSLYESWTKKSP
SPEFSGMPRISKLGSGNDFEVFFQRLGIASGRARYTKNWETNKFSGYPLYHSVYETY
ELVEKFYDPMFKYHLTVAQVRGGMVFELANSIVLPFDCRDYAVVLRKYADKIYSISMK
HPQEMKTYSVSFDSLFSAVKNFTEIASKFSERLQDFDKSNPIVLRMMNDQLMFLERAF
IDPLGLPDRPFYRHVIYAPSSHNKYAGESFPGIYDALFDIESKVDPSKAWGEVKRQIYV
AAFTVQAAAETLSEVA SEQ ID NO: 12. NUCLEOTIDE SEQEUNCE ENCODING AMINO ACID SEQUENCE
OF THE CYTOSOLIC PSMA ANTIGEN OF SEQ ID NO: 11
atggctagcaaatcctccaatgaagctactaacattactccaaagcataatatgaaagcattttttggatgaattgaaagct
gagaacatcaagaagttcttatatataattttacacagataccacatttagcaggaacagaacaaaactttcagcttgcaaa
gcaaattcaatcccagtggaaagaatttggcctggattctgttgagctggcacattatgatgtcctgttgtcctacccaaata
agactcatcccaactacatctcaataattaatgaagatggaaatgagattttcaacacatcattatttgaaccacctcctcc
aggatatgaaaatgtttcggatattgtaccacctttcagtgctttctctcctcaaggaatgccagagggcgatctagtgtatgt
taactatgcacgaactgaagacttctttaaattggaacgggacatgaaaatcaattgctctgggaaaattgtaattgccag
atatgggaaagttttcagaggaaataaggttaaaaatgcccagctggcaggggccaaaggagtcattctctactccgac
cctgctgactactttgctcctggggtgaagtcctatccagatggttggaatcttcctggaggtggtgtccagcgtggaaatat
cctaaatctgaatggtgcaggagaccctctcacaccaggttacccagcaaatgaatatgcttataggcgtggaattgcag
aggctgttggtcttccaagtattcctgttcatccaattggatactatgatgcacagaagctcctagaaaaaatgggtggctc
agcaccaccagatagcagctggagaggaagtctcaaagtgccctacaatgttggacctggcttactggaaacttttcta
cacaaaaagtcaagatgcacatccactctaccaatgaagtgacaagaatttacaatgtgataggtactctcagaggac
agtggaaccagacagatatgtcattctgggaggtcaccgggactcatgggtgtttggtggtattgaccctcagagtgga
gcagctgttgttcatgaaattgtgaggagctttggaacactgaaaaaggaagggtggagacctagaagaacaattttgttt
gcaagctgggatgcagaagaatttggtcttcttggttctactgagtgggcagaggagaattcaagactccttcaagagcgt
ggcgtggcttatattaatgctgactcatctatagaaggaaactacactctgagagttgattgtacaccgctgatgtacagctt
ggtacacaacctaacaaaagagctgaaaagccctgatgaaggcttgaaggcaaatctctttatgaaagttggactaaa
aaaagtccttccccagagttcagtggcatgcccaggataagcaaattgggatctggaaatgattttgaggtgttcttccaa
cgacttggaattgcttcaggcagagcacggtatactaaaaattgggaaacaaacaaattcagcggctatccactgtatc
acagtgtctatgaaacatatgagttggtggaaaagttttatgatccaatgtttaaatatcacctcactgtggcccaggttcga
ggagggatggtgtttgagctggccaattccatagtgctccctttttgattgtcgagattatgctgtagttttaagaaagtatgctg
acaaaatctacagtatttctatgaaacatccacaggaaatgaagacatacagtgtatcatttgattcactttttctgcagtaa
agaattttacagaaattgcttccaagttcagtgagagactccaggactttgacaaaagcaacccaatagtattaagaatg
atgaatgatcaactcatgtttctggaaagagcatttattgatccattagggttaccagacaggccttttataggcatgtcatct
atgctccaagcagccacaacaagtatgcagggagtcattcccaggaatttatgatgctctgtttgatattgaaagcaaa
gtggaccctccaaggcctggggagaagtgaagagacagatttatgttgcagccttcacagtgcaggcagctgcagag
actttgagtgaagtagcc

RAW SEQUENCE LISTING

SEQ ID NO: 13. AMINO ACID SEQUENCE OF A SECRETED PSMA ANTIGEN
MASETDTLLLWVLLLWVPGSTGDAAKSSNEATNITPKHNMKAFLDELKAENIKKFLYN
FTQIPHLAGTEQNFQLAKQIQSQWKEFGLDSVELAHYDVLLSYPNKTHPNYISIINEDG
NEIFNTSLFEPPPPGYENVSDIVPPFSAFSPQGMPEGDLVYVNYARTEDFFKLERDMK
INCSGKIVIARYGKVFRGNKVKNAQLAGAKGVILYSDPADYFAPGVKSYPDGWNLPG
GGVQRGNILNLNGAGDPLTPGYPANEYAYRRGIAEAVGLPSIPVHPIGYYDAQKLLEK
MGGSAPPDSSWRGSLKVPYNVGPGFTGNFSTQKVKMHIHSTNEVTRIYNVIGTLRGA
VEPDRYVILGGHRDSWVFGGIDPQSGAAVVHEIVRSFGTLKKEGWRPRRTILFASWD
AEEFGLLGSTEWAEENSRLLQERGVAYINADSSIEGNYTLRVDCTPLMYSLVHNLTKE
LKSPDEGFEGKSLYESWTKKSPSPEFSGMPRISKLGSGNDFEVFFQRLGIASGRARY
TKNWETNKFSGYPLYHSVYETYELVEKFYDPMFKYHLTVAQVRGGMVFELANSIVLP
FDCRDYAVVLRKYADKIYSISMKHPQEMKTYSVSFDSLFSAVKNFTEIASKFSERLQD
FDKSNPIVLRMMNDQLMFLERAFIDPLGLPDRPFYRHVIYAPSSHNKYAGESFPGIYD
ALFDIESKVDPSKAWGEVKRQIYVAAFTVQAAAETLSEVA

SEQ ID NO: 14. NUCLEOTIDE SEQUENCE ENCODING AMINO ACID SEQUENCE
OF THE SECRETED PSMA ANTIGEN OF SEQ ID NO: 13
atggctagcgaaaccgacactttgttgttgtgggtgcttttgctttgggtacccggatctactggtgatgctgctaaatcctcca
atgaagctactaacattactccaaagcataatatgaaagcattttggatgaattgaaagctgagaacatcaagaagttct
tatataatttttacacagataccacattttagcaggaacagaacaaaacttttcagcttgcaaagcaaattcaatcccagtgg
aaagaatttggcctggattctgttgagctagcacattatgatgtcctgttgtcctacccaaataagactcatcccaactacat
ctcaataattaatgaagatggaaatgagattttcaacacatcattatttgaaccacctcctccaggatatgaaaatgtttcgg
atattgtaccacctttcagtgctttctctcctcaaggaatgccagagggcgatctagtgtatgttaactatgcacgaactgaa
gacttctttaaattgaacgggacatgaaaatcaattgctctgggaaaatttaattgccagatatgggaaagttttcagag
gaaataaggttaaaaatgcccagctggcagggcaaaggagtcattctctactccgaccctgctgactactttgctcct
gggtgaagtcctatccagatggttggaatcttcctggaggtggtgtccagcgtggaaatatcctaaatctgaatggtgca
ggagaccctctcacaccaggttacccagcaaatgaatatgcttataggcgtggaattgcagaggctgttggtcttccaagt
attcctgttcatccaattggatactatgatgcacagaagctcctagaaaaaaatgggtggctcagcaccaccagatagcag
ctggagaggaagtctcaaagtgccctacaatgttggacctggcttttactggaaacttttctacacaaaaagtcaagatgc
acatccactctaccaatgaagtgacaagaatttacaatgtgataggtactctcagaggagcagtggaaccagacagat
atgtcattctgggaggtcaccgggactcatgggtgtttggtggtattgaccctcagagtggagcagctgttgttcatgaaatt
gtgaggagctttggaacactgaaaaaggaagggtggaacctagaagaacaattttgtttgcaagctgggatgcagaa
gaatttggtcttcttggttctactgagtgggcagaggagaattcaagactccttcaagagcgtgcgtggcttatattaatgct
gactcatctataagaaggaaactacactctgagagttgattgtacaccgctgatgtacagcttggtacacaacctaacaaa
agagctgaaaagccctgatgaaggctttgaaggcaaatctctttatgaaagttggactaaaaaaagtccttcccccagagt
tcagtggcatgcccaggataagcaaattgggatctggaaatgattttgaggtgttcttccaacgacttggaattgcttcagg
cagagcacggtatactaaaaattgggaaacaaacaaattcagcggctatccactgtatcacagtgtctatgaaacatat
gagttggtggaaaagttttatgatccaatgtttaaatatcacctcactgtgcccaggttcgaggagggatggtgtttgagct
agccaattccatagtgctccctttgattgtcgagattatgctgtagttttaagaaagtatgctgacaaaatctacagtatttcta
tgaaacatccacaggaaatgaagacatacagtgtatcatttgattcactttttctgcagtaaagaattttacagaaattgctt
ccaagttcagtgagagactccaggactttgacaaaagcaaccaatagtattaagaatgatgaatgatcaactcatgttt
ctggaaagagcatttattgatccattagggttaccagacaggcctttttataggcatgtcatctatgctccaagcagccaca
acaagtatgcagggagtcattcccaggaatttatgatgctctgtttgatattgaaagcaaagtggaccttccaaggcct
ggggagaagtgaagagacagatttatgttgcagccttcacagtgcaggcagctgcagagactttgagtgaagtagcc SEQ ID NO: 15. AMINO ACID SEQUENCE OF THE FULL LENGTH HUMAN PSA
MASWVPVVFLTLSVTWIGAAPLILSRIVGGWECEKHSQPWQVLVASRGRAVCGGVLV
HPQWVLTAAHCIRNKSVILLGRHSLFHPEDTGQVFQVSHSFPHPLYDMSLLKNRFLRP
GDDSSHDLMLLRLSEPAELTDAVKVMDLPTQEPALGTTCYASGWGSIEPEEFLTPKK
LQCVDLHVISNDVCAQVHPQKVTKFMLCAGRWTGGKSTCSGDSGGPLVCNGVLQGI
TSWGSEPCALPERPSLYTKVVHYRKWIKDTIVANP SEQ ID NO: 16. NUCLEOTIDE SEQUENCE ENCODING AMINO ACID SEQUENCE
OF THE FULL LENGTH HUMAN PSA OF SEQ ID NO: 15
atggctagctgggtcccggttgtcttcctcaccctgtccgtgacgtggattggcgctgcgcccctcatcctgtctcggattgtg
ggaggctgggagtgcgagaagcattcccaaccctggcaggtgcttgtggcctctcgtggcagggcagtctgcggcggt
gttctggtgcaccccccagtgggtcctcacagctgcccactgcatcaggaacaaaagcgtgatcttgctgggtcggcaca
gcttgtttcatcctgaagacacaggccaggtatttcaggtcagccacagcttcccacacccgctctacgatatgagcctcct
gaagaatcgattcctcaggccaggtgatgactccagccacgacctcatgctgctccgcctgtcagagcctgccgagctc
acggatgctgtgaaggtcatggacctgccacccaggagccagcactgggaccacctgctacgcctcaggctgggg
cagcattgaaccagaggagttcttgaccccaaagaaacttcagtgtgtggacctccatgtatttccaatgacgtgtgtgcg
caagttcaccctcagaaggtgaccaagttcatgctgtgtgctgcagggcagcaaaagcacctgctcgggt
gattctggggcccacttgtctgtaatggtgtgcttcaaggtatcacgtcatgggcagtgaaccatgtgccctgcccgaa
aggccttccctgtacaccaaggtggtgcattaccggaagtggatcaaggacaccatcgtggccaacccc SEQ ID NO: 17. AMINO ACID SEQUENCE OF A CYTOSOLIC PSA ANTIGEN
MASIVGGWECEKHSQPWQVLVASRGRAVCGGVLVHPQWVLTAAHCIRNKSVILLGR
HSLFHPEDTGQVFQVSHSFPHPLYDMSLLKNRFLRPGDDSSHDLMLLRLSEPAELTD
AVKVMDLPTQEPALGTTCYASGWGSIEPEEFLTPKKLQCVDLHVISNDVCAQVHPQK
VTKFMLCAGRWTGGKSTCSGDSGGPLVCNGVLQGITSWGSEPCALPERPSLYTKVV
HYRKWIKDTIVANP SEQ ID NO: 18. NUCLEOTIDE SEQEUNCE ENCODING AMINO ACID SEQUENCE
OF THE CYTOSOLIC PSA ANTIGEN OF SEQ ID NO: 17
atggctagcattgtgggaggctgggagtgcgagaagcattcccaaccctggcaggtgcttgtggcctctcgtggcaggg
cagtctgcggcggtgttctggtgcaccccccagtgggtcctcacagctgcccactgcatcaggaacaaaagcgtgatcttg
ctgggtcggcacagcttgtttcatcctgaagacacaggccaggtatttcaggtcagccacagcttcccacacccgctctac

```
gatatgagcctcctgaagaatcgattcctcaggccaggtgatgactccagccacgacctcatgctgctccgcctgtcaga
gcctgccgagctcacggatgctgtgaaggtcatggacctgcccacccaggagccagcactggggaccacctgctacg
cctcaggctggggcagcattgaaccagaggagttcttgacccaaagaaacttcagtgtgtggacctccatgttatttcca
atgacgtgtgtgcgcaagttcaccctcagaaggtgaccaagttcatgctgtgtgctggacgctggacaggggcaaaa
gcacctgctcgggtgattctggggggcccacttgtctgtaatggtgtgcttcaaggtatcacgtcatgggcagtgaaccatg
tgccctgcccgaaaggccttccctgtacaccaaggtggtgcattaccggaagtggatcaaggacaccatcgtggccaa
cccc SEQ ID NO: 19. AMINO ACID SEQUENCE OF A MEMBRANE-BOUND PSA
ANTIGEN
MASARRPRWLCAGALVLAGGFFLLGFLFGWFIKSSNEATNITPGIVGGWECEKHSQP
WQVLVASRGRAVCGGVLVHPQWVLTAAHCIRNKSVILLGRHSLFHPEDTGQVFQVS
HSFPHPLYDMSLLKNRFLRPGDDSSHDLMLLRLSEPAELTDAVKVMDLPTQEPALGT
TCYASGWGSIEPEEFLTPKKLQCVDLHVISNDVCAQVHPQKVTKFMLCAGRWTGGK
STCSGDSGGPLVCNGVLQGITSWGSEPCALPERPSLYTKVVHYRKWIKDTIVANP SEQ ID NO: 20. NUCLEOTIDE SEQUENCE ENCODING AMINO ACID SEQUENCE
OF THE MEMBRANE-BOUND PSA ANTIGEN OF SEQ ID NO: 19
atggctagcgcgcgccgcccgcgctggctgtgcgctggggcgctggtgctggcgggtggcttctttctcctcggcttcctctt
cgggtggtttataaaatcctccaatgaagctactaacattactccaggaattgtgggaggctgggagtgcgagaagcatt
cccaaccctggcaggtgcttgtggcctctcgtggcagggcagtctgcgcggtgttctggtgcaccccagtgggtcctc
acagctgcccactgcatcaggaacaaaagcgtgatcttgctgggtcggcacagcttgtttcatcctgaagacacaggcc
aggtatttcaggtcagccacagcttcccacacccgctctacgatatgagcctcctgaagaatcgattcctcaggccaggt
gatgactccagccacgacctcatgctgctccgcctgtcagagcctgccgagctcacggatgctgtgaaggtcatggacc
tgcccacccaggagccagcactggggaccacctgctacgcctcaggctggggcagcattgaaccagaggagttcttg
acccaaagaaacttcagtgtgtggacctccatgttatttccaatgacgtgtgtgcgcaagttcaccctcagaaggtgacc
aagttcatgctgtgtgctggacgctggacaggggcaaaagcacctgctcgggtgattctggggggcccacttgtctgtaat
ggtgtgcttcaaggtatcacgtcatgggcagtgaaccatgtgccctgcccgaaaggccttccctgtacaccaaggtggt
gcattaccggaagtggatcaaggacaccatcgtggccaaccctga SEQ ID NO: 21. AMINO ACID SEQUENCE OF THE FULL LENGTH HUMAN PSCA
MASKAVLLALLMAGLALQPGTALLCYSCKAQVSNEDCLQVENCTQLGEQCWTARIRA
VGLLTVISKGCSLNCVDDSQDYYVGKKNITCCDTDLCNASGAHALQPAAAILALLPAL
GLLLWGPGQL SEQ ID NO: 22. NUCLEOTIDE SEQUENCE ENCODING AMINO ACID SEQUENCE
OF THE FULL LENGTH HUMAN PSCA OF SEQ ID NO: 21
atggctagcaaggctgtgctgcttgccctgttgatggcaggcttggcctgcagccaggcactgccctgctgtgctactcct
gcaaagcccaggtgagcaacgaggactgcctgcaggtggagaactgcacccagctgggggagcagtgctggaccg
cgcgcatccgcgcagttggcctcctgaccgtcatcagcaaggctgcagcttgaactgcgtggatgactcacaggacta
ctacgtgggcaagaagaacatcacgtgctgtgacaccgacttgtgcaacgccagcggggcccatgccctgcagccgg
ctgccgccatccttgcgctgctccctgcactcggcctgctgctctggggaccccggccagcta SEQ ID NO: 23. NUCLEOTIDE SEQUENCE OF PLASMID 5166
GGCGTAATGCTCTGCCAGTGTTACAACCAATTAACCAATTCTGATTAGAAAAACTC
ATCGAGCATCAAATGAAACTGCAATTTATTCATATCAGGATTATCAATACCATATTT
TTGAAAAAGCCGTTTCTGTAATGAAGGAGAAAACTCACCGAGGCAGTTCCATAGG
ATGGCAAGATCCTGGTATCGGTCTGCGATTCCGACTCGTCCAACATCAATACAAC
CTATTAATTTCCCCTCGTCAAAAATAAGGTTATCAAGTGAGAAATCACCATGAGTG
ACGACTGAATCCGGTGAGAATGGCAAAAGCTTATGCATTTCTTTCCAGACTTGTTC
AACAGGCCAGCCATTACGCTCGTCATCAAAATCACTCGCATCAACCAAACCGTTA
TTCATTCGTGATTGCGCCTGAGCGAGACGAAATACGCGATCGCTGTTAAAAGGAC
AATTACAAACAGGAATCAAATGCAACCGGCGCAGGAACACTGCCAGCGCATCAAC
AATATTTTCACCTGAATCAGGATATTCTTCTAATACCTGGAATGCTGTTTTCCCGG
GGATCGCAGTGGTGAGTAACCATGCATCATCAGGAGTACGGATAAAATGCTTGAT
GGTCGGAAGAGGCATAAATTCCGTCAGCCAGTTTAGTCTGACCATCTCATCTGTA
ACATCATTGGCAACGCTACCTTTGCCATGTTTCAGAAACAACTCTGGCGCATCGG
GCTTCCCATACAATCGATAGATTGTCGCACCTGATTGCCCGACATTATCGCGAGC
CCATTTATACCCATATAAATCAGCATCCATGTTGGAATTTAATCGCGGCCTCGAGC
AAGACGTTTCCCGTTGAATATGGCTCATAACACCCCTTGTATTACTGTTTATGTAA
GCAGACAGGTCGACAATATTGGCTATTGGCCATTGCATACGTTGTATCTATATCAT
AATATGTACATTTATATTGGCTCATGTCCAATATGACCGCCATGTTGACATTGATTA
TTGACTAGTTATTAATAGTAATCAATTACGGGGTCATTAGTTCATAGCCCATATATG
GAGTTCCGCGTTACATAACTTACGGTAAATGGCCCGCCTGGCTGACCGCCCAAC
GACCCCCGCCCATTGACGTCAATAATGACGTATGTTCCCATAGTAACGCCAATAG
GGACTTTCCATTGACGTCAATGGGTGGAGTATTTACGGTAAACTGCCCACTTGGC
AGTACATCAAGTGTATCATATGCCAAGTCCGCCCCCTATTGACGTCAATGACGGT
AAATGGCCCGCCTGGCATTATGCCCAGTACATGACCTTACGGGACTTTCCTACTT
GGCAGTACATCTACGTATTAGTCATCGCTATTACCATGGTGATGCGGTTTTGGCA
GTACACCAATGGGCGTGGATAGCGGTTTGACTCACGGGGATTTCCAAGTCTCCAC
CCCATTGACGTCAATGGGAGTTTGTTTTGGCACCAAAATCAACGGGACTTTCCAA
AATGTCGTAATAACCCCGCCCCGTTGACGCAAATGGGCGGTAGGCGTGTACGGT
GGGAGGTCTATATAAGCAGAGCTCGTTTAGTGAACCGTCAGATCGCCTGGAGAC
GCCATCCACGCTGTTTTGACCTCCATAGAAGACACCGGGACCGATCCAGCCTCC
GCGGCCGGGAACGGTGCATTGGAACGCGGATTCCCCGTGCCAAGAGTGACTCA
CCGTCCGGATCTCAGCAAGCAGGTATGTACTCTCCAGGGTGGGCCTGGCTTCCC
CAGTCAAGACTCCAGGGATTTGAGGGACGCTGTGGGCTCTTCTCTTACATGTACC
```

RAW SEQUENCE LISTING

```
TTTTGCTTGCCTCAACCCTGACTATCTTCCAGGTCAGGATCCCAGAGTCAGGGGT
CTGTATTTTCCTGCTGGTGGCTCCAGTTCAGGAACAGTAAACCCTGCTCCGAATA
TTGCCTCTCACATCTCGTCAATCTCCGCGAGGACTGGGGACCCTGTGACGAACAT
GGCTAGCGCGCCGCCCGCGCTGGCTGTGCGCTGGGGCGCTGGTGCTGGCG
GGTGGCTTCTTTCTCCTCGGCTTCCTCTTCGGGTGGTTTATAAAATCCTCCAATGA
AGCTACTAACATTACTCCAAAGCATAATATGAAAGCATTTTTGGATGAATTGAAAG
CTGAGAACATCAAGAAGTTCTTATATAATTTTACACAGATACCACATTTAGCAGGA
ACAGAACAAAACTTTCAGCTTGCAAAGCAAATTCAATCCCAGTGGAAAGAATTTGG
CCTGGATTCTGTTGAGCTGGCACATTATGATGTCCTGTTGTCCTACCCAAATAAGA
CTCATCCCAACTACATCTCAATAATTAATGAAGATGGAAATGAGATTTTCAACACAT
CATTATTTGAACCACCTCCTCCAGGATATGAAAATGTTTCGGATATTGTACCACCT
TTCAGTGCTTTCTCTCCTCAAGGAATGCCAGAGGGCGATCTAGTGTATGTTAACTA
TGCACGAACTGAAGACTTCTTTAAATTGGAACGGGACATGAAAATCAATTGCTCTG
GGAAAATTGTAATTGCCAGATATGGGAAAGTTTTCAGAGGAAATAAGGTTAAAAAT
GCCCAGCTGGCAGGGGCCAAAGGAGTCATTCTCTACTCCGACCCTGCTGACTAC
TTTGCTCCTGGGGTGAAGTCCTATCCAGATGGTTGGAATCTTCCTGGAGGTGGTG
TCCAGCGTGGAAATATCCTAAATCTGAATGGTGCAGGAGACCCTCTCACACCAGG
TTACCCAGCAAATGAATATGCTTATAGGCGTGGAATTGCAGAGGCTGTTGGTCTT
CCAAGTATTCCTGTTCATCCAATTGGATACTATGATGCACAGAAGCTCCTAGAAAA
AATGGGTGGCTCAGCACCACCAGATAGCAGCTGGAGAGGAAGTCTCAAAGTGCC
CTACAATGTTGGACCTGGCTTTACTGAAACTTTTCTACACAAAAAGTCAAGATGC
ACATCCACTCTACCAATGAAGTGACAAGAATTTACAATGTGATAGGTACTCTCAGA
GGAGCAGTGGAACCAGACAGATATGTCATTCTGGGAGGTCACCGGGACTCATGG
GTGTTTGGTGGTATTGACCCTCAGAGTGGAGCAGCTGTTGTTCATGAAATTGTGA
GGAGCTTTGGAACACTGAAAAAGGAAGGGTGGAGACCTAGAAGAACAATTTTGTT
TGCAAGCTGGGATGCAGAAGAATTTGGTCTTCTTGGTTCTACTGAGTGGGCAGAG
GAGAATTCAAGACTCCTTCAAGAGCGTGGCGTGGCTTATATTAATGCTGACTCAT
CTATAGAAGGAAACTACACTCTGAGAGTTGATTGTACACCGCTGATGTACAGCTT
GGTACACAACCTAACAAAAGAGCTGAAAAGCCCTGATGAAGGCTTTGAAGGCAAA
TCTCTTTATGAAAGTTGGACTAAAAAAAGTCCTTCCCCAGAGTTCAGTGGCATGCC
CAGGATAAGCAAATTGGGATCTGGAAATGATTTTGAGGTGTTCTTCCAACGACTTG
GAATTGCTTCAGGCAGAGCACGGTATACTAAAAATTGGGAAACAAACAAATTCAG
CGGCTATCCACTGTATCACAGTGTCTATGAAACATATGAGTTGGTGGAAAAGTTTT
ATGATCCAATGTTTAAATATCACCTCACTGTGGCCCAGGTTCGAGGAGGGATGGT
GTTTGAGCTGGCCAATTCCATAGTGCTCCCTTTTGATTGTCGAGATTATGCTGTAG
TTTTAAGAAAGTATGCTGACAAAATCTACAGTATTTCTATGAAACATCCACAGGAAA
TGAAGACATACAGTGTATCATTTGATTCACTTTTTTCTGCAGTAAAGAATTTTACAG
AAATTGCTTCCAAGTTCAGTGAGAGACTCCAGGACTTTGACAAAAGCAACCCAATA
GTATTAAGAATGATGAATGATCAACTCATGTTTCTGGAAAGAGCATTTATTGATCC
ATTAGGGTTACCAGACAGGCCTTTTTATAGGCATGTCATCTATGCTCCAAGCAGC
CACAACAAGTATGCAGGGGAGTCATTCCCAGGAATTTATGATGCTCTGTTTGATAT
TGAAAGCAAAGTGGACCCTTCCAAGGCCTGGGGAGAAGTGAAGAGACAGATTTAT
GTTGCAGCCTTCACAGTGCAGGCAGCTGCAGAGACTTTGAGTGAAGTAGCCTAAA
GATCTGGCCCTAACAAAACAAAAAGATGGGGTTATTCCCTAAACTTCATGGGTTA
CGTAATTGGAAGTTGGGGGACATTGCCACAAGATCATATTGTACAAAAGATCAAA
CACTGTTTTAGAAAACTTCCTGTAAACAGGCCTATTGATTGGAAAGTATGTCAAAG
GATTGTGGGTCTTTTGGGCTTTGCTGCTCCATTTACACAATGTGGATATCCTGCCT
TAATGCCTTTGTATGCATGTATACAAGCTAAACAGGCTTTCACTTTCTCGCCAACT
TACAAGGCCTTTCTAAGTAAACAGTACATGAACCTTTACCCCGTTGCTCGGCAAC
GGCCTGGTCTGTGCCAAGTGTTTGCTGACGCAACCCCCACTGGCTGGGGCTTGG
CCATAGGCCATCAGCGCATGCGTGGAACCTTTGTGGCTCCTCTGCCGATCCATAC
TGCGGAACTCCTAGCCGCTTGTTTTGCTCGCAGCCGGTCTGGAGCAAAGCTCATA
GGAACTGACAATTCTGTCGTCCTCTCGCGGAAATATACATCGTTTCGATCTACGTA
TGATCTTTTTCCCTCTGCCAAAAATTATGGGGACATCATGAAGCCCCTTGAGCATC
TGACTTCTGGCTAATAAAGGAAATTTATTTTCATTGCAATAGTGTGTTGGAATTTTT
TGTGTCTCTCACTCGGAAGGAATTCTGCATTAATGAATCGGCCAACGCGCGGGGA
GAGGCGGTTTGCGTATTGGGCGCTCTTCCGCTTCCTCGCTCACTGACTCGCTGC
GCTCGGTCGTTCGGCTGCGGCGAGCGGTATCAGCTCACTCAAAGGCGGTAATAC
GGTTATCCACAGAATCAGGGGATAACGCAGGAAAGAACATGTGAGCAAAAGGCC
AGCAAAAGGCCAGGAACCGTAAAAAGGCCGCGTTGCTGGCGTTTTTCCATAGGC
TCCGCCCCCTGACGAGCATCACAAAAATCGACGCTCAAGTCAGAGGTGGCGAA
ACCCGACAGGACTATAAAGATACCAGGCGTTTCCCCCTGGAAGCTCCCTCGTGC
GCTCTCCTGTTCCGACCCTGCCGCTTACCGGATACCTGTCCGCCTTTCTCCCTTC
GGGAAGCGTGGCGCTTTCTCATAGCTCACGCTGTAGGTATCTCAGTTCGGTGTAG
GTCGTTCGCTCCAAGCTGGGCTGTGTGCACGAACCCCCCGTTCAGCCCGACCGC
TGCGCCTTATCCGGTAACTATCGTCTTGAGTCCAACCCGGTAAGACACGACTTAT
CGCCACTGGCAGCAGCCACTGGTAACAGGATTAGCAGAGCGAGGTATGTAGGCG
GTGCTACAGAGTTCTTGAAGTGGTGGCCTAACTACGGCTACACTAGAAGAACAGT
ATTTGGTATCTGCGCTCTGCTGAAGCCAGTTACCTTCGGAAAAAGAGTTGGTAGC
TCTTGATCCGGCAAACAAACCACCGCTGGTAGCGGTGGTTTTTTTGTTTGCAAGC
AGCAGATTACGCGCAGAAAAAAAGGATCTCAAGAAGATCCTTTGATCTTTTCTACG
GGGTCTGACGCTCAGTGGAACGAAAACTCACGTTAAGGGATTTTGGTCATGAGAT
TATCAAAAAGGATCTTCACCTAGATCCTTTTAAATTAAAAATGAAGTTTTAAATCAA
TCTAAAGTATATATGAGTAAACTTGGTCTGACAGTTACCAATGCTTAATCAGTGAG
GCACCTATCTCAGCGATCTGTCTATTTCGTTCATCCATAGTTGCCTGACTC
```

| RAW SEQUENCE LISTING |
|---|
| SEQ ID NO: 24. NUCLEOTIDE SEQUENCE OF PLASMID 5259<br>GGCGTAATGCTCTGCCAGTGTTACAACCAATTAACCAATTCTGATTAGAAAAACTC<br>ATCGAGCATCAAATGAAACTGCAATTTATTCATATCAGGATTATCAATACCATATTT<br>TTGAAAAAGCCGTTTCTGTAATGAAGGAGAAAACTCACCGAGGCAGTTCCATAGG<br>ATGGCAAGATCCTGGTATCGGTCTGCGATTCCGACTCGTCCAACATCAATACAAC<br>CTATTAATTTCCCTCGTCAAAAATAAGGTTATCAAGTGAGAAATCACCCATGAGTG<br>ACGACTGAATCCGGTGAGAATGGCAAAAGCTTATGCATTTCTTTCCAGACTTGTTC<br>AACAGGCCAGCCATTACGCTCGTCATCAAAATCACTCGCATCAACCAAACCGTTA<br>TTCATTCGTGATTGCGCCTGAGCGAGACGAAATACGCGATCGCTGTTAAAAGGAC<br>AATTACAAACAGGAATCAAATGCAACCGGCGCAGGAACACTGCCAGCGCATCAAC<br>AATATTTTCACCTGAATCAGGATATTCTTCTAATACCTGGAATGCTGTTTTCCCGG<br>GGATCGCAGTGGTGAGTAACCATGCATCATCAGGAGTACGGATAAAATGCTTGAT<br>GGTCGGAAGAGGCATAAATTCCGTCAGCCAGTTTAGTCTGACCATCTCATCTGTA<br>ACATCATTGGCAACGCTACCTTTGCCATGTTTCAGAAACAACTCTGGCGCATCGG<br>GCTTCCCATACAATCGATAGATTGTCGCACCTGATTGCCCGACATTATCGCGAGC<br>CCATTTATACCCATATAAATCAGCATCCATGTTGGAATTTAATCGCGGCCTCGAGC<br>AAGACGTTTCCCGTTGAATATGGCTCATAACACCCCTTGTATTACTGTTTATGTAA<br>GCAGACAGGTCGACAATATTGGCTATTGGCCATTGCATACGTTGTATCTATATCAT<br>AATATGTACATTTATATTGGCTCATGTCCAATATGACCGCCATGTTGACATTGATTA<br>TTGACTAGTTATTAATAGTAATCAATTACGGGGTCATTAGTTCATAGCCCATATATG<br>GAGTTCCGCGTTACATAACTTACGGTAAATGGCCCGCCTGGCTGACCGCCCAAC<br>GACCCCCGCCCATTGACGTCAATAATGACGTATGTTCCCATAGTAACGCCAATAG<br>GGACTTTCCATTGACGTCAATGGGTGGAGTATTTACGGTAAACTGCCCACTTGGC<br>AGTACATCAAGTGTATCATATGCCAAGTCCGCCCCCTATTGACGTCAATGACGGT<br>AAATGGCCCGCCTGGCATTATGCCCAGTACATGACCTTACGGGACTTTCCTACTT<br>GGCAGTACATCTACGTATTAGTCATCGCTATTACCATGGTGATGCGGTTTTGGCA<br>GTACACCAATGGGCGTGGATAGCGGTTTGACTCACGGGGATTTCCAAGTCTCCAC<br>CCCATTGACGTCAATGGGAGTTTGTTTTGGCACCAAAATCAACGGGACTTTCCAA<br>AATGTCGTAATAACCCCGCCCCGTTGACGCAAATGGGCGGTAGGCGTGTACGGT<br>GGGAGGTCTATATAAGCAGAGCTCGTTTAGTGAACCGTCAGATCGCCTGGAGAC<br>GCCATCCACGCTGTTTTGACCTCCATAGAAGACACCGGGACCGATCCAGCCTCC<br>GCGGCCGGGAACGGTGCATTGGAACGCGGATTCCCCGTGCCAAGAGTGACTCA<br>CCGTCCGGATCTCAGCAAGCAGGTATGTACTCTCCAGGGTGGGCCTGGCTTCCC<br>CAGTCAAGACTCCAGGGATTTGAGGGACGCTGTGGGCTCTTCTCTTACATGTACC<br>TTTTGCTTGCCTCAACCCTGACTATCTTCCAGGTCAGGATCCCAGAGTCAGGGGT<br>CTGTATTTTCCTGCTGGTGGCTCCAGTTCAGGAACAGTAAACCCTGCTCCGAATA<br>TTGCCTCTCACATCTCGTCAATCTCCGCGAGGACTGGGGACCCTGTGACGAACAT<br>GGCTAGCAAGGCTGTGCTGCTTGCCCTGTTGATGGCAGGCTTGGCCCTGCAGCC<br>AGGCACTGCCCTGCTGTGCTACTCCTGCAAAGCCCAGGTGAGCAACGAGGACTG<br>CCTGCAGGTGGAGAACTGCACCCAGCTGGGGGAGCAGTGCTGGACCGCGCGCA<br>TCCGCGCAGTTGGCCTCCTGACCGTCATCAGCAAAGGCTGCAGCTTGAACTGCG<br>TGGATGACTCACAGGACTACTACGTGGGCAAGAAGAACATCACGTGCTGTGACAC<br>CGACTTGTGCAACGCCAGCGGGCCCATGCCCTGCAGCCGGCTGCCGCCATCC<br>TTGCGCTGCTCCCTGCACTCGGCCTGCTGCTCTGGGGACCCGGCCAGCTATAGA<br>GATCTGGGCCTAACAAAACAAAAAGATGGGGTTATTCCCTAAACTTCATGGGTTA<br>CGTAATTGGAAGTTGGGGGACATTGCCACAAGATCATATTGTACAAAAGATCAAA<br>CACTGTTTTAGAAAACTTCCTGTAAACAGGCCTATTGATTGGAAAGTATGTCAAAG<br>GATTGTGGGTCTTTTGGGCTTTGCTGCTCCATTTACACAATGTGGATATCCTGCCT<br>TAATGCCTTTGTATGCATGTATACAAGCTAAACAGGCTTTCACTTTCTCGCCAACT<br>TACAAGGCCTTTCTAAGTAAACAGTACATGAACCTTTACCCCGTTGCTCGGCAAC<br>GGCCTGGTCTGTGCCAAGTGTTTGCTGACGCAACCCCCACTGGCTGGGGCTTGG<br>CCATAGGCCATCAGCGCATGCGTGGAACCTTTGTGGCTCCTCTGCCGATCCATAC<br>TGCGGAACTCCTAGCCGCTTGTTTTGCTCGCAGCCGGTCTGGAGCAAAGCTCATA<br>GGAACTGACAATTCTGTCGTCCTCTCGCGGAAATATACATCGTTTCGATCTACGTA<br>TGATCTTTTTCCCTCTGCCAAAAATTATGGGGACATCATGAAGCCCCTTGAGCATC<br>TGACTTCTGGCTAATAAAGGAAATTTATTTTCATTGCAATAGTGTGTTGGAATTTTT<br>TGTGTCTCTCACTCGGAAGGAATTCTGCATTAATGAATCGGCCAACGCGCGGGGA<br>GAGGCGGTTTGCGTATTGGGCGCTCTTCCGCTTCCTCGCTCACTGACTCGCTGC<br>GCTCGGTCGTTCGGCTGCGGCGAGCGGTATCAGCTCACTCAAAGGCGGTAATAC<br>GGTTATCCACAGAATCAGGGGATAACGCAGGAAAGAACATGTGAGCAAAAGGCC<br>AGCAAAAGGCCAGGAACCGTAAAAAGGCCGCGTTGCTGGCGTTTTTCCATAGGC<br>TCCGCCCCCTGACGAGCATCACAAAAATCGACGCTCAAGTCAGAGGTGGCGAA<br>ACCCGACAGGACTATAAAGATACCAGGCGTTTCCCCTGGAAGCTCCCTCGTGC<br>GCTCTCCTGTTCCGACCCTGCCGCTTACCGGATACCTGTCCGCCTTTCTCCCTTC<br>GGGAAGCGTGGCGCTTTCTCATAGCTCACGCTGTAGGTATCTCAGTTCGGTGTAG<br>GTCGTTCGCTCCAAGCTGGGCTGTGTGCACGAACCCCCCGTTCAGCCCGACCGC<br>TGCGCCTTATCCGGTAACTATCGTCTTGAGTCCAACCCGGTAAGACACGACTTAT<br>CGCCACTGGCAGCAGCCACTGGTAACAGGATTAGCAGAGCGAGGTATGTAGGCG<br>GTGCTACAGAGTTCTTGAAGTGGTGGCCTAACTACGGCTACACTAGAAGAACAGT<br>ATTTGGTATCTGCGCTCTGCTGAAGCCAGTTACCTTCGGAAAAAGAGTTGGTAGC<br>TCTTGATCCGGCAAACAAACCACCGCTGGTAGCGGTGGTTTTTTTGTTTGCAAGC<br>AGCAGATTACGCGCAGAAAAAAAGGATCTCAAGAAGATCCTTTGATCTTTTCTACG<br>GGGTCTGACGCTCAGTGGAACGAAAACTCACGTTAAGGGATTTTGGTCATGAGAT<br>TATCAAAAAGGATCTTCACCTAGATCCTTTTAAATTAAAAATGAAGTTTTAAATCAA<br>TCTAAAGTATATATGAGTAAACTTGGTCTGACAGTTACCAATGCTTAATCAGTGAG<br>GCACCTATCTCAGCGATCTGTCTATTTCGTTCATCCATAGTTGCCTGACTC |

RAW SEQUENCE LISTING

SEQ ID NO: 25. NUCLEOTIDE SEQUENCE OF PLASMID 5297
GGCGTAATGCTCTGCCAGTGTTACAACCAATTAACCAATTCTGATTAGAAAAACTC
ATCGAGCATCAAATGAAACTGCAATTTATTCATATCAGGATTATCAATACCATATTT
TTGAAAAAGCCGTTTCTGTAATGAAGGAGAAAACTCACCGAGGCAGTTCCATAGG
ATGGCAAGATCCTGGTATCGGTCTGCGATTCCGACTCGTCCAACATCAATACAAC
CTATTAATTTCCCCTCGTCAAAAATAAGGTTATCAAGTGAGAAATCACCATGAGTG
ACGACTGAATCCGGTGAGAATGGCAAAAGCTTATGCATTTCTTTCCAGACTTGTTC
AACAGGCCAGCCATTACGCTCGTCATCAAAATCACTCGCATCAACCAAACCGTTA
TTCATTCGTGATTGCGCCTGAGCGAGACGAAATACGCGATCGCTGTTAAAAGGAC
AATTACAAACAGGAATCAAATGCAACCGGCGCAGGAACACTGCCAGCGCATCAAC
AATATTTTCACCTGAATCAGGATATTCTTCTAATACCTGGAATGCTGTTTTCCCGG
GGATCGCAGTGGTGAGTAACCATGCATCATCAGGAGTACGGATAAAATGCTTGAT
GGTCGGAAGAGGCATAAATTCCGTCAGCCAGTTTAGTCTGACCATCTCATCTGTA
ACATCATTGGCAACGCTACCTTTGCCATGTTTCAGAAACAACTCTGGCGCATCGG
GCTTCCCATACAATCGATAGATTGTCGCACCTGATTGCCCGACATTATCGCGAGC
CCATTTATACCCATATAAATCAGCATCCATGTTGGAATTTAATCGCGGCCTCGAGC
AAGACGTTTCCCGTTGAATATGGCTCATAACACCCCTTGTATTACTGTTTATGTAA
GCAGACAGGTCGACAATATTGGCTATTGGCCATTGCATACGTTGTATCTATATCAT
AATATGTACATTTATATTGGCTCATGTCCAATATGACCGCCATGTTGACATTGATTA
TTGACTAGTTATTAATAGTAATCAATTACGGGGTCATTAGTTCATAGCCCATATATG
GAGTTCCGCGTTACATAACTTACGGTAAATGGCCCGCCTGGCTGACCGCCCAAC
GACCCCCGCCCATTGACGTCAATAATGACGTATGTTCCCATAGTAACGCCAATAG
GGACTTTCCATTGACGTCAATGGGTGGAGTATTTACGGTAAACTGCCCACTTGGC
AGTACATCAAGTGTATCATATGCCAAGTCCGCCCCCTATTGACGTCAATGACGGT
AAATGGCCCGCCTGGCATTATGCCCAGTACATGACCTTACGGGACTTTCCTACTT
GGCAGTACATCTACGTATTAGTCATCGCTATTACCATGGTGATGCGGTTTTGGCA
GTACACCAATGGGCGTGGATAGCGGTTTGACTCACGGGGATTTCCAAGTCTCCAC
CCCATTGACGTCAATGGGAGTTTGTTTTGGCACCAAAATCAACGGGACTTTCCAA
AATGTCGTAATAACCCCGCCCCGTTGACGCAAATGGGCGGTAGGCGTGTACGGT
GGGAGGTCTATATAAGCAGAGCTCGTTTAGTGAACCGTCAGATCGCCTGGAGAC
GCCATCCACGCTGTTTTGACCTCCATAGAAGACACCGGGACCGATCCAGCCTCC
GCGGCCGGGAACGGTGCATTGGAACGCGGATTCCCCGTGCCAAGAGTGACTCA
CCGTCCGGATCTCAGCAAGCAGGTATGTACTCTCCAGGGTGGGCCTGGCTTCCC
CAGTCAAGACTCCAGGGATTTGAGGGACGCTGTGGGCTCTTCTCTTACATGTACC
TTTTGCTTGCCTCAACCCTGACTATCTTCCAGGTCAGGATCCCAGAGTCAGGGGT
CTGTATTTTCCTGCTGGTGGCTCCAGTTCAGGAACAGTAAACCCTGCTCCGAATA
TTGCCTCTCACATCTCGTCAATCTCCGCGAGGACTGGGGACCCTGTGACGAACAT
GGCTAGCATTGTGGGAGGCTGGGAGTGCGAGAAGCATTCCCAACCCTGGCAGGT
GCTTGTGGCCTCTCGTGGCAGGGCAGTCTGCGGCGGTGTTCTGGTGCACCCCCA
GTGGGTCCTCACAGCTGCCCACTGCATCAGGAACAAAAGCGTGATCTTGCTGGG
TCGGCACAGCTTGTTTCATCCTGAAGACACAGGCCAGGTATTTCAGGTCAGCCAC
AGCTTCCCACACCCGCTCTACGATATGAGCCTCCTGAAGAATCGATTCCTCAGGC
CAGGTGATGACTCCAGCCACGACCTCATGCTGCTCCGCCTGTCAGAGCCTGCCG
AGCTCACGGATGCTGTGAAGGTCATGGACCTGCCCACCCAGGAGCCAGCACTGG
GGACCACCTGCTACGCCTCAGGCTGGGGCAGCATTGAACCAGAGGAGTTCTTGA
CCCCAAAGAAACTTCAGTGTGTGGACCTCCATGTTATTTCCAATGACGTGTGTGC
GCAAGTTCACCCTCAGAAGGTGACCAAGTTCATGCTGTGTGCTGGACGCTGGAC
AGGGGGCAAAAGCACCTGCTCGGGTGATTCTGGGGGCCCACTTGTCTGTAATGG
TGTGCTTCAAGGTATCACGTCATGGGGCAGTGAACCATGTGCCCTGCCCGAAAG
GCCTTCCCTGTACACCAAGGTGGTGCATTACCGGAAGTGGATCAAGGACACCATC
GTGGCCAACCCCTGAAGATCTGGGCCCTAACAAAACAAAAAGATGGGGTTATTCC
CTAAACTTCATGGGTTACGTAATTGGAAGTTGGGGGACATTGCCACAAGATCATAT
TGTACAAAAGATCAAACACTGTTTTAGAAAACTTCCTGTAAACAGGCCTATTGATT
GGAAAGTATGTCAAAGGATTGTGGGTCTTTTGGGCTTTGCTGCTCCATTTACACAA
TGTGGATATCCTGCCTTAATGCCTTTGTATGCATGTATACAAGCTAAACAGGCTTT
CACTTTCTCGCCAACTTACAAGGCCTTTCTAAGTAAACAGTACATGAACCTTTACC
CCGTTGCTCGGCAACGGCCTGGTCTGTGCCAAGTGTTTGCTGACGCAACCCCCA
CTGGCTGGGGCTTGGCCATAGGCCATCAGCGCATGCGTGGAACCTTTGTGGCTC
CTCTGCCGATCCATACTGCGGAACTCCTAGCCGCTTGTTTTGCTCGCAGCCGGTC
TGGAGCAAAGCTCATAGGAACTGACAATTCTGTCGTCCTCTCGCGGAAATATACA
TCGTTTCGATCTACGTATGATCTTTTTCCCTCTGCCAAAAATTATGGGGACATCAT
GAAGCCCCTTGAGCATCTGACTTCTGGCTAATAAAGGAAATTTATTTTCATTGCAA
TAGTGTGTTGGAATTTTTTGTGTCTCTCACTCGGAAGGAATTCTGCATTAATGAAT
CGGCCAACGCGCGGGGAGAGGCGGTTTGCGTATTGGGCGCTCTTCCGCTTCCTC
GCTCACTGACTCGCTGCGCTCGGTCGTTCGGCTGCGGCGAGCGGTATCAGCTCA
CTCAAAGGCGGTAATACGGTTATCCACAGAATCAGGGGATAACGCAGGAAAGAAC
ATGTGAGCAAAAGGCCAGCAAAAGGCCAGGAACCGTAAAAAGGCCGCGTTGCTG
GCGTTTTTCCATAGGCTCCGCCCCCCTGACGAGCATCACAAAAATCGACGCTCAA
GTCAGAGGTGGCGAAACCCGACAGGACTATAAAGATACCAGGCGTTTCCCCCTG
GAAGCTCCCTCGTGCGCTCTCCTGTTCCGACCCTGCCGCTTACCGGATACCTGTC
CGCCTTTCTCCCTTCGGGAAGCGTGGCGCTTTCTCATAGCTCACGCTGTAGGTAT
CTCAGTTCGGTGTAGGTCGTTCGCTCCAAGCTGGGCTGTGTGCACGAACCCCCC
GTTCAGCCCGACCGCTGCGCCTTATCCGGTAACTATCGTCTTGAGTCCAACCCGG
TAAGACACGACTTATCGCCACTGGCAGCAGCCACTGGTAACAGGATTAGCAGAG
CGAGGTATGTAGGCGGTGCTACAGAGTTCTTGAAGTGGTGGCCTAACTACGGCT
ACACTAGAAGAACAGTATTTGGTATCTGCGCTCTGCTGAAGCCAGTTACCTTCGG
AAAAAGAGTTGGTAGCTCTTGATCCGGCAAACAAACCACCGCTGGTAGCGGTGGT

| RAW SEQUENCE LISTING |
|---|
| TTTTTTGTTTGCAAGCAGCAGATTACGCGCAGAAAAAAGGATCTCAAGAAGATCC
TTTGATCTTTTCTACGGGGTCTGACGCTCAGTGGAACGAAAACTCACGTTAAGGG
ATTTTGGTCATGAGATTATCAAAAAGGATCTTCACCTAGATCCTTTTAAATTAAAA
TGAAGTTTTAAATCAATCTAAAGTATATATGAGTAAACTTGGTCTGACAGTTACCAA
TGCTTAATCAGTGAGGCACCTATCTCAGCGATCTGTCTATTTCGTTCATCCATAGT
TGCCTGACTC

SEQ ID NO: 26. NUCLEOTIDE SEQUENCE OF PLASMID 460
GAATTCTGCATTAATGAATCGGCCAACGCGCGGGGAGAGGCGGTTTGCGTATTG
GGCGCTCTTCCGCTTCCTCGCTCACTGACTCGCTGCGCTCGGTCGTTCGGCTGC
GGCGAGCGGTATCAGCTCACTCAAAGGCGGTAATACGGTTATCCACAGAATCAG
GGGATAACGCAGGAAAGAACATGTGAGCAAAAGGCCAGCAAAAGGCCAGGAACC
GTAAAAAGGCCGCGTTGCTGGCGTTTTTCCATAGGCTCCGCCCCCCTGACGAGC
ATCACAAAAATCGACGCTCAAGTCAGAGGTGGCGAAACCCGACAGGACTATAAAG
ATACCAGGCGTTTCCCCCTGGAAGCTCCCTCGTGCGCTCTCCTGTTCCGACCCTG
CCGCTTACCGGATACCTGTCCGCCTTTCTCCCTTCGGGAAGCGTGGCGCTTTCTC
ATAGCTCACGCTGTAGGTATCTCAGTTCGGTGTAGGTCGTTCGCTCCAAGCTGGG
CTGTGTGCACGAACCCCCCGTTCAGCCCGACCGCTGCGCCTTATCCGGTAACTA
TCGTCTTGAGTCCAACCCGGTAAGACACGACTTATCGCCACTGGCAGCAGCCACT
GGTAACAGGATTAGCAGAGCGAGGTATGTAGGCGGTGCTACAGAGTTCTTGAAG
TGGTGGCCTAACTACGGCTACACTAGAAGAACAGTATTTGGTATCTGCGCTCTGC
TGAAGCCAGTTACCTTCGGAAAAAGAGTTGGTAGCTCTTGATCCGGCAAACAAAC
CACCGCTGGTAGCGGTGGTTTTTTTGTTTGCAAGCAGCAGATTACGCGCAGAAAA
AAAGGATCTCAAGAAGATCCTTTGATCTTTTCTACGGGGTCTGACGCTCAGTGGA
ACGAAAACTCACGTTAAGGGATTTTGGTCATGAGATTATCAAAAAGGATCTTCACC
TAGATCCTTTTAAATTAAAAATGAAGTTTTAAATCAATCTAAAGTATATATGAGTAAA
CTTGGTCTGACAGTTACCAATGCTTAATCAGTGAGGCACCTATCTCAGCGATCTGT
CTATTTCGTTCATCCATAGTTGCCTGACTCGGCGTAATGCTCTGCCAGTGTTACAA
CCAATTAACCAATTCTGATTAGAAAAACTCATCGAGCATCAAATGAAACTGCAATTT
ATTCATATCAGGATTATCAATACCATATTTTTGAAAAAGCCGTTTCTGTAATGAAGG
AGAAAACTCACCGAGGCAGTTCCATAGGATGGCAAGATCCTGGTATCGGTCTGC
GATTCCGACTCGTCCAACATCAATACAACCTATTAATTTCCCCTCGTCAAAAATAA
GGTTATCAAGTGAGAAATCACCATGAGTGACGACTGAATCCGGTGAGAATGGCAA
AAGCTTATGCATTTCTTTCCAGACTTGTTCAACAGGCCAGCCATTACGCTCGTCAT
CAAAATCACTCGCATCAACCAAACCGTTATTCATTCGTGATTGCGCCTGAGCGAG
ACGAAATACGCGATCGCTGTTAAAAGGACAATTACAAACAGGAATCAAATGCAAC
CGGCGCAGGAACACTGCCAGCGCATCAACAATATTTTCACCTGAATCAGGATATT
CTTCTAATACCTGGAATGCTGTTTTCCCGGGGATCGCAGTGGTGAGTAACCATGC
ATCATCAGGAGTACGGATAAAATGCTTGATGGTCGGAAGAGGCATAAATTCCGTC
AGCCAGTTTAGTCTGACCATCTCATCTGTAACATCATTGGCAACGCTACCTTTGCC
ATGTTTCAGAAACAACTCTGGCGCATCGGGCTTCCCATACAATCGATAGATTGTC
GCACCTGATTGCCCGACATTATCGCGAGCCCATTTATACCCATATAAATCAGCATC
CATGTTGGAATTTAATCGCGGCCTCGAGCAAGACGTTTCCCGTTGAATATGGCTC
ATAACACCCCTTGTATTACTGTTTATGTAAGCAGACAGGGTACCAATCTTCCGAGT
GAGAGACACAAAAAATTCCAACACACTATTGCAATGAAAATAAATTTCCTTTATTAG
CCAGAAGTCAGATGCTCAAGGGGCTTCATGATGTCCCCATAATTTTTGGCAGAGG
GAAAAAGATCATACGTAGATCGAAACGATGTATATTTCCGCGAGAGGACGACAGA
ATTGTCAGTTCCTATGAGCTTTGCTCCAGACCGGCTGCGAGCAAAACAAGCGGCT
AGGAGTTCCGCAGTATGGATCGGCAGAGGAGCCACAAAGGTTCCACGCATGCGC
TGATGGCCTATGGCCAAGCCCCAGCCAGTGGGGGTTGCGTCAGCAAACACTTGG
CACAGACCAGGCCGTTGCCGAGCAACGGGGTAAAGGTTCATGTACTGTTTACTTA
GAAAGGCCTTGTAAGTTGGCGAGAAAGTGAAAGCCTGTTTAGCTTGTATACATGC
ATACAAAGGCATTAAGGCAGGATATCCACATTGTGTAAATGGAGCAGCAAAGCCC
AAAAGACCCCACAATCCTTTGACATACTTTCCAATCAATAGGCCTGTTTACAGGAAG
TTTTCTAAAACAGTGTTTGATCTTTTGTACAATATGATCTTGTGGCAATGTCCCCCA
ACTTCCAATTACGTAACCCATGAAGTTTAGGGAATAACCCCATCTTTTTGTTTTGTT
AGGGCCCAGATCTTTAGGCTACTTCACTCAAAGTCTCTGCAGCTGCCTGCACTGT
GAAGGCTGCAACATAAATCTGTCTCTTCACTTCTCCCCAGGCCTTGGAAGGGTCC
ACTTTGCTTTCAATATCAAACAGAGCATCATAAATTCCTGGGAATGACTCCCCTGC
ATACTTGTTGTGGCTGCTTGGAGCATAGATGACATGCCTATAAAAGGCCTGTCT
GGTAACCCTAATGGATCAATAAATGCTCTTTCCAGAAACATGAGTTGATCATTCAT
CATTCTTAATACTATTGGGTTGCTTTTGTCAAAGTCCTGGAGTCTCTCACTGAACTT
GGAAGCAATTTCTGTAAAATTCTTTACTGCAGAAAAAAGTGAATCAAATGATACAC
TGTATGTCTTCATTTCCTGTGGATGTTTCATAGAAATACTGTAGATTTTGTCAGCAT
ACTTTCTTAAAACTACAGCATAATCTCGACAATCAAAGGGAGCACTATGGAATTG
GCCAGCTCAAACACCATCCCTCCTCGAACCTGGGCCACAGTGAGGTGATATTTAA
ACATTGGATCATAAAACTTTTCCACCAACTCATATGTTTCATAGACACTGTGATACA
GTGGATAGCCGCTGAATTTGTTTGTTTCCCAATTTTTAGTATACCGTGCTCTGCCT
GAAGCAATTCCAAGTCGTTGGAAGAACACCTCAAAATCATTTCCAGATCCCAATTT
GCTTATCCTGGGCATGCCACTGAACTCTGGGGAAGGACTTTTTTTAGTCCAACTTT
CATAAAGAGATTTGCCTTCAAAGCCTTCATCAGGGCTTTTCAGCTCTTTTGTTAGG
TTGTGTACCAAGCTGTACATCAGCGGTGTACAATCAACTCTCAGAGTGTAGTTTCC
TTCTATAGATGAGTCAGCATTAATATAAGCCACGCCACGCTCTTGAAGGAGTCTTG
AATTCTCCTCTGCCCACTCAGTAGAACCAAGAAGACCAAATTCTTCTGCATCCCAG
CTTGCAAACAAAATTGTTCTTCTAGGTCTCCACCCTTCCTTTTTCAGTGTTCCAAAG
CTCCTCACAATTTCATGAACAACAGCTGCTCCACTCTGAGGGTCAATACCACCAAA
CACCCATGAGTCCCGGTGACCTCCCAGAATGACATATCTGTCTGGTTCCACTGCT |

| RAW SEQUENCE LISTING |
|---|
| CCTCTGAGAGTACCTATCACATTGTAAATTCTTGTCACTTCATTGGTAGAGTGGAT |
| GTGCATCTTGACTTTTTGTGTAGAAAAGTTTCCAGTAAAGCCAGGTCCAACATTGT |
| AGGGCACTTTGAGACTTTCCTCTCCAGCTGCTATCTGGTGGTGCTGAGCCACCCAT |
| TTTTTCTAGGAGCTTCTGTGCATCATAGTATCCAATTGGATGAACAGGAATACTTG |
| GAAGACCAACAGCCTCTGCAATTCCACGCCTATAAGCATATTCATTTGCTGGGTAA |
| CCTGGTGTGAGAGGGTCTCCTGCACCATTCAGATTTAGGATATTTCCACGCTGGA |
| CACCACCTCCAGGAAGATTCCAACCATCTGGATAGGACTTCACCCCAGGAGCAAA |
| GTAGTCAGCAGGGTCGGAGTAGAGAATGACTCCTTTGGCCCCTGCCAGCTGGGC |
| ATTTTTAACCTTATTTCCTCTGAAAACTTTCCCATATCTGGCAATTACAATTTTCCCA |
| GAGCAATTGATTTTCATGTCCCGTTCCAATTTAAAGAAGTCTTCAGTTCGTGCATA |
| GTTAACATACACTAGATCGCCCTCTGGCATTCCTTGAGGAGAGAAAGCACTGAAA |
| GGTGGTACAATATCCGAAACATTTTCATATCCTGGAGGAGGTGGTTCAAATAATGA |
| TGTGTTGAAAATCTCATTTCCATCTTCATTAATTATTGAGATGTAGTTGGGATGAGT |
| CTTATTTGGGTAGGACAACAGGACATCATAATGTGCCAGCTCAACAGAATCCAGG |
| CCAAATTCTTTCCACTGGGATTGAATTTGCTTTGCAAGCTGAAAGTTTTGTTCTGTT |
| CCTGCTAAATGTGGTATCTGTGTAAAATTATATAAGAACTTCTTGATGTTCTCAGCT |
| TTCAATTCATCCAAAAATGCTTTCATATTATGCTTTGGAGTAATGTTAGTAGCTTCA |
| TTGGAGGATTTTATAAACCACCCGAAGAGGAAGCCGAGGAGAAAGAAGCCACCC |
| GCCAGCACCAGCGCCCCAGCGCACAGCCAGCGCGGGCGGCGCGCGCTAGCCA |
| TGTTCGTCACAGGGTCCCCAGTCCTCGCGGAGATTGACGAGATGTGAGAGGCAA |
| TATTCGGAGCAGGGTTTACTGTTCCTGAACTGGAGCCACCAGCAGGAAAATACAG |
| ACCCCTGACTCTGGGATCCTGACCTGGAAGATAGTCAGGGTTGAGGCAAGCAAA |
| AGGTACATGTAAGAGAAGAGCCCACAGCGTCCCTCAAATCCCTGGAGTCTTGACT |
| GGGGAAGCCAGGCCCACCCTGGAGAGTACATACCTGCTTGCTGAGATCCGGACG |
| GTGAGTCACTCTTGGCACGGGGAATCCGCGTTCCAATGCACCGTTCCCGGCCGC |
| GGAGGCTGGATCGGTCCCGGTGTCTTCTATGGAGGTCAAAACAGCGTGGATGGC |
| GTCTCCAGGCGATCTGACGGTTCACTAAACGAGCTCTGCTTATATAGACCTCCCA |
| CCGTACACGCCTACCGCCCATTTGCGTCAACGGGGCGGGGTTATTACGACATTTT |
| GGAAAGTCCCGTTGATTTTGGTGCTCGACCTGCAGGGTACCAATATTGGCTATTG |
| GCCATTGCATACGTTGTATCTATATCATAATATGTACATTTATATTGGCTCATGTCC |
| AATATGACCGCCATGTTGACATTGATTATTGACTAGTTATTAATAGTAATCAATTAC |
| GGGGTCATTAGTTCATAGCCCATATATGGAGTTCCGCGTTACATAACTTACGGTAA |
| ATGGCCCGCCTGGCTGACCGCCCAACGACCCCCGCCCATTGACGTCAATAATGA |
| CGTATGTTCCCATAGTAACGCCAATAGGGACTTTCCATTGACGTCAATGGGTGGA |
| GTATTTACGGTAAACTGCCCACTTGGCAGTACATCAAGTGTATCATATGCCAAGTC |
| CGCCCCCTATTGACGTCAATGACGGTAAATGGCCCGCCTGGCATTATGCCCAGTA |
| CATGACCTTACGGGACTTTCCTACTTGGCAGTACATCTACGTATTAGTCATCGCTA |
| TTACCATGGTGATGCGGTTTTGGCAGTACACCAATGGGCGTGGATAGCGGTTTGA |
| CTCACGGGGATTTCCAAGTCTCCACCCCATTGACGTCAATGGGAGTTTGTTTTGG |
| CACCAAAATCAACGGGACTTTCCAAAATGTCGTAATAACCCCGCCCCGTTGACGC |
| AAATGGGCGGTAGGCGTGTACGGTGGGAGGTCTATATAAGCAGAGCTCGTTTAG |
| TGAACCGTCAGATCGCCTGGAGACGCCATCCACGCTGTTTTGACCTCCATAGAAG |
| ACACCGGGACCGATCCAGCCTCCGCGGCCGGGAACGGTGCATTGGAACGCGGA |
| TTCCCCGTGCCAAGAGTGACTCACCGTCCGGATCTCAGCAAGCAGGTATGTACTC |
| TCCAGGGTGGGCCTGGCTTCCCCAGTCAAGACTCCAGGGATTTGAGGGACGCTG |
| TGGGCTCTTCTCTTACATGTACCTTTTGCTTGCCTCAACCCTGACTATCTTCCAGG |
| TCAGGATCCCAGAGTCAGGGGTCTGTATTTTCCTGCTGGTGGCTCCAGTTCAGGA |
| ACAGTAAACCCTGCTCCGAATATTGCCTCTCACATCTCGTCAATCTCCGCGAGGA |
| CTGGGGACCCTGTGACGAACATGGCTAGCAAGGCTGTGCTGCTTGCCCTGTTGA |
| TGGCAGGCTTGGCCCTGCAGCCAGGCACTGCCCTGCTGTGCTACTCCTGCAAAG |
| CCCAGGTGAGCAACGAGGACTGCCTGCAGGTGGAGAACTGCACCCAGCTGGGG |
| GAGCAGTGCTGGACCGCGCGCATCCGCGCAGTTGGCCTCCTGACCGTCATCAGC |
| AAAGGCTGCAGCTTGAACTGCGTGGATGACTCACAGGACTACTACGTGGGCAAG |
| AAGAACATCACGTGCTGTGACACCGACTTGTGCAACGCCAGCGGGCCCATGCC |
| CTGCAGCCGGCTGCCGCCATCCTTGCGCTGCTCCCTGCACTCGGCCTGCTGCTC |
| TGGGGACCCGGCCAGCTATAGAGATCTGGGCCCTAACAAAACAAAAAGATGGGG |
| TTATTCCCTAAACTTCATGGGTTACGTAATTGGAAGTTGGGGGACATTGCCACAAG |
| ATCATATTGTACAAAAGATCAAACACTGTTTTAGAAAACTTCCTGTAAACAGGCCTA |
| TTGATTGGAAAGTATGTCAAAGGATTGTGGGTCTTTTGGGCTTTGCTGCTCCATTT |
| ACACAATGTGGATATCCTGCCTTAATGCCTTTGTATGCATGTATACAAGCTAAACA |
| GGCTTTCACTTTCTCGCCAACTTACAAGGCCTTTCTAAGTAAACAGTACATGAACC |
| TTTACCCCGTTGCTCGGCAACGGCCTGGTCTGTGCCAAGTGTTTGCTGACGCAAC |
| CCCCACTGGCTGGGGCTTGGCCATAGGCCATCAGCGCATGCGTGGAACCTTTGT |
| GGCTCCTCTGCCGATCCATACTGCGGAACTCCTAGCCGCTTGTTTTGCTCGCAGC |
| CGGTCTGGAGCAAAGCTCATAGGAACTGACAATTCTGTCGTCCTCTCGCGGAAAT |
| ATACATCGTTTCGATCTACGTATGATCTTTTTCCCTCTGCCAAAAATTATGGGGAC |
| ATCATGAAGCCCCTTGAGCATCTGACTTCTGGCTAATAAAGGAAATTTATTTTCATT |
| GCAATAGTGTGTTGGAATTTTTTGTGTCTCTCACTCGGAAGC |

SEQ ID NO: 27. NUCLEOTIDE SEQUENCE OF PLASMID 451
GGCGTAATGCTCTGCCAGTGTTACAACCAATTAACCAATTCTGATTAGAAAAACTC
ATCGAGCATCAAATGAAACTGCAATTTATTCATATCAGGATTATCAATACCATATTT
TTGAAAAAGCCGTTTCTGTAATGAAGGAGAAAACTCACCGAGGCAGTTCCATAGG
ATGGCAAGATCCTGGTATCGGTCTGCGATTCCGACTCGTCCAACATCAATACAAC
CTATTAATTTCCCCTCGTCAAAAATAAGGTTATCAAGTGAGAAATCACCATGAGTG
ACGACTGAATCCGGTGAGAATGGCAAAAGCTTATGCATTTCTTTCCAGACTTGTTC
AACAGGCCAGCCATTACGCTCGTCATCAAAATCACTCGCATCAACCAAACCGTTA

-continued

RAW SEQUENCE LISTING

```
TTCATTCGTGATTGCGCCTGAGCGAGACGAAATACGCGATCGCTGTTAAAAGGAC
AATTACAAACAGGAATCAAATGCAACCGGCGCAGGAACACTGCCAGCGCATCAAC
AATATTTTCACCTGAATCAGGATATTCTTCTAATACCTGGAATGCTGTTTTCCCGG
GGATCGCAGTGGTGAGTAACCATGCATCATCAGGAGTACGGATAAAATGCTTGAT
GGTCGGAAGAGGCATAAATTCCGTCAGCCAGTTTAGTCTGACCATCTCATCTGTA
ACATCATTGGCAACGCTACCTTTGCCATGTTTCAGAAACAACTCTGGCGCATCGG
GCTTCCCATACAATCGATAGATTGTCGCACCTGATTGCCCGACATTATCGCGAGC
CCATTTATACCCATATAAATCAGCATCCATGTTGGAATTTAATCGCGGCCTCGAGC
AAGACGTTTCCCGTTGAATATGGCTCATAACACCCCTTGTATTACTGTTTATGTAA
GCAGACAGGTCGACAATATTGGCTATTGGCCATTGCATACGTTGTATCTATATCAT
AATATGTACATTTATATTGGCTCATGTCCAATATGACCGCCATGTTGACATTGATTA
TTGACTAGTTATTAATAGTAATCAATTACGGGGTCATTAGTTCATAGCCCATATATG
GAGTTCCGCGTTACATAACTTACGGTAAATGGCCCGCCTGGCTGACCGCCCAAC
GACCCCCGCCCATTGACGTCAATAATGACGTATGTTCCCATAGTAACGCCAATAG
GGACTTTCCATTGACGTCAATGGGTGGAGTATTTACGGTAAACTGCCCACTTGGC
AGTACATCAAGTGTATCATATGCCAAGTCCGCCCCCTATTGACGTCAATGACGGT
AAATGGCCCGCCTGGCATTATGCCCAGTACATGACCTTACGGGACTTTCCTACTT
GGCAGTACATCTACGTATTAGTCATCGCTATTACCATGGTGATGCGGTTTTGGCA
GTACACCAATGGGCGTGGATAGCGGTTTGACTCACGGGGATTTCCAAGTCTCCAC
CCCATTGACGTCAATGGGAGTTTGTTTTGGCACCAAAATCAACGGGACTTTCCAA
AATGTCGTAATAACCCCGCCCCGTTGACGCAAATGGGCGGTAGGCGTGTACGGT
GGGAGGTCTATATAAGCAGAGCTCGTTTAGTGAACCGTCAGATCGCCTGGAGAC
GCCATCCACGCTGTTTTGACCTCCATAGAAGACACCGGGACCGATCCAGCCTCC
GCGGCCGGGAACGGTGCATTGGAACGCGGATTCCCCGTGCCAAGAGTGACTCA
CCGTCCGGATCTCAGCAAGCAGGTATGTACTCTCCAGGGTGGGCCTGGCTTCCC
CAGTCAAGACTCCAGGGATTTGAGGGACGCTGTGGGCTCTTCTCTTACATGTACC
TTTTGCTTGCCTCAACCCTGACTATCTTCCAGGTCAGGATCCCAGAGTCAGGGGT
CTGTATTTTCCTGCTGGTGGCTCCAGTTCAGGAACAGTAAACCCTGCTCCGAATA
TTGCCTCTCACATCTCGTCAATCTCCGCGAGGACTGGGGACCCTGTGACGAACAT
GGCTAGCGCGCCGCCCGCGCTGGCTGTGCGCTGGGGCGCTGGTGCTGGCG
GGTGGCTTCTTTCTCCTCGGCTTCCTCTTCGGGTGGTTTATAAAATCCTCCAATGA
AGCTACTAACATTACTCCAAAGCATAATATGAAAGCATTTTTGGATGAATTGAAAG
CTGAGAACATCAAGAAGTTCTTATATAATTTTACACAGATACCACATTTAGCAGGA
ACAGAACAAAACTTTCAGCTTGCAAAGCAAATTCAATCCCAGTGGAAAGAATTTGG
CCTGGATTCTGTTGAGCTGGCACATTATGATGTCCTGTTGTCCTACCCAAATAAGA
CTCATCCCAACTACATCTCAATAATTAATGAAGATGGAAATGAGATTTTCAACACAT
CATTATTTGAACCACCTCCTCCAGGATATGAAAATGTTTCGGATATTGTACCACCT
TTCAGTGCTTTCTCTCCTCAAGGAATGCCAGAGGGCGATCTAGTGTATGTTAACTA
TGCACGAACTGAAGACTTCTTTAAATTGGAACGGGACATGAAAATCAATTGCTCTG
GGAAAATTGTAATTGCCAGATATGGGAAAGTTTTCAGAGGGAAATAAGGTTAAAAAT
GCCCAGCTGGCAGGGGCCAAAGGAGTCATTCTCTACTCCGACCCTGCTGACTAC
TTTGCTCCTGGGGTGAAGTCCTATCCAGATGGTTGGAATCTTCCTGGAGGTGGTG
TCCAGCGTGGAAATATCCTAAATCTGAATGGTGCAGGAGACCCTCTCACACCAGG
TTACCCAGCAAATGAATATGCTTATAGGCGTGGAATTGCAGAGGCTGTTGGTCTT
CCAAGTATTCCTGTTCATCCAATTGGATACTATGATGCACAGAAGCTCCTAGAAAA
AATGGGTGGCTCAGCACCACCAGATAGCAGCTGGAGAGGAAGTCTCAAAGTGCC
CTACAATGTTGGACCTGGCTTTACTGGAAACTTTTCTACACAAAAAGTCAAGATGC
ACATCCACTCTACCAATGAAGTGACAAGAATTTACAATGTGATAGGTACTCTCAGA
GGAGCAGTGGAACCAGACAGATATGTCATTCTGGGAGGTCACCGGGACTCATGG
GTGTTTGGTGGTATTGACCCTCAGAGTGGAGCAGCTGTTGTTCATGAAATTGTGA
GGAGCTTTGGAACACTGAAAAAGGAAGGGTGGAGACCTAGAAGAACAATTTTGTT
TGCAAGCTGGGATGCAGAAGAATTTGGTCTTCTTGGTTCTACTGAGTGGGCAGAG
GAGAATTCAAGACTCCTTCAAGAGCGTGGCGTGGCTTATATTAATGCTGACTCAT
CTATAGAAGGAAACTACACTCTGAGAGTTGATTGTACACCGCTGATGTACAGCTT
GGTACACAACCTAACAAAAGAGCTGAAAAGCCCTGATGAAGGCTTTGAAGGCAAA
TCTCTTTATGAAAGTTGGACTAAAAAAAGTCCTTCCCCAGAGTTCAGTGGCATGCC
CAGGATAAGCAAATTGGGATCTGGAAATGATTTTGAGGTGTTCTTCCAACGACTTG
GAATTGCTTCAGGCAGAGCACGGTATACTAAAAATTGGGAAACAAACAAATTCAG
CGGCTATCCACTGTATCACAGTGTCTATGAAACATATGAGTTGGTGGAAAAGTTTT
ATGATCCAATGTTTAAATATCACCTCACTGTGGCCCAGGTTCGAGGAGGGATGGT
GTTTGAGCTGGCCAATTCCATAGTGCTCCCTTTTGATTGTCGAGATTATGCTGTAG
TTTTAAGAAAGTATGCTGACAAAATCTACAGTATTTCTATGAAACATCCACAGGAAA
TGAAGACATACAGTGTATCATTTGATTCACTTTTTTCTGCAGTAAAGAATTTTACAG
AAATTGCTTCCAAGTTCAGTGAGAGACTCCAGGACTTTGACAAAAGCAACCCAATA
GTATTAAGAATGATGAATGATCAACTCATGTTTCTGGAAAGAGCATTTATTGATCC
ATTAGGGTTACCAGACAGGCCTTTTTATAGGCATGTCATCTATGCTCCAAGCAGC
CACAACAAGTATGCAGGGGAGTCATTCCCAGGAATTTATGATGCTCTGTTTGATAT
TGAAAGCAAAGTGGACCCTTCCAAGGCCTGGGGAGAAGTGAAGAGACAGATTTAT
GTTGCAGCCTTCACAGTGCAGGCAGCTGCAGAGACTTTGAGTGAAGTAGCCGGA
TCCGAAGGTAGGGGTTCATTATTGACCTGTGGAGATGTCGAAGAAACCCAGGAC
CCGCAAGCAAGGCTGTGCTGCTTGCCCTGTTGATGGCAGGCTTGGCCCTGCAGC
CAGGCACTGCCCTGCTGTGCTACTCCTGCAAAGCCCAGGTGAGCAACGAGGACT
GCCTGCAGGTGGAGAACTGCACCCAGCTGGGGGAGCAGTGCTGGACCGCGCGC
ATCCGCGCAGTTGGCCTCCTGACCGTCATCAGCAAAGGCTGCAGCTTGAACTGC
GTGGATGACTCACAGGACTACTACGTGGGCAAGAAGAACATCACGTGCTGTGAC
ACCGACTTGTGCAACGCCAGCGGGGCCCATGCCCTGCAGCCGGCTGCCGCCAT
CCTTGCGCTGCTCCCTGCACTCGGCCTGCTGCTCTGGGGACCCGGCCAGCTATA
```

RAW SEQUENCE LISTING

```
GAGATCTGGGCCCTAACAAAACAAAAAGATGGGGTTATTCCCTAAACTTCATGGG
TTACGTAATTGGAAGTTGGGGGACATTGCCACAAGATCATATTGTACAAAAGATCA
AACACTGTTTTAGAAAACTTCCTGTAAACAGGCCTATTGATTGGAAAGTATGTCAA
AGGATTGTGGGTCTTTTGGGCTTTGCTGCTCCATTTACACAATGTGGATATCCTGC
CTTAATGCCTTTGTATGCATGTATACAAGCTAAACAGGCTTTCACTTTCTCGCCAA
CTTACAAGGCCTTTCTAAGTAAACAGTACATGAACCTTTACCCCGTTGCTCGGCAA
CGGCCTGGTCTGTGCCAAGTGTTTGCTGACGCAACCCCCACTGGCTGGGGCTTG
GCCATAGGCCATCAGCGCATGCGTGGAACCTTTGTGGCTCCTCTGCCGATCCATA
CTGCGGAACTCCTAGCCGCTTGTTTTGCTCGCAGCCGGTCTGGAGCAAAGCTCAT
AGGAACTGACAATTCTGTCGTCCTCTCGCGGAAATATACATCGTTTCGATCTACGT
ATGATCTTTTTCCCTCTGCCAAAAATTATGGGGACATCATGAAGCCCCTTGAGCAT
CTGACTTCTGGCTAATAAAGGAAATTTATTTTCATTGCAATAGTGTGTTGGAATTTT
TTGTGTCTCTCACTCGGAAGGAATTCTGCATTAATGAATCGGCCAACGCGCGGGG
AGAGGCGGTTTGCGTATTGGGCGCTCTTCCGCTTCCTCGCTCACTGACTCGCTG
CGCTCGGTCGTTCGGCTGCGGCGAGCGGTATCAGCTCACTCAAAGGCGGTAATA
CGGTTATCCACAGAATCAGGGGATAACGCAGGAAAGAACATGTGAGCAAAAGGC
CAGCAAAAGGCCAGGAACCGTAAAAAGGCCGCGTTGCTGGCGTTTTTCCATAGG
CTCCGCCCCCTGACGAGCATCACAAAAATCGACGCTCAAGTCAGAGGTGGCGA
AACCCGACAGGACTATAAAGATACCAGGCGTTTCCCCCTGGAAGCTCCCTCGTGC
GCTCTCCTGTTCCGACCCTGCCGCTTACCGGATACCTGTCCGCCTTTCTCCCTTC
GGGAAGCGTGGCGCTTTCTCATAGCTCACGCTGTAGGTATCTCAGTTCGGTGTAG
GTCGTTCGCTCCAAGCTGGGCTGTGTGCACGAACCCCCCGTTCAGCCCGACCGC
TGCGCCTTATCCGGTAACTATCGTCTTGAGTCCAACCCGGTAAGACACGACTTAT
CGCCACTGGCAGCAGCCACTGGTAACAGGATTAGCAGAGCGAGGTATGTAGGCG
GTGCTACAGAGTTCTTGAAGTGGTGGCCTAACTACGGCTACACTAGAAGAACAGT
ATTTGGTATCTGCGCTCTGCTGAAGCCAGTTACCTTCGGAAAAAGAGTTGGTAGC
TCTTGATCCGGCAAACAAACCACCGCTGGTAGCGGTGGTTTTTTTGTTTGCAAGC
AGCAGATTACGCGCAGAAAAAAAGGATCTCAAGAAGATCCTTTGATCTTTTCTACG
GGGTCTGACGCTCAGTGGAACGAAAACTCACGTTAAGGGATTTTGGTCATGAGAT
TATCAAAAAGGATCTTCACCTAGATCCTTTTAAATTAAAAATGAAGTTTTAAATCAA
TCTAAAGTATATATGAGTAAACTTGGTCTGACAGTTACCAATGCTTAATCAGTGAG
GCACCTATCTCAGCGATCTGTCTATTTCGTTCATCCATAGTTGCCTGACTC

SEQ ID NO: 28. NUCLEOTIDE SEQUENCE OF PLASMID 454
GGCGTAATGCTCTGCCAGTGTTACAACCAATTAACCAATTCTGATTAGAAAAACTC
ATCGAGCATCAAATGAAACTGCAATTTATTCATATCAGGATTATCAATACCATATTT
TTGAAAAAGCCGTTTCTGTAATGAAGGAGAAAACTCACCGAGGCAGTTCCATAGG
ATGGCAAGATCCTGGTATCGGTCTGCGATTCCGACTCGTCCAACATCAATACAAC
CTATTAATTTCCCCTCGTCAAAAATAAGGTTATCAAGTGAGAAATCACCATGAGTG
ACGACTGAATCCGGTGAGAATGGCAAAAGCTTATGCATTTCTTTCCAGACTTGTTC
AACAGGCCAGCCATTACGCTCGTCATCAAAATCACTCGCATCAACCAAACCGTTA
TTCATTCGTGATTGCGCCTGAGCGAGACGAAATACGCGATCGCTGTTAAAGGAC
AATTACAAACAGGAATCAAATGCAACCGGCGCAGGAACACTGCCAGCGCATCAAC
AATATTTTCACCTGAATCAGGATATTCTTCTAATACCTGGAATGCTGTTTTCCCGG
GGATCGCAGTGGTGAGTAACCATGCATCATCAGGAGTACGGATAAAATGCTTGAT
GGTCGGAAGAGGCATAAATTCCGTCAGCCAGTTTAGTCTGACCATCTCATCTGTA
ACATCATTGGCAACGCTACCTTTGCCATGTTTCAGAAACAACTCTGGCGCATCGG
GCTTCCCATACAATCGATAGATTGTCGCACCTGATTGCCCGACATTATCGCGAGC
CCATTTATACCCATATAAATCAGCATCCATGTTGGAATTTAATCGCGGCCTCGAGC
AAGACGTTTCCCGTTGAATATGGCTCATAACACCCCTTGTATTACTGTTTATGTAA
GCAGACAGGTCGACAATATTGGCTATTGGCCATTGCATACGTTGTATCTATATCAT
AATATGTACATTTATATTGGCTCATGTCCAATATGACCGCCATGTTGACATTGATTA
TTGACTAGTTATTAATAGTAATCAATTACGGGGTCATTAGTTCATAGCCCATATATG
GAGTTCCGCGTTACATAACTTACGGTAAATGGCCCGCCTGGCTGACCGCCCAAC
GACCCCCGCCCATTGACGTCAATAATGACGTATGTTCCCATAGTAACGCCAATAG
GGACTTTCCATTGACGTCAATGGGTGGAGTATTTACGGTAAACTGCCCACTTGGC
AGTACATCAAGTGTATCATATGCCAAGTCCGCCCCCTATTGACGTCAATGACGGT
AAATGGCCCGCCTGGCATTATGCCCAGTACATGACCTTACGGGACTTTCCTACTT
GGCAGTACATCTACGTATTAGTCATCGCTATTACCATGGTGATGCGGTTTTGGCA
GTACACCAATGGGCGTGGATAGCGGTTTGACTCACGGGGATTTCCAAGTCTCCAC
CCCATTGACGTCAATGGGAGTTTGTTTTGGCACCAAAATCAACGGGACTTTCCAA
AATGTCGTAATAACCCCGCCCCGTTGACGCAAATGGGCGGTAGGCGTGTACGGT
GGGAGGTCTATATAAGCAGAGCTCGTTTAGTGAACCGTCAGATCGCCTGGAGAC
GCCATCCACGCTGTTTTGACCTCCATAGAAGACACCGGGACCGATCCAGCCTCC
GCGGCCGGGAACGGTGCATTGGAACGCGGATTCCCCGTGCCAAGAGTGACTCA
CCGTCCGGATCTCAGCAAGCAGGTATGTACTCTCCAGGGTGGGCCTGGCTTCCC
CAGTCAAGACTCCAGGGATTTGAGGGACGCTGTGGGCTCTTCTCTTACATGTACC
TTTTGCTTGCCTCAACCCTGACTATCTTCCAGGTCAGGATCCCAGAGTCAGGGGT
CTGTATTTTCCTGCTGGTGGCTCCAGTTCAGGAACAGTAAACCCTGCTCCGAATA
TTGCCTCTCACATCTCGTCAATCTCCGCGAGGACTGGGGACCCTGTGACGAACAT
GGCTAGCAAGGCTGTGCTGCTTGCCCTGTTGATGGCAGGCTTGGCCCTGCAGCC
AGGCACTGCCCTGCTGTGCTACTCCTGCAAAGCCCAGGTGAGCAACGAGGACTG
CCTGCAGGTGGAGAACTGCACCCAGCTGGGGGAGCAGTGCTGGACCGCGCGCA
TCCGCGCAGTTGGCCTCCTGACCGTCATCAGCAAAGGCTGCAGCTTGAACTGCG
TGGATGACTCACAGGACTACTACGTGGGCAAGAAGAACATCACGTGCTGTGACAC
CGACTTGTGCAACGCCAGCGGGGCCCATGCCCTGCAGCCGGCTGCCGCCATCC
TTGCGCTGCTCCCTGCACTCGGCCTGCTGCTCTGGGGACCCGGCCAGCTAGGAT
```

RAW SEQUENCE LISTING

```
CCCAGACCCTGAACTTTGATCTGCTGAAACTGGCAGGCGATGTGGAAAGCAACC
CAGGCCCAATGGCAAGCGCGCGCCGCCCGCGCTGGCTGTGCGCTGGGGCGCT
GGTGCTGGCGGGTGGCTTCTTTCTCCTCGGCTTCCTCTTCGGGTGGTTTATAAAA
TCCTCCAATGAAGCTACTAACATTACTCCAAAGCATAATATGAAAGCATTTTTGGAT
GAATTGAAAGCTGAGAACATCAAGAAGTTCTTATATAATTTTACACAGATACCACAT
TTAGCAGGAACAGAACAAAACTTTCAGCTTGCAAAGCAAATTCAATCCCAGTGGAA
AGAATTTGGCCTGGATTCTGTTGAGCTGGCACATTATGATGTCCTGTTGTCCTACC
CAAATAAGACTCATCCCAACTACATCTCAATAATTAATGAAGATGGAAATGAGATTT
TCAACACATCATTATTTGAACCACCTCCTCCAGGATATGAAAATGTTTCGGATATT
GTACCACCTTTCAGTGCTTTCTCTCCTCAAGGAATGCCAGAGGGCGATCTAGTGT
ATGTTAACTATGCACGAACTGAAGACTTCTTTAAATTGGAACGGGACATGAAAATC
AATTGCTCTGGGAAAATTGTAATTGCCAGATATGGGAAAGTTTTCAGAGGAAATAA
GGTTAAAAATGCCCAGCTGGCAGGGGCCAAAGGAGTCATTCTCTACTCCGACCCT
GCTGACTACTTTGCTCCTGGGGTGAAGTCCTATCCAGATGGTTGGAATCTTCCTG
GAGGTGGTGTCCAGCGTGGAAATATCCTAAATCTGAATGGTGCAGGAGACCCTCT
CACACCAGGTTACCCAGCAAATGAATATGCTTATAGGCGTGGAATTGCAGAGGCT
GTTGGTCTTCCAAGTATTCCTGTTCATCCAATTGGATACTATGATGCACAGAAGCT
CCTAGAAAAAATGGGTGGCTCAGCACCACCAGATAGCAGCTGGAGAGGAAGTCT
CAAAGTGCCCTACAATGTTGGACCTGGCTTTACTGGAAACTTTTCTACACAAAAAG
TCAAGATGCACATCCACTCTACCAATGAAGTGACAAGAATTTACAATGTGATAGGT
ACTCTCAGAGGAGCAGTGGAACCAGACAGATATGTCATTCTGGGAGGTCACCGG
GACTCATGGGTGTTTGGTGGTATTGACCCTCAGAGTGGAGCAGCTGTTGTTCATG
AAATTGTGAGGAGCTTTGGAACACTGAAAAAGGAAGGGTGGAGACCTAGAAGAAC
AATTTTGTTTGCAAGCTGGGATGCAGAAGAATTTGGTCTTCTTGGTTCTTACTGAGT
GGGCAGAGGAGAATTCAAGACTCCTTCAAGAGCGTGGCGTGGCTTATATTAATGC
TGACTCATCTATAGAAGGAAACTACACTCTGAGAGTTGATTGTACACCGCTGATGT
ACAGCTTGGTACACAACCTAACAAAAGAGCTGAAAAGCCCTGATGAAGGCTTTGA
AGGCAAATCTCTTTATGAAAGTTGGACTAAAAAAAGTCCTTCCCCAGAGTTCAGTG
GCATGCCCAGGATAAGCAAATTGGGATCTGGAAATGATTTTGAGGTGTTCTTCCA
ACGACTTGGAATTGCTTCAGGCAGAGCACGGTATACTAAAAATTGGGAAACAAAC
AAAATTCAGCGGCTATCCACTGTATCACAGTGTCTATGAAACATATGAGTTGGTGGA
AAAGTTTTATGATCCAATGTTTAAATATCACCTCACTGTGGCCCAGGTTCGAGGAG
GGATGGTGTTTGAGCTGGCCAATTCCATAGTGCTCCCTTTTGATTGTCGAGATTAT
GCTGTAGTTTTAAGAAAGTATGCTGACAAAATCTACAGTATTTCTATGAAACATCCA
CAGGAAATGAAGACATACAGTGTATCATTTGATTCACTTTTTTCTGCAGTAAAGAAT
TTTACAGAAATTGCTTCCAAGTTCAGTGAGAGACTCCAGGACTTTGACAAAAGCAA
CCCAATAGTATTAAGAATGATGAATGATCAACTCATGTTTCTGGAAAGAGCATTTA
TTGATCCATTAGGGTTACCAGACAGGCCTTTTTATAGGCATGTCATCTATGCTCCA
AGCAGCCACAACAAGTATGCAGGGGAGTCATTCCCAGGAATTTATGATGCTCTGT
TTGATATTGAAAGCAAAGTGGACCCTTCCAAGGCCTGGGGAGAAGTGAAGAGACA
GATTTATGTTGCAGCCTTCACAGTGCAGGCAGCTGCAGAGACTTTGAGTGAAGTA
GCCTAAAGATCTGGGCCCTAACAAAACAAAAAGATGGGGTTATTCCCTAAACTTCA
TGGGTTACGTAATTGGAAGTTGGGGGACATTGCCACAAGATCATATTGTACAAAA
GATCAAACACTGTTTTAGAAAACTTCCTGTAAACAGGCCTATTGATTGGAAAGTAT
GTCAAAGGATTGTGGGTCTTTTGGGCTTTGCTGCTCCATTTACACAATGTGGATAT
CCTGCCTTAATGCCTTTGTATGCATGTATACAAGCTAAACAGGCTTTCACTTTCTC
GCCAACTTACAAGGCCTTTCTAAGTAAACAGTACATGAACCTTTACCCCGTTGCTC
GGCAACGGCCTGGTCTGTGCCAAGTGTTTGCTGACGCAACCCCCACTGGCTGGG
GCTTGGCCATAGGCCATCAGCGCATGCGTGGAACCTTTGTGGCTCCTCTGCCGA
TCCATACTGCGGAACTCCTAGCCGCTTGTTTTGCTCGCAGCCGGTCTGGAGCAAA
GCTCATAGGAACTGACAATTCTGTCGTCCTCTCGCGGAAATATACATCGTTTCGAT
CTACGTATGATCTTTTTCCCTCTGCCAAAAATTATGGGGACATCATGAAGCCCCTT
GAGCATCTGACTTCTGGCTAATAAAGGAAATTTATTTTCATTGCAATAGTGTGTTG
GAATTTTTTGTGTCTCTCACTCGGAAGGAATTCTGCATTAATGAATCGGCCAACGC
GCGGGGAGAGGCGGTTTGCGTATTGGGCGCTCTTCCGCTTCCTCGCTCACTGAC
TCGCTGCGCTCGGTCGTTCGGCTGCGGCGAGCGGTATCAGCTCACTCAAAGGCG
GTAATACGGTTATCCACAGAATCAGGGGATAACGCAGGAAAGAACATGTGAGCAA
AAGGCCAGCAAAAGGCCAGGAACCGTAAAAAGGCCGCGTTGCTGGCGTTTTTCC
ATAGGCTCCGCCCCCCTGACGAGCATCACAAAAATCGACGCTCAAGTCAGAGGT
GGCGAAACCCGACAGGACTATAAAGATACCAGGCGTTTCCCCCTGGAAGCTCCC
TCGTGCGCTCTCCTGTTCCGACCCTGCCGCTTACCGGATACCTGTCCGCCTTTCT
CCCTTCGGGAAGCGTGGCGCTTTCTCATAGCTCACGCTGTAGGTATCTCAGTTCG
GTGTAGGTCGTTCGCTCCAAGCTGGGCTGTGTGCACGAACCCCCCGTTCAGCCC
GACCGCTGCGCCTTATCCGGTAACTATCGTCTTGAGTCCAACCCGGTAAGACACG
ACTTATCGCCACTGGCAGCAGCCACTGGTAACAGGATTAGCAGAGCGAGGTATG
TAGGCGGTGCTACAGAGTTCTTGAAGTGGTGGCCTAACTACGGCTACACTAGAAG
AACAGTATTTGGTATCTGCGCTCTGCTGAAGCCAGTTACCTTCGGAAAAAGAGTT
GGTAGCTCTTGATCCGGCAAACAAACCACCGCTGGTAGCGGTGGTTTTTTTGTTT
GCAAGCAGCAGATTACGCGCAGAAAAAAAGGATCTCAAGAAGATCCTTTGATCTT
TTCTACGGGGTCTGACGCTCAGTGGAACGAAAACTCACGTTAAGGGATTTTGGTC
ATGAGATTATCAAAAAGGATCTTCACCTAGATCCTTTTAAATTAAAAATGAAGTTTT
AAATCAATCTAAAGTATATATGAGTAAACTTGGTCTGACAGTTACCAATGCTTAATC
AGTGAGGCACCTATCTCAGCGATCTGTCTATTTCGTTCATCCATAGTTGCCTGACTC
```

SEQ ID NO: 29. NUCLEOTIDE SEQUENCE OF PLASMID 5300
```
GGCGTAATGCTCTGCCAGTGTTACAACCAATTAACCAATTCTGATTAGAAAACTC
ATCGAGCATCAAATGAAACTGCAATTTATTCATATCAGGATTATCAATACCATATTT
```

RAW SEQUENCE LISTING

```
TTGAAAAAGCCGTTTCTGTAATGAAGGAGAAAACTCACCGAGGCAGTTCCATAGG
ATGGCAAGATCCTGGTATCGGTCTGCGATTCCGACTCGTCCAACATCAATACAAC
CTATTAATTTCCCCTCGTCAAAAATAAGGTTATCAAGTGAGAAATCACCATGAGTG
ACGACTGAATCCGGTGAGAATGGCAAAAGCTTATGCATTTCTTTCCAGACTTGTTC
AACAGGCCAGCCATTACGCTCGTCATCAAAATCACTCGCATCAACCAAACCGTTA
TTCATTCGTGATTGCGCCTGAGCGAGACGAAATACGCGATCGCTGTTAAAAGGAC
AATTACAAACAGGAATCAAATGCAACCGGCGCAGGAACACTGCCAGCGCATCAAC
AATATTTTCACCTGAATCAGGATATTCTTCTAATACCTGGAATGCTGTTTTCCCGG
GGATCGCAGTGGTGAGTAACCATGCATCATCAGGAGTACGGATAAAATGCTTGAT
GGTCGGAAGAGGCATAAATTCCGTCAGCCAGTTTAGTCTGACCATCTCATCTGTA
ACATCATTGGCAACGCTACCTTTGCCATGTTTCAGAAACAACTCTGGCGCATCGG
GCTTCCCATACAATCGATAGATTGTCGCACCTGATTGCCCGACATTATCGCGAGC
CCATTTATACCCATATAAATCAGCATCCATGTTGGAATTTAATCGCGGCCTCGAGC
AAGACGTTTCCCGTTGAATATGGCTCATAACACCCCTTGTATTACTGTTTATGTAA
GCAGACAGGTCGACAATATTGGCTATTGGCCATTGCATACGTTGTATCTATATCAT
AATATGTACATTTATATTGGCTCATGTCCAATATGACCGCCATGTTGACATTGATTA
TTGACTAGTTATTAATAGTAATCAATTACGGGGTCATTAGTTCATAGCCCATATATG
GAGTTCCGCGTTACATAACTTACGGTAAATGGCCCGCCTGGCTGACCGCCCAAC
GACCCCCGCCCATTGACGTCAATAATGACGTATGTTCCCATAGTAACGCCAATAG
GGACTTTCCATTGACGTCAATGGGTGGAGTATTTACGGTAAACTGCCCACTTGGC
AGTACATCAAGTGTATCATATGCCAAGTCCGCCCCCTATTGACGTCAATGACGGT
AAATGGCCCGCCTGGCATTATGCCCAGTACATGACCTTACGGGACTTTCCTACTT
GGCAGTACATCTACGTATTAGTCATCGCTATTACCATGGTGATGCGGTTTTGGCA
GTACACCAATGGGCGTGGATAGCGGTTTGACTCACGGGGATTTCCAAGTCTCCAC
CCCATTGACGTCAATGGGAGTTTGTTTTGGCACCAAAATCAACGGGACTTTCCAA
AATGTCGTAATAACCCCGCCCCGTTGACGCAAATGGGCGGTAGGCGTGTACGGT
GGGAGGTCTATATAAGCAGAGCTCGTTTAGTGAACCGTCAGATCGCCTGGAGAC
GCCATCCACGCTGTTTTGACCTCCATAGAAGACACCGGGACCGATCCAGCCTCC
GCGGCCGGGAACGGTGCATTGGAACGCGGATTCCCCGTGCCAAGAGTGACTCA
CCGTCCGGATCTCAGCAAGCAGGTATGTACTCTCCAGGGTGGGCCTGGCTTCCC
CAGTCAAGACTCCAGGGATTTGAGGGACGCTGTGGGCTCTTCTCTTACATGTACC
TTTTGCTTGCCTCAACCCTGACTATCTTCCAGGTCAGGATCCCAGAGTCAGGGGT
CTGTATTTTCCTGCTGGTGGCTCCAGTTCAGGAACAGTAAACCCTGCTCCGAATA
TTGCCTCTCACATCTCGTCAATCTCCGCGAGGACTGGGGACCCTGTGACGAACAT
GGCTAGCATTGTGGGAGGCTGGGAGTGCGAGAAGCATTCCCAACCCTGGCAGGT
GCTTGTGGCCTCTCGTGGCAGGGCAGTCTGCGGCGGTGTTCTGGTGCACCCCCA
GTGGGTCCTCACAGCTGCCCACTGCATCAGGAACAAAAGCGTGATCTTGCTGGG
TCGGCACAGCTTGTTTCATCCTGAAGACACAGGCCAGGTATTTCAGGTCAGCCAC
AGCTTCCCACACCCGCTCTACGATATGAGCCTCCTGAAGAATCGATTCCTCAGGC
CAGGTGATGACTCCAGCCACGACCTCATGCTGCTCCGCCTGTCAGAGCCTGCCG
AGCTCACGGATGCTGTGAAGGTCATGGACCTGCCCACCCAGGAGCCAGCACTGG
GGACCACCTGCTACGCCTCAGGCTGGGGCAGCATTGAACCAGAGGAGTTCTTGA
CCCCAAAGAAACTTCAGTGTGTGGACCTCCATGTTATTTCCAATGACGTGTGTGC
GCAAGTTCACCCTCAGAAGGTGACCAAGTTCATGCTGTGTGCTGGACGCTGGAC
AGGGGGCAAAAGCACCTGCTCGGGTGATTCTGGGGGCCCACTTGTCTGTAATGG
TGTGCTTCAAGGTATCACGTCATGGGGCAGTGAACCATGTGCCCTGCCCGAAAG
GCCTTCCCTGTACACCAAGGTGGTGCATTACCGGAAGTGGATCAAGGACACCATC
GTGGCCAACCCCGGATCCCAGACCCTGAACTTTGATCTGCTGAAACTGGCAGGC
GATGTGGAAAGCAACCCAGGCCCAATGGCAAGCGCGCGCCCGCCCGCGCTGGCT
GTGCGCTGGGGCGCTGGTGCTGGCGGGTGGCTTCTTTCTCCTCGGCTTCCTCTT
CGGGTGGTTTATAAAATCCTCAATGAAGCTACTAACATTACTCCAAAGCATAATA
TGAAAGCATTTTTGGATGAATTGAAAGCTGAGAACATCAAGAAGTTCTTATATAATT
TTACACAGATACCACATTTAGCAGGAACAGAACAAAACTTTCAGCTTGCAAAGCAA
ATTCAATCCCAGTGGAAAGAATTTGGCCTGGATTCTGTTGAGCTGGCACATTATGA
TGTCCTGTTGTCCTACCCAAATAAGACTCATCCCAACTACATCTCAATAATTAATGA
AGATGGAAATGAGATTTTCAACACATCATTATTTGAACCACCTCCTCCAGGATATG
AAAATGTTTCGGATATTGTACCACCTTTCAGTGCTTTCTCTCCTCAAGGAATGCCA
GAGGGCGATCTAGTGTATGTTAACTATGCACGAACTGAAGACTTCTTTAAATTGGA
ACGGGACATGAAATCAATTGCTCTGGGAAAATTGTAATTGCCAGATATGGGAAA
GTTTTCAGAGGAAATAAGGTTAAAAATGCCCAGCTGGCAGGGGCCAAAGGAGTCA
TTCTCTACTCCGACCCTGCTGACTACTTTGCTCCTGGGGTGAAGTCCTATCCAGA
TGGTTGGAATCTTCCTGGAGGTGGTGTCCAGCGTGGAAATATCCTAAATCTGAAT
GGTGCAGGAGACCCTCTCACACCAGGTTACCCAGCAAATGAATATGCTTATAGGC
GTGGAATTGCAGAGGCTGTTGGTCTTCCAAGTATTCCTGTTCATCCAATTGGATAC
TATGATGCACAGAAGCTCCTAGAAAAAATGGGTGGCTCAGCACCACCAGATAGCA
GCTGGAGAGGAAGTCTCAAAGTGCCCTACAATGTTGGACCTGGCTTTACTGGAAA
CTTTTCTACACAAAAAGTCAAGATGCACATCCACTCTACCAATGAAGTGACAAGAA
TTTACAATGTGATAGGTACTCTCAGAGGAGCAGTGGAACCAGACAGATATGTCAT
TCTGGGAGGTCACCGGGACTCATGGGTGTTTGGTGGTATTGACCCTCAGAGTGG
AGCAGCTGTTGTTCATGAAATTGTGAGGAGCTTTGGAACACTGAAAAAGGAAGGG
TGGAGACCTAGAAGAACAATTTTGTTTGCAAGCTGGGATGCAGAAGAATTTGGTC
TTCTTGGTTCTACTGAGTGGGCAGAGGAGAATTCAAGACTCCTTCAAGAGCGTGG
CGTGGCTTATATTAATGCTGACTCATCTATAGAAGGAAACTACACTCTGAGAGTTG
ATTGTACACCGCTGATGTACAGCTTGGTACAACCTAACAAAAGAGCTGAAAAG
CCCTGATGAAGGCTTTGAAGGCAAATCTCTTTATGAAAGTTGGACTAAAAAAGTC
CTTCCCCAGAGTTCAGTGGCATGCCCAGGATAAGCAAATTGGGATCTGGAAATGA
TTTTGAGGTGTTCTTCCAACGACTTGGAATTGCTTCAGGCAGAGCACGGTATACTA
```

| RAW SEQUENCE LISTING |
|---|
| AAAATTGGGAAACAAACAAATTCAGCGGCTATCCACTGTATCACAGTGTCTATGAA |
| ACATATGAGTTGGTGGAAAAGTTTTATGATCCAATGTTTAAATATCACCTCACTGT |
| GGCCCAGGTTCGAGGAGGGATGGTGTTTGAGCTGGCCAATTCCATAGTGCTCCC |
| TTTTGATTGTCGAGATTATGCTGTAGTTTTAAGAAAGTATGCTGACAAAATCTACAG |
| TATTTCTATGAAACATCCACAGGAAATGAAGACATACAGTGTATCATTTGATTCACT |
| TTTTTCTGCAGTAAAGAATTTTACAGAAATTGCTTCCAAGTTCAGTGAGAGACTCC |
| AGGACTTTGACAAAAGCAACCCAATAGTATTAAGAATGATGAATGATCAACTCATG |
| TTTCTGGAAAGAGCATTTATTGATCCATTAGGGTTACCAGACAGGCCTTTTTATAG |
| GCATGTCATCTATGCTCCAAGCAGCCACAACAAGTATGCAGGGGAGTCATTCCCA |
| GGAATTTATGATGCTCTGTTTGATATTGAAAGCAAAGTGGACCCTTCCAAGGCCTG |
| GGGAGAAGTGAAGAGACAGATTTATGTTGCAGCCTTCACAGTGCAGGCAGCTGC |
| AGAGACTTTGAGTGAAGTAGCCTAAAGATCTGGGCCCTAACAAAACAAAAAGATG |
| GGGTTATTCCCTAAACTTCATGGGTTACGTAATTGGAAGTTGGGGGACATTGCCA |
| CAAGATCATATTGTACAAAAGATCAAACACTGTTTTAGAAAACTTCCTGTAAACAG |
| GCCTATTGATTGGAAAGTATGTCAAAGGATTGTGGGTCTTTTGGGCTTTGCTGCTC |
| CATTTACACAATGTGGATATCCTGCCTTAATGCCTTTGTATGCATGTATACAAGCT |
| AAACAGGCTTTCACTTTCTCGCCAACTTACAAGGCCTTTCTAAGTAAACAGTACAT |
| GAACCTTTACCCCGTTGCTCGGCAACGGCCTGGTCTGTGCCAAGTGTTTGCTGAC |
| GCAACCCCCACTGGCTGGGGCTTGGCCATAGGCCATCAGCGCATGCGTGGAACC |
| TTTGTGGCTCCTCTGCCGATCCATACTGCGGAACTCCTAGCCGCTTGTTTTGCTC |
| GCAGCCGGTCTGGAGCAAAGCTCATAGGAACTGACAATTCTGTCGTCCTCTCGC |
| GGAAATATACATCGTTTCGATCTACGTATGATCTTTTTCCCTCTGCCAAAATTATG |
| GGGACATCATGAAGCCCCTTGAGCATCTGACTTCTGGCTAATAAAGGAAATTTATT |
| TTCATTGCAATAGTGTGTTGGAATTTTTTGTGTCTCTCACTCGGAAGGAATTCTGC |
| ATTAATGAATCGGCCAACGCGCGGGGAGAGGCGGTTTGCGTATTGGGCGCTCTT |
| CCGCTTCCTCGCTCACTGACTCGCTGCGCTCGGTCGTTCGGCTGCGGCGAGCGG |
| TATCAGCTCACTCAAAGGCGGTAATACGGTTATCCACAGAATCAGGGGATAACGC |
| AGGAAAGAACATGTGAGCAAAAGGCCAGCAAAAGGCCAGGAACCGTAAAAAGGC |
| CGCGTTGCTGGCGTTTTTCCATAGGCTCCGCCCCCCTGACGAGCATCACAAAAAT |
| CGACGCTCAAGTCAGAGGTGGCGAAACCCGACAGGACTATAAAGATACCAGGCG |
| TTTCCCCCTGGAAGCTCCCTCGTGCGCTCTCCTGTTCCGACCCTGCCGCTTACCG |
| GATACCTGTCCGCCTTTCTCCCTTCGGGAAGCGTGGCGCTTTCTCATAGCTCACG |
| CTGTAGGTATCTCAGTTCGGTGTAGGTCGTTCGCTCCAAGCTGGGCTGTGTGCAC |
| GAACCCCCCGTTCAGCCCGACCGCTGCGCCTTATCCGGTAACTATCGTCTTGAGT |
| CCAACCCGGTAAGACACGACTTATCGCCACTGGCAGCAGCCACTGGTAACAGGA |
| TTAGCAGAGCGAGGTATGTAGGCGGTGCTACAGAGTTCTTGAAGTGGTGGCCTA |
| ACTACGGCTACACTAGAAGAACAGTATTTGGTATCTGCGCTCTGCTGAAGCCAGT |
| TACCTTCGGAAAAAGAGTTGGTAGCTCTTGATCCGGCAAACAAACCACCGCTGGT |
| AGCGGTGGTTTTTTGTTTGCAAGCAGCAGATTACGCGCAGAAAAAAAGGATCTC |
| AAGAAGATCCTTTGATCTTTTCTACGGGGTCTGACGCTCAGTGGAACGAAAACTC |
| ACGTTAAGGGATTTTGGTCATGAGATTATCAAAAAGGATCTTCACCTAGATCCTTT |
| TAAATTAAAAATGAAGTTTTAAATCAATCTAAAGTATATATGAGTAAACTTGGTCTG |
| ACAGTTACCAATGCTTAATCAGTGAGGCACCTATCTCAGCGATCTGTCTATTTCGT |
| TCATCCATAGTTGCCTGACTC |
| |
| SEQ ID NO: 30. NUCLEOTIDE SEQUENCE OF PLASMID 449 |
| GGCGTAATGCTCTGCCAGTGTTACAACCAATTAACCAATTCTGATTAGAAAAACTC |
| ATCGAGCATCAAATGAAACTGCAATTTATTCATATCAGGATTATCAATACCATATTT |
| TTGAAAAAGCCGTTTCTGTAATGAAGGAGAAAACTCACCGAGGCAGTTCCATAGG |
| ATGGCAAGATCCTGGTATCGGTCTGCGATTCCGACTCGTCCAACATCAATACAAC |
| CTATTAATTTCCCCTCGTCAAAAATAAGGTTATCAAGTGAGAAATCACCATGAGTG |
| ACGACTGAATCCGGTGAGAATGGCAAAAGCTTATGCATTTCTTTCCAGACTTGTTC |
| AACAGGCCAGCCATTACGCTCGTCATCAAAATCACTCGCATCAACCAAACCGTTA |
| TTCATTCGTGATTGCGCCTGAGCGAGACGAAATACGCGATCGCTGTTAAAAGGAC |
| AATTACAAACAGGAATCAAATGCAACCGGCGCAGGAACACTGCCAGCGCATCAAC |
| AATATTTTCACCTGAATCAGGATATTCTTCTAATACCTGGAATGCTGTTTTCCCGG |
| GGATCGCAGTGGTGAGTAACCATGCATCATCAGGAGTACGGATAAAATGCTTGAT |
| GGTCGGAAGAGGCATAAATTCCGTCAGCCAGTTTAGTCTGACCATCTCATCTGTA |
| ACATCATTGGCAACGCTACCTTTGCCATGTTTCAGAAACAACTCTGGCGCATCGG |
| GCTTCCCATACAATCGATAGATTGTCGCACCTGATTGCCCGACATTATCGCGAGC |
| CCATTTATACCCATATAAATCAGCATCCATGTTGGAATTTAATCGCGGCCTCGAGC |
| AAGACGTTTCCCGTTGAATATGGCTCATAACACCCCTTGTATTACTGTTTATGTAA |
| GCAGACAGGTCGACAATATTGGCTATTGGCCATTGCATACGTTGTATCTATATCAT |
| AATATGTACATTTATATTGGCTCATGTCCAATATGACCGCCATGTTGACATTGATTA |
| TTGACTAGTTATTAATAGTAATCAATTACGGGGTCATTAGTTCATAGCCCATATATG |
| GAGTTCCGCGTTACATAACTTACGGTAAATGGCCCGCCTGGCTGACCGCCCAAC |
| GACCCCCGCCCATTGACGTCAATAATGACGTATGTTCCCATAGTAACGCCAATAG |
| GGACTTTCCATTGACGTCAATGGGTGGAGTATTTACGGTAAACTGCCCACTTGGC |
| AGTACATCAAGTGTATCATATGCCAAGTCCGCCCCCTATTGACGTCAATGACGGT |
| AAATGGCCCGCCTGGCATTATGCCCAGTACATGACCTTACGGGACTTTCCTACTT |
| GGCAGTACATCTACGTATTAGTCATCGCTATTACCATGGTGATGCGGTTTTGGCA |
| GTACACCAATGGGCGTGGATAGCGGTTTGACTCACGGGGATTTCCAAGTCTCCAC |
| CCCATTGACGTCAATGGGAGTTTGTTTTGGCACCAAAATCAACGGGACTTTCCAA |
| AATGTCGTAATAACCCCGCCCCGTTGACGCAAATGGGCGGTAGGCGTGTACGGT |
| GGGAGGTCTATATAAGCAGAGCTCGTTTAGTGAACCGTCAGATCGCCTGGAGAC |
| GCCATCCACGCTGTTTTGACCTCCATAGAAGACACCGGGACCGATCCAGCCTCC |
| GCGGCCGGGAACGGTGCATTGGAACGCGGATTCCCCGTGCCAAGAGTGACTCA |

-continued

RAW SEQUENCE LISTING

```
CCGTCCGGATCTCAGCAAGCAGGTATGTACTCTCCAGGGTGGGCCTGGCTTCCC
CAGTCAAGACTCCAGGGATTTGAGGGACGCTGTGGGCTCTTCTCTTACATGTACC
TTTTGCTTGCCTCAACCCTGACTATCTTCCAGGTCAGGATCCCAGAGTCAGGGGT
CTGTATTTTCCTGCTGGTGGCTCCAGTTCAGGAACAGTAAACCCTGCTCCGAATA
TTGCCTCTCACATCTCGTCAATCTCCGCGAGGACTGGGGACCCTGTGACGAACAT
GGCTAGCGCGCGCCGCCCGCGCTGGCTGTGCGCTGGGGCGCTGGTGCTGGCG
GGTGGCTTCTTTCTCCTCGGCTTCCTCTTCGGGTGGTTTATAAAATCCTCCAATGA
AGCTACTAACATTACTCCAAAGCATAATATGAAAGCATTTTTGGATGAATTGAAAG
CTGAGAACATCAAGAAGTTCTTATATAATTTTACACAGATACCACATTTAGCAGGA
ACAGAACAAAACTTTCAGCTTGCAAAGCAAATTCAATCCCAGTGGAAAGAATTTGG
CCTGGATTCTGTTGAGCTGGCACATTATGATGTCCTGTTGTCCTACCCAAATAAGA
CTCATCCCAACTACATCTCAATAATTAATGAAGATGGAAATGAGATTTTCAACACAT
CATTATTTGAACCACCTCCTCCAGGATATGAAATGTTTCGGATATTGTACCACCT
TTCAGTGCTTTCTCTCCTCAAGGAATGCCAGAGGGCGATCTAGTGTATGTTAACTA
TGCACGAACTGAAGACTTCTTTAAATTGGAACGGGACATGAAAATCAATTGCTCTG
GGAAAATTGTAATTGCCAGATATGGGAAAGTTTTCAGAGGGAAATAAGGTTAAAAAT
GCCCAGCTGGCAGGGGCCAAAGGAGTCATTCTCTACTCCGACCCTGCTGACTAC
TTTGCTCCTGGGGTGAAGTCCTATCCAGATGGTTGGAATCTTCCTGGAGGTGGTG
TCCAGCGTGGAAATATCCTAAATCTGAATGGTGCAGGAGACCCTCTCACACCAGG
TTACCCAGCAAATGAATATGCTTATAGGCGTGGAATTGCAGAGGCTGTTGGTCTT
CCAAGTATTCCTGTTCATCCAATTGGATACTATGATGCACAGAAGCTCCTAGAAAA
AATGGGTGGCTCAGCACCACCAGATAGCAGCTGGAGAGGAAGTCTCAAAGTGCC
CTACAATGTTGGACCTGGCTTTACTGGAAACTTTTCTACACAAAAAGTCAAGATGC
ACATCCACTCTACCAATGAAGTGACAAGAATTTACAATGTGATAGGTACTCTCAGA
GGAGCAGTGGAACCAGACAGATATGTCATTCTGGGAGGTCACCGGGACTCATGG
GTGTTTGGTGGTATTGACCCTCAGAGTGGAGCAGCTGTTGTTCATGAAATTGTGA
GGAGCTTTGGAACACTGAAAAAGGAAGGGTGGAGACCTAGAAGAACAATTTTGTT
TGCAAGCTGGGATGCAGAAGAATTTGGTCTTCTTGGTTCTACTGAGTGGGCAGAG
GAGAATTCAAGACTCCTTCAAGAGCGTGGCGTGGCTTATATTAATGCTGACTCAT
CTATAGAAGGAAACTACACTCTGAGAGTTGATTGTACACCGCTGATGTACAGCTT
GGTACACAACCTAACAAAAGAGCTGAAAAGCCCTGATGAAGGCTTTGAAGGCAAA
TCTCTTTATGAAAGTTGGACTAAAAAAAGTCCTTCCCCAGAGTTCAGTGGCATGCC
CAGGATAAGCAAATTGGGATCTGGAAATGATTTTGAGGTGTTCTTCCAACGACTTG
GAATTGCTTCAGGCAGAGCACGGTATACTAAAAATTGGGAAACAAACAAATTCAG
CGGCTATCCACTGTATCACAGTGTCTATGAAACATATGAGTTGGTGGAAAAGTTTT
ATGATCCAATGTTTAAATATCACCTCACTGTGGCCCAGGTTCGAGGAGGGATGGT
GTTTGAGCTGGCCAATTCCATAGTGCTCCCTTTTGATTGTCGAGATTATGCTGTAG
TTTTAAGAAAGTATGCTGACAAAATCTACAGTATTTCTATGAAACATCCACAGGAAA
TGAAGACATACAGTGTATCATTTGATTCACTTTTTTCTGCAGTAAAGAATTTTACAG
AAAATTGCTTCCAAGTTCAGTGAGAGACTCCAGGACTTTGACAAAAGCAACCCAATA
GTATTAAGAATGATGAATGATCAACTCATGTTTCTGGAAAGAGCATTTATTGATCC
ATTAGGGTTACCAGACAGGCCTTTTTATAGGCATGTCATCTATGCTCCAAGCAGC
CACAACAAGTATGCAGGGGAGTCATTCCCAGGAATTTATGATGCTCTGTTTGATAT
TGAAAGCAAAGTGGACCCTTCCAAGGCCTGGGGAGAAGTGAAGAGACAGATTTAT
GTTGCAGCCTTCACAGTGCAGGCAGCTGCAGAGACTTTGAGTGAAGTAGCCTAAA
GATCTGACCCCCTAACGTTACTGGCCGAAGCCGCTTGGAATAAGGCCGGTGTGC
GTTTGTCTATATGTTATTTTCCACCATATTGCCGTCTTTTGGCAATGTGAGGGCCC
GGAAACCTGGCCCTGTCTTCTTGACGAGCATTCCTAGGGGTCTTTCCCCTCTCGC
CAAAGGAATGCAAGGTCTGTTGAATGTCGTGAAGGAAGCAGTTCCTCTGGAAGCT
TCTTGAAGACAAACAACGTCTGTAGCGACCCTTTGCAGGCAGCGGAACCCCCCA
CCTGGCGACAGGTGCCTCTGCGGCCAAAAGCCACGTGTATAAGATACACCTGCA
AAGGCGGCACAACCCCAGTGCCACGTTGTGAGTTGGATAGTTGTGGAAAGAGTC
AAATGGCTCTCCTCAAGCGTATTCAACAAGGGGCTGAAGGATGCCCAGAAGGTAC
CCCATTGTATGGGATCTGATCTGGGGCCTCGGTGCACATGCTTTACATGTGTTTA
GTCGAGGTTAAAAAACGTCTAGGCCCCCCGAACCACGGGGACGTGGTTTTCCTTT
GAAAAACACGATGATAATATGGCCAGCAAGGCTGTGCTGCTTGCCCTGTTGATGG
CAGGCTTGGCCCTGCAGCCAGGCACTGCCCTGCTGTGCTACTCCTGCAAAGCCC
AGGTGAGCAACGAGGACTGCCTGCAGGTGGAGAACTGCACCCAGCTGGGGGAG
CAGTGCTGGACCGCGCGCATCCGCGCAGTTGGCCTCCTGACCGTCATCAGCAAA
GGCTGCAGCTTGAACTGCGTGGATGACTCACAGGACTACTACGTGGGCAAGAAG
AACATCACGTGCTGTGACACCGACTTGTGCAACGCCAGCGGGCCCATGCCCTG
CAGCCGGCTGCCGCCATCCTTGCGCTGCTCCCTGCACTCGGCCTGCTGCTCTGG
GGACCCGGCCAGCTATAGGGATCTGGGCCCTAACAAAACAAAAAGATGGGGTTA
TTCCCTAAACTTCATGGGTTACGTAATTGGAAGTTGGGGGACATTGCCACAAGAT
CATATTGTACAAAAGATCAAACACTGTTTTAGAAAACTTCCTGTAAACAGGCCTATT
GATTGGAAAGTATGTCAAAGGATTGTGGGTCTTTTGGGCTTTGCTGCTCCATTTAC
ACAATGTGGATATCCTGCCTTAATGCCTTTGTATGCATGTATACAAGCTAAACAGG
CTTTCACTTTCTCGCCAACTTACAAGGCCTTTCTAAGTAAACAGTACATGAACCTTT
ACCCCGTTGCTCGGCAACGGCCTGGTCTGTGCCAAGTGTTTGCTGACGCAACCC
CCACTGGCTGGGGCTTGGCCATAGGCCATCAGCGCATGCGTGGAACCTTTGTGG
CTCCTCTGCCGATCCATACTGCGGAACTCCTAGCCGCTTGTTTTGCTGCAGCCG
GTCTGGAGCAAAGCTCATAGGAACTGACAATTCTGTCGTCCTCTCGCGGAAATAT
ACATCGTTTCGATCTACGTATGATCTTTTCCCTCTGCCAAAAATTATGGGGACAT
CATGAAGCCCTTGAGCATCTGACTTCTGGCTAATAAAGGAAATTTATTTTCATTG
CAATAGTGTGTTGGAATTTTTTGTGTCTCTCACTCGGAAGGAATTCTGCATTAATG
AATCGGCCAACGCGCGGGGAGAGGCGGTTTGCGTATTGGGCGCTCTTCCGCTTC
CTCGCTCACTGACTCGCTGCGCTCGGTCGTTCGGCTGCGGCGAGCGGTATCAGC
```

| RAW SEQUENCE LISTING |
| --- |
| TCACTCAAAGGCGGTAATACGGTTATCCACAGAATCAGGGGATAACGCAGGAAAG
AACATGTGAGCAAAAGGCCAGCAAAAGGCCAGGAACCGTAAAAAGGCCGCGTTG
CTGGCGTTTTTCCATAGGCTCCGCCCCCCTGACGAGCATCACAAAAATCGACGCT
CAAGTCAGAGGTGGCGAAACCCGACAGGACTATAAAGATACCAGGCGTTTCCCC
CTGGAAGCTCCCTCGTGCGCTCTCCTGTTCCGACCCTGCCGCTTACCGGATACCT
GTCCGCCTTTCTCCCTTCGGGAAGCGTGGCGCTTTCTCATAGCTCACGCTGTAGG
TATCTCAGTTCGGTGTAGGTCGTTCGCTCCAAGCTGGGCTGTGTGCACGAACCCC
CCGTTCAGCCCGACCGCTGCGCCTTATCCGGTAACTATCGTCTTGAGTCCAACCC
GGTAAGACACGACTTATCGCCACTGGCAGCAGCCACTGGTAACAGGATTAGCAG
AGCGAGGTATGTAGGCGGTGCTACAGAGTTCTTGAAGTGGTGGCCTAACTACGG
CTACACTAGAAGAACAGTATTTGGTATCTGCGCTCTGCTGAAGCCAGTTACCTTC
GGAAAAAGAGTTGGTAGCTCTTGATCCGGCAAACAAACCACCGCTGGTAGCGGT
GGTTTTTTTGTTTGCAAGCAGCAGATTACGCGCAGAAAAAAAGGATCTCAAGAAG
ATCCTTTGATCTTTTCTACGGGGTCTGACGCTCAGTGGAACGAAAACTCACGTTAA
GGGATTTTGGTCATGAGATTATCAAAAAGGATCTTCACCTAGATCCTTTTAAATTAA
AAATGAAGTTTTAAATCAATCTAAAGTATATATGAGTAAACTTGGTCTGACAGTTAC
CAATGCTTAATCAGTGAGGCACCTATCTCAGCGATCTGTCTATTTCGTTCATCCAT
AGTTGCCTGACTC

SEQ ID NO: 31. NUCLEOTIDE SEQUENCE OF PLASMID 603
GGCGTAATGCTCTGCCAGTGTTACAACCAATTAACCAATTCTGATTAGAAAAACTC
ATCGAGCATCAAATGAAACTGCAATTTATTCATATCAGGATTATCAATACCATATTT
TGAAAAAGCCGTTTCTGTAATGAAGGAGAAAACTCACCGAGGCAGTTCCATAGG
ATGGCAAGATCCTGGTATCGGTCTGCGATTCCGACTCGTCCAACATCAATACAAC
CTATTAATTTCCCCTCGTCAAAAATAAGGTTATCAAGTGAGAAATCACCATGAGTG
ACGACTGAATCCGGTGAGAATGGCAAAAGCTTATGCATTTCTTTCCAGACTTGTTC
AACAGGCCAGCCATTACGCTCGTCATCAAAATCACTCGCATCAACCAAACCGTTA
TTCATTCGTGATTGCGCCTGAGCGAGACGAAATACGCGATCGCTGTTAAAAGGAC
AATTACAAACAGGAATCAAATGCAACCGGCGCAGGAACACTGCCAGCGCATCAAC
AATATTTTCACCTGAATCAGGATATTCTTCTAATACCTGGAATGCTGTTTTCCCGG
GGATCGCAGTGGTGAGTAACCATGCATCATCAGGAGTACGGATAAAATGCTTGAT
GGTCGGAAGAGGCATAAATTCCGTCAGCCAGTTTAGTCTGACCATCTCATCTGTA
ACATCATTGGCAACGCTACCTTTGCCATGTTTCAGAAACAACTCTGGCGCATCGG
GCTTCCCATACAATCGATAGATTGTCGCACCTGATTGCCCGACATTATCGCGAGC
CCATTTATACCCATATAAATCAGCATCCATGTTGGAATTTAATCGCGGCCTCGAGC
AAGACGTTTCCCGTTGAATATGGCTCATAACACCCCTTGTATTACTGTTTATGTAA
GCAGACAGGTCGACAATATTGGCTATTGGCCATTGCATACGTTGTATCTATATCAT
AATATGTACATTTATATTGGCTCATGTCCAATATGACCGCCATGTTGACATTGATTA
TTGACTAGTTATTAATAGTAATCAATTACGGGGTCATTAGTTCATAGCCCATATATG
GAGTTCCGCGTTACATAACTTACGGTAAATGGCCCGCCTGGCTGACCGCCCAAC
GACCCCCGCCCATTGACGTCAATAATGACGTATGTTCCCATAGTAACGCCAATAG
GGACTTTCCATTGACGTCAATGGGTGGAGTATTTACGGTAAACTGCCCACTTGGC
AGTACATCAAGTGTATCATATGCCAAGTCCGCCCCCTATTGACGTCAATGACGGT
AAATGGCCCGCCTGGCATTATGCCCAGTACATGACCTTACGGGACTTTCCTACTT
GGCAGTACATCTACGTATTAGTCATCGCTATTACCATGGTGATGCGGTTTTGGCA
GTACACCAATGGGCGTGGATAGCGGTTTGACTCACGGGGATTTCCAAGTCTCCAC
CCCATTGACGTCAATGGGAGTTTGTTTTGGCACCAAAATCAACGGGACTTTCCAA
AATGTCGTAATAACCCCGCCCCGTTGACGCAAATGGGCGGTAGGCGTGTACGGT
GGGAGGTCTATATAAGCAGAGCTCGTTTAGTGAACCGTCAGATCGCCTGGAGAC
GCCATCCACGCTGTTTTGACCTCCATAGAAGACACCGGGACCGATCCAGCCTCC
GCGGCCGGGAACGGTGCATTGGAACGCGGATTCCCCGTGCCAAGAGTGACTCA
CCGTCCGGATCTCAGCAAGCAGGTATGTACTCTCCAGGGTGGGCCTGGCTTCCC
CAGTCAAGACTCCAGGGATTTGAGGGACGCTGTGGGCTCTTCTCTTACATGTACC
TTTTGCTTGCCTCAACCCTGACTATCTTCCAGGTCAGGATCCCAGAGTCAGGGGT
CTGTATTTTCCTGCTGGTGGCTCCAGTTCAGGAACAGTAAACCCTGCTCCGAATA
TTGCCTCTCACATCTCGTCAATCTCCGCGAGGACTGGGGACCCTGTGACGAACAT
GGCTAGCAAGGCTGTGCTGCTTGCCCTGTTGATGGCAGGCTTGGCCCTGCAGCC
AGGCACTGCCCTGCTGTGCTACTCCTGCAAAGCCCAGGTGAGCAACGAGGACTG
CCTGCAGGTGGAGAACTGCACCCAGCTGGGGGAGCAGTGCTGGACCGCGCGCA
TCCGCGCAGTTGGCCTCCTGACCGTCATCAGCAAAGGCTGCAGCTTGAACTGCG
TGGATGACTCACAGGACTACTACGTGGGCAAGAAGAACATCACGTGCTGTGACAC
CGACTTGTGCAACGCCAGCGGGCCCATGCCCTGCAGCCGGCTGCCGCCATCC
TTGCGCTGCTCCCTGCACTCGGCCTGCTGCTCTGGGGACCCGGCCAGCTATAGA
GATCTGACCCCTAACGTTACTGGCCGAAGCCGCTTGGAATAAGGCCGGTGTGC
GTTTGTCTATATGTTATTTTCCACCATATTGCCGTCTTTTGGCAATGTGAGGGCCC
GGAAACCTGGCCCTGTCTTCTTGACGAGCATTCCTAGGGGTCTTTCCCCTCTCGC
CAAAGGAATGCAAGGTCTGTTGAATGTCGTGAAGGAAGCAGTTCCTCTGGAAGCT
TCTTGAAGACAAACAACGTCTGTAGCGACCCTTTGCAGGCAGCGGAACCCCCCA
CCTGGCGACAGGTGCCTCTGCGGCCAAAAGCCACGTGTATAAGATACACCTGCA
AAGGCGGCACAACCCCAGTGCCACGTTGTGAGTTGGATAGTTGTGGAAAGAGTC
AAATGGCTCTCCTCAAGCGTATTCAACAAGGGGCTGAAGGATGCCCAGAAGGTAC
CCCATTGTATGGGATCTGATCTGGGGCCTCGGTGCACATGCTTTACATGTGTTTA
GTCGAGGTTAAAAAACGTCTAGGCCCCCCGAACCACGGGGACGTGGTTTTCCTTT
GAAAAACACGATGATAATATGCCACAACCATGGCGCGCCGCCCGCGCTGGCTG
TGCGCTGGGCGCTGGTGCTGGCGGGTGGCTTCTTTCTCCTCGGCTTCCTCTTC
GGGTGGTTTATAAAATCCTCCAATGAAGCTACTAACATTACTCCAAAGCATAATAT
GAAAGCATTTTTGGATGAATTGAAAGCTGAGAACATCAAGAAGTTCTTATATAATTT |

```
TACACAGATACCACATTTAGCAGGAACAGAACAAAACTTTCAGCTTGCAAAGCAAA
TTCAATCCCAGTGGAAAGAATTTGGCCTGGATTCTGTTGAGCTGGCACATTATGAT
GTCCTGTTGTCCTACCCAAATAAGACTCATCCCAACTACATCTCAATAATTAATGA
AGATGGAAATGAGATTTTCAACACATCATTATTTGAACCACCTCCTCCAGGATATG
AAAATGTTTCGGATATTGTACCACCTTTCAGTGCTTTCTCTCCTCAAGGAATGCCA
GAGGGCGATCTAGTGTATGTTAACTATGCACGAACTGAAGACTTCTTTAAATTGGA
ACGGGACATGAAAATCAATTGCTCTGGGAAAATTGTAATTGCCAGATATGGGAAA
GTTTTCAGAGGAAATAAGGTTAAAAATGCCCAGCTGGCAGGGGCCAAAGGAGTCA
TTCTCTACTCCGACCCTGCTGACTACTTTGCTCCTGGGGTGAAGTCCTATCCAGA
TGGTTGGAATCTTCCTGGAGGTGGTGTCCAGCGTGGAAATATCCTAAATCTGAAT
GGTGCAGGAGACCCTCTCACACCAGGTTACCCAGCAAATGAATATGCTTATAGGC
GTGGAATTGCAGAGGCTGTTGGTCTTCCAAGTATTCCTGTTCATCCAATTGGATAC
TATGATGCACAGAAGCTCCTAGAAAAAATGGGTGGCTCAGCACCACCAGATAGCA
GCTGGAGAGGAAGTCTCAAAGTGCCCTACAATGTTGGACCTGGCTTTACTGGAAA
CTTTTCTACACAAAAAGTCAAGATGCACATCCACTCTACCAATGAAGTGACAAGAA
TTTACAATGTGATAGGTACTCTCAGAGGAGCAGTGGAACCAGACAGATATGTCAT
TCTGGGAGGTCACCGGGACTCATGGGTGTTTGGTGGTATTGACCCTCAGAGTGG
AGCAGCTGTTGTTCATGAAATTGTGAGGAGCTTTGGAACACTGAAAAGGAAGGG
TGGAGACCTAGAAGAACAATTTTGTTTGCAAGCTGGGATGCAGAAGAATTTGGTC
TTCTTGGTTCTACTGAGTGGGCAGAGGAGAATTCAAGACTCCTTCAAGAGCGTGG
CGTGGCTTATATTAATGCTGACTCATCTATAGAAGGAAACTACACTCTGAGAGTTG
ATTGTACACCGCTGATGTACAGCTTGGTACACAACCTAACAAAAGAGCTGAAAAG
CCCTGATGAAGGCTTTGAAGGCAAATCTCTTTATGAAAGTTGGACTAAAAAAAGTC
CTTCCCCAGAGTTCAGTGGCATGCCCAGGATAAGCAAATTGGGATCTGGAAATGA
TTTTGAGGTGTTCTTCCAACGACTTGGAATTGCTTCAGGCAGAGCACGGTATACTA
AAAATTGGGAAACAAACAAATTCAGCGGCTATCCACTGTATCACAGTGTCTATGAA
ACATATGAGTTGGTGGAAAAGTTTTATGATCCAATGTTTAAATATCACCTCACTGT
GGCCCAGGTTCGAGGAGGGATGGTGTTTGAGCTGGCCAATTCCATAGTGCTCCC
TTTTGATTGTCGAGATTATGCTGTAGTTTTAAGAAAGTATGCTGACAAAATCTACAG
TATTTCTATGAAACATCCACAGGAAATGAAGACATACAGTGTATCATTTGATTCACT
TTTTTCTGCAGTAAAGAATTTTACAGAAATTGCTTCCAAGTTCAGTGAGAGACTCC
AGGACTTTGACAAAAGCAACCCAATAGTATTAAGAATGATGAATGATCAACTCATG
TTTCTGGAAAGAGCATTTATTGATCCATTAGGGTTACCAGACAGGCCTTTTTATAG
GCATGTCATCTATGCTCCAAGCAGCCACAACAAGTATGCAGGGGAGTCATTCCCA
GGAATTTATGATGCTCTGTTTGATATTGAAAGCAAAGTGGACCCTTCCAAGGCCTG
GGGAGAAGTGAAGAGACAGATTTATGTTGCAGCCTTCACAGTGCAGGCAGCTGC
AGAGACTTTGAGTGAAGTAGCCTAAAGATCTGGGCCCTAACAAAACAAAAGATG
GGGTTATTCCCTAAACTTCATGGGTTACGTAATTGGAAGTTGGGGGACATTGCCA
CAAGATCATATTGTACAAAAGATCAAACACTGTTTTAGAAAACTTCCTGTAAACAG
GCCTATTGATTGGAAAGTATGTCAAAGGATTGTGGGTCTTTTGGGCTTTGCTGCTC
CATTTACACAATGTGGATATCCTGCCTTAATGCCTTTGTATGCATGTATACAAGCT
AAACAGGCTTTCACTTTCTCGCCAACTTACAAGGCCTTTCTAAGTAAACAGTACAT
GAACCTTTACCCCGTTGCTCGGCAACGGCCTGGTCTGTGCCAAGTGTTTGCTGAC
GCAACCCCCACTGGCTGGGGCTTGGCCATAGGCCATCAGCGCATGCGTGGAACC
TTTGTGGCTCCTCTGCCGATCCATACTGCGGAACTCCTAGCCGCTTGTTTTGCTC
GCAGCCGGTCTGGAGCAAAGCTCATAGGAACTGACAATTCTGTCGTCCTCTCGC
GGAAATATACATCGTTTCGATCTACGTATGATCTTTTTCCCTCTGCCAAAAATTATG
GGGACATCATGAAGCCCCTTGAGCATCTGACTTCTGGCTAATAAAGGAAATTTATT
TTCATTGCAATAGTGTGTTGGAATTTTTTGTGTCTCTCACTCGGAAGGAATTCTGC
ATTAATGAATCGGCCAACGCGCGGGGAGAGGCGGTTTGCGTATTGGGCGCTCTT
CCGCTTCCTCGCTCACTGACTCGCTGCGCTCGGTCGTTCGGCTGCGGCGAGCGG
TATCAGCTCACTCAAAGGCGGTAATACGGTTATCCACAGAATCAGGGGATAACGC
AGGAAAGAACATGTGAGCAAAAGGCCAGCAAAAGGCCAGGAACCGTAAAAAGGC
CGCGTTGCTGGCGTTTTTCCATAGGCTCCGCCCCCCTGACGAGCATCACAAAAAT
CGACGCTCAAGTCAGAGGTGGCGAAACCCGACAGGACTATAAAGATACCAGGCG
TTTCCCCCTGGAAGCTCCCTCGTGCGCTCTCCTGTTCCGACCCTGCCGCTTACCG
GATACCTGTCCGCCTTTCTCCCTTCGGGAAGCGTGGCGCTTTCTCATAGCTCACG
CTGTAGGTATCTCAGTTCGGTGTAGGTCGTTCGCTCCAAGCTGGGCTGTGTGCAC
GAACCCCCCGTTCAGCCCGACCGCTGCGCCTTATCCGGTAACTATCGTCTTGAGT
CCAACCCGGTAAGACACGACTTATCGCCACTGGCAGCAGCCACTGGTAACAGGA
TTAGCAGAGCGAGGTATGTAGGCGGTGCTACAGAGTTCTTGAAGTGGTGGCCTA
ACTACGGCTACACTAGAAGAACAGTATTTGGTATCTGCGCTCTGCTGAAGCCAGT
TACCTTCGGAAAAAGAGTTGGTAGCTCTTGATCCGGCAAACAAACCACCGCTGGT
AGCGGTGGTTTTTTTGTTTGCAAGCAGCAGATTACGCGCAGAAAAAAAGGATCTC
AAGAAGATCCTTTGATCTTTTCTACGGGGTCTGACGCTCAGTGGAACGAAAACTC
ACGTTAAGGGATTTTGGTCATGAGATTATCAAAAAGGATCTTCACCTAGATCCTTT
TAAATTAAAAATGAAGTTTTAAATCAATCTAAAGTATATATGAGTAAACTTGGTCTG
ACAGTTACCAATGCTTAATCAGTGAGGCACCTATCTCAGCGATCTGTCTATTTCGT
TCATCCATAGTTGCCTGACTC

SEQ ID NO: 32. NUCLEOTIDE SEQUENCE OF PLASMID 455
GGCGTAATGCTCTGCCAGTGTTACAACCAATTAACCAATTCTGATTAGAAAAACTC
ATCGAGCATCAAATGAAACTGCAATTTATTCATATCAGGATTATCAATACCATATTT
TTGAAAAAGCCGTTTCTGTAATGAAGGAGAAAACTCACCGAGGCAGTTCCATAGG
ATGGCAAGATCCTGGTATCGGTCTGCGATTCCGACTCGTCCAACATCAATACAAC
CTATTAATTTCCCCTCGTCAAAAATAAGGTTATCAAGTGAGAAATCACCATGAGTG
ACGACTGAATCCGGTGAGAATGGCAAAAGCTTATGCATTTCTTTCCAGACTTGTTC
```

RAW SEQUENCE LISTING

```
AACAGGCCAGCCATTACGCTCGTCATCAAAATCACTCGCATCAACCAAACCGTTA
TTCATTCGTGATTGCGCCTGAGCGAGACGAAATACGCGATCGCTGTTAAAAGGAC
AATTACAAACAGGAATCAAATGCAACCGGCGCAGGAACACTGCCAGCGCATCAAC
AATATTTTCACCTGAATCAGGATATTCTTCTAATACCTGGAATGCTGTTTTCCCGG
GGATCGCAGTGGTGAGTAACCATGCATCATCAGGAGTACGGATAAAATGCTTGAT
GGTCGGAAGAGGCATAAATTCCGTCAGCCAGTTTAGTCTGACCATCTCATCTGTA
ACATCATTGGCAACGCTACCTTTGCCATGTTTCAGAAACAACTCTGGCGCATCGG
GCTTCCCATACAATCGATAGATTGTCGCACCTGATTGCCCGACATTATCGCGAGC
CCATTTATACCCATATAAATCAGCATCCATGTTGGAATTTAATCGCGGCCTCGAGC
AAGACGTTTCCCGTTGAATATGGCTCATAACACCCCTTGTATTACTGTTTATGTAA
GCAGACAGGTCGACAATATTGGCTATTGGCCATTGCATACGTTGTATCTATATCAT
AATATGTACATTTATATTGGCTCATGTCCAATATGACCGCCATGTTGACATTGATTA
TTGACTAGTTATTAATAGTAATCAATTACGGGGTCATTAGTTCATAGCCCATATATG
GAGTTCCGCGTTACATAACTTACGGTAAATGGCCCGCCTGGCTGACCGCCCAAC
GACCCCCGCCCATTGACGTCAATAATGACGTATGTTCCCATAGTAACGCCAATAG
GGACTTTCCATTGACGTCAATGGGTGGAGTATTTACGGTAAACTGCCCACTTGGC
AGTACATCAAGTGTATCATATGCCAAGTCCGCCCCCTATTGACGTCAATGACGGT
AAATGGCCCGCCTGGCATTATGCCCAGTACATGACCTTACGGGACTTTCCTACTT
GGCAGTACATCTACGTATTAGTCATCGCTATTACCATGGTGATGCGGTTTTGGCA
GTACACCAATGGGCGTGGATAGCGGTTTGACTCACGGGGATTTCCAAGTCTCCAC
CCCATTGACGTCAATGGGAGTTTGTTTTGGCACCAAAATCAACGGGACTTTCCAA
AATGTCGTAATAACCCCGCCCCGTTGACGCAAATGGGCGGTAGGCGTGTACGGT
GGGAGGTCTATATAAGCAGAGCTCGTTTAGTGAACCGTCAGATCGCCTGGAGAC
GCCATCCACGCTGTTTTGACCTCCATAGAAGACACCGGGACCGATCCAGCCTCC
GCGGCCGGGAACGGTGCATTGGAACGCGGATTCCCCGTGCCAAGAGTGACTCA
CCGTCCGGATCTCAGCAAGCAGGTATGTACTCTCCAGGGTGGGCCTGGCTTCCC
CAGTCAAGACTCCAGGGATTTGAGGGACGCTGTGGGCTCTTCTCTTACATGTACC
TTTTGCTTGCCTCAACCCTGACTATCTTCCAGGTCAGGATCCCAGAGTCAGGGGT
CTGTATTTTCCTGCTGGTGGCTCCAGTTCAGGAACAGTAAACCCTGCTCCGAATA
TTGCCTCTCACATCTCGTCAATCTCCGCGAGGACTGGGGACCCTGTGACGAACAT
GGCTAGCAAGGCTGTGCTGCTTGCCCTGTTGATGGCAGGCTTGGCCCTGCAGCC
AGGCACTGCCCTGCTGTGCTACTCCTGCAAAGCCCAGGTGAGCAACGAGGACTG
CCTGCAGGTGGAGAACTGCACCCAGCTGGGGGAGCAGTGCTGGACCGCGCGCA
TCCGCGCAGTTGGCCTCCTGACCGTCATCAGCAAAGGCTGCAGCTTGAACTGCG
TGGATGACTCACAGGACTACTACGTGGGCAAGAAGAACATCACGTGCTGTGACAC
CGACTTGTGCAACGCCAGCGGGCCCATGCCCTGCAGCCGGCTGCCGCCATCC
TTGCGCTGCTCCCTGCACTCGGCCTGCTGCTCTGGGGACCCGGCCAGCTATAGA
GATCTGACCCCTAACGTTACTGGCCGAAGCCGCTTGGAATAAGGCCGGTGTGC
GTTTGTCTATATGTTATTTTCCACCATATTGCCGTCTTTTGGCAATGTGAGGGCCC
GGAAACCTGGCCCTGTCTTCTTGACGAGCATTCCTAGGGGTCTTTCCCCTCTCGC
CAAAGGAATGCAAGGTCTGTTGAATGTCGTGAAGGAAGCAGTTCCTCTGGAAGCT
TCTTGAAGACAAACAACGTCTGTAGCGACCCTTTGCAGGCAGCGGAACCCCCCA
CCTGGCGACAGGTGCCTCTGCGGCCAAAAGCCACGTGTATAAGATACACCTGCA
AAGGCGGCACAACCCCAGTGCCACGTTGTGAGTTGGATAGTTGTGGAAAGAGTC
AAATGGCTCTCCTCAAGCGTATTCAACAAGGGGCTGAAGGATGCCCAGAAGGTAC
CCCATTGTATGGGATCTGATCTGGGGCCTCGGTGCACATGCTTTACATGTGTTTA
GTCGAGGTTAAAAAACGTCTAGGCCCCCCGAACCACGGGGACGTGGTTTTCCTTT
GAAAAACACGATGATAATATGGCCAGCATTGTGGGAGGCTGGGAGTGCGAGAAG
CATTCCCAACCCTGGCAGGTGCTTGTGGCCTCTCGTGGCAGGGCAGTCTGCGGC
GGTGTTCTGGTGCACCCCCAGTGGGTCCTCACAGCTGCCCACTGCATCAGGAAC
AAAAGCGTGATCTTGCTGGGTCGGCACAGCTTGTTTCATCCTGAAGACACAGGCC
AGGTATTTCAGGTCAGCCACAGCTTCCCACACCCGCTCTACGATATGAGCCTCCT
GAAGAATCGATTCCTCAGGCCAGGTGATGACTCCAGCCACGACCTCATGCTGCTC
CGCCTGTCAGAGCCTGCCGAGCTCACGGATGCTGTGAAGGTCATGGACCTGCCC
ACCCAGGAGCCAGCACTGGGGACCACCTGCTACGCCTCAGGCTGGGGCAGCAT
TGAACCAGAGGAGTTCTTGACCCCAAAGAAACTTCAGTGTGTGGACCTCCATGTT
ATTTCCAATGACGTGTGTCGCAAGTTCACCCTCAGAAGGTGACCAAGTTCATGC
TGTGTGCTGGACGCTGGACAGGGGGCAAAAGCACCTGCTCGGGTGATTCTGGG
GGCCCACTTGTCTGTAATGGTGTGCTTCAAGGTATCACGTCATGGGGCAGTGAAC
CATGTGCCCTGCCCGAAAGGCCTTCCCTGTACACCAAGGTGGTGCATTACCGGA
AGTGGATCAAGGACACCATCGTGGCCAACCCCTGAGGATCTGGGCCCTAACAAA
ACAAAAAGATGGGGTTATTCCCTAAACTTCATGGGTTACGTAATTGGAAGTTGGG
GGACATTGCCACAAGATCATATTGTACAAAAGATCAAACACTGTTTTAGAAAACTT
CCTGTAAACAGGCCTATTGATTGGAAAGTATGTCAAAGGATTGTGGGTCTTTTGG
GCTTTGCTGCTCCATTTACACAATGTGGATATCCTGCCTTAATGCCTTTGTATGCA
TGTATACAAGCTAAACAGGCTTTCACTTTCTCGCCAACTTACAAGGCCTTTCTAAG
TAAACAGTACATGAACCTTTACCCCGTTGCTCGGCAACGGCCTGGTCTGTGCCAA
GTGTTTGCTGACGCAACCCCCACTGGCTGGGGCTTGGCCATAGGCCATCAGCGC
ATGCGTGGAACCTTTGTGGCTCCTCTGCCGATCCATACTGCGGAACTCCTAGCCG
CTTGTTTTGCTCGCAGCCGGTCTGGAGCAAAGCTCATAGGAACTGACAATTCTGT
CGTCCTCTCGCGGAAATATACATCGTTTCGATCTACGTATGATCTTTTTCCCTCTG
CCAAAAATTATGGGGACATCATGAAGCCCCTTGAGCATCTGACTTCTGGCTAATAA
AGGAAATTTATTTTCATTGCAATAGTGTGTTGGAATTTTTTGTGTCTCTCACTCGGA
AGGAATTCTGCATTAATGAATCGGCCAACGCGCGGGGAGAGGCGGTTTGCGTAT
TGGGCGCTCTTCCGCTTCCTCGCTCACTGACTCGCTGCGCTCGGTCGTTCGGCT
GCGGCGAGCGGTATCAGCTCACTCAAAGGCGGTAATACGGTTATCCACAGAATC
AGGGGATAACGCAGGAAAGAACATGTGAGCAAAAGGCCAGCAAAAGGCCAGGAA
```

| RAW SEQUENCE LISTING |
|---|
| CCGTAAAAAGGCCGCGTTGCTGGCGTTTTTCCATAGGCTCCGCCCCCCTGACGA |
| GCATCACAAAAATCGACGCTCAAGTCAGAGGTGGCGAAACCCGACAGGACTATAA |
| AGATACCAGGCGTTTCCCCCTGGAAGCTCCCTCGTGCGCTCTCCTGTTCCGACC |
| CTGCCGCTTACCGGATACCTGTCCGCCTTTCTCCCTTCGGGAAGCGTGGCGCTTT |
| CTCATAGCTCACGCTGTAGGTATCTCAGTTCGGTGTAGGTCGTTCGCTCCAAGCT |
| GGGCTGTGTGCACGAACCCCCCGTTCAGCCCGACCGCTGCGCCTTATCCGGTAA |
| CTATCGTCTTGAGTCCAACCCGGTAAGACACGACTTATCGCCACTGGCAGCAGCC |
| ACTGGTAACAGGATTAGCAGAGCGAGGTATGTAGGCGGTGCTACAGAGTTCTTGA |
| AGTGGTGGCCTAACTACGGCTACACTAGAAGAACAGTATTTGGTATCTGCGCTCT |
| GCTGAAGCCAGTTACCTTCGGAAAAAGAGTTGGTAGCTCTTGATCCGGCAAACAA |
| ACCACCGCTGGTAGCGGTGGTTTTTTTGTTTGCAAGCAGCAGATTACGCGCAGAA |
| AAAAAGGATCTCAAGAAGATCCTTTGATCTTTTCTACGGGGTCTGACGCTCAGTG |
| GAACGAAAACTCACGTTAAGGGATTTTGGTCATGAGATTATCAAAAAGGATCTTCA |
| CCTAGATCCTTTTAAATTAAAAATGAAGTTTTAAATCAATCTAAAGTATATATGAGTA |
| AACTTGGTCTGACAGTTACCAATGCTTAATCAGTGAGGCACCTATCTCAGCGATCT |
| GTCTATTTCGTTCATCCATAGTTGCCTGACTC |
| |
| SEQ ID NO: 33. NUCLEOTIDE SEQUENCE OF PLASMID 456 |
| GGCGTAATGCTCTGCCAGTGTTACAACCAATTAACCAATTCTGATTAGAAAAACTC |
| ATCGAGCATCAAATGAAACTGCAATTTATTCATATCAGGATTATCAATACCATATTT |
| TTGAAAAAGCCGTTTCTGTAATGAAGGAGAAAACTCACCGAGGCAGTTCCATAGG |
| ATGGCAAGATCCTGGTATCGGTCTGCGATTCCGACTCGTCCAACATCAATACAAC |
| CTATTAATTTCCCCTCGTCAAAAATAAGGTTATCAAGTGAGAAATCACCATGAGTG |
| ACGACTGAATCCGGTGAGAATGGCAAAAGCTTATGCATTTCTTTCCAGACTTGTTC |
| AACAGGCCAGCCATTACGCTCGTCATCAAAATCACTCGCATCAACCAAACCGTTA |
| TTCATTCGTGATTGCGCCTGAGCGAGACGAAATACGCGATCGCTGTTAAAGGAC |
| AATTACAAACAGGAATCAAATGCAACCGGCGCAGGAACACTGCCAGCGCATCAAC |
| AATATTTTCACCTGAATCAGGATATTCTTCTAATACCTGGAATGCTGTTTTCCCGG |
| GGATCGCAGTGGTGAGTAACCATGCATCATCAGGAGTACGGATAAAATGCTTGAT |
| GGTCGGAAGAGGCATAAATTCCGTCAGCCAGTTTAGTCTGACCATCTCATCTGTA |
| ACATCATTGGCAACGCTACCTTTGCCATGTTTCAGAAACAACTCTGGCGCATCGG |
| GCTTCCCATACAATCGATAGATTGTCGCACCTGATTGCCCGACATTATCGCGAGC |
| CCATTTATACCCCATATAAATCAGCATCCATGTTGGAATTTAATCGCGGCCTCGAGC |
| AAGACGTTTCCCGTTGAATATGGCTCATAACACCCCTTGTATTACTGTTTATGTAA |
| GCAGACAGGTCGACAATATTGGCTATTGGCCATTGCATACGTTGTATCTATATCAT |
| AATATGTACATTTATATTGGCTCATGTCCAATATGACCGCCATGTTGACATTGATTA |
| TTGACTAGTTATTAATAGTAATCAATTACGGGGTCATTAGTTCATAGCCCATATATG |
| GAGTTCCGCGTTACATAACTTACGGTAAATGGCCCGCCTGGCTGACCGCCCAAC |
| GACCCCCGCCCATTGACGTCAATAATGACGTATGTTCCCATAGTAACGCCAATAG |
| GGACTTTCCATTGACGTCAATGGGTGGAGTATTTACGGTAAACTGCCCACTTGGC |
| AGTACATCAAGTGTATCATATGCCAAGTCCGCCCCCTATTGACGTCAATGACGGT |
| AAATGGCCCGCCTGGCATTATGCCCAGTACATGACCTTACGGGACTTTCCTACTT |
| GGCAGTACATCTACGTATTAGTCATCGCTATTACCATGGTGATGCGGTTTTGGCA |
| GTACACCAATGGGCGTGGATAGCGGTTTGACTCACGGGGATTTCCAAGTCTCCAC |
| CCCATTGACGTCAATGGGAGTTTGTTTTGGCACCAAAATCAACGGGACTTTCCAA |
| AATGTCGTAATAACCCCGCCCCGTTGACGCAAATGGGCGGTAGGCGTGTACGGT |
| GGGAGGTCTATATAAGCAGAGCTCGTTTAGTGAACCGTCAGATCGCCTGGAGAC |
| GCCATCCACGCTGTTTTGACCTCCATAGAAGACACCGGGACCGATCCAGCCTCC |
| GCGGCCGGGAACGGTGCATTGGAACGCGGATTCCCCGTGCCAAGAGTGACTCA |
| CCGTCCGGATCTCAGCAAGCAGGTATGTACTCTCCAGGGTGGGCCTGGCTTCCC |
| CAGTCAAGACTCCAGGGATTTGAGGGACGCTGTGGGCTCTTCTCTTACATGTACC |
| TTTTGCTTGCCTCAACCCTGACTATCTTCCAGGTCAGGATCCCAGAGTCAGGGGT |
| CTGTATTTTCCTGCTGGTGGCTCCAGTTCAGGAACAGTAAACCCTGCTCCGAATA |
| TTGCCTCTCACATCTCGTCAATCTCCGCGAGGACTGGGGACCCTGTGACGAACAT |
| GGCTAGCATTGTGGGAGGCTGGGAGTGCGAGAAGCATTCCCAACCCTGGCAGGT |
| GCTTGTGGCCTCTCGTGGCAGGGCAGTCTGCGGCGGTGTTCTGGTGCACCCCCA |
| GTGGGTCCTCACAGCTGCCCACTGCATCAGGAACAAAAGCGTGATCTTGCTGGG |
| TCGGCACAGCTTGTTTCATCCTGAAGACACAGGCCAGGTATTTCAGGTCAGCCAC |
| AGCTTCCCACACCCGCTCTACGATATGAGCCTCCTGAAGAATCGATTCCTCAGGC |
| CAGGTGATGACTCCAGCCACGACCTCATGCTGCTCCGCCTGTCAGAGCCTGCCG |
| AGCTCACGGATGCTGTGAAGGTCATGGACCTGCCCACCCAGGAGCCAGCACTGG |
| GGACCACCTGCTACGCCTCAGGCTGGGGCAGCATTGAACCAGAGGAGTTCTTGA |
| CCCCAAAGAAACTTCAGTGTGTGGACCTCCATGTTATTTCCAATGACGTGTGTGC |
| GCAAGTTCACCCTCAGAAGGTGACCAAGTTCATGCTGTGTGCTGGACGCTGGAC |
| AGGGGGCAAAAGCACCTGCTCGGGTGATTCTGGGGGCCCACTTGTCTGTAATGG |
| TGTGCTTCAAGGTATCACGTCATGGGGCAGTGAACCATGTGCCTGCCCCGAAAG |
| GCCTTCCCTGTACACCAAGGTGGTGCATTACCGGAAGTGGATCAAGGACACCATC |
| GTGGCCAACCCCGGATCCCAGACCCTGAACTTTGATCTGCTGAAACTGGCAGGC |
| GATGTGGAAAGCAACCCAGGCCCAATGGCAAGCGCGCCGCCCGCGCTGGCT |
| GTGCGCTGGGGCGCTGGTGCTGGCGGGTGGCTTCTTTCTCCTCGGCTTCCTCTT |
| CGGGTGGTTTATAAAATCCTCCAAATGAAGCTACTAACATTACTCCAAAGCATAATA |
| TGAAAGCATTTTTGGATGAATTGAAAGCTGAGAACATCAAGAAGTTCTTATATAATT |
| TTACACAGATACCACATTTAGCAGGAACAGAACAAAACTTTCAGCTTGCAAAGCAA |
| ATTCAATCCAGTGGAAAGAATTTGGCCTGGATTCTGTTGAGCTGGCACATTATGA |
| TGTCCTGTTGTCCTACCCAAATAAGACTCATCCCAACTACATCTCAATAATTAATGA |
| AGATGGAAATGAGATTTTCAACACATCATTATTTGAACCACCTCCTCCAGGATATG |
| AAAATGTTTCGGATATTGTACCACCTTTCAGTGCTTTCTCTCCTCAAGGAATGCCA |

-continued

```
RAW SEQUENCE LISTING

GAGGGCGATCTAGTGTATGTTAACTATGCACGAACTGAAGACTTCTTTAAATTGGA
ACGGGACATGAAAATCAATTGCTCTGGGAAAATTGTAATTGCCAGATATGGGAAA
GTTTTCAGAGGAAATAAGGTTAAAAATGCCCAGCTGGCAGGGGCCAAAGGAGTCA
TTCTCTACTCCGACCCTGCTGACTACTTTGCTCCTGGGGTGAAGTCCTATCCAGA
TGGTTGGAATCTTCCTGGAGGTGGTGTCCAGCGTGGAAATATCCTAAATCTGAAT
GGTGCAGGAGACCCTCTCACACCAGGTTACCCAGCAAATGAATATGCTTATAGGC
GTGGAATTGCAGAGGCTGTTGGTCTTCCAAGTATTCCTGTTCATCCAATTGGATAC
TATGATGCACAGAAGCTCCTAGAAAAAATGGGTGGCTCAGCACCACCAGATAGCA
GCTGGAGAGGAAGTCTCAAAGTGCCCTACAATGTTGGACCTGGCTTTACTGGAAA
CTTTTCTACACAAAAAGTCAAGATGCACATCCACTCTACCAATGAAGTGACAAGAA
TTTACAATGTGATAGGTACTCTCAGAGGAGCAGTGGAACCAGACAGATATGTCAT
TCTGGGAGGTCACCGGGACTCATGGGTGTTTGGTGGTATTGACCCTCAGAGTGG
AGCAGCTGTTGTTCATGAAATTGTGAGGAGCTTTGGAACACTGAAAAAGGAAGGG
TGGAGACCTAGAAGAACAATTTTGTTTGCAAGCTGGGATGCAGAAGAATTTGGTC
TTCTTGGTTCTACTGAGTGGGCAGAGGAGAATTCAAGACTCCTTCAAGAGCGTGG
CGTGGCTTATATTAATGCTGACTCATCTATAGAAGGAAACTACACTCTGAGAGTTG
ATTGTACACCGCTGATGTACAGCTTGGTACACAACCTAACAAAAGAGCTGAAAAG
CCCTGATGAAGGCTTTGAAGGCAAATCTCTTTATGAAAGTTGGACTAAAAAAAGTC
CTTCCCCAGAGTTCAGTGGCATGCCCAGGATAAGCAAATTGGGATCTGGAAATGA
TTTTGAGGTGTTCTTCCAACGACTTGGAATTGCTTCAGGCAGAGCACGGTATACTA
AAAATTGGGAAACAAACAAATTCAGCGGCTATCCACTGTATCACAGTGTCTATGAA
ACATATGAGTTGGTGGAAAAGTTTTATGATCCAATGTTTAAATATCACCTCACTGT
GGCCCAGGTTCGAGGAGGGATGGTGTTTGAGCTGGCCAATTCCATAGTGCTCCC
TTTTGATTGTCGAGATTATGCTGTAGTTTTAAGAAAGTATGCTGACAAAATCTACAG
TATTTCTATGAAACATCCACAGGAAATGAAGACATACAGTGTATCATTTGATTCACT
TTTTTCTGCAGTAAAGAATTTTACAGAAATTGCTTCCAAGTTCAGTGAGAGACTCC
AGGACTTTGACAAAAGCAACCCAATAGTATTAAGAATGATGAATGATCAACTCATG
TTTCTGGAAAGAGCATTTATTGATCCATTAGGGTTACCAGACAGGCCTTTTTATAG
GCATGTCATCTATGCTCCAAGCAGCCACAACAAGTATGCAGGGGAGTCATTCCCA
GGAATTTATGATGCTCTGTTTGATATTGAAAGCAAAGTGGACCCTTCCAAGGCCTG
GGGAGAAGTGAAGAGACAGATTTATGTTGCAGCCTTCACAGTGCAGGCAGCTGC
AGAGACTTTGAGTGAAGTAGCCTAAAGATCTGACCCCCTAACGTTACTGGCCGAA
GCCGCTTGGAATAAGGCCGGTGTGCGTTTGTCTATATGTTATTTTCCACCATATTG
CCGTCTTTTGGCAATGTGAGGGCCCGGAAACCTGGCCCTGTCTTCTTGACGAGC
ATTCCTAGGGGTCTTTCCCCTCTCGCCAAAGGAATGCAAGGTCTGTTGAATGTCG
TGAAGGAAGCAGTTCCTCTGGAAGCTTCTTGAAGACAAACAACGTCTGTAGCGAC
CCTTTGCAGGCAGCGGAACCCCCCACCTGGCGACAGGTGCCTCTGCGGCCAAAA
GCCACGTGTATAAGATACACCTGCAAAGGCGGCACAACCCCAGTGCCACGTTGT
GAGTTGGATAGTTGTGGAAAGAGTCAAATGGCTCTCCTCAAGCGTATTCAACAAG
GGGCTGAAGGATGCCCAGAAGGTACCCCATTGTATGGGATCTGATCTGGGGCCT
CGGTGCACATGCTTTACATGTGTTTAGTCGAGGTTAAAAAACGTCTAGGCCCCCC
GAACCACGGGGACGTGGTTTTCCTTTGAAAAACACGATGATAATATGGCCAGCAA
GGCTGTGCTGCTTGCCCTGTTGATGGCAGGCTTGGCCCTGCAGCCAGGCACTGC
CCTGCTGTGCTACTCCTGCAAAGCCCAGGTGAGCAACGAGGACTGCCTGCAGGT
GGAGAACTGCACCCAGCTGGGGGAGCAGTGCTGGACCGCGCGCATCCGCGCAG
TTGGCCTCCTGACCGTCATCAGCAAAGGCTGCAGCTTGAACTGCGTGGATGACTC
ACAGGACTACTACGTGGGCAAGAAGAACATCACGTGCTGTGACACCGACTTGTG
CAACGCCAGCGGGGCCCATGCCCTGCAGCCGGCTGCCGCCATCCTTGCGCTGC
TCCCTGCACTCGGCCTGCTGCTCTGGGGACCCGGCCAGCTATAGGGATCTGGGC
CCTAACAAAACAAAAAGATGGGGTTATTCCCTAAACTTCATGGGTTACGTAATTGG
AAGTTGGGGGACATTGCCACAAGATCATATTGTACAAAAGATCAAACACTGTTTTA
GAAAACTTCCTGTAAACAGGCCTATTGATTGGAAAGTATGTCAAAGGATTGTGGGT
CTTTTGGGCTTTGCTGCTCCATTTACACAATGTGGATATCCTGCCTTAATGCCTTT
GTATGCATGTATACAAGCTAAACAGGCTTTCACTTTCTCGCCAACTTACAAGGCCT
TTCTAAGTAAACAGTACATGAACCTTTACCCCGTTGCTCGGCAACGGCCTGGTCT
GTGCCAAGTGTTTGCTGACGCAACCCCCACTGGCTGGGGCTTGGCCATAGGCCA
TCAGCGCATGCGTGGAACCTTTGTGGCTCCTCTGCCGATCCATACTGCGGAACTC
CTAGCCGCTTGTTTTGCTCGCAGCCGGTCTGGAGCAAAGCTCATAGGAACTGACA
ATTCTGTCGTCCTCTCGCGGAAATATACATCGTTTCGATCTACGTATGATCTTTTTC
CCTCTGCCAAAAATTATGGGGACATCATGAAGCCCCTTGAGCATCTGACTTCTGG
CTAATAAAGGAAATTTATTTTCATTGCAATAGTGTGTTGGAATTTTTTGTGTCTCTC
ACTCGGAAGGAATTCTGCATTAATGAATCGGCCAACGCGCGGGGAGAGGCGGTT
TGCGTATTGGGCGCTCTTCCGCTTCCTCGCTCACTGACTCGCTGCGCTCGGTCGT
TCGGCTGCGGCGAGCGGTATCAGCTCACTCAAAGGCGGTAATACGGTTATCCAC
AGAATCAGGGGATAACGCAGGAAAGAACATGTGAGCAAAAGGCCAGCAAAAGGC
CAGGAACCGTAAAAAGGCCGCGTTGCTGGCGTTTTTCCATAGGCTCCGCCCCCC
TGACGAGCATCACAAAAATCGACGCTCAAGTCAGAGGTGGCGAAACCCGACAGG
ACTATAAAGATACCAGGCGTTTCCCCCTGGAAGCTCCCTCGTGCGCTCTCCTGTT
CCGACCCTGCCGCTTACCGGATACCTGTCCGCCTTTCTCCCTTCGGGAAGCGTG
GCGCTTTCTCATAGCTCACGCTGTAGGTATCTCAGTTCGGTGTAGGTCGTTCGCT
CCAAGCTGGGCTGTGTGCACGAACCCCCCGTTCAGCCCGACCGCTGCGCCTTAT
CCGGTAACTATCGTCTTGAGTCCAACCCGGTAAGACACGACTTATCGCCACTGGC
AGCAGCCACTGGTAACAGGATTAGCAGAGCGAGGTATGTAGGCGGTGCTACAGA
GTTCTTGAAGTGGTGGCCTAACTACGGCTACACTAGAAGAACAGTATTTGGTATCT
GCGCTCTGCTGAAGCCAGTTACCTTCGGAAAAAGAGTTGGTAGCTCTTGATCCGG
CAAACAAACCACCGCTGGTAGCGGTGGTTTTTTTGTTTGCAAGCAGCAGATTACG
CGCAGAAAAAAAGGATCTCAAGAAGATCCTTTGATCTTTTCTACGGGGTCTGACG
```

| RAW SEQUENCE LISTING |
| --- |
| CTCAGTGGAACGAAAACTCACGTTAAGGGATTTTGGTCATGAGATTATCAAAAAG |
| GATCTTCACCTAGATCCTTTTAAATTAAAAATGAAGTTTTAAATCAATCTAAAGTATA |
| TATGAGTAAACTTGGTCTGACAGTTACCAATGCTTAATCAGTGAGGCACCTATCTC |
| AGCGATCTGTCTATTTCGTTCATCCATAGTTGCCTGACTC |
| |
| SEQ ID NO: 34. NUCLEOTIDE SEQUENCE OF PLASMID 457 |
| GGCGTAATGCTCTGCCAGTGTTACAACCAATTAACCAATTCTGATTAGAAAAACTC |
| ATCGAGCATCAAATGAAACTGCAATTTATTCATATCAGGATTATCAATACCATATTT |
| TTGAAAAAGCCGTTTCTGTAATGAAGGAGAAAACTCACCGAGGCAGTTCCATAGG |
| ATGGCAAGATCCTGGTATCGGTCTGCGATTCCGACTCGTCCAACATCAATACAAC |
| CTATTAATTTCCCCTCGTCAAAAATAAGGTTATCAAGTGAGAAATCACCATGAGTG |
| ACGACTGAATCCGGTGAGAATGGCAAAAGCTTATGCATTTCTTTCCAGACTTGTTC |
| AACAGGCCAGCCATTACGCTCGTCATCAAAATCACTCGCATCAACCAAACCGTTA |
| TTCATTCGTGATTGCGCCTGAGCGAGACGAAATACGCGATCGCTGTTAAAAGGAC |
| AATTACAAACAGGAATCAAATGCAACCGGCGCAGGAACACTGCCAGCGCATCAAC |
| AATATTTTCACCTGAATCAGGATATTCTTCTAATACCTGGAATGCTGTTTTCCCGG |
| GGATCGCAGTGGTGAGTAACCATGCATCATCAGGAGTACGGATAAAATGCTTGAT |
| GGTCGGAAGAGGCATAAATTCCGTCAGCCAGTTTAGTCTGACCATCTCATCTGTA |
| ACATCATTGGCAACGCTACCTTTGCCATGTTTCAGAAACAACTCTGGCGCATCGG |
| GCTTCCCATACAATCGATAGATTGTCGCACCTGATTGCCCGACATTATCGCGAGC |
| CCATTTATACCCATATAAATCAGCATCCATGTTGGAATTTAATCGCGGCCTCGAGC |
| AAGACGTTTCCCGTTGAATATGGCTCATAACACCCCTTGTATTACTGTTTATGTAA |
| GCAGACAGGTCGACAATATTGGCTATTGGCCATTGCATACGTTGTATCTATATCAT |
| AATATGTACATTTATATTGGCTCATGTCCAATATGACCGCCATGTTGACATTGATTA |
| TTGACTAGTTATTAATAGTAATCAATTACGGGGTCATTAGTTCATAGCCCATATATG |
| GAGTTCCGCGTTACATAACTTACGGTAAATGGCCCGCCTGGCTGACCGCCCAAC |
| GACCCCCGCCCATTGACGTCAATAATGACGTATGTTCCCATAGTAACGCCAATAG |
| GGACTTTCCATTGACGTCAATGGGTGGAGTATTTACGGTAAACTGCCCACTTGGC |
| AGTACATCAAGTGTATCATATGCCAAGTCCGCCCCCTATTGACGTCAATGACGGT |
| AAATGGCCCGCCTGGCATTATGCCCAGTACATGACCTTACGGGACTTTCCTACTT |
| GGCAGTACATCTACGTATTAGTCATCGCTATTACCATGGTGATGCGGTTTTGGCA |
| GTACACCAATGGGCGTGGATAGCGGTTTGACTCACGGGGATTTCCAAGTCTCCAC |
| CCCATTGACGTCAATGGGAGTTTGTTTTGGCACCAAAATCAACGGGACTTTCCAA |
| AATGTCGTAATAACCCCGCCCCGTTGACGCAAATGGGCGGTAGGCGTGTACGGT |
| GGGAGGTCTATATAAGCAGAGCTCGTTTAGTGAACCGTCAGATCGCCTGGAGAC |
| GCCATCCACGCTGTTTTGACCTCCATAGAAGACACCGGGACCGATCCAGCCTCC |
| GCGGCCGGGAACGGTGCATTGGAACGCGGATTCCCCGTGCCAAGAGTGACTCA |
| CCGTCCGGATCTCAGCAAGCAGGTATGTACTCTCCAGGGTGGGCCTGGCTTCCC |
| CAGTCAAGACTCCAGGGATTTGAGGGACGCTGTGGGCTCTTCTCTTACATGTACC |
| TTTTGCTTGCCTCAACCCTGACTATCTTCCAGGTCAGGATCCCAGAGTCAGGGGT |
| CTGTATTTTCCTGCTGGTGGCTCCAGTTCAGGAACAGTAAACCCTGCTCCGAATA |
| TTGCCTCTCACATCTCGTCAATCTCCGCGAGGACTGGGGACCCTGTGACGAACAT |
| GGCTAGCATTGTGGGAGGCTGGGAGTGCGAGAAGCATTCCCAACCCTGGCAGGT |
| GCTTGTGGCCTCTCGTGGCAGGGCAGTCTGCGGCGGTGTTCTGGTGCACCCCA |
| GTGGGTCCTCACAGCTGCCCACTGCATCAGGAACAAAAGCGTGATCTTGCTGGG |
| TCGGCACAGCTTGTTTCATCCTGAAGACACAGGCCAGGTATTTCAGGTCAGCCAC |
| AGCTTCCCACACCCGCTCTACGATATGAGCCTCCTGAAGAATCGATTCCTCAGGC |
| CAGGTGATGACTCCAGCCACGACCTCATGCTGCTCCGCCTGTCAGAGCCTGCCG |
| AGCTCACGGATGCTGTGAAGGTCATGGACCTGCCCACCCAGGAGCCAGCACTGG |
| GGACCACCTGCTACGCCTCAGGCTGGGGCAGCATTGAACCAGAGGAGTTCTTGA |
| CCCCAAAGAAACTTCAGTGTGTGGACCTCCATGTTATTTCCAATGACGTGTGTGC |
| GCAAGTTCACCCTCAGAAGGTGACCAAGTTCATGCTGTGTGCTGGACGCTGGAC |
| AGGGGGCAAAAGCACCTGCTCGGGTGATTCTGGGGGCCCACTTGTCTGTAATGG |
| TGTGCTTCAAGGTATCACGTCATGGGCAGTGAACCATGTGCCCTGCCCGAAAG |
| GCCTTCCCTGTACACCAAGGTGGTGCATTACCGGAAGTGGATCAAGGACACCATC |
| GTGGCCAACCCCGGATCCCAGACCCTGAACTTTGATCTGCTGAAACTGGCAGGC |
| GATGTGGAAAGCAACCCAGGCCCAATGGCAAGCGCGCGCCGCCCGGCTGGCT |
| GTGCGCTGGGGCGCTGGTGCTGGCGGGTGGCTTCTTTCTCCTCGGCTTCCTCTT |
| CGGGTGGTTTATAAAATCCTCAATGAAGCTACTAACATTACTCCAAAGCATAATA |
| TGAAAGCATTTTTGGATGAATTGAAAGCTGAGAACATCAAGAAGTTCTTATATAATT |
| TTACACAGATACCACATTTAGCAGGAACAGAACAAAACTTTCAGCTTGCAAAGCAA |
| ATTCAATCCCAGTGGAAAGAATTTGGCCTGGATTCTGTTGAGCTGGCACATTATGA |
| TGTCCTGTTGTCCTACCCAAATAAGACTCATCCCAACTACATCTCAATAATTAATGA |
| AGATGGAAATGAGATTTTCAACACATCATTATTTGAACCACCTCCTCCAGGATATG |
| AAAATGTTTCGGATATTGTACCACCTTTCAGTGCTTTCTCTCCTCAAGGAATGCCA |
| GAGGGCGATCTAGTGTATGTTAACTATGCACGAACTGAAGACTTCTTTAAATTGGA |
| ACGGGACATGAAAATCAATTGCTCTGGGAAAATTGTAATTGCCAGATATGGGAAA |
| GTTTTCAGAGGAAATAAGGTTAAAAATGCCCAGCTGGCAGGGGCAAAGGAGTCA |
| TTCTCTACTCCGACCCTGCTGACTACTTTGCTCCTGGGGTGAAGTCCTATCCAGA |
| TGGTTGGAATCTTCCTGGAGGTGGTGTCCAGCGTGGAAATATCCTAAATCTGAAT |
| GGTGCAGGAGACCCTCTCACACCAGGTTACCCAGCAAATGAATATGCTTATAGGC |
| GTGGAATTGCAGAGGCTGTTGGTCTTCCAAGTATTCCTGTTCATCCAATTGGATAC |
| TATGATGCACAGAAGCTCCTAGAAAAAATGGGTGGCTCAGCACCACCAGATAGCA |
| GCTGGAGAGGAAGTCTCAAAGTGCCCTACAATGTTGGACCTGGCTTTACTGGAAA |
| CTTTTCTACACAAAAAGTCAAGATGCACATCCACTCTACCAATGAAGTGACAAGAA |
| TTTACAATGTGATAGGTACTCTCAGAGGAGCAGTGGAACCAGACAGATATGTCAT |
| TCTGGGAGGTCACCGGGACTCATGGGTGTTTGGTGGTATTGACCCTCAGAGTGG |

-continued

RAW SEQUENCE LISTING

```
AGCAGCTGTTGTTCATGAAATTGTGAGGAGCTTTGGAACACTGAAAAAGGAAGGG
TGGAGACCTAGAAGAACAATTTTGTTTGCAAGCTGGGATGCAGAAGAATTTGGTC
TTCTTGGTTCTACTGAGTGGGCAGAGGAGAATTCAAGACTCCTTCAAGAGCGTGG
CGTGGCTTATATTAATGCTGACTCATCTATAGAAGGAAACTACACTCTGAGAGTTG
ATTGTACACCGCTGATGTACAGCTTGGTACACAACCTAACAAAAGAGCTGAAAAG
CCCTGATGAAGGCTTTGAAGGCAAATCTCTTTATGAAAGTTGGACTAAAAAAAGTC
CTTCCCCAGAGTTCAGTGGCATGCCCAGGATAAGCAAATTGGGATCTGGAAATGA
TTTTGAGGTGTTCTTCCAACGACTTGGAATTGCTTCAGGCAGAGCACGGTATACTA
AAAATTGGGAAACAAACAAATTCAGCGGCTATCCACTGTATCACAGTGTCTATGAA
ACATATGAGTTGGTGGAAAAGTTTTATGATCCAATGTTTAAATATCACCTCACTGT
GGCCCAGGTTCGAGGAGGGATGGTGTTTGAGCTGGCCAATTCCATAGTGCTCCC
TTTTGATTGTCGAGATTATGCTGTAGTTTTAAGAAAGTATGCTGACAAAATCTACAG
TATTTCTATGAAACATCCACAGGAAATGAAGACATACAGTGTATCATTTGATTCACT
TTTTTCTGCAGTAAAGAATTTTACAGAAATTGCTTCCAAGTTCAGTGAGAGACTCC
AGGACTTTGACAAAAGCAACCCAATAGTATTAAGAATGATGAATGATCAACTCATG
TTTCTGGAAAGAGCATTTATTGATCCATTAGGGTTACCAGACAGGCCTTTTTATAG
GCATGTCATCTATGCTCCAAGCAGCCACAACAAGTATGCAGGGGAGTCATTCCCA
GGAATTTATGATGCTCTGTTTGATATTGAAAGCAAAGTGGACCCTTCCAAGGCCTG
GGGAGAAGTGAAGAGACAGATTTATGTTGCAGCCTTCACAGTGCAGGCAGCTGC
AGAGACTTTGAGTGAAGTAGCCGGATCCGAAGGTAGGGGTTCATTATTGACCTGT
GGGAGATGTCGAAGAAAACCCAGGACCCGCAAGCAAGGCTGTGCTGCTTGCCCTG
TTGATGGCAGGCTTGGCCCTGCAGCCAGGCACTGCCCTGCTGTGCTACTCCTGC
AAAGCCCAGGTGAGCAACGAGGACTGCCTGCAGGTGGAGAACTGCACCCAGCTG
GGGGAGCAGTGCTGGACCGCGCGCATCCGCGCAGTTGGCCTCCTGACCGTCAT
CAGCAAAGGCTGCAGCTTGAACTGCGTGGATGACTCACAGGACTACTACGTGGG
CAAGAAGAACATCACGTGCTGTGACACCGACTTGTGCAACGCCAGCGGGGCCCA
TGCCCTGCAGCCGGCTGCCGCCATCCTTGCGCTGCTCCCTGCACTCGGCCTGCT
GCTCTGGGGACCCGGCCAGCTATAGAGATCTGGGCCCTAACAAAACAAAAAGAT
GGGGTTATTCCCTAAACTTCATGGGTTACGTAATTGGAAGTTGGGGGACATTGCC
ACAAGATCATATTGTACAAAAGATCAAACACTGTTTTAGAAAACTTCCTGTAAACAG
GCCTATTGATTGGAAAGTATGTCAAAGGATTGTGGGTCTTTTGGGCTTTGCTGCTC
CATTTACACAATGTGGATATCCTGCCTTAATGCCTTTGTATGCATGTATACAAGCT
AAACAGGCTTTCACTTTCTCGCCAACTTACAAGGCCTTTCTAAGTAAACAGTACAT
GAACCTTTACCCCGTTGCTCGGCAACGGCCTGGTCTGTGCCAAGTGTTTGCTGAC
GCAACCCCACTGGCTGGGGCTTGGCCATAGGCCATCAGCGCATGCGTGGAACC
TTTGTGGCTCCTCTGCCGATCCATACTGCGGAACTCCTAGCCGCTTGTTTTGCTC
GCAGCCGGTCTGGAGCAAAGCTCATAGGAACTGACAATTCTGTCGTCCTCTCGC
GGAAATATACATCGTTTCGATCTACGTATGATCTTTTTCCCTCTGCCAAAAATTATG
GGGACATCATGAAGCCCCTTGAGCATCTGACTTCTGGCTAATAAAGGAAATTTATT
TTCATTGCAATAGTGTGTTGGAATTTTTTGTGTCTCTCACTCGGAAGGAATTCTGC
ATTAATGAATCGGCCAACGCGCGGGGAGAGGCGGTTTGCGTATTGGGCGCTCTT
CCGCTTCCTCGCTCACTGACTCGCTGCGCTCGGTCGTTCGGCTGCGGCGAGCGG
TATCAGCTCACTCAAAGGCGGTAATACGGTTATCCACAGAATCAGGGGATAACGC
AGGAAAGAACATGTGAGCAAAAGGCCAGCAAAAGGCCAGGAACCGTAAAAAGGC
CGCGTTGCTGGCGTTTTTCCATAGGCTCCGCCCCCCTGACGAGCATCACAAAAAT
CGACGCTCAAGTCAGAGGTGGCGAAACCCGACAGGACTATAAAGATACCAGGCG
TTTCCCCCTGGAAGCTCCCTCGTGCGCTCTCCTGTTCCGACCCTGCCGCTTACCG
GATACCTGTCCGCCTTTCTCCCTTCGGGAAGCGTGGCGCTTTCTCATAGCTCACG
CTGTAGGTATCTCAGTTCGGTGTAGGTCGTTCGCTCCAAGCTGGGCTGTGTGCAC
GAACCCCCCGTTCAGCCCGACCGCTGCGCCTTATCCGGTAACTATCGTCTTGAGT
CCAACCCGGTAAGACACGACTTATCGCCACTGGCAGCAGCCACTGGTAACAGGA
TTAGCAGAGCGAGGTATGTAGGCGGTGCTACAGAGTTCTTGAAGTGGTGGCCTA
ACTACGGCTACACTAGAAGAACAGTATTTGGTATCTGCGCTCTGCTGAAGCCAGT
TACCTTCGGAAAAAGAGTTGGTAGCTCTTGATCCGGCAAACAAACCACCGCTGGT
AGCGGTGGTTTTTTTGTTTGCAAGCAGCAGATTACGCGCAGAAAAAAAGGATCTC
AAGAAGATCCTTTGATCTTTTCTACGGGGTCTGACGCTCAGTGGAACGAAAACTC
ACGTTAAGGGATTTTGGTCATGAGATTATCAAAAAGGATCTTCACCTAGATCCTTT
TAAATTAAAAATGAAGTTTTAAATCAATCTAAAGTATATATGAGTAAACTTGGTCTG
ACAGTTACCAATGCTTAATCAGTGAGGCACCTATCTCAGCGATCTGTCTATTTCGT
TCATCCATAGTTGCCTGACTC
```

SEQ ID NO: 35. NUCLEOTIDE SEQUENCE OF PLASMID 458

```
GGCGTAATGCTCTGCCAGTGTTACAACCAATTAACCAATTCTGATTAGAAAACTC
ATCGAGCATCAAATGAAACTGCAATTTATTCATATCAGGATTATCAATACCATATTT
TTGAAAAAGCCGTTTCTGTAATGAAGGAGAAAACTCACCGAGGCAGTTCCATAGG
ATGGCAAGATCCTGGTATCGGTCTGCGATTCCGACTCGTCCAACATCAATACAAC
CTATTAATTTCCCCTCGTCAAAAATAAGGTTATCAAGTGAGAAATCACCATGAGTG
ACGACTGAATCCGGTGAGAATGGCAAAAGCTTATGCATTTCTTTCCAGACTTGTTC
AACAGGCCAGCCATTACGCTCGTCATCAAAATCACTCGCATCAACCAAACCGTTA
TTCATTCGTGATTGCGCCTGAGCGAGACGAAATACGCGATCGCTGTTAAAAGGAC
AATTACAAACAGGAATCGAATGCAACCGGCGCAGGAACACTGCCAGCGCATCAAC
AATATTTTCACCTGAATCAGGATATTCTTCTAATACCTGGAATGCTGTTTTCCCGG
GGATCGCAGTGGTGAGTAACCATGCATCATCAGGAGTACGGATAAAATGCTTGAT
GGTCGGAAGAGGCATAAATTCCGTCAGCCAGTTTAGTCTGACCATCTCATCTGTA
ACATCATTGGCAACGCTACCTTTGCCATGTTTCAGAAACAACTCTGGCGCATCGG
GCTTCCCATACAATCGATAGATTGTCGCACCTGATTGCCCGACATTATCGCGAGC
CCATTTATACCCATATAAATCAGCATCCATGTTGGAATTTAATCGCGGCCTCGAGC
```

RAW SEQUENCE LISTING

```
AAGACGTTTCCCGTTGAATATGGCTCATAACACCCCTTGTATTACTGTTTATGTAA
GCAGACAGGTCGACAATATTGGCTATTGGCCATTGCATACGTTGTATCTATATCAT
AATATGTACATTTATATTGGCTCATGTCCAATATGACCGCCATGTTGACATTGATTA
TTGACTAGTTATTAATAGTAATCAATTACGGGGTCATTAGTTCATAGCCCATATATG
GAGTTCCGCGTTACATAACTTACGGTAAATGGCCCGCCTGGCTGACCGCCCAAC
GACCCCCGCCCATTGACGTCAATAATGACGTATGTTCCCATAGTAACGCCAATAG
GGACTTTCCATTGACGTCAATGGGTGGAGTATTTACGGTAAACTGCCCACTTGGC
AGTACATCAAGTGTATCATATGCCAAGTCCGCCCCCTATTGACGTCAATGACGGT
AAATGGCCCGCCTGGCATTATGCCCAGTACATGACCTTACGGGACTTTCCTACTT
GGCAGTACATCTACGTATTAGTCATCGCTATTACCATGGTGATGCGGTTTTGGCA
GTACACCAATGGGCGTGGATAGCGGTTTGACTCACGGGGATTTCCAAGTCTCCAC
CCCATTGACGTCAATGGGAGTTTGTTTTGGCACCAAAATCAACGGGACTTTCCAA
AATGTCGTAATAACCCCGCCCCGTTGACGCAAATGGGCGGTAGGCGTGTACGGT
GGGAGGTCTATATAAGCAGAGCTCGTTTAGTGAACCGTCAGATCGCCTGGAGAC
GCCATCCACGCTGTTTTGACCTCCATAGAAGACACCGGGACCGATCCAGCCTCC
GCGGCCGGGAACGGTGCATTGGAACGCGGATTCCCCGTGCCAAGAGTGACTCA
CCGTCCGGATCTCAGCAAGCAGGTATGTACTCTCCAGGGTGGGCCTGGCTTCCC
CAGTCAAGACTCCAGGGATTTGAGGGACGCTGTGGGCTCTTCTCTTACATGTACC
TTTTGCTTGCCTCAACCCTGACTATCTTCCAGGTCAGGATCCCAGAGTCAGGGGT
CTGTATTTTCCTGCTGGTGGCTCCAGTTCAGGAACAGTAAACCCTGCTCCGAATA
TTGCCTCTCACATCTCGTCAATCTCCGCGAGGACTGGGGACCCTGTGACGAACAT
GGCTAGCATTGTGGGAGGCTGGGAGTGCGAGAAGCATTCCCAACCCTGGCAGGT
GCTTGTGGCCTCTCGTGGCAGGGCAGTCTGCGGCGGTGTTCTGGTGCACCCCA
GTGGGTCCTCACAGCTGCCCACTGCATCAGGAACAAAAGCGTGATCTTGCTGGG
TCGGCACAGCTTGTTTCATCCTGAAGACACAGGCCAGGTATTTCAGGTCAGCCAC
AGCTTCCCACACCCGCTCTACGATATGAGCCTCCTGAAGAATCGATTCCTCAGGC
CAGGTGATGACTCCAGCCACGACCTCATGCTGCTCCGCCTGTCAGAGCCTGCCG
AGCTCACGGATGCTGTGAAGGTCATGGACCTGCCCACCCAGGAGCCAGCACTGG
GGACCACCTGCTACGCCTCAGGCTGGGGCAGCATTGAACCAGAGGAGTTCTTGA
CCCCAAAGAAACTTCAGTGTGTGGACCTCCATGTTATTTCCAATGACGTGTGTGC
GCAAGTTCACCCTCAGAAGGTGACCAAGTTCATGCTGTGTGCTGGACGCTGGAC
AGGGGGCAAAAGCACCTGCTCGGGTGATTCTGGGGGCCCACTTGTCTGTAATGG
TGTGCTTCAAGGTATCACGTCATGGGGCAGTGAACCATGTGCCCTGCCCGAAAG
GCCTTCCCTGTACACCAAGGTGGTGCATTACCGGAAGTGGATCAAGGACACCATC
GTGGCCAACCCCGGATCCGAAGGTAGGGGTTCATTATTGACCTGTGGAGATGTC
GAAGAAAACCCAGGACCCGCTAGCAAGGCTGTGCTGCTTGCCCTGTTGATGGCA
GGCTTGGCCCTGCAGCCAGGCACTGCCCTGCTGTGCTACTCCTGCAAAGCCCAG
GTGAGCAACGAGGACTGCCTGCAGGTGGAGAACTGCACCCAGCTGGGGGAGCA
GTGCTGGACCGCGCATCCGCGCAGTTGGCCTCCTGACCGTCATCAGCAAAGG
CTGCAGCTTGAACTGCGTGGATGACTCACAGGACTACTACGTGGGCAAGAAGAA
CATCACGTGCTGTGACACCGACTTGTGCAACGCCAGCGGGGCCCATGCCCTGCA
GCCGGCTGCCGCCATCCTTGCGCTGCTCCCTGCACTCGGCCTGCTGCTCTGGGG
ACCCGGCCAGCTAGGATCCCAGACCCTGAACTTTGATCTGCTGAAACTGGCAGG
CGATGTGGAAAGCAACCCAGGCCCAATGGCAAGCGCGCGCCGCCCGCGCTGGC
TGTGCGCTGGGGCGCTGGTGCTGGCGGGTGGCTTCTTTCTCCTCGGCTTCCTCT
TCGGGTGGTTTATAAAATCCTCCAATGAAGCTACTAACATTACTCCAAAGCATAAT
ATGAAAGCATTTTTGGATGAATTGAAAGCTGAGAACATCAAGAAGTTCTTATATAAT
TTTACACAGATACCACATTTAGCAGGAACAGAACAAAACTTTCAGCTTGCAAAGCA
AATTCAATCCCAGTGGAAAGAATTTGGCCTGGATTCTGTTGAGCTGGCACATTATG
ATGTCCTGTTGTCCTACCCAAATAAGACTCATCCCAACTACATCTCAATAATTAATG
AAGATGGAAATGAGATTTTCAACACATCATTATTTGAACCACCTCCTCCAGGATAT
GAAAATGTTTCGGATATTGTACCACCTTTCAGTGCTTTCTCTCCTCAAGGAATGCC
AGAGGGCGATCTAGTGTATGTTAACTATGCACGAACTGAAGACTTCTTTAAATTGG
AACGGGACATGAAAATCAATTGCTCTGGGAAAATTGTAATTGCCAGATATGGGAA
AGTTTTCAGAGGAAATAAGGTTAAAAATGCCCAGCTGGCAGGGGCAAAGGAGTC
ATTCTCTACTCCGACCCTGCTGACTACTTTGCTCCTGGGGTGAAGTCCTATCCAG
ATGGTTGGAATCTTCCTGGAGGTGGTGTCCAGCGTGGAAATATCCTAAATCTGAA
TGGTGCAGGAGACCCTCTCACACCAGGTTACCCAGCAAATGAATATGCTTATAGG
CGTGGAATTGCAGAGGCTGTTGGTCTTCCAAGTATTCCTGTTCATCCAATTGGATA
CTATGATGCACAGAAGCTCCTAGAAAAAATGGGTGGCTCAGCACCACCAGATAGC
AGCTGGAGAGGAAGTCTCAAAGTGCCCTACAATGTTGGACCTGGCTTTACTGGAA
ACTTTTCTACACAAAAAGTCAAGATGCACATCCACTCTACCAATGAAGTGACAAGA
ATTTACAATGTGATAGGTACTCTCAGAGGAGCAGTGGAACCAGACAGATATGTCA
TTCTGGGAGGTCACCGGGACTCATGGGTGTTTGGTGGTATTGACCCTCAGAGTG
GAGCAGCTGTTGTTCATGAAATTGTGAGGAGCTTTGGAACACTGAAAAAGGAAGG
GTGGAGACCTAGAAGAACAATTTTGTTTGCAAGCTGGGATGCAGAAGAATTTGGT
CTTCTTGGTTCTACTGAGTGGGCAGAGGAGAATTCAAGACTCCTTCAAGAGCGTG
GCGTGGCTTATATTAATGCTGACTCATCTATAGAAGGAAACTACACTCTGAGAGTT
GATTGTACACCGCTGATGTACAGCTTGGTACACAACCTAACAAAAGAGCTGAAAA
GCCCTGATGAAGGCTTTGAAGGCAAATCTCTTTATGAAAGTTGGACTAAAAAAGT
CCTTCCCCAGAGTTCAGTGGCATGCCCAGGATAAGCAAATTGGGATCTGGAAATG
ATTTTGAGGTGTTCTTCCAACGACTTGGAATTGCTTCAGGCAGAGCACGGTATACT
AAAAATTGGGAAACAAACAAATTCAGCGGCTATCCACTGTATCACAGTGTCTATGA
AACATATGAGTTGGTGGAAAAGTTTTATGATCCAATGTTTAAATATCACCTCACTGT
GGCCCAGGTTCGAGGAGGGATGGTGTTTGAGCTGGCCAATTCCATAGTGCTCCC
TTTTGATTGTCGAGATTATGCTGTAGTTTTAAGAAAGTATGCTGACAAAATCTACAG
TATTTCTATGAAACATCCACAGGAAATGAAGACATACAGTGTATCATTTGATTCACT
```

| RAW SEQUENCE LISTING |
|---|
| TTTTTCTGCAGTAAAGAATTTTACAGAAATTGCTTCCAAGTTCAGTGAGAGACTCC
AGGACTTTGACAAAAGCAACCCAATAGTATTAAGAATGATGAATGATCAACTCATG
TTTCTGGAAAGAGCATTTATTGATCCATTAGGGTTACCAGACAGGCCTTTTTATAG
GCATGTCATCTATGCTCCAAGCAGCCACAACAAGTATGCAGGGGAGTCATTCCCA
GGAATTTATGATGCTCTGTTTGATATTGAAAGCAAAGTGGACCCTTCCAAGGCCTG
GGGAGAAGTGAAGAGACAGATTTATGTTGCAGCCTTCACAGTGCAGGCAGCTGC
AGAGACTTTGAGTGAAGTAGCCTAAAGATCTGGGCCCTAACAAAACAAAAAGATG
GGGTTATTCCCTAAACTTCATGGGTTACGTAATTGGAAGTTGGGGGACATTGCCA
CAAGATCATATTGTACAAAAGATCAAACACTGTTTTAGAAAACTTCCTGTAAACAG
GCCTATTGATTGGAAAGTATGTCAAAGGATTGTGGGTCTTTTGGGCTTTGCTGCTC
CATTTACACAATGTGGATATCCTGCCTTAATGCCTTTGTATGCATGTATACAAGCT
AAACAGGCTTTCACTTTCTCGCCAACTTACAAGGCCTTTCTAAGTAAACAGTACAT
GAACCTTTACCCCGTTGCTCGGCAACGGCCTGGTCTGTGCCAAGTGTTTGCTGAC
GCAACCCCCACTGGCTGGGGCTTGGCCATAGGCCATCAGCGCATGCGTGGAACC
TTTGTGGCTCCTCTGCCGATCCATACTGCGGAACTCCTAGCCGCTTGTTTTGCTC
GCAGCCGGTCTGGAGCAAAGCTCATAGGAACTGACAATTCTGTCGTCCTCTCGC
GGAAATATACATCGTTTCGATCTACGTATGATCTTTTTCCCTCTGCCAAAAATTATG
GGGACATCATGAAGCCCCTTGAGCATCTGACTTCTGGCTAATAAAGGAAATTTATT
TTCATTGCAATAGTGTGTTGGAATTTTTTGTGTCTCTCACTCGGAAGGAATTCTGC
ATTAATGAATCGGCCAACGCGCGGGGAGAGGCGGTTTGCGTATTGGGCGCTCTT
CCGCTTCCTCGCTCACTGACTCGCTGCGCTCGGTCGTTCGGCTGCGGCGAGCGG
TATCAGCTCACTCAAAGGCGGTAATACGGTTATCCACAGAATCAGGGGATAACGC
AGGAAAGAACATGTGAGCAAAAGGCCAGCAAAAGGCCAGGAACCGTAAAAAGGC
CGCGTTGCTGGCGTTTTTCCATAGGCTCCGCCCCCCTGACGAGCATCACAAAAAT
CGACGCTCAAGTCAGAGGTGGCGAAACCCGACAGGACTATAAAGATACCAGGCG
TTTCCCCCTGGAAGCTCCCTCGTGCGCTCTCCTGTTCCGACCCTGCCGCTTACCG
GATACCTGTCCGCCTTTCTCCCTTCGGGAAGCGTGGCGCTTTCTCATAGCTCACG
CTGTAGGTATCTCAGTTCGGTGTAGGTCGTTCGCTCCAAGCTGGGCTGTGTGCAC
GAACCCCCCGTTCAGCCCGACCGCTGCGCCTTATCCGGTAACTATCGTCTTGAGT
CCAACCCGGTAAGACACGACTTATCGCCACTGGCAGCAGCCACTGGTAACAGGA
TTAGCAGAGCGAGGTATGTAGGCGGTGCTACAGAGTTCTTGAAGTGGTGGCCTA
ACTACGGCTACACTAGAAGAACAGTATTTGGTATCTGCGCTCTGCTGAAGCCAGT
TACCTTCGGAAAAAGAGTTGGTAGCTCTTGATCCGGCAAACAAACCACCGCTGGT
AGCGGTGGTTTTTTTGTTTGCAAGCAGCAGATTACGCGCAGAAAAAAAGGATCTC
AAGAAGATCCTTTGATCTTTTCTACGGGGTCTGACGCTCAGTGGAACGAAAACTC
ACGTTAAGGGATTTTGGTCATGAGATTATCAAAAAGGATCTTCACCTAGATCCTTT
TAAATTAAAAATGAAGTTTTAAATCAATCTAAAGTATATATGAGTAAACTTGGTCTG
ACAGTTACCAATGCTTAATCAGTGAGGCACCTATCTCAGCGATCTGTCTATTTCGT
TCATCCATAGTTGCCTGACTC

SEQ ID NO: 36. NUCLEOTIDE SEQUENCE OF PLASMID 459
GGCGTAATGCTCTGCCAGTGTTACAACCAATTAACCAATTCTGATTAGAAAACTC
ATCGAGCATCAAATGAAACTGCAATTTATTCATATCAGGATTATCAATACCATATTT
TTGAAAAAGCCGTTTCTGTAATGAAGGAGAAAACTCACCGAGGCAGTTCCATAGG
ATGGCAAGATCCTGGTATCGGTCTGCGATTCCGACTCGTCCAACATCAATACAAC
CTATTAATTTCCCCTCGTCAAAAATAAGGTTATCAAGTGAGAAATCACCATGAGTG
ACGACTGAATCCGGTGAGAATGGCAAAAGCTTATGCATTTCTTTCCAGACTTGTTC
AACAGGCCAGCCATTACGCTCGTCATCAAAATCACTCGCATCAACCAAACCGTTA
TTCATTCGTGATTGCGCCTGAGCGAGACGAAATACGCGATCGCTGTTAAAAGGAC
AATTACAAACAGGAATCAAATGCAACCGGCGCAGGAACACTGCCAGCGCATCAAC
AATATTTTCACCTGAATCAGGATATTCTTCTAATACCTGGAATGCTGTTTTCCCGG
GGATCGCAGTGGTGAGTAACCATGCATCATCAGGAGTACGGATAAAATGCTTGAT
GGTCGGAAGAGGCATAAATTCCGTCAGCCAGTTTAGTCTGACCATCTCATCTGTA
ACATCATTGGCAACGCTACCTTTGCCATGTTTCAGAAACAACTCTGGCGCATCGG
GCTTCCCATACAATCGATAGATTGTCGCACCTGATTGCCCGACATTATCGCGAGC
CCATTTATACCCATATAAATCAGCATCCATGTTGGAATTTAATCGCGGCCTCGAGC
AAGACGTTTCCCGTTGAATATGGCTCATAACACCCCTTGTATTACTGTTTATGTAA
GCAGACAGGTCGACAATATTGGCTATTGGCCATTGCATACGTTGTATCTATATCAT
AATATGTACATTTATATTGGCTCATGTCCAATATGACCGCCATGTTGACATTGATTA
TTGACTAGTTATTAATAGTAATCAATTACGGGGTCATTAGTTCATAGCCCATATATG
GAGTTCCGCGTTACATAACTTACGGTAAATGGCCCGCCTGGCTGACCGCCCAAC
GACCCCCGCCCATTGACGTCAATAATGACGTATGTTCCCATAGTAACGCCAATAG
GGACTTTCCATTGACGTCAATGGGTGGAGTATTTACGGTAAACTGCCCACTTGGC
AGTACATCAAGTGTATCATATGCCAAGTCCGCCCCCTATTGACGTCAATGACGGT
AAATGGCCCGCCTGGCATTATGCCCAGTACATGACCTTACGGGACTTTCCTACTT
GGCAGTACATCTACGTATTAGTCATCGCTATTACCATGGTGATGCGGTTTTGGCA
GTACACCAATGGGCGTGGATAGCGGTTTGACTCACGGGGATTTCCAAGTCTCCAC
CCCATTGACGTCAATGGGAGTTTGTTTTGGCACCAAAATCAACGGGACTTTCCAA
AATGTCGTAATAACCCCGCCCCGTTGACGCAAATGGGCGGTAGGCGTGTACGGT
GGGAGGTCTATATAAGCAGAGCTCGTTTAGTGAACCGTCAGATCGCCTGGAGAC
GCCATCCACGCTGTTTTGACCTCCATAGAAGACACCGGGACCGATCCAGCCTCC
GCGGCCGGGAACGGTGCATTGGAACGCGGATTCCCCGTGCCAAGAGTGACTCA
CCGTCCGGATCTCAGCAAGCAGGTATGTACTCTCCAGGGTGGGCCTGGCTTCCC
CAGTCAAGACTCCAGGGATTTGAGGGACGCTGTGGGCTCTTCTCTTACATGTACC
TTTTGCTTGCCTCAACCCTGACTATCTTCCAGGTCAGGATCCCAGAGTCAGGGGT
CTGTATTTTCCTGCTGGTGGCTCCAGTTCAGGAACAGTAAACCCTGCTCCGAATA
TTGCCTCTCACATCTCGTCAATCTCCGCGAGGACTGGGGACCCTGTGACGAACAT |

-continued

RAW SEQUENCE LISTING

```
GGCTAGCAAGGCTGTGCTGCTTGCCCTGTTGATGGCAGGCTTGGCCCTGCAGCC
AGGCACTGCCCTGCTGTGCTACTCCTGCAAAGCCCAGGTGAGCAACGAGGACTG
CCTGCAGGTGGAGAACTGCACCCAGCTGGGGGAGCAGTGCTGGACCGCGCGCA
TCCGCGCAGTTGGCCTCCTGACCGTCATCAGCAAAGGCTGCAGCTTGAACTGCG
TGGATGACTCACAGGACTACTACGTGGGCAAGAAGAACATCACGTGCTGTGACAC
CGACTTGTGCAACGCCAGCGGGGCCCATGCCCTGCAGCCGGCTGCCGCCATCC
TTGCGCTGCTCCCTGCACTCGGCCTGCTGCTCTGGGGACCCGGCCAGCTAGGAT
CCCAGACCCTGAACTTTGATCTGCTGAAACTGGCAGGCGATGTGGAAAGCAACC
CAGGCCCAATGGCAAGCGCGCGCCGCCCGCGCTGGCTGTGCGCTGGGCGCT
GGTGCTGGCGGGTGGCTTCTTTCTCCTCGGCTTCCTCTTCGGGTGGTTTATAAAA
TCCTCCAATGAAGCTACTAACATTACTCCAAAGCATAATATGAAAGCATTTTTGGAT
GAATTGAAAGCTGAGAACATCAAGAAGTTCTTATATAATTTTACACAGATACCACAT
TTAGCAGGAACAGAACAAAACTTTCAGCTTGCAAAGCAAATTCAATCCCAGTGGAA
AGAATTTGGCCTGGATTCTGTTGAGCTGGCACATTATGATGTCCTGTTGTCCTACC
CAAATAAGACTCATCCCAACTACATCTCAATAATTAATGAAGATGGAAATGAGATTT
TCAACACATCATTATTTGAACCACCTCCTCCAGGATATGAAAATGTTTCGGATATT
GTACCACCTTTCAGTGCTTTCTCTCCTCAAGGAATGCCAGAGGGCGATCTAGTGT
ATGTTAACTATGCACGAACTGAAGACTTCTTTAAATTGGAACGGGACATGAAAATC
AATTGCTCTGGGAAAATTGTAATTGCCAGATATGGGAAAGTTTTCAGAGGAAATAA
GGTTAAAAATGCCCAGCTGGCAGGGGCCAAAGGAGTCATTCTCTACTCCGACCCT
GCTGACTACTTTGCTCCTGGGGTGAAGTCCTATCCAGATGGTTGGAATCTTCCTG
GAGGTGGTGTCCAGCGTGGAAATATCCTAAATCTGAATGGTGCAGGAGACCCTCT
CACACCAGGTTACCCAGCAAATGAATATGCTTATAGGCGTGGAATTGCAGAGGCT
GTTGGTCTTCCAAGTATTCCTGTTCATCCAATTGGATACTATGATGCACAGAAGCT
CCTAGAAAAAATGGGTGGCTCAGCACCACCAGATAGCAGCTGGAGAGGAAGTCT
CAAAGTGCCCTACAATGTTGGACCTGGCTTTACTGGAAACTTTTCTACACAAAAAG
TCAAGATGCACATCCACTCTACCAATGAAGTGACAAGAATTTACAATGTGATAGGT
ACTCTCAGAGGAGCAGTGGAACCAGACAGATATGTCATTCTGGGAGGTCACCGG
GACTCATGGGTGTTTGGTGGTATTGACCCTCAGAGTGGAGCAGCTGTTGTTCATG
AAATTGTGAGGAGCTTTGGAACACTGAAAAAGGAAGGGTGGAGACCTAGAAGAAC
AATTTTGTTTGCAAGCTGGGATGCAGAAGAATTTGGTCTTCTTGGTTCTACTGAGT
GGGCAGAGGAGAATTCAAGACTCCTTCAAGAGCGTGGCGTGGCTTATATTAATGC
TGACTCATCTATAGAAGGAAACTACACTCTGAGAGTTGATTGTACACCGCTGATGT
ACAGCTTGGTACACAACCTAACAAAGAGCTGAAAAGCCCTGATGAAGGCTTTGA
AGGCAAATCTCTTTATGAAAGTTGGACTAAAAAAAGTCCTTCCCCAGAGTTCAGTG
GCATGCCCAGGATAAGCAAATTGGGATCTGGAAATGATTTTGAGGTGTTCTTCCA
ACGACTTGGAATTGCTTCAGGCAGAGCACGGTATACTAAAAATTGGGAAACAAAC
AAATTCAGCGGCTATCCACTGTATCACAGTGTCTATGAAACATATGAGTTGGTGGA
AAAGTTTTATGATCCAATGTTTAAATATCACCTCACTGTGGCCCAGGTTCGAGGAG
GGATGGTGTTTGAGCTGGCCAATTCCATAGTGCTCCCTTTTGATTGTGCGAGATTAT
GCTGTAGTTTTAAGAAAGTATGCTGACAAAATCTACAGTATTTCTATGAAACATCCA
CAGGAAATGAAGACATACAGTGTATCATTTGATTCACTTTTTCTGCAGTAAAGAAT
TTTACAGAAATTGCTTCCAAGTTCAGTGAGAGACTCCAGGACTTTGACAAAAGCAA
CCCAATAGTATTAAGAATGATGAATGATCAACTCATGTTTCTGGAAAGAGCATTTA
TTGATCCATTAGGGTTACCAGACAGGCCTTTTATAGGCATGTCATCTATGCTCCA
AGCAGCCACAACAAGTATGCAGGGGAGTCATTCCCAGGAATTTATGATGCTCTGT
TTGATATTGAAAGCAAAGTGGACCCTTCCAAGGCCTGGGGAGAAGTGAAGAGACA
GATTTATGTTGCAGCCTTCACAGTGCAGGCAGCTGCAGAGACTTTGAGTGAAGTA
GCCTAAAGATCTGACCCCCTAACGTTACTGGCCGAAGCCGCTTGGAATAAGGCC
GGTGTGCGTTTGTCTATATGTTATTTTCCACCCATATTGCCGTCTTTTGGCAATGTG
AGGGCCCGGAAACCTGGCCCTGTCTTCTTGACGAGCATTCCTAGGGGTCTTTCC
CCTCTCGCCAAAGGAATGCAAGGTCTGTTGAATGTCGTGAAGGAAGCAGTTCCTC
TGGAAGCTTCTTGAAGACAAACAACGTCTGTAGCGACCCTTTGCAGGCAGCGGAA
CCCCCCACCTGGCGACAGGTGCCTCTGCGGCCAAAAGCCACGTGTATAAGATAC
ACCTGCAAAGGCGGCACAACCCCAGTGCCACGTTGTGAGTTGGATAGTTGTGGA
AAGAGTCAAATGGCTCTCCTCAAGCGTATTCAACAAGGGGCTGAAGGATGCCCAG
AAGGTACCCCATTGTATGGGATCTGATCTGGGGCCTCGGTGCACATGCTTTACAT
GTGTTTAGTCGAGGTTAAAAAACGTCTAGGCCCCCCGAACCACGGGGACGTGGT
TTTCCTTTGAAAAACACGATGATAATATGGCCAGCATTGTGGGAGGCTGGGAGTG
CGAGAAGCATTCCCAACCCTGGCAGGTGCTTGTGGCCTCTCGTGGCAGGGCAGT
CTGCGGCGGTGTTCTGGTGCACCCCCAGTGGGTCCTCACAGCTGCCCACTGCAT
CAGGAACAAAAGCGTGATCTTGCTGGGTCGGCACAGCTTGTTTCATCCTGAAGAC
ACAGGCCAGGTATTTCAGGTCAGCCACAGCTTCCCACACCCGCTCTACGATATGA
GCCTCCTGAAGAATCGATTCCTCAGGCCAGGTGATGACTCCAGCCACGACCTCAT
GCTGCTCCGCCTGTCAGAGCCTGCCGAGCTCACGGATGCTGTGAAGGTCATGGA
CCTGCCCACCCAGGAGCCAGCACTGGGGACCACCTGCTACGCCTCAGGCTGGG
GCAGCATTGAACCAGAGGAGTTCTTGACCCCAAAGAAACTTCAGTGTGTGGACCT
CCATGTTATTTCCAATGACGTGTGTGCGCAAGTTCACCCTCAGAAGGTGACCAAG
TTCATGCTGTGTGCTGGACGCTGGACAGGGGGCAAAAGCACCTGCTCGGGTGAT
TCTGGGGGCCCACTTGTCTGTAATGGTGTGCTTCAAGGTATCACGTCATGGGGCA
GTGAACCATGTGCCCTGCCCGAAAGGCCTTCCCTGTACACCAAGGTGGTGCATTA
CCGGAAGTGGATCAAGGACACCATCGTGGCCAACCCCCTGAGGATCTGGGCCCTA
ACAAAACAAAAGATGGGGTTATTCCCTAAACTTCATGGGTTACGTAATTGGAAGT
TGGGGGACATTGCCACAAGATCATATTGTACAAAAGATCAAACACTGTTTTAGAAA
ACTTCCTGTAAACAGGCCTATTGATTGGAAAGTATGTCAAAGGATTGTGGGTCTTT
TGGGCTTTGCTGCTCCATTTACACAATGTGGATATCCTGCCTTAATGCCTTTGTAT
GCATGTATACAAGCTAAACAGGCTTTCACTTTCTCGCCAACTTACAAGGCCTTTCT
```

| RAW SEQUENCE LISTING |
|---|
| AAGTAAACAGTACATGAACCTTTACCCCGTTGCTCGGCAACGGCCTGGTCTGTGC |
| CAAGTGTTTGCTGACGCAACCCCCACTGGCTGGGGCTTGGCCATAGGCCATCAG |
| CGCATGCGTGGAACCTTTGTGGCTCCTCTGCCGATCCATACTGCGGAACTCCTAG |
| CCGCTTGTTTTGCTCGCAGCCGGTCTGGAGCAAAGCTCATAGGAACTGACAATTC |
| TGTCGTCCTCTCGCGGAAATATACATCGTTTCGATCTACGTATGATCTTTTTCCCT |
| CTGCCAAAAATTATGGGGACATCATGAAGCCCCTTGAGCATCTGACTTCTGGCTA |
| ATAAAGGAAATTTATTTTCATTGCAATAGTGTGTTGGAATTTTTTGTGTCTCTCACT |
| CGGAAGGAATTCTGCATTAATGAATCGGCCAACGCGCGGGGAGAGGCGGTTTGC |
| GTATTGGGCGCTCTTCCGCTTCCTCGCTCACTGACTCGCTGCGCTCGGTCGTTCG |
| GCTGCGGCGAGCGGTATCAGCTCACTCAAAGGCGGTAATACGGTTATCCACAGA |
| ATCAGGGGATAACGCAGGAAAGAACATGTGAGCAAAAGGCCAGCAAAAGGCCAG |
| GAACCGTAAAAAGGCCGCGTTGCTGGCGTTTTTCCATAGGCTCCGCCCCCCTGA |
| CGAGCATCACAAAAATCGACGCTCAAGTCAGAGGTGGCGAAACCCGACAGGACT |
| ATAAAGATACCAGGCGTTTCCCCCTGGAAGCTCCCTCGTGCGCTCTCCTGTTCCG |
| ACCCTGCCGCTTACCGGATACCTGTCCGCCTTTCTCCCTTCGGGAAGCGTGGCG |
| CTTTCTCATAGCTCACGCTGTAGGTATCTCAGTTCGGTGTAGGTCGTTCGCTCCA |
| AGCTGGGCTGTGTGCACGAACCCCCCGTTCAGCCCGACCGCTGCGCCTTATCCG |
| GTAACTATCGTCTTGAGTCCAACCCGGTAAGACACGACTTATCGCCACTGGCAGC |
| AGCCACTGGTAACAGGATTAGCAGAGCGAGGTATGTAGGCGGTGCTACAGAGTT |
| CTTGAAGTGGTGGCCTAACTACGGCTACACTAGAAGAACAGTATTTGGTATCTGC |
| GCTCTGCTGAAGCCAGTTACCTTCGGAAAAAGAGTTGGTAGCTCTTGATCCGGCA |
| AACAAACCACCGCTGGTAGCGGTGGTTTTTTTGTTTGCAAGCAGCAGATTACGCG |
| CAGAAAAAAAGGATCTCAAGAAGATCCTTTGATCTTTTCTACGGGGTCTGACGCTC |
| AGTGGAACGAAAACTCACGTTAAGGGATTTTGGTCATGAGATTATCAAAAAGGATC |
| TTCACCTAGATCCTTTTAAATTAAAAATGAAGTTTTAAATCAATCTAAAGTATATATG |
| AGTAAACTTGGTCTGACAGTTACCAATGCTTAATCAGTGAGGCACCTATCTCAGC |
| GATCTGTCTATTTCGTTCATCCATAGTTGCCTGACTC |
| |
| SEQ ID NO: 37. NUCLEOTIDE SEQUENCE OF PSHUTTLE IRES |
| CATCATCAATAATATACCTTATTTTGGATTGAAGCCAATATGATAATGAGGGGGTG |
| GAGTTTGTGACGTGGCGCGGGGCGTGGGAACGGGGCGGGTGACGTAGTAGTGT |
| GGCGGAAGTGTGATGTTGCAAGTGTGGCGGAACACATGTAAGCGACGGATGTGG |
| CAAAAGTGACGTTTTTGGTGTGCGCCGGTGTACACAGGAAGTGACAATTTTCGCG |
| CGGTTTTAGGCGGATGTTGTAGTAAATTTGGGCGTAACCGAGTAAGATTTGGCCA |
| TTTTCGCGGGAAAACTGAATAAGAGGAAGTGAAATCTGAATAATTTTGTGTTACTC |
| ATAGCGCGTAATACTGTAATAGTAATCAATTACGGGGTCATTAGTTCATAGCCCAT |
| ATATGGAGTTCCGCGTTACATAACTTACGGTAAATGCCCGCCTGGCTGACCGCC |
| CAACGACCCCCGCCCATTGACGTCAATAATGACGTATGTTCCCATAGTAACGCCA |
| ATAGGGACTTTCCATTGACGTCAATGGGTGGAGTATTTACGGTAAACTGCCCACT |
| TGGCAGTACATCAAGTGTATCATATGCCAAGTACGCCCCCTATTGACGTCAATGA |
| CGGTAAATGGCCCGCCTGGCATTATGCCCAGTACATGACCTTATGGGACTTTCCT |
| ACTTGGCAGTACATCTACGTATTAGTCATCGCTATTACCATGGTGATGCGGTTTTG |
| GCAGTACATCAATGGGCGTGGATAGCGGTTTGACTCACGGGGATTTCCAAGTCTC |
| CACCCCATTGACGTCAATGGGAGTTTGTTTTGGCACCAAAATCAACGGGACTTTC |
| CAAAATGTCGTAACAACTCCGCCCCATTGACGCAAATGGGCGGTAGGCGTGTAC |
| GGTGGGAGGTCTATATAAGCAGAGCTGGTTTAGTGAACCGTCAGATCCGCTAGA |
| GATCCACCATGGCTAGCGGTGCCCCGACGTTGCCCCCTGCCTGGCAGCCCTTTC |
| TCAAGGACCACCGCATCTCTACATTCAAGAACTGGCCCTTCTTGGAGGGCTGCGC |
| CTGCGCCCCGGAGCGGATGGCCGAGGCTGGCTTCATCCACTGCCCCCACTGAGA |
| ACGAGCCAGACTTGGCCCAGTGTTTCTTCTGCTTCAAGGAGCTGGAAGGCTGGG |
| AGCCAGATGACGACCCCATAGAGGAACATAAAAAGCATTCGTCCGGTTGCGCTTT |
| CCTTTCTGTCAAGAAGCAGTTTGAAGAATTAACCCTTGGTGAATTTTTGAAACTGG |
| ACAGAGAAAGAGCCAAGAACAAAATTGCAAAGGAAACCAACAATAAGAAGAAAGA |
| ATTTGAGGAAACTGCGGAGAAAGTGCGCCGTGCCATCGAGCAGCTGGCTGCCAT |
| GGATTAGAGATCTGACCCCCTAACGTTACTGGCCGAAGCCGCTTGGAATAAGGC |
| CGGTGTGCGTTTGTCTATATGTTATTTTCCACCATATTGCCGTCTTTTGGCAATGT |
| GAGGGCCCGGAAACCTGGCCCTGTCTTCTTGACGAGCATTCCTAGGGGTCTTTC |
| CCCTCTCGCCAAAGGAATGCAAGGTCTGTTGAATGTCGTGAAGGAAGCAGTTCCT |
| CTGGAAGCTTCTTGAAGACAAACAACGTCTGTAGCGACCCTTTGCAGGCAGCGGA |
| ACCCCCCACCTGGCGACAGGTGCCTCTGCGGCCAAAAGCCACGTGTATAAGATA |
| CACCTGCAAAGGCGGCACAACCCCAGTGCCACGTTGTGAGTTGGATAGTTGTGG |
| AAAGAGTCAAATGGCTCTCCTCAAGCGTATTCAACAAGGGGCTGAAGGATGCCCA |
| GAAGGTACCCCATTGTATGGGATCTGATCTGGGGCCTCGGTGCACATGCTTTACA |
| TGTGTTTAGTCGAGGTTAAAAAACGTCTAGGCCCCCCGAACCACGGGGACGTGG |
| TTTTCCTTTGAAAAACACGATAATATGGCGGCCGCTCGAGCCTAAGCTTCTAGATA |
| AGATATCCGATCCACCGGATCTAGATAACTGATCATAATCAGCCATACCACATTTG |
| TAGAGGTTTTACTTGCTTTAAAAAACCTCCCACACCTCCCCCTGAACCTGAAACAT |
| AAAATGAATGCAATTGTTGTTGTTAACTTGTTTATTGCAGCTTATAATGGTTACAAA |
| TAAAGCAATAGCATCACAAATTTCACAAATAAAGCATTTTTTTCACTGCATTCTAGT |
| TGTGGTTTGTCCAAACTCATCAATGTATCTTAACGCGGATCTGGGCGTGGTTAAG |
| GGTGGGAAAGAATATATAAGGTGGGGGTCTTATGTAGTTTTGTATCTGTTTTGCAG |
| CAGCCGCCGCCGCCATGAGCACCAACTCGTTTGATGGAAGCATTGTGAGCTCAT |
| ATTTGACAACGCGCATGCCCCCATGGGCCGGGGTGCGTCAGAATGTGATGGGCT |
| CCAGCATTGATGGTCGCCCCGTCCTGCCCGCAAACTCTACTACCTTGACCTACGA |
| GACCGTGTCTGGAACGCCGTTGGAGACTGCAGCCTCCGCCGCCGCTTCAGCCG |
| CTGCAGCCACCGCCCGCGGGATTGTGACTGACTTTGCTTTCCTGAGCCCGCTTG |
| CAAGCAGTGCAGCTTCCCGTTCATCCGCCCGCGATGACAAGTTGACGGCTCTTTT |

-continued

RAW SEQUENCE LISTING

```
GGCACAATTGGATTCTTTGACCCGGGAACTTAATGTCGTTTCTCAGCAGCTGTTG
GATCTGCGCCAGCAGGTTTCTGCCCTGAAGGCTTCCTCCCCTCCCAATGCGGTTT
AAAACATAAATAAAAAACCAGACTCTGTTTGGATTTGGATCAAGCAAGTGTCTTGC
TGTCTTTATTTAGGGGTTTTGCGCGCGCGGTAGGCCCGGGACCAGCGGTCTCGG
TCGTTGAGGGTCCTGTGTATTTTTTCCAGGACGTGGTAAAGGTGACTCTGGATGT
TCAGATACATGGGCATAAGCCCGTCTCTGGGGTGGAGGTAGCACCACTGCAGAG
CTTCATGCTGCGGGGTGGTGTTGTAGATGATCCAGTCGTAGCAGGAGCGCTGGG
CGTGGTGCCTAAAAATGTCTTTCAGTAGCAAGCTGATTGCCAGGGGCAGGCCCTT
GGTGTAAGTGTTTACAAAGCGGTTAAGCTGGGATGGGTGCATACGTGGGGATAT
GAGATGCATCTTGGACTGTATTTTTAGGTTGGCTATGTTCCCAGCCATATCCCTCC
GGGGATTCATGTTGTGCAGAACCACCAGCACAGTGTATCCGGTGCACTTGGGAA
ATTTGTCATGTAGCTTAGAAGGAAATGCGTGGAAGAACTTGGAGACGCCCTTGTG
ACCTCCAAGATTTTCCATGCATTCGTCCATAATGATGGCAATGGGCCCACGGGCG
GCGGCCTGGGCGAAGATATTTCTGGGATCACTAACGTCATAGTTGTGTTCCAGGA
TGAGATCGTCATAGGCCATTTTTACAAAGCGCGGGCGGAGGGTGCCAGACTGCG
GTATAATGGTTCCATCCGGCCCAGGGGCGTAGTTACCCTCACAGATTTGCATTTC
CCACGCTTTGAGTTCAGATGGGGGGATCATGTCTACCTGCGGGGCGATGAAGAA
AACGGTTTCCGGGGTAGGGGAGATCAGCTGGGAAGAAAGCAGGTTCCTGAGCAG
CTGCGACTTACCGCAGCCGGTGGGCCCGTAAATCACACCTATTACCGGCTGCAA
CTGGTAGTTAAGAGAGCTGCAGCTGCCGTCATCCCTGAGCAGGGGGGCCACTTC
GTTAAGCATGTCCCTGACTCGCATGTTTTCCCTGACCAAATCCGCCAGAAGGCGC
TCGCCGCCCAGCGATAGCAGTTCTTGCAAGGAAGCAAAGTTTTTCAACGGTTTGA
GACCGTCCGCCGTAGGCATGCTTTTGAGCGTTTGACCAAGCAGTTCCAGGCGGT
CCCACAGCTCGGTCACCTGCTCTACGGCATCTCGATCCAGCATATCTCCTCGTTT
CGCGGGTTGGGGCGGCTTTCGCTGTACGGCAGTAGTCGGTGCTCGTCCAGACG
GGCCAGGGTCATGTCTTTCCACGGGCGCAGGGTCCTCGTCAGCGTAGTCTGGGT
CACGGTGAAGGGGTGCGCTCCGGGCTGCGCGCTGGCCAGGGTGCGCTTGAGGC
TGGTCCTGCTGGTGCTGAAGCGCTGCCGGTCTTCGCCCTGCGCGTCGGCCAGGT
AGCATTTGACCATGGTGTCATAGTCCAGCCCCTCCGCGGCGTGGCCCTTGGCGC
GCAGCTTGCCCTTGGAGGAGGCGCCGCACGAGGGGCAGTGCAGACTTTTGAGG
GCGTAGAGCTTGGGCGCGAGAAATACCGATTCCGGGGAGTAGGCATCCGCGCC
GCAGGCCCCGCAGACGGTCTCGCATTCCACGAGCCAGGTGAGCTCTGGCCGTTC
GGGGTCAAAAACCAGGTTTCCCCCATGCTTTTTGATGCGTTTCTTACCTCTGGTTT
CCATGAGCCGGTGTCCACGCTCGGTGACGAAAAGGCTGTCCGTGTCCCCGTATA
CAGACTTGAGAGGGAGTTTAAACGAATTCAATAGCTTGTTGCATGGGCGGCGATA
TAAAATGCAAGGTGCTGCTCAAAAAATCAGGCAAAGCCTCGCGCAAAAAAGAAAG
CACATCGTAGTCATGCTCATGCAGATAAAGGCAGGTAAGCTCCGGAACCACCACA
GAAAAAGACACCATTTTTCTCTCAAACATGTCTGCGGGTTTCTGCATAAACACAAA
ATAAAATAACAAAAAAACATTTAAACATTAGAAGCCTGTCTTACAACAGGAAAAACA
ACCCTTATAAGCATAAGACGGACTACGGCCATGCCGGCGTGACCGTAAAAAAACT
GGTCACCGTGATTAAAAAGCACCACCGACAGCTCCTCGGTCATGTCCGGAGTCAT
AATGTAAGACTCGGTAAACACATCAGGTTGATTCACATCGGTCAGTGCTAAAAAG
CGACCGAAATAGCCCGGGGGAATACATACCCGCAGGCGTAGAGACAACATTACA
GCCCCCATAGGAGGTATAACAAAATTAATAGGAGAGAAAAACACATAAACACCTG
AAAAACCCTCCTGCCTAGGCAAAATAGCACCCTCCCGCTCCAGAACAACATACAG
CGCTTCCACAGCGGCAGCCATAACAGTCAGCCTTACCAGTAAAAAAGAAAACCTA
TTAAAAAAACACCACTCGACACGGCACCAGCTCAATCAGTCACAGTGTAAAAAAG
GGCCAAGTGCAGAGCGAGTATATATAGGACTAAAAAATGACGTAACGGTTAAAGT
CCACAAAAAACACCCAGAAAACCGCACGCGAACCTACGCCCAGAAACGAAAGCC
AAAAAACCCACAACTTCCTCAAATCGTCACTTCCGTTTTCCCACGTTACGTCACTT
CCCATTTTAAGAAAACTACAATTCCCAACACATACAAGTTACTCCGCCCTAAAACC
TACGTCACCCGCCCCGTTCCCACGCCCCGCGCCACGTCACAAACTCCACCCCCT
CATTATCATATTGGCTTCAATCCAAAATAAGGTATATTATTGATGATGTTAATTAAC
ATGCATGGATCCATATGCGGTGTGAAATACCGCACAGATGCGTAAGGAGAAAATA
CCGCATCAGGCGCTCTTCCGCTTCCTCGCTCACTGACTCGCTGCGCTCGGTCGT
TCGGCTGCGGCGAGCGGTATCAGCTCACTCAAAGGCGGTAATACGGTTATCCAC
AGAATCAGGGGATAACGCAGGAAAGAACATGTGAGCAAAAGGCCAGCAAAAGGC
CAGGAACCGTAAAAAGGCCGCGTTGCTGGCGTTTTTCCATAGGCTCCGCCCCCC
TGACGAGCATCACAAAAATCGACGCTCAAGTCAGAGGTGGCGAAACCCGACAGG
ACTATAAAGATACCAGGCGTTTCCCCCTGGAAGCTCCCTCGTGCGCTCTCCTGTT
CCGACCCTGCCGCTTACCGGATACCTGTCCGCCTTTCTCCCTTCGGGAAGCGTG
GCGCTTTCTCATAGCTCACGCTGTAGGTATCTCAGTTCGGTGTAGGTCGTTCGCT
CCAAGCTGGGCTGTGTGCACGAACCCCCCGTTCAGCCCGACCGCTGCGCCTTAT
CCGGTAACTATCGTCTTGAGTCCAACCCGGTAAGACACGACTTATCGCCACTGGC
AGCAGCCACTGGTAACAGGATTAGCAGAGCGAGGTATGTAGGCGGTGCTACAGA
GTTCTTGAAGTGGTGGCCTAACTACGGCTACACTAGAAGGACAGTATTTGGTATC
TGCGCTCTGCTGAAGCCAGTTACCTTCGGAAAAAGAGTTGGTAGCTCTTGATCCG
GCAAACAAACCACCGCTGGTAGCGGTGGTTTTTTTGTTTGCAAGCAGCAGATTAC
GCGCAGAAAAAAAGGATCTCAAGAAGATCCTTTGATCTTTTCTACGGGGTCTGAC
GCTCAGTGGAACGAAAACTCACGTTAAGGGATTTTGGTCATGAGATTATCAAAAA
GGATCTTCACCTAGATCCTTTTAAATTAAAAATGAAGTTTTAAATCAATCTAAAGTA
TATATGAGTAAACTTGGTCTGACAGTTACCAATGCTTAATCAGTGAGGCACCTATC
TCAGCGATCTGTCTATTTCGTTCATCCATAGTTGCCTGACTCCCCGTCGTGTAGAT
AACTACGATACGGGAGGGCTTACCATCTGGCCCCAGTGCTGCAATGATACCGCG
AGACCCACGCTCACCGGCTCCAGATTTATCAGCAATAAACCAGCCAGCCGGAAG
GGCCGAGCGCAGAAGTGGTCCTGCAACTTTATCCGCCTCCATCCAGTCTATTAAT
TGTTGCCGGGAAGCTAGAGTAAGTAGTTCGCCAGTTAATAGTTTGCGCAACGTTG
```

-continued

RAW SEQUENCE LISTING

```
TTGCCATTGCTGCAGCCATGAGATTATCAAAAAGGATCTTCACCTAGATCCTTTTC
ACGTAGAAAGCCAGTCCGCAGAAACGGTGCTGACCCCGGATGAATGTCAGCTAC
TGGGCTATCTGGACAAGGGAAAACGCAAGCGCAAAGAGAAAGCAGGTAGCTTGC
AGTGGGCTTACATGGCGATAGCTAGACTGGGCGGTTTTATGGACAGCAAGCGAA
CCGGAATTGCCAGCTGGGGCGCCCTCTGGTAAGGTTGGGAAGCCCTGCAAAGTA
AACTGGATGGCTTTCTTGCCGCCAAGGATCTGATGGCGCAGGGGATCAAGCTCT
GATCAAGAGACAGGATGAGGATCGTTTCGCATGATTGAACAAGATGGATTGCACG
CAGGTTCTCCGGCCGCTTGGGTGGAGAGGCTATTCGGCTATGACTGGGCACAAC
AGACAATCGGCTGCTCTGATGCCGCCGTGTTCCGGCTGTCAGCGCAGGGGCGC
CCGGTTCTTTTTGTCAAGACCGACCTGTCCGGTGCCCTGAATGAACTGCAAGACG
AGGCAGCGCGGCTATCGTGGCTGGCCACGACGGGCGTTCCTTGCGCAGCTGTG
CTCGACGTTGTCACTGAAGCGGGAAGGGACTGGCTGCTATTGGGCGAAGTGCCG
GGGCAGGATCTCCTGTCATCTCACCTTGCTCCTGCCGAGAAAGTATCCATCATGG
CTGATGCAATGCGGCGGCTGCATACGCTTGATCCGGCTACCTGCCCATTCGACC
ACCAAGCGAAACATCGCATCGAGCGAGCACGTACTCGGATGGAAGCCGGTCTTG
TCGATCAGGATGATCTGGACATGAAGAGCATCAGGGGCTCGCGCCAGCCGAACTGT
TCGCCAGGCTCAAGGCGAGCATGCCCGACGGCGAGGATCTCGTCGTGACCCAT
GGCGATGCCTGCTTGCCGAATATCATGGTGGAAAATGGCCGCTTTTCTGGATTCA
TCGACTGTGGCCGGCTGGGTGTGGCGGACCGCTATCAGGACATAGCGTTGGCTA
CCCGTGATATTGCTGAAGAGCTTGGCGGCGAATGGGCTGACCGCTTCCTCGTGC
TTTACGGTATCGCCGCTCCCGATTCGCAGCGCATCGCCTTCTATCGCCTTCTTGA
CGAGTTCTTCTGAATTTTGTTAAAATTTTTGTTAAATCAGCTCATTTTTTAACCAATA
GGCCGAAATCGGCACCATCCCTTATAAATCAAAAGAATAGACCGAGATAGGGTTG
AGTGTTGTTCCAGTTTGGAACAAGAGTCCACTATTAAAGAACGTGGACTCCAACG
TCAAAGGGCGAAAAACCGTCTATCAGGGCGATGGCCCACTACGTGAACCATCAC
CCTAATCAAGTTTTTTGTGGTCGAGGTGCCGTAAAGCACTAAATCGGAACCCTAAA
GGGAGCCCCGATTTAGAGCTTGACGGGGAAAGCCGGCGAACGTGGCGAGAAA
GGAAGGGAAGAAAGCGAAAGGAGCGGGCGCTAGGGCGCTGGCAAGTGTAGCGG
TCACGCTGCGCGTAACCACCACACCCGCGCGCTTAATGCGCCGCTACAGGGCGC
GTCCATTCGCCATTCAGGATCGAATTAATTCTTAATTAA
```

SEQ ID NO: 38. Amino acid sequence of Her-2 antigen:
MASELAALCRWGLLLALLPPGAASTQVCTGTDMKLRLPASPETHLDMLRHLYQGCQ
VVQGNLELTYLPTNASLSFLQDIQEVQGYVLIAHNQVRQVPLQRLRIVRGTQLFEDNY
ALAVLDNGDPLDSVAPAAGATPGGLQELQLRSLTEILKGGVLIRRSPQLCHQDTVLWE
DVFRKNNQLALVLMDTNRSRACHPCAPMCKANHCWGESSQDCQTLTRTICTSACAR
CKAPLPTDCCHEQCAAGCTGPKHSDCLACLHFNHSGICELHCPALVTYNTDTFESMP
NPEGRYTFGASCVTACPYNYLSTDVGSCTLVCPLHNQEVTAEDGTQRCEKCSKPCA
RVCYGLGMEHLREARAITSANVQDFVGCKKIFGSLAFLPESFDGDPASGTAPLQPEQ
LQVFETLEEITGYLYISAWPDSFPNLSVFQNLRVIRGRILHNGAYSLTLQGLGISWLGL
RSLQELGSGLALVHRNARLCFVHTVPWDQLFRNPHQALLHSGNRPEEDCVGEGFVC
YSLCAHGHCWGPGPTQCVNCSHFLRGQECVEEECRVLQGLPREYVNARHCLPCHPE
CQPQNGSVTCFGPEADQCVACAHYKDPPFCVARCPSGVKPDLSYMPIWKFPDEEG
ACQPCPINCTHSCVDLDDKGCPAEQRASPLTSIISAVVGILLVVVLGVVFGILIKRRQQK
IRKYTMRRNEDLGPSSPMDSTFYRSLLEDEDMGELVDAEEYLVPQQGFFCPDPTPGT
GSTAHRRHSSSARNGGGDLTLGMEPSGEGPPRSPRAPSEGTGSDVFDGDLAVGV
TKGLQSLSPQDLSPLQRYSEDPTLPLPSETDGKVAPLSCSPQPEFVNQSDVQPKSPL
TPEGPPSPARPTGATLERAKTLSPGKNGVVKDVFTFGGAVENPEFLAPREGTASPPH
PSPAFSPAFDNLFFWDQNSSEQGPPPSNFEGTPTAENPEFLGLDPV
(signal sequence underlined)

SEQ ID NO: 39. Nucleic acid sequence encoding the Her-2 antigen amino acid sequence of SEQ ID NO: 38
```
ATGGCTAGCGAGCTGGCCGCCCTGTGTAGATGGGGACTGCTGCTGGCTCTGCTG
CCTCCTGGAGCCGCTTCTACACAGGTCTGCACCGGCACCGACATGAAGCTGAGA
CTGCCCGCCAGCCCCGAGACACACCTGGACATGCTGCGGCACCTGTACCAGGG
CTGCCAGGTGGTCCAGGGGAATCTGGAACTGACCTACCTGCCCACCAACGCCAG
CCTGAGCTTCCTGCAGGACATCCAGGAAGTGCAGGGCTACGTCCTGATCGCCCA
CAACCAGGTCCGCCAGGTGCCCCTGCAGCGGCTGAGAATCGTGCGGGGCACCC
AGCTGTTCGAGGACAACTACGCCCTGGCCGTGCTGGACAACGGCGACCCTCTGG
ATAGCGTGGCCCCTGCTGCTGGGGCTACACCTGGCGGACTGCAGGAACTGCAG
CTGCGGAGCCTGACCGAGATCCTGAAGGGCGGCGTGCTGATCAGGCGGAGCCC
TCAGCTGTGCCACCAGGACACCGTGCTGTGGGAGGACGTGTTCCGGAAGAACAA
CCAGCTGGCCCTCGTGCTGATGGACACCAACAGAAGCCGGGCCTGCCACCCCTG
CGCCCCCATGTGCAAGGCCAATCACTGCTGGGGAGAGAGCAGCCAGGACTGCC
AGACCCTGACCCGGACCATCTGCACCAGCGCCTGCGCCAGATGCAAGGCCCCC
CTGCCTACCGACTGCTGCCACGAACAGTGCGCCGCTGGCTGCACCGGCCCCAA
GCACAGCGATTGCCTGGCCTGCCTGCACTTCAACCACAGCGGCATCTGCGAGCT
GCACTGCCCTGCCCTGGTGACATACAACACCGACACCTTCGAGAGCATGCCCAA
CCCCGAGGGCCGGTACACCTTCGGCGCCAGCTGTGTGACCGCCTGCCCCTACAA
CTACCTGAGCACCGACGTGGGCAGCTGCACCCTGGTGTGCCCCCTGCACAACCA
GGAAGTGACCGCCGAGGACGGCACCCAGAGATGCGAGAAGTGCAGCAAGCCTT
GCGCCAGAGTGTGCTACGGCCTGGGCATGGAACACCTGAGAGAGGCCAGAGCC
ATCACCAGCGCCAACGTGCAGGACTTCGTGGGCTGCAAGAAGATTTTCGGCTCC
CTGGCCTTCCTGCCCGAGAGCTTCGACGGCGATCCTGCCTCTGGCACCGCCCCT
CTGCAGCCTGAGCAGCTGCAGGTCTTCGAGACACTGGAAGAGATCACCGGCTAC
```

| RAW SEQUENCE LISTING |
|---|
| CTGTACATCAGCGCCTGGCCCGACAGCTTCCCCAACCTGAGCGTGTTCCAGAAC
CTGAGAGTGATCCGGGGCAGAATCCTGCACAACGGCGCCTACAGCCTGACCCTG
CAGGGCCTGGGAATCAGCTGGCTGGGCCTGCGGAGCCTGCAGGGAACTGGGATC
TGGCCTGGCTCTGGTGCACCGGAACGCCCGGCTGTGCTTCGTGCACACCGTGCC
CTGGGACCAGCTGTTCAGAAACCCCCACCAGGCTCTGCTGCACAGCGGCAACCG
GCCCGAAGAGGATTGCGTGGGCGAGGGCTTCGTGTGCTACTCCCTGTGCGCCCA
CGGCCACTGTTGGGGACCTGGCCCTACCCAGTGCGTGAACTGCAGCCACTTCCT
GCGGGGCCAAGAATGCGTGGAAGAGTGCCGGGTGCTGCAGGGACTGCCCCGGG
AATACGTGAACGCCAGACACTGCCTGCCTTGCCACCCCGAGTGCCAGCCCCAGA
ATGGCAGCGTGACCTGCTTCGGACCCGAGGCCGATCAGTGTGTGGCCTGCGCC
CACTACAAGGACCCCCCATTCTGCGTGGCCAGATGCCCCAGCGGCGTGAAGCCC
GACCTGAGCTACATGCCCATCTGGAAGTTCCCCGACGAGGAAGGCGCCTGCCAG
CCTTGCCCCATCAACTGCACCCACAGCTGCGTGGACCTGGACGACAAGGGCTGC
CCTGCCGAGCAGAGAGCCAGCCCCCTGACCAGCATCATCAGCGCCGTGGTGGGG
AATCCTGCTGGTGGTGGTGCTGGGCGTGGTGTTCGGCATCCTGATCAAGCGGCG
GCAGCAGAAGATCCGGAAGTACACCATGCGGCGGAACGAGGACCTGGGCCCCT
CTAGCCCCATGGACAGCACCTTCTACCGGTCCCTGCTGGAAGATGAGGACATGG
GCGAGCTGGTGGACGCCGAGGAATACCTGGTGCCTCAGCAGGGCTTCTTCTGCC
CCGACCCTACCCCTGGCACCGGCTCTACCGCCCACAGACGGCACAGAAGCAGCA
GCGCCAGAAACGGCGGAGGCGACCTGACCCTGGGAATGAACCTAGCGGCGAG
GGACCTCCCAGAAGCCCTAGAGCCCCTAGCGAGGGCACCGGCAGCGACGTGTT
CGATGGCGATCTGGCCGTGGGCGTGACCAAGGGACTGCAGAGCCTGAGCCCCC
AGGACCTGTCCCCCTGCAGAGATACAGCGAGGACCCCACCCTGCCCCTGCCCA
GCGAGACAGATGGCAAGGTGGCCCCCCTGAGCTGCAGCCCTCAGCCCGAGTTC
GTGAACCAGAGCGACGTGCAGCCCAAGTCCCCCCTGACACCCGAGGGACCTCCA
AGCCCTGCCAGACCTACCGGCGCCACCCTGGAAAGAGCCAAGACCCTGAGCCC
CGGCAAGAACGGCGTGGTGAAAGACGTGTTCACCTTCGGAGGCGCCGTGGAAAA
CCCCGAGTTCCTGGCCCCAGAGAGGGCACAGCCAGCCCTCCACACCCCAGCC
CAGCCTTCTCCCCCGCCTTCGACAACCTGTTCTTCTGGGACCAGAACAGCAGCGA
GCAGGGCCCACCCCCAGCAATTTCGAGGGCACCCCCACCGCCGAGAATCCTGA
GTTCCTGGGCCTGGACGTGCCCGTGTGA |

SEQ ID NO: 40. Amino acid sequence of heavy chain of the anti-CD40 antibody
CP870,893:
MDWTWRILFLVAAATGAHSQVQLVQSGAEVKKPGASVKVSCKASGYTFTGYYMHW
VRQAPGQGLEWMGWINPDSGGTNYAQKFQGRVTMTRDTSISTAYMELNRLRSDDT
AVYYCARDQPLGYCTNGVCSYFDYWGQGTLVTVSSASTKGPSVFPLAPCSRSTSES
TAALGCLVKDYFPEPVTVSWNSGALTSGVHTFPAVLQSSGLYSLSSVVTVPSSNFGT
QTYTCNVDHKPSNTKVDKTVERKCCVECPPCPAPPVAGPSVFLFPPKPKDTLMISRT
PEVTCVVVDVSHEDPEVQFNWYVDGVEVHNAKTKPREEQFNSTFRVVSVLTVVHQD
WLNGKEYKCKVSNKGLPAPIEKTISKTKGQPREPQVYTLPPSREEMTKNQVSLTCLV
KGFYPSDIAVEWESNGQPENNYKTTPPMLDSDGSFFLYSKLTVDKSRWQQGNVFSC
SVMHEALHNHYTQKSLSLSPGK.

SEQ ID NO: 41. Acid sequence of the light chain of the anti-CD40 antibody
CP870,893:
MRLPAQLLGLLLLWFPGSRCDIQMTQSPSSVSASVGDRVTITCRASQGIYSWLAWYQ
QKPGKAPNLLIYTASTLQSGVPSRFSGSGSGTDFTLTISSLQPEDFATYYCQQANIFPL
TFGGGTKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNR
GEC.

SEQ ID NO: 42. Acid sequence of the heavy chain of the anti-CTLA-4 antibody
Tremelimumab
QVQLVESGGGVVQPGRSLRLSCAASGFTFSSYGMHWVRQAPGKGLEWVAVIWYDG
SNKYYADSVKGRFTISRDNSKNTLYLQMNSLRAEDTAVYYCARDPRGATLYYYYGM
DVWGQGTTVTVSSASTKGPSVFPLAPCSRSTSESTAALGCLVKDYFPEPVTVSWNS
GALTSGVHTFPAVLQSSGLYSLSSVVTVPSSNFGTQTYTCNVDHKPSNTKVDKTVER
KCCVECPPCPAPPVAGPSVFLFPPKPKDTLMISRTPEVTCVVVDVSHEDPEVQFNWY
VDGVEVHNAKTKPREEQFNSTFRVVSVLTVVHQDWLNGKEYKCKVSNKGLPAPIEKT
ISKTKGQPREPQVYTLPPSREEMTKNQVSLTCLVKGFYPSDIAVEWESNGQPENNYK
TTPPMLDSDGSFFLYSKLTVDKSRWQQGNVFSCSVMHEALHNHYTQKSLSLSPGK SEQ ID NO: 43. Acid sequence of the light chain of the anti-CTLA-4 antibody
Tremelimumab
DIQMTQSPSSLSASVGDRVTITCRASQSINSYLDWYQQKPGKAPKLLIYAASSLQSGV
PSRFSGSGSGTDFTLTISSLQPEDFATYYCQQYYSTPFTFGPGTKVEIKRTVAAPSVFI
FPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC SEQ ID NO: 44. Nucleotide sequence of CpG 7909
5' TCGTCGTTTTGTCGTTTTGTCGTT3'

SEQ ID NO: 45. Nucleotide sequence of CpG 24555
5' TCGTCGTTTTTCGGTGCTTTT3'

| RAW SEQUENCE LISTING |
|---|

SEQ ID NO: 46. Nucleotide sequence of CpG 10103
5' TCGTCGTTTTTCGGTCGTTTT3'

SEQ ID NO: 47. Amino acid sequence of eGFP
MVSKGEELFTGVVPILVELDGDVNGHKFSVSGEGEGDATYGKLTLKFICTTGKLPVP
WPTLVTTLTYGVQCFSRYPDHMKQHDFFKSAMPEGYVQERTIFFKDDGNYKTRAEV
KFEGDTLVNRIELKGIDFKEDGNILGHKLEYNYNSHNVYIMADKQKNGIKVNFKIRHNIE
DGSVQLADHYQQNTPIGDGPVLLPDNHYLSTQSALSKDPNEKRDHMVLLEFVTAAGI
TLGMDELYK SEQ ID NO: 48. Amino acid sequence of HBV core antigen
MDIDPYKEFGATVELLSFLPSDFFPSVRDLLDTASALYREALESPEHCSPHHTALRQAI
LCWGELMTLATWVGNNLEDPASRDLVVNYVNTNMGLKIRQLLWFHISCLTFGRETVL
EYLVSFGVWIRTPPAYRPPNAPILSTLPETTVVRRRGRGRSPRRRTPSPRRRRSQSP
RRRRSQSRESQC SEQ ID NO: 49. Amino acid sequence of HBV surface antigen
MENITSGFLGPLLVLQAGFFLLTRILTIPQSLDSWWTSLNFLGGSPVCLGQNSQSPTS
NHSPTSCPPICPGYRWMCLRRFIIFLFILLLCLIFLLVLLDYQGMLPVCPLIPGSTTTSTG
PCKTCTTPAQGNSMFPSCCCTKPTDGNCTCIPIPSSWAFAKYLWEWASVRFSWLSLL
VPFVQWFVGLSPTVWLSAIWMMWYWGPSLYSIVSPFIPLLPIFFCLWVYI SEQ ID NO: 50. Amino acid sequence of Rhesus PSMA ECD protein:
MASETDTLLLWVLLLWVPGSTGDAAHHHHHHKSSSEATNITPKHNMKAFLDELKAENI
KKFLHNFTQIPHLAGTEQNFQLAKQIQSQWKEFGLDSVELTHYDVLLSYPNKTHPNYI
SIINEDGNEIFNTSLFEPPPAGYENVSDIVPPFSAFSPQGMPEGDLVYVNYARTEDFFK
LERDMKINCSGKIVIARYGKVFRGNKVKNAQLAGATGVILYSDPADYFAPGVKSYPDG
WNLPGGGVQRGNILNLNGAGDPLTPGYPANEYAYRRGIAEAVGLPSIPVHPIGYYDA
QKLLEKMGGSASPDSSWRGSLKVPYNVGPGFTGNFSTQKVKMHIHSTSEVTRIYNVI
GTLRGAVEPDRYVILGGHRDSWVFGGIDPQSGAAVVHEIVRSFGTLKKEGWRPRRTI
LFASWDAEEFGLLGSTEWAEENSRLLQERGVAYINADSSIEGNYTLRVDCTPLMYSL
VYNLTKELESPDEGFEGKSLYESWTKSPSPEFSGMPRISKLGSGNDFEVFFQRLGIAS
GRARYTKNWETNKFSSYPLYHSVYETYELVEKFYDPMFKYHLTVAQVRGGMVFELA
NSVVLPFDCRDYAVVLRKYADKIYNISMKHPQEMKTYSVSFDSLFSAVKNFTEIASKFS
ERLRDFDKSNPILLRMMNDQLMFLERAFIDPLGLPDRPFYRHVIYAPSSHNKYAGESF
PGIYDALFDIESKVDPSQAWGEVKRQISIATFTVQAAAETLSEVA SEQ ID NO: 51. Amino acid sequence of rat Her-2 p66 peptide (H-2d T cell
epitope)
TYVPANASL SEQ ID NO: 52. Amino acid sequence of rat Her-2 p169 peptide (H-2d T cell
epitope)
DMVLWKDVFRKNNQL SEQ ID NO: 53. Amino acid sequence of HBV core antigen p87 peptide
SYVNTNMGL SEQ ID NO: 54. Amino acid sequence of a Rat Her-2 Antigen (rHer-2):
MASELAAWCRWGFLLALLPPGIAGTQVCTGTDMKLRLPASPETHLDMLRHLYQGCQ
VVQGNLELTYVPANASLSFLQDIQEVQGYMLIAHNQVKRVPLQRLRIVRGTQLFEDKY
ALAVLDNRDPQDNVAASTPGRTPEGLRELQLRSLTEILKGGVLIRGNPQLCYQDMVL
WKDVFRKNNQLAPVDIDTNRSRACPPCAPACKDNHCWGESPEDCQILTGTICTSGC
ARCKGRLPTDCCHEQCAAGCTGPKHSDCLACLHFNHSGICELHCPALVTYNTDTFES
MHNPEGRYTFGASCVTTCPYNYLSTEVGSCTLVCPPNNQEVTAEDGTQRCEKCSKP
CARVCYGLGMEHLRGARAITSDNVQEFDGCKKIFGSLAFLPESFDGDPSSGIAPLRPE
QLQVFETLEEITGYLYISAWPDSLRDLSVFQNLRIIRGRILHDGAYSLTLQGLGLINSLGL
RSLRELGSGLALIHRNAHLCFVHTVPWDQLFRNPHQALLHSGNRPEEDCGLEGLVCN
SLCAHGHCWGPGPTQCVNCSHFLRGQECVEECRVWKGLPREYVSDKRCLPCHPEC
QPQNSSETCFGSEADQCAACAHYKDSSSCVARCPSGVKPDLSYMPIWKYPDEEGIC
QPCPINCTHSCVDLDERGCPAEQRASPVTFIIATVVGVLLFLILVVVVGILIKRRRQKIRK
YTMRRNEDLGPSSPMDSTFYRSLLEDDDMGDLVDAEEYLVPQQGFFSPDPTPGTGS
TAHRRHRSSSTRSGGGELTLGLEPSEEGPPRSPLAPSEGAGSDVFDGDLAMGVTKG
LQSLSPHDLSPLQRYSEDPTLPLPPETDGYVAPLACSPQPEFVNQSEVPQPPLTPE
GPLPPVRPAGATLERPKTLSPGKNGVVKDVFAFGGAVENPEFLVPREGTASPPHPSP
AFSPAFDNLFFWDQNSSEQGPPPSNFEGTPTAENPEFLGLDVPV SEQ ID NO: 55. Amino Acid Sequence of Rhesus PSMA antigen:
MASARRPRWLCAGALVLAGGFFLLGFLFGWFIKSSSEATNITPKHNMKAFLDELKAENIK
KFLHNFTQIPHLAGTEQNFQLAKQIQSQWKEFGLDSVELTHYDVLLSYPNKTHPNYISII
NEDGNEIFNTSLFEPPPAGYENVSDIVPPFSAFSPQGMPEGDLVYVNYARTEDFFKLERD
MKINCSGKIVIARYGKVFRGNKVKNAQLAGATGVILYSDPADYFAPGVKSYPDGWNLPGG
GVQRGNILNLNGAGDPLTPGYPANEYAYRRGIAEAVGLPSIPVHPIGYYDAQKLLEKMGG
SASPDSSWRGSLKVPYNVGPGFTGNFSTQKVKMHIHSTSEVTRIYNVIGTLRGAVEPDRY
VILGGHRDSWVFGGIDPQSGAAVVHEIVRSFGTLKKEGWRPRRTILFASWDAEEFGLLGS
TEWAEENSRLLQERGVAYINADSSIEGNYTLRVDCTPLMYSLVYNLTKELESPDEGFEGK
SLYESWTKKSPSPEFSGMPRISKLGSGNDFEVFFQRLGIASGRARYTKNWETNKFSSYPL

RAW SEQUENCE LISTING

YHSVYETYELVEKFYDPMFKYHLTVAQVRGGMVFELANSVVLPFDCRDYAVVLRKYADKI
YNISMKHPQEMKTYSVSFDSLFSAVKNFTEIASKFSERLRDFDKSNPILLRMMNDQLMFL
ERAFIDPLGLPDRPFYRHVIYAPSSHNKYAGESFPGIYDALFDIESKVDPSQAWGEVKRQ
ISIATFTVQAAAETLSEVA

SEQ ID NO: 56 Nucleotide sequence encoding the rhesus PSMA antigen of SEQ ID
NO: 55"
ATGGCTAGCGCTAGAAGGCCCAGATGGCTGTGCGCTGGCGCCCTGGTGCTGGCTGGCGGATTCTT
CCTGCTGGGCTTCCTGTTCGGCTGGTTCATCAAGTCCTCCAGCAGGGCCACCAACATCACCCCCA
AGCACAACATGAAGGCCTTTCTGGACGAGCTGAAGGCCGAGAATATCAAGAAGTTCCTGCACAAC
TTCACCCAGATCCCCCACCTGGCCGGCACCGAGCAGAACTTCCAGCTGGCCAAGCAGATCCAGTC
CCAGTGGAAAGAGTTCGGCCTGGACTCCGTGGAACTGACCCACTACGACGTGCTGCTGTCCTACC
CCAACAAGACCCACCCCAACTACATCTCCATCATCAACGAGGACGGCAACGAAATCTTCAACACC
TCCCTGTTCGAGCCCCACCAGCCGGCTACGAGAACGTGTCCGACATCGTGCCCCCATTCTCCGC
ATTCAGTCCACAAGGCATGCCCGAGGGCGACCTGGTGTACGTGAACTACGCCAGGACCGAGGACT
TCTTCAAGCTGGAAAGGGACATGAAGATCAACTGCTCCGGCAAGATCGTGATCGCCAGATACGGC
AAGGTGTTCAGGGGCAACAAAGTGAAGAACGCTCAGCTGGCTGGGGCCACCGGCGTGATCCTGTA
CTCTGACCCCGCCGACTACTTCGCCCCAGGCGTGAAGTCCTACCCCGACGGCTGGAACCTGCCAG
GTGGCGGAGTGCAGAGGGGCAACATCCTGAACCTGAACGGCTGGCGACCCCCTGACCCCAGGA
TACCCCGCCAACGAGTACGCCTACAGAAGAGGAATCGCCGAGGCCGTGGGCCTGCCCTCTATCCC
AGTGCACCCCATCGGCTACTACGACGCCCAGAAACTGCTGGAAAAGATGGGCGGCTCCGCCTCCC
CCGACTCCTCTTGGAGAGGCTCCCTGAAGGTGCCCTACAACGTGGGCCCAGGCTTCACCGGCAAC
TTCTCCACCCAGAAAGTGAAGATGCACATCCACTCCACCTCCAAGTGACCAGGATCTACAACGT
GATCGGCACCCTGAGAGGCGCCGTGGAACCCGACAGATACGTGATCCTGGGCGGCCACAGGGACA
GCTGGGTGTTCGGCGGCATCGACCCACAGTCTGGCGCCGCTGTGGTGCACGAGATCGTGCGGTCC
TTCGGAACCCTGAAGAAAGAGGGATGGCGCCCCAGAAGGACAATCCTGTTCGCCTCCTGGGACGC
CGAGGAATTCGGCCTGCTGGGATCCACCGAGTGGGCCGAGGAAAACTCCAGGCTGCTGCAGGAAA
GGGGCGTCGCCTACATCAACGCCGACTCCTCCATCGAGGGCAACTACACCCTGAGGGTGGACTGC
ACCCCCCTGATGTACTCCCTGGTGTACAACCTGACCAAAGAGCTGGAATCCCCCGACGAGGGCTT
CGAGGGCAAGTCCCTGTACGAGTCCTGGACCAAGAAGTCCCCATCCCCGAGTTCTCCGGCATGC
CCAGGATCTCCAAGCTGGGCTCCGGCAACGACTTCGAGGTGTTCTTCCAGAGGCTGGGAATCGCC
TCCGGCAGGGCCAGATACACCAAGAACTGGGAGACAAACAAGTTCTCCTCCTACCCCCTGTACCA
CTCCGTGTACGAAACCTACGAGCTGGTGGAAAAGTTCTACGACCCCATGTTCAAGTACCACTGA
CCGTGGCCCAGGTCCGCGGAGGCATGGTGTTCGAGCTGGCCAACTCCGTGGTGCTGCCCTTCGAC
TGCAGAGACTATGCTGTGGTGCTGAGGAAGTACGCCGACAAAATCTACAACATCTCCATGAAGCA
CCCCCAGGAAATGAAGACCTACTCCGTGTCCTTCGACTCCCTGTTCTCCGCCGTGAAGAATTTCA
CCGAGATCGCCTCCAAGTTCTCCGAGAGGCTGAGGGACTTCGACAAGTCCAACCCCATCCTGCTG
AGGATGATGAACGACCAGCTGATGTTCCTGGAAAGGGCCTTCATCGACCCCCTGGGCCTGCCAGA
CAGGCCCTTCTACAGGCACGTGATCTACGCCCCATCCTCCCACAACAAATACGCCGGCGAGTCCT
TCCCCGGCATCTACGATGCCCTGTTCGACATCGAGTCCAAGGTGGACCCCTCCCAGGCTTGGGGC
GAAGTGAAGAGGCAGATCAGTATCGCCACATTCACAGTGCAGGCCGCTGCCGAAACCCTGTCCGA
GGTGGCC

The invention claimed is:

1. A method of treating prostate cancer in a human, comprising administering to the human an effective amount of a composition 1 comprising a multi-antigen construct, wherein the multi-antigen construct comprises:
   (a) at least one nucleotide sequence encoding an immunogenic PSA polypeptide;
   (b) at least one nucleotide sequence encoding an immunogenic PSCA polypeptide; and
   (c) at least one nucleotide sequence encoding an immunogenic PSMA polypeptide, wherein the immunogenic PSA polypeptide comprises amino acids 4-240 of SEQ ID NO:17, wherein the immunogenic PSCA polypeptide comprises the amino acid sequence of SEQ ID NO:21, and wherein the immunogenic PSMA polypeptide has at least 90% identity with amino acids 15-750 of the human PSMA of SEQ ID NO:1 and comprises the amino acids of at least 10 conserved T cell epitopes of the human PSMA at corresponding positions.

2. The method according claim 1, wherein the immunogenic PSMA polypeptide is selected from the group consisting of:
   1) a polypeptide comprising amino acids 15-750 of SEQ ID NO: 1;
   2) a polypeptide comprising the amino acid sequence of SEQ ID NO:3;
   3) a polypeptide comprising the amino acid sequence of SEQ ID NO:5;
   4) a polypeptide comprising the amino acid sequence of SEQ ID NO:7;
   5) a polypeptide comprising the amino acids 4-739 of SEQ ID NO:9;
   6) a polypeptide comprising the amino acids 4-739 of SEQ ID NO:3;
   7) a polypeptide comprising the amino acids 4-739 of SEQ ID NO:5;
   8) a polypeptide comprising the amino acids 4-739 of SEQ ID NO:7; and
   9) polypeptide comprising the amino acid sequence of SEQ ID NO: 9.

3. The method according to claim 2, wherein the nucleotide sequence encoding the immunogenic PSA polypeptide is set forth in SEQ ID NO:18.

4. The method according to claim 3, wherein the nucleotide sequence encoding the immunogenic PSMA polypeptide is selected from the group consisting of:
   1) the nucleotide sequence of SEQ ID NO:2;
   2) the nucleotide sequence of SEQ ID NO:4;
   3) the nucleotide sequence of SEQ ID NO:6;
   4) the nucleotide sequence of SEQ ID NO:8;
   5) the nucleotide sequence of SEQ ID NO:10;
   6) a nucleotide sequence comprising nucleotides 10-2217 of SEQ ID NO:4;
   7) a nucleotide sequence comprising nucleotides 10-2217 of SEQ ID NO:6;
   8) a nucleotide sequence comprising nucleotides 10-2217 of SEQ ID NO:8; and
   9) a nucleotide sequence comprising nucleotides 10-2217 of SEQ ID NO:10.

5. The method according to claim 1, wherein the multi-antigen construct is incorporated into a vector.

6. The method according to claim 5, wherein the multi-antigen construct further comprises:
   (a) a nucleotide sequence encoding a T2A peptide sequence; and
   (b) a nucleotide sequence encoding a F2A peptide sequence.

7. The method according to 6, wherein the order of the nucleotide sequences on the multi-antigen construct is shown in formula (I):

PSA-T2A-PSCA-F2A-PSMA     (I)

wherein in formula (I):
   PSA is the nucleotide sequence encoding the immunogenic PSA polypeptide;
   PSCA is the nucleotide sequence encoding the immunogenic PSCA polypeptide;
   PSMA is the nucleotide sequence encoding the immunogenic PSMA polypeptide;
   T2A is the nucleotide sequence encoding the T2A peptide sequence; and
   F2A is the nucleotide sequence encoding the F2A peptide sequence.

8. The method according to 7, wherein the immunogenic PSMA polypeptide comprises the amino acid sequence of SEQ ID NO: 9.

9. The method according to claim 7, wherein the nucleotide sequence encoding the immunogenic PSMA polypeptide is set forth in SEQ ID NO:10.

10. A method of treating prostate cancer in a human, comprising administering to the human an effective amount of a composition comprising multi-antigen construct, wherein the multi-antigen construct comprises the nucleotide sequence of SEQ ID NO:35 or a degenerate variant of the nucleotide sequence of SEQ ID NO:35.

11. The method according to claim 10, wherein the multi-antigen construct comprises a degenerate variant of the nucleotide sequence of SEQ ID NO:35.

12. The method according to claim 10, further comprising administering to the human an effective amount of an immune modulators.

13. The method according to claim 12, wherein the immune modulator is an immune-effector-cell enhancer.

14. The method according to claim 13, wherein the immune-effector-cell enhancer is selected from the group consisting of TNFR agonists, CTLA-4 antagonists, TLR agonists, programmed cell death protein 1 antagonists, programmed cell death protein 1 ligand antagonists.

15. The method according to claim 14, wherein the immune-effector-cell enhancer is a CTLA-4 antagonist.

16. The method according to claim 15, wherein the CTLA-4 antagonist is an anti-CTLA-4 antibody.

17. The method according to claim 14, wherein the immune-effector-cell enhancer is a TLR agonist.

18. The method according to claim 17, wherein the TLR agonist is a CpG oligonucleotide.

19. The method according to claim 12, wherein the immune modulator is an immune-suppressive-cell inhibitor.

20. The method according to claim 19, wherein the immune-suppressive-cell inhibitor is sunitinib malate.

* * * * *